United States Patent
Shimizu et al.

(10) Patent No.: US 11,952,422 B2
(45) Date of Patent: Apr. 9, 2024

(54) ANTIGEN-BINDING MOLECULE COMPRISING ALTERED ANTIBODY VARIABLE REGION BINDING CD3 AND CD137

(71) Applicant: Chugai Seiyaku Kabushiki Kaisha, Tokyo (JP)

(72) Inventors: Shun Shimizu, Shizuoka (JP); Shu Wen Samantha Ho, Singapore (SG); Naoka Hironiwa, Shizuoka (JP); Mika Sakurai, Shizuoka (JP); Taro Miyazaki, Kanagawa (JP); Tomoyuki Igawa, Shizuoka (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 16/769,299

(22) PCT Filed: Dec. 4, 2018

(86) PCT No.: PCT/JP2018/044493
§ 371 (c)(1),
(2) Date: Jun. 3, 2020

(87) PCT Pub. No.: WO2019/111871
PCT Pub. Date: Jun. 13, 2019

(65) Prior Publication Data
US 2020/0377595 A1    Dec. 3, 2020

(30) Foreign Application Priority Data
Dec. 5, 2017 (JP) ................. 2017-233104

(51) Int. Cl.
*C07K 16/28* (2006.01)
*C07K 16/30* (2006.01)
*C40B 30/04* (2006.01)

(52) U.S. Cl.
CPC ...... *C07K 16/2809* (2013.01); *C07K 16/2863* (2013.01); *C07K 16/2878* (2013.01); *C07K 16/303* (2013.01); *C07K 2317/24* (2013.01); *C07K 2317/31* (2013.01); *C07K 2317/33* (2013.01); *C07K 2317/526* (2013.01); *C07K 2317/55* (2013.01); *C07K 2317/56* (2013.01); *C07K 2317/622* (2013.01); *C07K 2317/71* (2013.01); *C07K 2317/75* (2013.01); *C07K 2317/92* (2013.01); *C40B 30/04* (2013.01)

(58) Field of Classification Search
None
See application file for complete search history.

(56) References Cited

U.S. PATENT DOCUMENTS

| 6,344,443 | B1 | 2/2002 | Liu et al. |
| 6,737,056 | B1 | 5/2004 | Presta |
| 8,568,726 | B2 | 10/2013 | Beaumont et al. |
| 8,735,545 | B2 | 5/2014 | Lazar et al. |
| 9,493,569 | B2 | 11/2016 | Igawa et al. |
| 9,890,218 | B2 | 2/2018 | Mimoto et al. |
| 11,142,563 | B2 | 10/2021 | Igawa et al. |
| 11,154,615 | B2 * | 10/2021 | Igawa ................ C07K 16/2848 |
| 11,274,151 | B2 * | 3/2022 | Naoi ...................... C07K 16/28 |
| 11,718,672 | B2 | 8/2023 | Naoi et al. |
| 11,739,149 | B2 | 8/2023 | Igawa et al. |
| 2006/0121042 | A1 | 6/2006 | Dallacqua et al. |
| 2006/0140934 | A1 | 6/2006 | Gegg et al. |
| 2007/0071675 | A1 | 3/2007 | Wu et al. |
| 2007/0148164 | A1 | 6/2007 | Farrington et al. |
| 2007/0237767 | A1 | 10/2007 | Lazar et al. |
| 2007/0286859 | A1 | 12/2007 | Lazar et al. |
| 2008/0014205 | A1 | 1/2008 | Horowitz et al. |
| 2008/0089892 | A1 | 4/2008 | Allan et al. |
| 2010/0150918 | A1 | 6/2010 | Kufer et al. |
| 2010/0316641 | A1 | 12/2010 | Dimitrov |
| 2010/0322946 | A1 | 12/2010 | Bostrom et al. |
| 2011/0111406 | A1 | 5/2011 | Igawa et al. |
| 2012/0149876 | A1 | 6/2012 | Kreudenstein et al. |
| 2012/0328624 | A1 | 12/2012 | Yoshida et al. |
| 2013/0101581 | A1 | 4/2013 | Kuramochi et al. |
| 2014/0112914 | A1 | 4/2014 | Nezu et al. |
| 2014/0112926 | A1 | 4/2014 | Liu |
| 2014/0199294 | A1 | 7/2014 | Mimoto et al. |
| 2014/0242077 | A1 | 8/2014 | Choi et al. |
| 2015/0166636 | A1 | 6/2015 | Igawa et al. |
| 2015/0344570 | A1 | 12/2015 | Igawa et al. |
| 2016/0280787 | A1 * | 9/2016 | Igawa ...................... A61P 35/00 |
| 2017/0037130 | A1 | 2/2017 | Raum et al. |

(Continued)

FOREIGN PATENT DOCUMENTS

| CN | 1069124 | 2/1993 |
| CN | 101123983 | 2/2008 |

(Continued)

OTHER PUBLICATIONS

Lloyd et al. Protein Engineering, Design & Selection 22:159-168 (Year: 2009).*
Edwards et al., J Mol Biol. 334(1): 103-118 (Year: 2003).*
Piche-Nicholas et al., MABS 10(1): 81-94 (Year: 2018).*
Chiu et al., Antibodies 8(55): 1-80 (Year: 2019).*
U.S. Appl. No. 15/035,098, Igawa et al., filed May 6, 2016 (abandoned).
U.S. Appl. No. 16/704,464, Igawa et al., filed Dec. 5, 2019.
U.S. Appl. No. 17/506,733, Igawa et al., filed Oct. 21, 2021.
U.S. Appl. No. 17/484,003, Igawa et al., filed Sep. 24, 2021.
U.S. Appl. No. 17/272,972, Ho et al., filed Mar. 3, 2021.
U.S. Appl. No. 17/280,239, Igawa et al., filed Mar. 26, 2021.
U.S. Appl. No. 17/670,917, Naoi et al., filed Feb. 14, 2022.

(Continued)

*Primary Examiner* — Phuong Huynh
(74) *Attorney, Agent, or Firm* — Fish & Richardson P.C.

(57) ABSTRACT

Antigen-binding domains that are capable of binding to CD3 and CD137 but do not bind to CD3 and CD137 at the same time and methods of using the same are provided. Methods to obtain antigen binding domains which bind to two or more different antigen more efficiently are also provided.

15 Claims, 44 Drawing Sheets
Specification includes a Sequence Listing.

(56) References Cited

U.S. PATENT DOCUMENTS

| | | |
|---|---|---|
| 2017/0274072 A1 | 9/2017 | Kumagai et al. |
| 2017/0306036 A1 | 10/2017 | Vu et al. |
| 2018/0201691 A1 | 7/2018 | Hudson |
| 2018/0296668 A1 | 10/2018 | Igawa et al. |
| 2020/0332001 A1 | 10/2020 | Igawa et al. |
| 2021/0301016 A1 | 9/2021 | Naoi et al. |
| 2021/0388087 A1 | 12/2021 | Ho et al. |
| 2022/0040297 A1 | 2/2022 | Igawa et al. |
| 2022/0112296 A1 | 4/2022 | Igawa et al. |
| 2022/0242934 A1 | 8/2022 | Igawa et al. |
| 2022/0251201 A1 | 8/2022 | Naoi et al. |
| 2023/0121511 A1 | 4/2023 | Chichili et al. |
| 2023/0147840 A1 | 5/2023 | Naoi et al. |

FOREIGN PATENT DOCUMENTS

| | | |
|---|---|---|
| EP | 1 293 514 | 3/2003 |
| EP | 1 752 471 | 2/2007 |
| EP | 2 241 578 A | 10/2010 |
| EP | 2 647 707 | 10/2013 |
| EP | 2 731 970 A | 5/2014 |
| EP | 3 070 168 | 9/2016 |
| EP | 3 130 606 A | 2/2017 |
| EP | 3 219 724 | 9/2017 |
| EP | 3 305 322 A | 4/2018 |
| EP | 3 831 854 A | 6/2021 |
| JP | 2007-536912 | 12/2007 |
| JP | 2008-514201 | 5/2008 |
| JP | 2008-518023 | 5/2008 |
| JP | 2008-526809 | 7/2008 |
| JP | 2009/511587 | 3/2009 |
| JP | 2009-538273 | 11/2009 |
| JP | 2009-540837 | 11/2009 |
| JP | 2010-524851 | 7/2010 |
| JP | 2012-501648 | 1/2012 |
| JP | 6628966 | 1/2020 |
| RU | 2014/109551 | 9/2015 |
| RU | 2016/143383 | 5/2018 |
| WO | WO 92/19973 | 11/1992 |
| WO | WO 94/18221 | 8/1994 |
| WO | WO 95/14714 | 6/1995 |
| WO | WO 00/42072 | 7/2000 |
| WO | WO 01/77342 | 10/2001 |
| WO | WO 2005/070966 | 8/2005 |
| WO | WO 2006/019447 | 2/2006 |
| WO | WO 2006/036834 | 4/2006 |
| WO | WO 2006/047340 | 5/2006 |
| WO | WO 2006/047639 | 5/2006 |
| WO | WO 2006/072620 | 7/2006 |
| WO | WO 2006/083706 | 8/2006 |
| WO | WO 2006/106905 | 10/2006 |
| WO | WO 2007/047291 | 4/2007 |
| WO | WO 2007/121354 | 10/2007 |
| WO | WO 2008/003103 | 1/2008 |
| WO | WO 2008/119567 | 10/2008 |
| WO | WO 2009/087978 | 7/2009 |
| WO | WO 2009/125825 | 10/2009 |
| WO | WO 2010/027981 | 3/2010 |
| WO | WO 2010/035012 | 4/2010 |
| WO | WO 2010/080538 | 7/2010 |
| WO | WO 2011/057788 | 5/2011 |
| WO | WO 2011/093097 | 8/2011 |
| WO | WO 2011/108714 | 9/2011 |
| WO | WO 2011/122011 | 10/2011 |
| WO | WO 2011/133886 | 10/2011 |
| WO | WO 2012/003956 | 1/2012 |
| WO | WO 2012/064792 | 5/2012 |
| WO | WO 2012/073985 | 6/2012 |
| WO | WO 2012/096994 | 7/2012 |
| WO | WO 2012/143524 | 10/2012 |
| WO | WO 2012/156018 | 11/2012 |
| WO | WO 2012/162067 | 11/2012 |
| WO | WO 2013/026833 | 2/2013 |
| WO | WO 2013/026839 | 2/2013 |
| WO | WO 2013/055958 | 4/2013 |
| WO | WO 2013/059593 | 4/2013 |
| WO | WO 2013/126746 | 8/2013 |
| WO | WO 2013/187495 | 12/2013 |
| WO | WO 2014/075697 | 5/2014 |
| WO | WO 2014/075788 | 5/2014 |
| WO | WO 2014/116846 | 7/2014 |
| WO | WO 2015/068847 | 5/2015 |
| WO | WO 2015/069794 | 5/2015 |
| WO | WO 2015/138615 | 9/2015 |
| WO | WO 2015/156268 | 10/2015 |
| WO | WO 2016/047722 | 3/2016 |
| WO | WO 2016/076345 | 5/2016 |
| WO | WO 2017/021349 | 2/2017 |
| WO | WO 2018/114748 | 6/2018 |
| WO | WO 2018/114754 | 6/2018 |
| WO | WO 2019/111871 | 6/2019 |
| WO | WO 2019/131988 | 7/2019 |
| WO | WO 2019/135404 | 7/2019 |
| WO | WO 2020/027330 | 2/2020 |
| WO | WO 2020/067399 | 4/2020 |
| WO | WO 2020/067419 | 4/2020 |
| WO | WO 2021/006328 | 1/2021 |
| WO | WO 2021/200896 | 10/2021 |
| WO | WO 2021/200898 | 10/2021 |
| WO | WO 2021/200939 | 10/2021 |
| WO | WO 2021/201087 | 10/2021 |

OTHER PUBLICATIONS

Amann et al., "Therapeutic window of an EpCAM/CD3-specific BiTE antibody in mice is determined by a subpopulation of EpCAM-expressing lymphocytes that is absent in humans," Cancer Immunol Immunother, Jan. 2009, 58(1):95-109. Epub Jul. 2, 2008.

Bulman et al., "Mutations in the human Delta homologue, DLL3, cause axial skeletal defects in spondylocostal dysostosis," Nat Genet, Apr. 2000, 24(4):438-441.

Campoli et al., "Immunotherapy of Malignant Disease with Tumor Antigen-Specific Monoclonal Antibodies," Clin Cancer Res, Jan. 1, 2010, 16(1):11-20. Epub Dec. 22, 2009.

Dreier et al., "Extremely Potent, Rapid and Costimulation-Independent Cytotoxic T-Cell Response Against Lymphoma Cells Catalyzed by a Single-Chain Bispecific Antibody," Int J Cancer, Aug. 20, 2002, 100(6):690-697.

Mack et al., "A small bispecific antibody construct expressed as a functional single-chain molecule with high tumor cell cytotoxicity," Proc Natl Acad Sci USA, Jul. 18, 1995, 92(15):7021-7025.

Mezzanzanica et al., "Human Ovarian Carcinoma Lysis by Cytotoxic T Cells Targeted by Bispecific Monoclonal Antibodies: Analysis of the Antibody Components," Int J Cancer, Apr. 15, 1988, 41(4):609-615.

Mullendore et al., "Ligand-dependent Notch Signaling is Involved in Tumor Initiation and Tumor Maintenance in Pancreatic Cancer," Clin Cancer Res, Apr. 1, 2009, 15(7):2291-2301.

Phillips et al., "Molecular subclasses of high-grade glioma predict prognosis, delineate a pattern of disease progression, and resemble stages in neurogenesis," Cancer Cell, Mar. 2006, 9(3):157-173.

Schlereth et al., "T-cell activation and B-cell depletion in chimpanzees treated with a bispecific anti-CD19/anti-CD3 single-chain antibody construct," Cancer Immunol Immunother, May 2006, 55(5):503-514. Epub Jul. 20, 2005.

Sebastian et al., "Treatment of non-small cell lung cancer patients with the trifunctional monoclonal antibody catumaxomab (anti-EpCAM x anti-CD3): a phase I study," Cancer Immunol Immunother, Oct. 2007, 56(10):1637-1644. Epub Apr. 5, 2007.

Staerz et al., "Hybrid antibodies can target sites for attack by T cells," Nature, Apr. 18-24, 1985, 314(6012):628-631.

Staerz et al., "Hybrid hybridoma producing a bispecific monoclonal antibody that can focus effector T-cell activity," Proc Natl Acad Sci USA, Mar. 1986, 83(5):1453-1457.

Turnpenny et al., "Novel mutations in DLL3, a somitogenesis gene encoding a ligand for the Notch signaling pathway, cause a consistent pattern of abnormal vertebral segmentation in spondylocostal dysostosis," J Med Genet, May 2003, 40(5):333-339.

(56) References Cited

OTHER PUBLICATIONS

Wolf et al., "BiTEs: bispecific antibody constructs with unique anti-tumor activity," Drug Discov Today, Sep. 15, 2005, 10(18):1237-1244.
U.S. Appl. No. 15/525,603, Igawa et al., filed May 10, 2017.
U.S. Appl. No. 14/406,232, Igawa et al., filed Dec. 8, 2014.
Abuazza et al., "Claudins 6, 9, and 13 are developmentally expressed renal tight junction proteins," Am J Physiol Renal Physiol, Dec. 2006, 291(6):F1132-1141.
Bardwell et al., "Potent and conditional redirected T cell killing of tumor cells using Half DVD-Ig," Protein Cell, Jan. 2018, 9(1):121-129.
Dickopf et al., "Format and geometries matter: Structure-based design defines the functionality of bispecific antibodies," Comput Struct Biotechnol J, May 14, 2020, 18:1221-1227.
Ellmark et al., "Selective FcKR engagement by human agonistic anti-CD40 antibodies," Transl Cancer Res, Oct. 2016, 5(Suppl 4):S839-S841.
Ferran et al., "Cytokine-related syndrome following injection of anti-CD3 monoclonal antibody: Further evidence for transient in vivo T cell activation," Eur J Immunol, Mar. 1990, 20(3):509-515.
Frey et al., "Cytokine release syndrome with novel therapeutics for acute lymphoblastic leukemia," Hematology Am Soc Hematol Educ Program, Dec. 2, 2016, 2016(1):567-572.
Furuse et al., "Claudins in occluding junctions of humans and flies," Trends Cell Biol, Apr. 2006, 16(4):181-188. Epub Mar. 14, 2006.
Hashizume et al., "Expression Patterns of Claudin Family of Tight Junction Membrane Proteins in Developing Mouse Submandibular Gland, " Dev Dyn, Oct. 2004, 231(2):425-431.
Micke et al., "Aberrantly activated claudin 6 and 18.2 as potential therapy targets in non-small-cell lung cancer," Int J Cancer, Nov. 1, 2014, 135(9):2206-2214.
Morita et al., "Claudin multigene family encoding four-transmembrane domain protein components of tight junction strands," Proc Natl Acad Sci USA, Jan. 19, 1999, 96(2):511-516.
Rahner et al., "Heterogeneity in Expression and Subcellular Localization of Claudins 2, 3, 4, and 5 in the Rat Liver, Pancreas, and Gut," Gastroenterology, Feb. 2001, 120(2):411-422.
Rendon-Huerta et al., "Distribution and Expression Pattern of Claudins 6, 7, and 9 in Diffuse- and Intestinal-Type Gastric Adenocarcinomas," J Gastrointest Cancer, Mar. 2010, 41(1):52-59.
Stadler et al., "Characterization of the first-in-class T-cell-engaging bispecific single-chain antibody for targeted immunotherapy of solid tumors expressing the oncofetal protein claudin 6," Oncoimmunology, Oct. 29, 2015, 5(3):e1091555. eCollection Mar. 2016.
Ushiku et al., "Distinct expression pattern of claudin-6, a primitive phenotypic tight junction molecule, in germ cell tumours and visceral carcinomas," Histopathology, Dec. 2012, 61(6):1043-1056.
Wilcox et al., "Mutations in the Gene Encoding Tight Junction Claudin-14 Cause Autosomal Recessive Deafness DFNB29," Cell, Jan. 12, 2001, 104(1):165-172.
Atwell et al., "Stable heterodimers from remodeling the domain interface of a homodimer using a phage display library," J Mol Biol, Jul. 4, 1997, 270(1):26-35.
Baeuerle et al., "Bispecific T-Cell Engaging Antibodies for Cancer Therapy," Cancer Res, Jun. 15, 2009, 69(12):4941-4. doi:10.1158/0008-5472.CAN-09-0547. Epub Jun. 9, 2009.
Beljaars et al., "The preferential homing of a platelet derived growth factor receptor-recognizing macromolecule to fibroblast-like cells in fibrotic tissue," Biochemical Pharmacology, Oct. 2003, 66(7):1307-17.
Berntzen et al., "Identification of a High Affinity FcγRIIA-binding Peptide that Distinguishes FcγRIIA from FcγRIIB and Exploits FcγRIIA-mediated Phagocytosis and Degradation," J Biol Chem, Jan. 2009, 284(2):1126-1135. doi: 10.1074/jbc.M803584200. Epub Oct. 28, 2008.
Binetruy-Tournaire et al., "Identification of a peptide blocking vascular endothelial growth factor (VEGF)-mediated angiogenesis," EMBO J, Apr. 3, 2000, 19(7):1525-33.
Boder et al., "Directed evolution of antibody fragments with monovalent femtomolar antigen-binding affinity," Proc Natl Acad Sci USA, Sep. 26, 2000, 97(20):10701-5.
Bostrom et al., "Variants of the Antibody Herceptin That Interact with HER2 and VEGF at the Antigen Binding Site," Science, Mar. 20, 2009, 323(5921):1610-4.
Brennand et al., "A cyclic peptide analogue of loop III of PDGF-BB causes an apoptosis in human fibroblasts," FEBS Lett, Dec. 15, 1997, 419(2-3):166-70.
Chamarthy et al., "Gene delivery to dendritic cells facilitated by a tumor necrosis factor alpha-competing peptide," Mol Immunol, Jul. 2004, 41(8):741-9.
Chan et al., "Therapeutic antibodies for autoimmunity and inflammation," Nat Rev Immunol, May 2010, 10(5):301-16. doi: 10.1038/nri2761.
Chen et al., "Characterization of human IgG repertoires in an acute HIV-1 infection," Exp Mol Pathol, Dec. 2012, 93(3):399-407. doi: 10.1016/j.yexmp.2012.09.022. Epub Oct. 1, 2012.
Chen et al., "Enhancement and destruction of antibody function by somatic mutation: unequal occurrence is controlled by V gene combinatorial associations," The EMBO Journal, Jun. 1995, 14(12):2784-2794.
Clackson et al., "Making antibody fragments using phage display libraries," Nature, Aug. 15, 1991, 352(6336):624-8.
Clark, "IgG effector mechanisms," Chem Immunol, 1997, 65:88-110.
Conrad et al, "TCR and CD3 antibody cross-reactivity in 44 species," Cytometry A, Nov. 2007, 71(11):925-33.
Dall'Acqua et al., "Modulation of the Effector Functions of a Human IgG1 through Engineering of Its Hinge Region," J Immunol, Jul. 15, 2006, 177(2):1129-38.
De Pascalis et al., "Grafting of 'Abbreviated' Complementarity-Determining Regions Containing Specificity-Determining Residues Essential for Ligand Contact to Engineer a Less Immunogenic Humanized Monoclonal Antibody," J Immunol, Sep. 15, 2002, 169(6):3076-3084.
Deambrosis et al., "Inhibition of CD40-CD154 costimulatory pathway by a cyclic peptide targeting CD154," J Mol Med, Feb. 2009, 87(2):181-97.
Dermer et al., "Another Anniversary for the War on Cancer," Bio/Technology, Mar. 1, 1994, 12:320.
Dubrot et al., "Treatment with anti-CD137 mAbs causes intense accumulations of liver T cells without selective antitumor immunotherapeutic effects in this organ," Cancer Immunol Immunother, Aug. 2010, 59(8):1223-33.
Dufner, "Harnessing phage and ribosome display for antibody optimization," Trends Biotechnol, Nov. 2006, 24(11):523-529.
Edelman et al., "A Covalent Structure of an Entire γG Immunoglobulin Molecule," Proc Natl Acad Sci USA, May 1969, 63(1):78-85.
Eigenbrot et al., "Two-in-One antibodies with dual action Fabs," Curr Opin Chem Biol, Jun. 2013, 17(3):400-5. doi: 10.1016/j.cbpa.2013.04.015. Epub May 14, 2013.
Faham et al., "Antigen-Containing Liposomes Engrafted with Flagellin-Related Peptides Are Effective Vaccines That Can Induce Potent Antitumor Immunity and Immunotherapeutic Effect," J Immunol, Jul. 7, 2010, 185:1744-1754.
Fukuda et al., "In vitro evolution of single-chain antibodies using mRNA display," Nucleic Acids Res, Oct. 1, 2006, 34(19):e127.
Greenwood et al., "Structural motifs involved in human IgG antibody effector functions," Eur J Immunol, May 1993, 23(5):1098-104.
Guilliams et al., "The function of Fcγ receptors in dendritic cells and macrophages," Nat Rev Immunol, Feb. 2014, 14(2):94-108. doi: 10.1038/nri3582. Epub Jan. 21, 2014.
Gura et al., "Systems for Identifying New Drugs Are Often Faulty," Science, Nov. 7, 1997, 278:1041-1042.
Hanes et al., "Picomolar affinity antibodies from a fully synthetic naïve library selected and evolved by ribosome display," Nat Biotechnol, Dec. 2000, 18(12):1287-92.

(56) References Cited

OTHER PUBLICATIONS

Harvey et al., "Anchored periplasmic expression, a versatile technology for the isolation of high-affinity antibodies from *Escherichia coli*-expressed libraries," Proc Natl Acad Sci USA, Jun. 22, 2004, 101(25):9193-8.
Hawkins et al., "Selection of Phage Antibodies by Binding Affinity—Mimicking Affinity Maturation," J Mol Biol, Aug. 5, 1992, 226(3):889-96.
Hess et al., "Cancer therapy with trifunctional antibodies: linking innate and adaptive immunity," Future Oncol, Jan. 2012, 8(1):73-85. doi: 10.2217/fon.11.138.
Hetian et al., "A Novel Peptide Isolated from a Phage Display Library Inhibits Tumor Growth and Metastasis by Blocking the Binding of Vascular Endothelial Growth Factor to Its Kinase Domain Receptor," J Biol Chem, Nov. 8, 2002, 277(45):43137-42.
Hezareh et al., "Effector Function Activities of a Panel of Mutants of a Broadly Neutralizing Antibody against Human Immunodeficiency Virus Type 1," J Virol, Dec. 2001, 75(24):12161-8.
Holen et al., "Activation of EphA receptors on CD4+CD45RO+ memory cells stimulates migration," J Leukoc Biol, Jun. 2010, 87(6):1059-68. doi: 10.1189/jlb.0709497. Epub Feb. 16, 2010.
Houot et al., "Therapeutic effect of CD137 immunomodulation in lymphoma and its enhancement by $T_{reg}$ depletion," Blood, Oct. 15, 2009, 114(16):3431-8.
Ikuta et al, "Expression of human immunodeficiency virus type 1 (HIV-1) gag antigens on the surface of a cell line persistently infected with HIV-1 that highly expresses HIV-1 antigens," Virology, Jun. 1989, 170(2):408-17.
Janeway et al., Chapter 3 "Structure of the Antibody Molecule and Immunoglobulin Genes," Immunobiology—The Immune System in Health and Disease, 3rd Edition, 1997 Garland Publishing Inc., pp. 3:1-3:11.
Jefferis et al., "Interaction sites on human IgG-Fc for Fc gamma R: current models," Immunol Lett, Jun. 3, 2002, 82(1-2):57-65.
Jones et al., "Growth factor receptor interplay and resistance in cancer," Endocr Relat Cancer, Dec. 2006, 13 Suppl 1:S45-51.
Kontermann, "Dual targeting strategies with bispecific antibodies," mAbs, Mar.-Apr. 2012, 4(2):182-97. doi: 10.4161/mabs.4.2.19000. Epub Mar. 1, 2012.
Kraft et al., "Definition of an Unexpected Ligand Recognition Motif for αvβ6 Integrin," J Biol Chem, Jan. 22, 1999, 274:1979-1985.
Kramer et al, "Molecular basis for the binding promiscuity of an anti-p24 (HIV-1) monoclonal antibody" Cell, Dec. 12, 1997, 91(6):799-809.
Kronqvist et al., "A novel affinity protein selection system based on *staphylococcal* cell surface display and flow cytometry," Protein Eng Des Sel, Apr. 2008, 21(4):247-55.
Kussie et al., "A Single Engineered Amino Acid Substitution Changes Antibody Fine Specificity," J Immunol, Jan. 1, 1994, 152(1):146-152.
Lazar et al., "Engineered antibody Fc variants with enhanced effector function," Proc Natl Acad Sci USA, Mar. 2006, 103(11):4005-10. Epub Mar. 6, 2006.
Lederman et al., "A Single Amino Acid Substitution in a Common African Allele of the CD4 Molecule Ablates Binding of the Monoclonal Antibody, OKT4," Molecular Immunology, Nov. 1991, 28(11):1171-1181.
Lightfield et al., "Critical function for Naip5 in inflammasome activation by a conserved carboxy-terminal domain of flagellin," Nature Immunology, Oct. 2008, 9(10): 1171-1178. doi: 10.1038/ni.1646. Epub Aug. 24, 2008.
Li et al., "β-Endorphin omission analogs: Dissociation of immunoreactivity from other biological activities," Proc Natl Acad Sci USA, Jun. 1, 1980, 77:3211-3214.
Li et al., "Activation of the Proapoptotic Death Receptor DR5 by Oligomeric Peptide and Antibody Agonists," J Mol Biol, Aug. 18, 2006, 361(3):522-536.
Li et al., "Antitumor activities of agonistic anti-TNFR antibodies require differential FcγRIIB coengagement in vivo," Proc Natl Acad Sci USA, Nov. 26, 2013, 110(48):19501-6.

Lum et al., "Targeting T Cells with Bispecific Antibodies for Cancer Therapy," BioDrugs, Dec. 1, 2011, 25(6):365-79. doi: 10.2165/11595950-000000000-00000.
Lutterbuese et al., "T cell-engaging BiTE antibodies specific for EGFR potently eliminate KRAS- and BRAF-mutated colorectal cancer cells," Proc Natl Acad Sci USA, Jul. 13, 2010, 107(28):12605-10. doi: 10.1073/pnas.1000976107. Epub Jun. 28, 2010.
Maccallum et al., "Antibody-antigen Interactions: Contact Analysis and Binding Site Topography," J Mol Biol, Oct. 11, 1996, 262(5):732-745.
Marino et al., "Prevention of systemic lupus erythematosus in MRL/1pr mice by administration of an immunoglobulin-binding peptide," Nat Biotechnol, Jul. 2000, 18(7):735-9.
Marks et al., "By-passing Immunization—Human Antibodies from V-gene Libraries Displayed on Phage," J Mol Biol, Dec. 5, 1991, 222(3):581-97.
Morgan et al., "The N-terminal end of the CH2 domain of chimeric human IgG1 anti-HLA-DR is necessary for C1q, Fc gamma RI and Fc gamma RIII binding," Immunology, Oct. 1995, 86(2):319-24.
Nakamura et al., "Peptide mimics of epidermal growth factor (EGF) with antagonistic activity," Journal of Biotechnology, Mar. 30, 2005, 116(3):211-219.
Natsume et al., "Engineered antibodies of IgG1/IgG3 mixed isotype with enhanced cytotoxic activities," Cancer Res, May 15, 2008, 68(10):3863-72. doi: 10.1158/0008-5472.CAN-07-6297.
Nimmerjahn et al., "Fcgamma receptors as regulators of immune responses," Nat Rev Immunol, Jan. 2008, 8(1):34-47.
Odegrip et al., "CIS display: In vitro selection of peptides from libraries of protein-DNA complexes," Proc Natl Acad Sci USA, Mar. 2, 2004, 101(9):2806-10.
Pavlou et al., "The therapeutic antibodies market to 2008," Eur J Pharm Biopharm, Apr. 2005, 59(3):389-96.
Porter et al., "Chimeric Antigen Receptor-Modified T Cells in Chronic Lymphoid Leukemia," N Engl J Med, Aug. 25, 2011, 365(8):725-33.
Rao et al., "Novel cyclic and linear oligopeptides that bind to integrin β1 chain and either inhibit or costimulate T lymphocytes," Int Immunopharmacol, Mar. 2003, 3(3):435-43.
Reichert et al., "Monoclonal antibody successes in the clinic," Nat Biotechnol, Sep. 2005, 23(9):1073-8.
Richards et al., "A peptide containing a novel FPGN CD40-binding sequence enhances adenoviral infection of murine and human dendritic cells," Eur J Biochem, May 2003, 70(10):2287-94.
Riechelmann et al., "Adoptive therapy of head and neck squamous cell carcinoma with antibody coated immune cells: a pilot clinical trial," Cancer Immunol Immunother, Sep. 2007, 56(9):1397-406. Epub Feb. 2, 2007.
Rothe et al., "Recombinant proteins in rheumatology—recent advances," N Biotechnol, Sep. 2011, 28(5):502-10. doi: 10.1016/j.nbt.2011.03.019. Epub Apr. 5, 2011.
Rudikoff et al., "Single amino acid substitution altering antigen-binding specificity," Proc Natl Acad Sci USA, Mar. 1982, 79(6):1979-83.
Schaefer et al., "A two-in-one antibody against HER3 and EGFR has superior inhibitory activity compared with monospecific antibodies," Cancer Cell, Oct. 18, 2011, 20(4):472-86. doi: 10.1016/j.ccr.2011.09.003.
Schabowsky et al., "A Novel Form of 4-1BBL Has Better Immunomodulatory Activity than an Agonistic Anti-4-1BB Ab without Ab Associated Severe Toxicity," Vaccine, Dec. 11, 2009, 28(2):512-22.
Schraa et al., "RGD-Modified Anti-CD3 Antibodies Redirect Cytolytic Capacity of Cytotoxic T Lymphocytes Toward $α_vβ_3$-Expressing Endothelial Cells," Int J Cancer, Nov. 1, 2004, 112(2):279-85.
Seimetz et al., "Development and approval of the trifunctional antibody catumaxomab (anti- EpCAM x anti-CD3) as a targeted cancer immunotherapy," Cancer Treat Rev, Oct. 2010, 36(6):458-67. doi: 10.1016/j.ctrv.2010.03.001. Epub Mar. 27, 2010.
Sepp et al., Chapter 12 "Cell-Free Selection of Domain Antibodies by In Vitro Compartmentalization," Methods Mol Biol, 2012, 911:183-98.

(56) References Cited

OTHER PUBLICATIONS

Shanmugam et al., "Synthetic Toll Like Receptor-4 (TLR-4) Agonist Peptides as a Novel Class of Adjuvants," PLoS One, Feb. 2012, 7(2):e30839.
Shinkawa et al., "The absence of fucose but not the presence of galactose or bisecting N-acetylglucosamine of human IgG1 complex-type oligosaccharides shows the critical role of enhancing antibody-dependent cellular cytotoxicity," J Biol Chem, Jan. 31, 2003, 278(5):3466-73. Epub Nov. 8, 2002.
Stancovski et al., "Mechanistic Aspects of the Opposing Effects of Monoclonal Antibodies to the ERBB2 Receptor on Tumor Growth," Proc Nat Acad Sci USA, Oct. 1, 1991, 88(19):8691-8695.
Stevenson et al., "A chimeric antibody with dual Fc regions (*bis*FabFc) prepared by manipulations at the IgG hinge," Anticancer Drug Des, Mar. 1989, 3(4): 219-30.
Traxlmayr et al., "Integrin binding human antibody constant domains—Probing the C-terminal structural loops for grafting the RGD motif," J Biotechnol, Sep. 10, 2011, 155(2):193-202. doi: 10.1016/j.jbiotec.2011.06.042. Epub Jul. 8, 2011.
Tutt et al., "Trispecific F(ab')3 derivatives that use cooperative signaling via the TCR/CD3 complex and CD2 to activate and redirect resting cytotoxic T cells," J Immunol, Jul. 1, 1991, 147(1):60-9.
Unkeless et al., "Structure and function of human and murine receptors for IgG," Annu Rev Immunol, 1988, 6:251-81.
Vajdos et al., "Comprehensive Functional Maps of the Antigen-binding Site of an Anti-ErbB2 Antibody Obtained with Shotgun Scanning Mutagenesis," J Mol Biol, Jul. 5, 2002, 320(2):415-428.
Vaughan et al., "Human Antibodies with Sub-nanomolar Affinities Isolated from a Large Non-immunized Phage Display Library," Nat Biotechnol, Mar. 1996, 14(3):309-14.
Vidarsson et al., "IgG subclasses and allotypes: from structure to effector functions," Front Immunol, Oct. 20, 2014, 5:520. doi: 10.3389/fimmu.2014.00520. eCollection 2014.
Vinay et al., "4-1BB signaling beyond T cells," Cell Mol Immunol, Jul. 2011, 8(4):281-4.
Werwitzke et al., "Treatment of lupus-prone NZB/NZW F1 mice with recombinant soluble Fc gamma receptor II (CD32)," Ann Rheum Dis, Feb. 2008, 67(2):154-61. Epub Jun. 8, 2007.
Witte et al., "Monoclonal antibodies targeting the VEGF receptor-2 (Flk1/KDR) as an anti-angiogenic therapeutic strategy," Cancer and Metastasis Reviews, Jun. 1998, 17(2):155-161.
Wozniak-Knopp et al., "Introducing antigen-binding sites in structural loops of immunoglobulin constant domains: Fc fragments with engineered HER2/neu-binding sites and antibody properties," Protein Eng Des Sel, Apr. 2010, 23(4):289-97. doi: 10.1093/protein/gzq005. Epub Feb. 11, 2010.
Wu et al., "Humanization of a Murine Monoclonal Antibody by Simultaneous Optimization of Framework and CDR Residues," J Mol Biol, Nov. 19, 1999, 294(1):151-162.
Wu et al., "Structures of the CXCR4 Chemokine GPCR with Small-Molecule and Cyclic Peptide Antagonists," Science, Nov. 19, 2010, 330:1066-1071.
Xi et al., "Increased survival and reduced renal injury in MRL/lpr mice treated with a human Fcγ receptor II (CD32) peptide," Immunology, May 2012, 136(1):46-53. doi: 10.1111/j.1365-2567.2012.03553.x.
Xiao et al., "A large library based on a novel (CH2) scaffold: Identification of HIV-1 inhibitors," Biochem Biophys Res Commun, Sep. 18, 2009, 387(2):387-92. doi: 10.1016/j.bbrc.2009.07.044. Epub Jul. 15, 2009.
Xie et al., "A new format of bispecific antibody: highly efficient heterodimerization, expression and tumor cell lysis," J Immunol Methods, Jan. 2005, 296(1-2):95-101. Epub Nov. 19, 2004.
Yu et al., "Interaction between Bevacizumab and Murine VEGF-A: A Reassessment," Investigative Ophthalmology and Visual Science, Feb. 2008, 49(2):522-527.
Zeidler et al., "Simultaneous activation of T cells and accessory cells by a new class of intact bispecific antibody results in efficient tumor cell killing," J Immunol, Aug. 1, 1999, 163(3):1246-52.
Zhou et al., "Development of a novel mammalian cell surface antibody display platform," mAbs, Sep.-Oct. 2010, 2(5):508-18.
International Preliminary Report on Patentability in International Application No. PCT/JP2018/044493, dated Jun. 9, 2020, 8 pages.
International Search Report for App. Ser. No. PCT/JP2018/044493, dated Feb. 26, 2019, 5 pages.
Sazinsky et al., "Aglycosylated immunoglobulin $G_1$ variants productively engage activating Fc receptors," Proc Natl Acad Sci USA, Dec. 23, 2008, 105(51):20167-20172. doi: 10.1073/pnas.0809257105. Epub Dec. 12, 2008.
Nezu, Chugai's Strategy for Drug Discovery Research, Dec. 9, 2019, pp. 1-80.
Mariuzza et al., "The Structural Basis of Antigen-Antibody Recognition," Annu Rev Biophys Biophys Chem, Jun. 1987, 16:139-159.
Roitt et al., "Antibody Structure and Function," Immunology, Moscow, Mir, 2000, pp. 110-111 (with what are believed to be the corresponding pages from an English version of Immunology).
Singer et al., "Structure of Proteins," Genes & Genomes, Moscow, Mir, 1998, pp. 63-64 (with what are believed to be the corresponding pages from an English version of Genes & Genomes).
Torres et al., "The immunoglobulin constant region contributes to affinity and specificity," Trends Immunol, Feb. 2008, 29(2):91-97. doi: 10.1016/j.it.2007.11.004. Epub Jan. 10, 2008. PMID: 18191616.
U.S. Appl. No. 17/914,432, Chichili et al., filed Sep. 26, 2022.
U.S. Appl. No. 17/914,855, Naoi et al., filed Sep. 27, 2022.
U.S. Appl. No. 17/913,899, Ishii et al., filed Sep. 23, 2022.
Garber, "Bispecific antibodies rise again," Nat Rev Drug Discov, Nov. 2014, 13(11):799-801.
Ishiguro et al., "Anti-Glypican 3 Antibody as a Potential Antitumor Agent for Human Liver Cancer," Cancer Res, Dec. 1, 2008, 68(23):9832-9838. doi: 10.1158/0008-5472.CAN-8-1973.
Nakano et al., "Anti-glypican 3 antibodies cause ADCC against human hepatocellular carcinoma cells," Biochem Biophys Res Commun, Jan. 9, 2009, 378(2):279-284. doi: 10.1016/j.bbrc.2008.11.033. Epub Nov. 18, 2008.
U.S. Appl. No. 18/343,850, Naoi et al., filed Jun. 29, 2023.
U.S. Appl. No. 18/345,750, Igawa et al., filed Jun. 30, 2023.
Diamond et al., "Somatic mutation of the T15 heavy chain gives rise to an antibody with autoantibody specificity," Proc Natl Acad Sci USA, Sep. 1984, 81(18):5841-5844.
Dirks, "Brain tumor stem cells: bringing order to the chaos of brain cancer," J Clin Oncol, Jun. 10, 2008, 26(17):2916-2924.
Kuznetsova, "Brackets in text of legal document as a linguo-cognitive phenomenon," Bulletin MGOU, Chapter: Russian Philology, 2015, 3:37-43 (with English translation).
Lopez-Lazaro et al., "The migration ability of stem cells can explain the existence of cancer of unknown primary site. Rethinking metastasis," Oncoscience, May 1, 2015, 2(5):467-475.
Mabey, "Epidemiology of sexually transmitted infections: worldwide," Medicine, 2014, 42(6):287-290.
Ohno et al., "Antigen-binding specificities of antibodies are primarily determined by seven residues of $V_H$," Proc Natl Acad Sci USA, May 1985, 82(9):2945-2949.
Rudzitis et al., Chemistry—Inorganic chemistry—8th grade, 2011, p. 15 (with English translation).
Solopova et al., "Bispecific Antibodies in Clinical Practice and Clinical Trials (Literature Review)," Clinical Oncohematology, 2019, 12(2):125-144 (with English translation).
Sundberg, "Structural basis of antibody-antigen interactions," Methods Mol Biol, 2009, 524:23-36.
Tran et al., "Survival comparison between glioblastoma multiforme and other incurable cancers," J Clin Neurosci, Apr. 2010, 17(4):417-421.
Yarilin, Fundamentals of Immunology, Moscow, Medicina, 1999, pp. 172-174 (with English translation).

\* cited by examiner

[Fig. 1]
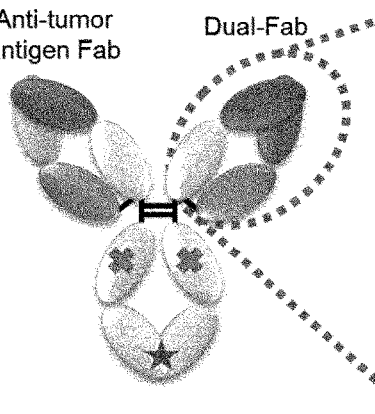
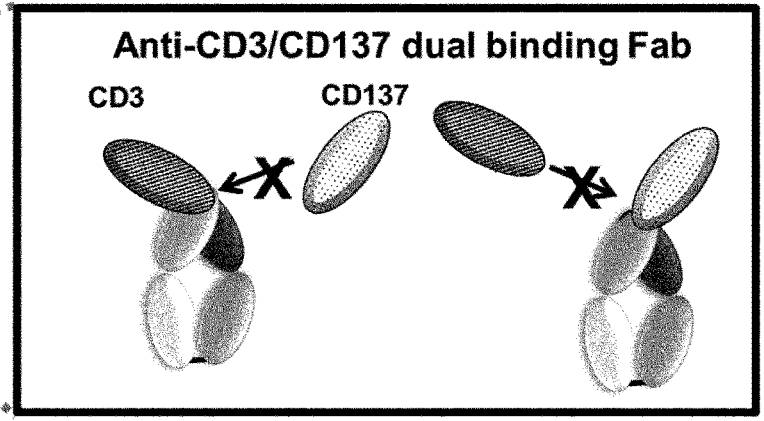
[Fig. 2]
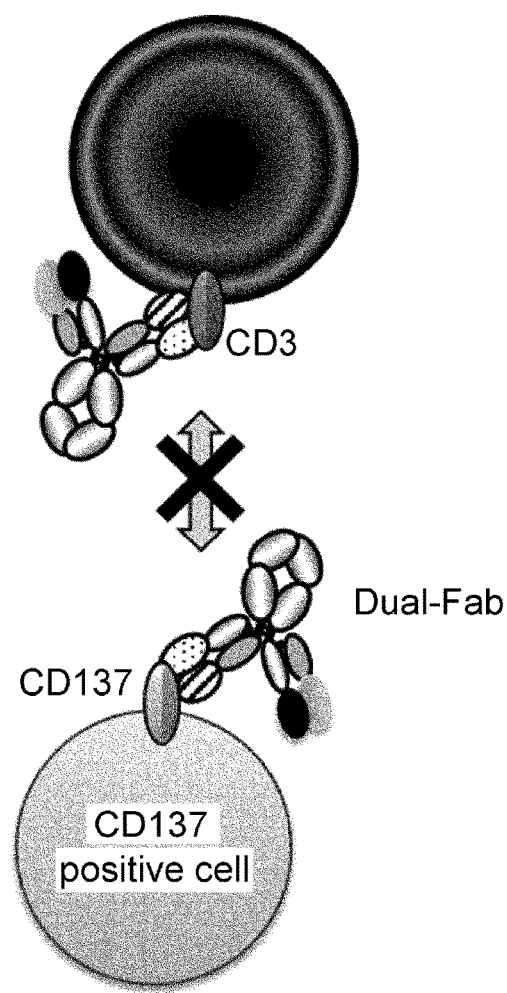
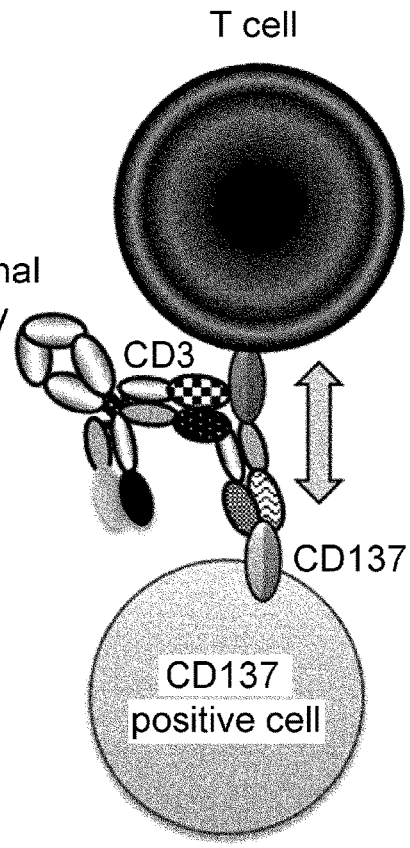

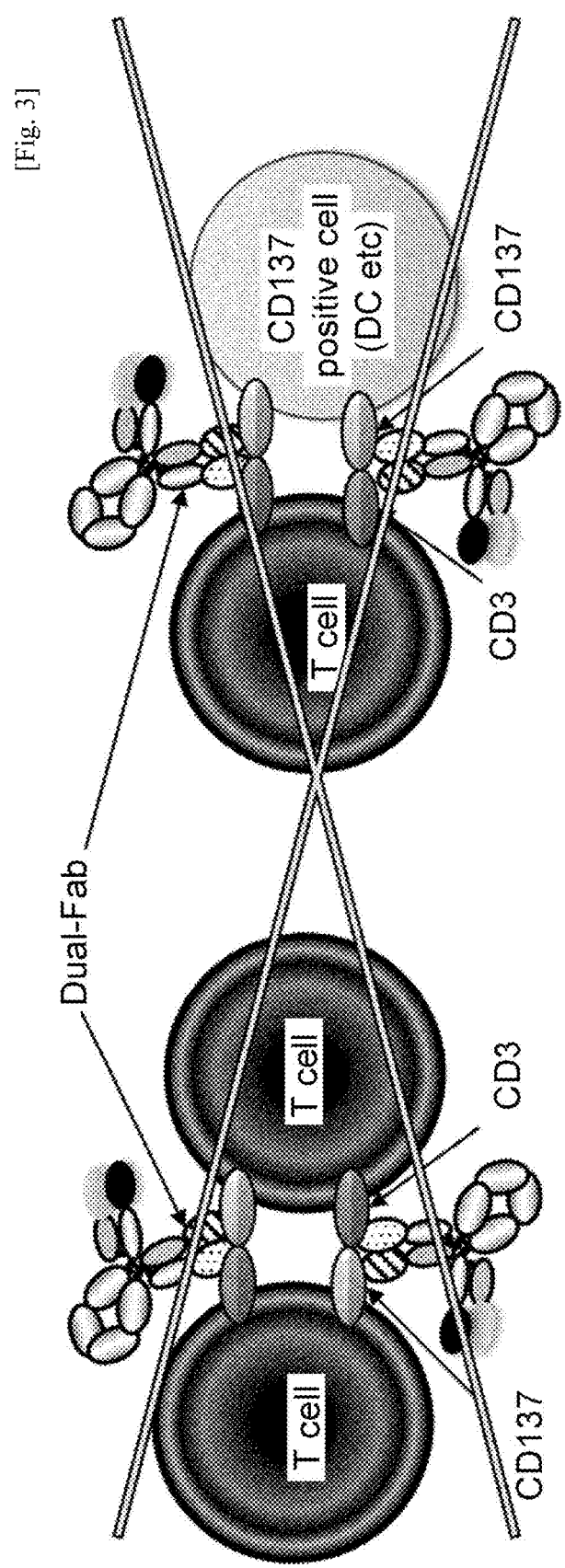

[Fig. 4]
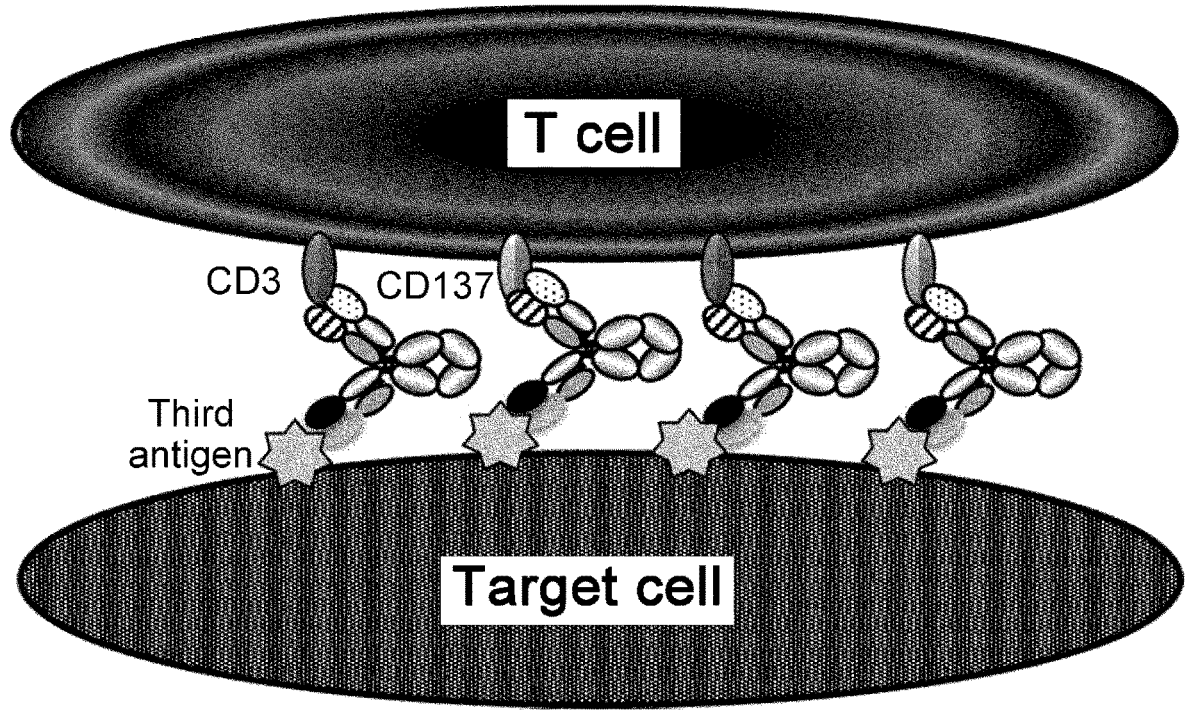
[Fig. 5]
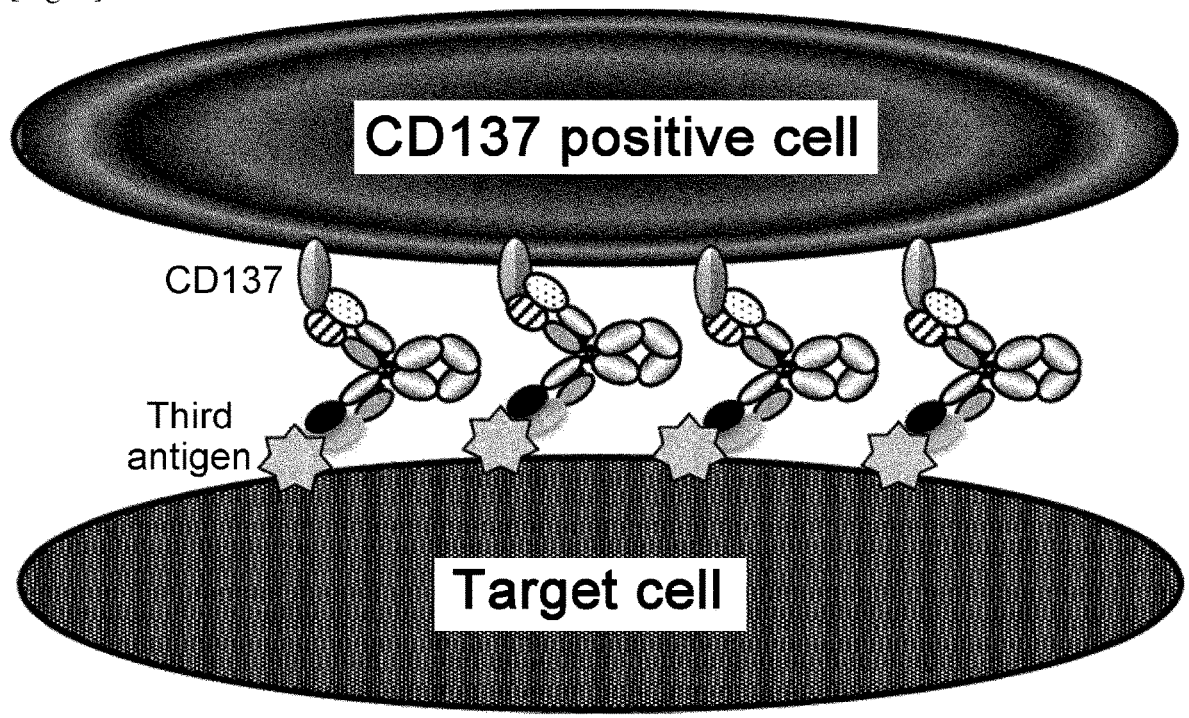

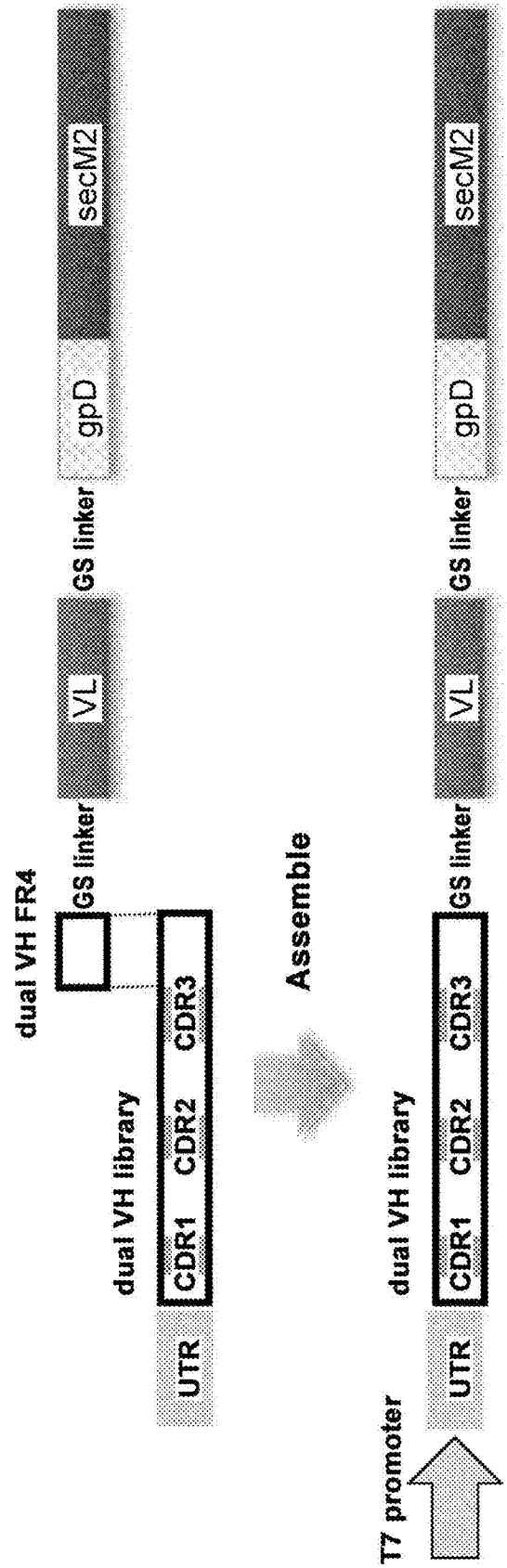
[Fig. 6]

[Fig. 7-1]
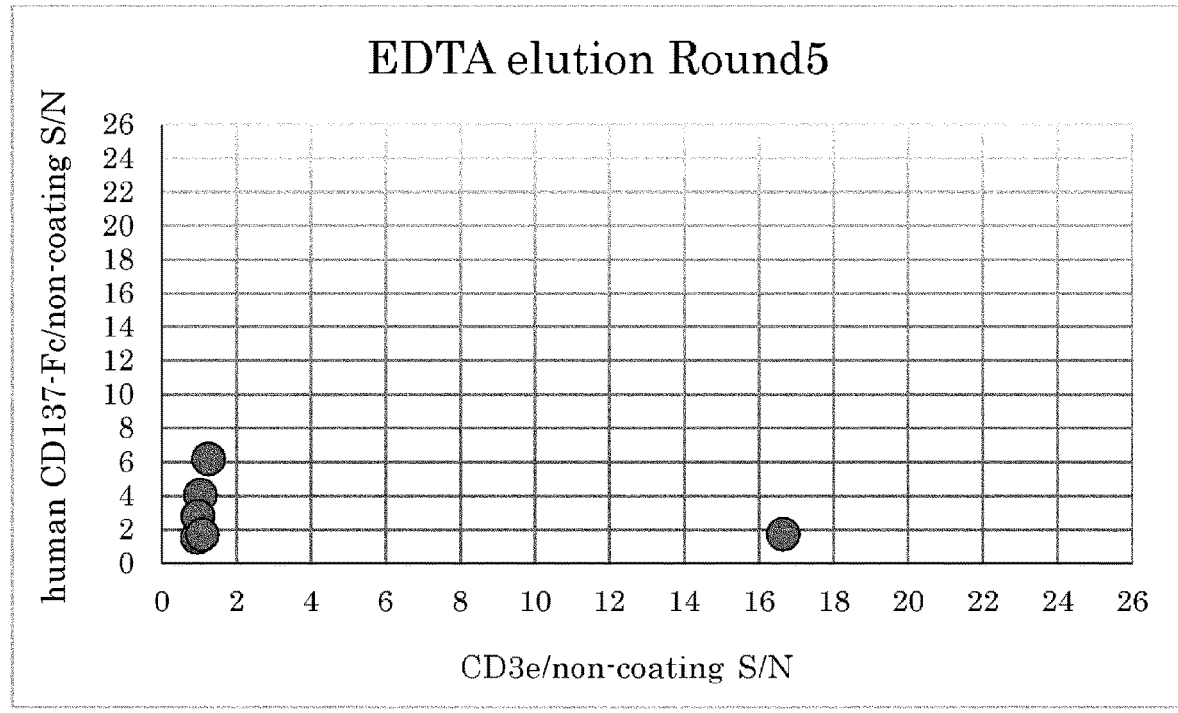
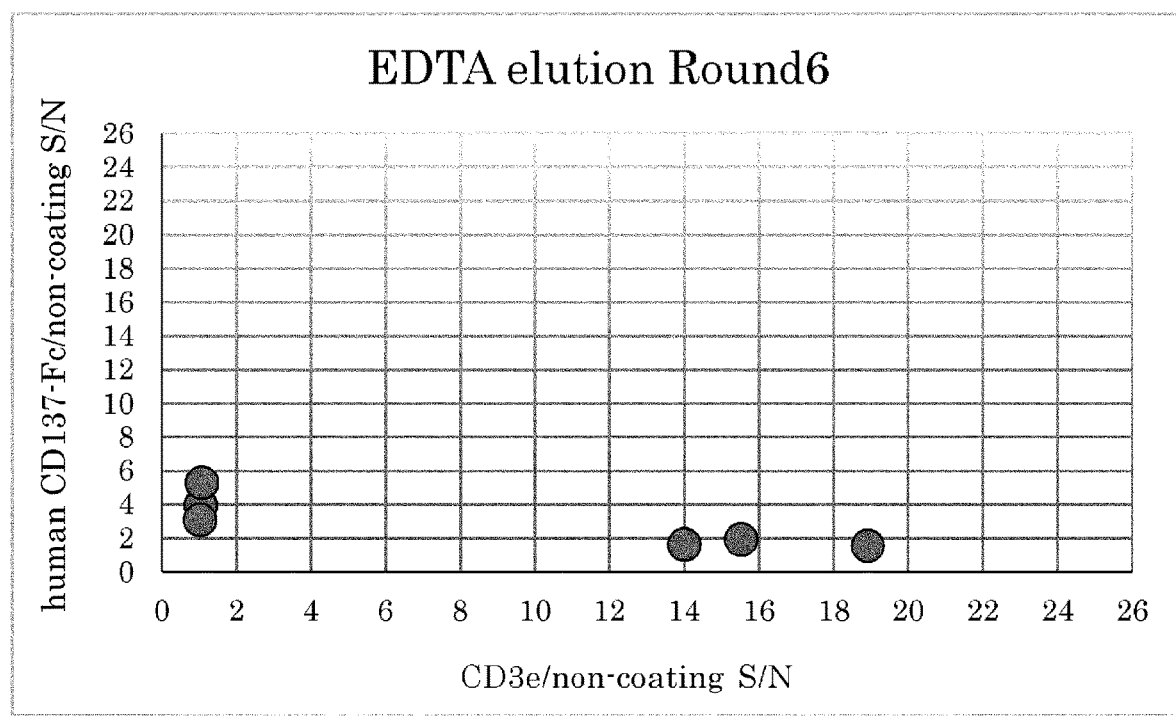

[Fig. 7-2]
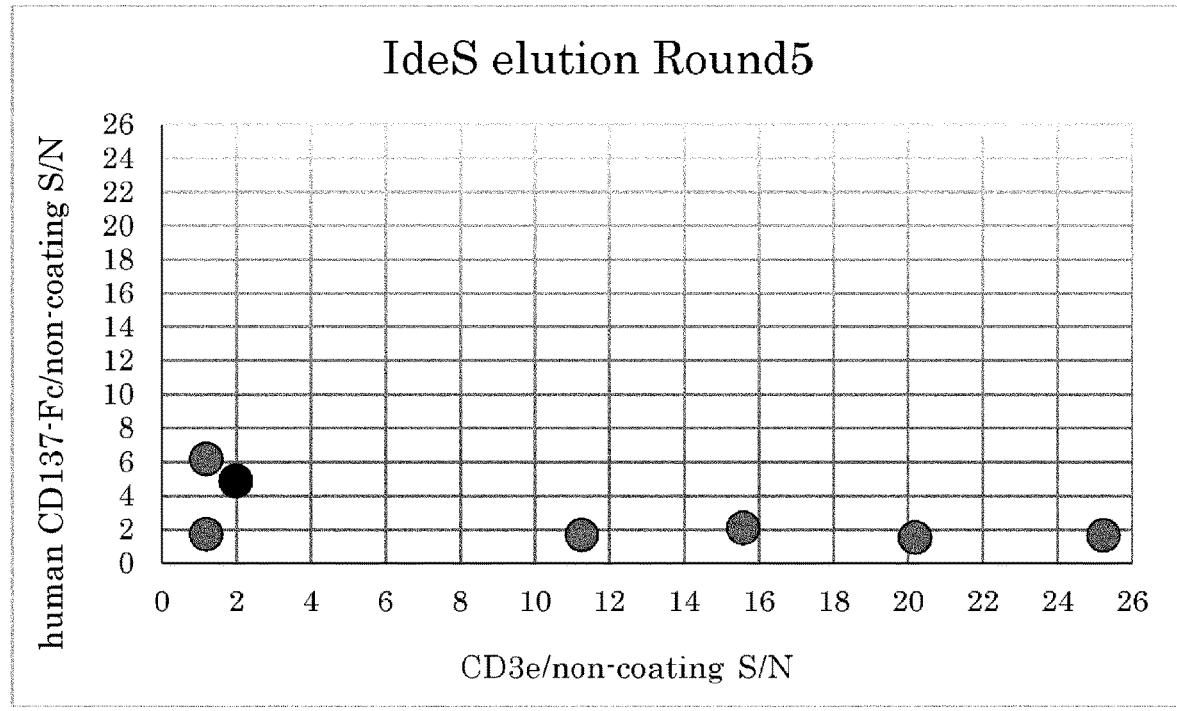
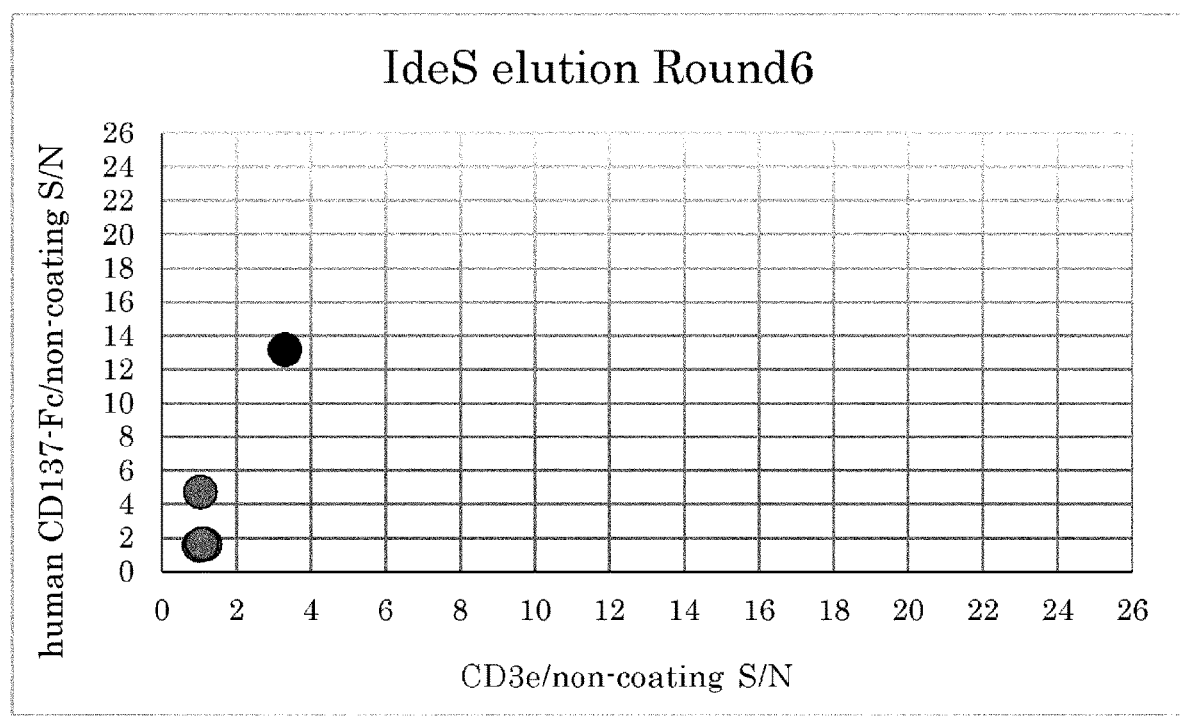

[Fig. 8]
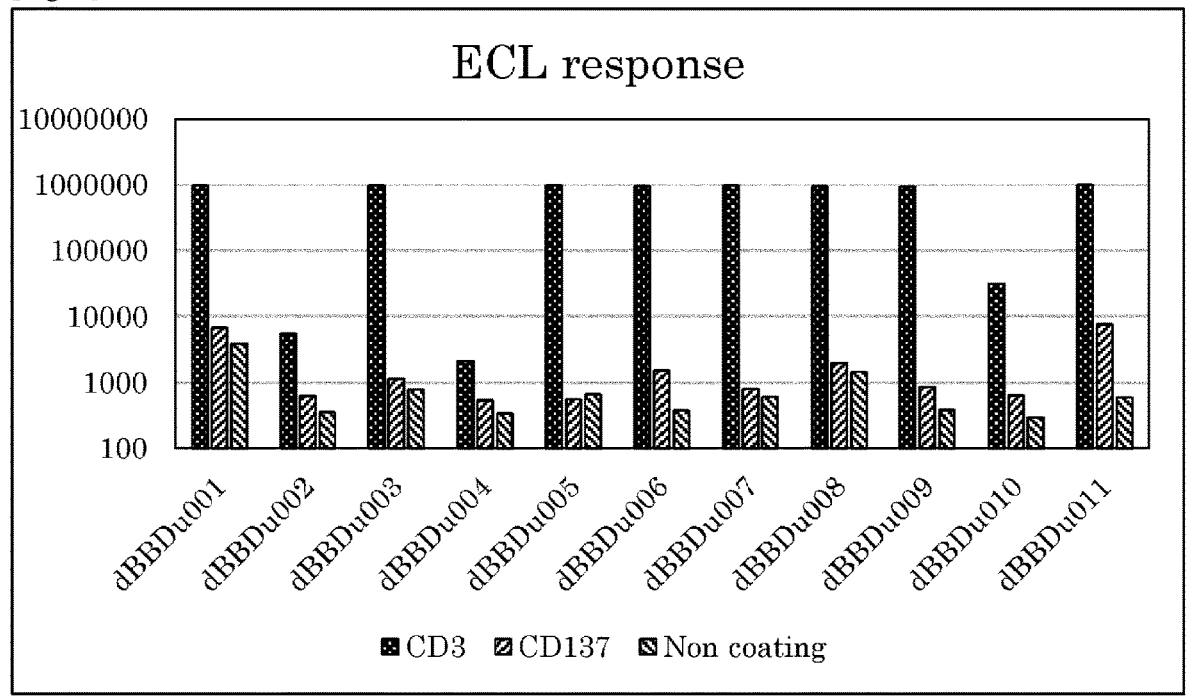
[Fig. 9-1]
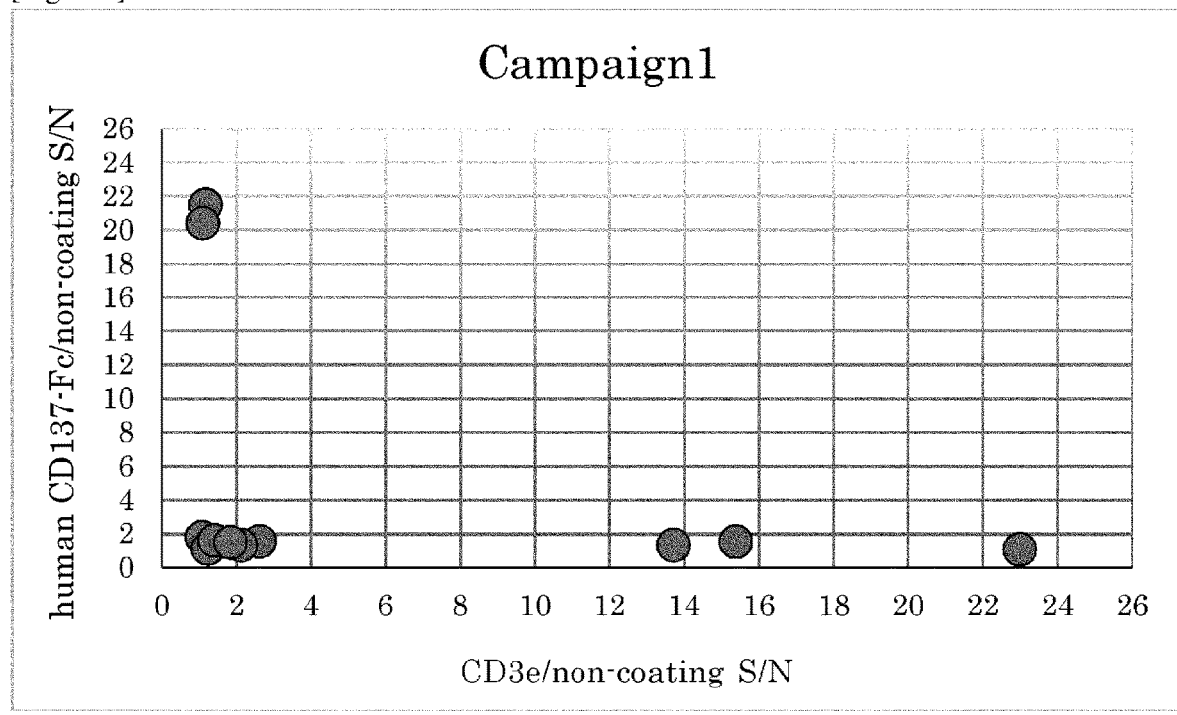

[Fig. 9-2]
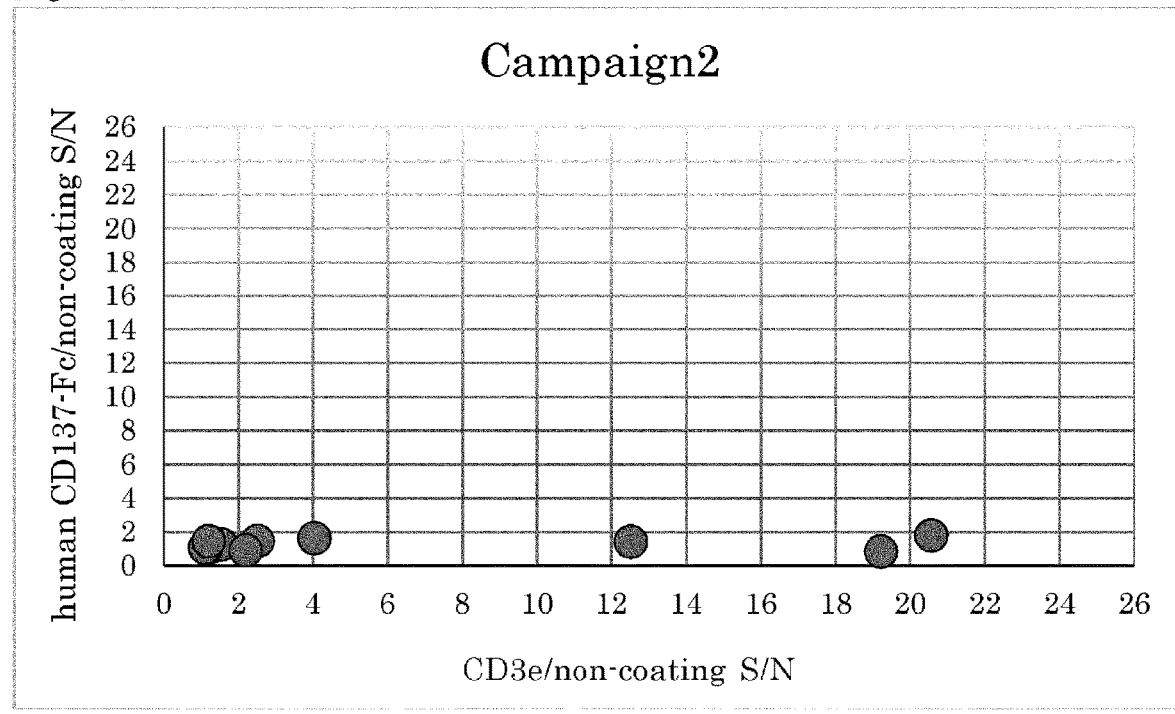
[Fig. 9-3]
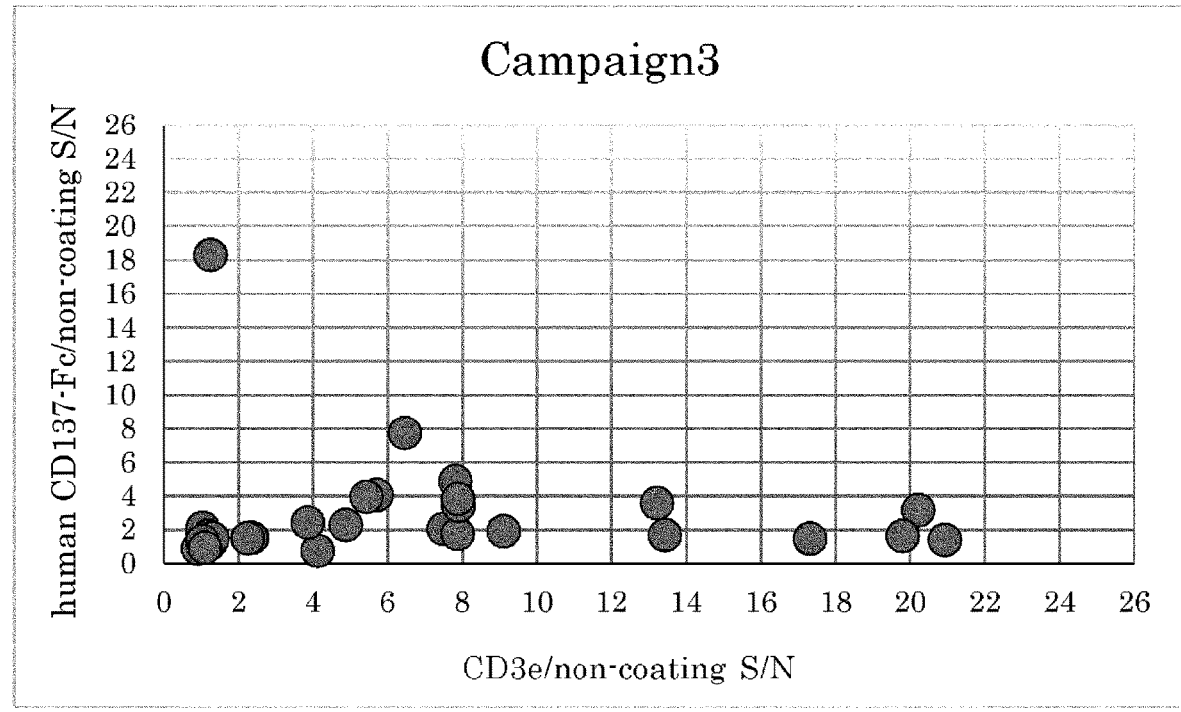

[Fig. 10]
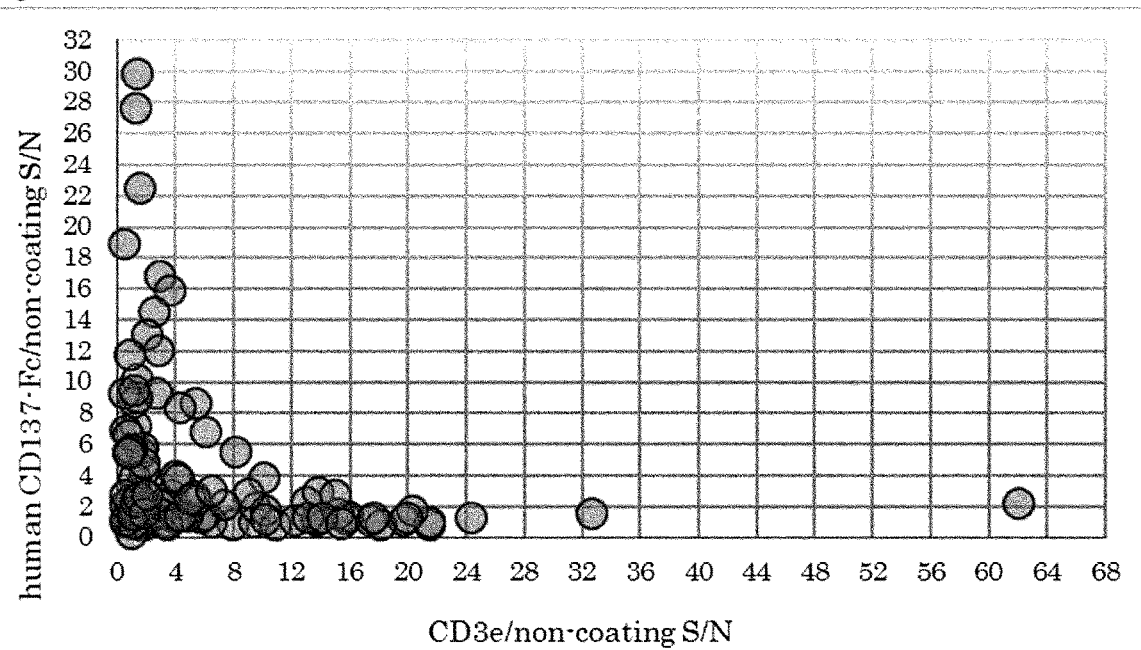
[Fig. 11]
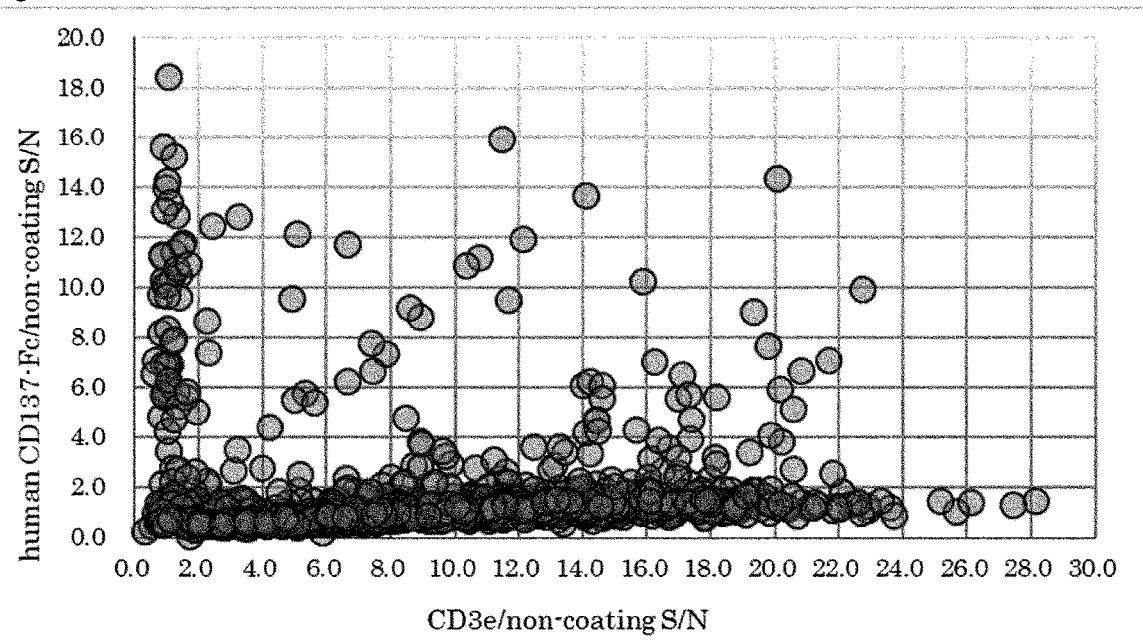

[Fig. 12]
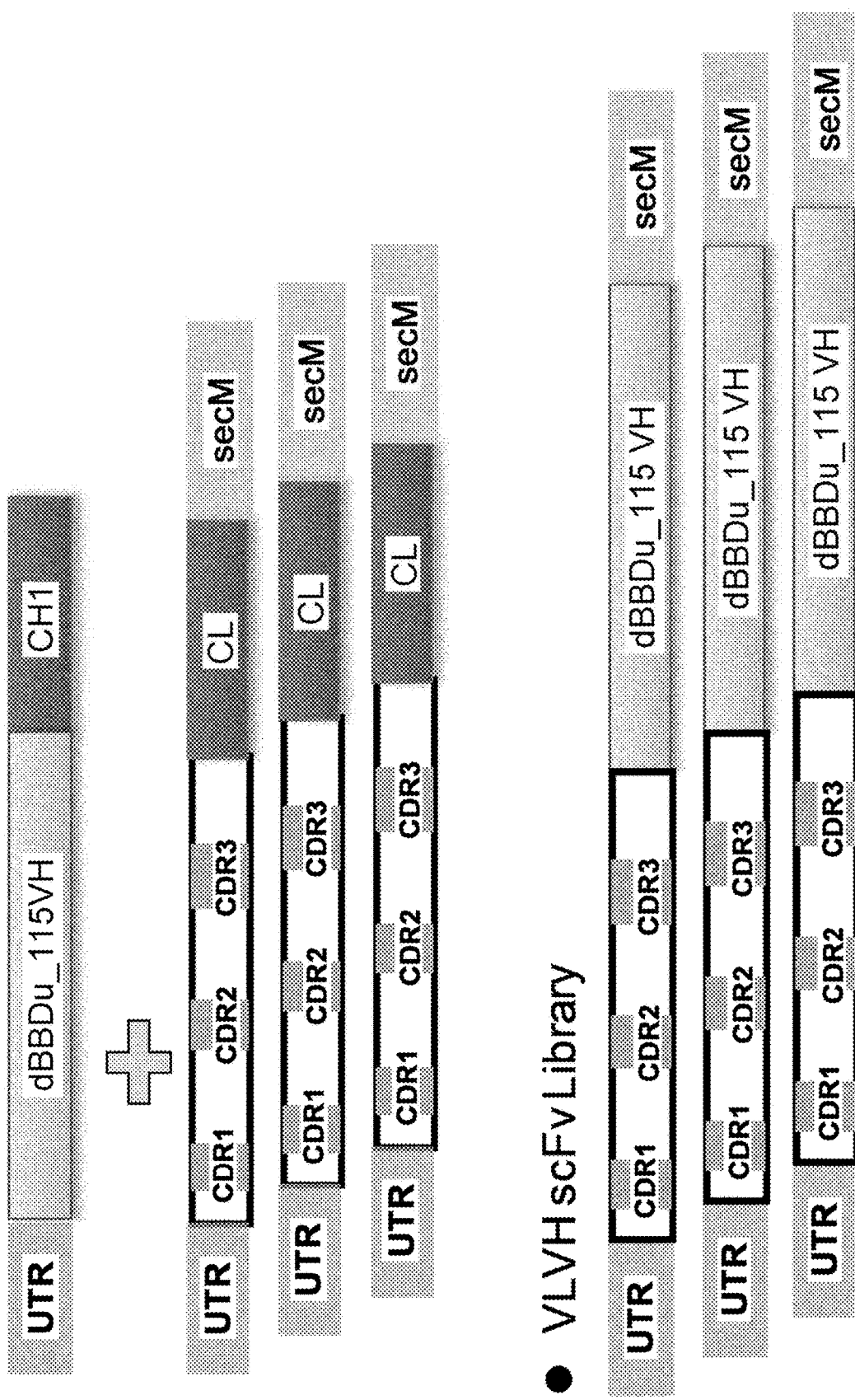

[Fig. 13]
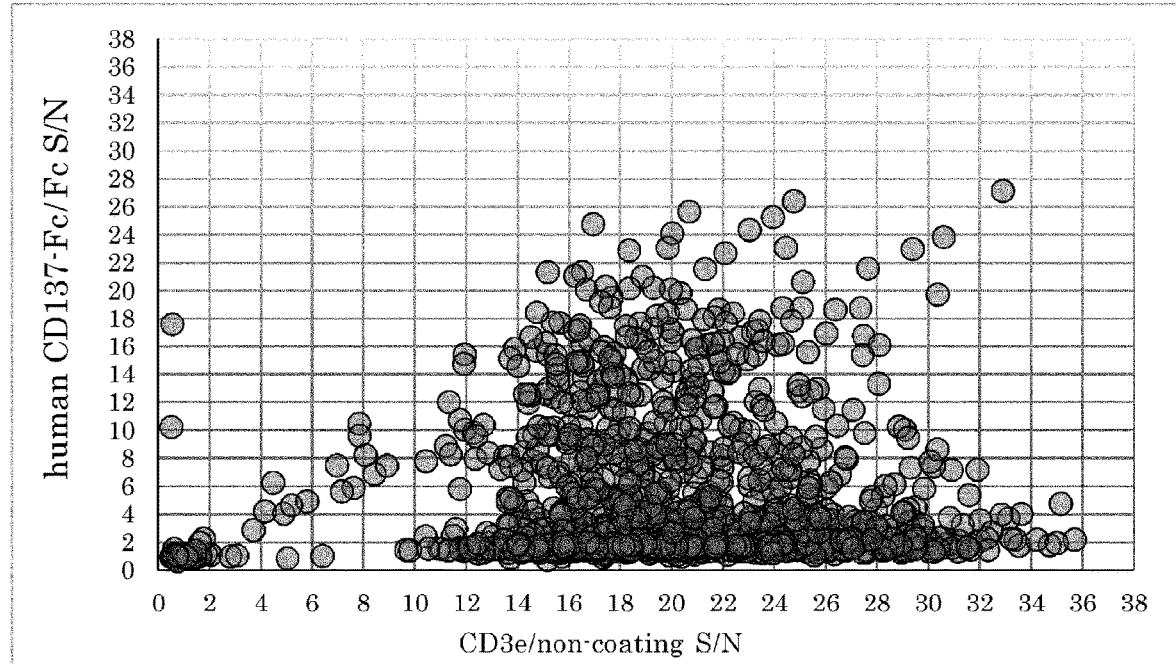
[Fig. 14]
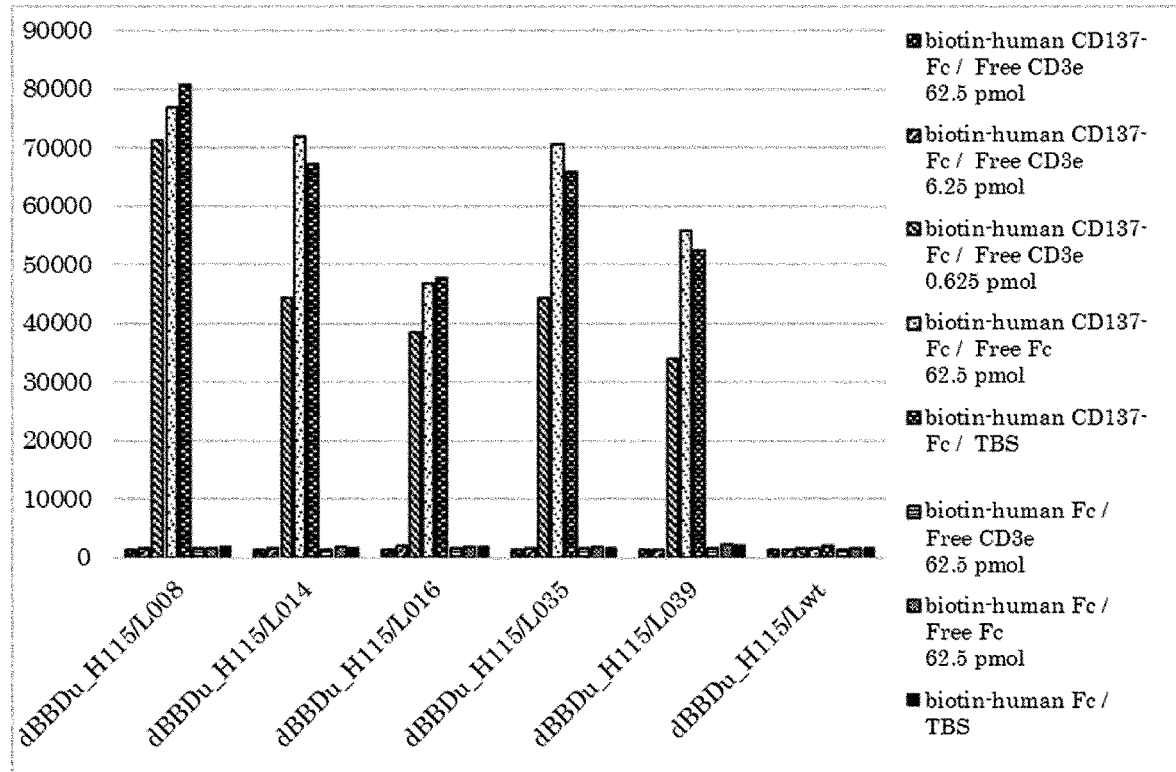

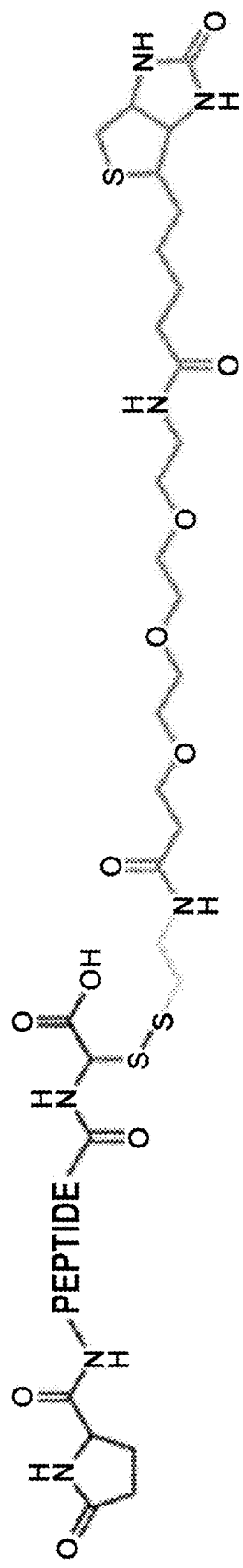
[Fig. 15]
C3NP1-27
Pyr-DGNEEMGGITQTPYKVSISGTTVILT-Cys (SEQ ID NO: 145)

[Fig. 16]
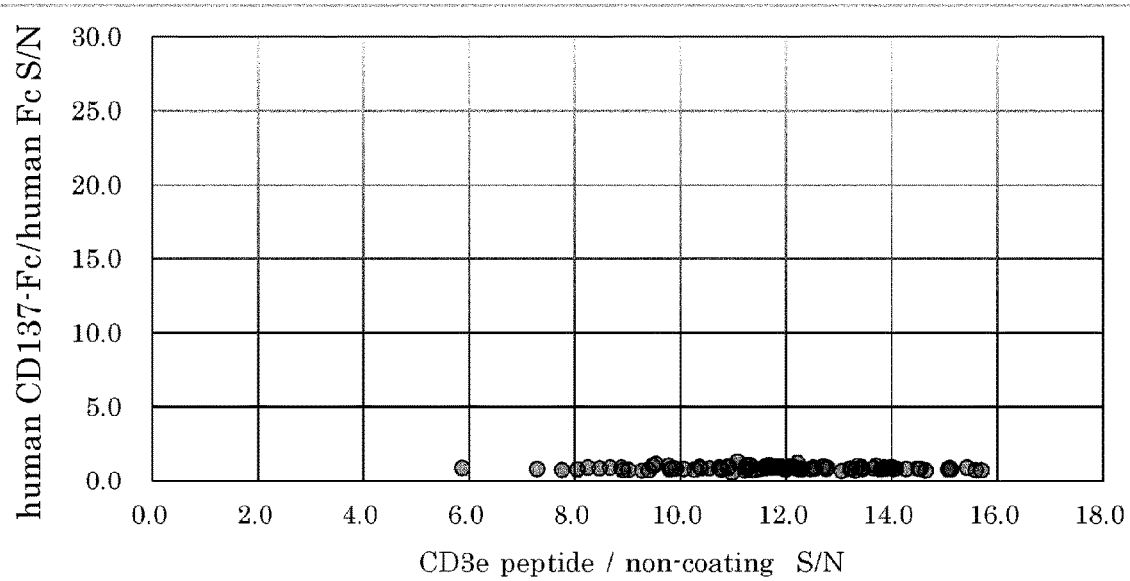
[Fig. 17]
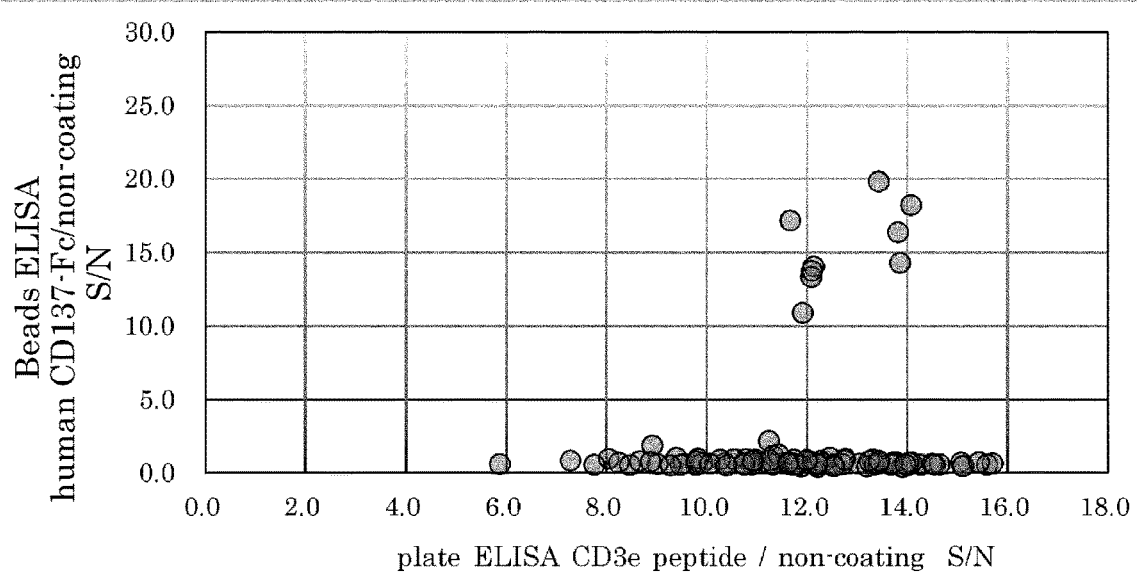

[Fig. 18]

| | | | |
|---|---|---|---|
| cyCD137 | 1 | LQDLCSNCPAGTFCDNNRSQICSPCPPNSFSSAGGQRTCDICRQCKGVFKTRKECSSTSN | 60 |
| huCD137 | 1 | LQDPCSNCPAGTFCDNNRNQICSPCPPNSFSSAGGQRTCDICRQCKGVFRTRKECSSTSN | 60 |
| cyCD137 | 61 | AECDCISGYHCLGAECSMCEQDCKQGQELTKKGCKDCCFGTFNDQKRGICRPWTNCSLDG | 120 |
| huCD137 | 61 | AECDCTPGFHCLGAGCSMCEQDCKQGQELTKKGCKDCCFGTFNDQKRGICRPWTNCSLDG | 120 |
| cyCD137 | 121 | KSVLVNGTKERDVVCGPSPADLSPGASSATPPAPAREPGHSPQ (SEQ ID NO : 18) | 163 |
| huCD137 | 121 | KSVLVNGTKERDVVCGPSPADLSPGASSVTPPAPAREPGHSPQ (SEQ ID NO : 146) | 163 |

[Fig. 19]
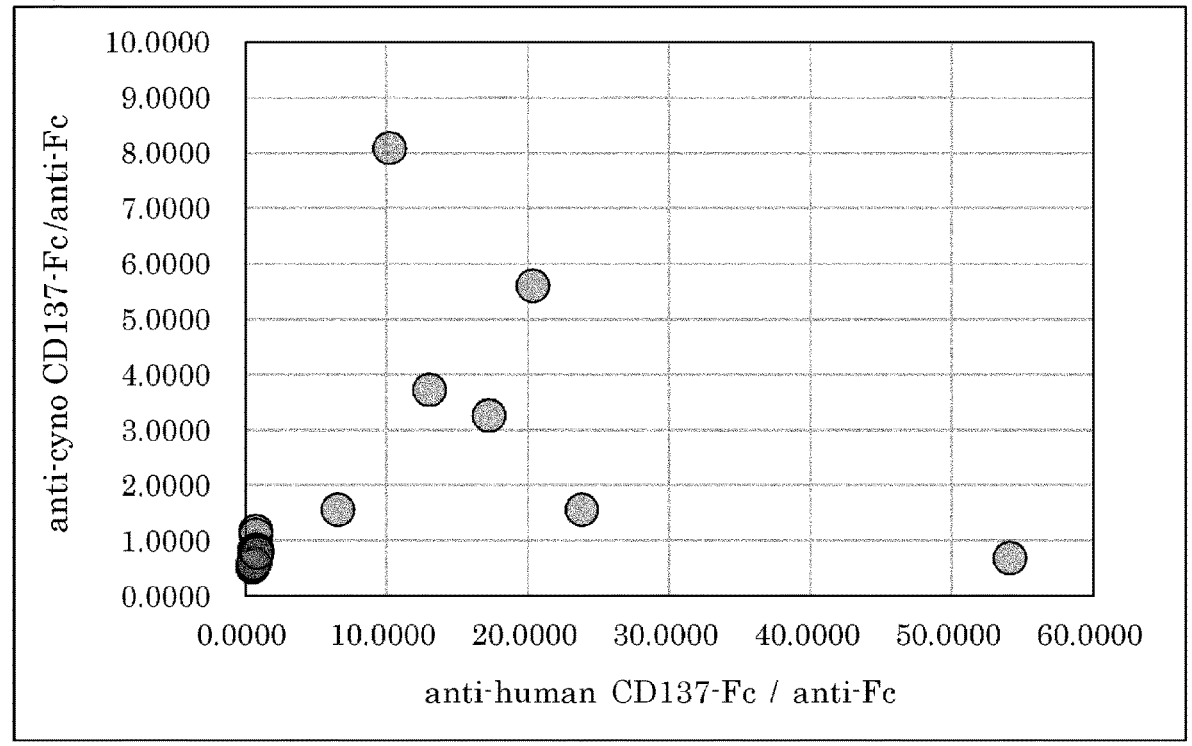
[Fig. 20]
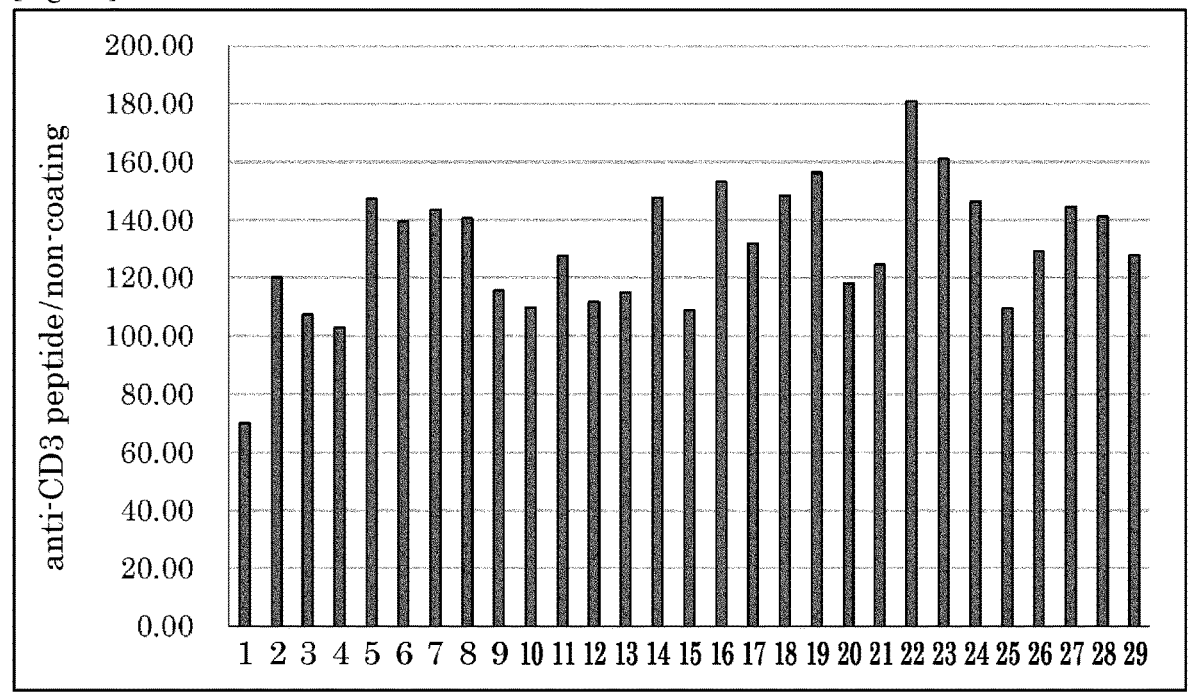

[Fig. 21]
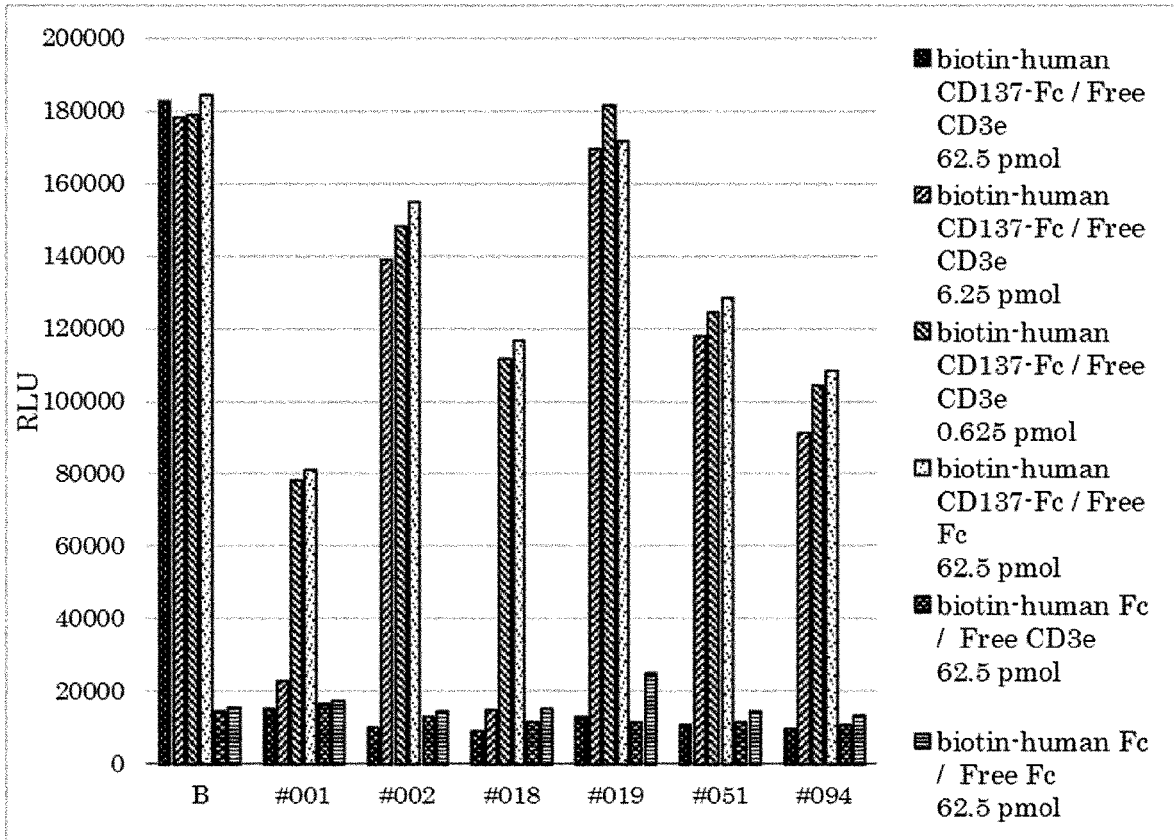
[Fig. 22A]
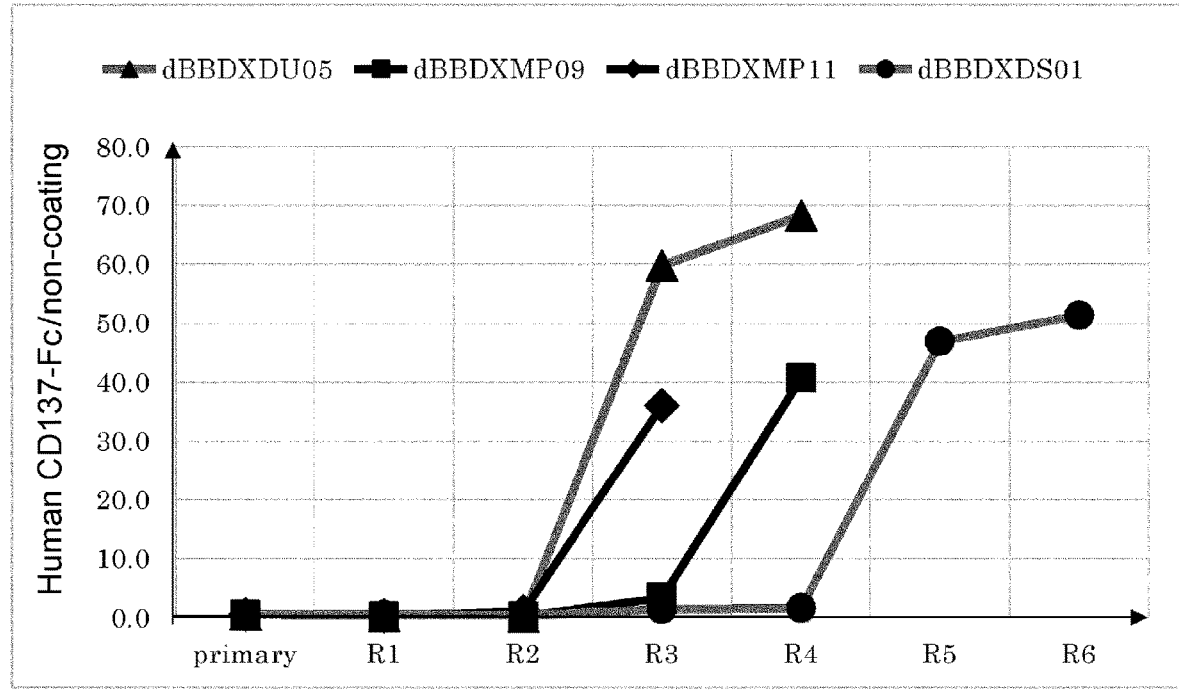

[Fig. 22B]
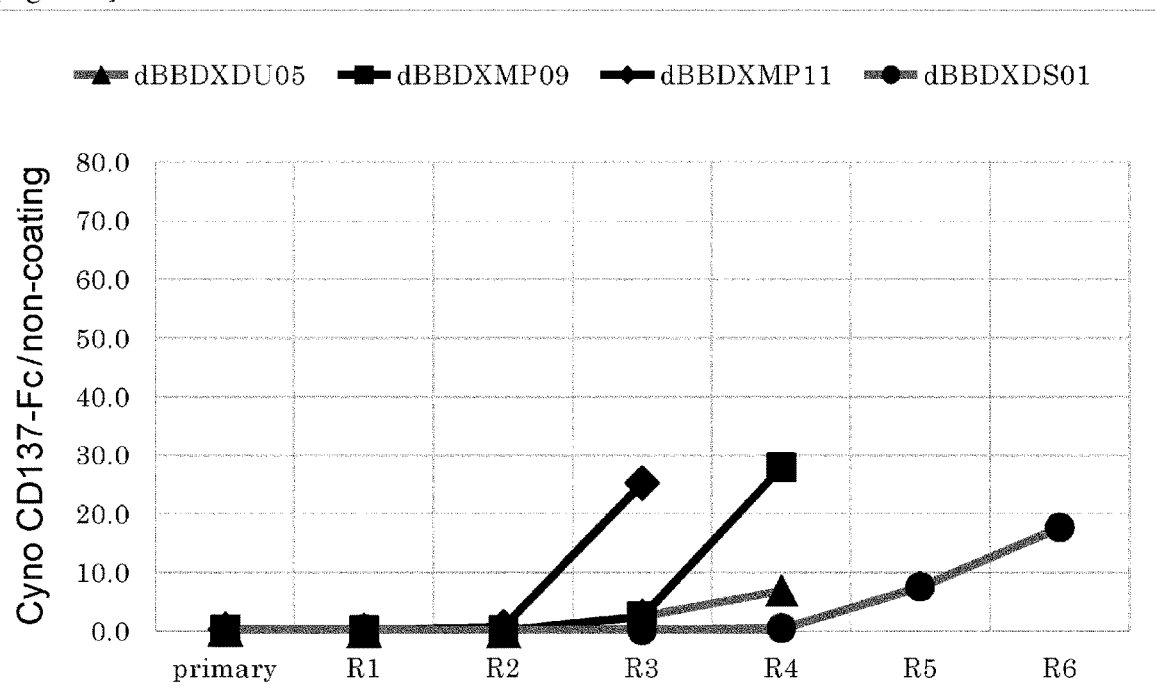
[Fig. 22C]
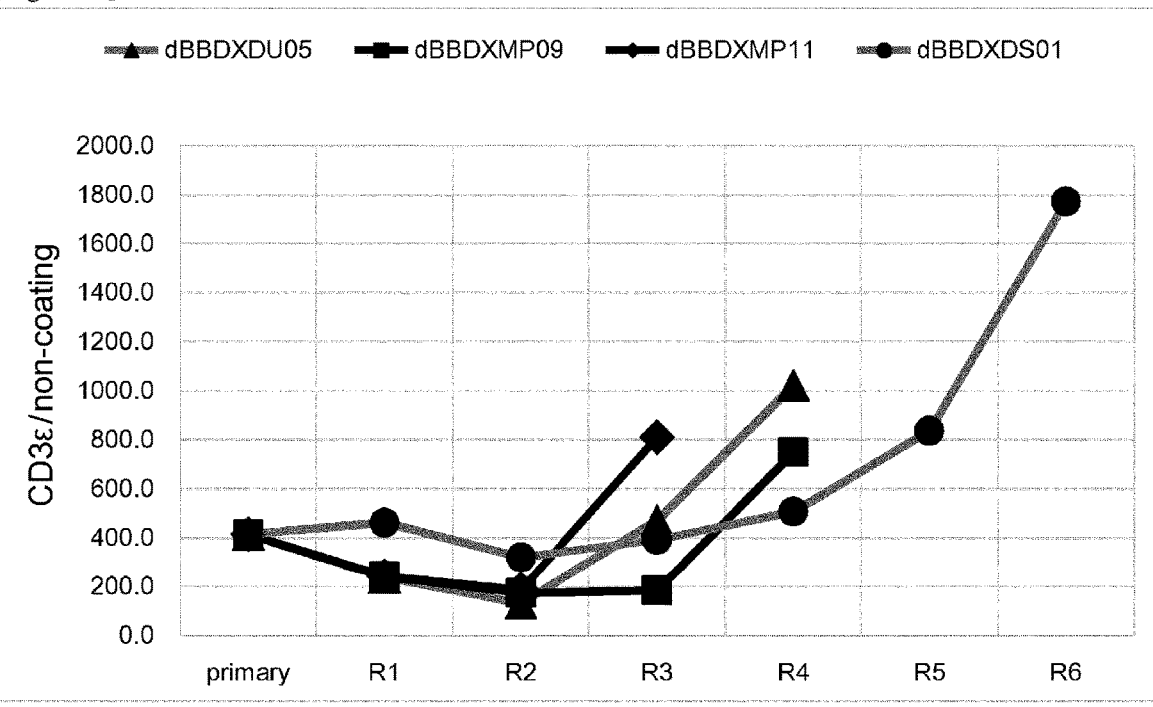

[Fig. 23-1]
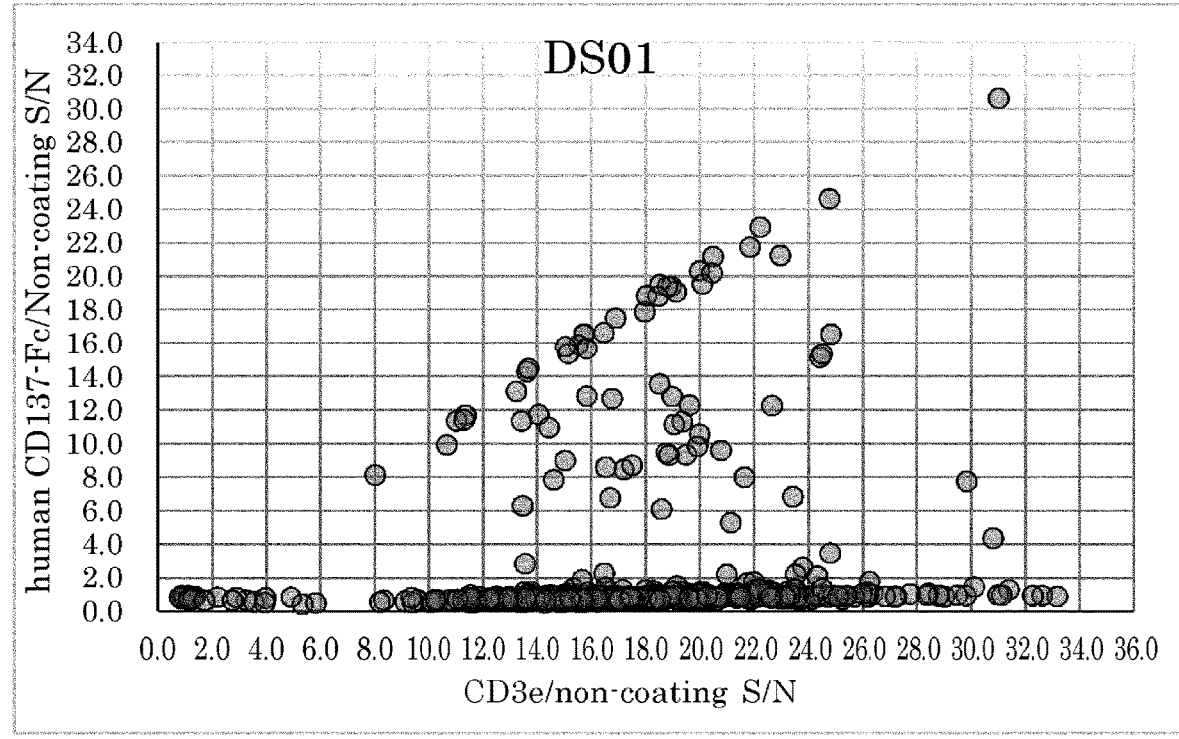
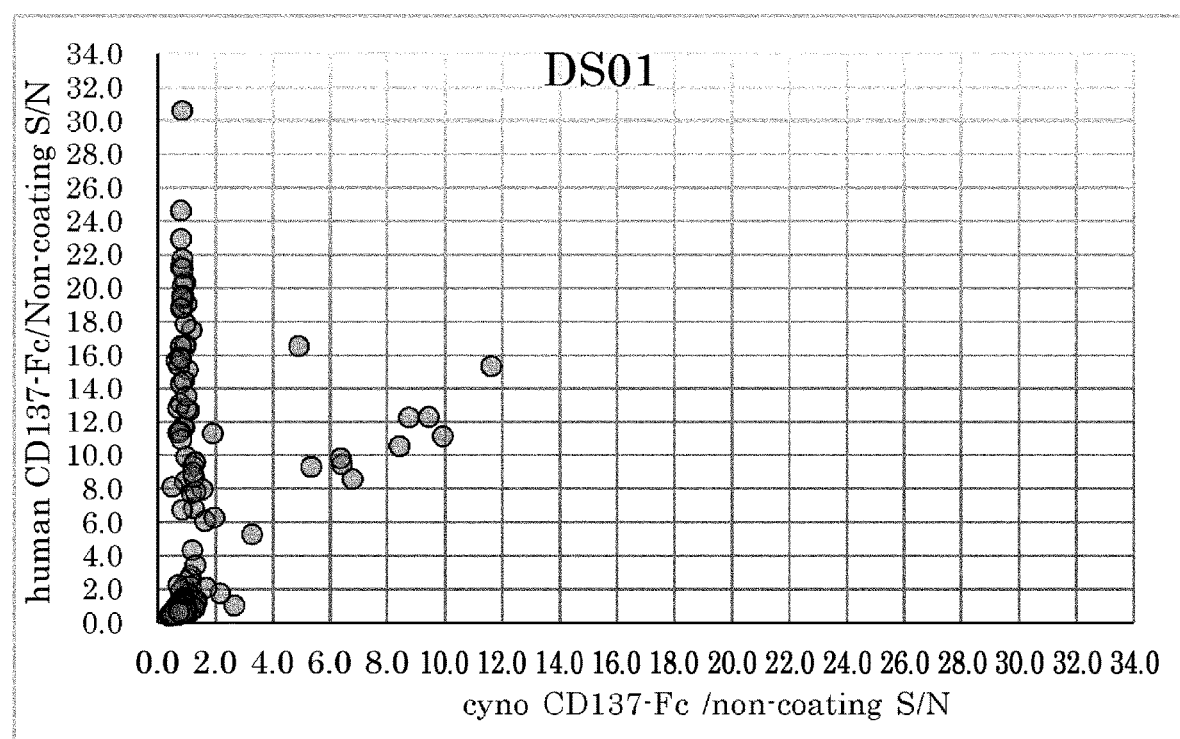

[Fig. 23-2]
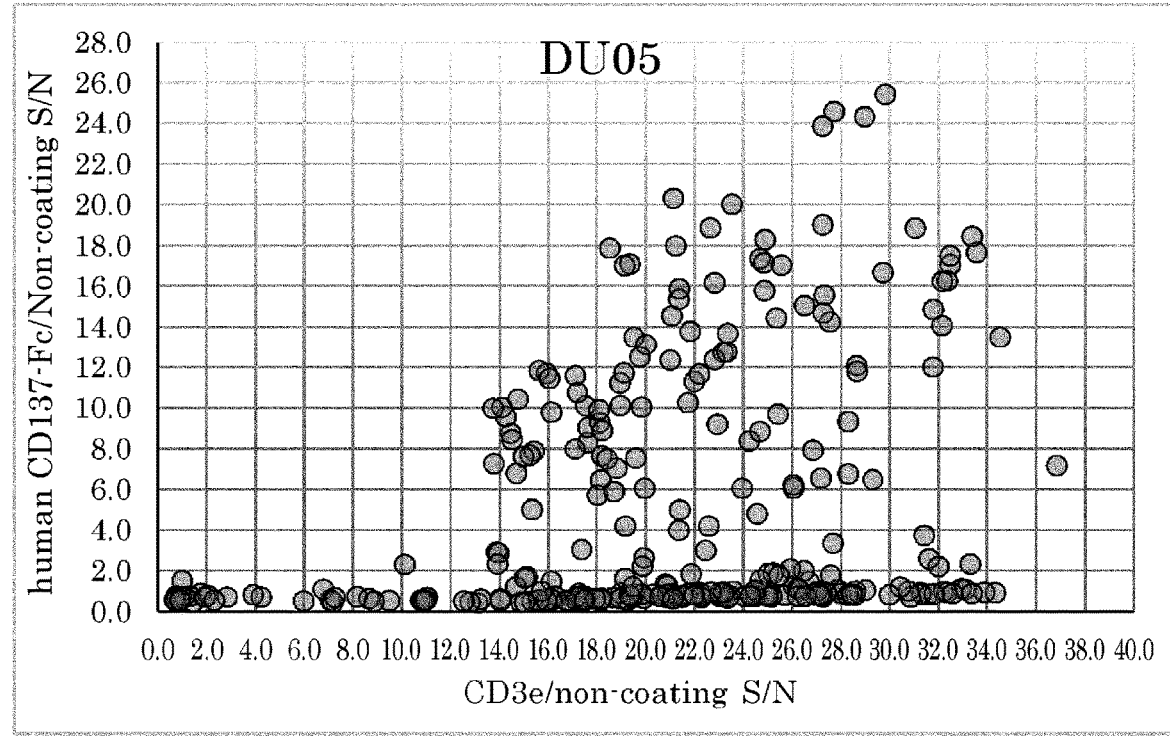
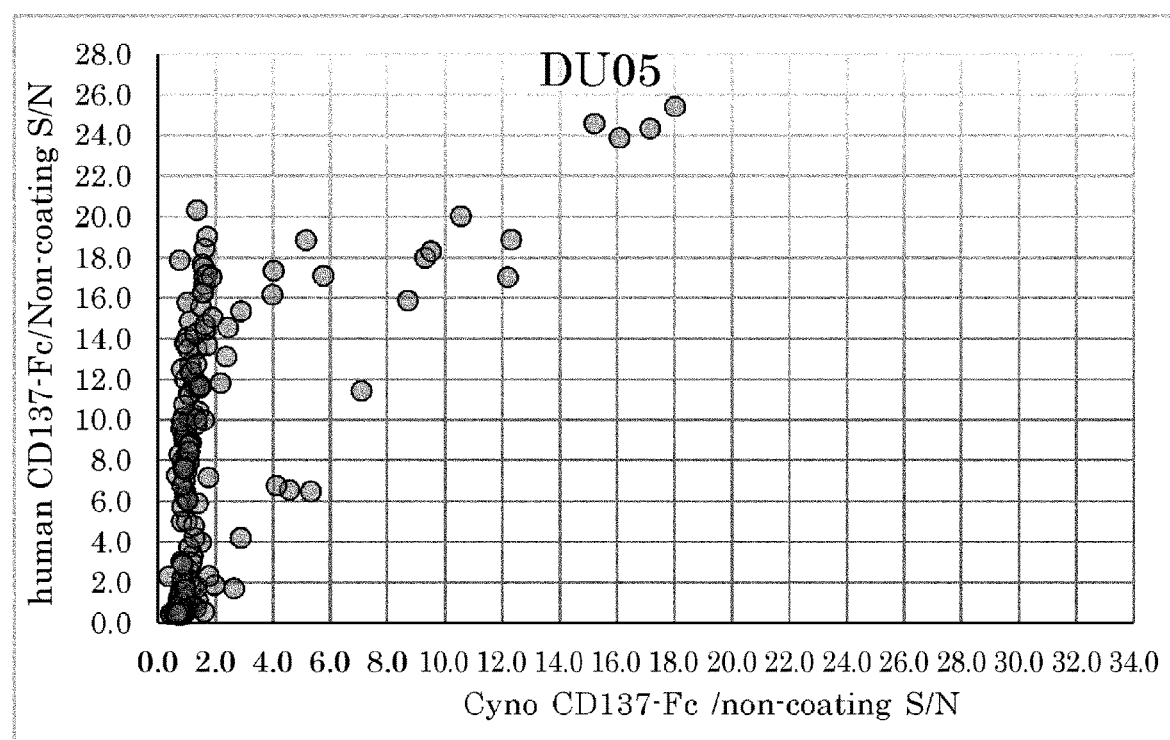

[Fig. 23-3]
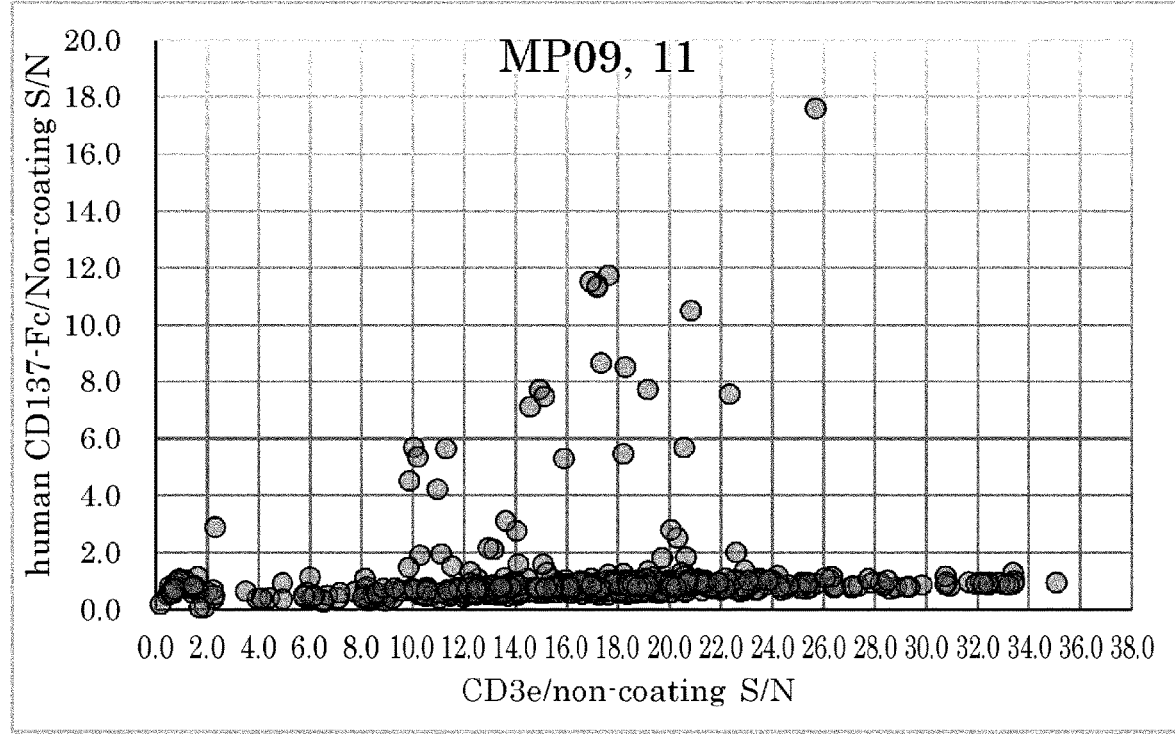
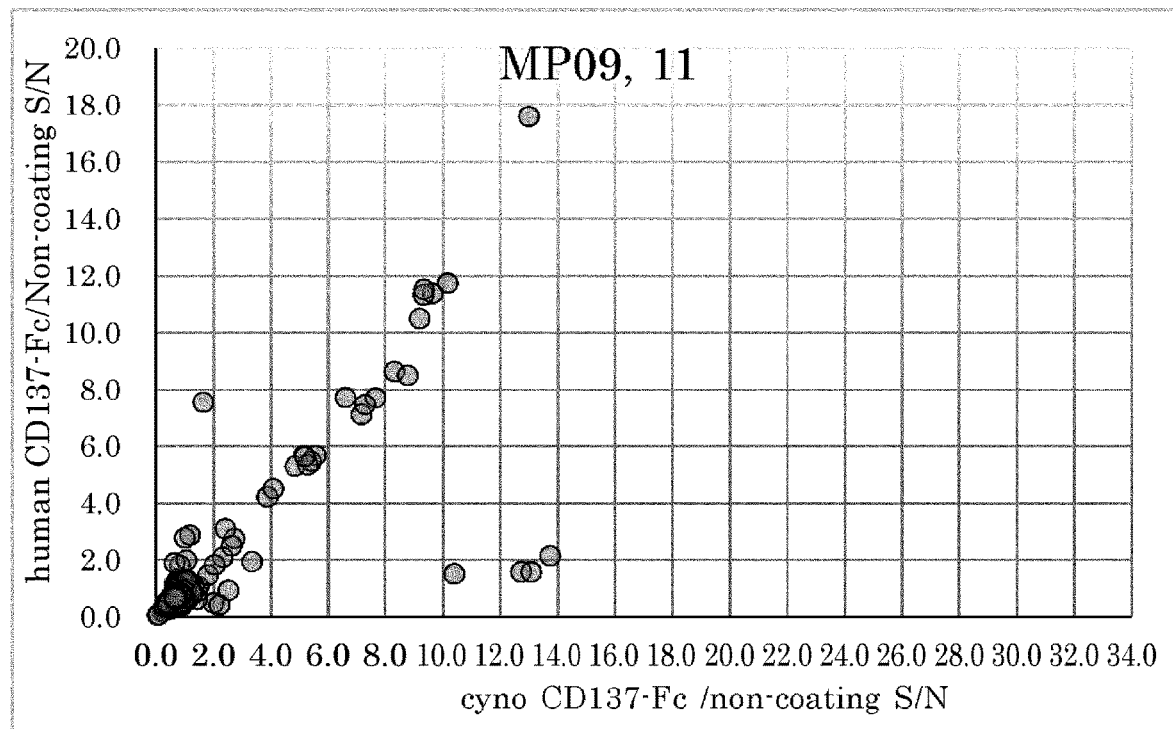

[Fig. 24]
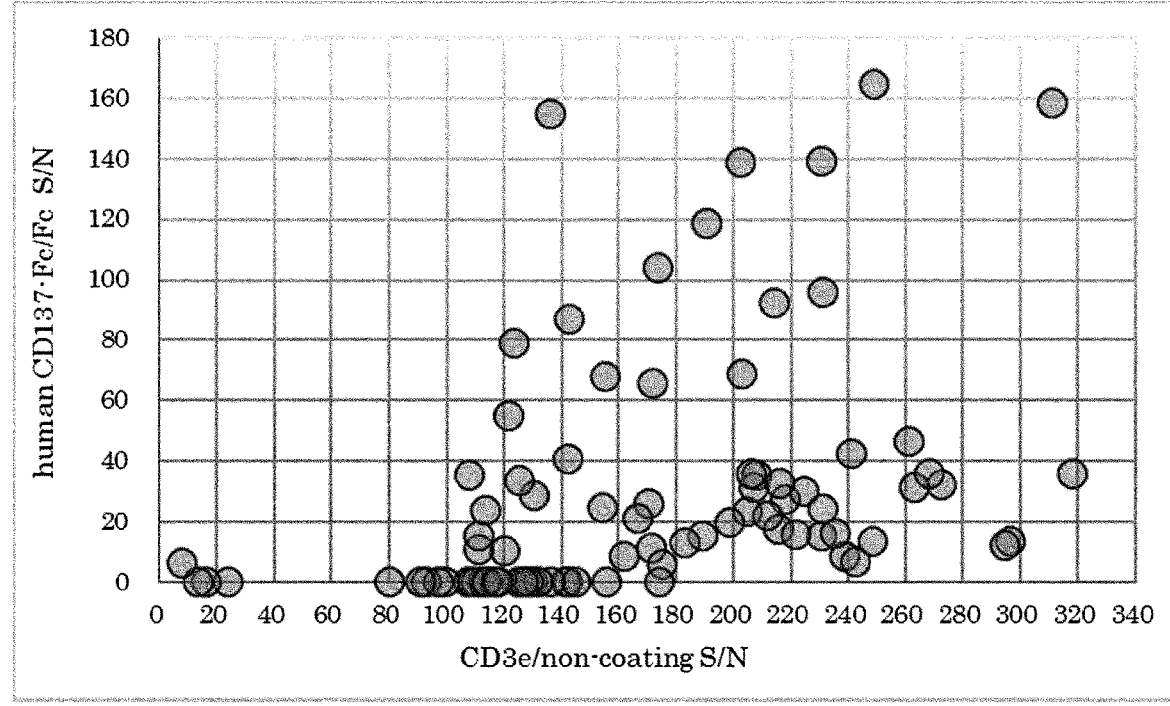
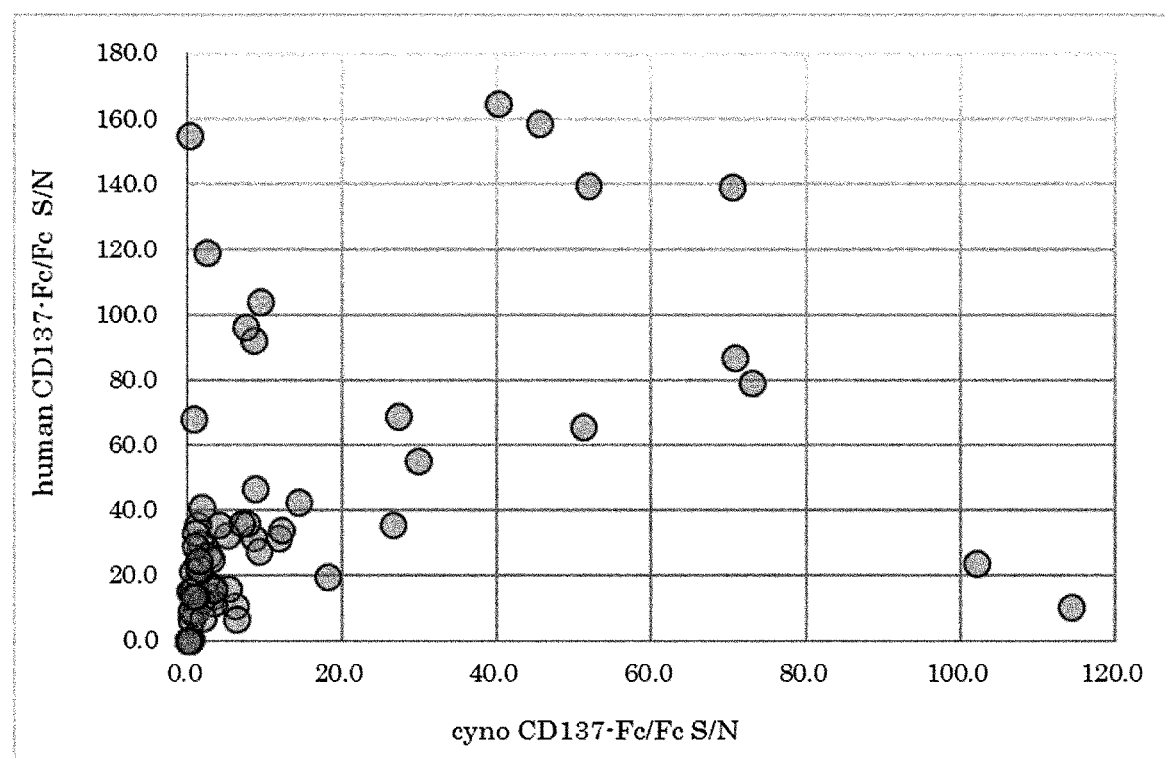

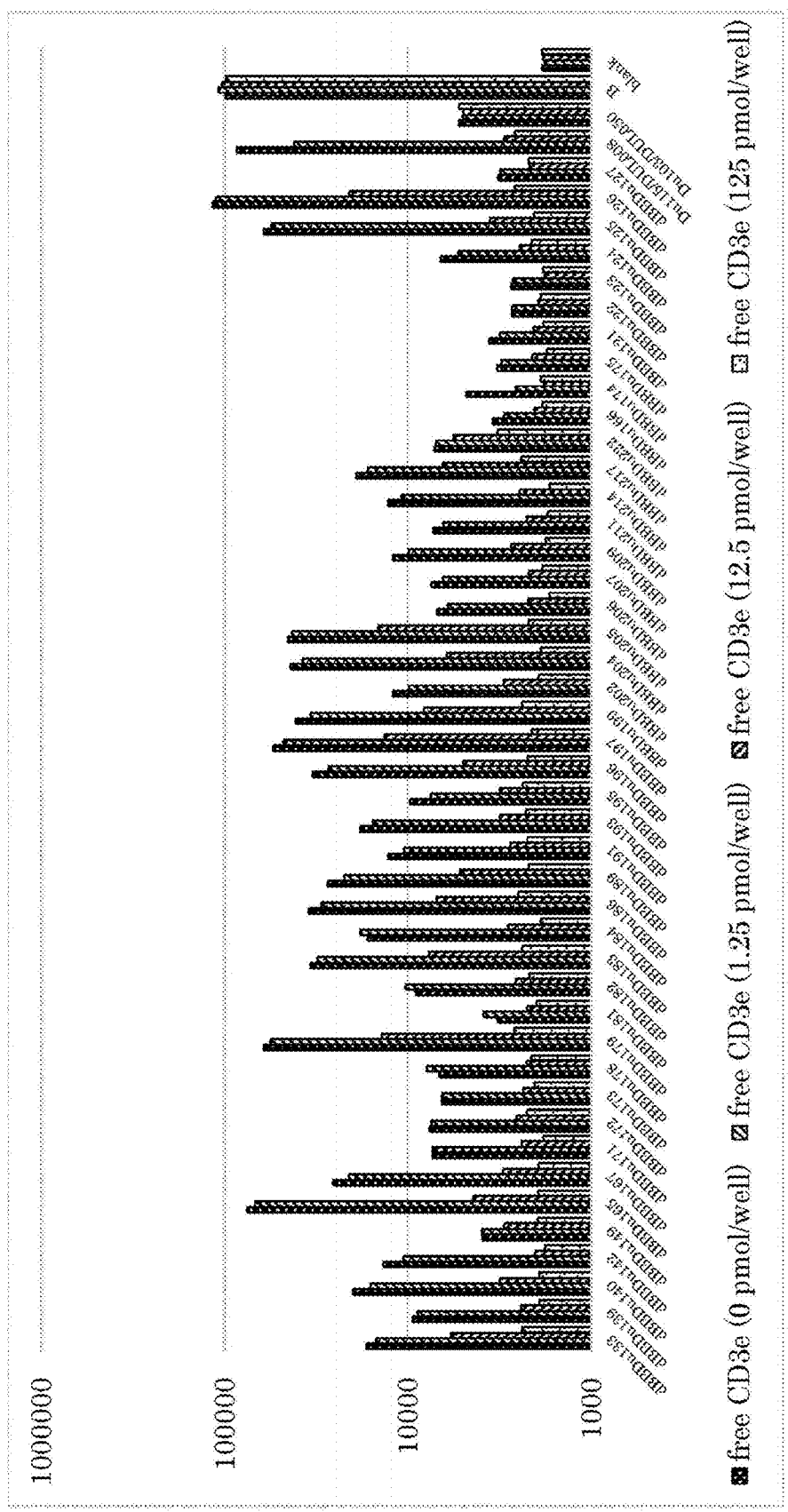
[Fig. 25]

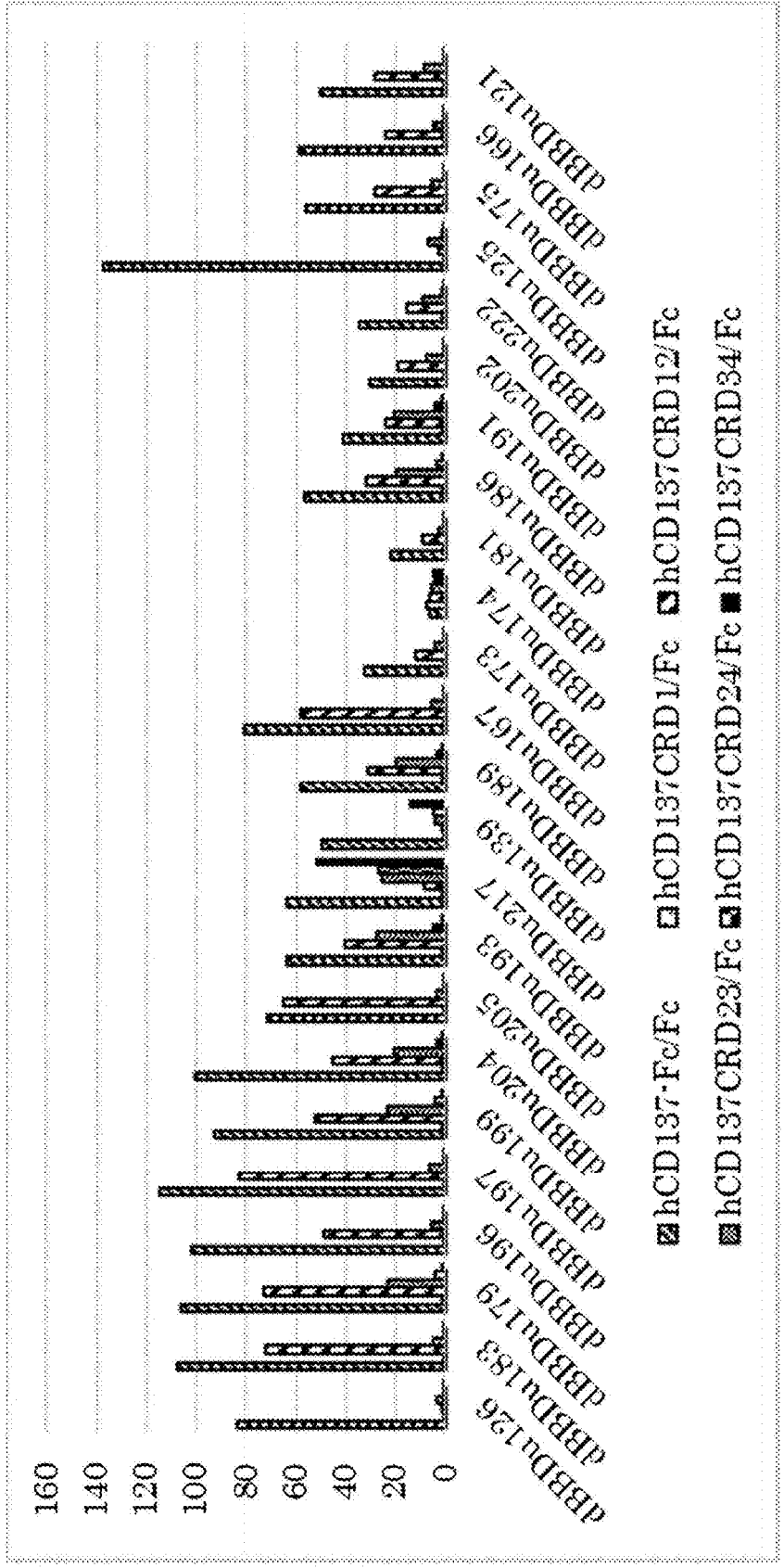

[Fig. 27]
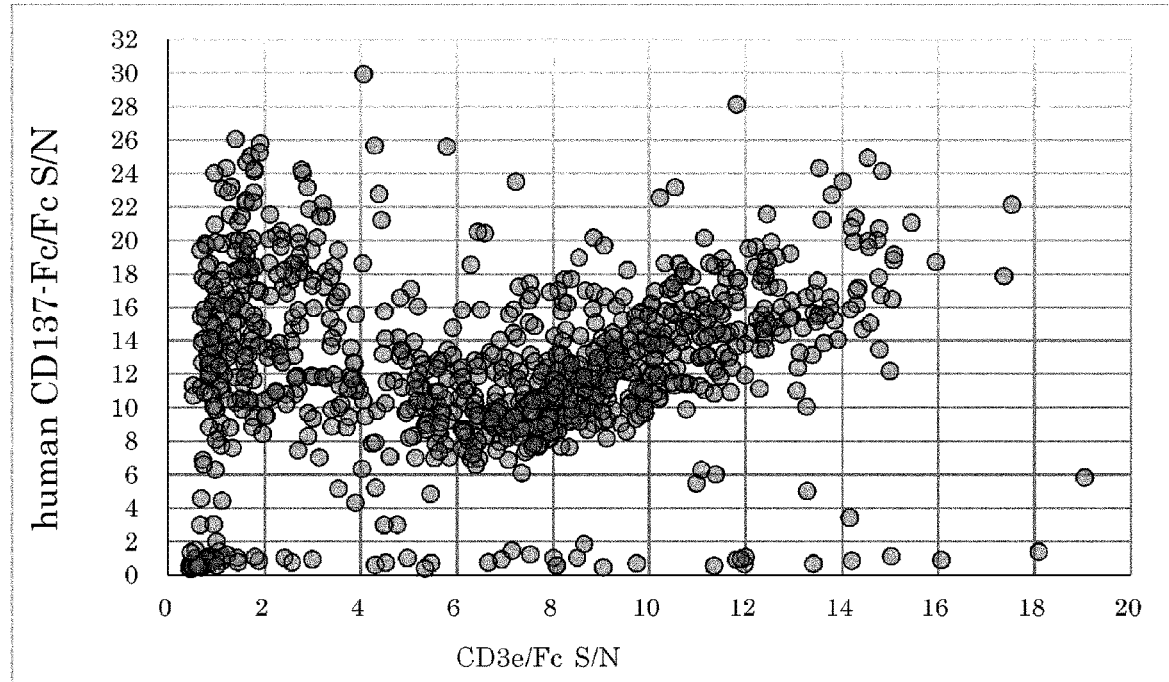
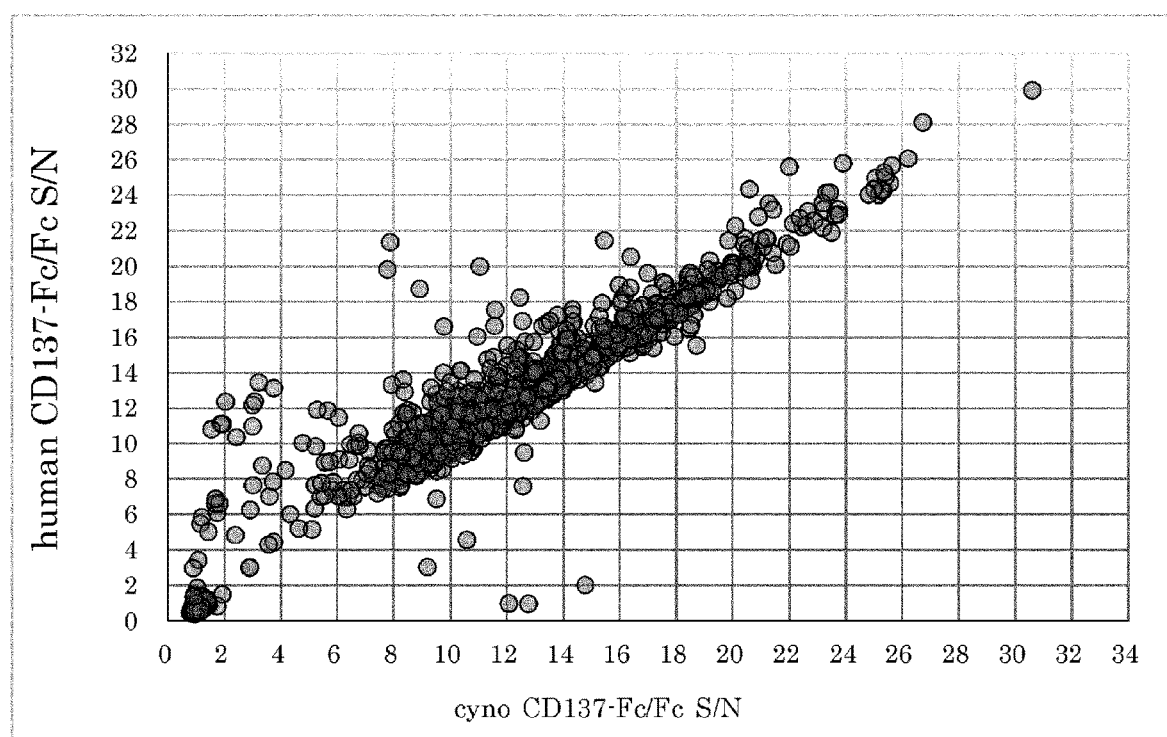

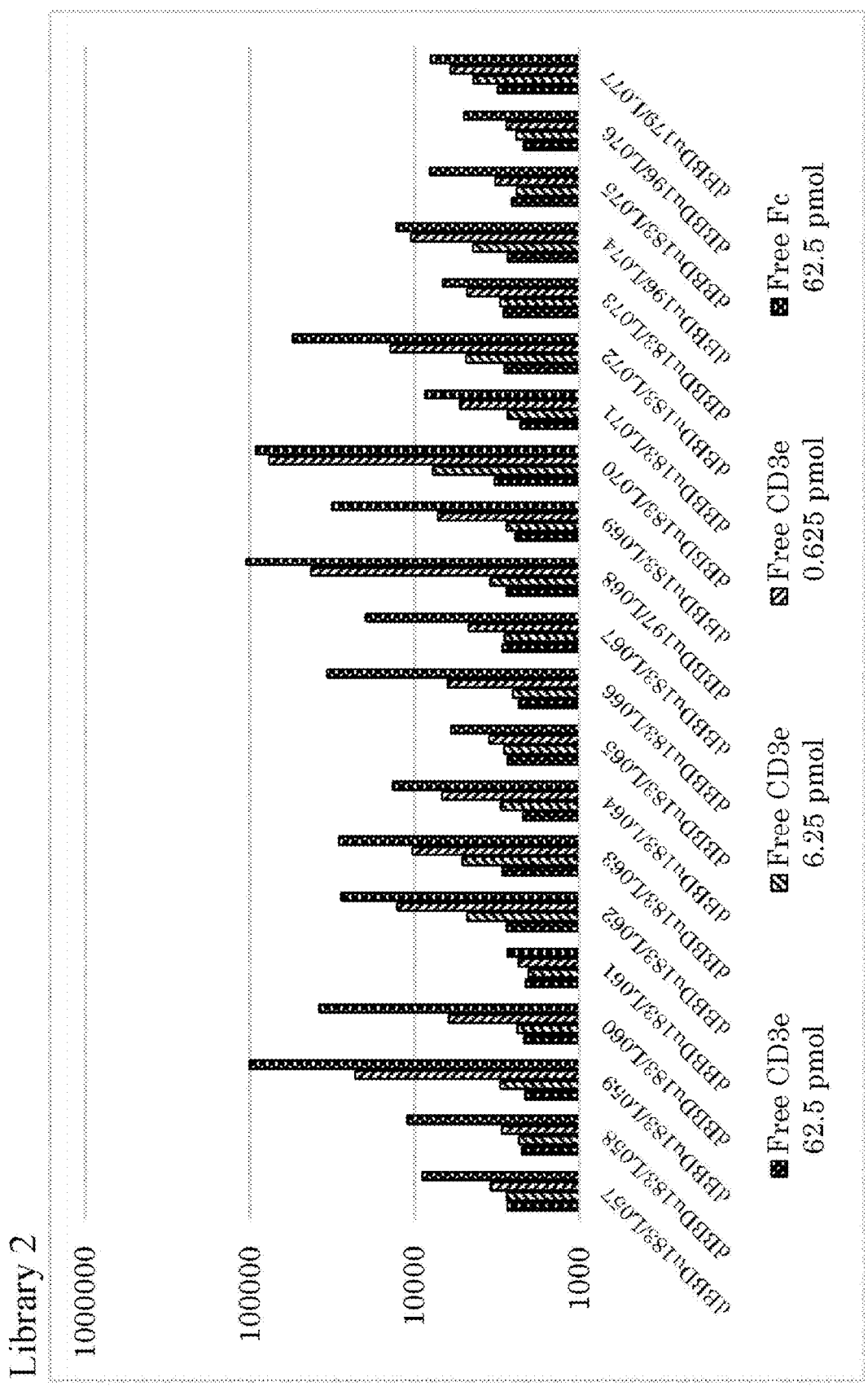
[Fig. 28-1]

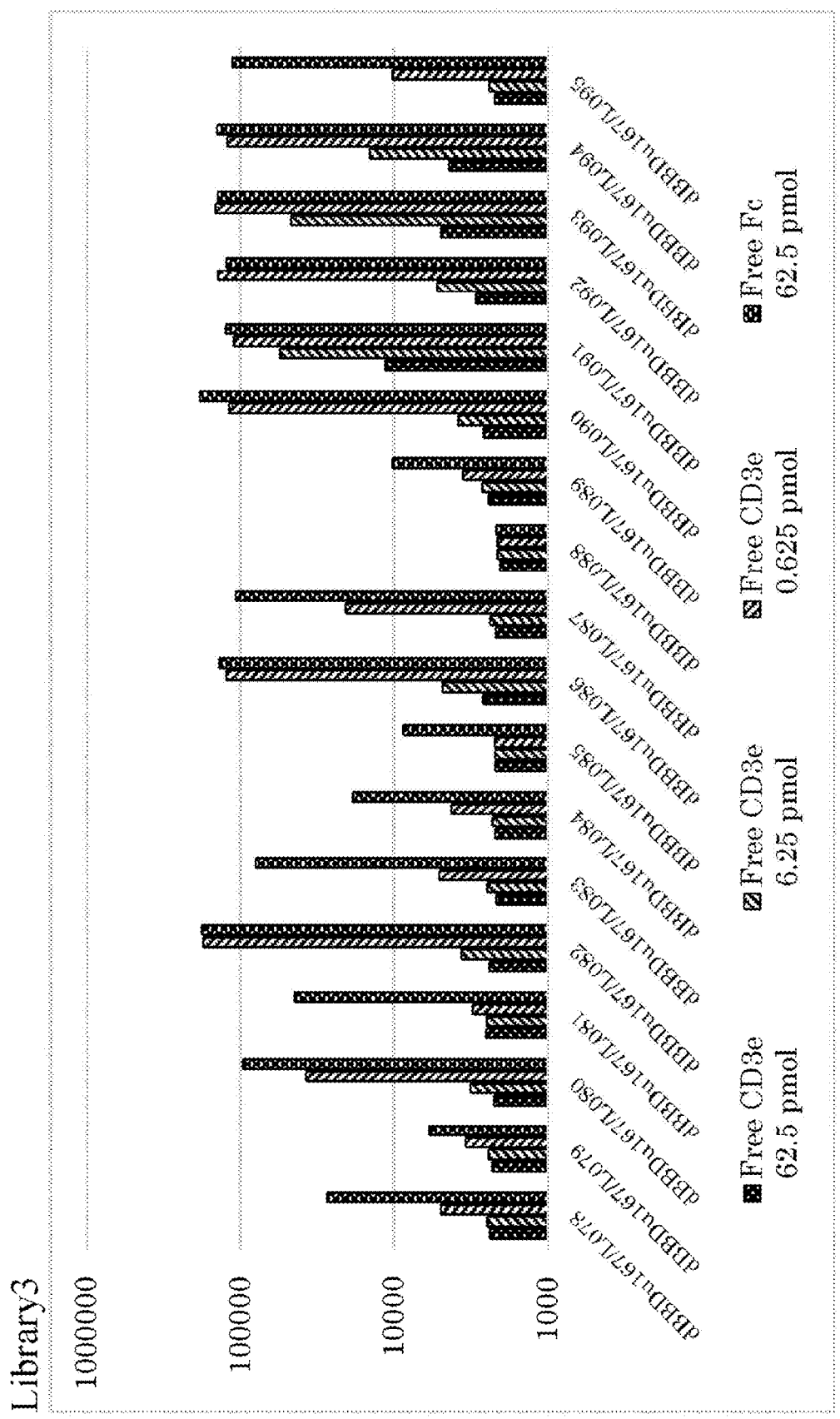
[Fig. 28-2]

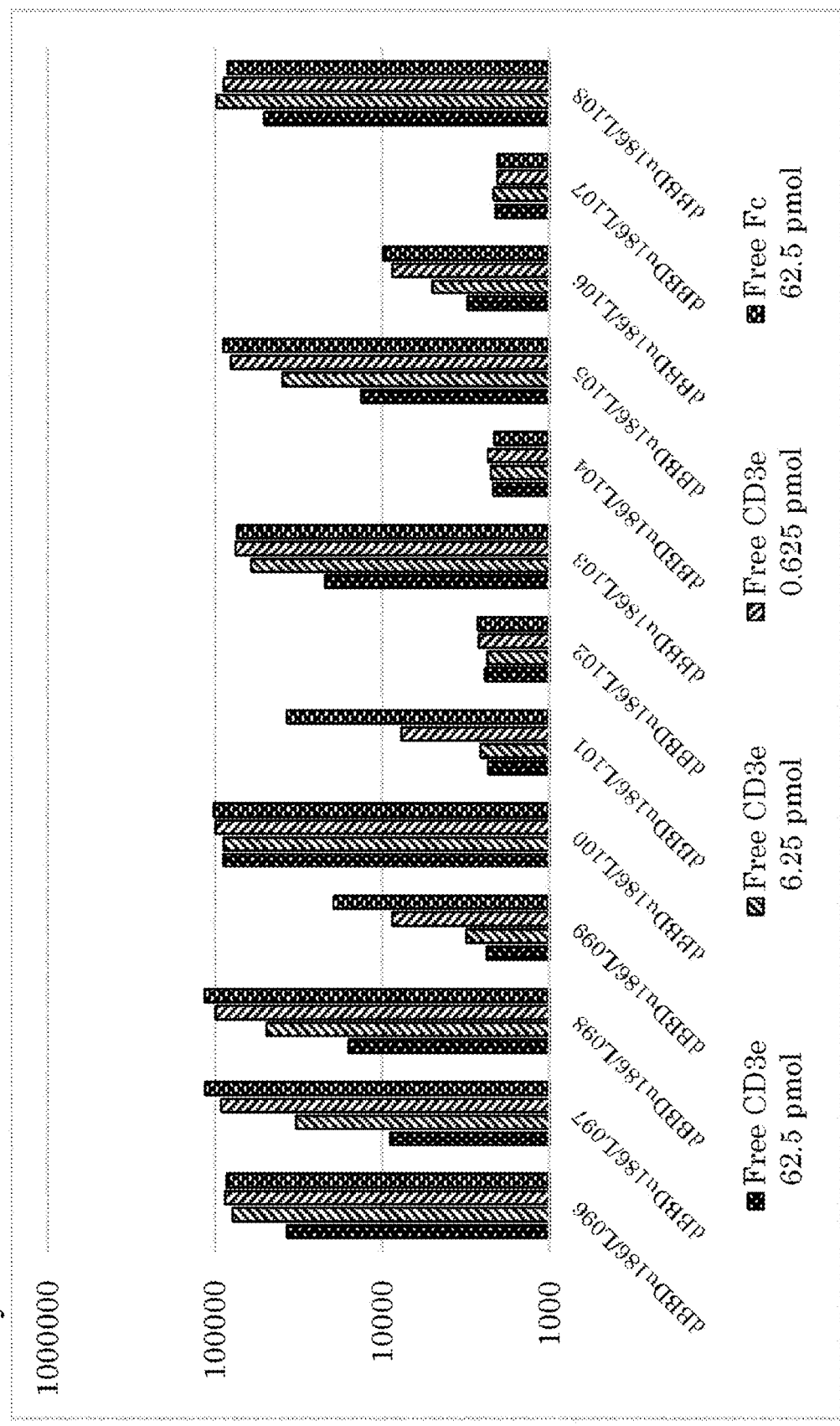
[Fig. 28-3]

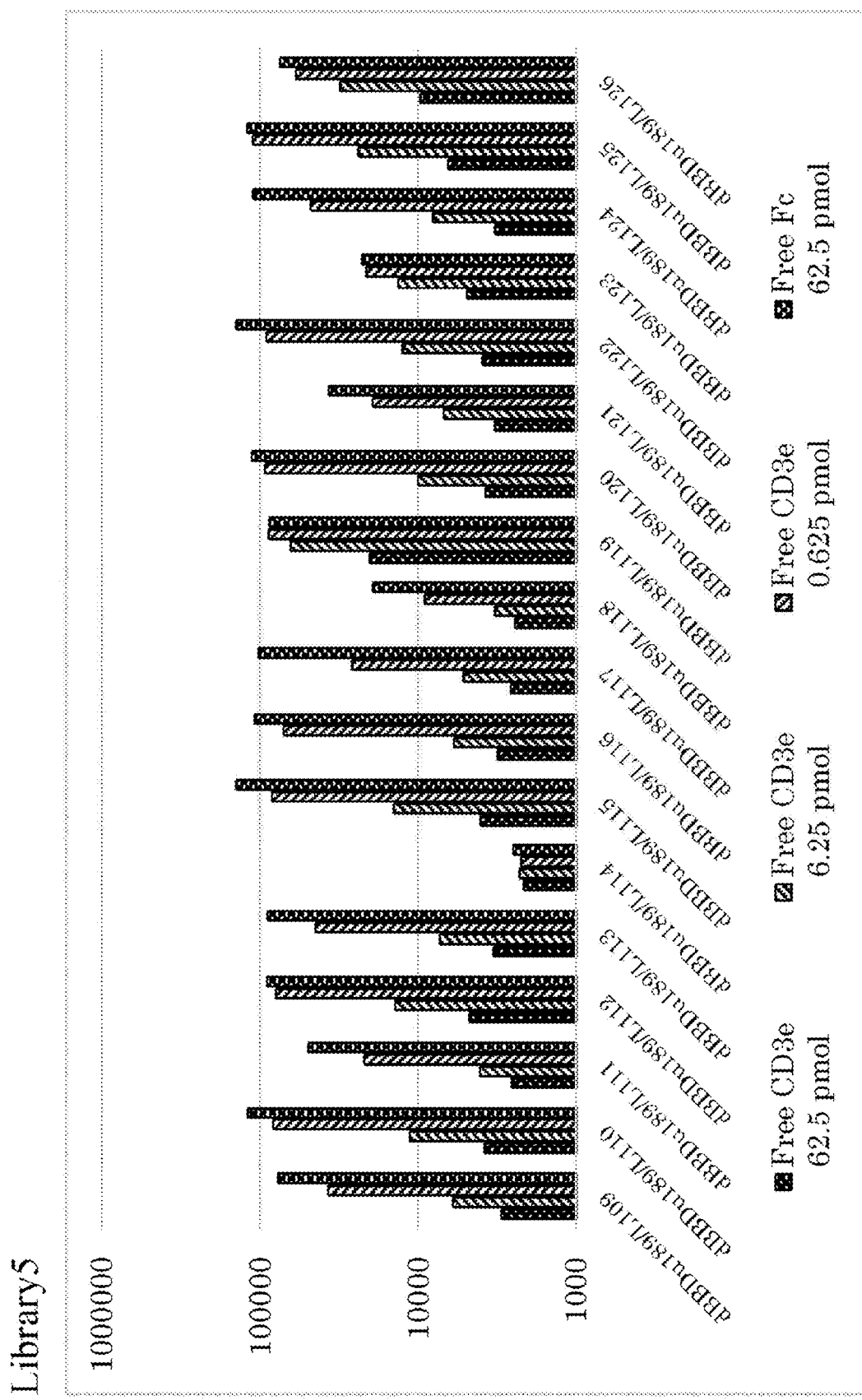
[Fig. 28-4]

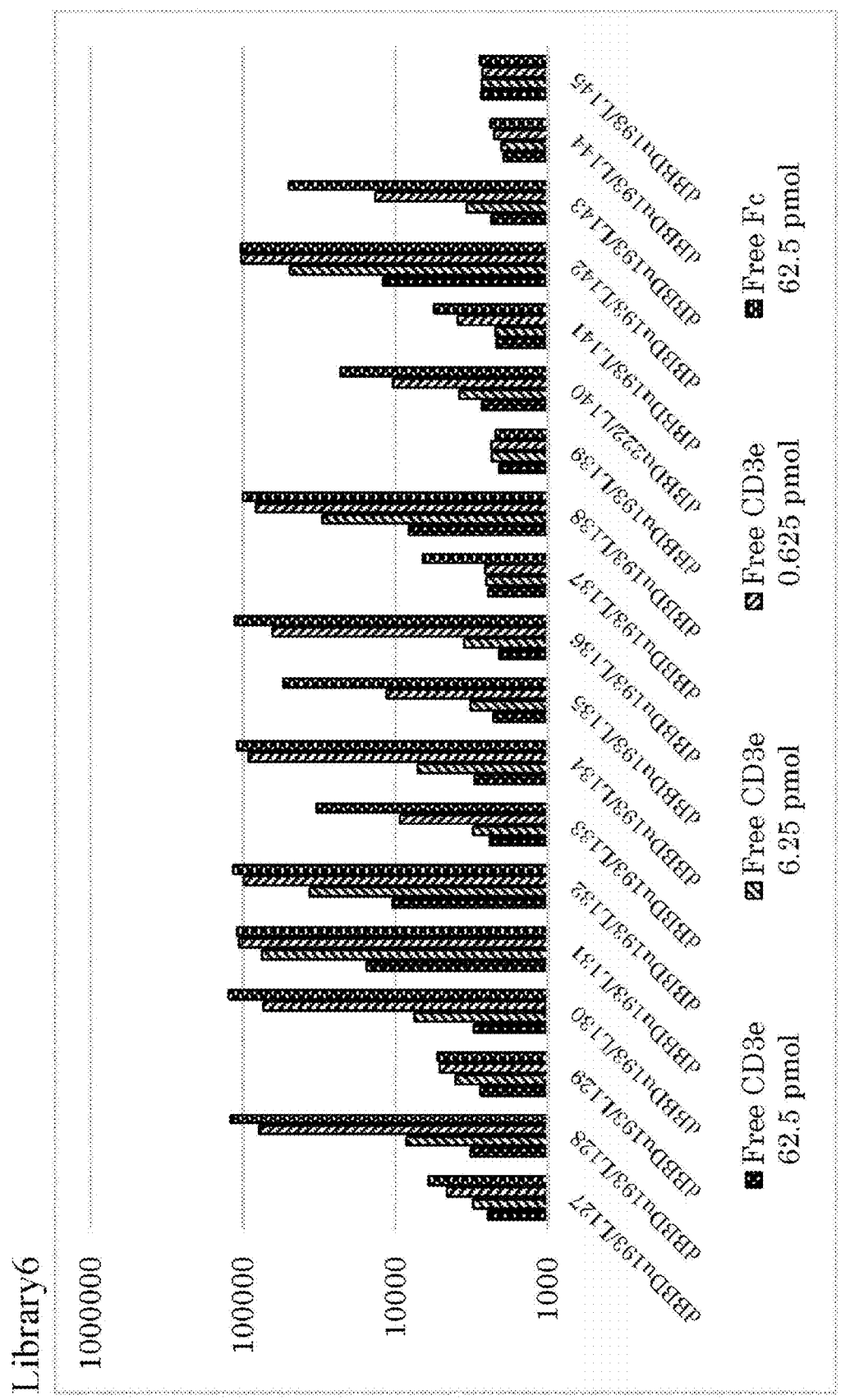
[Fig. 28-5]

[Fig. 29A]
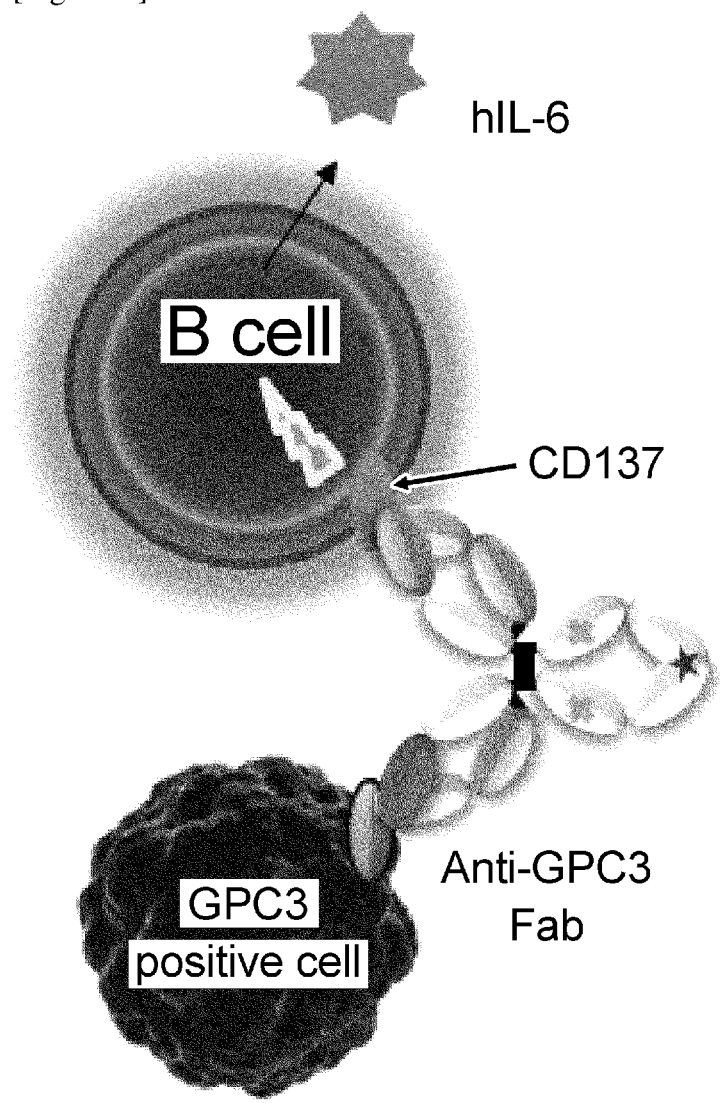

[Fig. 29B]
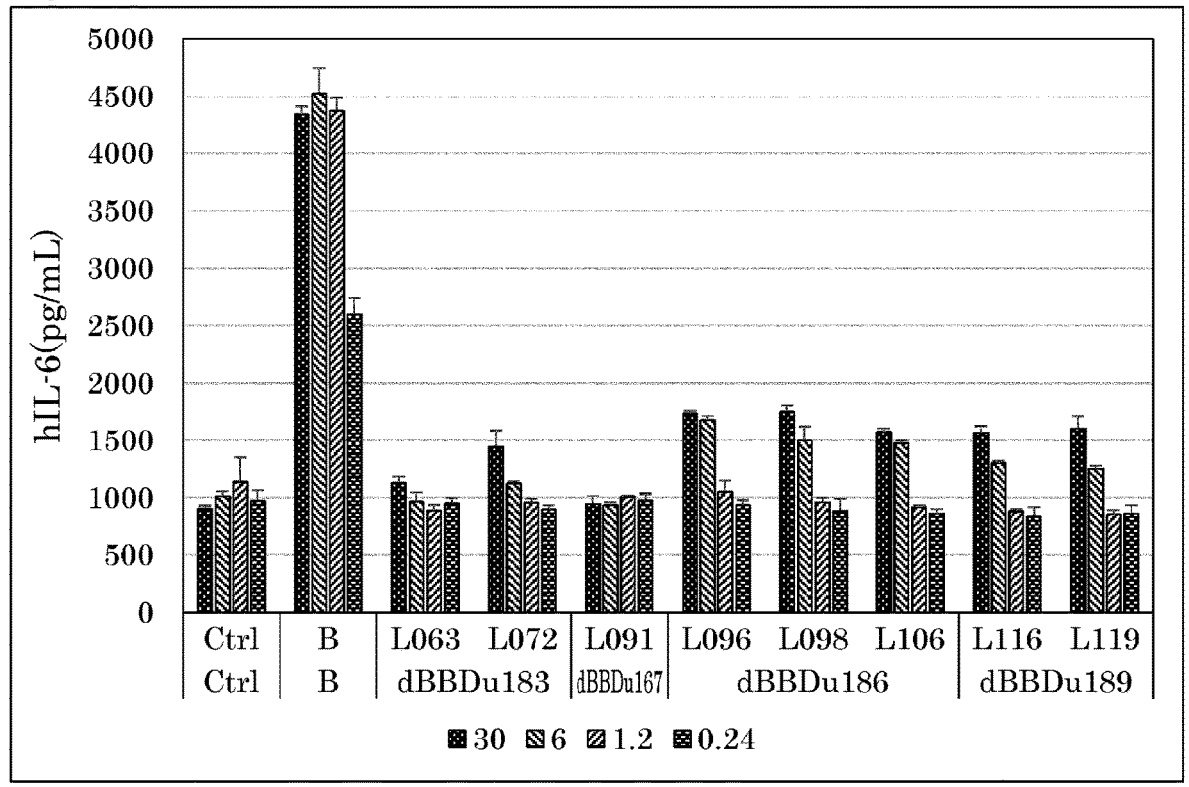
[Fig. 30A]
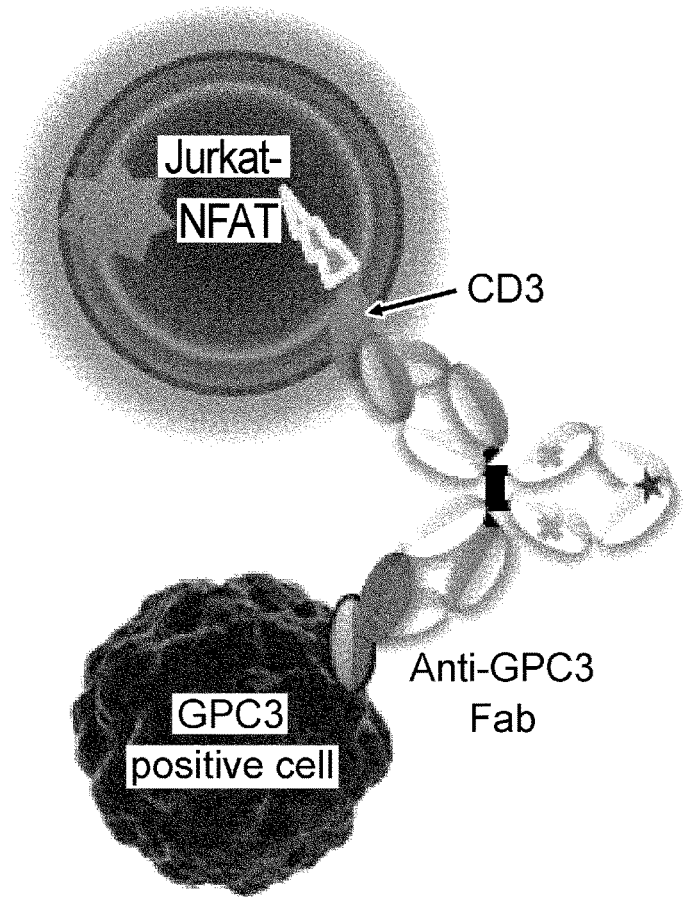

[Fig. 30B]
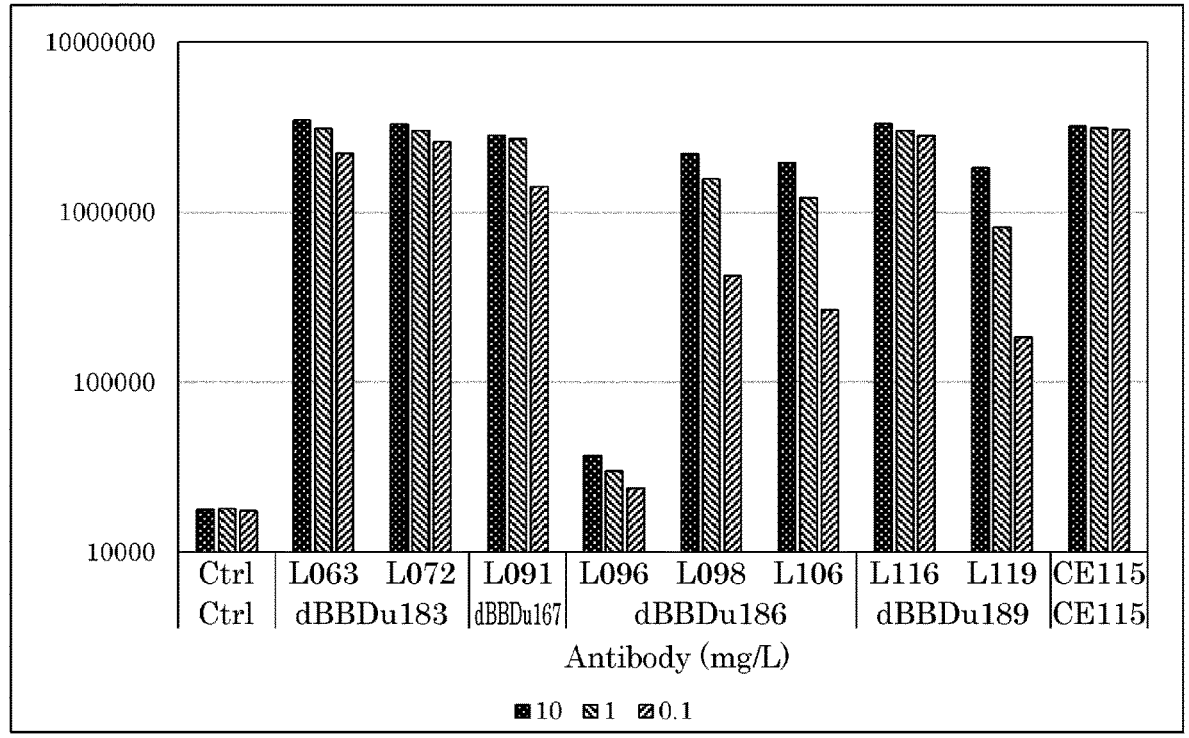
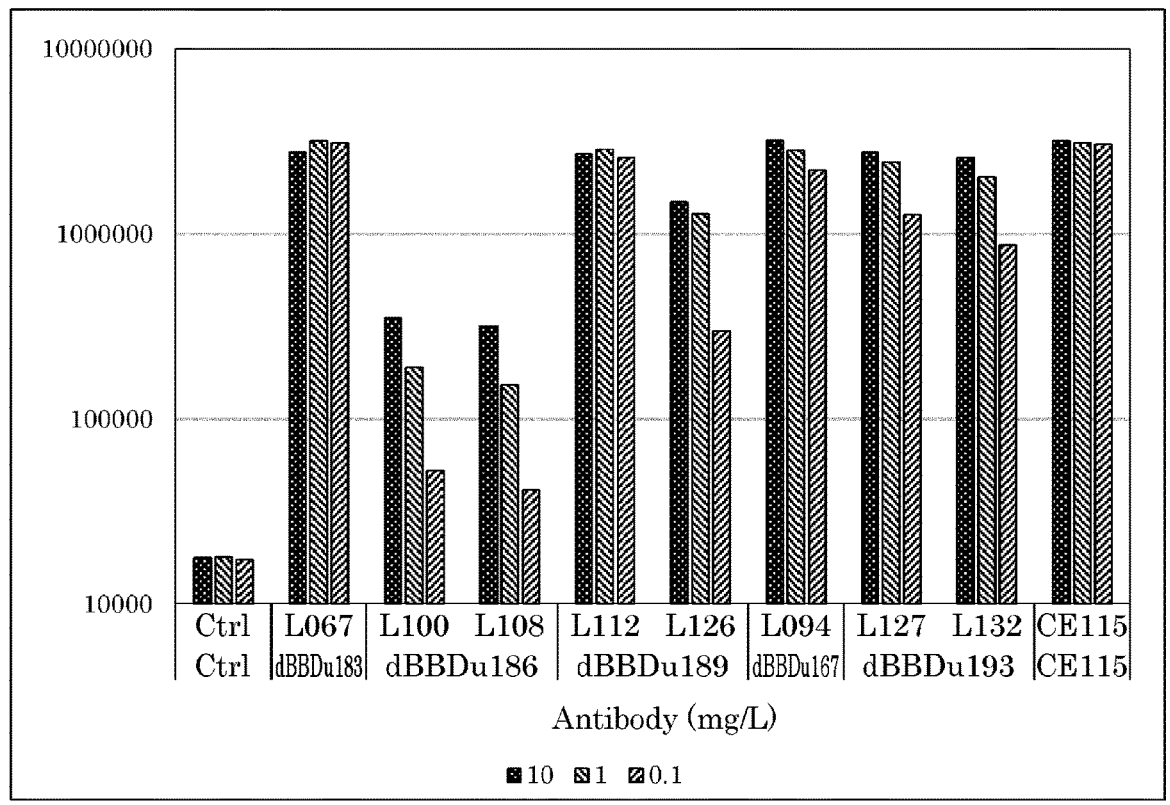

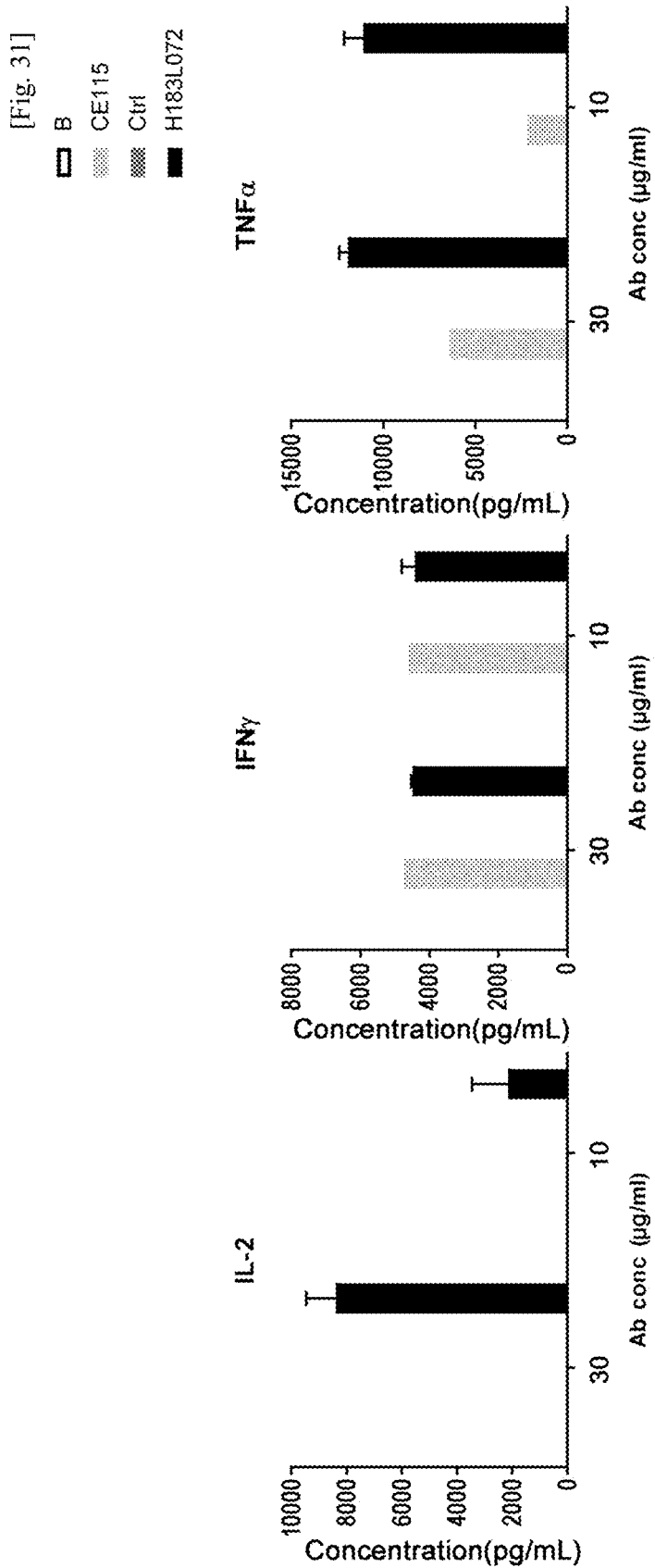

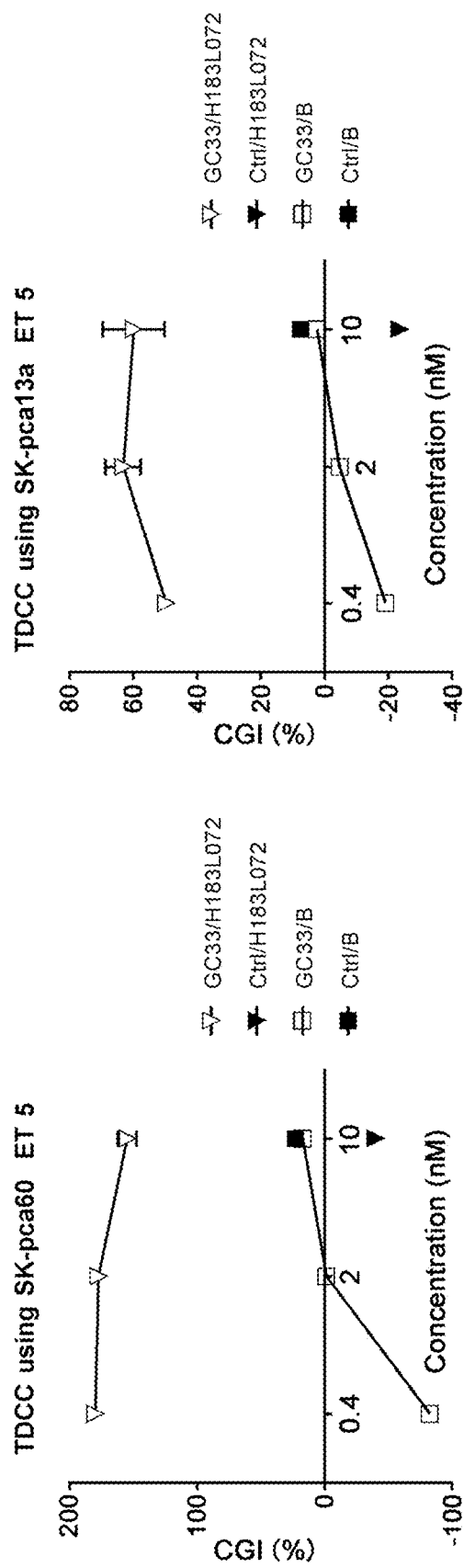

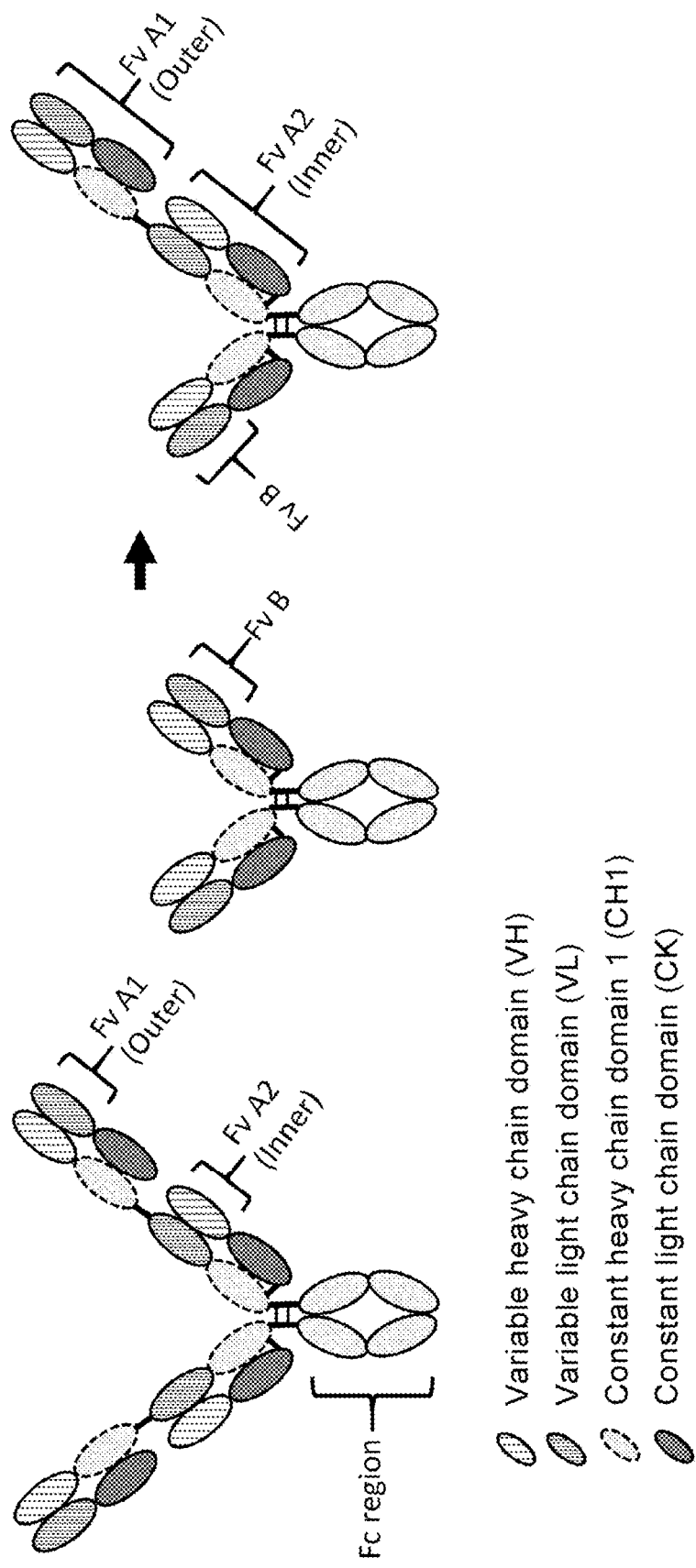

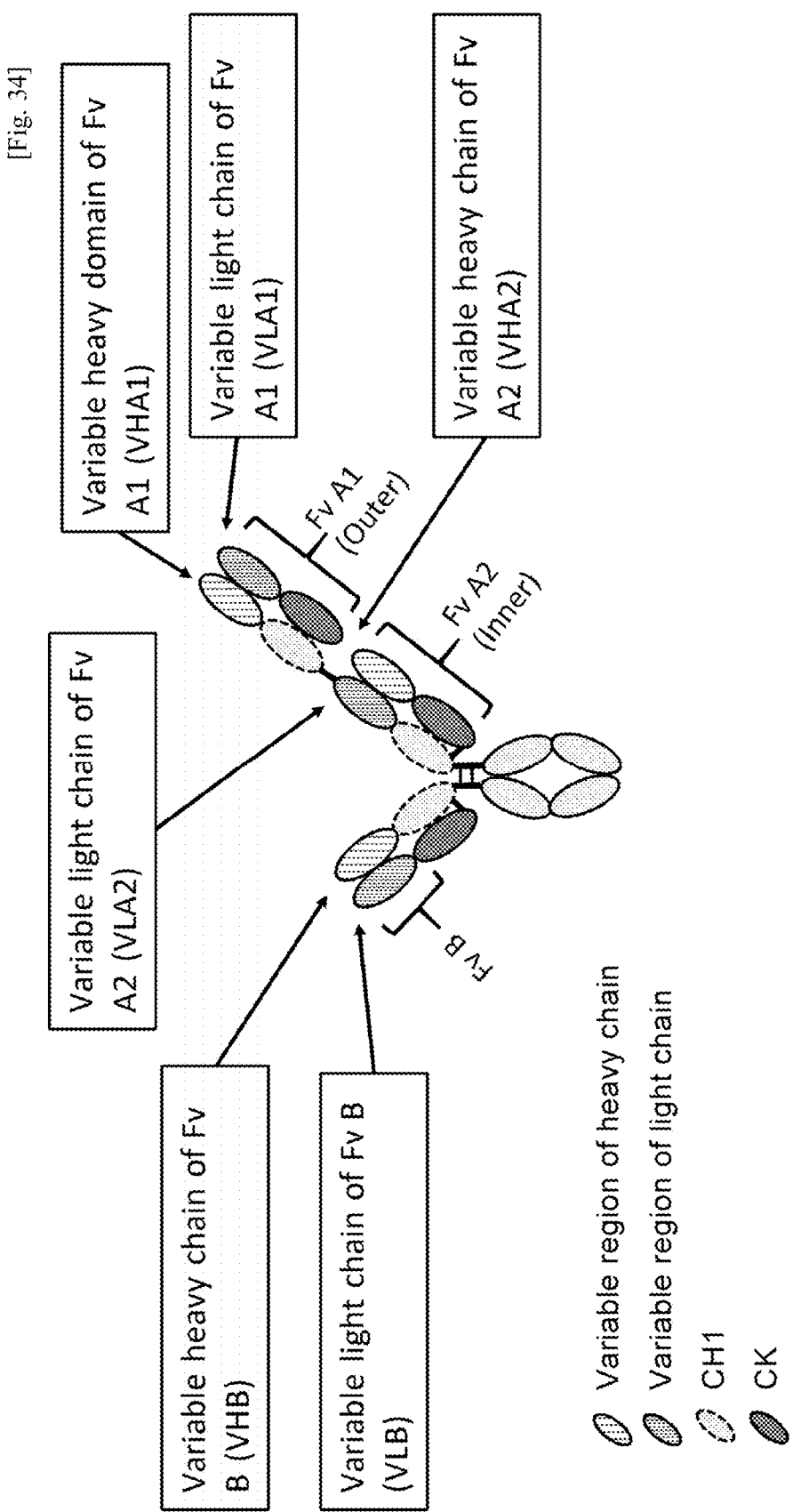
[Fig. 34]

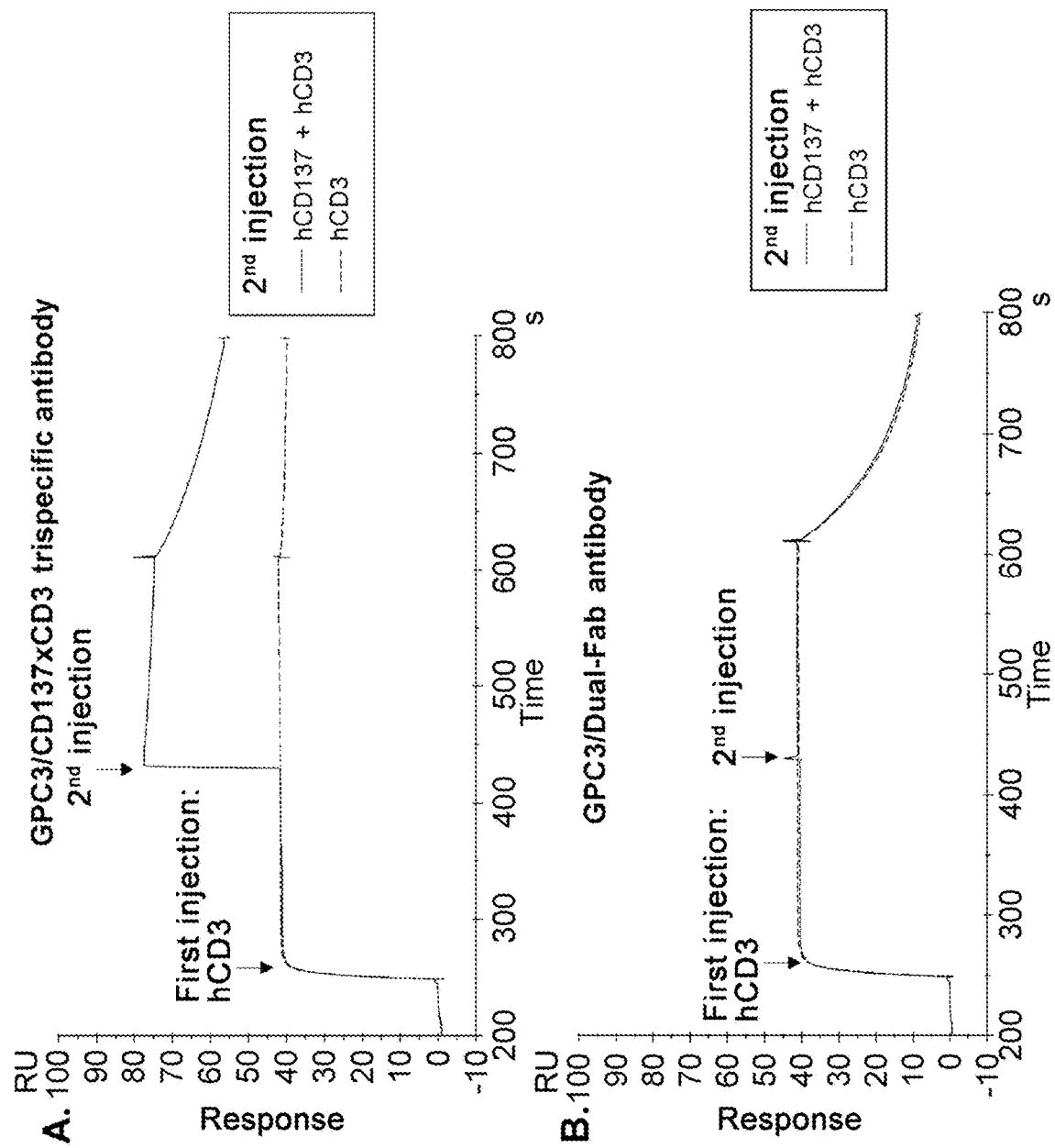
[Fig. 35]

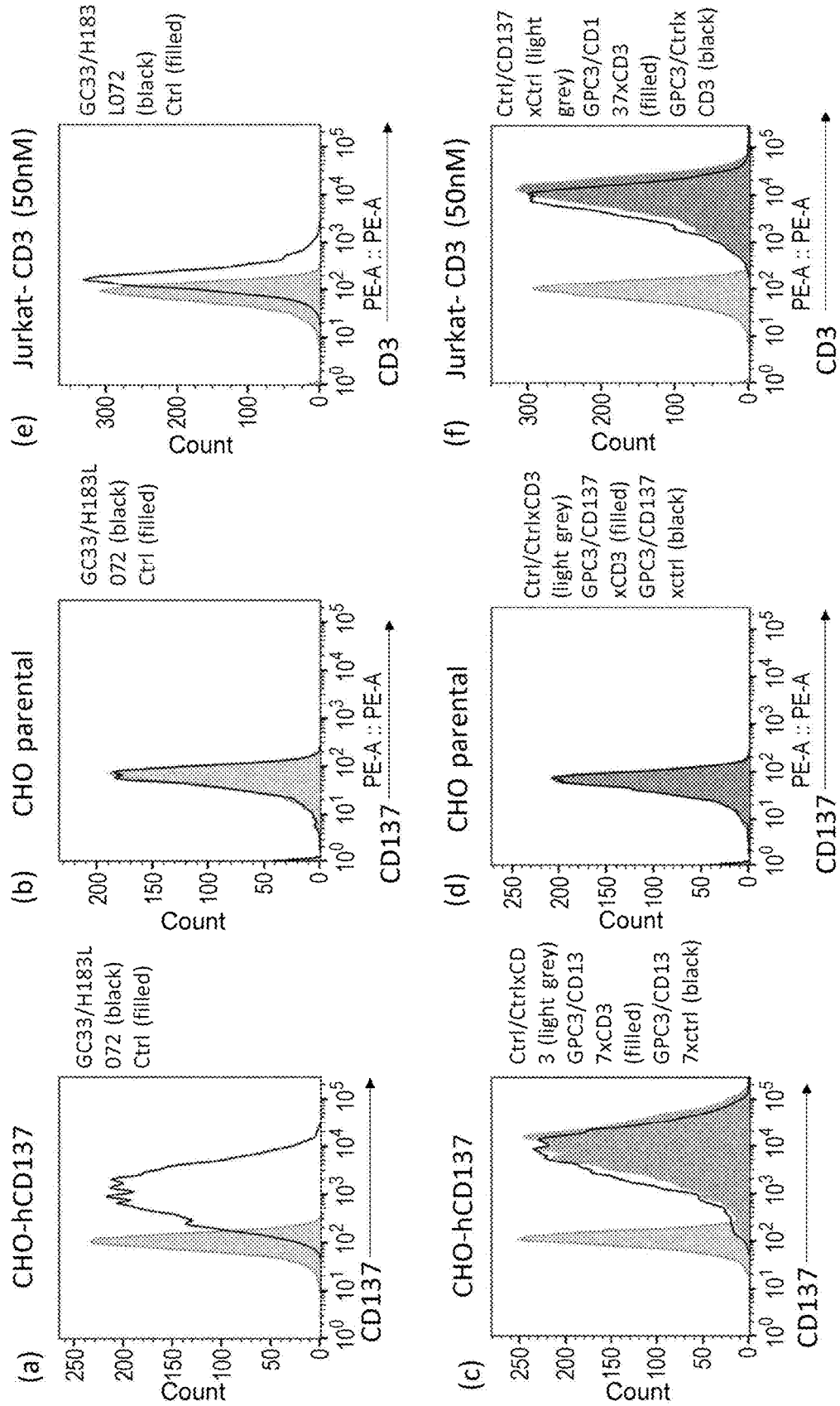
[Fig. 36]

[Fig. 37]
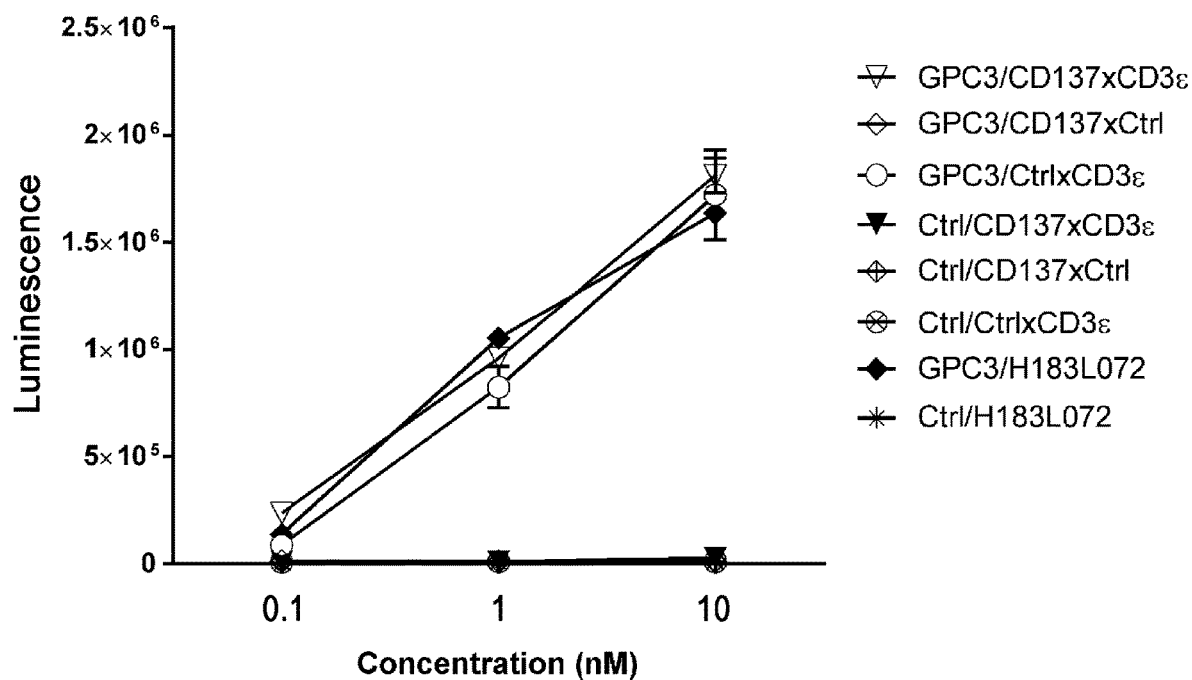

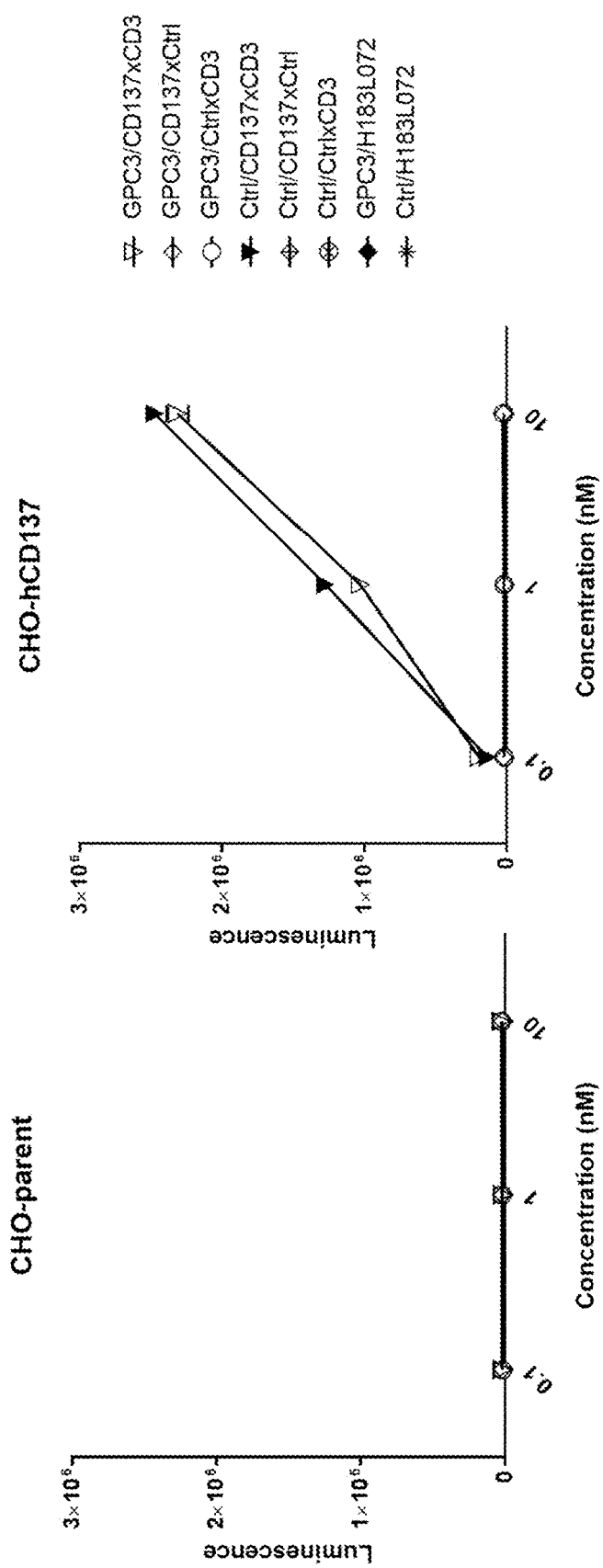
[Fig. 38]

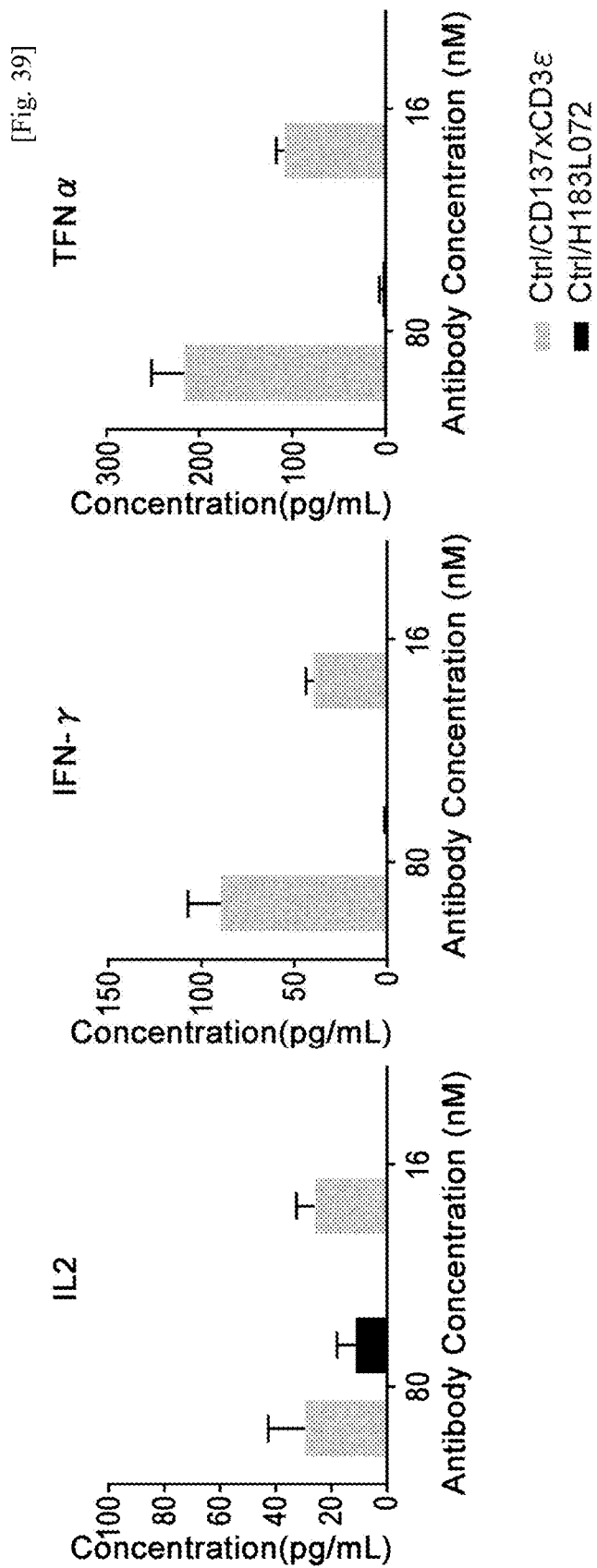

[Fig. 40]
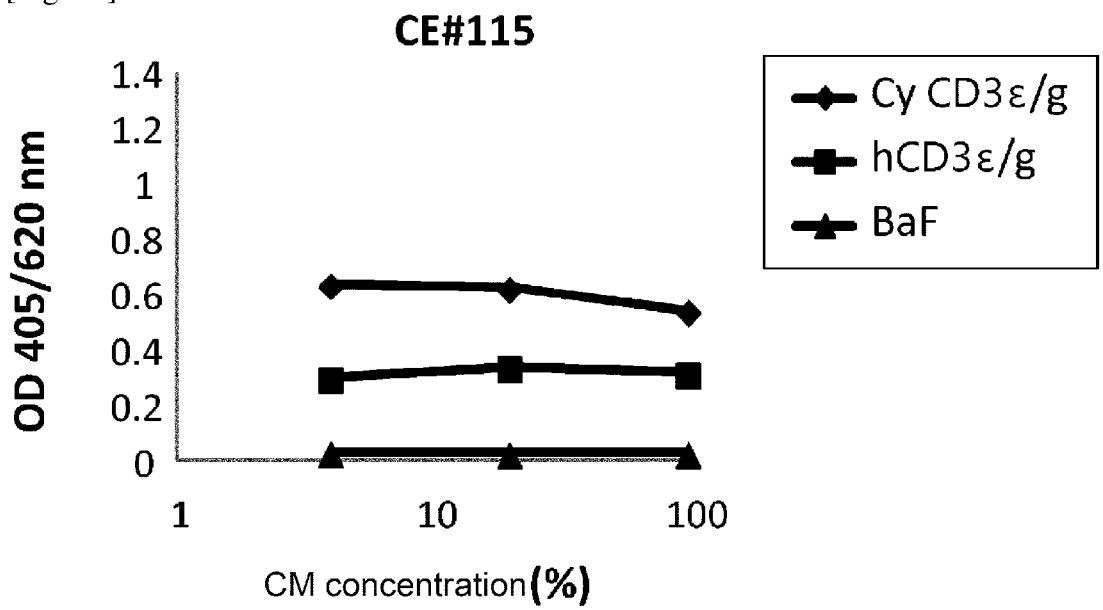
[Fig. 41]
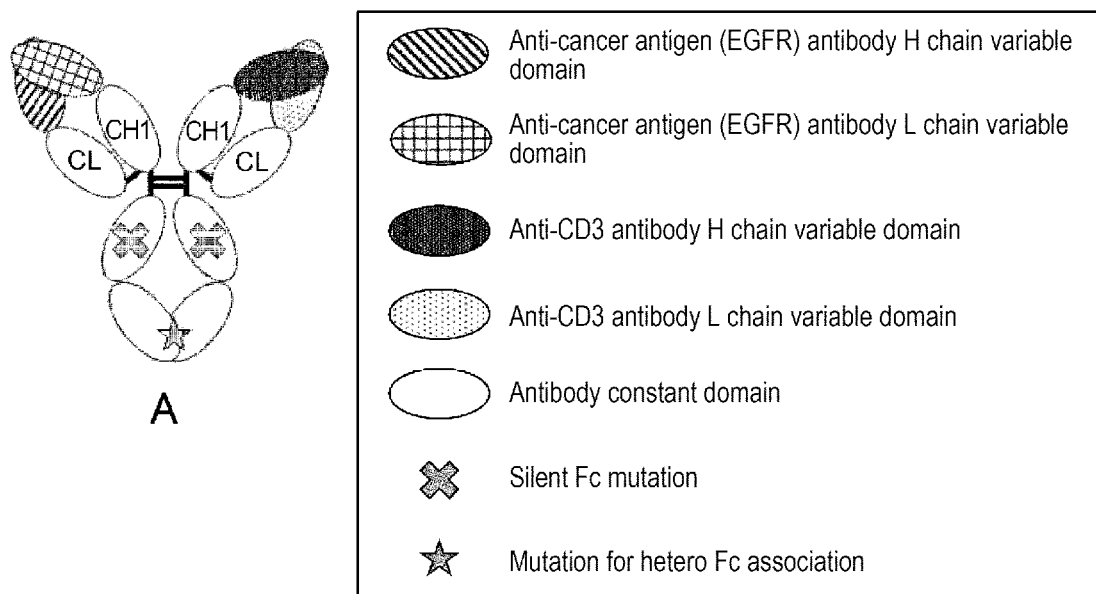

[Fig. 42]
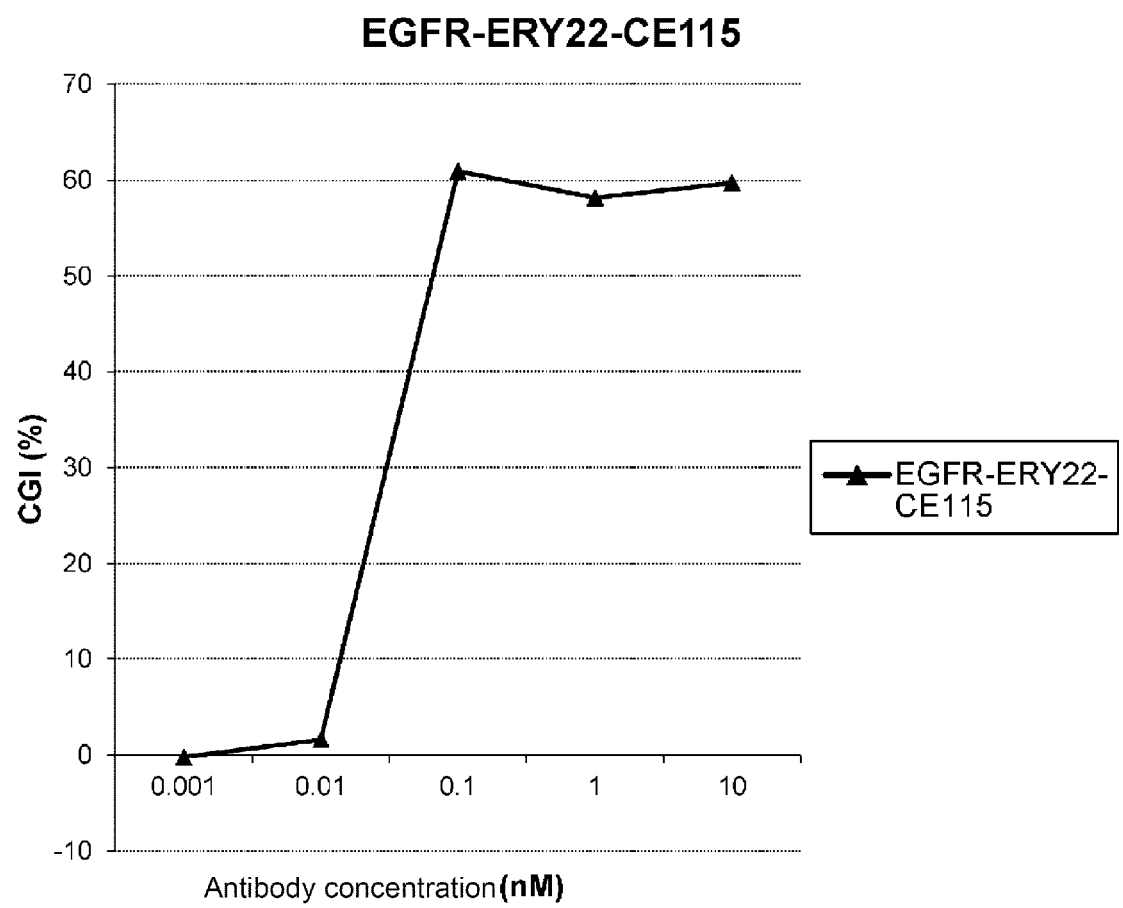

[Fig. 43]
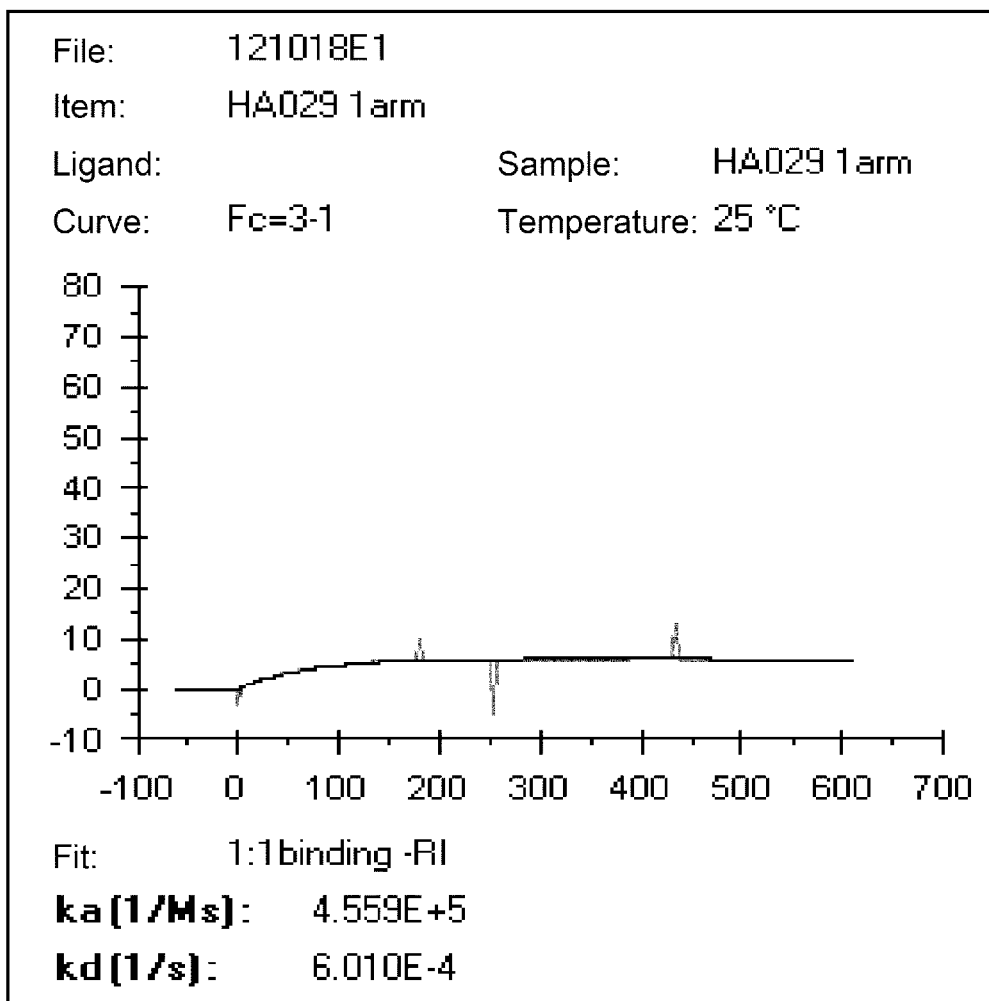

ANTIGEN-BINDING MOLECULE COMPRISING ALTERED ANTIBODY VARIABLE REGION BINDING CD3 AND CD137

CROSS-REFERENCE TO RELATED APPLICATIONS

This application is the National Stage of International Application No. PCT/JP2018/044493, filed on Dec. 4, 2018, which claims the benefit of Japanese Application No. 2017-233104, filed on Dec. 5, 2017.

TECHNICAL FIELD

The present invention relates to antigen-binding molecules binding to CD3 and CD137 (4-1BB) and methods of using the same.

BACKGROUND ART

Antibodies have received attention as drugs because of having high stability in plasma and producing few adverse reactions (Nat. Biotechnol. (2005) 23, 1073-1078 (NPL 1) and Eur J Pharm Biopharm. (2005) 59 (3), 389-396 (NPL 2)). The antibodies not only have an antigen-binding effect and an agonist or antagonist effect, but induce cytotoxic activity mediated by effector cells (also referred to as effector functions), such as ADCC (antibody dependent cytotoxicity), ADCP (antibody dependent cell phagocytosis), or CDC (complement dependent cytotoxicity). Particularly, antibodies of IgG1 subclass exhibit the effector functions for cancer cells. Therefore, a large number of antibody drugs have been developed in the field of oncology.

For exerting the ADCC, ADCP, or CDC of the antibodies, their Fc regions must bind to antibody receptors (Fc gamma R) present on effector cells (such as NK cells or macrophages) and various complement components. In humans, Fc gamma RIa, Fc gamma RIIa, Fc gamma RII, Fc gamma RIIIa, and Fc gamma RIIb isoforms have been reported as the protein family of Fc gamma R, and their respective allotypes have also been reported (Immunol. Lett. (2002) 82, 57-65 (NPL 3)). Of these isoforms, Fc gamma RIa, Fc gamma RIIa, and Fc gamma RIIIa have, in their intracellular domains, a domain called ITAM (immunoreceptor tyrosine-based activation motif), which transduces activation signals. By contrast, only Fc gamma RIIb has, in its intracellular domain, a domain called ITIM (immunoreceptor tyrosine-based inhibitory motif), which transduces inhibition signals. These isoforms of Fc gamma R are all known to transduce signals through cross-linking by immune complexes or the like (Nat. Rev. Immunol. (2008) 8, 34-47 (NPL 4)). In fact, when the antibodies exert effector functions against cancer cells, Fc gamma R molecules on effector cell membranes are clustered by the Fc regions of a plurality of antibodies bound onto cancer cell membranes and thereby transduce activation signals through the effector cells. As a result, a cell-killing effect is exerted. In this respect, the cross-linking of Fc gamma R is restricted to effector cells located near the cancer cells, showing that the activation of immunity is localized to the cancer cells (Ann. Rev. Immunol. (1988). 6. 251-81 (NPL 5)).

Naturally occurring immunoglobulins bind to antigens through their variable regions and bind to receptors such as Fc gamma R, FcRn, Fc alpha R, and Fc epsilon R or complements through their constant regions. Each molecule of FcRn (binding molecule that interacts with an IgG Fc region) binds to each heavy chain of an antibody in a one-to-one connection. Hence, two molecules of FcRn reportedly bind to one IgG-type antibody molecule. Unlike FcRn, etc., Fc gamma R interacts with an antibody hinge region and CH2 domains, and only one molecule of Fc gamma R binds to one IgG-type antibody molecule (J. Bio. Chem., (20001) 276, 16469-16477). For the binding between Fc gamma R and the Fc region of an antibody, some amino acid residues in the hinge region and the CH2 domains of the antibody and sugar chains added to Asn 297 (EU numbering) of the CH2 domains have been found to be important (Chem. Immunol. (1997), 65, 88-110 (NPL 6), Eur. J. Immunol. (1993) 23, 1098-1104 (NPL 7), and Immunol. (1995) 86, 319-324 (NPL 8)). Fc region variants having various Fc gamma R-binding properties have previously been studied by focusing on this binding site, to yield Fc region variants having higher binding activity against activating Fc gamma R (WO2000/042072 (PTL 1) and WO2006/019447 (PTL 2)). For example, Lazar et al. have successfully increased the binding activity of human IgG1 against human Fc gamma RIIIa (V158) to approximately 370 times by substituting Ser 239, Ala 330, and Ile 332 (EU numbering) of the human IgG1 by Asn, Leu, and Glu, respectively (Proc. Natl. Acad. Sci. U.S.A. (2006) 103, 4005-4010 (NPL 9) and WO2006/019447 (PTL 2)). This altered form has approximately 9 times the binding activity of a wild type in terms of the ratio of Fc gamma RIIIa to Fc gamma IIb (A/I ratio). Alternatively, Shinkawa et al. have successfully increased binding activity against Fc gamma RIIIa to approximately 100 times by deleting fucose of the sugar chains added to Asn 297 (EU numbering) (J. Biol. Chem. (2003) 278, 3466-3473 (NPL 10)). These methods can drastically improve the ADCC activity of human IgG1 compared with naturally occurring human IgG1.

A naturally occurring IgG-type antibody typically recognizes and binds to one epitope through its variable region (Fab) and can therefore bind to only one antigen. Meanwhile, many types of proteins are known to participate in cancer or inflammation, and these proteins may crosstalk with each other. For example, some inflammatory cytokines (TNF, IL1, and IL6) are known to participate in immunological disease (Nat. Biotech., (2011) 28, 502-10 (NPL 11)). Also, the activation of other receptors is known as one mechanism underlying the acquisition of drug resistance by cancer (Endocr Relat Cancer (2006) 13, 45-51 (NPL 12)). In such a case, the usual antibody, which recognizes one epitope, cannot inhibit a plurality of proteins.

Antibodies that bind to two or more types of antigens by one molecule (these antibodies are referred to as bispecific antibodies) have been studied as molecules inhibiting a plurality of targets. Binding activity against two different antigens (first antigen and second antigen) can be conferred by the modification of naturally occurring IgG-type antibodies (mAbs. (2012) March 1, 4 (2)). Therefore, such an antibody has not only the effect of neutralizing these two or more types of antigens by one molecule but the effect of enhancing antitumor activity through the cross-linking of cells having cytotoxic activity to cancer cells. A molecule with an antigen-binding site added to the N or C terminus of an antibody (DVD-Ig, TCB and scFv-IgG), a molecule having different sequences of two Fab regions of an antibody (common L-chain bispecific antibody and hybrid hybridoma), a molecule in which one Fab region recognizes two antigens (two-in-one IgG and DutaMab), and a molecule having a CH3 domain loop as another antigen-binding site (Fcab) have previously been reported as molecular forms of the bispecific antibody (Nat. Rev. (2010), 10, 301-316 (NPL 13) and Peds (2010), 23 (4), 289-297 (NPL 14)). Since any of these bispecific antibodies interact at their Fc regions with Fc gamma R, antibody effector functions are preserved therein.

Provided that all the antigens recognized by the bispecific antibody are antigens specifically expressed in cancer, the bispecific antibody binding to any of the antigens exhibits cytotoxic activity against cancer cells and can therefore be expected to have a more efficient anticancer effect than that of the conventional antibody drug that recognizes one antigen. However, in the case where any one of the antigens recognized by the bispecific antibody is expressed in a normal tissue or is a cell expressed on immunocytes, damage on the normal tissue or release of cytokines occurs due to cross-linking with Fc gamma R (J. Immunol. (1999) August 1, 163 (3), 1246-52 (NPL 15)). As a result, strong adverse reactions are induced.

For example, catumaxomab is known as a bispecific antibody that recognizes a protein expressed on T cells and a protein expressed on cancer cells (cancer antigen). Catumaxomab binds, at two Fabs, the cancer antigen (EpCAM) and a CD3 epsilon chain expressed on T cells, respectively. Catumaxomab induces T cell-mediated cytotoxic activity through binding to the cancer antigen and the CD3 epsilon at the same time and induces NK cell- or antigen-presenting cell (e.g., macrophage)-mediated cytotoxic activity through binding to the cancer antigen and Fc gamma R at the same time. By use of these two cytotoxic activities, catumaxomab exhibits a high therapeutic effect on malignant ascites by intraperitoneal administration and has thus been approved in Europe (Cancer Treat Rev. (2010) Oct. 36 (6), 458-67 (NPL 16)). In addition, the administration of catumaxomab reportedly yields cancer cell-reactive antibodies in some cases, demonstrating that acquired immunity is induced (Future Oncol. (2012) Jan. 8 (1), 73-85 (NPL 17)). From this result, such antibodies having both of T cell-mediated cytotoxic activity and the effect brought about by cells such as NK cells or macrophages via Fc gamma R (these antibodies are particularly referred to as trifunctional antibodies) have received attention because a strong antitumor effect and induction of acquired immunity can be expected.

The trifunctional antibodies, however, bind to CD3 epsilon and Fc gamma R at the same time even in the absence of a cancer antigen and therefore cross-link CD3 epsilon-expressing T cells to Fc gamma R-expressing cells even in a cancer cell-free environment to produce various cytokines in large amounts. Such cancer antigen-independent induction of production of various cytokines restricts the current administration of the trifunctional antibodies to an intraperitoneal route (Cancer Treat Rev. 2010 Oct. 36 (6), 458-67 (NPL 16)). The trifunctional antibodies are very difficult to administer systemically due to serious cytokine storm-like adverse reactions (Cancer Immunol Immunother. 2007 September; 56 (9): 1397-406 (NPL 18)).

The bispecific antibody of the conventional technique is capable of binding to both antigens, i.e., a first antigen cancer antigen (EpCAM) and a second antigen CD3 epsilon, at the same time with binding to Fc gamma R, and therefore, cannot circumvent, in view of its molecular structure, such adverse reactions caused by the binding to Fc gamma R and the second antigen CD3 epsilon at the same time.

In recent years, a modified antibody that causes cytotoxic activity mediated by T cells while circumventing adverse reactions has been provided by use of an Fc region having reduced binding activity against Fc gamma R (WO2012/073985).

Even such an antibody, however, fails to act on two immunoreceptors, i.e., CD3 epsilon and Fc gamma R, while binding to the cancer antigen, in view of its molecular structure.

An antibody that exerts both of cytotoxic activity mediated by T cells and cytotoxic activity mediated by cells other than the T cells in a cancer antigen-specific manner while circumventing adverse reactions has not yet been known.

T cells play important roles in tumor immunity, and are known to be activated by two signals: 1) binding of a T cell receptor (TCR) to an antigenic peptide presented by major histocompatibility complex (MHC) class I molecules and activation of TCR; and 2) binding of a costimulator on the surface of T cells to the ligands on antigen-presenting cells and activation of the costimulator. Furthermore, activation of molecules belonging to the tumor necrosis factor (TNF) superfamily and the TNF receptor superfamily, such as CD137(4-1BB) on the surface of T cells, has been described as important for T cell activation (Vinay, 2011, Cellular & Molecular Immunology, 8, 281-284 (NPL 19)).

CD137 agonist antibodies have already been demonstrated to show anti-tumor effects, and this has been shown experimentally to be mainly due to activation of CD8-positive T cells and NK cells (Houot, 2009, Blood, 114, 3431-8 (NPL 20)). It is also understood that T cells engineered to have chimeric antigen receptor molecules (CAR-T cells) which consist of a tumor antigen-binding domain as an extracellular domain and the CD3 and CD137 signal transducing domains as intracellular domains can enhance the persistence of the efficacy (Porter, N ENGL J MED, 2011, 365; 725-733 (NPL 21)). However, side effects of such CD137 agonist antibodies due to their non-specific hepatotoxicity have been a problem clinically and non-clinically, and development of pharmaceutical agents has not advanced (Dubrot, Cancer Immunol. Immunother., 2010, 28, 512-22 (NPL 22)). The main cause of the side effects has been suggested to involve binding of the antibody to the Fc gamma receptor via the antibody constant region (Schabowsky, Vaccine, 2009, 28, 512-22 (NPL 23)). Furthermore, it has been reported that for agonist antibodies targeting receptors that belong to the TNF receptor superfamily to exert an agonist activity in vivo, antibody cross-linking by Fc gamma receptor-expressing cells (Fc gamma RII-expressing cells) is necessary (Li, Proc Natl Acad Sci USA. 2013, 110(48), 19501-6 (NPL 24)). WO2015/156268 (PTL 3) describes that a bispecific antibody which has a binding domain with CD137 agonistic activity and a binding domain to a tumor specific antigen can exert CD137 agonistic activity and activate immune cells only in the presence of cells expressing the tumor specific antigen, by which hepatotoxic adverse events of CD137 agonist antibody can be avoided while retaining the anti-tumor activity of the antibody. WO2015/156268 further describes that the anti-tumor activity can be further enhanced and these adverse events can be avoided by using this bispecific antibody in combination with another bispecific antibody which has a binding domain with CD3 agonistic activity and a binding domain to a tumor specific antigen. A tri-specific antibody which has three binding domains to CD137, CD3 and a tumor specific antigen (EGFR) has also been reported (WO2014/116846 (PTL 4)). However, an antibody that exerts both cytotoxic activity mediated by T cells and activation activity of T cells and other immune cells via CD137 in a cancer antigen-specific manner while circumventing adverse reactions has not yet been known.

Techniques of obtaining binding domains to any antigens using libraries are well known (Clackson et al., Nature 352:624-628 (1991) (NPL 25); Marks et al., J. Mol. Biol. 222:581-597 (1991) (NPL 26)). For example, phage display, ribosome display, mRNA display, CIS display, E. coli display, cell display, and yeast display are known as techniques of obtaining binding domains using libraries (Nat Biotechnol. 1996 March; 14(3):309-14 (NPL 27); Nat Biotechnol. 2000 December; 18 (12): 1287-92 (NPL 28); Nucleic Acids Res. 2006; 34 (19): e127 (NPL 29); Proc Natl Acad Sci USA. 2004 Mar. 2; 101 (9): 2806-10 (NPL 30); Proc Natl Acad Sci USA. 2004 Jun. 22; 101 (25): 9193-8 (NPL 31); Protein Eng Des Sel. 2008 April; 21 (4): 247-55 (NPL 32); Proc Natl Acad Sci USA. 2000 Sep. 26; 97 (20): 10701-5 (NPL 33); MAbs. 2010 September-October; 2 (5): 508-18 (NPL 34); and Methods Mol Biol. 2012; 911: 183-98 (NPL 35)).

A binding domain which binds to two different antigens has also been acquired with a library method (Bostrom et al., Science 323:1610-4 (2009) (NPL 36)). There are some reported techniques to acquire such domains binding to two different antigens, such as a method of using different antigens alternately in different panning rounds, and a method of first obtaining a binding domain to the first antigen and then obtaining a binding domain to the second antigen from a library which is made by the randomization of the binding domain to the first antigen. However, those strategies require a gene amplification step after recovery of the first antigen-binding domains to amplify the recovered polynucleotides.

A phage display method in which selective pressure for one antigen is applied twice sequentially without an intervening step of amplifying nucleic acids, called double round selection, has been reported (Hawkins et al., J. Mol. Biol. 226:889-96 (1992) (NPL 37)). However, there is no known method to collect binding domains to two or more different antigens more efficiently by applying selective pressure for two or more different antigens twice or more times sequentially.

CITATION LIST

Patent Literature

PTL 1: WO2000/042072
PTL 2: WO2006/019447
PTL 3: WO2015/156268
PTL 4: WO2014/116846

Non Patent Literature

NPL 1: Nat. Biotechnol. (2005) 23, 1073-1078
NPL 2: Eur J Pharm Biopharm. (2005) 59 (3), 389-396
NPL 3: Immunol. Lett. (2002) 82, 57-65
NPL 4: Nat. Rev. Immunol. (2008) 8, 34-47
NPL 5: Ann. Rev. Immunol. (1988). 6. 251-81
NPL 6: Chem. Immunol. (1997), 65, 88-110
NPL 7: Eur. J. Immunol. (1993) 23, 1098-1104
NPL 8: Immunol. (1995) 86, 319-324
NPL 9: Proc. Natl. Acad. Sci. U.S.A. (2006) 103, 4005-4010
NPL 10: J. Biol. Chem. (2003) 278, 3466-3473
NPL 11: Nat. Biotech., (2011) 28, 502-10
NPL 12: Endocr Relat Cancer (2006) 13, 45-51
NPL 13: Nat. Rev. (2010), 10, 301-316
NPL 14: Peds (2010), 23 (4), 289-297
NPL 15: J. Immunol. (1999) August 1, 163 (3), 1246-52
NPL 16: Cancer Treat Rev. (2010) October 36 (6), 458-67
NPL 17: Future Oncol. (2012) January 8 (1), 73-85
NPL 18: Cancer Immunol Immunother. 2007 September; 56 (9): 1397-406
NPL 19: Vinay, 2011, Cellular & Molecular Immunology, 8, 281-284
NPL 20: Houot, 2009, Blood, 114, 3431-8
NPL 21: Porter, N ENGL J MED, 2011, 365; 725-733
NPL 22: Dubrot, Cancer Immunol. Immunother., 2010, 28, 512-22
NPL 23: Schabowsky, Vaccine, 2009, 28, 512-22
NPL 24: Li, Proc Natl Acad Sci USA. 2013, 110(48), 19501-6
NPL 25: Clackson et al., Nature 352:624-628 (1991)
NPL 26: Marks et al., J. Mol. Biol. 222:581-597 (1991)
NPL 27: Nat Biotechnol. 1996 March; 14(3):309-14
NPL 28: Nat Biotechnol. 2000 December; 18 (12): 1287-92
NPL 29: Nucleic Acids Res. 2006; 34 (19): e127
NPL 30: Proc Natl Acad Sci USA. 2004 Mar. 2; 101 (9): 2806-10
NPL 31: Proc Natl Acad Sci USA. 2004 Jun. 22; 101 (25): 9193-8
NPL 32: Protein Eng Des Sel. 2008 April; 21 (4): 247-55
NPL 33: Proc Natl Acad Sci USA. 2000 Sep. 26; 97 (20): 10701-5
NPL 34: MAbs. 2010 September-October; 2 (5): 508-18
NPL 35: Methods Mol Biol. 2012; 911: 183-98
NPL 36: Bostrom et al., Science 323:1610-4 (2009)
NPL 37: Hawkins et al., J. Mol. Biol. 226:889-96 (1992)

SUMMARY OF INVENTION

Technical Problem

Tri-specific antibodies comprising a tumor-specific antigen (EGFR)-binding domain, a CD137-binding domain, and a CD3-binding domain were already reported (WO2014116846). However, since antibodies with such a molecular format can bind to three different antigens at the same time, the present inventors speculated that those tri-specific antibodies could result in cross-linking between CD3 epsilon-expressing T cells and CD137-expressing cells (e.g. T cells, B cells, NK cells, DCs etc.) by binding to CD3 and CD137 at the same time.

Furthermore, it was already reported that bispecific antibodies against CD8 and CD3 epsilon induced mutual cytotoxicity among CD8 positive T cells because the antibodies cross-linked them (Wong, Clin. Immunol. Immunopathol. 1991, 58(2), 236-250). Therefore, the present inventors speculated that bispecific antibodies against a molecule expressed on T cells and CD3 epsilon would also induce mutual cytotoxicity among T cells because they would cross-link cells expressing the molecule and CD3 epsilon.

There are some previously reported techniques to acquire antigen domains binding to two different antigens, such as a method of using different antigens alternately in different panning rounds, and a method of first acquiring a binding domain to the first antigen and then acquiring a binding domain to the second antigen from a library which is made by the randomization of the binding domain to the first antigen. However, those strategies require a step of recovering binding domains to the first antigen and then amplifying the recovered nucleotides which encode the binding domains to the first antigen, and further recovering binding domains which can also bind to the second antigen and amplifying their nucleic acids. The present inventors considered that as a result of this step, each panning round step would end up concentrating binding domains which show stronger binding to one of the different antigens used therein than the other antigens more specifically than binding domains which show binding to each of the different antigens, and would therefore prevent desired molecules from being recovered efficiently.

It is understood that in some methodologies like cell display, yeast display or bacteria display, which can use FACS (fluorescence activated cell sorting) for selection, it is possible to apply two or more selective pressures for two or more different antigens at the same time. However, the present inventors considers that it has been difficult to apply two or more selective pressures for two or more different antigens at the same time in methodologies like phage display, ribosome display, mRNA display or CIS display, which cannot use FACS.

Solution to Problem

The present invention provides antigen-binding domains binding to CD3 and CD137 and methods of using the same. The invention also provides methods to obtain antigen binding domains which bind to two or more different antigens more efficiently.

In some embodiments, an antigen-binding molecule of the present invention is an antigen-binding molecule comprising an antibody variable region that is capable of binding to CD3 and CD137 (4-1BB) but does not bind to CD3 and CD137 at the same time, and a variable region binding to a third antigen different from CD3 and CD137.

In some embodiments, an antigen-binding molecule of the present invention is an antigen-binding molecule comprising an antibody variable region that is capable of binding to a T cell receptor and CD137 (4-1BB) but does not bind to the T cell receptor and CD137 at the same time; and a variable region binding to a third antigen different from the T cell receptor and CD137.

In some embodiments, an antigen-binding molecule of the present invention is an antigen-binding molecule comprising an antibody variable region that is capable of binding to CD3 and CD137 but does not bind to CD3 and CD137 at the same time, and a variable region binding to a molecule specifically expressed in a cancer tissue.

In some embodiments, an antigen-binding domain of the present invention is a variable region that is capable of binding to CD3 and CD137 but does not bind to CD3 and CD137 at the same time. In some embodiments, an antibody variable region of the present invention is a variable region that is capable of binding to CD3 and CD137 but does not bind to CD3 and CD137 at the same time.

In some embodiments, the present invention also provides an antigen-binding domain that does not bind to CD3 and CD137 at the same time, which is a variable region that does not bind to CD3 and CD137 each expressed on a different cell, at the same time.

In some embodiments, an antigen-binding molecule of the present invention comprises an antibody Fc region. In further embodiments, an antigen-binding molecule of the present invention comprises an antibody Fc region having reduced binding activity against Fc gamma R as compared with the Fc region of a naturally occurring human IgG1 antibody.

In some embodiments, an antigen-binding molecule of the present invention has at least one characteristic selected from the group consisting of (1) to (4) below:
  (1) the variable region binds to an extracellular domain of CD3 epsilon comprising the amino acid sequence of SEQ ID NO: 91,
  (2) the antigen-binding molecule has an agonistic activity against CD137,
  (3) the antigen-binding molecule induces CD3 activation of a T cell against a cell expressing the molecule of the third antigen, but does not induce activation of a T cell against a cell expressing CD137, and
  (4) the antigen-binding molecule does not induce a cytokine release from PBMC in the absence of a cell expressing the molecule of the third antigen.

In some embodiments, an antigen-binding molecule of the present invention has at least one characteristic selected from the group consisting of (1) to (2) below:
  (1) the antigen-binding molecule does not compete for binding to CD137 with CD137 ligand, and
  (2) the antigen-binding molecule induces cytotoxicity of a T cell against a cell expressing the molecule of the third antigen, but does not induce cytotoxicity of a T cell against a cell expressing CD137.

In some embodiments, an antigen-binding molecule of the present invention competes for binding to CD137 with an antibody selected from the group consisting of:
  (a) an antibody comprising a VH sequence having the amino acid sequence of SEQ ID NO: 30 and a VL sequence having the amino acid sequence of SEQ ID NO: 51,
  (b) an antibody comprising a VH sequence having the amino acid sequence of SEQ ID NO: 46 and a VL sequence having the amino acid sequence of SEQ ID NO: 53,
  (c) an antibody comprising a VH sequence having the amino acid sequence of SEQ ID NO: 40 and a VL sequence having the amino acid sequence of SEQ ID NO: 56,
  (d) an antibody comprising a VH sequence having the amino acid sequence of SEQ ID NO: 30 and a VL sequence having the amino acid sequence of SEQ ID NO: 58, and
  (e) an antibody comprising a VH sequence having the amino acid sequence of SEQ ID NO: 40 and a VL sequence having the amino acid sequence of SEQ ID NO: 61.

In some embodiments, an antigen-binding molecule of the present invention comprises an amino acid sequence resulting from introducing alteration of one or more amino acids into a template sequence consisting of a heavy chain variable domain sequence described in SEQ ID NO: 92 and/or a light chain variable domain sequence described in SEQ ID NO: 93, wherein the one or more amino acids comprises at least one amino acid selected from the following positions:
  H chain: 31, 52b, 52c, 53, 54, 56, 57, 61, 98, 99, 100, 100a, 100b, 100c, 100d, 100e, 100f, and 100g (Kabat numbering); and
  L chain: 24, 25, 26, 27, 27a, 27b, 27c, 27e, 30, 31, 33, 34, 51, 52, 53, 54, 55, 56, 74, 77, 89, 90, 92, 93, 94, and 96 (Kabat numbering),
  wherein the HVR-H3 of the altered heavy chain variable domain sequence comprises at least one amino acid selected from:
  Ala, Pro, Ser, Arg, His or Thr at amino acid position 98;
  Ala, Ser, Thr, Gln, His or Leu at amino acid position 99;
  Tyr, Ala, Ser, Pro or Phe at amino acid position 100;
  Tyr, Val, Ser, Leu or Gly at amino acid position 100a;
  Asp, Ser, Thr, Leu, Gly or Tyr at amino acid position 100b;
  Val, Leu, Phe, Gly, His or Ala at amino acid position 100c;
  Leu, Phe, Ile or Tyr at amino acid position 100d;
  Gly, Pro, Tyr, Gln, Ser or Phe at amino acid position 100e;

Tyr, Ala, Gly, Ser or Lys at amino acid position 100f;
Gly, Tyr, Phe or Val at amino acid position 100g (Kabat numbering).

In some embodiments, an antigen-binding molecule of the present invention comprises (a) a VH sequence having at least 95% sequence identity to the amino acid sequence of SEQ ID NO: 41, 30, 46 or 40; (b) a VL sequence having at least 95% sequence identity to the amino acid sequence of SEQ ID NO: 51, 52, 53, 54, 55, 56 or 57; or (c) the VH sequence of (a) and the VL sequence of (b).

In some embodiments, an antigen-binding molecule of the present invention is a monoclonal antibody. In some embodiments, an antigen-binding molecule of the present invention is a human, humanized, or chimeric antibody. In further embodiments, an antigen-binding molecule of the present invention is a full length IgG1, IgG2, IgG3 or IgG4 antibody.

The invention also provides isolated nucleic acids encoding an antigen-binding molecule of the present invention. The invention also provides host cells comprising a nucleic acid of the present invention. The invention also provides a method of producing an antibody comprising culturing a host cell of the present invention so that the antibody is produced.

The invention also provides a pharmaceutical formulation comprising the antigen-binding molecule of the present invention and a pharmaceutically acceptable carrier.

Antigen-binding molecules of the present invention may be for use as a medicament. Antigen-binding molecules of the present invention may be for use in treating various types of cancer.

Antigen-binding molecules of the present invention may be used in the manufacture of a medicament. In some embodiments, the medicament is for treatment of various types of cancer.

The invention also provides a method of treating an individual having various types of cancer. In some embodiments, the method comprises administering to the individual an effective amount of an antigen-binding molecule of the present invention.

The present inventors have successfully prepared an antigen-binding molecule comprising: an antibody variable region that has binding activity against two different antigens (CD3 and CD137) but does not bind to these antigens at the same time, and a variable region binding to an antigen (third antigen) different from these antigens, and have found that it leads to an enhanced activity induced by this antigen-binding molecule through the use of its binding activity against the three different antigens. In addition, the present inventors have successfully prepared an antigen-binding molecule capable of circumventing the cross-linking between different cells resulting from the binding of a conventional multispecific antigen-binding molecule to antigens expressed on the different cells, which is considered to be responsible for adverse reactions when the multispecific antigen-binding molecule is used as a drug.

The present inventors have also successfully developed methods to obtain antigen binding domains which bind to two or more different antigens more efficiently.

In some embodiments, a method for screening an antigen-binding domain which binds to at least two or more different antigens of interest of the present invention comprises:
(a) providing a library comprising a plurality of antigen-binding domains,
(b) contacting the library provided in step (a) with the first antigen of interest and collecting antigen-binding domains bound to the first antigen,
(c) contacting the antigen-binding domain collected in step (b) with the second antigen of interest and collecting antigen-binding domains bound to the second antigen, and
(d) amplifying genes which encode the antigen binding domains collected in step (c) and identifying a candidate antigen-binding domain,
wherein the method does not comprise, between step (b) and step (c), amplifying nucleic acids that encode the antigen-binding domain collected in step (b).

In some embodiments, the antigen-binding domains of the present invention are Fab, scFv, Fab'2, VHH, VH, or VL.

In some embodiments, the antigen-binding domains of the present invention are fusion polypeptides formed by fusing antigen-binding domains with scaffolds to cross-link the antigen-binding domains with the nucleic acids that encode the antigen-binding domains.

In some embodiments, the scaffolds of the present invention are bacteriophages. In some embodiments, the scaffolds of the present invention are ribosomes, RepA proteins or DNA puromycin linkers.

In some embodiments, elution is performed in steps (b) and (c) above using an eluting solution that is an acid solution, a base solution, DTT, or IdeS.

In some embodiments, the eluting solution used in steps (b) and (c) above of the present invention is EDTA or IdeS.

In some embodiments, a method for screening an antigen-binding domain which binds to at least two or more different antigens of interest of the present invention comprises:
(a) providing a library comprising a plurality of antigen-binding domains,
(b) contacting the library provided in step (a) with the first antigen of interest and collecting antigen-binding domains bound to the first antigen,
(b)' translating nucleic acids that encode the antigen-binding domains collected in step (b),
(c) contacting the antigen-binding domains collected in step (b) with the second antigen of interest and collecting antigen-binding domains bound to the second antigen, and
(d) amplifying genes which encode the antigen binding domains collected in step (c) and identifying a candidate antigen-binding domain,
wherein the method does not comprise amplifying nucleic acids that encode the antigen-binding domains collected in step (b) between step (b) and step (c).

In some embodiments, a method for producing an antigen-binding domain which binds to at least two or more different antigens of interest of the present invention comprises:
(a) providing a library comprising a plurality of antigen-binding domains,
(b) contacting the library provided in step (a) with the first antigen of interest and collecting antigen-binding domains bound to the first antigen,
(c) contacting the antigen-binding domains collected in step (b) with the second antigen of interest and collecting antigen-binding domains bound to the second antigen, and
(d) amplifying genes which encode the antigen binding domains collected in step (c) and identifying a candidate antigen-binding domain,
(e) linking the polynucleotide that encodes the candidate antigen-binding domain selected in step (d) with a polynucleotide that encodes a polypeptide comprising an Fc region, (f) culturing a cell introduced with a vector in which the polynucleotide obtained in step (d) above is operably linked, and (g) collecting the antigen-binding molecule from the culture solution of the cell cultured in step (f) above, wherein the method does not comprise amplifying nucleic acids that encode the antigen-binding domains collected in step (b) between step (b) and step (c).

In some embodiments, the library provided in step (a) of the present invention is a design library.

In some embodiments, an antigen-binding molecule of the present invention is an antibody that prepared by the method described above.

More specifically, the present invention relates to the following:

[1] An antigen-binding molecule comprising:
an antibody variable region that is capable of binding to CD3 and CD137, but does not bind to CD3 and CD137 at the same time; and a variable region binding to a third antigen different from CD3 and CD137.

[2] The antigen-binding molecule of [1], wherein the third antigen is a molecule specifically expressed in a cancer tissue.

[3] The antigen-binding molecule of [1] or [2], wherein the variable region that does not bind to CD3 and CD137 at the same time is a variable region that does not bind to CD3 and CD137 each expressed on a different cell, at the same time.

[4] The antigen-binding molecule of any one of [1] to [3], further comprising an antibody Fc region.

[5] The antigen-binding molecule of [4], wherein the Fc region is an Fc region having reduced binding activity against Fc gamma R as compared with the Fc region of a naturally occurring human IgG1 antibody.

[6] The antigen-binding molecule of any one of [1] to [5], wherein the antigen-binding molecule has at least one characteristic selected from the group consisting of (1) to (4) below:

(1) the variable region binds to an extracellular domain of CD3 epsilon comprising the amino acid sequence of SEQ ID NO: 91, (2) the antigen-binding molecule has an agonistic activity against CD137, (3) the antigen-binding molecule induces CD3 activation of a T cell against a cell expressing the molecule of the third antigen, but does not induce CD3 activation of a T cell against a cell expressing CD137, and (4) the antigen-binding molecule does not induce a cytokine release from PBMC in the absence of a cell expressing the molecule of the third antigen.

[7] The antigen-binding molecule of any one of [1] to [6], which competes for binding to CD137 with an antibody selected from the group consisting of:

(a) an antibody comprising a VH sequence having the amino acid sequence of SEQ ID NO: 30 and a VL sequence having the amino acid sequence of SEQ ID NO: 51, (b) an antibody comprising a VH sequence having the amino acid sequence of SEQ ID NO: 46 and a VL sequence having the amino acid sequence of SEQ ID NO: 53, (c) an antibody comprising a VH sequence having the amino acid sequence of SEQ ID NO: 40 and a VL sequence having the amino acid sequence of SEQ ID NO: 56, (d) an antibody comprising a VH sequence having the amino acid sequence of SEQ ID NO: 30 and a VL sequence having the amino acid sequence of SEQ ID NO: 58, and (e) an antibody comprising a VH sequence having the amino acid sequence of SEQ ID NO: 40 and a VL sequence having the amino acid sequence of SEQ ID NO: 61.

[8] The antigen-binding molecule of any one of [1] to [7], comprising an amino acid sequence resulting from introducing alteration of one or more amino acids into a template sequence consisting of a heavy chain variable domain sequence described in SEQ ID NO: 92 and/or a light chain variable domain sequence described in SEQ ID NO: 93, wherein the one or more amino acids comprise at least one amino acid selected from the following positions:

H chain: 31, 52b, 52c, 53, 54, 56, 57, 61, 98, 99, 100, 100a, 100b, 100c, 100d, 100e, 100f, and 100g (Kabat numbering); and L chain: 24, 25, 26, 27, 27a, 27b, 27c, 27e, 30, 31, 33, 34, 51, 52, 53, 54, 55, 56, 74, 77, 89, 90, 92, 93, 94, and 96 (Kabat numbering), wherein the HVR-H3 of the altered heavy chain variable domain sequence comprises at least one amino acid selected from:

Ala, Pro, Ser, Arg, His or Thr at amino acid position 98;
Ala, Ser, Thr, Gln, His or Leu at amino acid position 99;
Tyr, Ala, Ser, Pro or Phe at amino acid position 100;
Tyr, Val, Ser, Leu or Gly at amino acid position 100a;
Asp, Ser, Thr, Leu, Gly or Tyr at amino acid position 100b;
Val, Leu, Phe, Gly, His or Ala at amino acid position 100c;
Leu, Phe, Ile or Tyr at amino acid position 100d;
Gly, Pro, Tyr, Gln, Ser or Phe at amino acid position 100e;
Tyr, Ala, Gly, Ser or Lys at amino acid position 100f;
Gly, Tyr, Phe or Val at amino acid position 100g (Kabat numbering).

[9] The antigen-binding molecule of any one of [1] to [8], comprising (a) a VH sequence having at least 95% sequence identity to the amino acid sequence of SEQ ID NO: 41, 30, 46 or 40; (b) a VL sequence having at least 95% sequence identity to the amino acid sequence of SEQ ID NO: 51, 52, 53, 54, 55, 56 or 57; or (c) the VH sequence of (a) and the VL sequence of (b).

[10] A pharmaceutical composition comprising the antigen-binding molecule according to any of [1] to [9] and a pharmaceutically acceptable carrier.

[11] A method of screening for an antigen-binding domain which binds to at least two or more different antigens of interest, comprising:

(a) providing a library comprising a plurality of antigen-binding domains, (b) contacting the library provided in step (a) with a first antigen of interest and collecting antigen-binding domains bound to the first antigen, (c) contacting the antigen-binding domains collected in step (b) with a second antigen of interest and collecting antigen-binding domains bound to the second antigen, and (d) amplifying genes which encode the antigen binding domains collected in step (c) and identifying a candidate antigen-binding domain, wherein the method does not comprise amplifying nucleic acids that encode the antigen-binding domains collected in step (b) between step (b) and step (c).

[12] The method of [11], wherein the antigen-binding domains are fusion polypeptides formed by fusing antigen-binding domains with scaffolds to cross-link the antigen-binding domains with the nucleic acids that encode the antigen-binding domains.

[13] The method of [12], wherein the scaffolds are bacteriophages.

[14] The method of [12], further comprising, between steps (b) and (c), a step comprising translating nucleic acids that encode the antigen-binding domains collected in step (b)

[15] The method of [12] or [14], wherein the scaffolds are ribosomes, RepA proteins or DNA puromycin linkers.

BRIEF DESCRIPTION OF DRAWINGS

FIG. 1 is a conceptual diagram of an antibody that binds to CD3 and CD137, but does not bind to these antigens at the same time.

FIG. 2 is a conceptual diagram of an antibody that does not cause cross-linking because the antibody does not bind to CD3 and CD137 at the same time. On the contrary, a tri-functional antibody to CD3, CD137 and third antigen causes cross-linking of a T cell with a CD137 positive cell.

FIG. 3 is a conceptual diagram of an antibody that binds to CD3 and CD137, but does not link two cells at the same time.

FIG. 4 is a conceptual diagram of an antibody that cross-links a third antigen positive cell to a T cell expressing CD3 and CD137.

FIG. 5 is a conceptual diagram of an antibody that cross-links a third antigen positive cell to a cell expressing CD137.

FIG. 6 is a scheme diagram of the design and construction flow of dual scFv VH ribosome display library.

FIG. 7-1 FIG. 7 is a set of graphs showing the results of ELISA of clones obtained with ribosome display to CD3 and CD137. Y axis means the specificity to CD137-Fc and X axis means the specificity to CD3 of each clone. Black colored clones were identified as positive scFv which show binding to both CD137 and CD3.

FIG. 7-2 Continuation of FIG. 7-1.

FIG. 8 is a graph showing the result of ECL analysis of IgGs obtained with ribosome display to CD3 and CD137. Y axis means the response to both CD137, CD3 and plate itself.

FIG. 9-1 FIG. 9 is a set of graphs showing the results of ELISA of clones obtained with ribosome display to CD3 and CD137. Y axis means the specificity to CD137-Fc and X axis means the specificity to CD3 of each clone. Campaign3 means ribosome display panning with double round selection.

FIG. 9-2 Continuation of FIG. 9-1.

FIG. 9-3 Continuation of FIG. 9-2.

FIG. 10 is a graph showing the result of ELISA of clones obtained with ribosome display to CD3 and CD137. Y axis means the specificity to CD137-Fc and X axis means the specificity to CD3 of each clone.

FIG. 11 is a graph showing the result of ELISA of IgGs obtained with ribosome display to CD3 and CD137. Y axis means the specificity to CD137-Fc and X axis means the specificity to CD3 of each clone.

FIG. 12 is a scheme diagram of the design of dual scFv VL ribosome display library and dual Fab VL ribosome display library.

FIG. 13 is a graph showing the result of ELISA of IgGs obtained with ribosome display affinity maturation to CD3 and CD137. Y axis means the specificity to CD137-Fc and X axis means the specificity to CD3 of each clone.

FIG. 14 is a graph showing the result of competitive ELISA of IgGs obtained with ribosome display affinity maturation to CD3 and CD137. Y axis means the response of ELISA to biotin-human CD137-Fc or biotin-human Fc. Excess amount of human CD3 or human Fc were used as competitor.

FIG. 15 shows a design of C3NP1-27, CD3 epsilon peptide antigen which is biotin-labeled through disulfide-bond linker.

FIG. 16 is a graph showing the result of phage ELISA of clones obtained with phage display to CD3 and CD137. Y axis means the specificity to CD137-Fc and X axis means the specificity to CD3 of each clone.

FIG. 17 is a graph showing the result of phage ELISA of clones obtained with phage display to CD3 and CD137. Y axis means the specificity to CD137-Fc in beads ELISA and X axis means the specificity to CD3 in plate ELISA as same as FIG. 16 of each clone.

FIG. 18 shows a comparison data of human CD137 amino acids sequence with cynomolgus monkey CD137 amino acids sequence.

FIG. 19 is a graph showing the result of ELISA of IgGs obtained with phage display to CD3 and CD137. Y axis means the specificity to cyno CD137-Fc and X axis means the specificity to human CD137 of each clone.

FIG. 20 is a graph showing the result of ELISA of IgGs obtained with phage display to CD3 and CD137. Y axis means the specificity to CD3e.

FIG. 21 is a graph showing the result of competitive ELISA of IgGs obtained with phage display to CD3 and CD137. Y axis means the response of ELISA to biotin-human CD137-Fc or biotin-human Fc. Excess amount of human CD3 or human Fc were used as competitor.

FIG. 22A is a graph showing the result of phage ELISA of phage display panning output pools to CD3 and CD137. Y axis means the specificity to human CD137. X axis means the panning output pools, Primary is a pool before phage display panning, and R1 to R6 means panning output pool after phage display panning Round1 to Round6, respectively.

FIG. 22B is a graph showing the result of phage ELISA of phage display panning output pools to CD3 and CD137. Y axis means the specificity to cyno CD137. X axis means the panning output pools, Primary is a pool before phage display panning, and R1 to R6 means panning output pool after phage display panning Round1 to Round6, respectively.

FIG. 22C is a graph showing the result of phage ELISA of phage display panning output pools to CD3 and CD137. Y axis means the specificity to CD3. X axis means the panning output pools, Primary is a pool before phage display panning, and R1 to R6 means panning output pool after phage display panning Round1 to Round6, respectively.

FIG. 23-1 FIG. 23 is a set of graphs showing the result of ELISA of IgGs obtained with phage display to CD3 and CD137. Y axis means the specificity to human CD137-Fc and X axis means the specificity to human CD137 or CD3 of each clone.

FIG. 23-2 Continuation of FIG. 23-1.

FIG. 23-3 Continuation of FIG. 23-2.

FIG. 24 is a set of graphs showing the result of ELISA of IgGs obtained with phage display to CD3 and CD137. Y axis means the specificity to human CD137-Fc and X axis means the specificity to human CD137 or CD3 of each clone.

FIG. 25 is a graph showing the result of competitive ELISA of IgGs obtained with phage display to CD3 and CD137. Y axis means the response of ELISA to biotin-human CD137-Fc or biotin-human Fc. Excess amount of human CD3 were used as competitor.

FIG. 26 is a graph showing the result of ELISA of IgGs obtained with phage display to CD3 and CD137 to identify the epitope domain of each clones. Y axis means the response of ELISA to each domain of human CD137.

FIG. 27 is a set of graphs showing the result of ELISA of IgGs obtained with phage display affinity maturation to CD3 and CD137. Y axis means the specificity to human CD137-Fc and X axis means the specificity to human CD137 or CD3 of each clone.

FIG. 28-1 FIG. 28 is a set of graphs showing the result of competitive ELISA of IgGs obtained with phage display to CD3 and CD137. Y axis means the response of ELISA to biotin-human CD137-Fc or biotin-human Fc. An excess amount of human CD3 was used as a competitor.

FIG. 28-2 Continuation of FIG. 28-1.

FIG. 28-3 Continuation of FIG. 28-2.

FIG. 28-4 Continuation of FIG. 28-3.

FIG. 28-5 Continuation of FIG. 28-4.

FIG. 29A shows the mechanism of IL-6 secretion from the activated B cell via anti-human GPC3/Dual-Fab antibodies.

FIG. 29B presents a graph showing the results of assessing the CD137-mediated agonist activity of various anti-human GPC3/Dual-Fab antibodies by the level of production of IL-6 which is secreted from the activated B cells. Ctrl indicates the negative control human IgG1 antibody.

FIG. 30A shows the mechanism of Luciferase expression in the activated Jurkat T cell via anti-human GPC3/Dual-Fab antibodies.

FIG. 30B presents graphs showing the results of assessing the CD3 mediated agonist activity of various anti-human GPC3/Dual-Fab antibodies by the level of production of Luciferase which is expressed in the activated Jurkat T cells. Ctrl indicates the negative control human IgG1 antibody.

FIG. 31 is a set of graphs showing the results of assessing the cytokine (IL-2, IFN-gamma and TNF-alpha) release from human PBMC derived T cells in the presence of each immobilized antibodies. Y axis means the concentration of secreted each cytokines and X-axis means the concentration of immobilized antibodies. Control anti-CD137 antibody (B), control anti-CD3 antibody (CE115), negative control antibody (Ctrl) and one of the dual antibody (L183L072) were used for assay.

FIG. 32 is a set of graphs showing the results of assessing the T-cell dependent cellular cytotoxicity (TDCC) against GPC3 positive target cells (SK-pca60 and SK-pca13a) with each bi-specific antibodies. Y axis means the ratio of Cell Growth Inhibition (CGI) and X-axis means the concentration of each bi-specific antibodies. Anti-GPC3/Dual Bi-specific antibody (GC33/H183L072), Negative control/Dual Bi-specific antibody (Ctrl/H183L072), Anti-GPC3/Anti-CD137 Bi-specific antibody (GC33/B) and Negative control/Anti-CD137 Bi-specific antibody (Ctrl/B) were used for this assay. 5-fold amount of effector (E) cells were added on tumor (T) cells (ET5).

FIG. 33 shows the design and construction procedure of trispecific antibodies (mAb AB).

FIG. 34 shows the naming rule of prepared trispecific antibodies.

FIG. 35 is a set of graphs showing the results of Biacore analysis of simultaneous binding of GPC3/CD137×CD3 trispecific antibody and anti-GPC3/dual-Fab antibody. Y-axis means the binding response to each antigen. At first human CD3 (hCD3) was used as analyte, and then also hCD3 (shown as broken line) or mixture of human CD137 (hCD137) and hCD3 (shown as solid line) were used as analyte.

FIG. 36 is a set of sensorgrams showing the results of FACS analysis to CD137 positive CHO cells or Jurkat cells of each antibodies. FIGS. 35(a) and (c) are the results of binding to human CD137 positive CHO cells, and FIGS. 35(b) and (d) are the results to parental CHO cells. In FIGS. 35(a) and (b), solid line shows the result of anti-GPC3/dual antibody (GC33/H183L072) and filled shows the result of control antibody (Ctrl). In FIGS. 35(c) and (d), solid line, filled with dark gray and filled with light grey shows the results of GPC3/CD137×Ctrl trispecific antibody, GPC3/CD137×CD3 trispecific antibody and Ctrl/Ctrl×CD3 trispecific antibody, respectively.

FIGS. 35(e) and (f) are the results of binding to Jurkat CD3 positive cells. In FIG. 35(e), solid line and filled shows the result of anti-GPC3/dual antibody (GC33/H183L072) and control antibody (Ctrl), respectively. In FIG. 35(f), solid line, filled with dark gray and filled with light grey shows the results of GPC3/Ctrl×CD3 trispecific antibody, GPC3/CD137×CD3 trispecific antibody and Ctrl/CD137×Ctrl trispecific antibody, respectively.

FIG. 37 presents graphs showing the results of assessing the CD3 mediated agonist activity of various a antibodies to GPC3 positive target cell SK-pca60 by the level of production of Luciferase which is expressed in the activated Jurkat T cells. Six kinds of tri-specific antibodies, anti-GPC3/Dual-Fab antibody (GPC3/H183L072) and control/Dual-Fab antibody (Ctrl/H183L072) were used for this assay. X-axis means the concentration used of each antibodies.

FIG. 38 presents graphs showing the results of assessing the CD3 mediated agonist activity of various a antibodies to human CD137 positive CHO cells and parental CHO cells by the level of production of Luciferase which is expressed in the activated Jurkat T cells. Six kinds of tri-specific antibodies, anti-GPC3/Dual-Fab antibody (GPC3/H183L072) and control/Dual-Fab antibody (Ctrl/H183L072) were used for this assay. X-axis means the concentration used of each antibodies.

FIG. 39 is a set of graphs showing the results of assessing the cytokine (IL-2, IFN-gamma and TNF-alpha) release from human PBMCs in the presence of each soluble antibodies. Y axis means the concentration of secreted each cytokines and X-axis means the concentration of antibodies used. Ctrl/CD137×CD3 trispecific antibody and control/Dual-Fab antibody (Ctrl/H183L072) were used for this assay FIG. 40 is a graph showing results of cell-ELISA of CE115 for CD3e.

FIG. 41 is a diagram showing the molecular form of EGFR_ERY22_CE115.

FIG. 42 is a graph showing results of TDCC (SK-pca13a) of EGFR_ERY22_CE115.

FIG. 43 is an exemplary sensorgram of an antibody having a ratio of the amounts bound of less than 0.8. The vertical axis depicts an RU value (response). The horizontal axis depicts time.

DESCRIPTION OF EMBODIMENTS

In one aspect, an antigen-binding molecule of the present invention is an antigen-binding molecule comprising an antibody variable region that is capable of binding to CD3 and CD137 (4-1BB) but does not bind to CD3 and CD137 at the same time, and a variable region binding to a third antigen different from CD3 and CD137.

In one aspect, an antigen-binding molecule of the present invention is an antigen-binding molecule comprising an antibody variable region that is capable of binding to a T cell receptor and CD137 (4-1BB) but does not bind to the T cell receptor and CD137 at the same time, and a variable region binding to a third antigen different from the T cell receptor and CD137.

In one aspect, an antigen-binding molecule of the present invention is an antigen-binding molecule comprising an antibody variable region that is capable of binding to CD3 and CD137 but does not bind to CD3 and CD137 at the same time, and a variable region binding to a molecule specifically expressed in a cancer tissue.

In one aspect, an antigen-binding domain of the present invention is a variable region that is capable of binding to CD3 and CD137 but does not bind to CD3 and CD137 at the same time. In one aspect, an antibody variable region of the present invention is a variable region that is capable of binding to CD3 and CD137 but does not bind to CD3 and CD137 at the same time.

In some embodiments, the antigen binding molecule of the present invention can activate T cells by its agonistic activity on CD3, and it can induce cytotoxicity of T cells against target cells, and strengthen T-cell activation, survival, and differentiation into memory T cells by its co-stimulatory agonistic activity on CD137 and CD3. Meanwhile, the antigen binding molecule of the present invention can avoid the adverse events caused by cross-linking of CD137 and CD3 because it does not bind to CD3 and CD137 at the same time.

In some embodiments, the antigen binding molecule of the present invention can also activate immune cells expressing CD137 and strengthen the immune response to target cells by the agonistic activity on CD137.

In the present invention, the "antibody variable region" usually means a region comprising a domain constituted by four framework regions (FRs) and three complementarity-determining regions (CDRs) flanked thereby, and also includes a partial sequence thereof as long as the partial sequence has the activity of binding to a portion or the whole of an antigen. Particularly, a region comprising an antibody light chain variable domain (VL) and an antibody heavy chain variable domain (VH) is preferred. The antibody variable region of the present invention may have an arbitrary sequence and may be a variable region derived from any antibody such as a mouse antibody, a rat antibody, a rabbit antibody, a goat antibody, a camel antibody, and a humanized antibody obtained by the humanization of any of these nonhuman antibodies, and a human antibody. The "humanized antibody", also called reshaped human antibody, is obtained by grafting complementarity determining regions (CDRs) of a non-human mammal-derived antibody, for example, a mouse antibody to human antibody CDRs. Methods for identifying CDRs are known in the art (Kabat et al., Sequence of Proteins of Immunological Interest (1987), National Institute of Health, Bethesda, Md.; and Chothia et al., Nature (1989) 342: 877). General gene recombination approaches therefor are also known in the art (see European Patent Application Publication No. EP 125023 and WO 96/02576).

The "antibody variable region" of the present invention that does "not bind to CD3 and CD137 (4-1BB) at the same time" means that the antibody variable region of the present invention cannot bind to CD137 in a state bound with CD3 whereas the variable region cannot bind to CD3 in a state bound with CD137. In this context, the phrase "not bind to CD3 and CD137 at the same time" also includes not cross-linking a cell expressing CD3 to a cell expressing CD137, or not binding to CD3 and CD137 each expressed on a different cell, at the same time. This phrase further includes the case where the variable region is capable of binding to both CD3 and CD137 at the same time when CD3 and CD137 are not expressed on cell membranes, as with soluble proteins, or both reside on the same cell, but cannot bind to CD3 and CD137 each expressed on a different cell, at the same time. Such an antibody variable region is not particularly limited as long as the antibody variable region has these functions. Examples thereof can include variable regions derived from an IgG-type antibody variable region by the alteration of a portion of its amino acids so as to bind to the desired antigen. The amino acid to be altered is selected from, for example, amino acids whose alteration does not cancel the binding to the antigen, in an antibody variable region binding to CD3 or CD137.

In this context, the phrase "expressed on different cells" merely means that the antigens are expressed on separate cells. The combination of such cells may be, for example, the same types of cells such as a T cell and another T cell, or may be different types of cells such as a T cell and an NK cell.

In the present invention, one amino acid alteration may be used alone, or a plurality of amino acid alterations may be used in combination.

In the case of using a plurality of amino acid alterations in combination, the number of the alterations to be combined is not particularly limited and can be appropriately set within a range that can attain the object of the invention. The number of the alterations to be combined is, for example, 2 or more and 30 or less, preferably 2 or more and 25 or less, 2 or more and 22 or less, 2 or more and 20 or less, 2 or more and 15 or less, 2 or more and 10 or less, 2 or more and 5 or less, or 2 or more and 3 or less.

The plurality of amino acid alterations to be combined may be added to only the antibody heavy chain variable domain or light chain variable domain or may be appropriately distributed to both of the heavy chain variable domain and the light chain variable domain.

One or more amino acid residues in the variable region are acceptable as the amino acid residue to be altered as long as the antigen-binding activity is maintained. In the case of altering an amino acid in the variable region, the resulting variable region preferably maintains the binding activity of the corresponding unaltered antibody and preferably has, for example, 50% or higher, more preferably 80% or higher, further preferably 100% or higher, of the binding activity before the alteration, though the variable region according to the present invention is not limited thereto. The binding activity may be increased by the amino acid alteration and may be, for example, 2 times, 5 times, or 10 times the binding activity before the alteration.

Examples of the region preferred for the amino acid alteration include solvent-exposed regions and loops in the variable region. Among others, CDR1, CDR2, CDR3, FR3, and loops are preferred. Specifically, Kabat numbering positions 31 to 35, 50 to 65, 71 to 74, and 95 to 102 in the H chain variable domain and Kabat numbering positions 24 to 34, 50 to 56, and 89 to 97 in the L chain variable domain are preferred. Kabat numbering positions 31, 52a to 61, 71 to 74, and 97 to 101 in the H chain variable domain and Kabat numbering positions 24 to 34, 51 to 56, and 89 to 96 in the L chain variable domain are more preferred. Also, an amino acid that increases antigen-binding activity may be further introduced at the time of the amino acid alteration.

The term "hypervariable region" or "HVR" as used herein refers to each of the regions of an antibody variable domain which are hypervariable in sequence ("complementarity determining regions" or "CDRs") and/or form structurally defined loops ("hypervariable loops") and/or contain the antigen-contacting residues ("antigen contacts"). Generally, antibodies comprise six HVRs: three in the VH (H1, H2, H3), and three in the VL (L1, L2, L3). Exemplary HVRs herein include:

(a) hypervariable loops occurring at amino acid residues 26-32 (L1), 50-52 (L2), 91-96 (L3), 26-32 (H1), 53-55 (H2), and 96-101 (H3) (Chothia and Lesk, J. Mol. Biol. 196:901-917 (1987));

(b) CDRs occurring at amino acid residues 24-34 (L1), 50-56 (L2), 89-97 (L3), 31-35b (H1), 50-65 (H2), and 95-102 (H3) (Kabat et al., Sequences of Proteins of Immunological Interest, 5th Ed. Public Health Service, National Institutes of Health, Bethesda, MD (1991));

(c) antigen contacts occurring at amino acid residues 27c-36 (L1), 46-55 (L2), 89-96 (L3), 30-35b (H1), 47-58 (H2), and 93-101 (H3) (MacCallum et al. J. Mol. Biol. 262: 732-745 (1996)); and (d) combinations of (a), (b), and/or (c), including HVR amino acid residues 46-56 (L2), 47-56 (L2), 48-56 (L2), 49-56 (L2), 26-35 (H1), 26-35b (H1), 49-65 (H2), 93-102 (H3), and 94-102 (H3).

Unless otherwise indicated, HVR residues and other residues in the variable domain (e.g., FR residues) are numbered herein according to Kabat et al., supra.

In the present invention, the "loop" means a region containing residues that are not involved in the maintenance of an immunoglobulin beta barrel structure.

In the present invention, the amino acid alteration means substitution, deletion, addition, insertion, or modification, or a combination thereof. In the present invention, the amino acid alteration can be used interchangeably with amino acid mutation and used in the same sense therewith.

The substitution of an amino acid residue is carried out by replacement with another amino acid residue for the purpose of altering, for example, any of the following (a) to (c): (a) the polypeptide backbone structure of a region having a sheet structure or helix structure; (b) the electric charge or hydrophobicity of a target site; and (c) the size of a side chain.

Amino acid residues are classified into the following groups on the basis of general side chain properties: (1) hydrophobic residues: norleucine, Met, Ala, Val, Leu, and Ile; (2) neutral hydrophilic residues: Cys, Ser, Thr, Asn, and Gln; (3) acidic residues: Asp and Glu; (4) basic residues: His, Lys, and Arg; (5) residues that influence chain orientation: Gly and Pro; and (6) aromatic residues: Trp, Tyr, and Phe.

The substitution of amino acid residues within each of these groups is called conservative substitution, while the substitution of an amino acid residue in one of these groups by an amino acid residue in another group is called non-conservative substitution.

The substitution according to the present invention may be the conservative substitution or may be the non-conservative substitution. Alternatively, the conservative substitution and the non-conservative substitution may be combined.

The alteration of an amino acid residue also includes: the selection of a variable region that is capable of binding to CD3 and CD137, but cannot bind to these antigens at the same time, from those obtained by the random alteration of amino acids whose alteration does not cancel the binding to the antigen, in the antibody variable region binding to CD3 or CD137; and alteration to insert a peptide previously known to have binding activity against the desired antigen, to the region mentioned above.

In the antibody variable region of the present invention, the alteration mentioned above may be combined with alteration known in the art. For example, the modification of N-terminal glutamine of the variable region to pyroglutamic acid by pyroglutamylation is a modification well known to those skilled in the art. Thus, the antibody of the present invention having glutamine at the N terminus of its heavy chain may contain a variable region with this N-terminal glutamine modified to pyroglutamic acid.

Such an antibody variable region may further have amino acid alteration to improve, for example, antigen binding, pharmacokinetics, stability, or antigenicity. The antibody variable region of the present invention may be altered so as to have pH dependent binding activity against an antigen and be thereby capable of repetitively binding to the antigen (WO2009/125825).

Also, amino acid alteration to change antigen-binding activity according to the concentration of a target tissue-specific compound may be added to, for example, such an antibody variable region binding to a third antigen (WO2013/180200).

The variable region may be further altered for the purpose of, for example, enhancing binding activity, improving specificity, reducing p, conferring pH-dependent antigen-binding properties, improving the thermal stability of binding, improving solubility, improving stability against chemical modification, improving heterogeneity derived from a sugar chain, avoiding a T cell epitope identified by use of in silico prediction or in vitro T cell-based assay for reduction in immunogenicity, or introducing a T cell epitope for activating regulatory T cells (mAbs 3: 243-247, 2011).

Whether the antibody variable region of the present invention is "capable of binding to CD3 and CD137" can be determined by a method known in the art.

This can be determined by, for example, an electrochemiluminescence method (ECL method) (BMC Research Notes 2011, 4: 281).

Specifically, for example, a low-molecular antibody composed of a region capable of binding to CD3 and CD137, for example, a Fab region, of a biotin-labeled antigen-binding molecule to be tested, or a monovalent antibody (antibody lacking one of the two Fab regions carried by a usual antibody) thereof is mixed with CD3 or CD137 labeled with sulfo-tag (Ru complex), and the mixture is added onto a streptavidin-immobilized plate. In this operation, the biotin-labeled antigen-binding molecule to be tested binds to streptavidin on the plate. Light is developed from the sulfo-tag, and the luminescence signal can be detected using Sector Imager 600 or 2400 (MSD K.K.) or the like to thereby confirm the binding of the aforementioned region of the antigen-binding molecule to be tested to CD3 or CD137.

Alternatively, this assay may be conducted by ELISA, FACS (fluorescence activated cell sorting), ALPHAScreen (amplified luminescent proximity homogeneous assay screen), the BIACORE method based on a surface plasmon resonance (SPR) phenomenon, etc. (Proc. Natl. Acad. Sci. USA (2006) 103 (11), 4005-4010).

Specifically, the assay can be conducted using, for example, an interaction analyzer Biacore (GE Healthcare Japan Corp.) based on a surface plasmon resonance (SPR) phenomenon. The Biacore analyzer includes any model such as Biacore T100, T200, X100, A100, 4000, 3000, 2000, 1000, or C. Any sensor chip for Biacore, such as a CM7, CM5, CM4, CM3, C1, SA, NTA, L1, HPA, or Au chip, can be used as a sensor chip. Proteins for capturing the antigen-binding molecule of the present invention, such as protein A, protein G, protein L, anti-human IgG antibodies, anti-human IgG-Fab, anti-human L chain antibodies, anti-human Fc antibodies, antigenic proteins, or antigenic peptides, are immobilized onto the sensor chip by a coupling method such as amine coupling, disulfide coupling, or aldehyde coupling. CD3 or CD137 is injected thereon as an analyte, and the interaction is measured to obtain a sensorgram. In this operation, the concentration of CD3 or CD137 can be selected within the range of a few micro M to a few pM according to the interaction strength (e.g., KD) of the assay sample.

Alternatively, CD3 or CD137 may be immobilized instead of the antigen-binding molecule onto the sensor chip, with which the antibody sample to be evaluated is in turn allowed to interact. Whether the antibody variable region of the antigen-binding molecule of the present invention has binding activity against CD3 or CD137 can be confirmed on the basis of a dissociation constant (KD) value calculated from the sensorgram of the interaction or on the basis of the degree of increase in the sensorgram after the action of the antigen-binding molecule sample over the level before the action.

The ALPHAScreen is carried out by the ALPHA technology using two types of beads (donor and acceptor) on the basis of the following principle: luminescence signals are detected only when these two beads are located in proximity through the biological interaction between a molecule bound with the donor bead and a molecule bound with the acceptor bead. A laser-excited photosensitizer in the donor bead converts ambient oxygen to singlet oxygen having an excited state. The singlet oxygen diffuses around the donor bead and reaches the acceptor bead located in proximity thereto to thereby cause chemiluminescent reaction in the bead, which finally emits light. In the absence of the interaction between the molecule bound with the donor bead and the molecule bound with the acceptor bead, singlet oxygen produced by the donor bead does not reach the acceptor bead. Thus, no chemiluminescent reaction occurs.

One (ligand) of the substances between which the interaction is to be observed is immobilized onto a thin gold film of a sensor chip. The sensor chip is irradiated with light from the back such that total reflection occurs at the interface between the thin gold film and glass. As a result, a site having a drop in reflection intensity (SPR signal) is formed in a portion of reflected light. The other (analyte) of the substances between which the interaction is to be observed is injected on the surface of the sensor chip. Upon binding of the analyte to the ligand, the mass of the immobilized ligand molecule is increased to change the refractive index of the solvent on the sensor chip surface. This change in the refractive index shifts the position of the SPR signal (on the contrary, the dissociation of the bound molecules gets the signal back to the original position). The Biacore system plots on the ordinate the amount of the shift, i.e., change in mass on the sensor chip surface, and displays time-dependent change in mass as assay data (sensorgram). The amount of the analyte bound to the ligand captured on the sensor chip surface (amount of change in response on the sensorgram between before and after the interaction of the analyte) can be determined from the sensorgram. However, since the amount bound also depends on the amount of the ligand, the comparison must be performed under conditions where substantially the same amounts of the ligand are used. Kinetics, i.e., an association rate constant (ka) and a dissociation rate constant (kd), can be determined from the curve of the sensorgram, while affinity (KD) can be determined from the ratio between these constants. Inhibition assay is also preferably used in the BIACORE method. Examples of the inhibition assay are described in Proc. Natl. Acad. Sci. USA (2006) 103 (11), 4005-4010.

Whether the antigen-binding molecule of the present invention does "not bind to CD3 and CD137 at the same time" can be confirmed by: confirming the antigen-binding molecule to have binding activity against both CD3 and CD137; then allowing either CD3 or CD137 to bind in advance to the antigen-binding molecule comprising the variable region having this binding activity; and then determining the presence or absence of its binding activity against the other one by the method mentioned above. Alternatively, this can also be confirmed by determining whether the binding of the antigen-binding molecule to either CD3 or CD137 immobilized on an ELISA plate or a sensor chip is inhibited by the addition of the other one into the solution. In some embodiments, the binding of the antigen-binding molecule of the present invention to either CD3 or CD137 is inhibited by binding of the antigen-binding molecule to the other by at least 50%, preferably 60% or more, more preferably 70% or more, more preferably 80% or more, further preferably 90% or more, or even more preferably 95% or more.

In one aspect, while one antigen (e.g. CD3) is immobilized, the inhibition of the binding of the antigen-binding molecule to CD3 can be determined in the presence of the other antigen (e.g. CD137) by methods known in prior art (i.e. ELISA, BIACORE, and so on). In another aspect, while CD137 is immobilized, the inhibition of the binding of the antigen-binding molecule to CD137 also can be determined in the presence of CD3. When either one of two aspects mentioned above is conducted, the antigen-binding molecule of the present invention is determined not to bind to CD3 and CD137 at the same time if the binding is inhibited by at least 50%, preferably 60% or more, preferably 70% or more, further preferably 80% or more, further preferably 90% or more, or even more preferably 95% or more.

In some embodiments, the concentration of the antigen injected as an analyte is at least 1-fold, 2-fold, 5-fold, 10-fold, 30-fold, 50-fold, or 100-fold higher than the concentration of the other antigen to be immobilized.

In preferable manner, the concentration of the antigen injected as an analyte is 100-fold higher than the concentration of the other antigen to be immobilized and the binding is inhibited by at least 80%.

In one embodiment, the ratio of the KD value for the CD3 (analyte)-binding activity of the antigen-binding molecule to the CD137 (immobilized)-binding activity of the antigen-binding molecule (KD (CD3)/KD (CD137)) is calculated and the CD3 (analyte) concentration which is 10-fold, 50-fold, 100-fold, or 200-fold of the ratio of the KD value (KD(CD3)/KD(CD137)) higher than the CD137 (immobilized) concentration can be used for the competition measurement above. (e.g. 1-fold, 5-fold, 10-fold, or 20-fold higher concentration can be selected when the ratio of the KD value is 0.1. Furthermore, 100-fold, 500-fold, 1000-fold, or 2000-fold higher concentration can be selected when the ratio of the KD value is 10.)

In one aspect, while one antigen (e.g. CD3) is immobilized, the attenuation of the binding signal of the antigen-binding molecule to CD3 can be determined in the presence of the other antigen (e.g. CD137) by methods known in prior art (i.e. ELISA, ECL and so on). In another aspect, while CD137 is immobilized, the attenuation of the binding signal of the antigen-binding molecule to CD137 also can be determined in the presence of CD3. When either one of two aspects mentioned above is conducted, the antigen-binding molecule of the present invention is determined not to bind to CD3 and CD137 at the same time if the binding signal is attenuated by at least 50%, preferably 60% or more, preferably 70% or more, further preferably 80% or more, further preferably 90% or more, or even more preferably 95% or more. (see Example 5-5, 7-5, 8-9, 9-4)

In some embodiments, the concentration of the antigen injected as an analyte is at least 1-fold, 2-fold, 5-fold, 10-fold, 30-fold, 50-fold, or 100-fold higher than the concentration of the other antigen to be immobilized.

In preferable manner, the concentration of the antigen injected as an analyte is 100-fold higher than the concentration of the other antigen to be immobilized and the binding is inhibited by at least 80%.

In one embodiment, the ratio of the KD value for the CD3 (analyte)-binding activity of the antigen-binding molecule to the CD137 (immobilized)-binding activity of the antigen-binding molecule (KD (CD3)/KD (CD137)) is calculated and the CD3 (analyte) concentration which is 10-fold, 50-fold, 100-fold, or 200-fold of the ratio of the KD value (KD(CD3)/KD(CD137)) higher than the CD137 (immobilized) concentration can be used for the measurement above. (e.g. 1-fold, 5-fold, 10-fold, or 20-fold higher concentration can be selected when the ratio of the KD value is 0.1. Furthermore, 100-fold, 500-fold, 1000-fold, or 2000-fold higher concentration can be selected when the ratio of the KD value is 10.)

Specifically, in the case of using, for example, the ECL method, a biotin-labeled antigen-binding molecule to be tested, CD3 labeled with sulfo-tag (Ru complex), and an unlabeled CD137 are prepared. When the antigen-binding molecule to be tested is capable of binding to CD3 and CD137, but does not bind to CD3 and CD137 at the same time, the luminescence signal of the sulfo-tag is detected in the absence of the unlabeled CD137 by adding the mixture of the antigen-binding molecule to be tested and labeled CD3 onto a streptavidin-immobilized plate, followed by light development. By contrast, the luminescence signal is decreased in the presence of unlabeled CD137. This decrease in luminescence signal can be quantified to determine relative binding activity. This analysis may be similarly conducted using the labeled CD137 and the unlabeled CD3.

In the case of the ALPHAScreen, the antigen-binding molecule to be tested interacts with CD3 in the absence of the competing CD137 to generate signals of 520 to 620 nm. The untagged CD137 competes with CD3 for the interaction with the antigen-binding molecule to be tested. Decrease in fluorescence caused as a result of the competition can be quantified to thereby determine relative binding activity. The polypeptide biotinylation using sulfo-NHS-biotin or the like is known in the art. CD3 can be tagged with GST by an appropriately adopted method which involves, for example: fusing a polynucleotide encoding CD3 in flame with a polynucleotide encoding GST; and allowing the resulting fusion gene to be expressed by cells or the like harboring vectors capable of expression thereof, followed by purification using a glutathione column. The obtained signals are preferably analyzed using, for example, software GRAPHPAD PRISM (GraphPad Software, Inc., San Diego) adapted to a one-site competition model based on nonlinear regression analysis. This analysis may be similarly conducted using the tagged CD137 and the untagged CD3.

Alternatively, a method using fluorescence resonance energy transfer (FRET) may be used. FRET is a phenomenon in which excitation energy is transferred directly between two fluorescent molecules located in proximity to each other by electron resonance. When FRET occurs, the excitation energy of a donor (fluorescent molecule having an excited state) is transferred to an acceptor (another fluorescent molecule located near the donor) so that the fluorescence emitted from the donor disappears (to be precise, the lifetime of the fluorescence is shortened) and instead, the fluorescence is emitted from the acceptor. By use of this phenomenon, whether or not bind to CD3 and CD137 at the same time can be analyzed. For example, when CD3 carrying a fluorescence donor and CD137 carrying a fluorescence acceptor bind to the antigen-binding molecule to be tested at the same time, the fluorescence of the donor disappears while the fluorescence is emitted from the acceptor. Therefore, change in fluorescence wavelength is observed. Such an antibody is confirmed to bind to CD3 and CD137 at the same time. On the other hand, if the mixing of CD3, CD137, and the antigen-binding molecule to be tested does not change the fluorescence wavelength of the fluorescence donor bound with CD3, this antigen-binding molecule to be tested can be regarded as antigen binding domain that is capable of binding to CD3 and CD137, but does not bind to CD3 and CD137 at the same time.

For example, a biotin-labeled antigen-binding molecule to be tested is allowed to bind to streptavidin on the donor bead, while CD3 tagged with glutathione S transferase (GST) is allowed to bind to the acceptor bead. The antigen-binding molecule to be tested interacts with CD3 in the absence of the competing second antigen to generate signals of 520 to 620 nm. The untagged second antigen competes with CD3 for the interaction with the antigen-binding molecule to be tested. Decrease in fluorescence caused as a result of the competition can be quantified to thereby determine relative binding activity. The polypeptide biotinylation using sulfo-NHS-biotin or the like is known in the art. CD3 can be tagged with GST by an appropriately adopted method which involves, for example: fusing a polynucleotide encoding CD3 in flame with a polynucleotide encoding GST; and allowing the resulting fusion gene to be expressed by cells or the like harboring vectors capable of expression thereof, followed by purification using a glutathione column. The obtained signals are preferably analyzed using, for example, software GRAPHPAD PRISM (GraphPad Software, Inc., San Diego) adapted to a one-site competition model based on nonlinear regression analysis.

The tagging is not limited to the GST tagging and may be carried out with any tag such as, but not limited to, a histidine tag, MBP, CBP, a Flag tag, an HA tag, a V5 tag, or a c-myc tag. The binding of the antigen-binding molecule to be tested to the donor bead is not limited to the binding using biotin-streptavidin reaction. Particularly, when the antigen-binding molecule to be tested comprises Fc, a possible method involves allowing the antigen-binding molecule to be tested to bind via an Fc-recognizing protein such as protein A or protein G on the donor bead.

Also, the case where the variable region is capable of binding to CD3 and CD137 at the same time when CD3 and CD137 are not expressed on cell membranes, as with soluble proteins, or both reside on the same cell, but cannot bind to CD3 and CD137 each expressed on a different cell, at the same time can also be assayed by a method known in the art.

Specifically, the antigen-binding molecule to be tested has been confirmed to be positive in ECL-ELISA for detecting binding to CD3 and CD137 at the same time is also mixed with a cell expressing CD3 and a cell expressing CD137. The antigen-binding molecule to be tested can be shown to be incapable of binding to CD3 and CD137 expressed on different cells, at the same time unless the antigen-binding molecule and these cells bind to each other at the same time. This assay can be conducted by, for example, cell-based ECL-ELISA. The cell expressing CD3 is immobilized onto a plate in advance. After binding of the antigen-binding molecule to be tested thereto, the cell expressing CD137 is added to the plate. A different antigen expressed only on the cell expressing CD137 is detected using a sulfo-tag-labeled antibody against this antigen. A signal is observed when the antigen-binding molecule binds to the two antigens respectively expressed on the two cells, at the same time. No signal is observed when the antigen-binding molecule does not bind to these antigens at the same time.

Alternatively, this assay may be conducted by the ALPHAScreen method. The antigen-binding molecule to be tested is mixed with a cell expressing CD3 bound with the donor bead and a cell expressing CD137 bound with the acceptor bead. A signal is observed when the antigen-binding molecule binds to the two antigens expressed on the two cells respectively, at the same time. No signal is observed when the antigen-binding molecule does not bind to these antigens at the same time.

Alternatively, this assay may also be conducted by an Octet interaction analysis method. First, a cell expressing CD3 tagged with a peptide tag is allowed to bind to a biosensor that recognizes the peptide tag. A cell expressing CD137 and the antigen-binding molecule to be tested are placed in wells and analyzed for interaction. A large wavelength shift caused by the binding of the antigen-binding molecule to be tested and the cell expressing CD137 to the biosensor is observed when the antigen-binding molecule binds to the two antigens expressed on the two cells respectively, at the same time. A small wavelength shift caused by the binding of only the antigen-binding molecule to be tested to the biosensor is observed when the antigen-binding molecule does not bind to these antigens at the same time.

Instead of these methods based on the binding activity, assay based on biological activity may be conducted. For example, a cell expressing CD3 and a cell expressing CD137 are mixed with the antigen-binding molecule to be tested, and cultured. The two antigens expressed on the two cells respectively are mutually activated via the antigen-binding molecule to be tested when the antigen-binding molecule binds to these two antigens at the same time. Therefore, change in activation signal, such as increase in the respective downstream phosphorylation levels of the antigens, can be detected. Alternatively, cytokine production is induced as a result of the activation. Therefore, the amount of cytokines produced can be measured to thereby confirm whether or not to bind to the two cells at the same time. Alternatively, cytotoxicity against a cell expressing CD137 is induced as a result of the activation. Alternatively, the expression of a reporter gene is induced by a promoter which is activated at the downstream of the signal transduction pathway of CD137 or CD3 as a result of the activation. Therefore, the cytotoxicity or the amount of reporter proteins produced can be measured to thereby confirm whether or not to bind to the two cells at the same time.

In the present invention, the "Fc region" refers to a region comprising a fragment consisting of a hinge or a portion thereof and CH2 and CH3 domains in an antibody molecule. The Fc region of IgG class means, but is not limited to, a region from, for example, cysteine 226 (EU numbering (also referred to as EU index herein)) to the C terminus or proline 230 (EU numbering) to the C terminus. The Fc region can be preferably obtained by the partial digestion of, for example, an IgG1, IgG2, IgG3, or IgG4 monoclonal antibody with a proteolytic enzyme such as pepsin followed by the re-elution of a fraction adsorbed on a protein A column or a protein G column. Such a proteolytic enzyme is not particularly limited as long as the enzyme is capable of digesting a whole antibody to restrictively form Fab or F(ab')$_2$ under appropriately set reaction conditions (e.g., pH) of the enzyme. Examples thereof can include pepsin and papain.

In some embodiments, the "antigen-binding molecule" is not particularly limited as long as the molecule comprises the "antibody variable region" of the present invention. The antigen-binding molecule may further comprise a peptide or a protein having a length of approximately 5 or more amino acids. The peptide or the protein is not limited to a peptide or a protein derived from an organism, and may be, for example, a polypeptide consisting of an artificially designed sequence. Also, a natural polypeptide, a synthetic polypeptide, a recombinant polypeptide, or the like may be used.

In some embodiments, the "antigen-binding molecule" of the present invention is not particularly limited to a molecule comprising the "antibody variable region". In certain embodiments, antigen-binding molecules that are other than antibodies comprising a variable region and can bind to two different antigens, for example, Affibody and so on, may be obtained by methods generally known to those skilled in the art (PLoS One. 2011; 6(10):e25791; PLoS One. 2012; 7(8):e42288; J Mol Biol. 2011 Aug. 5; 411(1):201-19; Proc Natl Acad Sci USA. 2011 Aug. 23; 108(34):14067-72).

Preferred examples of the antigen-binding molecule of the present invention can include an antigen-binding molecule comprising an antibody Fc region.

An Fc region derived from, for example, naturally occurring IgG can be used as the "Fc region" of the present invention. In this context, the naturally occurring IgG means a polypeptide that contains an amino acid sequence identical to that of IgG found in nature and belongs to a class of an antibody substantially encoded by an immunoglobulin gamma gene. The naturally occurring human IgG means, for example, naturally occurring human IgG1, naturally occurring human IgG2, naturally occurring human IgG3, or naturally occurring human IgG4. The naturally occurring IgG also includes variants or the like spontaneously derived therefrom. A plurality of allotype sequences based on gene polymorphism are described as the constant regions of human IgG1, human IgG2, human IgG3, and human IgG4 antibodies in Sequences of proteins of immunological interest, NIH Publication No. 91-3242, any of which can be used in the present invention. Particularly, the sequence of human IgG1 may have DEL or EEM as an amino acid sequence of EU numbering positions 356 to 358.

The antibody Fc region is found as, for example, an Fc region of IgA1, IgA2, IgD, IgE, IgG1 IgG2, IgG3, IgG4, or IgM type. For example, an Fc region derived from a naturally occurring human IgG antibody can be used as the antibody Fc region of the present invention. For example, an Fc region derived from a constant region of naturally occurring IgG, specifically, a constant region (SEQ ID NO: YY004) originated from naturally occurring human IgG1, a constant region (SEQ ID NO: YY005) originated from naturally occurring human IgG2, a constant region (SEQ ID NO: YY006) originated from naturally occurring human IgG3, or a constant region (SEQ ID NO: YY007) originated from naturally occurring human IgG4 can be used as the Fc region of the present invention. The constant region of naturally occurring IgG also includes variants or the like spontaneously derived therefrom.

The Fc region of the present invention is particularly preferably an Fc region having reduced binding activity against an Fc gamma receptor. In this context, the Fc gamma receptor (also referred to as Fc gamma R herein) refers to a receptor capable of binding to the Fc region of IgG1, IgG2, IgG3, or IgG4 and means any member of the protein family substantially encoded by Fc gamma receptor genes. In humans, this family includes, but is not limited to: Fc gamma RI (CD64) including isoforms Fc gamma RIa, Fc gamma RIb, and Fc gamma RIc; Fc gamma RII (CD32) including isoforms Fc gamma RIa (including allotypes H131 (H type) and R131 (R type)), Fc gamma RIb (including Fc gamma RIIb-1 and Fc gamma RIIb-2), and Fc gamma RIIc; and Fc gamma RIII (CD16) including isoforms Fc gamma RIIIa (including allotypes V158 and F158) and Fc gamma RIIb (including allotypes Fc gamma RIIIb-NA1 and Fc gamma RIIIb-NA2); and any yet-to-be-discovered human Fc gamma R or Fc gamma R isoform or allotype. The Fc gamma R includes those derived from humans, mice, rats, rabbits, and monkeys. The Fc gamma R is not limited to these molecules and may be derived from any organism. The mouse Fc gamma Rs include, but are not limited to, Fc gamma RI (CD64), Fc gamma RII (CD32), Fc gamma RIII (CD16), and Fc gamma RIII-2 (CD16-2), and any yet-to-be-discovered mouse Fc gamma R or Fc gamma R isoform or allotype. Preferred examples of such Fc gamma receptors include human Fc gamma RI (CD64), Fc gamma RIIa (CD32), Fc gamma RIb (CD32), Fc gamma RIIIa (CD16), and/or Fc gamma RIIIb (CD16).

The Fc gamma R is found in the forms of an activating receptor having ITAM (immunoreceptor tyrosine-based activation motif) and an inhibitory receptor having ITIM (immunoreceptor tyrosine-based inhibitory motif). The Fc gamma R is classified into activating Fc gamma R (Fc gamma RI, Fc gamma RIIa R, Fc gamma RIIa H, Fc gamma RIIIa, and Fc gamma RIIIb) and inhibitory Fc gamma R (Fc gamma RIIb).

The polynucleotide sequence and the amino acid sequence of Fc gamma RI are described in NM_000566.3 and NP_000557.1, respectively; the polynucleotide sequence and the amino acid sequence of Fc gamma RIIa are described in BC020823.1 and AAH20823.1, respectively; the polynucleotide sequence and the amino acid sequence of Fc gamma RIIb are described in BC146678.1 and AAI46679.1, respectively; the polynucleotide sequence and the amino acid sequence of Fc gamma RIIIa are described in BC033678.1 and AAH33678.1, respectively; and the polynucleotide sequence and the amino acid sequence of Fc gamma RII are described in BC128562.1 and AAI28563.1, respectively (RefSeq registration numbers). Fc gamma RIIa has two types of gene polymorphisms that substitute the 131st amino acid of Fc gamma RIIa by histidine (H type) or arginine (R type) (J. Exp. Med, 172, 19-25, 1990). Fc gamma RIIb has two types of gene polymorphisms that substitute the 232nd amino acid of Fc gamma RIb by isoleucine (I type) or threonine (T type) (Arthritis. Rheum. 46: 1242-1254 (2002)). Fc gamma RIIIa has two types of gene polymorphisms that substitute the 158th amino acid of Fc gamma RIIIa by valine (V type) or phenylalanine (F type) (J. Clin. Invest. 100 (5): 1059-1070 (1997)). Fc gamma RIIb has two types of gene polymorphisms (NA1 type and NA2 type) (J. Clin. Invest. 85: 1287-1295 (1990)).

The reduced binding activity against an Fc gamma receptor can be confirmed by a well-known method such as FACS, ELISA format, ALPHAScreen (amplified luminescent proximity homogeneous assay screen), or the BIA-CORE method based on a surface plasmon resonance (SPR) phenomenon (Proc. Natl. Acad. Sci. USA (2006) 103 (11), 4005-4010).

The ALPHAScreen method is carried out by the ALPHA technology using two types of beads (donor and acceptor) on the basis of the following principle: luminescence signals are detected only when these two beads are located in proximity through the biological interaction between a molecule bound with the donor bead and a molecule bound with the acceptor bead. A laser-excited photosensitizer in the donor bead converts ambient oxygen to singlet oxygen having an excited state. The singlet oxygen diffuses around the donor bead and reaches the acceptor bead located in proximity thereto to thereby cause chemiluminescent reaction in the bead, which finally emits light. In the absence of the interaction between the molecule bound with the donor bead and the molecule bound with the acceptor bead, singlet oxygen produced by the donor bead does not reach the acceptor bead. Thus, no chemiluminescent reaction occurs.

For example, a biotin-labeled antigen-binding molecule is allowed to bind to the donor bead, while a glutathione S transferase (GST)-tagged Fc gamma receptor is allowed to bind to the acceptor bead. In the absence of a competing antigen-binding molecule having a mutated Fc region, an antigen-binding molecule having a wild-type Fc region interacts with the Fc gamma receptor to generate signals of 520 to 620 nm. The untagged antigen-binding molecule having a mutated Fc region competes with the antigen-binding molecule having a wild-type Fc region for the interaction with the Fc gamma receptor. Decrease in fluorescence caused as a result of the competition can be quantified to thereby determine relative binding affinity. The antigen-binding molecule (e.g., antibody) biotinylation using sulfo-NHS-biotin or the like is known in the art. The Fc gamma receptor can be tagged with GST by an appropriately adopted method which involves, for example: fusing a polynucleotide encoding the Fc gamma receptor in flame with a polynucleotide encoding GST; and allowing the resulting fusion gene to be expressed by cells or the like harboring vectors capable of expression thereof, followed by purification using a glutathione column. The obtained signals are preferably analyzed using, for example, software GRAPHPAD PRISM (GraphPad Software, Inc., San Diego) adapted to a one-site competition model based on nonlinear regression analysis.

One (ligand) of the substances between which the interaction is to be observed is immobilized onto a thin gold film of a sensor chip. The sensor chip is irradiated with light from the back such that total reflection occurs at the interface between the thin gold film and glass. As a result, a site having a drop in reflection intensity (SPR signal) is formed in a portion of reflected light. The other (analyte) of the substances between which the interaction is to be observed is injected on the surface of the sensor chip. Upon binding of the analyte to the ligand, the mass of the immobilized ligand molecule is increased to change the refractive index of the solvent on the sensor chip surface. This change in the refractive index shifts the position of the SPR signal (on the contrary, the dissociation of the bound molecules gets the signal back to the original position). The Biacore system plots on the ordinate the amount of the shift, i.e., change in mass on the sensor chip surface, and displays time-dependent change in mass as assay data (sensorgram). Kinetics, i.e., an association rate constant (ka) and a dissociation rate constant (kd), can be determined from the curve of the sensorgram, while affinity (KD) can be determined from the ratio between these constants. Inhibition assay is also preferably used in the BIACORE method. Examples of the inhibition assay are described in Proc. Natl. Acad. Sci. USA (2006) 103 (11), 4005-4010.

In the present specification, the reduced binding activity against an Fc gamma receptor means that the antigen-binding molecule to be tested exhibits binding activity of, for example, 50% or lower, preferably 45% or lower, 40% or lower, 35% or lower, 30% or lower, 20% or lower, or 15% or lower, particularly preferably 10% or lower, 9% or lower, 8% or lower, 7% or lower, 6% or lower, 5% or lower, 4% or lower, 3% or lower, 2% or lower, or 1% or lower, compared with the binding activity of a control antigen-binding molecule comprising an Fc region on the basis of the analysis method described above.

An antigen-binding molecule having an IgG1, IgG2, IgG3, or IgG4 monoclonal antibody Fc region can be appropriately used as the control antigen-binding molecule. The structure of the Fc region is described in SEQ ID NO: 94 (RefSeq registration No. AAC82527.1 with A added to the N terminus), SEQ ID NO: 95 (RefSeq registration No. AAB59393.1 with A added to the N terminus), SEQ ID NO: 96 (RefSeq registration No. CAA27268.1 with A added to the N terminus), or SEQ ID NO: 97 (RefSeq registration No. AAB59394.1 with A added to the N terminus). In the case of using an antigen-binding molecule having a variant of the Fc region of an antibody of a certain isotype as a test substance, an antigen-binding molecule having the Fc region of the antibody of this certain isotype is used as a control to test the effect of the mutation in the variant on the binding activity against an Fc gamma receptor. The antigen-binding molecule having the Fc region variant thus confirmed to have reduced binding activity against an Fc gamma receptor is appropriately prepared.

For example, a 231A-238S deletion (WO 2009/011941), C226S, C229S, P238S, (C220S) (J. Rheumatol (2007) 34, 11), C226S, C229S (Hum. Antibod. Hybridomas (1990) 1 (1), 47-54), C226S, C229S, E233P, L234V, or L235A (Blood (2007) 109, 1185-1192) (these amino acids are defined according to the EU numbering) variant is known in the art as such a variant.

Preferred examples thereof include antigen-binding molecules having an Fc region derived from the Fc region of an antibody of a certain isotype by the substitution of any of the following constituent amino acids: amino acids at positions 220, 226, 229, 231, 232, 233, 234, 235, 236, 237, 238, 239, 240, 264, 265, 266, 267, 269, 270, 295, 296, 297, 298, 299, 300, 325, 327, 328, 329, 330, 331, and 332 defined according to the EU numbering. The isotype of the antibody from which the Fc region is originated is not particularly limited, and an Fc region originated from an IgG1, IgG2, IgG3, or IgG4 monoclonal antibody can be appropriately used. An Fc region originated from a naturally occurring human IgG1 antibody is preferably used.

For example, an antigen-binding molecule having an Fc region derived from an IgG1 antibody Fc region by any of the following substitution groups of the constituent amino acids (the number represents the position of an amino acid residue defined according to the EU numbering; the one-letter amino acid code positioned before the number represents an amino acid residue before the substitution; and the one-letter amino acid code positioned after the number represents an amino acid residue before the substitution):
  (a) L234F, L235E, and P331S,
  (b) C226S, C229S, and P238S,
  (c) C226S and C229S, and
  (d) C226S, C229S, E233P, L234V, and L235A
or by the deletion of an amino acid sequence from positions 231 to 238 defined according to the EU numbering can also be appropriately used.

An antigen-binding molecule having an Fc region derived from an IgG2 antibody Fc region by any of the following substitution groups of the constituent amino acids (the number represents the position of an amino acid residue defined according to the EU numbering; the one-letter amino acid code positioned before the number represents an amino acid residue before the substitution; and the one-letter amino acid code positioned after the number represents an amino acid residue before the substitution):
  (e) H268Q, V309L, A330S, and P331S,
  (f) V234A,
  (g) G237A,
  (h) V234A and G237A,
  (i) A235E and G237A, and
  (j) V234A, A235E, and G237A
defined according to the EU numbering can also be appropriately used.

An antigen-binding molecule having an Fc region derived from an IgG3 antibody Fc region by any of the following substitution groups of the constituent amino acids (the number represents the position of an amino acid residue defined according to the EU numbering; the one-letter amino acid code positioned before the number represents an amino acid residue before the substitution; and the one-letter amino acid code positioned after the number represents an amino acid residue before the substitution):
  (k) F241A,
  (l) D265A, and
  (m) V264A
defined according to the EU numbering can also be appropriately used.

An antigen-binding molecule having an Fc region derived from an IgG4 antibody Fc region by any of the following substitution groups of the constituent amino acids (the number represents the position of an amino acid residue defined according to the EU numbering; the one-letter amino acid code positioned before the number represents an amino acid residue before the substitution; and the one-letter amino acid code positioned after the number represents an amino acid residue before the substitution):
  (n) L235A, G237A, and E318A,
  (o) L235E, and
  (p) F234A and L235A
defined according to the EU numbering can also be appropriately used.

Other preferred examples thereof include antigen-binding molecules having an Fc region derived from the Fc region of a naturally occurring human IgG1 antibody by the substitution of any of the following constituent amino acids: amino acids at positions 233, 234, 235, 236, 237, 327, 330, and 331 defined according to the EU numbering, by an amino acid at the corresponding EU numbering position in the Fc region of the counterpart IgG2 or IgG4.

Other preferred examples thereof include antigen-binding molecules having an Fc region derived from the Fc region of a naturally occurring human IgG1 antibody by the substitution of any one or more of the following constituent amino acids: amino acids at positions 234, 235, and 297 defined according to the EU numbering, by a different amino acid. The type of the amino acid present after the substitution is not particularly limited. An antigen-binding molecule having an Fc region with any one or more of amino acids at positions 234, 235, and 297 substituted by alanine is particularly preferred.

Other preferred examples thereof include antigen-binding molecules having an Fc region derived from an IgG1 antibody Fc region by the substitution of the constituent amino acid at position 265 defined according to the EU numbering, by a different amino acid. The type of the amino acid present after the substitution is not particularly limited. An antigen-binding molecule having an Fc region with an amino acid at position 265 substituted by alanine is particularly preferred.

One preferred form of the "antigen-binding molecule" of the present invention can be, for example, a multispecific antibody comprising the antibody variable region of the present invention.

A technique of suppressing the unintended association between H chains by introducing electric charge repulsion to the interface between the second constant domains (CH2) or the third constant domains (CH3) of the antibody H chains (WO2006/106905) can be applied to association for the multispecific antibody.

In the technique of suppressing the unintended association between H chains by introducing electric charge repulsion to the CH2 or CH3 interface, examples of amino acid residues contacting with each other at the interface between the H chain constant domains can include a residue at EU numbering position 356, a residue at EU numbering position 439, a residue at EU numbering position 357, a residue at EU numbering position 370, a residue at EU numbering position 399, and a residue at EU numbering position 409 in one CH3 domain, and their partner residues in another CH3 domain.

More specifically, for example, an antibody comprising two H chain CH3 domains can be prepared as an antibody in which one to three pairs of amino acid residues selected from the following amino acid residue pairs (1) to (3) in the first H chain CH3 domain carry the same electric charge: (1) amino acid residues at EU numbering positions 356 and 439 contained in the H chain CH3 domain; (2) amino acid residues at EU numbering positions 357 and 370 contained in the H chain CH3 domain; and (3) amino acid residues at EU numbering positions 399 and 409 contained in the H chain CH3 domain.

The antibody can be further prepared as an antibody in which one to three pairs of amino acid residues are selected from the amino acid residue pairs (1) to (3) in the second H chain CH3 domain different from the first H chain CH3 domain so as to correspond to the amino acid residue pairs (1) to (3) carrying the same electric charge in the first H chain CH3 domain and to carry opposite electric charge from their corresponding amino acid residues in the first H chain CH3 domain.

Each amino acid residue described in the pairs (1) to (3) is located close to its partner in the associated H chains. Those skilled in the art can find positions corresponding to the amino acid residues described in each of the pairs (1) to (3) as to the desired H chain CH3 domains or H chain constant domains by homology modeling or the like using commercially available software and can appropriately alter amino acid residues at the positions.

In the antibody described above, each of the "amino acid residues carrying electric charge" is preferably selected from, for example, amino acid residues included in any of the following groups (a) and (b):

(a) glutamic acid (E) and aspartic acid (D); and
(b) lysine (K), arginine (R), and histidine (H).

In the antibody described above, the phrase "carrying the same electric charge" means that, for example, all of two or more amino acid residues are amino acid residues included in any one of the groups (a) and (b). The phrase "carrying opposite electric charge" means that, for example, at least one amino acid residue among two or more amino acid residues may be an amino acid residue included in any one of the groups (a) and (b), while the remaining amino acid residue(s) is amino acid residue(s) included in the other group.

In a preferred embodiment, the antibody may have the first H chain CH3 domain and the second H chain CH3 domain cross-linked through a disulfide bond.

The amino acid residue to be altered according to the present invention is not limited to the amino acid residues in the antibody variable region or the antibody constant region mentioned above. Those skilled in the art can find amino acid residues constituting the interface as to a polypeptide variant or a heteromultimer by homology modeling or the like using commercially available software and can alter amino acid residues at the positions so as to regulate the association.

The association for the multispecific antibody of the present invention can also be carried out by an alternative technique known in the art. An amino acid side chain present in the variable domain of one antibody H chain is substituted by a larger side chain (knob), and its partner amino acid side chain present in the variable domain of the other H chain is substituted by a smaller side chain (hole). The knob can be placed into the hole to efficiently associate the polypeptides of the Fc domains differing in amino acid sequence (WO1996/027011; Ridgway J B et al., Protein Engineering (1996) 9, 617-621; and Merchant A M et al. Nature Biotechnology (1998) 16, 677-681).

In addition to this technique, a further alternative technique known in the art may be used for forming the multispecific antibody of the present invention. A portion of CH3 of one antibody H chain is converted to its counterpart IgA-derived sequence, and its complementary portion in CH3 of the other H chain is converted to its counterpart IgA-derived sequence. Use of the resulting strand-exchange engineered domain CH3 can cause efficient association between the polypeptides differing in sequence through complementary CH3 association (Protein Engineering Design & Selection, 23; 195-202, 2010). By use of this technique known in the art, the multispecific antibody of interest can also be efficiently formed.

Alternatively, the multispecific antibody may be formed by, for example, an antibody preparation technique using antibody CH1-CL association and VH-VL association as described in WO2011/028952, a technique of preparing a bispecific antibody using separately prepared monoclonal antibodies (Fab arm exchange) as described in WO2008/119353 and WO2011/131746, a technique of controlling the association between antibody heavy chain CH3 domains as described in WO2012/058768 and WO2013/063702, a technique of preparing a bispecific antibody constituted by two types of light chains and one type of heavy chain as described in WO2012/023053, or a technique of preparing a bispecific antibody using two bacterial cell lines each expressing an antibody half-molecule consisting of one H chain and one L chain as described in Christoph et al. (Nature Biotechnology Vol. 31, p. 753-758 (2013)). In addition to these association techniques, CrossMab technology, a known hetero light chain association technique of associating a light chain forming a variable region binding to a first epitope and a light chain forming a variable region binding to a second epitope to a heavy chain forming the variable region binding to the first epitope and a heavy chain forming the variable region binding to the second epitope, respectively (Scaefer et al., Proc. Natl. Acad. Sci. U.S.A. (2011) 108, 11187-11192), can also be used for preparing a multispecific or multiparatopic antigen-binding molecule provided by the present invention. Examples of the technique of preparing a bispecific antibody using separately prepared monoclonal antibodies can include a method which involves promoting antibody heterodimerization by placing monoclonal antibodies with a particular amino acid substituted in a heavy chain CH3 domain under reductive conditions to obtain the desired bispecific antibody. Examples of the amino acid substitution site preferred for this method can include a residue at EU numbering position 392 and a residue at EU numbering position 397 in the CH3 domain. Furthermore, the bispecific antibody can also be prepared by use of an antibody in which one to three pairs of amino acid residues selected from the following amino acid residue pairs (1) to (3) in the first H chain CH3 domain carry the same electric charge: (1) amino acid residues at EU numbering positions 356 and 439 contained in the H chain CH3 domain; (2) amino acid residues at EU numbering positions 357 and 370 contained in the H chain CH3 domain; and (3) amino acid residues at EU numbering positions 399 and 409 contained in the H chain CH3 domain. The bispecific antibody can also be prepared by use of the antibody in which one to three pairs of amino acid residues are selected from the amino acid residue pairs (1) to (3) in the second H chain CH3 domain different from the first H chain CH3 domain so as to correspond to the amino acid residue pairs (1) to (3) carrying the same electric charge in the first H chain CH3 domain and to carry opposite electric charge from their corresponding amino acid residues in the first H chain CH3 domain.

Even if the multispecific antibody of interest cannot be formed efficiently, the multispecific antibody of the present invention may be obtained by the separation and purification of the multispecific antibody of interest from among produced antibodies. For example, the previously reported method involves introducing amino acid substitution to the variable domains of two types of H chains to impart thereto difference in isoelectric point so that two types of homodimers and the heterodimerized antibody of interest can be separately purified by ion-exchanged chromatography (WO2007114325). A method using protein A to purify a heterodimerized antibody consisting of a mouse IgG2a H chain capable of binding to protein A and a rat IgG2b H chain incapable of binding to protein A has previously been reported as a method for purifying the heterodimer (WO98050431 and WO95033844). Alternatively, amino acid residues at EU numbering positions 435 and 436 that constitute the protein A-binding site of IgG may be substituted by amino acids, such as Tyr and His, which offer the different strength of protein A binding, and the resulting H chain is used to change the interaction of each H chain with protein A. As a result, only the heterodimerized antibody can be efficiently purified by use of a protein A column.

A plurality of, for example, two or more of these techniques may be used in combination. Also, these techniques can be appropriately applied separately to the two H chains to be associated. On the basis of, but separately from the form thus altered, the antigen-binding molecule of the present invention may be prepared as an antigen-binding molecule having an amino acid sequence identical thereto.

The alteration of an amino acid sequence can be performed by various methods known in the art. Examples of these methods that may be performed can include, but are not limited to, methods such as site-directed mutagenesis (Hashimoto-Gotoh, T, Mizuno, T, Ogasahara, Y, and Nakagawa, M. (1995) An oligodeoxyribonucleotide-directed dual amber method for site-directed mutagenesis. Gene 152, 271-275; Zoller, M J, and Smith, M. (1983) Oligonucleotide-directed mutagenesis of DNA fragments cloned into M13 vectors. Methods Enzymol. 100, 468-500; Kramer, W, Drutsa, V, Jansen, H W, Kramer, B, Pflugfelder, M, and Fritz, H J (1984) The gapped duplex DNA approach to oligonucleotide-directed mutation construction. Nucleic Acids Res. 12, 9441-9456; Kramer W, and Fritz H J (1987) Oligonucleotide-directed construction of mutations via gapped duplex DNA Methods. Enzymol. 154, 350-367; and Kunkel, T A (1985) Rapid and efficient site-specific mutagenesis without phenotypic selection. Proc Natl Acad Sci USA. 82, 488-492), PCR mutagenesis, and cassette mutagenesis.

The "antigen-binding molecule" of the present invention may be an antibody fragment that comprises both of a heavy chain and a light chain constituting the "antibody variable region" of the present invention in a single polypeptide chain, but lacks a constant region. Such an antibody fragment may be, for example, diabody (db), a single-chain antibody, or sc(Fab')2.

db is a dimer constituted by two polypeptide chains (e.g., Holliger P et al., Proc. Natl. Acad. Sci. USA 90: 6444-6448 (1993); EP404,097; and WO93/11161). These polypeptide chains are linked through a linker as short as, for example, approximately 5 residues, such that an L chain variable domain (VL) and an H chain variable domain (VH) on the same polypeptide chain cannot be paired with each other.

Because of this short linker, VL and VH encoded on the same polypeptide chain cannot form single-chain Fv and instead, are dimerized with VH and VL, respectively, on another polypeptide chain, to form two antigen-binding sites.

Examples of the single-chain antibody include sc(Fv)2. The sc(Fv)2 is a single-chain antibody having one chain constituted by four variable domains, i.e., two VLs and two VHs, linked via linkers such as peptide linkers (J Immunol. Methods (1999) 231 (1-2), 177-189). These two VHs and VLs may be derived from different monoclonal antibodies. Preferred examples thereof include bispecific sc(Fv)2, which recognizes two types of epitopes present in the same antigen, as disclosed in Journal of Immunology (1994) 152 (11), 5368-5374. The sc(Fv)2 can be prepared by a method generally known to those skilled in the art. For example, the sc(Fv)2 can be prepared by connecting two scFvs via a linker such as a peptide linker.

Examples of the configuration of the antigen-binding domains constituting the sc(Fv)2 described herein include an antibody in which two VHs and two VLs are aligned as VH, VL, VH, and VL (i.e., [VH]-linker-[VL]-linker-[VH]-linker-[VL]) in this order starting at the N-terminus of the single-chain polypeptide. The order of two VHs and two VLs is not particularly limited to the configuration described above and may be any order of arrangement. Examples thereof can also include the following arrangements:

[VL]-linker-[VH]-linker-[VH]-linker-[VL],
[VH]-linker-[VL]-linker-[VL]-linker-[VH],
[VH]-linker-[VH]-linker-[VL]-linker-[VL],
[VL]-linker-[VL]-linker-[VH]-linker-[VH], and
[VL]-linker-[VH]-linker-[VL]-linker-[VH].

The molecular form of the sc(Fv)2 is also described in detail in WO2006/132352. On the basis of the description therein, those skilled in the art can appropriately prepare the desired sc(Fv)2 in order to prepare the antigen-binding molecule disclosed in the present specification.

The antigen-binding molecule of the present invention may be conjugated with a carrier polymer such as PEG or an organic compound such as an anticancer agent. Also, a sugar chain can be preferably added to the antigen-binding molecule of the present invention by the insertion of a glycosylation sequence for the purpose of producing the desired effects.

For example, an arbitrary peptide linker that can be introduced by genetic engineering, or a synthetic compound linker (e.g., a linker disclosed in Protein Engineering, 9 (3), 299-305, 1996) can be used as the linker to link the antibody variable domains. In the present invention, a peptide linker is preferred. The length of the peptide linker is not particularly limited and can be appropriately selected by those skilled in the art according to the purpose. The length is preferably 5 or more amino acids (the upper limit is not particularly limited and is usually 30 or less amino acids, preferably 20 or less amino acids), particularly preferably 15 amino acids. When the sc(Fv)2 contains three peptide linkers, all of these peptide linkers used may have the same lengths or may have different lengths.

Examples of the peptide linker can include
Ser,
Gly-Ser,
Gly-Gly-Ser,
Ser-Gly-Gly,
Gly-Gly-Gly-Ser (SEQ ID NO: 162),
Ser-Gly-Gly-Gly (SEQ ID NO: 163),
Gly-Gly-Gly-Gly-Ser (SEQ ID NO: 164),
Ser-Gly-Gly-Gly-Gly (SEQ ID NO: 165),
Gly-Gly-Gly-Gly-Gly-Ser (SEQ ID NO: 166),
Ser-Gly-Gly-Gly-Gly-Gly (SEQ ID NO: 167),
Gly-Gly-Gly-Gly-Gly-Gly-Ser (SEQ ID NO: 168),
Ser-Gly-Gly-Gly-Gly-Gly-Gly (SEQ ID NO: 169),
(Gly-Gly-Gly-Gly-Ser (SEQ ID NO: 164))n, and
(Ser-Gly-Gly-Gly-Gly (SEQ ID NO: 165))n,
wherein n is an integer of 1 or larger.

However, the length or sequence of the peptide linker can be appropriately selected by those skilled in the art according to the purpose.

The synthetic compound linker (chemical cross-linking agent) is a cross-linking agent usually used in the cross-linking of peptides, for example, N-hydroxysuccinimide (NHS), disuccinimidyl suberate (DSS), bis(sulfosuccinimidyl) suberate (BS3), dithiobis(succinimidyl propionate) (DSP), dithiobis(sulfosuccinimidyl propionate) (DTSSP), ethylene glycol bis(succinimidyl succinate) (EGS), ethylene glycol bis(sulfosuccinimidyl succinate) (sulfo-EGS), disuccinimidyl tartrate (DST), disulfosuccinimidyl tartrate (sulfo-DST), bis[2-(succinimidoxycarbonyloxy)ethyl]sulfone (BSOCOES), or bis[2-(sulfosuccinimidoxycarbonyloxy)ethyl]sulfone (sulfo-BSOCOES).

These cross-linking agents are commercially available.

Three linkers are usually necessary for linking four antibody variable domains. All of these linkers used may be the same linkers or may be different linkers.

The F(ab')2 comprises two light chains and two heavy chains containing a constant region (CH1 domains and a portion of CH2 domains) so as to form the interchain disulfide bond between these two heavy chains. The F(ab')2 constituting a polypeptide associate disclosed in the present specification can be preferably obtained by the partial digestion of, for example, a whole monoclonal antibody having the desired antigen-binding domains with a proteolytic enzyme such as pepsin followed by the removal of an Fc fragment adsorbed on a protein A column. Such a proteolytic enzyme is not particularly limited as long as the enzyme is capable of digesting a whole antibody to restrictively form $F(ab')_2$ under appropriately set reaction conditions (e.g., pH) of the enzyme. Examples thereof can include pepsin and ficin.

The antigen-binding molecule of the present invention can further contain additional alteration in addition to the amino acid alteration mentioned above. The additional alteration can be selected from, for example, amino acid substitution, deletion, and modification, and a combination thereof.

For example, the antigen-binding molecule of the present invention can be further altered arbitrarily, substantially without changing the intended functions of the molecule. Such a mutation can be performed, for example, by the conservative substitution of amino acid residues. Alternatively, even alteration to change the intended functions of the antigen-binding molecule of the present invention may be carried out as long as the functions changed by such alteration fall within the object of the present invention.

The alteration of an amino acid sequence according to the present invention also includes posttranslational modification. Specifically, the posttranslational modification can refer to the addition or deletion of a sugar chain. The antigen-binding molecule of the present invention, for example, having an IgG1-type constant region, can have a sugar chain-modified amino acid residue at EU numbering position 297. The sugar chain structure for use in the modification is not limited. In general, antibodies expressed by eukaryotic cells involve sugar chain modification in their constant regions. Thus, antibodies expressed by the following cells are usually modified with some sugar chain:
mammalian antibody-producing cells; and
eukaryotic cells transformed with expression vectors comprising antibody-encoding DNAs.

In this context, the eukaryotic cells include yeast and animal cells. For example, CHO cells or HEK293H cells are typical animal cells for transformation with expression vectors comprising antibody-encoding DNAs. On the other hand, the antibody of the present invention also includes antibodies lacking sugar chain modification at the position. The antibodies having sugar chain-unmodified constant regions can be obtained by the expression of genes encoding these antibodies in prokaryotic cells such as E. coli.

The additional alteration according to the present invention may be more specifically, for example, the addition of sialic acid to a sugar chain in an Fc region (mAbs. 2010 September-October; 2 (5): 519-27).

When the antigen-binding molecule of the present invention has an Fc region, for example, amino acid substitution to improve binding activity against FcRn (J Immunol. 2006 Jan. 1; 176 (1): 346-56; J Biol Chem. 2006 Aug. 18; 281 (33): 23514-24; Int Immunol. 2006 December; 18 (12): 1759-69; Nat Biotechnol. 2010 February; 28 (2): 157-9; WO2006/019447; WO2006/053301; and WO2009/086320) or amino acid substitution to improve antibody heterogeneity or stability ((WO2009/041613)) may be added thereto.

In the present invention, the term "antibody" is used in the broadest sense and also includes any antibody such as monoclonal antibodies (including whole monoclonal antibodies), polyclonal antibodies, antibody variants, antibody fragments, multispecific antibodies (e.g., bispecific antibodies), chimeric antibodies, and humanized antibodies as long as the antibody exhibits the desired biological activity.

The antibody of the present invention is not limited by the type of its antigen, its origin, etc., and may be any antibody. Examples of the origin of the antibody can include, but are not particularly limited to, human antibodies, mouse antibodies, rat antibodies, and rabbit antibodies.

The antibody can be prepared by a method well known to those skilled in the art. For example, the monoclonal antibodies may be produced by a hybridoma method (Kohler and Milstein, Nature 256: 495 (1975)) or a recombination method (U.S. Pat. No. 4,816,567). Alternatively, the monoclonal antibodies may be isolated from phage-displayed antibody libraries (Clackson et al., Nature 352: 624-628 (1991); and Marks et al., J. Mol. Biol. 222: 581-597 (1991)). Also, the monoclonal antibodies may be isolated from single B cell clones (N. Biotechnol. 28 (5): 253-457 (2011)).

The humanized antibodies are also called reshaped human antibodies. Specifically, for example, a humanized antibody consisting of a non-human animal (e.g., mouse) antibody CDR-grafted human antibody is known in the art. General gene recombination approaches are also known for obtaining the humanized antibodies. Specifically, for example, overlap extension PCR is known in the art as a method for grafting mouse antibody CDRs to human FRs.

DNAs encoding antibody variable domains each comprising three CDRs and four FRs linked and DNAs encoding human antibody constant domains can be inserted into expression vectors such that the variable domain DNAs are fused in frame with the constant domain DNAs to prepare vectors for humanized antibody expression. These vectors having the inserts are transferred to hosts to establish recombinant cells. Then, the recombinant cells are cultured for the expression of the DNAs encoding the humanized antibodies to produce the humanized antibodies into the cultures of the cultured cells (see European Patent Publication No. EP 239400 and International Publication No. WO1996/002576).

If necessary, FR amino acid residue(s) may be substituted such that the CDRs of the reshaped human antibody form an appropriate antigen-binding site. For example, the amino acid sequence of FR can be mutated by the application of the PCR method used in the mouse CDR grafting to the human FRs.

The desired human antibody can be obtained by DNA immunization using transgenic animals having all repertoires of human antibody genes (see International Publication Nos. WO1993/012227, WO1992/003918, WO1994/002602, WO1994/025585, WO1996/034096, and WO1996/033735) as immunized animals.

In addition, a technique of obtaining human antibodies by panning using human antibody libraries is also known. For example, a human antibody V region is expressed as a single-chain antibody (scFv) on the surface of phages by a phage display method. A phage expressing antigen-binding scFv can be selected. The gene of the selected phage can be analyzed to determine a DNA sequence encoding the V region of the antigen-binding human antibody. After the determination of the DNA sequence of the antigen-binding scFv, the V region sequence can be fused in frame with the sequence of the desired human antibody C region and then inserted to appropriate expression vectors to prepare expression vectors. The expression vectors are transferred to the preferred expression cells listed above for the expression of the genes encoding the human antibodies to obtain the human antibodies. These methods are already known in the art (see International Publication Nos. WO1992/001047, WO1992/020791, WO1993/006213, WO1993/011236, WO1993/019172, WO1995/001438, and WO1995/015388).

In addition to the phage display technique, for example, a technique using a cell-free translation system, a technique of displaying an antigen-binding molecule on the surface of a cell or a virus, and a technique using an emulsion are known as techniques for obtaining a human antibody by panning using a human antibody library. For example, a ribosome display method which involves forming a complex of mRNA and a translated protein via a ribosome by the removal of a stop codon, etc., a cDNA or mRNA display method which involves covalently binding a translated protein to a gene sequence using a compound such as puromycin, or a CIS display method which involves forming a complex of a gene and a translated protein using a nucleic acid-binding protein, can be used as the technique using a cell-free translation system. The phage display method as well as an E. coli display method, a gram-positive bacterium display method, a yeast display method, a mammalian cell display method, a virus display method, or the like can be used as the technique of displaying an antigen-binding molecule on the surface of a cell or a virus. For example, an in vitro virus display method using a gene and a translation-related molecule enclosed in an emulsion can be used as the technique using an emulsion. These methods have already been known in the art (Nat Biotechnol. 2000 December; 18 (12): 1287-92; Nucleic Acids Res. 2006; 34 (19): e127; Proc Natl Acad Sci USA. 2004 Mar. 2; 101 (9): 2806-10; Proc Natl Acad Sci USA. 2004 Jun. 22; 101 (25): 9193-8; Protein Eng Des Sel. 2008 April; 21 (4): 247-55; Proc Natl Acad Sci USA. 2000 Sep. 26; 97 (20): 10701-5; MAbs. 2010 September-October; 2 (5): 508-18; and Methods Mol Biol. 2012; 911: 183-98).

The variable regions binding to a third antigen of the present invention can be variable regions that recognize an arbitrary antigen. The variable regions binding to a third antigen of the present invention can be variable regions that recognize a molecule specifically expressed in a cancer tissue.

In the present specification, the "third antigen" is not particularly limited and may be any antigen. Examples of the antigen include 17-IA, 4Dc, 6-keto-PGF1a, 8-iso-PGF2a, 8-oxo-dG, A1 Adenosine Receptor, A33, ACE, ACE-2, Activin, Activin A, Activin AB, Activin B, Activin C, Activin RIA, Activin RIA ALK-2, Activin RIB ALK-4, Activin RIIA, Activin RIIB, ADAM, ADAM10, ADAM12, ADAM15, ADAM17/TACE, ADAM8, ADAM9, ADAMTS, ADAMTS4, ADAMTS5, Addressins, adiponectin, ADP ribosyl cyclase-1, aFGF, AGE, ALCAM, ALK, ALK-1, ALK-7, allergen, alpha1-antichemotrypsin, alpha1-antitrypsin, alpha-synuclein, alpha-V/beta-1 antagonist, aminin, amylin, amyloid beta, amyloid immunoglobulin heavy chain variable region. amyloid immunoglobulin light chain variable region, Androgen, ANG, angiotensinogen, Angiopoietin ligand-2, anti-Id, antithrombinIII, Anthrax, APAF-1, APE, APJ, apo A, apo serum amyloid A, Apo-SAA, APP, APRIL, AR, ARC, ART, Artemin, ASPARTIC, Atrial natriuretic factor, Atrial natriuretic peptide, atrial natriuretic peptides A, atrial natriuretic peptides B, atrial natriuretic peptides C, av/b3 integrin, Ax1, B7-1, B7-2, B7-H, BACE, BACE-1, *Bacillus anthracis* protective antigen, Bad, BAFF, BAFF-R, Bag-1, BAK, Bax, BCA-1, BCAM, BcI, BCMA, BDNF, b-ECGF, beta-2-microglobulin, betalactamase, bFGF, BID, Bik, BIM, BLC, BL-CAM, BLK, B-lymphocyte Stimulator (BlyS), BMP, BMP-2 (BMP-2a), BMP-3 (Osteogenin), BMP-4 (BMP-2b), BMP-5, BMP-6 (Vgr-1), BMP-7 (OP-1), BMP-8 (BMP-8a), BMPR, BMPR-IA (ALK-3), BMPR-IB (ALK-6), BMPR-II (BRK-3), BMPs, BOK, Bombesin, Bone-derived neurotrophic factor, bovine growth hormone, BPDE, BPDE-DNA, BRK-2, BTC, B-lymphocyte cell adhesion molecule, C10, C1-inhibitor, C1q, C3, C3a, C4, C5, C5a (complement 5a), CA125, CAD-8, Cadherin-3, Calcitonin, cAMP, Carbonic anhydrase-IX, carcinoembryonic antigen (CEA), carcinoma-associated antigen, Cardiotrophin-1, Cathepsin A, Cathepsin B, Cathepsin C/DPPI, Cathepsin D, Cathepsin E, Cathepsin H, Cathepsin L, Cathepsin O, Cathepsin S, Cathepsin V, Cathepsin X/Z/P, CBL, CCI, CCK2, CCL, CCL1/I-309, CCL11/Eotaxin, CCL12/MCP-5, CCL13/MCP-4, CCL14/HCC-1, CCL15/HCC-2, CCL16/HCC-4, CCL17/TARC, CCL18/PARC, CCL19/ELC, CCL2/MCP-1, CCL20/MIP-3-alpha, CCL21/SLC, CCL22/MDC, CCL23/MPIF-1, CCL24/Eotaxin-2, CCL25/TECK, CCL26/Eotaxin-3, CCL27/CTACK, CCL28/MEC, CCL3/M1P-1-alpha, CCL3L1/LD-78-beta, CCL4/MIP-1-beta, CCL5/RANTES, CCL6/C10, CCL7/MCP-3, CCL8/MCP-2, CCL9/10/MTP-1-gamma, CCR, CCR1, CCR10, CCR2, CCR3, CCR4, CCR5, CCR6, CCR7, CCR8, CCR9, CD1, CD10, CD105, CD11a, CD11b, CD11c, CD123, CD13, CD137, CD138, CD14, CD140a, CD146, CD147, CD148, CD15, CD152, CD16, CD164, CD18, CD19, CD2, CD20, CD21, CD22, CD23, CD25, CD26, CD27L, CD28, CD29, CD3, CD30, CD30L, CD32, CD33 (p67 proteins), CD34, CD37, CD38, CD3E, CD4, CD40, CD40L, CD44, CD45, CD46, CD49a, CD49b, CD5, CD51, CD52, CD54, CD55, CD56, CD6, CD61, CD64, CD66e, CD7, CD70, CD74, CD8, CD80 (B7-1), CD89, CD95, CD105, CD158a, CEA, CEACAM5, CFTR, cGMP, CGRP receptor, CINC, CKb8-1, Claudin18, CLC, *Clostridium botulinum* toxin, *Clostridium difficile* toxin, *Clostridium perfringens* toxin, c-Met, CMV, CMV UL, CNTF, CNTN-1, complement factor 3 (C3), complement factor D, corticosteroid-binding globulin, Colony stimulating factor-1 receptor, COX, C-Ret, CRG-2, CRTH2, CT-1, CTACK, CTGF, CTLA-4, CX3CL1/Fractalkine, CX3CR1, CXCL, CXCL1/Gro-alpha, CXCL10, CXCL11/I-TAC, CXCL12/SDF-1-alpha/beta, CXCL13/BCA-1, CXCL14/BRAK, CXCL15/Lungkine. CXCL16, CXCL16, CXCL2/Gro-beta CXCL3/Gro-gamma, CXCL3, CXCL4/PF4, CXCL5/ENA-78, CXCL6/GCP-2, CXCL7/NAP-2, CXCL8/IL-8, CXCL9/Mig, CXCLlO/IP-10, CXCR, CXCR1, CXCR2, CXCR3, CXCR4, CXCR5, CXCR6, cystatin C, cytokeratin tumor-associated antigen, DAN, DCC, DcR3, DC-SIGN, Decay accelerating factor, Delta-like protein ligand 4, des(1-3)-IGF-1 (brain IGF-1), Dhh, DHICA oxidase, Dickkopf-1, digoxin, Dipeptidyl peptidase IV, DKl, DNAM-1, Dnase, Dpp, DPPIV/CD26, Dtk, ECAD, EDA, EDAA1, EDA-A2, EDAR, EGF, EGFR (ErbB-1), EGF like domain containing protein 7, Elastase, elastin, EMA, EMMPRIN, ENA, ENA-78, Endosialin, endothelin receptor, endotoxin, Enkephalinase, eNOS, Eot, Eotaxin, Eotaxin-2, eotaxini, EpCAM, Ephrin B2/EphB4, Epha2 tyrosine kinase receptor, epidermal growth factor receptor (EGFR), ErbB2 receptor, ErbB3 tyrosine kinase receptor, ERCC, EREG, erythropoietin (EPO), Erythropoietin receptor, E-selectin, ET-1, Exodus-2, F protein of RSV, F10, F11, F12, F13, F5, F9, Factor Ia, Factor IX, Factor Xa, Factor VII, factor VIII, Factor VIIIc, Fas, FcalphaR, FcepsilonRI, FcgammaIIb, FcgammaRI, FcgammaRIIa, FcgammaRIIIa, FcgammaRIIIb, FcRn, FEN-1, Ferritin, FGF, FGF-19, FGF-2, FGF-2 receptor, FGF-3, FGF-8, FGF-acidic, FGF-basic, Fibrin, fibroblast activation protein (FAP), fibroblast growth factor, fibroblast growth factor-10, fibronectin, FL, FLIP, Flt-3, FLT3 ligand, Folate receptor, follicle stimulating hormone (FSH), Fractalkine (CX3C), free heavy chain, free light chain, FZD1, FZD10, FZD2, FZD3, FZD4, FZD5, FZD6, FZD7, FZD8, FZD9, G250, Gas 6, GCP-2, GCSF, G-CSF, G-CSF receptor, GD2, GD3, GDF, GDF-1, GDF-15 (MIC-1), GDF-3 (Vgr-2), GDF-5 (BMP-14/CDMP-1), GDF-6 (BMP-13/CDMP-2), GDF-7 (BMP-12/CDMP-3), GDF-8 (Myostatin), GDF-9, GDNF, Gelsolin, GFAP, GF-CSF, GFR-alphal, GFR-alpha2, GFR-alpha3, GF-beta 1, gH envelope glycoprotein, GITR, Glucagon, Glucagon receptor, Glucagon-like peptide 1 receptor, Glut 4, Glutamate carboxypeptidase II, glycoprotein hormone receptors, glycoprotein IIb/IIIa (GP IIb/IIIa), Glypican-3, GM-CSF, GM-CSF receptor, gp130, gp140, gp72, granulocyte-CSF (G-CSF), GRO/MGSA, Growth hormone releasing factor, GRO-beta, GRO-gamma, *H. pylori*, Hapten (NP-cap or NIP-cap), HB-EGF, HCC, HCC 1, HCMV gB envelope glycoprotein, HCMV UL, Hemopoietic growth factor (HGF), Hep B gp120, heparanase, heparin cofactor II, hepatic growth factor, *Bacillus anthracis* protective antigen, Hepatitis C virus E2 glycoprotein, Hepatitis E, Hepcidin, Her1, Her2/neu (ErbB-2), Her3 (ErbB-3), Her4 (ErbB-4), herpes simplex virus (HSV) gB glycoprotein, HGF, HGFA, High molecular weight melanoma-associated antigen (HMW-MAA), HIV envelope proteins such as GP120, HIV MIB gp 120 V3 loop, HLA, HLA-DR, HM1.24, HMFG PEM, HMGB-1, HRG, Hrk, HSP47, Hsp90, HSV gD glycoprotein, human cardiac myosin, human cytomegalovirus (HCMV), human growth hormone (hGH), human serum albumin, human tissue-type plasminogen activator (t-PA), Huntingtin, HVEM, IAP, ICAM, ICAM-1, ICAM-3, ICE, ICOS, IFN-alpha, IFN-beta, IFN-gamma, IgA, IgA receptor, IgE, IGF, IGF binding proteins, IGF-1, IGF-1 R, IGF-2, IGFBP, IGFR, IL, IL-1, IL-10, IL-10 receptors, IL-11, IL-11 receptors, IL-12, IL-12 receptors, IL-13, IL-13 receptors, IL15, IL-15 receptors, IL-16, IL-16 receptors, IL-17, IL-17 receptors, IL-18 (IGIF), IL18 receptors, IL-1alpha, IL-1beta, IL-1 receptors, IL-2, IL-2 receptors, IL-20, IL-20 receptors, IL-21, IL-21 receptors, IL-23, IL-23 receptors, IL-2 receptors, IL-3, IL-3 receptors, IL-31, IL-31 receptors, IL-3 receptors, IL-4, IL-4 receptors IL-5, IL-5 receptors, IL-6, IL-6 receptors, IL-7, IL-7 receptors, IL-8, IL-8 receptors, IL-9, IL-9 receptors, immunoglobulin immune complex, immunoglobulins, INF-alpha, INF-alpha receptors, INF-beta, INF-beta receptors, INF-gamma, INF-gamma receptors, IFN type-I, IFN type-I receptor, influenza, inhibin, Inhibin alpha, Inhibin beta, iNOS, insulin, Insulin A-chain, Insulin B-chain, Insulin-like growth factor 1, insulin-like growth factor 2, insulin-like growth factor binding proteins, integrin, integrin alpha2, integrin alpha3, integrin alpha4, integrin alpha4/beta1, integrin alpha-V/beta-3, integrin alpha-V/beta-6, integrin alpha4/beta7, integrin alpha5/beta1, integrin alpha5/beta3, integrin alpha5/beta6, integrin alpha sigma (alphaV), integrin alpha theta, integrin beta1, integrin beta2, integrin beta3(GPIIb-IIIa), IP-10, I-TAC, JE, kalliklein, Kallikrein 11, Kallikrein 12, Kallikrein 14, Kallikrein 15, Kallikrein 2, Kallikrein 5, Kallikrein 6, Kallikrein L1, Kallikrein L2, Kallikrein L3, Kallikrein L4, kallistatin, KC, KDR, Keratinocyte Growth Factor (KGF), Keratinocyte Growth Factor-2 (KGF-2), KGF, killer immunoglobulin-like receptor, kit ligand (KL), Kit tyrosine kinase, laminin 5, LAMP, LAPP (Amylin, islet-amyloid polypeptide), LAP (TGF-1), latency associated peptide, Latent TGF-1, Latent TGF-1 bp, LBP, LDGF, LDL, LDL receptor, LECT2, Lefty, Leptin, leutinizing hormone (LH), Lewis-Y antigen, Lewis-Y related antigen, LFA-1, LFA-3, LFA-3 receptors, Lfo, LIF, LIGHT, lipoproteins, LIX, LKN, Lptn, L-Selectin, LT-a, LT-b, LTB4, LTBP-1, Lung surfactant, Luteinizing hormone, Lymphotactin, Lymphotoxin Beta Receptor, Lysosphingolipid receptor, Mac-1, macrophage-CSF (M-CSF), MAdCAM, MAG, MAP2, MARC, maspin, MCAM, MCK-2, MCP, MCP-1, MCP-2, MCP-3, MCP-4, MCP-I (MCAF), M-CSF, MDC, MDC (67 a.a.), MDC (69 a.a.), megsin, Mer, MET tyrosine kinase receptor family, METALLOPRO- TEASES, Membrane glycoprotein OX2, Mesothelin, MGDF receptor, MGMT, MHC (HLA-DR), microbial protein, MIF, MIG, MIP, MIP-1 alpha, MIP-1 beta, MIP-3 alpha, MIP-3 beta, MIP-4, MK, MMAC1, MMP, MMP-1, MMP-10, MMP-11, MMP12, MMP-13, MMP-14, MMP-15, MMP-2, MMP-24, MMP-3, MMP-7, MMP-8, MMP-9, monocyte attractant protein, monocyte colony inhibitory factor, mouse gonadotropin-associated peptide, MPIF, Mpo, MSK, MSP, MUC-16, MUC18, mucin (Mud), Muellerian-inhibiting substance, Mug, MuSK, Myelin associated glycoprotein, myeloid progenitor inhibitor factor-1 (MPIF-I), NAIP, Nanobody, NAP, NAP-2, NCA 90, NCAD, N-Cadherin, NCAM, Neprilysin, Neural cell adhesion molecule, neroserpin, Neuronal growth factor (NGF), Neurotrophin-3, Neurotrophin-4, Neurotrophin-6, Neuropilin 1, Neurturin, NGF-beta, NGFR, NKG20, N-methionyl human growth hormone, nNOS, NO, Nogo-A, Nogo receptor, non-structural protein type 3 (NS3) from the hepatitis C virus, NOS, Npn, NRG-3, NT, NT-3, NT-4, NTN, OB, OGG1, Oncostatin M, OP-2, OPG, OPN, OSM, OSM receptors, osteoinductive factors, osteopontin, OX40L, OX40R, oxidized LDL, p150, p95, PADPr, parathyroid hormone, PARC, PARP, PBR, PBSF, PCAD, P-Cadherin, PCNA, PCSK9, PDGF, PDGF receptor, PDGF-AA, PDGF-AB, PDGF-BB, PDGF-D, PDK-1, PECAM, PEDF, PEM, PF-4, PGE, PGF, PGI2, PGJ2, PIGF, PIN, PLA2, Placenta growt h factor, placental alkaline phosphatase (PLAP), placental lactogen, plasminogen activator inhibitor-1, platelet-growth factor, plgR, PLP, poly glycol chains of different size (e.g. PEG-20, PEG-30, PEG40), PP14, prekallikrein, prion protein, procalcitonin, Programmed cell death protein 1, proinsulin, prolactin, Proprotein convertase PC9, prorelaxin, prostate specific membrane antigen (PSMA), Protein A, Protein C, Protein D, Protein S, Protein Z, PS, PSA, PSCA, PsmAr, PTEN, PTHrp, Ptk, PTN, P-selectin glycoprotein ligand-1, R51, RAGE, RANK, RANKL, RANTES, relaxin, Relaxin A-chain, Relaxin B-chain, renin, respiratory syncytial virus (RSV) F, Ret, reticulon 4, Rheumatoid factors, RLI P76, RPA2, RPK-1, RSK, RSV Fgp, 5100, RON-8, SCF/KL, SCGF, Sclerostin, SDF-1, SDF1 alpha, SDF1 beta, SERINE, Serum Amyloid P, Serum albumin, sFRP-3, Shh, Shiga like toxin II, SIGIRR, SK-1, SLAM, SLPI, SMAC, SMDF, SMOH, SOD, SPARC, sphingosine 1-phosphate receptor 1, Staphylococcal lipoteichoic acid, Stat, STEAP, STEAP-II, stem cell factor (SCF), streptokinase, superoxide dismutase, syndecan-1, TACE, TACI, TAG-72 (tumor-associated glycoprotein-72), TARC, TB, TCA-3, T-cell receptor alpha/beta, TdT, TECK, TEM1, TEM5, TEM7, TEM8, Tenascin, TERT, testicular PLAP-like alkaline phosphatase, TfR, TGF, TGF-alpha, TGF-beta, TGF-beta Pan Specific, TGF-beta RII, TGF-beta RIb, TGF-beta RIII, TGF-beta R1 (ALK-5), TGF-beta1, TGF-beta2, TGF-beta3, TGF-beta4, TGF-beta5, TGF-I, Thrombin, thrombopoietin (TPO), Thymic stromal lymphoprotein receptor, Thymus Ck-1, thyroid stimulating hormone (TSH), thyroxine, thyroxine-binding globulin, Tie, TIMP, TIQ, Tissue Factor, tissue factor protease inhibitor, tissue factor protein, TMEFF2, Tmpo, TMPRSS2, TNF receptor I, TNF receptor II, TNF-alpha, TNF-beta, TNF-beta2, TNFc, TNF-RI, TNF-RII, TNFRSF10A (TRAIL R1 Apo-2/DR4), TNFRSF10B (TRAIL R2 DR5/KILLER/TRICK-2A/TRICK-B), TNFRSF10C (TRAIL R3 DcR1/LIT/TRID), TNFRSF10D (TRAIL R4 DcR2/TRUNDD), TNFRSF11A (RANK ODF R/TRANCE R), TNFRSF11B (OPG OCIF/TR1), TNFRSF12 (TWEAK R FN14), TNFRSF12A, TNFRSF13B (TACI), TNFRSF13C (BAFF R), TNFRSF14 (HVEM ATAR/HveA/LIGHT R/TR2), TNFRSF16 (NGFR p75NTR), TNFRSF17 (BCMA), TNFRSF18 (GITR AITR), TNFRSF19 (TROY TAJ/TRADE), TNFRSF19L (RELT), TNFRSF1A (TNF R1 CD120a/p55-60), TNFRSF1B (TNF RII CD120b/p75-80), TNFRSF21 (DR6), TNFRSF22 (DcTRAIL R2 TNFRH2), TNFRSF25 (DR3 Apo-3/LARD/TR-3/TRAMP/WSL-1), TNFRSF26 (TNFRH3), TNFRSF3 (LTbR TNF RIII/TNFC R), TNFRSF4 (OX40 ACT35/TXGP1 R), TNFRSF5 (CD40 p50), TNFRSF6 (Fas Apo-1/APT1/CD95), TNFRSF6B (DcR3 M68/TR6), TNFRSF7 (CD27), TNFRSF8 (CD30), TNFRSF9 (4-1 BB CD137/ILA), TNFRST23 (DcTRAIL R1 TNFRH1), TNFSF10 (TRAIL Apo-2 Ligand/TL2), TNFSF11 (TRANCE/RANK Ligand ODF/OPG Ligand), TNFSF12 (TWEAK Apo-3 Ligand/DR3 Ligand), TNFSF13 (APRIL TALL2), TNFSF13B (BAFF BLYS/TALL1/THANK/TNFSF20), TNFSF14 (LIGHT HVEM Ligand/LTg), TNFSF15 (TL1A/VEGI), TNFSF18 (GITR Ligand AITR Ligand/TL6), TNFSF1A (TNF-α Conectin/DIF/TNFSF2), TNFSF1B (TNF-b LTa/TNFSF1), TNFSF3 (LTb TNFC/p33), TNFSF4 (OX40 Ligand gp34/TXGP1), TNFSF5 (CD40 Ligand CD154/gp39/HIGM1/IMD3/TRAP), TNFSF6 (Fas Ligand Apo-1 Ligand/APT1 Ligand), TNFSF7 (CD27 Ligand CD70), TNFSF8 (CD30 Ligand CD153), TNFSF9 (4-1 BB Ligand CD137 Ligand), TNF-alpha, TNF-beta, TNIL-I, toxic metabolite, TP-1, t-PA, Tpo, TRAIL, TRAIL R, TRAIL-R1, TRAIL-R2, TRANCE, transferrin receptor, transforming growth factors (TGF) such as TGF-alpha and TGF-beta, Transmembrane glycoprotein NMB, Transthyretin, TRF, Trk, TROP-2, Trophoblast glycoprotein, TSG, TSLP, Tumor Necrosis Factor (TNF), tumor-associated antigen CA 125, tumor-associated antigen expressing Lewis Y related carbohydrate, TWEAK, TXB2, Ung, uPAR, uPAR-1, Urokinase, VAP-1, vascular endothelial growth factor (VEGF), vaspin, VCAM, VCAM-1, VECAD, VE-Cadherin, VE-Cadherin-2, VEFGR-1 (flt-1), VEFGR-2, VEGF receptor (VEGFR), VEGFR-3 (flt-4), VEGI, VIM, Viral antigens, VitB12 receptor, Vitronectin receptor, VLA, VLA-1, VLA-4, VNR integrin, von Willebrand Factor (vWF), WIF-1, WNT1, WNT10A, WNT10B, WNT11, WNT16, WNT2, WNT2B/13, WNT3, WNT3A, WNT4, WNT5A, WNT5B, WNT6, WNT7A, WNT7B, WNT8A, WNT8B, WNT9A, WNT9B, XCL1, XCL2/SCM-1-beta, XCLl/Lymphotactin, XCR1, XEDAR, XIAP, and XPD.

Specific examples of the molecule specifically expressed on a T cell include CD3 and T cell receptors. Particularly, CD3 is preferred. In the case of, for example, human CD3, a site in the CD3 to which the antigen-binding molecule of the present invention binds may be any epitope present in a gamma chain, delta chain, or epsilon chain sequence constituting the human CD3. Particularly, an epitope present in the extracellular region of an epsilon chain in a human CD3 complex is preferred. The polynucleotide sequences of the gamma chain, delta chain, and epsilon chain structures constituting CD3 are shown in SEQ ID NOs: 170 (NM_000073.2), 172 (NM_000732.4), and 174 (NM_000733.3), and the polypeptide sequences thereof are shown in SEQ ID NOs: 171 (NP_000064.1), 173 (NP_000723.1), and 175 (NP_000724.1) (RefSeq registration numbers are shown within the parentheses).

One of the two variable regions of the antibody included in the antigen-binding molecule of the present invention binds to a "third antigen" that is different from the "CD3" and the "CD137" mentioned above. In some embodiments, the third antigen is derived from humans, mice, rats, monkeys, rabbits, or dogs. In some embodiments, the third antigen is a molecule specifically expressed on the cell or the organ derived from humans, mice, rats, monkeys, rabbits, or dogs. The third antigen is preferably, a molecule not systemically expressed on the cell or the organ. The third antigen is preferably, for example, a tumor cell-specific antigen and also includes an antigen expressed in association with the malignant alteration of cells as well as an abnormal sugar chain that appears on cell surface or a protein molecule during the malignant transformation of cells. Specific examples thereof include ALK receptor (pleiotrophin receptor), pleiotrophin, KS 1/4 pancreatic cancer antigen, ovary cancer antigen (CA125), prostatic acid phosphate, prostate-specific antigen (PSA), melanoma-associated antigen p97, melanoma antigen gp75, high-molecular-weight melanoma antigen (HMW-MAA), prostate-specific membrane antigen, carcinoembryonic antigen (CEA), polymorphic epithelial mucin antigen, human milk fat globule antigen, colorectal tumor-associated antigen (e.g., CEA, TAG-72, CO17-A, GICA 19-9, CTA-1, and LEA), Burkitt's lymphoma antigen 38.13, CD19, human B lymphoma antigen CD20, CD33, melanoma-specific antigen (e.g., ganglioside GD2, ganglioside GD3, ganglioside GM2, and ganglioside GM3), tumor-specific transplantation antigen (TSTA), T antigen, virus-induced tumor antigen (e.g., envelope antigens of DNA tumor virus and RNA tumor virus), colon CEA, oncofetal antigen alpha-fetoprotein (e.g., oncofetal trophoblastic glycoprotein 5T4 and oncofetal bladder tumor antigen), differentiation antigen (e.g., human lung cancer antigens L6 and L20), fibrosarcoma antigen, human T cell leukemia-associated antigen Gp37, newborn glycoprotein, sphingolipid, breast cancer antigen (e.g., EGFR (epithelial growth factor receptor)), NYBR-16, NY-BR-16 and HER2 antigen (p185HER2), polymorphic epithelial mucin (PEM), malignant human lymphocyte antigen APO-1, differentiation antigen such as I antigen found in fetal erythrocytes, primary endoderm I antigen found in adult erythrocytes, I (Ma) found in embryos before transplantation or gastric cancer, M18 found in mammary gland epithelium, M39, SSEA-1 found in bone marrow cells, VEP8, VEP9, Myl, VIM-D5, D156-22 found in colorectal cancer, TRA-1-85 (blood group H), SCP-1 found in testis and ovary cancers, C14 found in colon cancer, F3 found in lung cancer, AH6 found in gastric cancer, Y hapten, Ley found in embryonic cancer cells, TL5 (blood group A), EGF receptor found in A431 cells, E1 series (blood group B) found in pancreatic cancer, FC10.2 found in embryonic cancer cells, gastric cancer antigen, CO-514 (blood group Lea) found in adenocarcinoma, NS-10 found in adenocarcinoma, CO-43 (blood group Leb), G49 found in A431 cell EGF receptor, MH2 (blood group ALeb/Ley) found in colon cancer, 19.9 found in colon cancer, gastric cancer mucin, T5A7 found in bone marrow cells, R24 found in melanoma, 4.2, GD3, D1.1, OFA-1, GM2, OFA-2, GD2, and M1:22:25:8 found in embryonic cancer cells, SSEA-3 and SSEA-4 found in 4-cell to 8-cell embryos, cutaneous T cell lymphoma-associated antigen, MART-1 antigen, sialyl Tn (STn) antigen, colon cancer antigen NYCO-45, lung cancer antigen NY-LU-12 variant A, adenocarcinoma antigen ART1, paraneoplastic associated brain-testis-cancer antigen (onconeuronal antigen MA2 and paraneoplastic neuronal antigen), neuro-oncological ventral antigen 2 (NOVA2), blood cell cancer antigen gene 520, tumor-associated antigen CO-029, tumor-associated antigen MAGE-C1 (cancer/testis antigen CT7), MAGE-B1 (MAGE-XP antigen), MAGE-B2 (DAM6), MAGE-2, MAGE-4a, MAGE-4b MAGE-X2, cancer-testis antigen (NY-EOS-1), YKL-40, and any fragment of these polypeptides, and modified structures thereof (aforementioned modified phosphate groups, sugar chains, etc.), EpCAM, EREG, CA19-9, CA15-3, sialyl SSEA-1 (SLX), HER2, PSMA, CEA, and CLEC12A.

The term "CD137" herein, also called 4-1BB, is a member of the tumor necrosis factor (TNF) receptor family. Examples of factors belonging to the TNF superfamily or the TNF receptor superfamily include CD137, CD137L, CD40, CD40L, OX40, OX40L, CD27, CD70, HVEM, LIGHT, RANK, RANKL, CD30, CD153, GITR, and GITRL.

In one aspect, an antigen-binding molecule of the present invention has at least one characteristic selected from the group consisting of (1) to (4) below:
(1) the variable region binds to an extracellular domain of CD3 epsilon comprising the amino acid sequence of SEQ ID NO: 91,
(2) the antigen-binding molecule has an agonistic activity against CD137,
(3) the antigen-binding molecule induces CD3 activation of a T cell against a cell expressing the molecule of the third antigen, but does not induce activation of a T cell against a cell expressing CD137, and
(4) the antigen-binding molecule does not induce release of a cytokine from PBMC in the absence of a cell expressing the molecule of the third antigen.

In one aspect, an antigen-binding molecule of the present invention has at least one characteristic selected from the group consisting of (1) to (4) below:
(1) the variable region binds to an extracellular domain of CD3 epsilon comprising the amino acid sequence of SEQ ID NO: 91,
(2) the antigen-binding molecule has an agonistic activity against CD137,
(3) the antigen-binding molecule induces cytotoxicity of a T cell against a cell expressing the molecule of the third antigen, but does not induce activation of a T cell against a cell expressing CD137, and
(4) the antigen-binding molecule does not induce release of a cytokine from PBMC in the absence of a cell expressing the molecule of the third antigen.

In some embodiments, an antigen-binding molecule of the present invention has at least one characteristic selected from the group consisting of (1) to (2) below:
(1) the antigen-binding molecule does not compete for binding to CD137 with CD137 ligand, and
(2) the antigen-binding molecule induces cytotoxicity of a T cell against a cell expressing the molecule of the third antigen, but does not induce cytotoxicity of a T cell against a cell expressing CD137.

In one aspect, the "CD137 agonist antibody" or "antigen-binding molecule having an agonistic activity against CD137" of the present invention refers to an antibody or an antigen-binding molecule that activates cells expressing CD137 by at least about 5%, specifically at least about 10%, or more specifically at least about 15% when added to the cells, tissues, or living bodies that express CD137, where 0% activation is the background level (e.g. IL6 secretion and so on) of the non-activation cells expressing CD137. In various specific examples, the CD137 agonist antibody for use as a pharmaceutical composition of the present invention can activate the activity of the cells by at least about 20%, 30%, 40%, 50%, 60%, 70%, 80%, 90%, 100%, 125%, 150%, 175%, 200%, 250%, 300%, 350%, 400%, 450%, 500%, 750%, or 1000%.

In one aspect, the "CD137 agonist antibody" or "antigen-binding molecule having an agonistic activity against CD137" of the present invention also refers to an antibody or an antigen-binding molecule that activates cells expressing CD137 by at least about 5%, specifically at least about 10%, or more specifically at least about 15% when added to the cells, tissues, or living bodies that express CD137, where 100% activation is the level of activation achieved by an equimolar amount of a binding partner under physiological conditions. In various specific examples, the CD137 agonist antibody for use as a pharmaceutical composition of the present invention can activate the activity of the cells by at least about 5%, 10%, 20%, 30%, 40%, 50%, 60%, 70%, 80%, 90%, 100%, 125%, 150%, 175%, 200%, 250%, 300%, 350%, 400%, 450%, 500%, 750%, or 1000%. In some embodiments, "a binding partner" used herein is a molecule which is known to bind to CD137 and induce the activation of cells expressing CD137. In further embodiments, examples of the binding partner include Urelumab (CAS Registry No. 934823-49-1) and its variants described in WO2005/035584A1, Utomilumab (CAS Registry No. 1417318-27-4) and its variants described in WO2012/032433A1, and various known CD137 agonist antibodies. In certain embodiments, examples of the binding partner include CD137 ligands. In further embodiments, the activation of cells expressing CD137 by an anti-CD137 agonist antibody may be determined using an ELISA to characterize IL6 secretion (See, e.g., Example 10-2, herein). The anti-CD137 antibody used as the binding partner and the antibody concentration for the measurements can be referred to Example 10-2, where 100% activation is the level of activation achieved by the antibody. In further embodiments, an antibody comprising the heavy chain amino acid sequence of SEQ ID NO: 69 and the light chain amino acid sequence of SEQ ID NO: 71 can be used at 30 ug/mL for the measurements as the binding partner (See, e.g., Example 10-2, herein).

As a non-limiting embodiment, the present invention provides a "CD137 agonist antibody" comprising an Fc region, wherein the Fc region has an enhanced binding activity towards an inhibitory Fc gamma receptor.

As a non-limiting embodiment, the CD137 agonistic activity can be confirmed using B cells, which are known to express CD137 on their surface. As a non-limiting embodiment, HDLM-2 B cell line can be used as B cells. The CD137 agonistic activity can be evaluated by the amount of human Interleukin-6 (IL-6) produced because the expression of IL-6 is induced as a result of the activation of CD137. In this evaluation, it is possible to determine how much % of CD137 agonistic activity the evaluated molecule has by evaluating the increased amount of IL-6 expression by using the amount of IL-6 from non-activating B cells as 0% background level.

In some embodiments, the antigen-binding molecule of the present invention induces CD3 activation of T cells against cells expressing the molecule of a third antigen, but does not induce CD3 activation of T cells against cells expressing CD137. Whether an antigen-binding molecule induces CD3 activation of T cells against cells expressing a third antigen can be determined by, for example, co-culturing T cells with cells expressing the third antigen in the presence of the antigen-binding molecule, and assaying CD3 activation of the T cells. T cell activation can be assayed by, for example, using recombinant T cells that express a reporter gene (e.g. luciferase) in response to CD3 signaling, and detecting the expression of the reporter gene or the activity of the reporter gene product as an index of the activation of the T cells. When recombinant T cells that express a reporter gene in response to CD3 signaling are co-cultured with cells expressing a third antigen in the presence of an antigen-binding molecule, detection of the expression of the reporter gene or the activity of the reporter gene product in a manner dependent on the dose of the antigen-binding molecule indicates that the antigen-binding molecule induces activation of T cells against cells expressing the third antigen. Similarly, whether an antigen-binding molecule does not induce CD3 activation of T cells against cells expressing CD137 can be determined by, for example, co-culturing T cells with cells expressing CD137 in the presence of the antigen-binding molecule, and assaying CD3 activation of the T cells as described above. When recombinant T cells that express a reporter gene in response to CD3 signaling are co-cultured with cells expressing CD137 in the presence of an antigen-binding molecule, the antigen-binding molecule is determined not to induce activation of T cells against cells expressing CD137 if the expression of the reporter gene or the activity of the reporter gene product is absent or below a detection limit or below that of negative control. In one aspect, when recombinant T cells that express a reporter gene in response to CD3 signaling are co-cultured with cells expressing CD137 in the presence of an antigen-binding molecule, the antigen-binding molecule is determined not to induce activation of T cells against cells expressing CD137 if the expression of the reporter gene or the activity of the reporter gene product is at most about 50%, 30%, 20%, 10%, 5% or 1%, where 100% activation is the level of activation achieved by an antigen-binding molecule which binds to CD3 and CD137 at the same time. In one aspect, when recombinant T cells that express a reporter gene in response to CD3 signaling are co-cultured with cells expressing CD137 in the presence of an antigen-binding molecule, the antigen-binding molecule is determined not to induce activation of T cells against cells expressing CD137 if the expression of the reporter gene or the activity of the reporter gene product is at most about 50%, 30%, 20%, 10%, 5% or 1%, where 100% activation is the level of activation achieved by the same antigen-binding molecule against cells expressing the molecule of a third antigen.

In some embodiments, the antigen-binding molecule of the present invention does not induce a cytokine release from PBMCs in the absence of cells expressing the molecule of a third antigen. Whether an antigen-binding molecule does not induce release of cytokines in the absence of cells expressing a third antigen can be determined by, for example, incubating PBMCs with the antigen-binding molecule in the absence of cells expressing a third antigen, and measuring cytokines such as IL-2, IFN gamma, and TNF alpha released from the PBMCs into the culture supernatant using methods known in the art. If no significant levels of cytokines are detected or no significant induction of cytokines expression occurred in the culture supernatant of PBMCs that have been incubated with an antigen-binding molecule in the absence of cells expressing a third antigen, the antigen-binding molecule is determined not to induce a cytokine release from PBMCs in the absence of cells expressing a third antigen. In one aspect, "no significant levels of cytokines" also refers to the level of cytokines concentration that is about at most 50%, 30%, 20%, 10%, 5% or 1%, where 100% is the cytokine concentration achieved by an antigen-binding molecule which binds to CD3 and CD137 at the same time. In one aspect, "no significant levels of cytokines" also refers to the level of cytokines concentration that is about at most 50%, 30%, 20%, 10%, 5% or 1%, where 100% is the cytokine concentration achieved in the presence of cells expressing the molecule of a third antigen. In one aspect, "no significant induction of cytokines expression" also refers to the level of cytokines concentration increase that is at most 5-fold, 2-fold or 1-fold of the concentration of each cytokines before adding the antigen-binding molecules.

In some embodiments, an antigen-binding molecule of the present invention competes for binding to CD137 with an antibody selected from the group consisting of:
- (a) an antibody comprising a VH sequence having the amino acid sequence of SEQ ID NO: 30 and a VL sequence having the amino acid sequence of SEQ ID NO: 51,
- (b) an antibody comprising a VH sequence having the amino acid sequence of SEQ ID NO: 46 and a VL sequence having the amino acid sequence of SEQ ID NO: 53,
- (c) an antibody comprising a VH sequence having the amino acid sequence of SEQ ID NO: 40 and a VL sequence having the amino acid sequence of SEQ ID NO: 56,
- (d) an antibody comprising a VH sequence having the amino acid sequence of SEQ ID NO: 30 and a VL sequence having the amino acid sequence of SEQ ID NO: 58, and
- (e) an antibody comprising a VH sequence having the amino acid sequence of SEQ ID NO: 40 and a VL sequence having the amino acid sequence of SEQ ID NO: 61.

In some embodiments, an antigen-binding molecule of the present invention binds to the same epitope as an antibody selected from the group consisting of:
- [1] an antibody comprising the amino acid sequence of SEQ ID NO: 98 as the heavy-chain variable region and the amino acid sequence of SEQ ID NO: 99 as the light-chain variable region;
- [2] an antibody comprising the amino acid sequence of SEQ ID NO: 100 as the heavy-chain variable region and the amino acid sequence of SEQ ID NO: 101 as the light-chain variable region;
- [3] an antibody comprising the amino acid sequence of SEQ ID NO: 102 as the heavy-chain variable region and the amino acid sequence of SEQ ID NO: 103 as the light-chain variable region;
- [4] an antibody comprising the amino acid sequence of SEQ ID NO: 104 as the heavy-chain variable region and the amino acid sequence of SEQ ID NO: 105 as the light-chain variable region;
- [5] an antibody comprising the amino acid sequence of SEQ ID NO: 106 as the heavy-chain variable region and the amino acid sequence of SEQ ID NO: 107 as the light-chain variable region;
- [6] an antibody comprising the amino acid sequence of SEQ ID NO: 108 as the heavy-chain variable region and the amino acid sequence of SEQ ID NO: 109 as the light-chain variable region;
- [7] the antibody of any one of [1] to [6], which comprises the amino acid sequence of SEQ ID NO: 110 as the heavy-chain constant region and the amino acid sequence of SEQ ID NO: 111 or the amino acid sequence of SEQ ID NO: 112 as the light-chain constant region; and
- [8] an antibody that has an activity equivalent to that of the antibody of any one of [1] to [7]; and
- [9] an antibody that binds to the same epitope as the epitope bound by the antibody of any one of [1] to [7].

In the antibody of [8], the "equivalent activity" refers to a CD137 agonist activity that is 70% or more, preferably 80% or more, and more preferably 90% or more of the binding activity of the antibody of any one of [1] to [7].

Whether a test antibody shares a common epitope with a certain antibody can be assessed based on competition between the two antibodies for the same epitope. The competition between antibodies can be detected by a cross-blocking assay or the like. For example, the competitive ELISA assay is a preferred cross-blocking assay. Specifically, in a cross-blocking assay, the CD137 protein used to coat the wells of a microtiter plate is pre-incubated in the presence or absence of a candidate competitor antibody, and then an anti-CD137 antibody of the present invention is added thereto. The amount of the anti-CD137 antibody of the present invention bound to the CD137 protein in the wells is indirectly correlated with the binding ability of a candidate competitor antibody (test antibody) that competes for the binding to the same epitope. That is, the greater the affinity of the test antibody for the same epitope, the lower the amount of the anti-CD137 antibody of the present invention bound to the CD137 protein-coated wells, and the higher the amount of the test antibody bound to the CD137 protein-coated wells.

The amount of the antibody bound to the wells can be readily determined by labeling the antibody in advance. For example, a biotin-labeled antibody can be measured using an avidin/peroxidase conjugate and an appropriate substrate. In particular, a cross-blocking assay that uses enzyme labels such as peroxidase is called a "competitive ELISA assay". The antibody can be labeled with other labeling substances that enable detection or measurement. Specifically, radiolabels, fluorescent labels, and such are known.

Furthermore, when the test antibody has a constant region derived from a species different from that of the anti-CD137 antibody of the present invention, the amount of antibody bound to the wells can be measured by using a labeled antibody that recognizes the constant region of that antibody. Alternatively, if the antibodies are derived from the same species but belong to different classes, the amount of the antibodies bound to the wells can be measured using antibodies that distinguish individual classes.

If a candidate antibody can block binding of an anti-CD137 antibody by at least 20%, preferably by at least 20% to 50%, and even more preferably, by at least 50%, as compared to the binding activity obtained in a control experiment performed in the absence of the candidate competing antibody, the candidate competing antibody is either an antibody that binds substantially to the same epitope or an antibody that competes for binding to the same epitope as an anti-CD137 antibody of the present invention.

In another embodiment, the ability of a test antibody to competitively or cross competitively bind with another antibody can be appropriately determined by those skilled in the art using a standard binding assay such as BIAcore analysis or flow cytometry known in the art.

Methods for determining the spatial conformation of an epitope include, for example, X ray crystallography and two-dimensional nuclear magnetic resonance (see, Epitope Mapping Protocols in Methods in Molecular Biology, G. E. Morris (ed.), Vol. 66 (1996)).

Whether a test antibody shares a common epitope with a CD137 ligand can also be assessed based on competition between the test antibody and CD137 ligand for the same epitope. The competition between antibody and CD137 ligand can be detected by a cross-blocking assay or the like as mentioned above. In another embodiment, the ability of a test antibody to competitively or cross competitively bind with CD137 ligand can be appropriately determined by those skilled in the art using a standard binding assay such as BIAcore analysis or flow cytometry known in the art In some embodiments, favorable examples of an antigen-binding molecule of the present invention include antigen-binding molecules that bind to the same epitope as the human CD137 epitope bound by the antibody selected from the group consisting of:
- antibody that recognize a region comprising the SPCPPNSFSSAGGQRTCD ICRQCKGVFRTRKECSSTSNAECDCTPGFHCLGAGCSMCEQDCKQGQELTK KGC sequence (SEQ ID NO: 81),
- antibody that recognize a region comprising the DCTPGFHCLGAGCSMCEQDC KQGQELTKKGC sequence (SEQ ID NO: 76),
- antibody that recognize a region comprising the LQDPCSNC PAGTFCDNNRNQICSPCPPNSFSSAGGQRTCDICRQCKGVFRTRKECSSTSNA EC sequence (SEQ ID NO: 79), and
- antibody that recognize a region comprising the LQDPCSNCPAGTFCDNNRN QIC sequence (SEQ ID NO: 74) in the human CD137 protein.

Depending on the targeted cancer antigen, those skilled in the art can appropriately select a heavy chain variable region sequence and a light chain variable region sequence that bind to the cancer antigen for the heavy chain variable region and the light chain variable region to be included in the cancer-specific antigen-binding domain. When an epitope bound by an antigen-binding domain is contained in multiple different antigens, antigen-binding molecules containing the antigen-binding domain can bind to various antigens that have the epitope.

"Epitope" means an antigenic determinant in an antigen, and refers to an antigen site to which various binding domains in antigen-binding molecules disclosed herein bind. Thus, for example, an epitope can be defined according to its structure. Alternatively, the epitope may be defined according to the antigen-binding activity of an antigen-binding molecule that recognizes the epitope. When the antigen is a peptide or polypeptide, the epitope can be specified by the amino acid residues that form the epitope. Alternatively, when the epitope is a sugar chain, the epitope can be specified by its specific sugar chain structure.

A linear epitope is an epitope that contains an epitope whose primary amino acid sequence is recognized. Such a linear epitope typically contains at least three and most commonly at least five, for example, about 8 to 10 or 6 to 20 amino acids in its specific sequence.

In contrast to the linear epitope, "conformational epitope" is an epitope in which the primary amino acid sequence containing the epitope is not the only determinant of the recognized epitope (for example, the primary amino acid sequence of a conformational epitope is not necessarily recognized by an epitope-defining antibody). Conformational epitopes may contain a greater number of amino acids compared to linear epitopes. A conformational epitope-recognizing antibody recognizes the three-dimensional structure of a peptide or protein. For example, when a protein molecule folds and forms a three dimensional structure, amino acids and/or polypeptide main chains that form a conformational epitope become aligned, and the epitope is made recognizable by the antibody. Methods for determining epitope conformations include, for example, X ray crystallography, two-dimensional nuclear magnetic resonance spectroscopy, site-specific spin labeling, and electron paramagnetic resonance spectroscopy, but are not limited thereto. See, for example, Epitope Mapping Protocols in Methods in Molecular Biology (1996), Vol. 66, Morris (ed.).

Examples of a method for assessing the binding of an epitope in a cancer-specific antigen by a test antigen-binding molecule are shown below. According to the examples below, methods for assessing the binding of an epitope in a target antigen by another binding domain can also be appropriately conducted.

For example, whether a test antigen-binding molecule that comprises an antigen-binding domain for a cancer-specific antigen recognizes a linear epitope in the antigen molecule can be confirmed for example as mentioned below. For example, a linear peptide comprising an amino acid sequence forming the extracellular domain of a cancer-specific antigen is synthesized for the above purpose. The peptide can be synthesized chemically, or obtained by genetic engineering techniques using a region in a cDNA of a cancer-specific antigen encoding the amino acid sequence that corresponds to the extracellular domain. Then, a test antigen-binding molecule containing an antigen-binding domain for a cancer-specific antigen is assessed for its binding activity towards a linear peptide comprising the extracellular domain-constituting amino acid sequence. For example, an immobilized linear peptide can be used as an antigen to evaluate the binding activity of the antigen-binding molecule towards the peptide by ELISA. Alternatively, the binding activity towards a linear peptide can be assessed based on the level at which the linear peptide inhibits binding of the antigen-binding molecule to cancer-specific antigen-expressing cells. The binding activity of the antigen-binding molecule towards the linear peptide can be demonstrated by these tests.

Whether the above-mentioned test antigen-binding molecule containing an antigen-binding domain towards an antigen recognizes a conformational epitope can be confirmed as below. For example, an antigen-binding molecule that comprises an antigen-binding domain for a cancer-specific antigen strongly binds to cancer-specific antigen-expressing cells upon contact, but does not substantially bind to an immobilized linear peptide comprising an amino acid sequence forming the extracellular domain of the cancer-specific antigen. Herein, "does not substantially bind" means that the binding activity is 80% or less, generally 50% or less, preferably 30% or less, and particularly preferably 15% or less compared to the binding activity to antigen-expressing cells. of ELISA or fluorescence activated cell sorting (FACS) using antigen-expressing cells as antigen.

In the ELISA format, the binding activity of a test antigen-binding molecule comprising an antigen-binding domain towards antigen-expressing cells can be assessed quantitatively by comparing the levels of signals generated by enzymatic reaction. Specifically, a test antigen-binding molecule is added to an ELISA plate onto which antigen-expressing cells are immobilized. Then, the test antigen-binding molecule bound to the cells is detected using an enzyme-labeled antibody that recognizes the test antigen-binding molecule. Alternatively, when FACS is used, a dilution series of a test antigen-binding molecule is prepared, and the antibody-binding titer for antigen-expressing cells can be determined to compare the binding activity of the test antigen-binding molecule towards antigen-expressing cells.

The binding of a test antigen-binding molecule to an antigen expressed on the surface of cells suspended in buffer or the like can be detected using a flow cytometer. Known flow cytometers include, for example, the following devices:

FACSCanto™ II
FACSAria™
FACSArray™
FACSVantage™ SE
FACSCalibur™ (all are trade names of BD Biosciences)
EPICS ALTRA HyPerSort
Cytomics FC 500
EPICS XL-MCL ADC EPICS XL ADC
Cell Lab Quanta/Cell Lab Quanta SC (all are trade names of Beckman Coulter).

Suitable methods for assaying the binding activity of the above-mentioned test antigen-binding molecule comprising an antigen-binding domain towards an antigen include, for example, the method below. First, antigen-expressing cells are reacted with a test antigen-binding molecule, and then this is stained with an FITC-labeled secondary using FACSCalibur (BD). The fluorescence intensity obtained by analysis using the CELL QUEST Software (BD), i.e., the Geometric Mean value, reflects the quantity of antibody bound to the cells. That is, the binding activity of a test antigen-binding molecule, which is represented by the quantity of the test antigen-binding molecule bound, can be measured by determining the Geometric Mean value.

Whether a test antigen-binding molecule comprising an antigen-binding domain of the present invention shares a common epitope with another antigen-binding molecule can be assessed based on competition between the two molecules for the same epitope. The competition between antigen-binding molecules can be detected by a cross-blocking assay or the like. For example, the competitive ELISA assay is a preferred cross-blocking assay.

Specifically, in a cross-blocking assay, the antigen coating the wells of a microtiter plate is pre-incubated in the presence or absence of a candidate competitor antigen-binding molecule, and then a test antigen-binding molecule is added thereto. The quantity of test antigen-binding molecule bound to the antigen in the wells indirectly correlates with the binding ability of a candidate competitor antigen-binding molecule that competes for the binding to the same epitope. That is, the greater the affinity of the competitor antigen-binding molecule for the same epitope, the lower the binding activity of the test antigen-binding molecule towards the antigen-coated wells.

The quantity of the test antigen-binding molecule bound to the wells via the antigen can be readily determined by labeling the antigen-binding molecule in advance. For example, a biotin-labeled antigen-binding molecule can be measured using an avidin/peroxidase conjugate and appropriate substrate. In particular, a cross-blocking assay that uses enzyme labels such as peroxidase is called "competitive ELISA assay". The antigen-binding molecule can also be labeled with other labeling substances that enable detection or measurement. Specifically, radiolabels, fluorescent labels, and such are known.

When the candidate competitor antigen-binding molecule can block the binding of a test antigen-binding molecule comprising an antigen-binding domain by at least 20%, preferably at least 20 to 50%, and more preferably at least 50% compared to the binding activity in a control experiment conducted in the absence of the competitor antigen-binding molecule, the test antigen-binding molecule is determined to substantially bind to the same epitope bound by the competitor antigen-binding molecule, or to compete for binding to the same epitope.

When the structure of an epitope bound by a test antigen-binding molecule comprising an antigen-binding domain of the present invention is already identified, whether the test and control antigen-binding molecules share a common epitope can be assessed by comparing the binding activities of the two antigen-binding molecules towards a peptide prepared by introducing amino acid mutations into the peptide forming the epitope.

As a method for measuring such binding activities, for example, the binding activities of test and control antigen-binding molecules towards a linear peptide into which a mutation is introduced are measured by comparison in the above ELISA format. Besides the ELISA methods, the binding activity towards the mutant peptide bound to a column can be determined by passing the test and control antigen-binding molecules through the column, and then quantifying the antigen-binding molecule eluted in the eluate. Methods for adsorbing a mutant peptide to a column, for example, in the form of a GST fusion peptide, are known.

Alternatively, when the identified epitope is a conformational epitope, whether test and control antigen-binding molecules share a common epitope can be assessed by the following method. First, cells expressing an antigen targeted by an antigen-binding domain and cells expressing an antigen having an epitope introduced with a mutation are prepared. The test and control antigen-binding molecules are added to a cell suspension prepared by suspending these cells in an appropriate buffer such as PBS. Then, the cell suspension is appropriately washed with a buffer, and an FITC-labeled antibody that can recognize the test and control antigen-binding molecules is added thereto. The fluorescence intensity and number of cells stained with the labeled antibody are determined using FACSCalibur (BD). The test and control antigen-binding molecules are appropriately diluted using a suitable buffer, and used at desired concentrations. For example, they may be used at a concentration within the range of 10 micro g/ml to 10 ng/ml. The fluorescence intensity determined by analysis using the CELL QUEST Software (BD), i.e., the Geometric Mean value, reflects the quantity of the labeled antibody bound to the cells. That is, the binding activities of the test and control antigen-binding molecules, which are represented by the quantity of the labeled antibody bound, can be measured by determining the Geometric Mean value.

In some embodiments, an antigen-binding molecule of the present invention comprises an amino acid sequence resulting from introducing alteration of one or more amino acids into a template sequence consisting of a heavy chain variable domain sequence described in SEQ ID NO: 92 and/or a light chain variable domain sequence described in SEQ ID NO: 93, and the one or more amino acids to be altered are selected from the following positions:

H chain: 31, 52b, 52c, 53, 54, 56, 57, 61, 98, 99, 100, 100a, 100b, 100c, 100d, 100e, 100f, and 100g (Kabat numbering); and L chain: 24, 25, 26, 27, 27a, 27b, 27c, 27e, 30, 31, 33, 34, 51, 52, 53, 54, 55, 56, 74, 77, 89, 90, 92, 93, 94, and 96 (Kabat numbering), wherein the HVR-H3 of the altered heavy chain variable domain sequence comprises at least one amino acid selected from:

Ala, Pro, Ser, Arg, His or Thr at amino acid position 98;
Ala, Ser, Thr, Gln, His or Leu at amino acid position 99;
Tyr, Ala, Ser, Pro or Phe at amino acid position 100;
Tyr, Val, Ser, Leu or Gly at amino acid position 100a;
Asp, Ser, Thr, Leu, Gly or Tyr at amino acid position 100b;
Val, Leu, Phe, Gly, His or Ala at amino acid position 100c;
Leu, Phe, Ile or Tyr at amino acid position 100d;
Gly, Pro, Tyr, Gln, Ser or Phe at amino acid position 100e;

Tyr, Ala, Gly, Ser or Lys at amino acid position 100f;
Gly, Tyr, Phe or Val at amino acid position 100g (Kabat numbering).

In some embodiments, an antigen-binding molecule of the present invention comprises (a) a VH sequence having at least 95% sequence identity to the amino acid sequence of SEQ ID NO: 41, 30, 46 or 40; (b) a VL sequence having at least 95% sequence identity to the amino acid sequence of SEQ ID NO: 51, 52, 53, 54, 55, 56 or 57; or (c) the VH sequence of (a) and the VL sequence of (b).

The antigen-binding molecule of the present invention can be produced by a method generally known to those skilled in the art. For example, the antibody can be prepared by a method given below, though the method for preparing the antibody of the present invention is not limited thereto. Many combinations of host cells and expression vectors are known in the art for antibody preparation by the transfer of isolated genes encoding polypeptides into appropriate hosts. All of these expression systems can be applied to the isolation of the antigen-binding molecule of the present invention. In the case of using eukaryotic cells as the host cells, animal cells, plant cells, or fungus cells can be appropriately used. Specifically, examples of the animal cells can include the following cells:

(1) mammalian cells such as CHO (Chinese hamster ovary cell line), COS (monkey kidney cell line), myeloma cells (Sp2/O, NS0, etc.), BHK (baby hamster kidney cell line), HEK293 (human embryonic kidney cell line with sheared adenovirus (Ad)5 DNA), PER.C6 cell (human embryonic retinal cell line transformed with the adenovirus type 5 (Ad5) E1A and E1B genes), Hela, and Vero (Current Protocols in Protein Science (May, 2001, Unit 5.9, Table 5.9.1));
(2) amphibian cells such as *Xenopus* oocytes; and
(3) insect cells such as sf9, sf21, and Tn5.

The antibody can also be prepared using *E. coli* (mAbs 2012 March-April; 4 (2): 217-225) or yeast (WO2000023579). The antibody prepared using *E. coli* is not glycosylated. On the other hand, the antibody prepared using yeast is glycosylated.

An antibody heavy chain-encoding DNA that encodes a heavy chain with one or more amino acid residues in a variable domain substituted by different amino acids of interest, and a DNA encoding a light chain of the antibody are expressed. The DNA that encodes a heavy chain or a light chain with one or more amino acid residues in a variable domain substituted by different amino acids of interest can be obtained, for example, by obtaining a DNA encoding an antibody variable domain prepared by a method known in the art against a certain antigen, and appropriately introducing substitution such that codons encoding the particular amino acids in the domain encode the different amino acids of interest.

Alternatively, a DNA encoding a protein in which one or more amino acid residues in an antibody variable domain prepared by a method known in the art against a certain antigen are substituted by different amino acids of interest may be designed in advance and chemically synthesized to obtain the DNA that encodes a heavy chain with one or more amino acid residues in a variable domain substituted by different amino acids of interest. The amino acid substitution site and the type of the substitution are not particularly limited. Examples of the region preferred for the amino acid alteration include solvent-exposed regions and loops in the variable region. Among others, CDR1, CDR2, CDR3, FR3, and loops are preferred. Specifically, Kabat numbering positions 31 to 35, 50 to 65, 71 to 74, and 95 to 102 in the H chain variable domain and Kabat numbering positions 24 to 34, 50 to 56, and 89 to 97 in the L chain variable domain are preferred. Kabat numbering positions 31, 52a to 61, 71 to 74, and 97 to 101 in the H chain variable domain and Kabat numbering positions 24 to 34, 51 to 56, and 89 to 96 in the L chain variable domain are more preferred.

The amino acid alteration is not limited to the substitution and may be deletion, addition, insertion, or modification, or a combination thereof.

The DNA that encodes a heavy chain with one or more amino acid residues in a variable domain substituted by different amino acids of interest can also be produced as separate partial DNAs. Examples of the combination of the partial DNAs include, but are not limited to: a DNA encoding a variable domain and a DNA encoding a constant domain; and a DNA encoding a Fab domain and a DNA encoding an Fc domain. Likewise, the light chain-encoding DNA can also be produced as separate partial DNAs.

These DNAs can be expressed by the following method: for example, a DNA encoding a heavy chain variable domain, together with a DNA encoding a heavy chain constant domain, is integrated to an expression vector to construct a heavy chain expression vector. Likewise, a DNA encoding a light chain variable domain, together with a DNA encoding a light chain constant domain, is integrated to an expression vector to construct a light chain expression vector. These heavy chain and light chain genes may be integrated to a single vector.

The DNA encoding the antibody of interest is integrated to expression vectors so as to be expressed under the control of expression control regions, for example, an enhancer and a promoter. Next, host cells are transformed with the resulting expression vectors and allowed to express antibodies. In this case, appropriate hosts and expression vectors can be used in combination.

Examples of the vectors include M13 series vectors, pUC series vectors, pBR322, pBluescript, and pCR-Script. In addition to these vectors, for example, pGEM-T, pDIRECT, or pT7 can also be used for the purpose of cDNA subcloning and excision.

Particularly, expression vectors are useful for using the vectors for the purpose of producing the antibody of the present invention. For example, when the host is *E. coli* such as JM109, DH5 alpha, HB101, or XL1-Blue, the expression vectors indispensably have a promoter that permits efficient expression in *E. coli*, for example, lacZ promoter (Ward et al., Nature (1989) 341, 544-546; and FASEB J. (1992) 6, 2422-2427, which are incorporated herein by reference in their entirety), araB promoter (Better et al., Science (1988) 240, 1041-1043, which is incorporated herein by reference in its entirety), or T7 promoter. Examples of such vectors include the vectors mentioned above as well as pGEX-5X-1 (manufactured by Pharmacia), "QIAexpress system" (manufactured by Qiagen N.V.), pEGFP, and pET (in this case, the host is preferably BL21 expressing T7 RNA polymerase).

The vectors may contain a signal sequence for polypeptide secretion. In the case of production in the periplasm of *E. coli*, pelB signal sequence (Lei, S. P. et al., J. Bacteriol. (1987) 169, 4397, which is incorporated herein by reference in its entirety) can be used as the signal sequence for polypeptide secretion. The vectors can be transferred to the host cells by use of, for example, a Lipofectin method, a calcium phosphate method, or a DEAE-dextran method.

In addition to the expression vectors for *E. coli*, examples of the vectors for producing the polypeptide of the present invention include mammal-derived expression vectors (e.g., pcDNA3 (manufactured by Invitrogen Corp.), pEGF-BOS (Nucleic Acids. Res. 1990, 18 (17), p. 5322, which is incorporated herein by reference in its entirety), pEF, and pCDM8), insect cell-derived expression vectors (e.g., "Bac-to-BAC baculovirus expression system" (manufactured by GIBCO BRL), and pBacPAK8), plant-derived expression vectors (e.g., pMH1 and pMH2), animal virusderived expression vectors (e.g., pHSV, pMV, and pAdexLcw), retrovirus-derived expression vectors (e.g., pZIPneo), yeast-derived expression vectors (e.g., "Pichia Expression Kit" (manufactured by Invitrogen Corp.), pNV11, and SP-Q01), and Bacillus subtilis-derived expression vectors (e.g., pPL608 and pKTH50).

For the purpose of expression in animal cells such as CHO cells, COS cells, NIH3T3 cells, or HEK293 cells, the vectors indispensably have a promoter necessary for intracellular expression, for example, SV40 promoter (Mulligan et al., Nature (1979) 277, 108, which is incorporated herein by reference in its entirety), MMTV-LTR promoter, EF1 alpha promoter (Mizushima et al., Nucleic Acids Res. (1990) 18, 5322, which is incorporated herein by reference in its entirety), CAG promoter (Gene. (1991) 108, 193, which is incorporated herein by reference in its entirety), or CMV promoter and, more preferably, have a gene for screening for transformed cells (e.g., a drug resistance gene that can work as a marker by a drug (neomycin, G418, etc.)). Examples of the vectors having such properties include pMAM, pDR2, pBK-RSV, pBK-CMV, pOPRSV, and pOP13. In addition, EBNA1 protein may be coexpressed therewith for the purpose of increasing the number of gene copies. In this case, vectors having a replication origin OriP are used (Biotechnol Bioeng. 2001 Oct. 20; 75 (2): 197-203; and Biotechnol Bioeng. 2005 Sep. 20; 91 (6): 670-7).

An exemplary method intended to stably express the gene and increase the number of intracellular gene copies involves transforming CHO cells deficient in nucleic acid synthesis pathway with vectors having a DHFR gene serving as a complement thereto (e.g., pCHOI) and using methotrexate (MTX) in the gene amplification. An exemplary method intended to transiently express the gene involves using COS cells having an SV40 T antigen gene on their chromosomes to transform the cells with vectors having a replication origin of SV40 (pcD, etc.). A replication origin derived from polyomavirus, adenovirus, bovine papillomavirus (BPV), or the like can also be used. In order to increase the number of gene copies in the host cell system, the expression vectors can contain a selective marker such as an aminoglycoside phosphotransferase (APH) gene, a thymidine kinase (TK) gene, an E. coli xanthine guanine phosphoribosyltransferase (Ecogpt) gene, or a dihydrofolate reductase (dhfr) gene.

The antibody can be recovered, for example, by culturing the transformed cells and then separating the antibody from within the molecule-transformed cells or from the culture solution thereof. The antibody can be separated and purified by appropriately using in combination methods such as centrifugation, ammonium sulfate fractionation, salting out, ultrafiltration, C1q, FcRn, protein A and protein G columns, affinity chromatography, ion-exchanged chromatography, and gel filtration chromatography.

The technique mentioned above, such as the knobs-into-holes technology (WO1996/027011; Ridgway J B et al., Protein Engineering (1996) 9, 617-621; and Merchant A M et al., Nature Biotechnology (1998) 16, 677-681) or the technique of suppressing the unintended association between H chains by the introduction of electric charge repulsion (WO2006/106905), can be applied to a method for efficiently preparing the multispecific antibody.

The present invention further provides a method for producing the antigen-binding molecule of the present invention and specifically provides a method for producing an antigen-binding molecule comprising: an antibody variable region that is capable of binding to two different antigens (first antigen and second antigen), but does not bind to CD3 and CD137 at the same time (this variable region is referred to as a first variable region); and a variable region binding to a third antigen different from CD3 and CD137 (this variable region is referred to as a second variable region), the method comprising the step of preparing an antigen-binding molecule library containing diverse amino acid sequences of the first variable region.

Examples thereof can include a production method comprising the following steps:
  (i) preparing a library of antigen-binding molecules with at least one amino acid altered in their antibody variable regions each binding to CD3 or CD137, wherein the altered variable regions differ in at least one amino acid from each other;
  (ii) selecting, from the prepared library, an antigen-binding molecule comprising a variable region that has binding activity against CD3 and CD137, but does not bind to CD3 and CD137 at the same time;
  (iii) culturing a host cell comprising a nucleic acid encoding the variable region of the antigen-binding molecule selected in the step (ii), and a nucleic acid encoding a variable region of an antigen-binding molecule binding to the third antigen, to express an antigen-binding molecule comprising the antibody variable region that is capable of binding to CD3 and CD137, but does not bind to CD3 and CD137 at the same time, and the variable region binding to the third antigen; and
  (iv) recovering the antigen-binding molecule from the host cell cultures.

In this production method, the step (ii) may be the following selection step:
  (v) selecting, from the prepared library, an antigen-binding molecule comprising a variable region that has binding activity against CD3 and CD137, but does not bind to CD3 and CD137 each expressed on a different cell, at the same time.

The antigen-binding molecules used in the step (i) are not particularly limited as long as these molecules each comprise an antibody variable region. The antigen-binding molecules may be antibody fragments such as Fv, Fab, or Fab' or may be Fc region-containing antibodies.

The amino acid to be altered is selected from, for example, amino acids whose alteration does not cancel the binding to the antigen, in the antibody variable region binding to CD3 or CD137.

In the present invention, one amino acid alteration may be used alone, or a plurality of amino acid alterations may be used in combination.

In the case of using a plurality of amino acid alterations in combination, the number of the alterations to be combined is not particularly limited and is, for example, 2 or more and 30 or less, preferably 2 or more and 25 or less, 2 or more and 22 or less, 2 or more and 20 or less, 2 or more and 15 or less, 2 or more and 10 or less, 2 or more and 5 or less, or 2 or more and 3 or less.

The plurality of amino acid alterations to be combined may be added to only the antibody heavy chain variable domain or light chain variable domain or may be appropriately distributed to both of the heavy chain variable domain and the light chain variable domain.

Examples of the region preferred for the amino acid alteration include solvent-exposed regions and loops in the variable region. Among others, CDR1, CDR2, CDR3, FR3, and loops are preferred. Specifically, Kabat numbering positions 31 to 35, 50 to 65, 71 to 74, and 95 to 102 in the H chain variable domain and Kabat numbering positions 24 to 34, 50 to 56, and 89 to 97 in the L chain variable domain are preferred. Kabat numbering positions 31, 52a to 61, 71 to 74, and 97 to 101 in the H chain variable domain and Kabat numbering positions 24 to 34, 51 to 56, and 89 to 96 in the L chain variable domain are more preferred.

The alteration of an amino acid residue also include: the random alteration of amino acids in the region mentioned above in the antibody variable region binding to CD3 or CD137; and the insertion of a peptide previously known to have binding activity against the CD3 or CD137, to the region mentioned above. The antigen-binding molecule of the present invention can be obtained by selecting a variable region that is capable of binding to CD3 and CD137, but cannot bind to these antigens at the same time, from among the antigen-binding molecules thus altered.

Whether the variable region is capable of binding to CD3 and CD137, but cannot bind to these antigens at the same time, and further, whether the variable region is capable of binding to both CD3 and CD137 at the same time when any one of CD3 and CD137 resides on a cell and the other antigen exists alone, both of the antigens each exist alone, or both of the antigens reside on the same cell, but cannot bind to these antigens each expressed on a different cell, at the same time, can also be confirmed according to the method mentioned above.

The present inventors have also successfully developed the methods to obtain antigen binding domains which bind to two or more different antigens more efficiently.

In some embodiments, a method of screening for an antigen-binding domain which binds to at least two or more different antigens of interest of the present invention comprises:
  (a) providing a library comprising a plurality of antigen-binding domains,
  (b) contacting the library provided in step (a) with a first antigen of interest and collecting antigen-binding domains bound to the first antigen,
  (c) contacting the antigen-binding domains collected in step (b) with a second antigen of interest and collecting antigen-binding domains bound to the second antigen, and
  (d) amplifying genes which encode the antigen binding domains collected in step (c) and identifying a candidate antigen-binding domain,
  wherein the method does not comprise amplifying nucleic acids that encode the antigen-binding domains collected in step (b) between step (b) and step (c).

In the above method, the number of steps of contacting antigen-binding domains with antigens is not particularly limited. In some embodiments, the method of screening of the present invention may comprise three or more contacting steps when the number of the antigens of interest is two or more. In further embodiments, the method of screening of the present invention may comprise two or more steps of contacting antigen-binding domains with each of one or more of the antigens of interest. In this case, the antigen-binding domains can be contacted with each antigen in an arbitrary order. For example, the antigen-binding domains may be contacted with each antigen twice or more consecutively, or may be first contacted with one antigen once or more times and then contacted with other antigen(s) before being contacted with the same antigen again. Even when the method of screening of the present invention comprises three or more steps of contacting the antigen-binding domains with the antigens, the method does not comprise amplifying nucleic acids that encode the collected antigen-binding domains between any consecutive two of the contacting steps.

In some embodiments, the antigen-binding domains of the present invention are Fab, scFv, Fab'2, VHH, VH, or VL.

In some embodiments, the antigen-binding domains of the present invention are fusion polypeptides formed by fusing antigen-binding domains with scaffolds to cross-link the antigen-binding domains with the nucleic acids that encode the antigen-binding domains.

In some embodiments, the scaffolds of the present invention are bacteriophages. In some embodiments, the scaffolds of the present invention are ribosomes, RepA proteins or DNA puromycin linkers.

In some embodiments, elution is performed in steps (b) and (c) above using an eluting solution that is an acid solution, a base solution, DTT, or IdeS.

In some embodiments, the eluting solution used in steps (b) and (c) above of the present invention is EDTA or IdeS.

In some embodiments, a method of screening for an antigen-binding domain which binds to at least two or more different antigens of interest of the present invention comprises:
  (a) providing a library comprising a plurality of antigen-binding domains,
  (b) contacting the library provided in step (a) with a first antigen of interest and collecting antigen-binding domains bound to the first antigen,
  (b)' translating nucleic acids that encode the antigen-binding domains collected in step (b),
  (c) contacting the antigen-binding domains collected in step (b) with a second antigen of interest and collecting antigen-binding domains bound to the second antigen, and
  (d) amplifying genes which encode the antigen binding domains collected in step (c) and identifying a candidate antigen-binding domain,
  wherein the method does not comprise amplifying nucleic acids that encode the antigen-binding domains collected in step (b) between step (b) and step (c).

In some embodiments, a method for producing an antigen-binding domain which binds to at least two or more different antigens of interest of the present invention comprises:
  (a) providing a library comprising a plurality of antigen-binding domains,
  (b) contacting the library provided in step (a) with a first antigen of interest and collecting antigen-binding domains bound to the first antigen,
  (c) contacting the antigen-binding domains collected in step (b) with a second antigen of interest and collecting antigen-binding domains bound to the second antigen, and
  (d) amplifying genes which encode the antigen binding domains collected in step (c) and identifying a candidate antigen-binding domain,
  (e) linking the polynucleotide that encodes the candidate antigen-binding domain selected in step (d) with a polynucleotide that encodes a polypeptide comprising an Fc region,
  (f) culturing a cell introduced with a vector in which the polynucleotide obtained in step (d) above is operably linked, and (g) collecting the antigen-binding molecule from the culture solution of the cell cultured in step (f) above, wherein the method does not comprise amplifying nucleic acids that encode the antigen-binding domains collected in step (b) between step (b) and step (c).

In some embodiments, an antigen-binding molecule of the present invention is an antibody prepared by the method described above.

In one aspect, the method of screening of the present invention makes it possible to acquire an antigen-binding domain which binds to at least two or more different antigens of interest more efficiently.

In the present specification, the "library" refers to a plurality of antigen-binding molecules or a plurality of fusion polypeptides comprising the antigen-binding molecules, or nucleic acids or polynucleotides encoding these sequences. The plurality of antigen-binding molecules or the plurality of fusion polypeptides comprising the antigen-binding molecules, included in the library are antigen-binding molecules differing in sequence from each other, not having single sequences, or fusion polypeptides comprising the antigen-binding molecules. In some embodiments, the library of the present invention is a design library. In further embodiments, the design library is a design library disclosed in WO2016/076345.

In one embodiment of the present invention, a fusion polypeptide of the antigen-binding molecule of the present invention and a heterologous polypeptide can be prepared. In one embodiment, the fusion polypeptide can comprise the antigen-binding molecule of the present invention fused with at least a portion of a viral coat protein selected from the group consisting of, for example, viral coat proteins pIII, pVIII, pVII, pIX, Soc, Hoc, gpD, and pVI, and variants thereof.

In one embodiment, the antigen-binding molecule of the present invention can be ScFv, a Fab fragment, $F(ab)_2$, or $F(ab')_2$. In another embodiment, the present invention provides a library consisting essentially of a plurality of fusion polypeptides differing in sequence from each other, the fusion polypeptides each comprising any of these antigen-binding molecules and a heterologous polypeptide. Specifically, the present invention provides a library consisting essentially of a plurality of fusion polypeptides differing in sequence from each other, the fusion polypeptides each comprising any of these antigen-binding molecules fused with at least a portion of a viral coat protein selected from the group consisting of, for example, viral coat proteins pIII, pVIII, pVII, pIX, Soc, Hoc, gpD, and pVI, and variants thereof. The antigen-binding molecule of the present invention may further comprise a dimerization domain. In one embodiment, the dimerization domain can be located between the antibody heavy chain or light chain variable domain and at least a portion of the viral coat protein. This dimerization domain may comprise at least one dimerization sequence and/or a sequence comprising one or more cysteine residues. This dimerization domain can be preferably linked to the C terminus of the heavy chain variable domain or constant domain. The dimerization domain can assume various structures, depending on whether the antibody variable domain is prepared as a fusion polypeptide component with the viral coat protein component (an amber stop codon following the dimerization domain is absent) or depending on whether the antibody variable domain is prepared predominantly without comprising the viral coat protein component (e.g., an amber stop codon following the dimerization domain is present). When the antibody variable domain is prepared predominantly as a fusion polypeptide with the viral coat protein component, bivalent display is brought about by one or more disulfide bonds and/or a single dimerization sequence.

The term "differing in sequence from each other" in a plurality of antigen-binding molecules differing in sequence from each other as described herein means that the individual antigen-binding molecules in the library have distinct sequences. Specifically, the number of the distinct sequences in the library reflects the number of independent clones differing in sequences in the library and may also be referred to as a "library size". The library size of a usual phage display library is $10^6$ to $10^{12}$ and can be expanded to $10^{14}$ by the application of a technique known in the art such as a ribosome display method. The actual number of phage particles for use in panning selection for the phage library, however, is usually 10 to 10,000 times larger than the library size. This excessive multiple, also called the "number of equivalents of the library", represents that 10 to 10,000 individual clones may have the same amino acid sequence. Accordingly, the term "differing in sequence from each other" described in the present invention means that the individual antigen-binding molecules in the library excluding the number of equivalents of the library have distinct sequences and more specifically means that the library has $10^6$ to $10^{14}$, preferably $10^7$ to $10^{12}$, more preferably $10^8$ to $10^{11}$, particularly preferably $10^8$ to $10^{10}$ antigen-binding molecules differing in sequence from each other.

The "phage display" as described herein refers to an approach by which variant polypeptides are displayed as fusion proteins with at least a portion of coat proteins on the particle surface of phages, for example, filamentous phages. The phage display is useful because a large library of randomized protein variants can be rapidly and efficiently screened for a sequence binding to a target antigen with high affinity. The display of peptide and protein libraries on the phages has been used for screening millions of polypeptides for ones with specific binding properties. A polyvalent phage display method has been used for displaying small random peptides and small proteins through fusion with filamentous phage gene III or gene VIII (Wells and Lowman, Curr. Opin. Struct. Biol. (1992) 3, 355-362; and references cited therein). Monovalent phage display involves fusing a protein or peptide library to gene III or a portion thereof, and expressing fusion proteins at low levels in the presence of wild-type gene III protein so that each phage particle displays one copy or none of the fusion proteins. The monovalent phages have a lower avidity effect than that of the polyvalent phages and are therefore screened on the basis of endogenous ligand affinity using phagemid vectors, which simplify DNA manipulation (Lowman and Wells, Methods: A Companion to Methods in Enzymology (1991) 3, 205-216).

The "phagemid" refers to a plasmid vector having a bacterial replication origin, for example, ColE1, and a copy of an intergenic region of a bacteriophage. A phagemid derived from any bacteriophage known in the art, for example, a filamentous bacteriophage or a lambdoid bacteriophage, can be appropriately used. Usually, the plasmid also contains a selective marker for antibiotic resistance. DNA fragments cloned into these vectors can grow as plasmids. When cells harboring these vectors possess all genes necessary for the production of phage particles, the replication pattern of plasmids is shifted to rolling circle replication to form copies of one plasmid DNA strand and package phage particles. The phagemid can form infectious or non-infectious phage particles. This term includes a phagemid comprising a phage coat protein gene or a fragment thereof bound with a heterologous polypeptide gene by gene fusion such that the heterologous polypeptide is displayed on the surface of the phage particle.

The term "phage vector" means a double-stranded replicative bacteriophage that comprises a heterologous gene and is capable of replicating. The phage vector has a phage replication origin that permits phage replication and phage particle formation. The phage is preferably a filamentous bacteriophage, for example, an M13, f1, fd, or Pf3 phage or a derivative thereof, or a lambdoid phage, for example, lambda, 21, phi80, phi81, 82, 424, 434, or any other phage or a derivative thereof.

The term "coat protein" refers to a protein, at least a portion of which is present on the surface of a viral particle. From a functional standpoint, the coat protein is an arbitrary protein that binds to viral particles in the course of construction of viruses in host cells and remains bound therewith until viral infection of other host cells. The coat protein may be a major coat protein or may be a minor coat protein. The minor coat protein is usually a coat protein present in viral capsid at preferably at least approximately 5, more preferably at least approximately 7, further preferably at least approximately 10 or more protein copies per virion. The major coat protein can be present at tens, hundreds, or thousands of copies per virion. Examples of the major coat protein include filamentous phage p8 protein.

The "ribosome display" as described herein refers to an approach by which variant polypeptides are displayed on the ribosome (Nat. Methods 2007 March; 4(3):269-79, Nat. Biotechnol. 2000 December; 18(12):1287-92, Methods Mol. Biol. 2004; 248:177-89). Preferably, ribosome display methods require that the nucleic acid encoding the variant polypeptide has the appropriate ribosome stalling sequence like *Eschericha coli*. secM (J. Mol. Biol. 2007 Sep. 14; 372(2): 513-24) or does not have stop codon. Preferably, the nucleic acid encoding variant polypeptide also has a spacer sequence. As used herein the term "spacer sequence" means a series of nucleic acids that encode a peptide that is fused to the variant polypeptide to make the variant polypeptide go through the ribosomal tunnel after translation and which allows the variant polypeptides to express its function. Any of the in vitro translation systems can be used to ribosome display, e.g., *Eschericha coli*. S30 system, PUREsystem, Rabbit reticulocyte lysate system or wheat germ cell free translation system.

The term "oligonucleotide" refers to a short single- or double-stranded polydeoxynucleotide that is chemically synthesized by a method known in the art (e.g., phosphotriester, phosphite, or phosphoramidite chemistry using a solid-phase approach such as an approach described in EP266032; or a method via deoxynucleotide H-phosphonate intermediates described in Froeshler et al., Nucl. Acids. Res. (1986) 14, 5399-5407). Other methods for oligonucleotide synthesis include the polymerase chain reaction described below and other autoprimer methods and oligonucleotide syntheses on solid supports. All of these methods are described in Engels et al., Agnew. Chem. Int. Ed. Engl. (1989) 28, 716-734. These methods are used if the whole nucleic acid sequence of the gene is known or if a nucleic acid sequence complementary to the coding strand is available. Alternatively, a possible nucleic acid sequence may be appropriately predicted using known and preferred residues encoding each amino acid residue, if the target amino acid sequence is known. The oligonucleotide can be purified using polyacrylamide gels or molecular sizing columns or by precipitation.

The terms "amplification of nucleic acids" refers to an experimental procedure to increase the mole number of nucleic acids. As a non-limiting embodiment, nucleic acids include single-stranded RNA (ssRNA), double-stranded DNA (dsDNA) or single-stranded DNA (ssDNA) As a non-limiting embodiment, PCR (polymerase chain reaction) method is used generically as a method to amplify nucleic acids although any methods which can amplify nucleic acids can be used. Alternatively, nucleic acids can be amplified in host cells when the nucleic acid vector was introduced into those host cells. As a non-limiting embodiment, electroporation, heat shock, infection of phages or viruses which have the vector, or chemical reagents can be used to introduce nucleic acids into cells. Alternatively, transcription of DNA, or reverse transcription of mRNA and then transcription of it can also amplify nucleic acids. As a non-limiting embodiment, introduction of phagemid vectors into *Escherichia coli*. is generically used to amplify nucleic acids encoding binding domains, but PCR is also able to be used in phage display technique. In ribosome display, cDNA display, mRNA display and CIS display, PCR method or transcription is generically used to amplify nucleic acids.

The terms "fusion protein" and "fusion polypeptide" refer to a polypeptide having two segments linked to each other. These segments in the polypeptide differ in character. This character may be, for example, a biological property such as in vitro or in vivo activity. Alternatively, this character may be a single chemical or physical property, for example, binding to a target antigen or catalysis of reaction. These two segments may be linked either directly through a single peptide bond or via a peptide linker containing one or more amino acid residues. Usually, these two segments and the linker are located in the same reading frame. Preferably, the two segments of the polypeptide are obtained from heterologous or different polypeptides.

The terms "scaffold" in "fusion polypeptides formed by fusing antigen-binding domains with scaffolds" refer to a molecule which cross-link the antigen-biding domain with the nucleic acids that encode the antigen-binding domain. As a non-limiting embodiment, phage coat protein in phage display, ribosome in ribosome display, puromycin in mRNA or cDNA display, RepA protein in CIS display, virus coat protein in virus display, mammalian cell membrane anchoring protein in mammalian cell display, yeast cell membrane anchoring protein in yeast display, bacterial cell membrane anchoring protein in bacteria display or *E. coli* display, etc. can be used as scaffold in each display methodology.

In the present invention, the term "one or more amino acids" is not limited to a particular number of amino acids and may be 2 or more types of amino acids, 5 or more types of amino acids, 10 or more types of amino acids, 15 or more types of amino acids, or 20 types of amino acids.

As for fusion polypeptide display, the fusion polypeptide of the variable region of the antigen-binding molecule can be displayed in various forms on the surface of cells, viruses, ribosomes, DNAs, RNAs or phagemid particles. These forms include single-chain Fv fragments (scFvs), F(ab) fragments, and multivalent forms of these fragments. The multivalent forms are preferably ScFv, Fab, and F(ab') dimers, which are referred to as (ScFv)2, F(ab)2, and F(ab')2, respectively, herein. The display of the multivalent forms is preferred, probably in part because the displayed multivalent forms usually permit identification of low-affinity clones and/or have a plurality of antigen-binding sites that permit more efficient selection of rare clones in the course of selection.

Methods for displaying fusion polypeptides comprising antibody fragments on the surface of bacteriophages are known in the art and described in, for example, WO1992001047 and the present specification. Other related methods are described in WO1992020791, WO1993006213, WO1993011236, and 1993019172. Those skilled in the art can appropriately use these methods. Other public literatures (H. R. Hoogenboom & G. Winter (1992) J. Mol. Biol. 227, 381-388, WO1993006213, and WO1993011236) disclose the identification of antibodies using artificially rearranged variable region gene repertoires against various antigens displayed on the surface of phages.

In the case of constructing a vector for display in the form of scFv, this vector comprises nucleic acid sequences encoding the light chain variable domain and the heavy chain variable domain of the antigen-binding molecule. In general, the nucleic acid sequence encoding the heavy chain variable domain of the antigen-binding molecule is fused with a nucleic acid sequence encoding a viral coat protein constituent. The nucleic acid sequence encoding the light chain variable domain of the antigen-binding molecule is linked to the heavy chain variable domain nucleic acid of the antigen-binding molecule through a nucleic acid sequence encoding a peptide linker. The peptide linker generally contains approximately 5 to 15 amino acids. Optionally, an additional sequence encoding, for example, a tag useful in purification or detection, may be fused with the 3' end of the nucleic acid sequence encoding the light chain variable domain of the antigen-binding molecule or the nucleic acid sequence encoding the heavy chain variable domain of the antigen-binding molecule, or both.

In the case of constructing a vector for display in the form of F(ab), this vector comprises nucleic acid sequences encoding the variable domains of the antigen-binding molecule and the constant domains of the antigen-binding molecule. The nucleic acid sequence encoding the light chain variable domain is fused with the nucleic acid sequence encoding the light chain constant domain. The nucleic acid sequence encoding the heavy chain variable domain of the antigen-binding molecule is fused with the nucleic acid sequence encoding the heavy chain constant CH1 domain. In general, the nucleic acid sequence encoding the heavy chain variable domain and constant domain is fused with a nucleic acid sequence encoding the whole or a portion of a viral coat protein. The heavy chain variable domain and constant domain are preferably expressed as a fusion product with at least a portion of the viral coat protein, while the light chain variable domain and constant domain are expressed separately from the heavy chain-viral coat fusion protein. The heavy chain and the light chain may be associated with each other through a covalent bond or a non-covalent bond. Optionally, an additional sequence encoding, for example, a polypeptide tag useful in purification or detection, may be fused with the 3' end of the nucleic acid sequence encoding the light chain constant domain of the antigen-binding molecule or the nucleic acid sequence encoding the heavy chain constant domain of the antigen-binding molecule, or both.

As for vector transfer to host cells, the vectors constructed as described above are transferred to host cells for amplification and/or expression. The vectors can be transferred to host cells by a transformation method known in the art, including electroporation, calcium phosphate precipitation, and the like. When the vectors are infectious particles such as viruses, the vectors themselves invade the host cells. Fusion proteins are displayed on the surface of phage particles by the transfection of host cells with replicable expression vectors having inserts of polynucleotides encoding the fusion proteins and the production of the phage particles by an approach known in the art.

The replicable expression vectors can be transferred to host cells by use of various methods. In a non-limiting embodiment, the vectors can be transferred to the cells by electroporation as described in WO2000106717. The cells are cultured at 37 degrees C., optionally for approximately 6 to 48 hours (or until OD at 600 nm reaches 0.6 to 0.8) in a standard culture medium. Next, the culture medium is centrifuged, and the culture supernatant is removed (e.g., by decantation). At the initial stage of purification, the cell pellet is preferably resuspended in a buffer solution (e.g., 1.0 mM HEPES (pH 7.4)). Next, the suspension is centrifuged again to remove the supernatant. The obtained cell pellet is resuspended in glycerin diluted to, for example, 5 to 20% V/V. The suspension is centrifuged again for the removal of the supernatant to obtain cell pellet. The cell pellet is resuspended in water or diluted glycerin. On the basis of the measured cell density of the resulting suspension, the final cell density is adjusted to a desired density using water or diluted glycerin.

Examples of preferred recipient cells include an *E. coli* strain SS320 capable of responding to electroporation (Sidhu et al., Methods Enzymol. (2000) 328, 333-363). The *E. coli* strain SS320 has been prepared by the coupling of MC1061 cells with XL1-BLUE cells under conditions sufficient for transferring fertility episome (F' plasmid) or XL1-BLUE into the MC1061 cells. The *E. coli* strain SS320 has been deposited with ATCC (10801 University Boulevard, Manassas, Virginia) under deposition No. 98795. Any F' episome that permits phage replication in this strain can be used in the present invention. Appropriate episome may be obtained from strains deposited with ATCC or may be obtained as a commercially available product (TG1, CJ236, CSH18, DHF', ER2738, JM101, JM103, JM105, JM107, JM109, JM110, KS1000, XL1-BLUE, 71-18, etc.).

Use of higher DNA concentrations (approximately 10 times) in electroporation improves transformation frequency and increases the amount of DNAs transforming the host cells. Use of high cell densities also improves the efficiency (approximately 10 times). The increased amount of transferred DNAs can yield a library having greater diversity and a larger number of independent clones differing in sequence. The transformed cells are usually selected on the basis of the presence or absence of growth on a medium containing an antibiotic.

The present invention further provides a nucleic acid encoding the antigen-binding molecule of the present invention. The nucleic acid of the present invention may be in any form such as DNA or RNA.

The present invention further provides a vector comprising the nucleic acid of the present invention. The type of the vector can be appropriately selected by those skilled in the art according to host cells that receive the vector. For example, any of the vectors mentioned above can be used.

The present invention further relates to a host cell transformed with the vector of the present invention. The host cell can be appropriately selected by those skilled in the art. For example, any of the host cells mentioned above can be used.

The present invention also provides a pharmaceutical composition comprising the antigen-binding molecule of the present invention and a pharmaceutically acceptable carrier. The pharmaceutical composition of the present invention can be formulated according to a method known in the art by supplementing the antigen-binding molecule of the present invention with the pharmaceutically acceptable carrier. For example, the pharmaceutical composition can be used in the form of a parenteral injection of an aseptic solution or suspension with water or any other pharmaceutically acceptable solution. For example, the pharmaceutical composition may be formulated with the antigen-binding molecule mixed in a unit dosage form required for generally accepted pharmaceutical practice, in appropriate combination with pharmacologically acceptable carriers or media, specifically, sterilized water, physiological saline, plant oil, an emulsifier, a suspending agent, a surfactant, a stabilizer, a flavoring agent, an excipient, a vehicle, a preservative, a binder, etc. Specific examples of the carrier can include light anhydrous silicic acid, lactose, crystalline cellulose, mannitol, starch, carmellose calcium, carmellose sodium, hydroxypropylcellulose, hydroxypropylmethylcellulose, polyvinyl acetal diethylaminoacetate, polyvinylpyrrolidone, gelatin, medium-chain fatty acid triglyceride, polyoxyethylene hydrogenated castor oil 60, saccharide, carboxymethylcellulose, cornstarch, and inorganic salts. The amount of the active ingredient in such a preparation is determined such that an appropriate dose within the prescribed range can be achieved.

An aseptic composition for injection can be formulated according to conventional pharmaceutical practice using a vehicle such as injectable distilled water. Examples of aqueous solutions for injection include physiological saline, isotonic solutions containing glucose and other adjuvants, for example, D-sorbitol, D-mannose, D-mannitol, and sodium chloride. These solutions may be used in combination with an appropriate solubilizer, for example, an alcohol (specifically, ethanol) or a polyalcohol (e.g., propylene glycol and polyethylene glycol), or a nonionic surfactant, for example, polysorbate 80™ or HCO-50.

Examples of oily solutions include sesame oil and soybean oil. These solutions may be used in combination with benzyl benzoate or benzyl alcohol as a solubilizer. The solutions may be further mixed with a buffer (e.g., a phosphate buffer solution and a sodium acetate buffer solution), a soothing agent (e.g., procaine hydrochloride), a stabilizer (e.g., benzyl alcohol and phenol), and an antioxidant. The injection solutions thus prepared are usually charged into appropriate ampules. The pharmaceutical composition of the present invention is preferably administered parenterally. Specific examples of its dosage forms include injections, intranasal administration agents, transpulmonary administration agents, and percutaneous administration agents. Examples of the injections include intravenous injection, intramuscular injection, intraperitoneal injection, and subcutaneous injection, through which the pharmaceutical composition can be administered systemically or locally.

The administration method can be appropriately selected depending on the age and symptoms of a patient. The dose of a pharmaceutical composition containing a polypeptide or a polynucleotide encoding the polypeptide can be selected within a range of, for example, 0.0001 to 1000 mg/kg of body weight per dose. Alternatively, the dose can be selected within a range of, for example, 0.001 to 100000 mg/body of a patient, though the dose is not necessarily limited to these numeric values. Although the dose and the administration method vary depending on the weight, age, symptoms, etc. of a patient, those skilled in the art can appropriately select the dose and the method.

The present invention also provides a method for treating cancer, comprising the step of administering the antigen-binding molecule of the present invention, the antigen-binding molecule of the present invention for use in the treatment of cancer, use of the antigen-binding molecule of the present invention in the production of a therapeutic agent for cancer, and a process for producing a therapeutic agent for cancer, comprising the step of using the antigen-binding molecule of the present invention.

The three-letter codes and corresponding one-letter codes of amino acids used herein are defined as follows: alanine: Ala and A, arginine: Arg and R, asparagine: Asn and N, aspartic acid: Asp and D, cysteine: Cys and C, glutamine: Gln and Q, glutamic acid: Glu and E, glycine: Gly and G, histidine: His and H, isoleucine: Ile and I, leucine: Leu and L, lysine: Lys and K, methionine: Met and M, phenylalanine: Phe and F, proline: Pro and P, serine: Ser and S, threonine: Thr and T, tryptophan: Trp and W, tyrosine: Tyr and Y, and valine: Val and V.

Those skilled in the art should understand that one of or any combination of two or more of the aspects described herein is also included in the present invention unless a technical contradiction arises on the basis of the technical common sense of those skilled in the art.

All references cited herein are incorporated herein by reference in their entirety.

The present invention will be further illustrated with reference to Examples below. However, the present invention is not intended to be limited by Examples below.

EXAMPLES

[Example 1] Concept of Altered Immunoglobulin Variable (Fab) Region that Binds CD3 and CD137, but does not Bind to CD3 and CD137 at Same Time T cells play important roles in tumor immunity, and are known to be activated by two signals: 1) binding of a T cell receptor (TCR) to an antigenic peptide presented by major histocompatibility complex (MHC) class I molecules and activation of TCR; and 2) binding of a costimulator on the surface of T cells to the ligands on antigen-presenting cells and activation of the costimulator. Furthermore, activation of molecules belonging to the tumor necrosis factor (TNF) superfamily and the TNF receptor superfamily, such as CD137(4-1BB) on the surface of T cells, has been described as important for T cell activation (Vinay, 2011, Cellular & Molecular Immunology, 8, 281-284).

CD137 agonist antibodies have already been demonstrated to show anti-tumor effects, and this has been shown experimentally to be mainly due to activation of CD8-positive T cells and NK cells (Houot, 2009, Blood, 114, 3431-8). It is also understood that T cell engineered to have chimeric antigen receptor molecules (CAR-T cells) which consist of a tumor antigen-binding domain as an extracellular domain and CD3 and CD137 signal transducing domains as intracellular domains can enhance the persistence of the efficacy (Porter, N ENGL J MED, 2011, 365; 725-733). However, side effects of such CD137 agonist antibodies due to their non-specific hepatotoxicity have been a problem clinically and non-clinically, and development of pharmaceutical agents has not advanced (Dubrot, Cancer Immunol. Immunother., 2010, 28, 512-22). The main cause of the side effects has been suggested to involve binding of the antibody to the Fc gamma receptor via the antibody constant region (Schabowsky, Vaccine, 2009, 28, 512-22). Furthermore, it has been reported that for agonist antibodies targeting receptors that belong to the TNF receptor superfamily to exert an agonist activity in vivo, antibody cross-linking by Fc gamma receptor-expressing cells (Fc gamma RII-expressing cells) is necessary (Li, Proc Natl Acad Sci USA. 2013, 110(48), 19501-6). WO2015/156268 describes that a bispecific antibody which has a binding domain with CD137 agonistic activity and a binding domain to a tumor specific antigen can exert CD137 agonistic activity activate immune cells only in the presence of cells expressing the tumor specific antigen, by which hepatotoxic adverse events of CD137 agonist antibody can be avoided while retaining the anti-tumor activity of the antibody. WO2015/156268 further describes that the anti-tumor activity can be further enhanced and these adverse events can be avoided by using this bispecific antibody in combination with another bispecific antibody which has a binding domain with CD3 agonistic activity and a binding domain to a tumor specific antigen. A tri-specific antibody which has three binding domains to CD137, CD3 and a tumor specific antigen (EGFR) has also been reported (WO2014/116846). However it is expected that this molecule will cross-link CD3 epsilon-expressing T cells and CD137 expressing cells (T cells, B cells, NK cells, DCs etc.) even in the absence of tumor specific antigen expressing cells because it will bind to CD3 epsilon and CD137 at the same time (FIG. 2). In fact, it has been reported that a bispecific antibody to CD3 and CD8 cross-linked CD8 positive T cells and induced cytotoxicity among those cells (Wong, Clin. Immunol. Immunopathol. 1991, 58(2), 236-250). So it is also expected that the cross-link of CD3 and an antigen which is expressed on T cells will induce cross-link of T cells and cause the T cells to kill each other.

Catumaxomab is known as a bispecific antibody that recognizes a protein expressed on T cells and a protein expressed on cancer cells (cancer antigen) and it binds, at two Fabs, to the cancer antigen (EpCAM) and a CD3 epsilon chain expressed on T cells, respectively, is known to bind to CD3 epsilon and Fc gamma R at the same time even in the absence of a cancer antigen and therefore cross-link CD3 epsilon-expressing T cells to Fc gamma R-expressing cells even in a cancer cell-free environment to produce various cytokines in large amounts. Such cancer antigen-independent induction of production of various cytokines restricts the current administration of the trifunctional antibodies to an intraperitoneal route (Cancer Treat Rev. 2010 Oct. 36 (6), 458-67 (NPL 16)). So the trifunctional antibodies are very difficult to administer systemically due to serious cytokine storm-like adverse reactions (Cancer Immunol Immunother. 2007 September; 56 (9): 1397-406 (NPL 18)).

Meanwhile, a conventional multispecific antibody binds to a plurality of antigens at the same time. Depending on the combination of the antigens, the binding to a plurality of antigens at the same time may not be favorable. An antibody that exerts both of cytotoxic activity mediated by T cells and activation activity of T cells and other immune cells via CD137 in a cancer antigen-specific manner while circumventing adverse reactions has not yet been known.

Accordingly, a possible method for controlling such unfavorable cross-linking reaction was dual binding Fab, which is one variable (Fab) region that binds to the CD3 through a portion thereof and binds to the CD137 through a different portion that does not participate in this binding to the first antigen (FIG. 1). Provided that two proximally positioned moieties in one variable (Fab) region are essential for the binding to their respective antigens, as shown in FIG. 1, the binding to the CD3 inhibits the binding to the CD137 while the binding to the CD137 also inhibits the binding to the CD3. Thus, a modified antibody having the properties of such dual binding Fab cannot bind to the CD3 and the CD137 at the same time and therefore, presumably causes no cross-linking reaction between the CD3 and the CD137 (FIG. 2). Also, the dual binding Fab is considered to be capable of binding to both the CD3 and the CD137 at the same time when the CD3 and the CD137 are not expressed on cell membranes, as with soluble proteins, or both reside on the same cell, but to neither bind to these antigens each expressed on a different cell at the same time nor cross-link these two cells (FIG. 3). On the other hand, an antigen (third antigen) binding to another variable (Fab) region may undergo cross-linking reaction with the CD3 and CD137 on T cells (FIG. 4) or may undergo cross-linking reaction with the CD137 on CD137 positive immune cells (FIG. 5). For this antibody, an Fc region binding to Fc gamma R may be used as a constant region, or an Fc region having reduced binding activity against Fc gamma R may be used as a constant region.

By use of the properties of such dual CD3/CD137 binding Fab, for example, a technique of damaging cancer cells expressing a cancer antigen by the antibody-mediated redirection of T cells can be further provided with a function of activation of T cells, NK cells and/or other immune cells and thereby achieve higher anti-cancer potential.

Briefly, if a variable (Fab) region can be modified as dual binding Fab to confer the following properties, an antibody having the effects as shown in FIG. 1 can be developed:
1. having binding activity against the CD3;
2. having binding activity against the CD137; and
3. not binding to the CD3 and the CD137 at the same time.

The phrase "not bind to the CD3 and the CD137 at the same time" also includes not cross-linking a cell expressing the CD3 to a cell expressing the CD137, or not binding to the CD3 and the CD137 each expressed on a different cell, at the same time. This phrase further includes the case where the variable region is capable of binding to both the CD3 and the CD137 at the same time when the CD3 and the CD137 are not expressed on cell membranes, as with soluble proteins, or both reside on the same cell, but cannot bind to the CD3 and the CD137 each expressed on a different cell, at the same time.

Likewise, if a variable (Fab) region can be modified as dual binding Fab to confer the following properties, an antibody having, for example, the effects as shown in both FIGS. 3, 4 and 5 can be developed:
1. having binding activity against the CD3 on a T cell;
2. having binding activity against the CD137 on the CD137 expressing cell; and
3. not binding to the CD3 and the CD137 at the same time.

[Example 2] Construction of Dual scFv Library for Ribosome Display

The antibody library fragments synthesized in Reference Example 3 was used to construct the dual scFv library for ribosome display. The dual library was prepared as a library in which H chains are diversified as shown in Table 38 (in Reference Example 4) while L chains are fixed to the original sequence GLS3000 (SEQ ID NO: 1). The design of ribosome display dual antibody library is shown in FIG. 6. A part of bacteriophage lambda gpD gene and *Escherichia coli* secM gene were used as spacer gene to display scFv library on ribosome efficiently (SEQ ID NO: 2). The VL fragment of GLS3000 was assembled with that spacer gene and Gly/Ser rich linker gene by PCR (SEQ ID NO: 3). The synthesized antibody VH library fragments were then fused to the VL-spacer gene at 3' terminus and T7 promoter with 5' untranslated region (UTR) (SEQ ID NO: 4) at 5' terminus by PCR amplification.

[Example 3] Obtainment of scFv Domain Binding to CD3 Epsilon and Human CD137 from Dual scFv Library (3-1) Obtainment of scFv Domain Binding to Human CD137 scFv domains binding to human CD137 were identified from the dual scFv library designed and constructed in Example 2. Biotin-labeled human CD137 fused to human IgG1 Fc fragment (Called as human CD137-Fc, SEQ ID NO 16) was used as an antigen.

scFv ribosome display library constructed in Example 2 was used for in vitro transcription (T7 RiboMAX™ Express Large scale RNA production system, P1320, Promega) to prepare mRNA scFv library. Synthesized mRNA are purified by RNeasy mini kit (Cat. No. 74104, QIAGEN). Obtained mRNA library was translated by PUREfrex1.0 (PF001-0.25, Genefrontier) cell-free in vitro translation system with DnaK GroE Mix and DS supplement (PF003-0.5, PF004-0.5, PF005-0.5, Genefrontier). After that WBTH buffer (50 mM Tris-Acetate, 150 mM NaCl, 70 mM Mg-Acetate, 0.1% Tween, 2.5 mg/mL Heparin) was added to stop the translation and Blocking buffer (One pack of SuperBlock Dry Blend Blocking buffer in TBS (Cat. No. 37545, Pierce) in 200 mL milliQ) was also added. The panning method was performed with reference to a general panning method with magnetic beads (Nat Methods. 2007 March; 4(3):269-79; Methods Mol Biol. 2012; 805:261-86). The magnetic beads used were NeutrAvidin coated beads (Sera-Mag Speed Beads NeutrAvidin-corted or FG NeutrAvidin beads) or Streptavidin coated beads (Dynabeads M-280 Streptavidin or Dynabeads MyOne Streptavidin T1 beads).

Specifically, 250 pmol of the biotin-labeled antigen and 2 nmol of free human IgG Fe domain (in those "free" means "non-biotin-labeled") was added to the prepared ribosome display library solution and thereby contacted with the library solution at 4 degrees Celsius for 60 minutes. After addition of SuperBlock-blocked magnetic beads, the antigen-scFv complex were attached to the magnetic beads at 4 degrees Celsius for 15 minutes. The beads were washed three times with WBT buffer (50 mM Tris-Acetate, 150 mM NaCl, 50 mM Mg-Acetate, 0.1% Tween). After addition of Elution buffer (50 mM Tris-Acetate, 150 mM NaCl, 50 mM EDTA and 50 micro g/mL S. cerevisiae RNA(SIGMA)), the beads were suspended at 50 degrees Celsius for 15 minutes, immediately after which the beads were separated using a magnetic stand to recover mRNA solution. Purified mRNA library was converted to cDNA reverse transcription using the primer of SEQ ID NO: 147 and SuperScript III Reverse Transcriptase (Thermo Fisher Scientific) and then amplified by PCR with the primer of SEQ ID NO: 148 and KOD-FX polymerase (TOYOBO). T7 promoter gene was added to the amplified DNA library by PCR with the primers of SEQ ID NOs: 149 and 150. This cycle, called panning, was repeated several times. In the second and subsequent rounds of panning, 150 to 50 pmol of the biotin-labeled human CD137-Fc was used, and either Elution buffer (named as EDTA elution campaign) or FabRICATOR (IdeS, protease for hinge region of IgG, GENOVIS)(named as IdeS elution campaign) was used to recover mRNA. In that procedure, 10 units/micro L Fabricator 5 uL with 95 uL WBT buffer was added and beads were suspended at 37 degrees Celsius for 10 minutes, immediately after which the beads were separated using a magnetic stand to recover mRNA solution. And then 100 micro L of Elution Buffer was added to the recovered mRNA and incubated at 50 degrees Celsius for 10 minutes.

(3-2) Binding of scFv Domain to CD3 Epsilon or CD137 (scFv ELISA)

To evaluate the binding of scFv domain by ELISA, FLAG-tag was added to the recovered DNA library in round five and six by PCR with the primers of SEQ ID NOs: 148 and 151. Obtained scFv-FLAG DNA fragment was ligated into the TOPO TA cloning kit dual promoter (Invitrogen) vector and DH5alpha Escherichia coli was transformed. The VH sequence from each single colony of the E. coli was analyzed. Then five to seven clones which had different VH sequence each other from both EDTA and IdeS elution campaign in round five and round six were picked up. Each scFv-FLAG gene were amplified from each colony with the primers of SEQ ID NOs: 148 and 151. PUREfrex1.0ss was added to the each amplified scFv gene and incubated at 37 degrees Celsius for 2 hours. After addition of 2% Skim-milk buffer, the scFv containing solution was subjected to ELISA by the following procedures: StreptaWell 96 microtiter plate (F. Hoffmann-La Roche Ltd.) was coated with biotinylated CD3 epsilon peptide (SEQ ID NO: 6) or biotinylated human CD137-Fc at room temperature for 30 minutes. Each well of the plate was washed with TBST (TBS containing 0.1% Tween 20; TBS was available from Takara Bio Inc.) to remove unbound antigen. Then, the well was blocked with 250 micro L of 2% skim-milk-TBS for 1 hour or longer. After removal of 2% skim-milk-TBS, the prepared scFv solution was added to each well, and the plate was left standing at room temperature for 1 hour so that the scFv bound to the antigen contained in each well. Each well was washed with TBST, MONOCLONAL ANTI-FLAG® M2, ANTIBODY (SIGMA, 1000-fold diluted with TBS) was then added to each well. The plate was incubated for 1 hour. Each well was washed with TBST, Goat Anti-Mouse IgG, IgA, IgM (H+L), HRP Conjugate (Invitrogen, 2000-fold diluted with TBS) was then added to each well. The plate was incubated for 1 hour. After washing with TBST, TMB single solution (ZYMED Laboratories, Inc.) was added to the well. The chromogenic reaction of the solution in each well was terminated by the addition of sulfuric acid. Then, the developed color was assayed on the basis of absorbance at 450 nm. The results are shown in FIG. 7. Most of scFv bound to either CD3 epsilon or CD137 but two scFv, painted as black in FIG. 7, from IdeS elution campaign, showed binding to both human CD137 and CD3 epsilon. In other words, clones exhibiting binding activity against the second antigen (human CD137) were successfully selected by use of the dual scFv library.

(3-3) Analysis of Binding of IgG to CD3 Epsilon or CD137

Eleven clones(dBBDu_001 to 011) were selected to be evaluated further. These clones were converted to IgG (the VH and VL sequences of each clone are linked to human H chain and L chain constant domains, respectively), and evaluated for their binding activity against CD3 epsilon and CD137. The VH fragment of each clone was amplified by PCR using primers specifically binding to the H chain in the library. The amplified VH fragment was assembled to CH1 gene of human IgG1 and integrated into an animal expression plasmid. The prepared plasmids were used for expression in animal cells by the method of Reference Example 1. GLS3000 was used as Light chain and its expression plasmid was prepared as shown in Reference Example 4-2.

Antigen binding of each molecule was tested by the electrochemiluminescence method (ECL method). Specifically, biotinylated CD3 epsilon peptide or biotinylated human CD137 diluted to 18 pmol/mL with a TBS solution containing 0.1% Tween 20, referred as to TBST, and each antibody solution adjusted to 2 micro g/mL, and SULFO-TAG labeled (MESO SCALE DIAGNOSTICS, Ruthenium (II) trisbipyridine, N-hydroxysuccinimide) anti-human IgG antibody (Invitrogen #628400) adjusted to 18 pmol/mL were each added at 25 micro L/well to Nunc-Immuno™ MicroWell™ 96 well round plates (Nunc), and mixed, and the plate was then incubated for one hour at room temperature to form an antibody-antigen complex. A TBST solution containing 0.5% BSA was added at 150 micro L/well to streptavidin plate (MSD K.K., L15SA-1), and the plate was incubated overnight at 4 degrees C. After removal of the blocking solution, each well was washed three times with 250 micro L of a TBST solution. The antibody-antigen complex solution was added thereto at 75 micro L/well, and the plate was incubated at room temperature for one hour so that the biotin-anti human IgG Ab bound to the streptavidin plate. After removal of the antibody-antigen complex solution, each well was washed three times with a TBST solution, and READ buffer (MSD K.K.) was added thereto at 150 micro L/well, followed by the detection of the luminescence signal of the sulfo-tag using Sector Imager 2400 (MSD K.K.).

Among those 11 clones, clone 011 (SEQ ID NO: 5) showed obvious binding to both CD3 epsilon and human CD137, and some other clones also showed binding to both CD3 epsilon and human CD137 (FIG. 8), so this result proves those dual antibodies which bind to two different antigen could be obtained with this designed dual scFv library.

[Example 4] Obtainment of scFv Domain Binding to CD3 Epsilon and Human CD137 from Dual scFv Library with Double Round Selection (4-1) Panning Strategy to Improve the Efficiency to Obtain scFv Domain Binding to Human CD137 scFv domain binding to CD3 epsilon and CD137 were successfully obtained in Example 3, but the acquisition efficiency was not so high. One of the considerable strategy to improve it is alternative panning, in which different antigens would be used in different panning rounds. By this method selection pressure to both CD3 epsilon and CD137 could be put on dual scFv library in each different round, but not simultaneously. To resolve this flaw, we used double round selection which was reported that twice panning was conducted to an antigen in 1 round (1 round mean from phage recovery from *E. coli* to phage infection to *E. coli*. in phage display and from in vitro transcription to PCR amplification in ribosome display) (J Mol Biol. 1992 Aug. 5; 226(3):889-96). They used only one type of antigen in each panning round, but we considered we will be able to recover two different antigen specific antibodies more efficiently by double round selection in which two different antigen were used in each panning procedure.

(4-2) Obtainment of scFv Domain Binding to Human CD137 with Double Round Selection Panning conditions were shown in Table 1. Campaign.1 and 2 were alternative panning condition and Campaign 3 were double round selection condition in which double round selection was conducted in round 3, 5 and 7. Biotin-labeled CD3 epsilon peptide antigen (amino acid sequence: SEQ ID NO: 6) and biotin-labeled human CD137 fused to human IgG1 Fc fragment (named as human CD137-Fc) was used as an antigen. In the Table 1, CD3 means panning with biotin-labeled CD3 peptide, CD137 means panning with biotin-labeled human CD137-Fc, and Double means double round selection.

TABLE 1

| Campaign name | Round1 | Round2 | Round3 | Round4 | Round5 | Round6 | Round7 |
|---|---|---|---|---|---|---|---|
| 1 | CD3 | CD137 | CD137 | CD3 | CD137 | CD137 | CD137 |
| 2 | CD137 |  | CD3 | CD137 |  | CD3 |  |
| 3 |  |  | Double |  | Double | CD137 | Double | scFv ribosome display library constructed in Example 2 was used for in vitro transcription (T7 RiboMAX™ Express Large scale RNA production system, P1320, Promega) to prepare mRNA scFv library. Synthesized mRNA are purified by RNeasy mini kit (Cat. No. 74104, QIAGEN). Obtained mRNA library was translated by PUREfrex1.0 (PF001-0.25, Genefrontier) cell-free in vitro translation system with DnaK GroE Mix and DS supplement (PF003-0.5, PF004-0.5, PF005-0.5, Genefrontier). After that WBTH buffer (50 mM Tris-Acetate, 150 mM NaCl, 70 mM Mg-Acetate, 0.1% Tween, 2.5 mg/mL Heparin) was added to stop the translation and Blocking buffer (One pack of SuperBlock Dry Blend Blocking buffer in TBS(Cat. No. 37545, Pierce) in 200 mL milliQ) was also added. The panning method was performed with reference to a general panning method with magnetic beads (Nat Methods. 2007 March; 4(3):269-79; Methods Mol Biol. 2012; 805:261-86). The magnetic beads used were NeutrAvidin coated beads (Sera-Mag Speed Beads NeutrAvidin-corted or FG NeutrAvidin beads) or Streptavidin coated beads (Dynabeads M-280 Streptavidin or Dynabeads MyOne Streptavidin T1 beads).

Specifically, 250 pmol of the biotin-labeled antigen and 2 nmol of free human IgG Fc domain (when biotin-labeled antigen was human CD137-Fc) was added to the prepared ribosome display library solution and thereby contacted with the library solution at 4 degrees Celsius for 60 minutes. After addition of SuperBlock-blocked magnetic beads, the antigen-scFv complex were attached to the magnetic beads at 4 degrees Celsius for 15 minutes. The beads were washed two or three times with WBT buffer (50 mM Tris-Acetate, 150 mM NaCl, 50 mM Mg-Acetate, 0.1% Tween). After addition of Elution buffer (50 mM Tris-Acetate, 150 mM NaCl, 50 mM EDTA and 50 micro g/mL *S. cerevisiae* RNA (SIGMA)), the beads were suspended at 50 degrees Celsius for 15 minutes, immediately after which the beads were separated using a magnetic stand to recover mRNA solution. The recovered mRNA was purified using High Pure RNA Isolation kit (Roche). Purified mRNA library was converted to cDNA reverse transcription using the primer of SEQ ID NO: 147 and SuperScript III Reverse Transcriptase (Thermo Fisher Scientific) and then amplified by PCR with the primer of SEQ ID NO: 148 and KOD-FX polymerase (TOYOBO). T7 promoter gene was added to the amplified DNA library by PCR with the primers of SEQ ID NOs: 149 and 150. This cycle was repeated several times. In the second and subsequent rounds of panning, 150 to 50 pmol of the biotin-labeled human CD137-Fc or 250 pmol of the biotin-labeled CD3 epsilon peptide was used.

In the round 3, 5 and 7 of Campaign3, double round selection was conducted. Specifically, 250 pmol of the biotin-labeled CD3 epsilon peptide was added to the prepared ribosome display library solution and thereby contacted with the library solution at 4 degrees Celsius for 60 minutes. After addition of SuperBlock-blocked magnetic beads, the antigen-scFv complex were attached to the magnetic beads at 4 degrees Celsius for 15 minutes. The beads were washed six to ten times (depend on the panning round) with WBT buffer. After addition of Elution buffer, the beads were suspended at 50 degrees Celsius for 15 minutes, immediately after which the beads were separated using a magnetic stand to recover mRNA solution. The recovered mRNA was purified using High Pure RNA Isolation kit (Roche). Purified mRNA library was subsequently translated by PUREfrex1.0 (GeneFrontier) again. 250 pmol or 100 pmol of the biotin-labeled CD137-Fc and 2 nmol of free human IgG Fc domain was added to the prepared ribosome display library solution and thereby contacted with the library solution at 4 degrees Celsius for 60 minutes. After addition of SuperBlock-blocked magnetic beads, the antigen-scFv complex were attached to the magnetic beads at 4 degrees Celsius for 15 minutes. The beads were washed three to ten times (depend on the panning round) with WBT buffer. After addition of Elution buffer, the beads were suspended at 50 degrees Celsius for 15 minutes, immediately after which the beads were separated using a magnetic stand to recover mRNA solution. The recovered mRNA was purified using High Pure RNA Isolation kit (Roche). Purified mRNA library converted to cDNA reverse transcription using the primer of SEQ ID NO: 147 and SuperScript III Reverse Transcriptase (Thermo Fisher Scientific) and then amplified by PCR with the primer of SEQ ID NO: 148 and KOD-FX polymerase (TOYOBO). T7 promoter gene was added to the amplified DNA library by PCR with the primers of SEQ ID NOs: 149 and 150.

(XX-2) Binding of scFv Domain to CD3 Epsilon or CD137 (scFv ELISA)

To evaluate the binding of scFv domain by ELISA, FLAG-tag was added to the recovered DNA library in round six and seven by PCR with the primers of SEQ ID NOs: 149 and 151. Obtained scFv-FLAG DNA fragment was ligated into the TOPO TA cloning kit dual promoter (Invitrogen) and transformed to DH5alpha *Escherichia coli*. The VH sequence from each single colony of the *E. coli* was analyzed. Then some clones which had different VH sequence each other from each panning campaign in round six and seven were picked up. Each scFv-FLAG gene were amplified from each colony with the primers of SEQ ID NOs: 149 and 151. PUREfrex1.0ss was added to the each amplified scFv gene and incubated at 37 degrees Celsius for 2 hours. After addition of 2% Skim-milk buffer, the scFv containing solution was subjected to ELISA by the following procedures: StreptaWell 96 microtiter plate (F. Hoffmann-La Roche Ltd.) was coated with biotinylate CD3 epsilon peptide or biotinylated human CD137-Fc at room temperature for 30 minutes. Each well of the plate was washed with TBST (TBS containing 0.1% Tween 20; TBS was available from Takara Bio Inc.) to remove unbound antigen. Then, the well was blocked with 250 micro L of 2% skim-milk-TBS for 1 hour or longer. After removal of 2% skim-milk-TBS, the prepared scFv solution was added to each well, and the plate was left standing at room temperature for 1 hour so that the scFv bound to the antigen contained in each well. Each well was washed with TBST, MONOCLONAL ANTI-FLAG® M2, ANTIBODY(SIGMA, 1000-fold diluted with TBS) was then added to each well. The plate was incubated for 1 hour. Each well was washed with TBST, Goat Anti-Mouse IgG, IgA, IgM (H+L), HRP Conjugate (Invitrogen, 2000-fold diluted with TBS) was then added to each well. The plate was incubated for 1 hour. After washing with TBST, TMB single solution (ZYMED Laboratories, Inc.) was added to the well. The chromogenic reaction of the solution in each well was terminated by the addition of sulfuric acid. Then, the developed color was assayed on the basis of absorbance at 450 nm. The results are shown in FIG. 9. All scFv in campaign 1 and 2 bound to either CD3 epsilon or CD137. On the other hand, many scFv in campaign 3 showed binding to both human CD137 and CD3 epsilon. In other words, the efficiency to obtain clones exhibiting binding activity against both CD3 epsilon and the second antigen (human CD137) was successfully improved by double round selection in which two different antigen were used in each panning round.

(4-3) Additional Panning to Obtain More scFv Domain Binding to Human CD137 with Double Round Selection To produce much more scFv domain binding to human CD137 and CD3 epsilon, additional round of panning was conducted on campaign2 and 3. In round 8, both conventional selection and double round selection was used on campaign2 round 7 output library, and only double round selection was conducted on campaign3 round 7 output library. The each panning procedure was as same as Example 4-2.

(4-4) Obtainment of scFv Domain Binding to Human CD137 with Double Round Selection and IdeS Elution.

Panning conditions were shown in Table 2. Campaign.4 and 5 were alternative panning condition and Campaign 6 were double round selection condition in which double round selection was conducted in round 3, 5 and 7. Biotin-labeled CD3 epsilon peptide antigen (amino acid sequence: SEQ ID NO: 6) and biotin-labeled human CD137 fused to human IgG1 Fc fragment (named as human CD137-Fc) was used as an antigen. In the Table 2, CD3 means panning with biotin-labeled CD3 peptide, CD137 means panning with biotin-labeled human CD137-Fc, and Double means double round selection.

TABLE 2

| Campaign | Round1 | Round2 | Round3 | Round4 | Round5 | Round6 | Round7 |
|---|---|---|---|---|---|---|---|
| 4 | CD3 | CD137 | CD137 | CD3 | CD137 | CD137 | CD137 |
| 5 | CD137 | | CD3 | CD137 | | CD3 | |
| 6 | | | Double | | Double | CD137 | Double | scFv ribosome display library constructed in Example 2 was used for in vitro transcription (T7 RiboMAX™ Express Large scale RNA production system, P1320, Promega) to prepare mRNA scFv library. Synthesized mRNA are purified by RNeasy mini kit (Cat. No. 74104, QIAGEN). Obtained mRNA library was translated by PUREfrex1.0 (PF001-0.25, Genefrontier) cell-free in vitro translation system with DnaK GroE Mix and DS supplement (PF003-0.5, PF004-0.5, PF005-0.5, Genefrontier). After that WBTH buffer (50 mM Tris-Acetate, 150 mM NaCl, 70 mM Mg-Acetate, 0.1% Tween, 2.5 mg/mL Heparin) was added to stop the translation and Blocking buffer (One pack of SuperBlock Dry Blend Blocking buffer in TBS (Cat. No. 37545, Pierce) in 200 mL milliQ) was also added. The panning method was performed with reference to a general panning method with magnetic beads (Nat Methods. 2007 March; 4(3):269-79; Methods Mol Biol. 2012; 805:261-86). The magnetic beads used were NeutrAvidin coated beads (Sera-Mag Speed Beads NeutrAvidin-corted or FG NeutrAvidin beads) or Streptavidin coated beads (Dynabeads M-280 Streptavidin or Dynabeads MyOne Streptavidin T1 beads).

Specifically, 250 pmol of the biotin-labeled antigen and 2 nmol of free human IgG Fc domain (when biotin-labeled antigen was human CD137-Fc) was added to the prepared ribosome display library solution and thereby contacted with the library solution at 4 degrees Celsius for 60 minutes. After addition of SuperBlock-blocked magnetic beads, the antigen-scFv complex were attached to the magnetic beads at 4 degrees Celsius for 15 minutes. The beads were washed two or three times with WBT buffer. After addition of Elution buffer, the beads were suspended at 50 degrees Celsius for 15 minutes, immediately after which the beads were separated using a magnetic stand to recover mRNA solution. The recovered mRNA and the mRNA was purified using High Pure RNA Isolation kit (Roche). Purified mRNA library was converted to cDNA reverse transcription using the primer of SEQ ID NO: 147 and SuperScript III Reverse Transcriptase (Thermo Fisher Scientific) and then amplified by PCR with the primer of SEQ ID NO: 148 and KOD-FX polymerase (TOYOBO). T7 promoter gene was added to the amplified DNA library by PCR with the primers of SEQ ID NOs: 149 and 150. This cycle was repeated several times. In the second and subsequent rounds of panning, 150 to 50 pmol of the biotin-labeled human CD137 Fc or 250 pmol of the biotin-labeled CD3 epsilon peptide was used. When antigen was the biotin-labeled human CD137-Fc in second and subsequent round, FabRICATOR (IdeS, protease for hinge region of IgG, GENOVIS) was used to recover mRNA. In that procedure, 10 units/micro L Fabricator 5 micro L with 95 micro L WBT buffer was added and beads were suspended at 37 degrees Celsius for 10 minutes, immediately after which the beads were separated using a magnetic stand to recover mRNA solution. And then 100 micro L of Elution Buffer was added to the recovered mRNA and incubated at 50 degrees Celsius for 10 minutes. When antigen was the biotin-labeled CD3 epsilon peptide, only elution buffer was used as same as round 1.

In the round 3, 5 and 7 of Campaign6, double round selection was conducted. Specifically, 250 pmol of the biotin-labeled CD3 epsilon peptide was added to the prepared ribosome display library solution and thereby contacted with the library solution at 4 degrees Celsius for 60 minutes. After addition of SuperBlock-blocked magnetic beads, the antigen-scFv complex were attached to the magnetic beads at 4 degrees Celsius for 15 minutes. The beads were washed six to ten times (depend on the panning round) with WBT buffer. After addition of Elution buffer, the beads were suspended at 50 degrees Celsius for 15 minutes, immediately after which the beads were separated using a magnetic stand to recover mRNA solution.

Ribosome (GeneFrontier) was added to the recovered mRNA and the mRNA was purified using High Pure RNA Isolation kit (Roche). Purified mRNA library was subsequently translated by PUREfrex1.0 (GeneFrontier) again. 250 pmol or 100 pmol of the biotin-labeled CD137-Fc and 2 nmol of free human IgG Fc domain was added to the prepared ribosome display library solution and thereby contacted with the library solution at 4 degrees Celsius for 60 minutes. After addition of SuperBlock-blocked magnetic beads, the antigen-scFv complex were attached to the magnetic beads at 4 degrees Celsius for 15 minutes. The beads were washed three to ten times (depend on the panning round) with WBT buffer. 10 units/micro L Fabricator 5 micro L with 95 micro L WBT buffer was added and beads were suspended at 37 degrees Celsius for 10 minutes, immediately after which the beads were separated using a magnetic stand to recover mRNA solution. And then 100 micro L of Elution Buffer was added to the recovered mRNA and incubated at 50 degrees Celsius for 10 minutes. The recovered mRNA was purified using High Pure RNA Isolation kit (Roche). Purified mRNA library converted to cDNA reverse transcription using the primer of SEQ ID NO: 147 and SuperScript III Reverse Transcriptase (Thermo Fisher Scientific) and then amplified by PCR with the primer of SEQ ID NO: 148 and KOD-FX polymerase (TOYOBO). T7 promoter gene was added to the amplified DNA library by PCR with the primers of SEQ ID NOs: 149 and 150.

(4-5) Additional Panning to Obtain More scFv Domain Binding to Human CD137 with Double Round Selection and IdeS Elution To produce much more scFv domain binding to human CD137 and CD3 epsilon, additional round of panning was conducted as same as Example 4-3 on campaign4, 5 and 6. Both conventional selection and double round selection was used on both campaign5 and campaign6 round 7 output library and double round selection was conducted on campaign4 round 6 output library. The each panning procedure was as same as Example. 4-4.

(4-6) Binding of scFv Domain to CD3 Epsilon or CD137 (scFv ELISA)

To evaluate the binding of scFv domain by ELISA, FLAG-tag was added to the recovered DNA library in round six to eight in Example. 4-3, 4 and 5 by PCR with the primers of SEQ ID NOs: 149 and 151. Obtained scFv-FLAG DNA fragment was ligated into the TOPO TA cloning kit dual promoter (Invitrogen) and transformed to DH5alpha *Escherichia coli*. The VH sequence from each single colony of the *E. coli* was analyzed. Then we picked up some clones which had different VH sequence each other from each panning campaign. Each scFv-FLAG gene were amplified from each colony with the primers of SEQ ID NOs: 149 and 151. PUREfrex1.0ss was added to the each amplified scFv gene and incubated at 37 degrees Celsius for 2 hours. After addition of 2% Skim-milk buffer, the scFv containing solution was subjected to ELISA by the following procedures: StreptaWell 96 microtiter plate (F. Hoffmann-La Roche Ltd.) was coated with biotinylate CD3 epsilon peptide or biotinylated human CD137-human IgG1 Fc fusion at room temperature for 30 minutes. Each well of the plate was washed with TBST (TBS containing 0.1% Tween 20; TBS was available from Takara Bio Inc.) to remove unbound antigen. Then, the well was blocked with 250 micro L of 2% skim-milk-TBS for 1 hour or longer. After removal of 2% skim-milk-TBS, the prepared scFv solution was added to each well, and the plate was left standing at room temperature for 1 hour so that the scFv bound to the antigen contained in each well. Each well was washed with TBST, MONOCLONAL ANTIFLAG® M2, ANTIBODY(SIGMA, 1000-fold diluted with TBS) was then added to each well. The plate was incubated for 1 hour. Each well was washed with TBST, Goat Anti-Mouse IgG, IgA, IgM (H+L), HRP Conjugate (Invitrogen, 2000-fold diluted with TBS) was then added to each well. The plate was incubated for 1 hour. After washing with TBST, TMB single solution (ZYMED Laboratories, Inc.) was added to the well. The chromogenic reaction of the solution in each well was terminated by the addition of sulfuric acid. Then, the developed color was assayed on the basis of absorbance at 450 nm.

The results are shown in FIG. 10. Many scFvs showed binding to both human CD137 and CD3 epsilon in each panning campaign.

(4-7) Conversion of Antibody Format into IgG1 and Preparation of Each IgG1 Molecules.

Eleven pools (shown in Table 3) were selected to be evaluated further. scFvs included in these pools were converted to IgG (the VH and VL sequences of each clone are linked to human H chain and L chain constant domains, respectively), and evaluated for their binding activity against CD3 epsilon and CD137. The VH fragments of each pool were amplified by PCR using primers specifically binding to the H chain in the library (SEQ ID NOs: 152 and 153). The amplified VH fragment was integrated into an animal expression plasmid which have already had human IgG1 CH1-Fc region. The prepared plasmids were used for expression in animal cells by the method of Reference Example 1. GLS3000 (SEQ ID NO: 1) was used as Light chain and its expression plasmid was prepared as shown in Reference Example 4-2.

TABLE 3

| Campaign | Additional panning | Round | Picked colony number |
|---|---|---|---|
| 3 | — | 6 | 288 |
| 3 | — | 7 | 192 |
| 3 | Double round | 8 | 288 |
| 4 | — | 6 | 96 |
| 4 | Double round | 7 | 288 |
| 5 | — | 7 | 192 |
| 5 | Conventional | 8 | 96 |
| 5 | Double round | 8 | 96 |
| 6 | — | 6 | 96 |
| 6 | — | 7 | 96 |
| 6 | Conventional | 8 | 96 |

(4-8) Assessment of the Obtained Antibodies for their CD3 Epsilon and Human CD137 Binding Activity The prepared antibodies were subjected to ELISA to evaluate their binding capacity to CD3 epsilon and human CD137.

First, a Streptavidin-coated microplate (384 well, Greiner) was coated with 20 micro L of TBS containing biotin-labeled CD3 epsilon peptide or biotin labeled human CD137-Fc at room temperature for one or more hours. After removing biotin-labeled antigen that are not bound to the plate by washing each well of the plate with TBST, the wells were blocked with 20 micro L of Blocking Buffer (2% skim milk/TBS) for one or more hours. Blocking Buffer was removed from each well. 10 micro L each of the IgG containing mammalian cell supernatant twice diluted with 1% Skim milk/TBS were added to the wells, and the plate was allowed to stand at room temperature for one hour to allow each IgG to bind to biotin-labeled antigen in each well. After that each well was washed with TBST. Goat anti-human kappa Light chain alkaline phosphatase conjugate (BETHYL, A80-115AP) diluted with TBS was added to each well. The plate was incubated for one hour. After washing with TBST, the chromogenic reaction of the solution in each well added with Blue Phos Microwell Phosphatase Substrate System (KPL) was terminated by adding Blue Phos Stop Solution (KPL). Then, the color development was measured by absorbance at 615 nm. The measurement results are shown in FIG. 11.

Many clones showed binding to both CD3 epsilon and human CD137 even in the IgG1 format. Then The VH sequence from each single colony of the E. coli was analyzed. In total, 19 different HCDR3 sequence were contained in these antibodies that bind to both CD3 epsilon and CD137, and in which many HCDR1 or 2 sequence variants were existed.

This suggests that antibodies that bind to two different antigen, CD3 epsilon and human CD137, were obtained from the rationally designed library constructed using a CD3 binding antibody as a template as described in Reference Example 4, and double round selection could improve the efficiency to obtain such antibodies much more. In conventional alternative panning, selection pressure changes in each panning round so condensation of ideal clones become slower and slower or the loss of ideal clones might be occurred. By using double round selection with two different antigens we can uniform the selection pressure in each panning round so that ideal clones prone to collect smoothly and more directly.

[Example 5] Affinity Maturation of Antibody Domain Binding to CD3 Epsilon and Human CD137 from Dual scFv Library with Designed Light Chain Library (5-1) Construction of Light Chain Library with Obtained Heavy Chain Many antibodies which bind to both CD3 epsilon and human CD137 were obtained in Example 4, but their affinity to human CD137 were still weak so affinity maturation to improve their affinity was conducted.

To achieve that, designed light chain library described in Reference Example 4 was combined with Heavy chain of one candidate antibodies which bind to both CD3 epsilon and human CD137. We selected an antibodies, named as dBBDu_115 (SEQ ID NO: 7), as candidate antibody for affinity maturation because of its better binding to both CD3 epsilon and human CD137 among these 19 antibodies described in Example 4.

We constructed two different antibody format library, VL-GS linker-VH scFv format and Fab format. The design of ribosome display dual antibody library is shown in FIG. 12. A part of bacteriophage lambda gpD gene and Escherichia coli secM gene were used as spacer gene to display scFv or Fab library on ribosome efficiently as same as Example 2.

The synthesized antibody VL library fragments described in Reference Example 4 were fused with Gly/Ser rich linker-dBBDu_115 VH-Spacer gene (SEQ ID NO: 8) at 3' terminus and T7 promoter with 5' untranslated region (SEQ ID NO: 4) at 5' terminus by PCR amplification to create VL-VH scFv format library.

The synthesized antibody VL library fragments described in Reference Example 4 were fused with CL-Spacer gene (SEQ ID NO: 9) at 3' terminus and T7 promoter with 5' untranslated region (SEQ ID NO: 4) at 5' terminus by PCR amplification to create Fab format library. VH gene fragment of dBBDu_115 was also fused with CH1 gene (SEQ ID NO: 10) at 3' terminus and T7 promoter with 5' untranslated region (SEQ ID NO: 4) at 5' terminus by PCR amplification to create Hch fragment of Fab format.

(5-2) Obtainment of Antibody Domain Binding to Both CD3 Epsilon and Human CD137

Panning conditions were shown in Table 4. In this Table 4, double means double round selection and CD137Fc means conventional panning against biotin-labeled human CD137-Fc. Biotin-labeled CD3 epsilon peptide antigen (amino acid sequence: SEQ ID NO: 6) and biotin-labeled human CD137 fused to human IgG1 Fc fragment (named as human CD137-Fc) was used as an antigen.

TABLE 4

| Antibody format | Campaign name | Elution | Round1 | Round2 | Round3 | Round4 | Round5 | Round6 | Round7 | Round8 |
|---|---|---|---|---|---|---|---|---|---|---|
| Fab | 5 | Elution buffer | CD137Fc | double | CD137Fc | double | CD137Fc | double | double | double |
| Fab | 6 | IdeS | CD137Fc | double | CD137Fc | double | CD137Fc | double | CD137Fc | double |
| Fab | 9 | IdeS | CD137Fc | double | CD137Fc | double | CD137Fc | double | double | double |
| VL-VH scFv | 10 | IdeS | CD137Fc | CD137Fc | double | CD137Fc | double | double | double | | scFv ribosome display library, Fab Light chain ribosome display library and Fab Heavy chain constructed in Example 5-1 was used for in vitro transcription (T7 RiboMAX™ Express Large scale RNA production system, P1320, Promega) to prepare mRNA library and Heavy chain mRNA. Synthesized mRNA are purified by RNeasy mini kit (Cat. No. 74104, QIAGEN). Obtained mRNA library and Fab Heavy chain were translated by PUREfrex1.0 (PF001-0.25, Genefrontier) cell-free in vitro translation system with DnaK GroE Mix and DS supplement (PF003-0.5, PF004-0.5, PF005-0.5, Genefrontier). After that WBTH buffer was added to stop the translation and Blocking buffer (2×c-block-e, Beacle) was also added. The magnetic beads used were NeutrAvidin coated beads (Sera-Mag Speed Beads NeutrAvidin-corted or FG NeutrAvidin beads) or Streptavidin coated beads (Dynabeads M-280 Streptavidin or Dynabeads MyOne Streptavidin T1 beads).

Specifically, 60 pmol of the biotin-labeled human CD137-Fc was added to the magnetic beads at 4 degrees Celsius for 60 minutes and then c-block-e (Beacle) was added to block the beads at 4 degrees Celsius for 60 minutes. This antigen coated magnetic beads and 2 nmol of free human IgG Fc domain was added to the prepared ribosome display library solution and thereby contacted with the library solution at 4 degrees Celsius for 75 minutes. The beads were incubated with WBT buffer for 2 (Campaign 10) or 10 (Campaign 5, 6 and 9) minutes and then discord the WBT buffer. This wash procedure was repeated ten times with WBT buffer. After addition of Elution buffer, the beads were suspended at 50 degrees Celsius for 15 minutes, immediately after which the beads were separated using a magnetic stand to recover mRNA solution. The recovered mRNA was purified using High Pure RNA Isolation kit (Roche). Purified mRNA library was converted to cDNA reverse transcription using the primer of SEQ ID NO: 147 and SuperScript III Reverse Transcriptase (Thermo Fisher Scientific) and then amplified by PCR with the primer of SEQ ID NO: 148 and KOD-FX polymerase (TOYOBO). T7 promoter gene was added to the amplified DNA library by PCR with the primers of SEQ ID NOs: 149 and 150. This cycle, called panning, was repeated several times.

In the second and subsequent rounds of panning, amount of the biotin-labeled human CD137-Fc was changed as shown in Table 5, and the number of washing was also changed as shown in Table 6. When antigen was the biotin-labeled human CD137-Fc in second and subsequent round in Campaign 6, 9 and 10, FabRICATOR (IdeS, protease for hinge region of IgG, GENOVIS) was used to recover mRNA. In that procedure, 10 units/micro L Fabricator 5 micro L with 95 micro L WBT buffer was added and beads were suspended at 37 degrees Celsius for 10 minutes, immediately after which the beads were separated using a magnetic stand to recover mRNA solution. And then 100 micro L of Elution Buffer was added to the recovered mRNA and incubated at 50 degrees Celsius for 10 minutes.

TABLE 5

The amount of biotin-labeled human CD137-Fc (pmol)

| Antibody format | Campaign name | Elution | Round1 | Round2 | Round3 | Round4 | Round5 | Round6 | Round7 | Round8 |
|---|---|---|---|---|---|---|---|---|---|---|
| Fab | 5 | Elution buffer | 60 | *40* | 30 | *40* | 30 | *40* | *40* | *40* |
| Fab | 6 | IdeS | 60 | *40* | 30 | *40* | 30 | *40* | 30 | *40* |
| Fab | 9 | IdeS | 60 | *40* | 3 | *4* | 3 | *4* | *4* | *4* |
| VL-VH scFv | 10 | IdeS | 100 | 60 | *80* | 60 | *80* | *80* | *80* | |

TABLE 6

The number of wash

| Antibody format | Campaign name | Elution | Round1 | Round2 | Round3 | Round4 | Round5 | Round6 | Round7 | Round8 |
|---|---|---|---|---|---|---|---|---|---|---|
| Fab | 5 | Elution buffer | 10 minutes 10 times | 10 minutes 10 times | 10 minutes 16 times | 10 minutes 10 times | 10 minutes 16 times | 10 minutes 10 times | 10 minutes 10 times | 10 minutes 10 times |
| Fab | 6 | IdeS | 10 minutes 10 times | 10 minutes 10 times | 10 minutes 16 times | 10 minutes 10 times | 10 minutes 16 times | 10 minutes 10 times | 10 minutes 16 times | 10 minutes 10 times |
| Fab | 9 | IdeS | 10 minutes 10 times | 10 minutes 10 times | 10 minutes 16 times | 10 minutes 10 times | 10 minutes 16 times | 10 minutes 10 times | 10 minutes 10 times | 10 minutes 10 times |
| VL-VH scFv | 10 | IdeS | 2 minutes 10 times | 10 minutes 10 times | 10 minutes 10 times | 10 minutes 10 times | 10 minutes 10 times | 10 minutes 10 times | 10 minutes 10 times | |

Double round selection was conducted in some campaign. Specifically, 150 pmol of the biotin-labeled CD3 epsilon peptide was added to the magnetic beads at 4 degrees Celsius for 60 minutes and then c-block-e (Beacle) was added to block the beads at 4 degrees Celsius for 60 minutes. This antigen coated magnetic beads were added to the prepared ribosome display library solution and thereby contacted with the library solution at 4 degrees Celsius for 60 minutes. The beads were washed ten times with WBT buffer. After addition of Elution buffer, the beads were suspended at 50 degrees Celsius for 15 minutes, immediately after which the beads were separated using a magnetic stand to recover mRNA solution. The recovered mRNA was purified using High Pure RNA Isolation kit (Roche). Purified mRNA library was subsequently translated by PUREfrex1.0 (GeneFrontier) again. The biotin-labeled CD137-Fc was added to the magnetic beads at 4 degrees Celsius for 60 minutes and then c-block-e (Beacle) was added to block the beads at 4 degrees Celsius for 60 minutes. This antigen coated magnetic beads and 2 nmol of free human IgG Fc domain were added to the prepared ribosome display library solution and thereby contacted with the library solution at 4 degrees Celsius for 60 minutes. The beads were incubated with WBT buffer for 10 minutes and then discord the WBT buffer. This wash procedure was repeated ten times with WBT buffer. In Campaign 6, 9 and 10, 10 units/micro L Fabricator 5 micro L with 95 micro L WBT buffer was added and beads were suspended at 37 degrees Celsius for 10 minutes, immediately after which the beads were separated using a magnetic stand to recover mRNA solution. And then 100 micro L of Elution Buffer was added to the recovered mRNA and incubated at 50 degrees Celsius for 10 minutes. The recovered mRNA was purified using High Pure RNA Isolation kit (Roche). Purified mRNA library converted to cDNA reverse transcription using the primer of SEQ ID NO: 147 and SuperScript III Reverse Transcriptase (Thermo Fisher Scientific) and then amplified by PCR with the primer of SEQ ID NO: 148 and KOD-FX polymerase (TOYOBO). T7 promoter gene was added to the amplified DNA library by PCR with the primers of SEQ ID NOs: 149 and 150.

(5-3) Conversion of Antibody Format into IgG1 and Preparation of Each IgG1 Molecules.

Light chain gene of scFv or Fab domain library from the affinity maturation panning written in Example 5-2 were converted to IgG, and evaluated for their binding activity against CD3 epsilon and CD137. The VL-CL fragments of Campaign 5, 6 and 9 pool were amplified by PCR using primers specifically binding to the L chain in the library (SEQ ID NOs: 154 and 155). The amplified VL-CL fragment was integrated into an animal expression plasmid and DH5 alpha *Escherichia coli* strain were transformed. Obtained plasmid was also used for construction of Light chain expression vector from Campaign 10. VL region gene was eliminated from obtained expression vector with restriction enzyme SfiI and KpnI. The VL fragments of Campaign 10 pool were amplified by PCR using primers specifically binding to the VL region in the library (SEQ ID NOs: 154 and 156). Prepared VL fragment was introduced into digested expression plasmid. Picked colony number was shown in Table 7. The prepared plasmids were used for expression in animal cells by the method of Reference Example 1. dBBDu_115 Heavy chain expression plasmid constructed in Example 4 was also used to express full length IgG.

TABLE 7

| Campaign | Picked clone number |
| --- | --- |
| 5 | 288 |
| 6 | 288 |
| 9 | 384 |
| 10 | 192 |

(5-4) Assessment of the Obtained Antibodies for their CD3 Epsilon and Human CD137 Binding Activity The prepared antibodies were subjected to ELISA to evaluate their binding capacity to CD3 epsilon and human CD137.

First, a Streptavidin-coated microplate (384 well, Greiner) was coated with 20 micro L of TBS containing biotin-labeled CD3 epsilon peptide, biotin labeled human CD137-Fc and biotin labeled human IgG1 Fc region at room temperature for one or more hours. After removing biotin-labeled antigen that are not bound to the plate by washing each well of the plate with TBST, the wells were blocked with 20 micro L of Blocking Buffer (2% skim milk/TBS) for one or more hours. Blocking Buffer was removed from each well. 10 micro L each of the 20 micro g/mL IgG containing mammalian cell supernatant twice diluted with 2% Skim milk/TBS were added to the wells, and the plate was allowed to stand at room temperature for one hour to allow each IgG to bind to biotin-labeled antigen in each well. After that each well was washed with TBST. Goat anti-human kappa Light chain alkaline phosphatase conjugate (BETHYL, A80-115AP) diluted with TBS was added to each well. The plate was incubated for one hour. After washing with TBST, the chromogenic reaction of the solution in each well added with Blue Phos Microwell Phosphatase Substrate System (KPL) was terminated by adding Blue Phos Stop Solution (KPL). Then, the color development was measured by absorbance at 615 nm. The measurement results are shown in FIG. 13.

(5-5) Evaluation of Binding of IgG Having Obtained Fab Domain to CD3 Epsilon and Human CD137 at Same Time Five antibodies (shown in Table 8) were selected to evaluate further. These antibodies were expressed and purified according to Example 5-3 and Reference Example 1. Purified antibodies were subjected to ELISA to evaluate their binding capacity to CD3 epsilon and human CD137 at same time.

TABLE 8

| Lch name | SEQ ID NO |
| --- | --- |
| L008 | 11 |
| L014 | 12 |
| L016 | 13 |
| L035 | 14 |
| L039 | 15 |

First, a MyOne-T1 streptavidin beads were mixed with 0.625 pmol of biotin-labeled human CD137-Fc or biotin-labeled human Fc and incubated at room temperature for 10 minutes, then 2% skim-milk/TBS was added to block the magnetic beads. Mixed solution was dispended to each well of 96 well plate (Corning, 3792 black round bottom PS plate) and incubated at room temperature for 60 minutes or more. After that magnetic beads were washed by TBS once. 100 ng of purified IgG was mixed with 62.5, 6.25 or 0.625 pmol of free human CD3 epsilon or 62.5 pmol of free human Fc (in this example "free" means "non-biotin-labeled") or TBS and then added to the magnetic beads in each well, and the plate was allowed to stand at room temperature for one hour to allow each IgG to bind to biotin-labeled antigen in each well. After that each well was washed with TBST. Goat anti-human kappa Light chain alkaline phosphatase conjugate (BETHYL, A80-115AP) diluted with TBS was added to each well. The plate was incubated for one hour. After washing with TBST, APS-5 (Lumigen) was added to each well. 2 minutes later the fluorescence of each well was detected. The measurement results are shown in FIG. 14 and Table 9.

TABLE 9

| | biotin-human CD137-Fc | | |
|---|---|---|---|
| | Free CD3e 62.5 pmol | Free Fc 62.5 pmol | Signal decrease |
| dBBDu_H115/L008 | 1448 | 76909 | 98.12% |
| dBBDu_H115/L014 | 1511 | 72060 | 97.90% |
| dBBDu_H115/L016 | 1541 | 46828 | 96.71% |
| dBBDu_H115/L035 | 1466 | 70610 | 97.92% |
| dBBDu_H115/L039 | 1546 | 55829 | 97.23% |
| dBBDu_H115/Lwt | 1512 | 1728 | 12.50% |

Inhibition of binding to human CD137-Fc by free CD3 epsilon peptide was observed in all tested antibodies but not observed by free Fc domain. This results means those obtained antibodies could not bind to human CD137-Fc in the presence of CD3 epsilon peptide, in other words, these antibody do not bind to human CD137 and CD3 epsilon peptide at same time. So it was proved that Fab domains which can bind to two different antigens, CD137 and CD3 epsilon, but not bind to at same time were successfully obtained with designed library and ribosome display double round selection.

[Example 6] Obtainment of Fab Domain Binding to CD3 Epsilon and Human CD137 from Dual Fab Phage Display Library (6-1) Construction of Heavy Chain Phage Display Library with GLS3000 Light Chain The antibody library fragments synthesized in Reference Example 4 was used to construct the dual Fab library for phage display. The dual library was prepared as a library in which H chains are diversified as shown in Reference Example 4 while L chains are fixed to the original sequence GLS3000 (SEQ ID NO: 1). The H chain library sequences derived from CE115HA000 by adding the V11L/L78I mutation to FR (framework) and further diversifying CDRs as shown in Table 38 (in Reference Example 4) were entrusted to the DNA synthesizing company DNA2.0, Inc. to obtain antibody library fragments (DNA fragments). The obtained antibody library fragments were inserted to phagemids for phage display amplified by PCR. GLS3000 was selected as L chains. The constructed phagemids for phage display were transferred to *E. coli* by electroporation to prepare *E. coli* harboring the antibody library fragments.

Phage library displaying Fab domain were produced from the *E. coli* harboring the constructed phagemids by infection of helper phage M13KO7TC/FkpA which code FkpA chaperone gene and then incubate in the presence of 0.002% arabinose at 25 degrees Celsius (this phage library named as DA library) or 0.02% arabinose at 20 degrees Celsius (this phage library named as DX library) for overnight. M13KO7TC is a helper phage which has an insert of the trypsin cleavage sequence between the N2 domain and the CT domain of the pIII protein on the helper phage (see National Publication of International Patent Application No. 2002-514413). Introduction of insert gene into M13KO7TC gene have been already disclosed elsewhere (see National Publication of International Patent Application No. WO2015046554).

(6-2) Obtainment of Fab Domain Binding to CD3 Epsilon and Human CD137 with Double Round Selection Fab domains binding to CD3 epsilon and human CD137 were identified from the dual Fab library constructed in Example 6-1. Biotin-labeled CD3 epsilon peptide antigen (amino acid sequence: SEQ ID NO: 6), CD3 epsilon peptide antigen biotin-labeled through disulfide-bond linker (FIG. 15, called C3NP1-27; amino acid sequence: SEQ ID NO: 145, synthesized by Genscript), biotin-labeled human CD137 fused to human IgG1 Fc fragment (named as human CD137-Fc) and SS-biotinylated human CD137 fused to human IgG1 Fc fragment (named as ss-human CD137-Fc) was used as an antigen. ss-human CD137-Fc was prepared by using EZ-Link Sulfo-NHS-SS-Biotinylation Kit (PIERCE, Cat. No. 21445) to human CD137 fused to human IgG1 Fc fragment. Biotinylation was conducted in accordance with the instruction manual.

Phages were produced from the *E. coli* harboring the constructed phagemids for phage display. 2.5 M NaCl/10% PEG was added to the culture solution of the *E. coli* that had produced phages, and a pool of the phages thus precipitated was diluted with TBS to obtain a phage library solution. Next, BSA (final concentration: 4%) was added to the phage library solution. The panning method was performed with reference to a general panning method using antigens immobilized on magnetic beads (J. Immunol. Methods. (2008) 332 (1-2), 2-9; J. Immunol. Methods. (2001) 247 (1-2), 191-203; Biotechnol. Prog. (2002) 18 (2) 212-20; and Mol. Cell Proteomics (2003) 2 (2), 61-9). The magnetic beads used were NeutrAvidin coated beads (Sera-Mag SpeedBeads NeutrAvidin-coated) or Streptavidin coated beads (Dynabeads M-280 Streptavidin). To eliminate antibodies displaying phage which bind to magnetic beads itself or human IgG1 Fc region, subtraction for magnetic beads and biotin labeled human Fc was conducted.

Specifically, Phage solution was mixed with 250 pmol of human CD137-Fc and 4 nmol of free human IgG1 Fc domain and incubated at room temperature for 60 minutes. Magnetic beads was blocked by 2% skim-milk/TBS with free Streptavidin (Roche) at room temperature for 60 minutes or more and washed three times with TBS, and then mixed with incubated phage solution. After incubation at room temperature for 15 minutes, the beads were washed three-times with TBST (TBS containing 0.1% Tween 20; TBS was available from Takara Bio Inc.) and then further washed twice with 1 mL of TBS. 5 micro L of 100 mg/mL Trypsin and 495 micro L of TBS were added and incubated at room temperature for 15 minutes, immediately after which the beads were separated using a magnetic stand to recover phage solution. The *E. coli* strain was infected by the phages through the gentle spinner culture of the strain at 37 degrees C. for 1 hour. The infected *E. coli* was inoculated to a plate of 225 mm×225 mm. Next, phages were recovered from the culture solution of the inoculated *E. coli* to prepare a phage library solution.

In this panning round 1 procedure antibody displaying phages which bind to human CD137 was concentrated. In the $2^{nd}$ round of panning, 250 pmol of ss-human CD137-Fc was used as biotin-labeled antigen and wash was conducted three-times with TBST and then two-times with TBS. Elution was conducted with 25 mM DTT at room temperature for 15 minutes and then digested by Trypsin.

In the 3$^{rd}$ round and 6$^{th}$ round of panning, 62.5 pmol of C3NP1-27 was used as biotin-labeled antigen and wash was conducted three-times with TBST and then two-times with TBS. Elution was conducted with 25 mM DTT at room temperature for 15 minutes and then digested by Trypsin.

In the 4$^{th}$, 5$^{th}$ and 7$^{th}$ round of panning, 62.5 pmol of ss-human CD137-Fc was used as biotin-labeled antigen and wash was conducted three-times with TBST and then two-times with TBS. Elution was conducted with 25 mM DTT at room temperature for 15 minutes and then digested by Trypsin.

(6-3) Binding of Fab Domain Displayed by Phage to CD3 Epsilon or Human CD137

A phage-containing culture supernatant was recovered according to a general method (Methods Mol. Biol. (2002) 178, 133-145) from each 96 single colony of the E. coli obtained by the method described above. The phage-containing culture supernatant was subjected to ELISA by the following procedures: Streptavidin-coated Microplate (384 well, greiner, Cat #781990) was coated overnight at 4 degrees C. or at room temperature for 1 hour with 10 micro L of TBS containing the biotin-labeled antigen (biotin-labeled CD3 epsilon peptide or biotin-labeled human CD137-Fc). Each well of the plate was washed with TBST to remove unbound antigens. Then, the well was blocked with 80 micro L of TBS/2% skim milk for 1 hour or longer. After removal of TBS/2% skim milk, the prepared culture supernatant was added to each well, and the plate was left standing at room temperature for 1 hour so that the phage-displayed antibody bound to the antigen contained in each well. Each well was washed with TBST, and HRP/Anti M13 (GE Healthcare 27-9421-01) were then added to each well. The plate was incubated for 1 hour. After washing with TBST, TMB single solution (ZYMED Laboratories, Inc.) was added to the well. The chromogenic reaction of the solution in each well was terminated by the addition of sulfuric acid. Then, the developed color was assayed on the basis of absorbance at 450 nm. The results are shown in FIG. 16.

As shown in FIG. 16, all clones showed binding to human CD3 epsilon but did not show binding to human CD137 even though panning procedure to human CD137 was conducted 5-times. It might depend on the less sensitivity of this phage ELISA analysis with Streptavidin-coated Microplate so phage ELISA with Streptavidin coated beads was also conducted.

(6-4) Binding of Fab Domain Displayed by Phage to Human CD137 (Phage Beads ELISA)

First, Streptavidin-coated magnetic beads MyOne-T1 beads was washed three-times with blocking buffer including 0.5× block Ace, 0.02% Tween and 0.05% ProClin 300 and then blocked with this blocking buffer at room temperature for 60 minutes or more. After washing once with TBST, 0.625 pmol of ss-human CD137-Fc was added to magnetic beads and incubated at room temperature for 10 minutes or more and then magnetic beads were applied to each well of 96 well plate (Corning, 3792 black round bottom PS plate). 12.5 micro L each of the Fab displaying phage solution with 12.5 micro L of TBS was added to the wells, and the plate was allowed to stand at room temperature for 30 minutes to allow each Fab to bind to biotin-labeled antigen in each well. After that each well was washed with TBST. Anti-M13(p8) Fab-HRP diluted with blocking buffer including 0.5× block Ace, 0.02% Tween and 0.05% ProClin 300 was added to each well. The plate was incubated for 10 minutes. After washing 3-times with TBST, LumiPhos-HRP (Lumigen) was added to each well. 2 minutes later the fluorescence of each well was detected. The measurement results are shown in FIG. 17.

Some clones showed obvious binding to human CD137. This result showed that some Fab domains which bind to both human CD3 epsilon and CD137 were also obtained from this designed library with phage display panning strategy. Nonetheless the binding to human CD137 was still weak compared to CD3 epsilon peptide. The VH fragment of each human CD137 binding clones were amplified by PCR using primers specifically binding to the phagemid vector (SEQ ID NOs: 157 and 158) and the DNA sequences were analyzed. The result showed all binding clones have same VH sequence, it meant only one Fab clone showed binding to both human CD137 and CD3 epsilon. To improve this, double round selection was also applied to phage display strategy in next experiment.

[Example 7] Obtainment of Fab Domain Binding to CD3 Epsilon and Human CD137 from Dual Fab Phage Display Library with Double Round Selection Method (7-1) Construction of Heavy Chain Phage Display Library with GLS3000 Light Chain Phage library displaying Fab domain were produced from the E. coli harboring the constructed phagemids by infection of helper phage M13KO7TC/FkpA which code FkpA chaperone (SEQ ID NO: 17) and then incubate in the presence of 0.002% arabinose at 25 degrees Celsius (this phage library named as DA library) or 0.02% arabinose at 20 degrees Celsius (this phage library named as DX library) for overnight. M13KO7TC is a helper phage which has an insert of the trypsin cleavage sequence between the N2 domain and the CT domain of the pIII protein on the helper phage (see Japanese Patent Application Kohyo Publication No. 2002-514413). Introduction of insert gene into M13KO7TC gene have been already disclosed elsewhere (see WO2015/046554).

(7-2) Obtainment of Fab Domain Binding to CD3 Epsilon and Human CD137 with Double Round Selection Fab domains binding to CD3 epsilon and human CD137 were identified from the dual Fab library constructed in Example 7-1. Biotin-labeled CD3 epsilon peptide antigen (amino acid sequence: SEQ ID NO: 6), CD3 epsilon peptide antigen biotin-labeled through disulfide-bond linker (C3NP1-27: SEQ ID NO: 145) and biotin-labeled human CD137 fused to human IgG1 Fc fragment (named as human CD137-Fc) was used as an antigen.

To produce much more Fab domain binding to human CD137 and CD3 epsilon, double round selection was also applied for phage display panning at panning round 2 and subsequent round.

Phages were produced from the E. coli harboring the constructed phagemids for phage display. 2.5 M NaCl/10% PEG was added to the culture solution of the E. coli that had produced phages, and a pool of the phages thus precipitated was diluted with TBS to obtain a phage library solution. Next, BSA (final concentration: 4%) was added to the phage library solution. The panning method was performed with reference to a general panning method using antigens immobilized on magnetic beads (J. Immunol. Methods. (2008) 332 (1-2), 2-9; J. Immunol. Methods. (2001) 247 (1-2), 191-203; Biotechnol. Prog. (2002) 18 (2) 212-20; and Mol. Cell Proteomics (2003) 2 (2), 61-9). The magnetic beads used were NeutrAvidin coated beads (Sera-Mag SpeedBeads NeutrAvidin-coated) or Streptavidin coated beads (Dynabeads M-280 Streptavidin). To eliminate antibodies displaying phage which bind to magnetic beads itself or human IgG1 Fc region, subtraction for magnetic beads and biotin labeled human Fc was conducted.

Specifically, at panning round 1, magnetic beads was blocked by 2% skim-milk/TBS at room temperature for 60 minutes or more and washed three times with TBS. Phage solution of DA library or DX library were added to blocked magnetic beads and incubated at room temperature for 60 minutes or more, then supernatant was recovered. 500 pmol of biotin labeled human IgG1 Fc was added to new magnetic beads and incubated at room temperature for 15 minutes and then add 2% skim-milk/TBS. After blocking at room temperature for 60 minutes or more, magnetic beads was washed three times with TBS. Recovered phage solution were added to blocked magnetic beads and incubated at room temperature for 60 minutes or more, then supernatant was recovered. 500 pmol of the biotin-labeled CD137-Fc was added to new magnetic beads and incubated at room temperature for 15 minutes and then add 2% skim-milk/TBS. After blocking at room temperature for 60 minutes or more, magnetic beads was washed three times with TBS. Recovered phage solution were added to blocked magnetic beads and 8 nmol of free human IgG1 Fc domain was also added, and then incubated at room temperature for 60 minutes. The beads were washed twice with TBST (TBS containing 0.1% Tween 20; TBS was available from Takara Bio Inc.) and then further washed once with 1 mL of TBS. After addition of 0.5 mL of 1 mg/mL trypsin, the beads were suspended at room temperature for 15 minutes, immediately after which the beads were separated using a magnetic stand to recover a phage solution. The recovered phage solution was added to an *E. coli* strain ER2738 in a logarithmic growth phase (OD600: 0.4-0.5). The *E. coli* strain was infected by the phages through the gentle spinner culture of the strain at 37 degrees C. for 1 hour. The infected *E. coli* was inoculated to a plate of 225 mm×225 mm. Next, phages were recovered from the culture solution of the inoculated *E. coli* to prepare a phage library solution.

In this panning round 1 procedure antibody displaying phages which bind to human CD137 was concentrated so from next round of panning procedure double round selection was conducted to recover antibody displaying phages which bind to both CD3 epsilon and human CD137.

Specifically, at panning round 2, magnetic beads was blocked by 2% skim-milk/TBS at room temperature for 60 minutes or more and washed three times with TBS. Phage solution were added to blocked magnetic beads and incubated at room temperature for 60 minutes or more, then supernatant was recovered. 500 pmol of biotin labeled human IgG1 Fc was added to new magnetic beads and incubated at room temperature for 15 minutes and then add 2% skim-milk/TBS. After blocking at room temperature for 60 minutes or more, magnetic beads was washed three times with TBS. Recovered phage solution were added to blocked magnetic beads and incubated at room temperature for 60 minutes or more, then supernatant was recovered. 500 pmol of the biotin-labeled CD137-Fc was added to new magnetic beads and incubated at room temperature for 15 minutes and then add 2% skim-milk/TBS. After blocking at room temperature for 60 minutes or more, magnetic beads was washed three times with TBS. Recovered phage solution were added to blocked magnetic beads and then incubated at room temperature for 60 minutes. The beads were washed three times with TBST (TBS containing 0.1% Tween 20; TBS was available from Takara Bio Inc.) and then further washed twice with 1 mL of TBS. FabRICATOR (IdeS, protease for hinge region of IgG, GENOVIS)(named as IdeS elution campaign) was used to recover antibody displaying phages. In that procedure, 10 units/micro L Fabricator 20 micro L with 80 micro L TBS buffer was added and beads were suspended at 37 degrees Celsius for 30 minutes, immediately after which the beads were separated using a magnetic stand to recover phage solution.

In this $1^{st}$ cycle of panning procedure antibody displaying phages which bind to human CD137 was concentrated so then move on to $2^{nd}$ cycle panning procedure to recover antibody displaying phages which also bind to CD3 epsilon before phage infection and amplification. 500 pmol of the biotin-labeled CD3 epsilon was added to new magnetic beads and incubated at room temperature for 15 minutes and then add 2% skim-milk/TBS. After blocking at room temperature for 60 minutes or more, magnetic beads was washed three times with TBS. Recovered phage solution, 50 micro L of TBS and 250 micro L of 8% BSA blocking buffer were added to blocked magnetic beads and then incubated at 37 degrees Celsius for 30 minutes, at room temperature for 60 minutes, 4 degrees Celsius for overnight and then at room temperature for 60 minutes to transfer antibody displaying phage from human CD137 to CD3 epsilon. The beads were washed three times with TBST (TBS containing 0.1% Tween 20; TBS was available from Takara Bio Inc.) and then further washed twice with 1 mL of TBS. The beads supplemented with 0.5 mL of 1 mg/mL trypsin were suspended at room temperature for 15 minutes, immediately after which the beads were separated using a magnetic stand to recover a phage solution. The phages recovered from the trypsin-treated phage solution were added to an *E. coli* strain ER2738 in a logarithmic growth phase (OD600: 0.4-0.7). The *E. coli* strain was infected by the phages through the gentle spinner culture of the strain at 37 degrees C. for 1 hour. The infected *E. coli* was inoculated to a plate of 225 mm×225 mm. Next, phages were recovered from the culture solution of the inoculated *E. coli* to recover a phage library solution.

In the third and fourth round of panning, wash number increased to fifth with TBST and then twice with TBS. In $2^{nd}$ cycle of double round selection, C3NP1-27 antigen was used instead of biotin labeled CD3 epsilon peptide antigen, and elution was conducted by DTT solution to cleave the disulfide bond between CD3 epsilon peptide and biotin. Precisely, after washing with TBS twice, 500 micro L of 25 mM DTT solution was added and beads were suspended at room temperature for 15 minutes, immediately after which the beads were separated using a magnetic stand to recover phage solution. 0.5 mL of 1 mg/mL trypsin were added to recovered phage solution and incubated at room temperature for 15 minutes (7-3) Binding of IgG Having Obtained Fab Domain to Human CD137 and Cynomolgus Monkey CD137

96 clones were picked from each panning output pools of DA and DX library at round 3 and round 4 and their VH gene sequence were analyzed. Twenty-nine VH sequence was obtained so all of them were converted into IgG format. The VH fragments of each clones were amplified by PCR using primers specifically binding to the phagemid vector (SEQ ID NOs: 157 and 158). The amplified VH fragment was integrated into an animal expression plasmid which have already had human IgG1 CH1-Fc region. The prepared plasmids were used for expression in animal cells by the method of Reference Example 1. GLS3000 was used as Light chain and its expression plasmid was prepared as shown in Reference Example 4-2).

The prepared antibodies were subjected to ELISA to evaluate their binding capacity to human CD137 (SEQ ID NO: 146) and cynomolgus monkey (called as cyno) CD137 (SEQ ID NO: 18). FIG. 18 shows the amino acids sequence difference between human and cynomolgus monkey CD137. There are 8 different residues among them.

First, 20 micro g of Streptavidin-coated magnetic beads MyOne-T1 beads was washed three-times with blocking buffer including 0.5× block Ace, 0.02% Tween and 0.05% ProClin 300 and then blocked with this blocking buffer at room temperature for 60 minutes or more. After washing once with TBST, magnetic beads were applied to each well of white round bottom PS plate (Corning, 3605) and 0.625 pmol of biotin labeled human CD137-Fc, biotin labeled cyno CD137-Fc or biotin labeled human Fc was added to magnetic beads and incubated at room temperature for 15 minutes or more. After washing once with TBST, 25 micro L each of the 50 ng/micro L purified IgG was added to the wells, and the plate was allowed to stand at room temperature for one hour to allow each IgG to bind to biotin-labeled antigen in each well. After that each well was washed with TBST. Goat anti-human kappa Light chain alkaline phosphatase conjugate (BETHYL, A80-115AP) diluted with TBS was added to each well. The plate was incubated for one hour. After washing with TBST, each sample were transferred to 96 well plate (Corning, 3792 black round bottom PS plate) and APS-5 (Lumigen) was added to each well. 2 minutes later the fluorescence of each well was detected. The measurement results are shown in Table 10 and FIG. 19. Among them, clones DXDU01_3#094, DXDU01_3#072, DADU01_3#018, DADU01_3#002, DXDU01_3#019 and DXDU01_3#051 showed binding to both human and cyno CD137. On the other hand, DADU01_3#001, which showed strongest binding to human CD137, did not show binding to cyno CD137.

TABLE 10

| | RLU | | | S/N ratio | | |
|---|---|---|---|---|---|---|
| | human CD137-Fc | cyno CD137-Fc | human Fc | human CD137-Fc/Fc | cyno CD137-Fc/Fc | SEQ ID NO |
| DADU01_3#031 | 2122 | 1633 | 1783 | 0.7696 | 0.8402 | |
| DXDU01_3#053 | 1935 | 1469 | 1555 | 0.7592 | 0.8036 | |
| DADU01_3#006 | 3202 | 1842 | 1886 | 0.5753 | 0.5890 | |
| DXDU01_3#035 | 2005 | 1424 | 1484 | 0.7102 | 0.7401 | |
| DXDU01_3#064 | 1826 | 1369 | 2150 | 0.7497 | 1.1774 | |
| DADU01_3#036 | 1960 | 1491 | 2173 | 0.7607 | 1.1087 | |
| DXDU01_3#043 | 2311 | 1533 | 1919 | 0.6633 | 0.8304 | |
| DXDU01_3#094 | 2367 | 24241 | 19145 | 10.2412 | 8.0883 | 23 |
| DADU01_3#003 | 2349 | 1596 | 1658 | 0.6794 | 0.7058 | |
| DADU01_3#051 | 2276 | 1595 | 1534 | 0.7008 | 0.6740 | |
| DADU01_4#089 | 3578 | 1970 | 1894 | 0.5506 | 0.5293 | |
| DADU01_3#013 | 2770 | 1707 | 1710 | 0.6162 | 0.6173 | |
| DXDU01_3#049 | 2586 | 1559 | 1578 | 0.6029 | 0.6102 | |
| DXDU01_3#072 | 2148 | 14137 | 3348 | 6.5815 | 1.5587 | 24 |
| DADU01_3#042 | 2570 | 1779 | 1600 | 0.6922 | 0.6226 | |
| DADU01_3#020 | 1970 | 1640 | 1641 | 0.8325 | 0.8330 | |
| DADU01_3#050 | 2246 | 1785 | 1689 | 0.7947 | 0.7520 | |
| DADU01_3#018 | 1899 | 32770 | 6205 | 17.2565 | 3.2675 | 25 |
| DADU01_3#002 | 1924 | 39141 | 10775 | 20.3436 | 5.6003 | 26 |
| DADU01_3#058 | 1931 | 1461 | 1363 | 0.7566 | 0.7059 | |
| DADU01_3#078 | 1689 | 1374 | 1326 | 0.8135 | 0.7851 | |
| DADU01_3#044 | 1992 | 1647 | 1606 | 0.8268 | 0.8062 | |
| DXDU01_3#019 | 3264 | 77805 | 5093 | 23.8373 | 1.5604 | 27 |
| DADU01_3#001 | 1760 | 95262 | 1209 | 54.1261 | 0.6869 | 28 |
| DADU01_3#071 | 3389 | 1927 | 1860 | 0.5686 | 0.5488 | |
| DADU01_3#024 | 3131 | 1783 | 1763 | 0.5695 | 0.5631 | |
| DXDU01_3#051 | 2914 | 38065 | 10870 | 13.0628 | 3.7303 | 29 |
| DADU01_3#004 | 3053 | 1918 | 1802 | 0.6282 | 0.5902 | |
| DADU01_3#045 | 1988 | 1662 | 1573 | 0.8360 | 0.7912 | |

(7-4) Binding of IgG Having Obtained Fab Domain to Human CD3 Epsilon

Each antibodies were also subjected to ELISA to evaluate their binding capacity to CD3 epsilon.

First, a MyOne-T1 streptavidin beads were mixed with 0.625 pmol of biotin-labeled CD3 epsilon and incubated at room temperature for 10 minutes, then blocking buffer including 0.5× block Ace, 0.02% Tween and 0.05% ProClin 300/TBS was added to block the magnetic beads. Mixed solution was dispensed to each well of 96 well plate (Corning, 3792 black round bottom PS plate) and incubated at room temperature for 60 minutes or more. After that magnetic beads were washed by TBS once, 100 ng of purified IgG was added to the magnetic beads in each well, and the plate was allowed to stand at room temperature for one hour to allow each IgG to bind to biotin-labeled antigen in each well. After that each well was washed with TBST, Goat anti-human kappa Light chain alkaline phosphatase conjugate (BETHYL, A80-115AP) diluted with TBS was added to each well. The plate was incubated for one hour. After washing with TBST, APS-5 (Lumigen) was added to each well. 2 minutes later the fluorescence of each well was detected. The measurement results are shown in Table 11 and FIG. 20. All clones showed obvious binding to CD3 epsilon peptide. These data proves the Fab domain which bind to both CD3 epsilon, human CD137 and cyno CD137 could be efficiently obtained by designed Dual Fab antibody phage display library with double round selection procedure with higher hit-rate than with conventional phage display panning procedure conducted in example 6.

TABLE 11

| | RLU | | S/N ratio CD3 peptide/ non coating |
|---|---|---|---|
| | Non coating | CD3 peptide | |
| DADU01_3#031 | 1505 | 142935 | 70.13 |
| DXDU01_3#053 | 2082 | 148836 | 120.32 |
| DADU01_3#006 | 3843 | 127079 | 107.42 |
| DXDU01_3#035 | 3302 | 119726 | 103.03 |
| DXDU01_3#064 | 3901 | 171861 | 147.52 |
| DADU01_3#036 | 1562 | 159897 | 139.65 |
| DXDU01_3#043 | 1147 | 168793 | 143.65 |
| DXDU01_3#094 | 2473 | 164780 | 140.72 |
| DADU01_3#003 | 3104 | 151738 | 115.65 |
| DADU01_3#051 | 2489 | 135224 | 109.85 |
| DADU01_4#089 | 1366 | 150267 | 127.67 |
| DADU01_3#013 | 4688 | 136821 | 111.78 |
| DXDU01_3#049 | 3205 | 141259 | 114.94 |
| DXDU01_3#072 | 2168 | 176615 | 147.67 |
| DADU01_3#042 | 4271 | 135203 | 108.86 |
| DADU01_3#020 | 1454 | 197301 | 153.18 |
| DADU01_3#050 | 1564 | 166509 | 132.05 |
| DADU01_3#018 | 2293 | 181896 | 148.73 |
| DADU01_3#002 | 2954 | 173838 | 156.47 |
| DADU01_3#058 | 2618 | 136587 | 118.05 |
| DADU01_3#078 | 1754 | 146653 | 124.49 |
| DADU01_3#044 | 1091 | 196612 | 180.88 |
| DXDU01_3#019 | 1919 | 190761 | 161.12 |
| DADU01_3#001 | 1840 | 198383 | 146.41 |
| DADU01_3#071 | 4237 | 144562 | 109.60 |
| DADU01_3#024 | 3782 | 152018 | 129.38 |
| DXDU01_3#051 | 1904 | 169289 | 144.69 |
| DADU01_3#004 | 2310 | 166261 | 141.26 |
| DADU01_3#045 | 1730 | 154444 | 127.85 |

(7-5) Evaluation of Binding of IgG Having Obtained Fab Domain to CD3 Epsilon and Human CD137 at Same Time Six antibodies (DXDU01_3#094(#094), DADU01_3#018(#018), DADU01_3#002(#002), DXDU01_3#019(#019), DXDU01_3#051(#051) and DADU01_3#001(#001 or dBBDu_126)) were selected to evaluate further. An anti-human CD137 antibody (SEQ ID NO: 19 for the Heavy chain and SEQ ID NO: 20 for the Light chain) described in WO2005/035584A1(abbreviated as B) was used as a control antibody. Purified antibodies were subjected to ELISA to evaluate their binding capacity to CD3 epsilon and human CD137 at same time.

First, a MyOne-T1 streptavidin beads were mixed with 0.625 pmol of biotin-labeled human CD137-Fc or biotin-labeled human Fc and incubated at room temperature for 10 minutes, then 2% skim-milk/TBS was added to block the magnetic beads. Mixed solution was dispended to each well of 96 well plate (Corning, 3792 black round bottom PS plate) and incubated at room temperature for 60 minutes or more. After that magnetic beads were washed by TBS once. 100 ng of purified IgG was mixed with 62.5, 6.25 or 0.625 pmol of free CD3 epsilon peptide or 62.5 pmol of free human Fc or TBS and then added to the magnetic beads in each well, and the plate was allowed to stand at room temperature for one hour to allow each IgG to bind to biotin-labeled antigen in each well. After that each well was washed with TBST. Goat anti-human kappa Light chain alkaline phosphatase conjugate (BETHYL, A80-115AP) diluted with TBS was added to each well. The plate was incubated for one hour. After washing with TBST, APS-5 (Lumigen) was added to each well. 2 minutes later the fluorescence of each well was detected. The measurement results are shown in FIG. 21 and Table 12.

TABLE 12

| | biotin-human CD137-Fc | | |
|---|---|---|---|
| | Free CD3e 62.5 pmol | Free Fc 62.5 pmol | Signal decrease |
| B | 182548 | 184279 | 0.94% |
| #001 | 15125 | 80997 | 81.33% |
| #002 | 9966 | 154791 | 93.56% |
| #018 | 9024 | 116919 | 92.28% |
| #019 | 12850 | 171835 | 92.52% |
| #051 | 10804 | 128260 | 91.58% |
| #094 | 9664 | 108313 | 91.08% |

Inhibition of binding to human CD137-Fc by free CD3 epsilon peptide was observed in all tested antibodies but not in control anti-CD137 antibody, and inhibition was not observed by free Fc domain. This results demonstrates those obtained antibodies could not bind to human CD137-Fc in the presence of CD3 epsilon peptide, in other words, these antibody do not bind to human CD137 and CD3 epsilon at same time. So it was proved that Fab domains which can bind to two different antigen, CD137 and CD3 epsilon, but not bind to at same time were successfully obtained with designed library and phage display double round selection.

[Example 8] Obtainment of Fab Domain Binding to CD3 Epsilon, Human CD137 and Cyno CD137 from Dual Fab Library with Double Round Alternative Selection or Quadruple Round Selection (8-1) Panning Strategy to Improve the Efficiency to Obtain Fab Domain Binding to Cyno CD137

Fab domain binding to CD3 epsilon, human CD137 and cyno CD137 were successfully obtained in Example 7, but binding to cyno CD137 was weaker than to human CD137. One of the considerable strategy to improve it is alternative panning with double round selection, in which different antigens would be used in different panning rounds. By this method selection pressure to both CD3 epsilon, human CD137 and cyno CD137 could be put on dual Fab library in each round with favorable antigen combination, CD3 epsilon with human CD137, CD3 epsilon with cyno CD137 or human CD137 with cyno CD137. And another strategy to improve it is the triple or quadruple round selection in which we can use all necessary antigens in one panning round.

In the double round selection procedure in Example 7, over-night incubation was used to make antibody displaying phage transfer from $1^{st}$ antigen to $2^{nd}$ antigen. This methods worked well, but when affinity to $1^{st}$ antigen is stronger than to $2^{nd}$ antigen, transfer may be hardly occur (for example when $1^{st}$ antigen was CD3 epsilon in this dual library). To deal with this, elution of binding phage with base solution was also conducted. The campaign names and conditions of each panning procedure are described in Table 13.

Fab domains binding to CD3 epsilon, human CD137 and cyno CD137 were identified from the dual Fab library constructed in Example 6-1. Biotin-labeled CD3 epsilon peptide antigen (amino acid sequence: SEQ ID NO: 6, CD3 epsilon peptide antigen biotin-labeled through disulfide-bond linker (C3NP1-27; amino acid sequence: SEQ ID NO: 145), heterodimer of biotin-labeled human CD3 epsilon fused to human IgG1 Fc fragment and biotin-labeled human CD3 delta fused to human IgG1 Fc fragment (named as CD3ed-Fc, amino acid sequence: SEQ ID NO: 21, 22), biotin-labeled human CD137 fused to human IgG1 Fc fragment (named as human CD137-Fc), biotin-labeled cynomolgus monkey CD137 fused to human IgG1 Fc fragment (named as cyno CD137-Fc) and biotin-labeled cynomolgus monkey CD137 (named as cyno CD137) was used as an antigen.

TABLE 13

| Campaign | | | Cycle 1 | | Cycle 2 | | Cycle 3 | | Cycle 4 | |
|---|---|---|---|---|---|---|---|---|---|---|
| Name | Round | panning | Antigen | Elution | Antigen | Elution | Antigen | Elution | Antigen | Elution |
| DU05 | Round1 | Double | human CD137-Fc | IdeS | C3NP1-27 | DTT | | | | |
| | Round2 | Double | cyno CD137-Fc | IdeS | C3NP1-27 | DTT | | | | |
| | Round3 | Double | human CD137-Fc | IdeS | C3NP1-27 | DTT | | | | |
| | Round4 | Double | cyno CD137-Fc | IdeS | C3NP1-27 | DTT | | | | |
| MP09 | Round1 | Double | cyno CD137-Fc | IdeS | CD3ed-Fc | IdeS | | | | |
| | Round2 | Double | human CD137-Fc | IdeS | cyno CD137 | Trypsin | | | | |
| | Round3 | Quadruple | human CD137-Fc | IdeS | CD3ed-Fc | IdeS | cyno CD137-Fc | IdeS | CD3ed-Fc | IdeS |
| | Round4 | Quadruple | cyno CD137-Fc | IdeS | CD3ed-Fc | IdeS | human CD137-Fc | IdeS | CD3ed-Fc | IdeS |
| MP11 | Round1 | Double | cyno CD137-Fc | IdeS | CD3ed-Fc | IdeS | | | | |
| | Round2 | Quadruple | human CD137-Fc | IdeS | CD3ed-Fc | IdeS | cyno CD137-Fc | IdeS | CD3ed-Fc | IdeS |
| | Round3 | Quadruple | cyno CD137-Fc | IdeS | CD3ed-Fc | IdeS | human CD137-Fc | IdeS | CD3ed-Fc | IdeS |

TABLE 13-continued

| Campaign | | | Cycle 1 | | Cycle 2 | | Cycle 3 | | Cycle 4 | |
|---|---|---|---|---|---|---|---|---|---|---|
| Name | Round | panning | Antigen | Elution | Antigen | Elution | Antigen | Elution | Antigen | Elution |
| DS01 | Round1 | Single | human CD137-Fc | Trypsin | | | | | | |
| | Round2 | Double | CD3 peptide | TEA | human CD137-Fc | Trypsin | | | | |
| | Round3 | Double | CD3 peptide | TEA | human CD137-Fc | Trypsin | | | | |
| | Round4 | Double | CD3 peptide | TEA | cyno CD137-Fc | Trypsin | | | | |
| | Round5 | Double | CD3 peptide | TEA | human CD137-Fc | Trypsin | | | | |
| | Round6 | Double | CD3 peptide | TEA | cyno CD137-Fc | Trypsin | | | | |

(8-2) Obtainment of Fab Domain Binding to CD3 Epsilon, Human CD137 and Cyno CD137 with Double Round Selection and Alternative Panning Panning condition named as campaign DU05 was conducted to obtain Fab domain binding to CD3 epsilon, human CD137 and cyno CD137 with double round selection and alternative panning as shown in Table 13.

Human CD137-Fc was used in even-numbered round and cyno CD137-Fc was used in odd-numbered round. Detailed panning procedure of double round selection was as same as it shown in Example 7. In DU05 campaign, double round selection was conducted since the $1^{st}$ round of panning.

(8-3) Obtainment of Fab Domain Binding to CD3 Epsilon, Human CD137 and Cyno CD137 with base-elution double round selection and alternative panning In previous double round selection with different antigens shown in Example 7, antibody displaying phages were eluted as the complex with its $1^{st}$ antigen because IdeS or DTT cleaved the linker region between antigen and biotin, so $1^{st}$ antigen were also brought to the $2^{nd}$ cycle of double round selection and compete with $2^{nd}$ antigen. To suppress the carry-in of $1^{st}$ antigen, elution with base buffer, which induce dissociation of binding antibodies from antigen and is very popular method in conventional phage display panning, was also conducted (name as campaign DS01).

Detailed panning procedure of panning round 1 was as same as it shown in Example 7. In round 1, conventional panning with biotin labeled human CD137-Fc was conducted.

In panning round 1 Fab displaying phages which bind to human CD137 were accumulated so from panning round 2 base-elution double round selection was conducted to obtain Fab domain which bind to CD3 epsilon, human CD137 and cyno CD137.

Specifically, at panning round 2, magnetic beads was blocked by 2% skim-milk/TBS at room temperature for 60 minutes or more and washed three times with TBS. Phage solution were added to blocked magnetic beads and incubated at room temperature for 60 minutes or more, then supernatant was recovered. 500 pmol of biotin labeled human IgG1 Fc was added to new magnetic beads and incubated at room temperature for 15 minutes and then add 2% skim-milk/TBS. After blocking at room temperature for 60 minutes or more, magnetic beads was washed three times with TBS. Recovered phage solution were added to blocked magnetic beads and incubated at room temperature for 60 minutes or more, then supernatant was recovered. 500 pmol of the biotin-labeled CD3 epsilon peptide was added to new magnetic beads and incubated at room temperature for 15 minutes and then add 2% skim-milk/TBS. After blocking at room temperature for 60 minutes or more, magnetic beads was washed three times with TBS. Recovered phage solution were added to blocked magnetic beads and then incubated at room temperature for 60 minutes or more. The beads were washed three times with TBST (TBS containing 0.1% Tween 20; TBS was available from Takara Bio Inc.) and then further washed twice with 1 mL of TBS. 0.1 M Triethylamine (TEA, Wako 202-02646) was used to recover antibody displaying phages. In that procedure, 500 micro L of 0.1 M TEA was added and beads were suspended at room temperature for 10 minutes, immediately after which the beads were separated using a magnetic stand to recover phage solution. 100 micro L of 1M Tris-HCl (pH 7.5) was added to neutralize phage solution for 15 minutes.

In this $1^{st}$ cycle of panning procedure antibody displaying phages which bind to CD3 epsilon was concentrated so then move on to $2^{nd}$ cycle panning procedure to recover antibody displaying phages which also bind to CD137 before phage infection and amplification. 500 pmol of the biotin-labeled human CD137-Fc was added to new magnetic beads and incubated at room temperature for 15 minutes and then add 2% skim-milk/TBS. After blocking at room temperature for 60 minutes or more, magnetic beads was washed three times with TBS. Recovered phage solution, 50 micro L of TBS and 250 micro L of 8% BSA blocking buffer were added to blocked magnetic beads and then incubated at room temperature for 60 minutes. The beads were washed three times with TBST (TBS containing 0.1% Tween 20; TBS was available from Takara Bio Inc.) and then further washed twice with 1 mL of TBS. The beads supplemented with 0.5 mL of 1 mg/mL trypsin were suspended at room temperature for 15 minutes, immediately after which the beads were separated using a magnetic stand to recover a phage solution. The phages recovered from the trypsin-treated phage solution were added to an *E. coli* strain ER2738 in a logarithmic growth phase (OD600: 0.4-0.7). The *E. coli* strain was infected by the phages through the gentle spinner culture of the strain at 37 degrees C. for 1 hour. The infected *E. coli* was inoculated to a plate of 225 mm×225 mm. Next, phages were recovered from the culture solution of the inoculated *E. coli* to recover a phage library solution.

In the $2^{nd}$ cycle of double round selection in fourth and sixth round of panning, biotin labeled cyno CD137-Fc was used instead of biotin labeled human CD137-Fc. Through panning round 4 to round 6, 250 pmol of biotin labeled human or cyno CD137-Fc was used in the $2^{nd}$ cycle of double round selection.

(8-4) Obtainment of Fab Domain Binding to CD3 Epsilon, Human CD137 and Cyno CD137 with Quadruple Round Selection In previous double round selection only two different antigens could be used in the panning one round. To break through this limitation, quadruple round selection was also conducted (name as campaign MP09 and MP11, shown in Table 13).

In panning round 1 of both MP09 and MP11 and panning round 2 of MP9, double round selection was conducted.

Specifically, magnetic beads was blocked by 2% skim-milk/TBS at room temperature for 60 minutes or more and washed three times with TBS. Phage solution were added to blocked magnetic beads and incubated at room temperature for 60 minutes or more, then supernatant was recovered. 500 pmol of biotin labeled human IgG1 Fc was added to new magnetic beads and incubated at room temperature for 15 minutes and then add 2% skim-milk/TBS. After blocking at room temperature for 60 minutes or more, magnetic beads was washed three times with TBS. Recovered phage solution were added to blocked magnetic beads and incubated at room temperature for 60 minutes or more, then supernatant was recovered. 268 pmol of the biotin-labeled cyno CD137-Fc was added to new magnetic beads and incubated at room temperature for 15 minutes and then add 2% skim-milk/TBS. After blocking at room temperature for 60 minutes or more, magnetic beads was washed three times with TBS. Recovered phage solution were added to blocked magnetic beads and then incubated at room temperature for 60 minutes. The beads were washed three times with TBST (TBS containing 0.1% Tween 20; TBS was available from Takara Bio Inc.) and then further washed twice with 1 mL of TBS. FabRICATOR (IdeS, protease for hinge region of IgG, GENOVIS)(named as IdeS elution campaign) was used to recover antibody displaying phages. In that procedure, 10 units/micro L Fabricator 20 micro L with 80 micro L TBS buffer was added and beads were suspended at 37 degrees Celsius for 30 minutes, immediately after which the beads were separated using a magnetic stand to recover phage solution.

In this $1^{st}$ cycle of panning procedure antibody displaying phages which bind to cyno CD137 was concentrated so then move on to $2^{nd}$ cycle panning procedure to recover antibody displaying phages which also bind to CD3 epsilon before phage infection and amplification. To remove IdeS protease from phage solution, 40 micro L of helper phage M13KO7 (1.2E+13 pfu) and 200 micro L of 10% PEG-2.5M NaCl was added and a pool of the phages thus precipitated was diluted with TBS to obtain a phage library solution. 500 pmol of the biotin-labeled CD3ed-Fc was added to new magnetic beads and incubated at room temperature for 15 minutes and then add 2% skim-milk/TBS. After blocking at room temperature for 60 minutes or more, magnetic beads was washed three times with TBS. Recovered phage solution and 500 micro L of 8% BSA blocking buffer were added to blocked magnetic beads and then incubated at room temperature for 60 minutes. The beads were washed three times with TBST (TBS containing 0.1% Tween 20; TBS was available from Takara Bio Inc.) and then further washed twice with 1 mL of TBS. 10 units/micro L Fabricator 20 micro L with 80 micro L TBS buffer was added and beads were suspended at 37 degrees Celsius for 30 minutes, immediately after which the beads were separated using a magnetic stand to recover phage solution. 5 micro L of 100 mg/mL trypsin and 395 micro L of TBS were added and incubated at room temperature for 15 minutes. The phages recovered from the trypsin-treated phage solution were added to an *E. coli* strain ER2738 in a logarithmic growth phase (OD600: 0.4-0.7). The *E. coli* strain was infected by the phages through the gentle spinner culture of the strain at 37 degrees C. for 1 hour. The infected *E. coli* was inoculated to a plate of 225 mm×225 mm. Next, phages were recovered from the culture solution of the inoculated *E. coli* to recover a phage library solution.

In the second round of panning campaign of MP09, biotin-labeled human CD137-Fc was used as $1^{st}$ cycle panning antigen and biotin-labeled cyno CD137 with elution by Trypsin was used as $2^{nd}$ cycle panning antigen as shown in Table 13.

Quadruple panning was conducted in panning round 3 and round 4 of MP09 campaign and panning round 2 and round 3 of MP11 campaign.

In panning round 3 of MP09 and round 2 of MP11 campaign, magnetic beads was blocked by 2% skim-milk/TBS at room temperature for 60 minutes or more and washed three times with TBS. Phage solution were added to blocked magnetic beads and incubated at room temperature for 60 minutes or more, then supernatant was recovered. 500 pmol of biotin labeled human IgG1 Fc was added to new magnetic beads and incubated at room temperature for 15 minutes and then add 2% skim-milk/TBS. After blocking at room temperature for 60 minutes or more, magnetic beads was washed three times with TBS. Recovered phage solution were added to blocked magnetic beads and incubated at room temperature for 60 minutes or more, then supernatant was recovered. 250 pmol of the biotin-labeled human CD137-Fc was added to new magnetic beads and incubated at room temperature for 15 minutes and then add 2% skim-milk/TBS. After blocking at room temperature for 60 minutes or more, magnetic beads was washed three times with TBS. Recovered phage solution were added to blocked magnetic beads and then incubated at room temperature for 60 minutes. The beads were washed three times with TBST (TBS containing 0.1% Tween 20; TBS was available from Takara Bio Inc.) and then further washed twice with 1 mL of TBS. FabRICATOR (IdeS, protease for hinge region of IgG, GENOVIS) (named as IdeS elution campaign) was used to recover antibody displaying phages. In that procedure, 10 units/micro L Fabricator 20 micro L with 80 micro L TBS buffer was added and beads were suspended at 37 degrees Celsius for 30 minutes, immediately after which the beads were separated using a magnetic stand to recover phage solution.

To remove IdeS protease from phage solution, 40 micro L of helper phage M13KO7 (1.2E+13 pfu) and 200 micro L of 10% PEG-2.5M NaCl was added and a pool of the phages thus precipitated was diluted with TBS to obtain a phage library solution. 250 pmol of the biotin-labeled CD3ed-Fc was added to new magnetic beads and incubated at room temperature for 15 minutes and then add 2% skim-milk/TBS. After blocking at room temperature for 60 minutes or more, magnetic beads was washed three times with TBS. Recovered phage solution and 500 micro L of 8% BSA blocking buffer were added to blocked magnetic beads and then incubated at room temperature for 60 minutes. The beads were washed three times with TBST (TBS containing 0.1% Tween 20; TBS was available from Takara Bio Inc.) and then further washed twice with 1 mL of TBS. 10 units/micro L Fabricator 20 micro L with 80 micro L TBS buffer was added and beads were suspended at 37 degrees Celsius for 30 minutes, immediately after which the beads were separated using a magnetic stand to recover phage solution. In $3^{rd}$ cycle of quadruple round selection, 40 micro L of helper phage M13KO7 (1.2E+13 pfu) and 200 micro L of 10% PEG-2.5M NaCl was added and a pool of the phages thus precipitated was diluted with TBS to obtain a phage library solution. 250 pmol of the biotin-labeled cyno CD137-Fc was added to new magnetic beads and incubated at room temperature for 15 minutes and then add 2% skim-milk/TBS. After blocking at room temperature for 60 minutes or more, magnetic beads was washed three times with TBS. Recovered phage solution and 500 micro L of 8% BSA blocking buffer were added to blocked magnetic beads and then incubated at room temperature for 60 minutes. The beads were washed three times with TBST (TBS containing 0.1% Tween 20; TBS was available from Takara Bio Inc.) and then further washed twice with 1 mL of TBS. 10 units/micro L Fabricator 20 micro L with 80 micro L TBS buffer was added and beads were suspended at 37 degrees Celsius for 30 minutes, immediately after which the beads were separated using a magnetic stand to recover phage solution.

In $4^{th}$ cycle of quadruple round selection, 40 micro L of helper phage M13KO7 (1.2E+13 pfu) and 200 micro L of 10% PEG-2.5M NaCl was added and a pool of the phages thus precipitated was diluted with TBS to obtain a phage library solution. 500 pmol of the biotin-labeled CD3ed-Fc was added to new magnetic beads and incubated at room temperature for 15 minutes and then add 2% skim-milk/TBS. After blocking at room temperature for 60 minutes or more, magnetic beads was washed three times with TBS. Recovered phage solution and 500 micro L of 8% BSA blocking buffer were added to blocked magnetic beads and then incubated at room temperature for 60 minutes. The beads were washed three times with TBST (TBS containing 0.1% Tween 20; TBS was available from Takara Bio Inc.) and then further washed twice with 1 mL of TBS. 10 units/micro L Fabricator 20 micro L with 80 micro L TBS buffer was added and beads were suspended at 37 degrees Celsius for 30 minutes, immediately after which the beads were separated using a magnetic stand to recover phage solution. 5 micro L of 100 mg/mL trypsin and 395 micro L of TBS were added and incubated at room temperature for 15 minutes. The phages recovered from the trypsin-treated phage solution were added to an *E. coli* strain ER2738 in a logarithmic growth phase (OD600: 0.4-0.7). The *E. coli* strain was infected by the phages through the gentle spinner culture of the strain at 37 degrees C. for 1 hour. The infected *E. coli* was inoculated to a plate of 225 mm×225 mm. Next, phages were recovered from the culture solution of the inoculated *E. coli* to recover a phage library solution.

In panning round 4 of MP09 and round 3 of MP11 campaign, biotin labeled human CD137-Fc was used as $1^{st}$ cycle antigen and biotin labeled cyno CD137-Fc was used as $3^{rd}$ cycle antigen.

(8-5) Binding of Fab Domain Displayed by Phage to Human and Cyno CD137 (Phage ELISA)

Fab displaying phage solution were prepared through panning procedure in Example 8-2, 8-3 and 8-4. First, 20 micro g of Streptavidin-coated magnetic beads MyOne-T1 beads was washed three-times with blocking buffer including 0.4% block Ace, 1% BSA, 0.02% Tween and 0.05% ProClin 300 and then blocked with this blocking buffer at room temperature for 60 minutes or more. After washing once with TBST, magnetic beads were applied to each well of 96 well plate (Corning, 3792 black round bottom PS plate) and 0.625 pmol of biotin labeled human CD137-Fc, biotin labeled cyno CD137-Fc or biotin labeled CD3 epsilon peptide was added to magnetic beads and incubated at room temperature for 15 minutes or more. After washing once with TBST, 250 nL each of the Fab displaying phage solution with 24.75 micro L of TBS was added to the wells, and the plate was allowed to stand at room temperature for one hour to allow each Fab to bind to biotin-labeled antigen in each well. After that each well was washed with TBST. Anti-M13(p8) Fab-HRP diluted with TBS was added to each well. The plate was incubated for 10 minutes. After washing with TBST, LumiPhos-HRP (Lumigen) was added to each well. 2 minutes later the fluorescence of each well was detected. The measurement results are shown in FIG. 22.

The binding to each antigens, human CD137, cyno CD137 and CD3 epsilon, were observed in each panning output phage solution. This result showed that double round selection with base elution worked as well as previous double round selection with IdeS elution method, and that double round selection with alternative panning also worked well to obtain Fab domain which bind to three different antigens. Nonetheless the binding to cyno CD137 was still weak compared to human CD137 although these methods collect Fab domains which bind to three different antigens. On the other hand, in MP09 or MP11 campaign, the binding to CD3 epsilon, human CD137 and cyno CD137 were observed at same round point and their binding to cyno CD137 was higher than other campaign. This result demonstrated that quadruple round selection can concentrate Fab domain which bind to three different antigens more efficiently.

(8-6) Preparation of IgG Having Obtained Fab Domain 96 clones were picked from each panning output pools and their VH gene sequence were analyzed. Thirty-two clones were selected because their VH sequence were appeared more than twice among all analyzed pools. Their VH gene were amplified by PCR and converted into IgG format. The VH fragments of each clones were amplified by PCR using primers specifically binding to the H chain in the library (SEQ ID NOs: 157 and 158). The amplified VH fragment was integrated into an animal expression plasmid which have already had human IgG1 CH1-Fc region. The prepared plasmids were used for expression in animal cells by the method of Reference Example 1. These sample were called as clone converted IgG. GLS3000 was used as Light chain.

VH genes of each panning output pools were also converted into IgG format. Phagemid vector library were prepared from the *E. coli* of each panning output pools DU05, DS01 and MP11, and digested with NheI and SalI restriction enzyme to extract VH genes directly. The extracted VH fragments were integrated into an animal expression plasmid which have already had human IgG1 CH1-Fc region. The prepared plasmids were introduced into *E. coli* and 192 or 288 colonies were picked from each panning output pools and their VH sequence were analyzed. In MP09 and 11 campaign, clones which had different VH sequences were picked up as possible. The prepared plasmids from each *E. coli* colonies were used for expression in animal cells by the method of Reference Example 1. These sample were called as bulk converted IgG. GLS3000 was used as Light chain.

(8-7) Assessment of the Obtained Antibodies for their CD3 Epsilon, Human CD137 and Cyno CD137 Binding Activity The prepared bulk converted IgG antibodies were subjected to ELISA to evaluate their binding capacity to CD3 epsilon, human CD137 and cyno CD137.

First, a Streptavidin-coated microplate (384 well, Greiner) was coated with 20 micro L of TBS containing biotin-labeled CD3 epsilon peptide, biotin labeled human CD137-Fc or biotin labeled cyno CD137-Fc at room temperature for one or more hours. After removing biotin-labeled antigen that are not bound to the plate by washing each well of the plate with TBST, the wells were blocked with 20 micro L of Blocking Buffer (2% skim milk/TBS) for one or more hours. Blocking Buffer was removed from each well. 20 micro L each of the IgG containing mammalian cell supernatant twice diluted with 2% Skim milk/TBS were added to the wells, and the plate was allowed to stand at room temperature for one hour to allow each IgG to bind to biotin-labeled antigen in each well. After that each well was washed with TBST. Goat anti-human kappa Light chain alkaline phosphatase conjugate (BETHYL, A80-115AP) diluted with TBS was added to each well. The plate was incubated for one hour. After washing with TBST, the chromogenic reaction of the solution in each well added with Blue Phos Microwell Phosphatase Substrate System (KPL) was terminated by adding Blue Phos Stop Solution (KPL). Then, the color development was measured by absorbance at 615 nm. The measurement results are shown in FIG. 23.

Many IgG clones which showed binding to both CD3 epsilon, human CD137 and cyno CD137 were obtained from each panning procedure so it proves that both double round selection with alternative panning, double selection with base elution and quadruple round selection were all worked as expected. Especially, Most of all clones from quadruple round selection which bound to human CD137 showed equality level of binding to cyno-CD137 compared to other two panning conditions. In those panning conditions it was likely to be obtained less clones which showed binding to both CD3 epsilon and human CD137, it mainly because clones which had same VH sequences each other were not picked up on purpose as possible in this campaign. Fifty-four clones which showed better binding to each protein and had different VH sequences each other were selected and evaluated further.

(8-8) Assessment of the Purified IgG Antibodies for their CD3 Epsilon, Human CD137 and Cyno CD137 Binding Activity The binding capability of purified IgG antibodies were evaluated. Thirty-two clone converted IgGs in Example 8-5 and fifty-four bulk converted IgGs which was selected in Example 8-6 were used.

First, 20 micro g of Streptavidin-coated magnetic beads MyOne-T1 beads was washed three-times with blocking buffer including 0.4% block Ace, 1% BSA, 0.02% Tween and 0.05% ProClin 300 and then blocked with this blocking buffer at room temperature for 60 minutes or more. After washing once with TBST, magnetic beads were applied to each well of white round bottom PS plate (Corning, 3605) and 0.625 pmol of biotin labeled CD3 epsilon peptide, 2.5 pmol of biotin labeled human CD137-Fc, 2.5 pmol of biotin labeled cyno CD137-Fc or 0.625 pmol of biotin labeled human Fc was added to magnetic beads and incubated at room temperature for 15 minutes or more. After washing once with TBST, 25 micro L each of the 50 ng/micro L purified IgG was added to the wells, and the plate was allowed to stand at room temperature for one hour to allow each IgG to bind to biotin-labeled antigen in each well. After that each well was washed with TBST. Goat anti-human kappa Light chain alkaline phosphatase conjugate (BETHYL, A80-115AP) diluted with TBS was added to each well. The plate was incubated for one hour. After washing with TBST, each sample were transferred to 96 well plate (Corning, 3792 black round bottom PS plate) and APS-5 (Lumigen) was added to each well. 2 minutes later the fluorescence of each well was detected. The measurement results are shown in FIG. 24. Many clones showed equal level of binding to both human and cyno CD137 and also showed binding to CD3 epsilon.

(8-9) Evaluation of Binding of IgG Having Obtained Fab Domain to CD3 Epsilon and Human CD137 at Same Time Thirty-seven antibodies which showed obvious binding to both CD3 epsilon, human CD137 and cyno CD137 in Example 8-7 were selected to evaluate further. Seven antibodies obtained in Example 7-3 were also evaluated (these 7 clones were renamed as in Table 14). Purified antibodies were subjected to ELISA to evaluate their binding capacity to CD3 epsilon and human CD137 at same time. Anti-human CD137 antibody named as B described in Example 7-5 was used as control antibody.

TABLE 14

| Old name | New name |
| --- | --- |
| DXDU01_3_#094 | dBBDu121 |
| DXDU01_3_#072 | dBBDu122 |
| DADU01_3_#018 | dBBDu123 |
| DADU01_3_#002 | dBBDu124 |
| DXDU01_3_#019 | dBBDu125 |
| DADU01_3_#001 | dBBDu126 |
| DXDU01_3_#051 | dBBDu127 |

First, 20 micro g of Streptavidin-coated magnetic beads MyOne-T1 beads was washed three-times with blocking buffer including 0.4% block Ace, 1% BSA, 0.02% Tween and 0.05% ProClin 300 and then blocked with this blocking buffer at room temperature for 60 minutes or more. After washing once with TBST, magnetic beads were applied to each well of black round bottom PS plate (Corning, 3792). 1.25 pmol of biotin-labeled human CD137-Fc was added and incubated at room temperature for 10 minute. After that magnetic beads were washed by TBS once. 1250 ng of purified IgG was mixed with 125, 12.5 or 1.25 pmol of free CD3 epsilon peptide or TBS and then added to the magnetic beads in each well, and the plate was allowed to stand at room temperature for one hour to allow each IgG to bind to biotin-labeled antigen in each well. After that each well was washed with TBST. Goat anti-human kappa Light chain alkaline phosphatase conjugate (BETHYL, A80-115AP) diluted with TBS was added to each well. The plate was incubated for 10 minutes. After washing with TBST, APS-5 (Lumigen) was added to each well. 2 minutes later the fluorescence of each well was detected. The measurement results are shown in FIG. 25 and Table 15.

TABLE 15

| | biotin-human CD137-Fc | | |
| --- | --- | --- | --- |
| | free CD3e (pmol/well) | | |
| | 0 | 125 | Signal decrease |
| dBBDu133 | 16927 | 2373 | 85.98% |
| dBBDu139 | 9436 | 1924 | 79.61% |
| dBBDu140 | 19960 | 1923 | 90.37% |
| dBBDu142 | 13665 | 1786 | 86.93% |
| dBBDu149 | 3915 | 1962 | 49.89% |
| dBBDu165 | 75488 | 1954 | 97.41% |
| dBBDu167 | 25731 | 1937 | 92.47% |
| dBBDu171 | 7394 | 1819 | 75.40% |
| dBBDu172 | 7589 | 2241 | 70.47% |
| dBBDu173 | 6544 | 2041 | 68.81% |
| dBBDu178 | 6777 | 2126 | 68.63% |
| dBBDu179 | 61009 | 2625 | 95.70% |
| dBBDu181 | 3241 | 1990 | 38.60% |
| dBBDu182 | 9081 | 2178 | 76.02% |
| dBBDu183 | 34000 | 2369 | 93.03% |
| dBBDu184 | 16701 | 1888 | 88.70% |
| dBBDu186 | 34783 | 2497 | 92.82% |
| dBBDu189 | 27434 | 2193 | 92.01% |
| dBBDu191 | 12863 | 2230 | 82.66% |
| dBBDu193 | 18193 | 2278 | 87.48% |
| dBBDu195 | 9715 | 2361 | 75.70% |
| dBBDu196 | 33099 | 2222 | 93.29% |
| dBBDu197 | 54367 | 2111 | 96.12% |
| dBBDu199 | 40880 | 2372 | 94.20% |
| dBBDu202 | 12055 | 1930 | 83.99% |
| dBBDu204 | 43663 | 1879 | 95.70% |

TABLE 15-continued

| | biotin-human CD137-Fc | | |
|---|---|---|---|
| | free CD3e (pmol/well) | | |
| | 0 | 125 | Signal decrease |
| dBBDu205 | 45191 | 2194 | 95.15% |
| dBBDu206 | 6967 | 1697 | 75.64% |
| dBBDu207 | 7466 | 1844 | 75.30% |
| dBBDu209 | 12051 | 1779 | 85.24% |
| dBBDu211 | 7284 | 1732 | 76.22% |
| dBBDu214 | 12852 | 1701 | 86.76% |
| dBBDu217 | 19093 | 2416 | 87.35% |
| dBBDu222 | 7188 | 3236 | 54.98% |
| dBBDu166 | 3437 | 1844 | 46.35% |
| dBBDu174 | 4804 | 1884 | 60.78% |
| dBBDu175 | 3257 | 1755 | 46.12% |
| dBBDu121 | 3609 | 1826 | 49.40% |
| dBBDu122 | 2698 | 1882 | 30.24% |
| dBBDu123 | 2746 | 1840 | 32.99% |
| dBBDu124 | 6621 | 2116 | 68.04% |
| dBBDu125 | 61364 | 2058 | 96.65% |
| dBBDu126 | 116289 | 2613 | 97.75% |
| dBBDu127 | 3232 | 2198 | 31.99% |
| Du115/DUL008 | 86183 | 2620 | 96.96% |
| Du103/DUL050 | 5273 | 5297 | −0.46% |
| B | 99359 | 98110 | 1.26% |
| blank | 1860 | 1850 | 0.54% |

The binding to human CD137 of all tested clones except for control anti-CD137 antibody B was inhibited by excess amount of free CD3 epsilon peptide, it demonstrated that obtained antibodies with dual Fab library did not bind to CD3 epsilon and human CD137 at same time.

(8-10) Evaluation of the Human CD137 Epitope of IgGs Having Obtained Fab Domain to CD3 Epsilon and Human CD137

Twenty-one antibodies in Example 8-8 were selected to evaluate further (Table 17). Purified antibodies were subjected to ELISA to evaluate their binding epitope of human CD137.

To analyze the epitope, a fusion protein of the fragmentation human CD137 and the Fc region of an antibody that domain divided by the structure formed by Cys-Cys called CRD reference (Table 16) as described in WO2015/156268. Fragmentation human CD137-Fc fusion protein to include the amino acid sequence shown in Table 16, the respective gene fragments by PCR from a polynucleotide encoding the full-length human CD137-Fc fusion protein (SEQ ID NO: 16) It Gets, incorporated into a plasmid vector for expression in animal cells by methods known to those skilled in the art. Fragmentation human CD137-Fc fusion protein was purified as an antibody by the method described in WO2015/156268.

TABLE 16

| Name of the fragmented human CD137 | Amino acid sequence of the fragmented human CD137 | Domanins that are included | SEQ ID NO |
|---|---|---|---|
| Full length | LQDPCSNCPAGTFCDNNRNQICSPCPPNSFSSA GGQRTCDICRQCKGVFRTRKECSSTSNAECDCT PGFHCLGAGCSMCEQDCKQGQELTKKGCKDC FGTFNDQKRGICRPWTNCSLDG KSVLVNGTKER DVVCGPSPADLSPGASSVTPPAPAREPGHSPQ | CRD1,2,3,4 | 16 |
| CRD1 | LQDPCSNCPAGTFCDNNRNQIC | CRD1 | 74 |
| CRD2 | SPCPPNSFSSAGGQRTCDICRQCKGVFRTRKEC SSTSNAEC | CRD2 | 75 |
| CRD3 | DCTPGFHCLGAGCSMCEQDCKQGQELTKKGC | CRD3 | 76 |
| CRD4 | KDCCFGTFNDQKRGICRPWTNCSLDGKSVLVNG TKERDVVCGPSPADLSPGASSVTPPAPAREPGH SPQ | CRD4 | 77 |
| CRD1-3 | LQDPCSNCPAGTFCDNNRNQICSPCPPNSFSSA GGQRTCDICRQCKGVFRTRKECSSTSNAECDCT PGFHCLGAGCSMCEQDCKQGQELTKKGC | CRD1,2,3 | 78 |
| CRD1-2 | LQDPCSNCPAGTFCDNNRNQICSPCPPNSFSSA GGQRTCDICRQCKGVFRTRKECSSTSNAEC | CRD1,2 | 79 |
| CRD2-4 | SPCPPNSFSSAGGQRTCDICRQCKGVFRTRKEC SSTSNAECDCTPGFHCLGAGCSMCEQDCKQGQ ELTKKGCKDCCFGTFNDQKRGICRPWTNCSLDG KSVLVNGTKERDVVCGPSPADLSPGASSVTPPA PAREPGHSPQ | CRD2,3,4 | 80 |
| CRD2-3 | SPCPPNSFSSAGGQRTCDICRQCKGVFRTRKEC SSTSNAECDCTPGFHCLGAGCSMCEQDCKQGQ ELTKKGC | CRD2,3 | 81 |
| CRD3-4 | DCTPGFHCLGAGCSMCEQDCKQGQELTKKGCK DCCFGTFNDQKRGICRPWTNCSLDGKSVLVNGT KERDVVCGPSPADLSPGASSVTPPAPAREPGHS PQ | CRD3,4 | 82 |

First, 20 micro g of Streptavidin-coated magnetic beads MyOne-Ti beads was washed three-times with blocking buffer including 0.4% block Ace, 1% BSA, 0.02% Tween and 0.05% ProClin 300 and then blocked with this blocking buffer at room temperature for 60 minutes or more. After washing once with TBST, magnetic beads were applied to each well of black round bottom PS plate (Corning, 3792). 1.25 pmol of biotin-labeled human CD137-Fc, human CD137 domain1-Fc, human CD137 domain1/2-Fc, human CD137 domain2/3-Fc, human CD137 domain2/3/4-Fc, human CD137 domain3/4-Fc and human Fc was added and incubated at room temperature for 10 minute. After that magnetic beads were washed by TBS once. 1250 ng of purified IgG was added to the magnetic beads in each well, and the plate was allowed to stand at room temperature for one hour to allow each IgG to bind to biotin-labeled antigen in each well. After that each well was washed with TBST. Goat anti-human kappa Light chain alkaline phosphatase conjugate (BETHYL, A80-115AP) diluted with TBS was added to each well. The plate was incubated for 10 minutes. After washing with TBST, APS-5 (Lumigen) was added to each well. 2 minutes later the fluorescence of each well was detected. The measurement results are shown in FIG. 26.

Each clones recognized different epitope domain of human CD137. Antibodies which recognize only domain1/2 (e.g. dBBDu183, dBBDu205), both domain1/2 and domain2/3 (e.g. dBBDu193, dBBDu 202, dBBDu222), both domain2/3, 2/3/4 and 3/4 (e.g. dBBDu139, dBBDu217), broadly human CD137 domains (dBBDu174) and which do not bind to each separated human CD137 domains (e.g. dBBDu126). This result demonstrates many dual binding antibodies to several human CD137 epitopes can be obtained with this designed library and double round selection procedure.

The practice epitope region of dBBDu126 cannot be decided by this ELISA assay, but it can be guessed that it will recognize position(s) in which human and cynomolgus monkey have different residues because dBBDu126 cannot cross-react with cyno CD137 as described in Example 7-3. As shown in FIG. 18, there are 8 different position between human and cyno, and 75E (75G in human) was identified as occasion which interfere the binding of dBBDu126 to cyno CD137 by the binding assay to cyno CD137/human CD137 hybrid molecules and the crystal structure analysis of binding complex. Crystal structure also reveal dBBDu126 mainly recognize CRD3 region of human CD137.

TABLE 17

| Clone name | SEQ ID NO |
| --- | --- |
| dBBDu126 | 28 |
| dBBDu183 | 30 |
| dBBDu179 | 31 |
| dBBDu196 | 32 |
| dBBDu197 | 33 |
| dBBDu199 | 34 |
| dBBDu204 | 35 |
| dBBDu205 | 36 |
| dBBDu193 | 37 |
| dBBDu217 | 38 |
| dBBDu139 | 39 |
| dBBDu189 | 40 |
| dBBDu167 | 41 |
| dBBDu173 | 43 |
| dBBDu174 | 44 |
| dBBDu181 | 45 |
| dBBDu186 | 46 |
| dBBDu191 | 47 |
| dBBDu202 | 48 |

TABLE 17-continued

| Clone name | SEQ ID NO |
| --- | --- |
| dBBDu222 | 49 |
| dBBDu125 | 27 |

[Example 9] Affinity Maturation of Antibody Domain Binding to CD3 Epsilon and Human CD137 from Dual Fab Library with Designed Light Chain Library (9-1) Construction of Light Chain Library with Obtained Heavy Chain Many antibodies which bind to both CD3 epsilon and human CD137 were obtained in Example 8, but their affinity to human CD137 were still weak so affinity maturation to improve their affinity was conducted.

Thirteen VH sequences, dBBDu_179, 183, 196, 197, 199, 204, 205, 167, 186, 189, 191, 193 and 222 were selected for affinity maturation. In those, dBBDu_179, 183, 196, 197, 199, 204 and 205 have same CDR3 sequence and different CDR1 or 2 sequences so these 7 phagemids were mixed to produce Light chain Fab library. dBBDu_191, 193 and 222 three phagemids were also mixed to produce Light chain Fab library although they had different CDR3 sequences. The list of light chain library was shown in Table 18.

TABLE 18

| Library name | VH |
| --- | --- |
| Library 2 | dBBDu_179, 183, 196, 197, 199, 204, 205 |
| Library 3 | dBBDu_167 |
| Library 4 | dBBDu_186 |
| Library 5 | dBBDu_189 |
| Library 6 | dBBDu_191, 193, 222 |

The synthesized antibody VL library fragments described in Reference Example 4 were amplified by PCR method with the primers of SEQ ID NO: 159 and 160. Amplified VL fragments were digested by SfiI and KpnI restriction enzyme and introduced into phagemid vectors which had each thirteen VH fragments. The constructed phagemids for phage display were transferred to *E. coli* by electroporation to prepare *E. coli* harboring the antibody library fragments.

Phage library displaying Fab domain were produced from the *E. coli* harboring the constructed phagemids by infection of helper phage M13KO7TC/FkpA which code FkpA chaperone gene and then incubation with 0.002% arabinose at 25 degrees Celsius for overnight. M13KO7TC is a helper phage which has an insert of the trypsin cleavage sequence between the N2 domain and the CT domain of the pIII protein on the helper phage (see Japanese Patent Application Kohyo Publication No. 2002-514413). Introduction of insert gene into M13KO7TC gene have been already disclosed elsewhere (see WO2015/046554).

(9-2) Obtainment of Fab Domain Binding to CD3 Epsilon and Human CD137 with Double Round Selection Fab domains binding to CD3 epsilon, human CD137 and cyno CD137 were identified from the dual Fab library constructed in Example 9-1. CD3 epsilon peptide antigen biotin-labeled through disulfide-bond linker (C3NP1-27), biotin-labeled human CD137 fused to human IgG1 Fc fragment (named as human CD137-Fc) and biotin-labeled cynomolgus monkey CD137 fused to human IgG1 Fc fragment (named as cyno CD137-Fc) was used as an antigen.

Phages were produced from the *E. coli* harboring the constructed phagemids for phage display. 2.5 M NaCl/10% PEG was added to the culture solution of the *E. coli* that had produced phages, and a pool of the phages thus precipitated was diluted with TBS to obtain a phage library solution. Next, BSA (final concentration: 4%) was added to the phage library solution. The panning method was performed with reference to a general panning method using antigens immobilized on magnetic beads (J. Immunol. Methods. (2008) 332 (1-2), 2-9; J. Immunol. Methods. (2001) 247 (1-2), 191-203; Biotechnol. Prog. (2002) 18 (2) 212-20; and Mol. Cell Proteomics (2003) 2 (2), 61-9). The magnetic beads used were NeutrAvidin coated beads (Sera-Mag SpeedBeads NeutrAvidin-coated) or Streptavidin coated beads (Dynabeads M-280 Streptavidin).

Specifically, Phage solution was mixed with 100 pmol of human CD137-Fc and 4 nmol of free human IgG1 Fc domain and incubated at room temperature for 60 minutes. Magnetic beads was blocked by 2% skim-milk/TBS with free Streptavidin (Roche) at room temperature for 60 minutes or more and washed three times with TBS, and then mixed with incubated phage solution. After incubation at room temperature for 15 minutes, the beads were washed three-times with TBST (TBS containing 0.1% Tween 20; TBS was available from Takara Bio Inc.) for 10 minutes and then further washed twice with 1 mL of TBS for 10 minutes. FabRICATOR (IdeS, protease for hinge region of IgG, GENOVIS)(named as IdeS elution campaign) was used to recover antibody displaying phages. In that procedure, 10 units/micro L Fabricator 20 micro L with 80 micro L TBS buffer was added and beads were suspended at 37 degrees Celsius for 30 minutes, immediately after which the beads were separated using a magnetic stand to recover phage solution. 5 micro L of 100 mg/mL Trypsin and 400 micro L of TBS were added and incubated at room temperature for 15 minutes. The recovered phage solution was added to an *E. coli* strain ER2738 in a logarithmic growth phase (OD600: 0.4-0.5). The *E. coli* strain was infected by the phages through the gentle spinner culture of the strain at 37 degrees C. for 1 hour. The infected *E. coli* was inoculated to a plate of 225 mm×225 mm. Next, phages were recovered from the culture solution of the inoculated *E. coli* to prepare a phage library solution.

In this panning round 1 procedure antibody displaying phages which bind to human CD137 was concentrated. In the $2^{nd}$ round of panning, 160 pmol of C3NP1-27 was used as biotin-labeled antigen and wash was conducted seven-times with TBST for 2 minutes and then three-times with TBS for 2 minutes. Elution was conducted with 25 mM DTT at room temperature for 15 minutes and then digested by Trypsin.

In the $3^{rd}$ round of panning, 16 or 80 pmol of biotin-labeled cyno CD137-Fc were used as antigen and wash was conducted seven-times with TBST for 10 minutes and then three-times with TBS for 10 minutes. Elution was conducted with IdeS as same as round 1.

In the $4^{th}$ round of panning, 16 or 80 pmol of biotin labeled human CD137-Fc were used as antigen and wash was conducted seven-times with TBST for 10 minutes and then three-times with TBS for 10 minutes. Elution was conducted with IdeS as same as round 1.

(9-3) Binding of IgG Having Obtained Fab Domain to Human CD137 and Cyno CD137

Fab genes of each panning output pools were converted into IgG format. The prepared mammalian expression plasmids were introduced into *E. coli* and 96 colonies were picked from each panning output pools and their VH and VL sequence were analyzed. Most of VH sequence in Library 2 had concentrated to dBBDu_183 and most of VH sequence in Library6 had concentrated to dBBDu_193, respectively. The prepared plasmids from each *E. coli* colonies were used for expression in animal cells by the method of Reference Example 1.

The prepared IgG antibodies were subjected to ELISA to evaluate their binding capacity to CD3 epsilon, human CD137 and cyno CD137.

First, a Streptavidin-coated microplate (384 well, Greiner) was coated with 20 micro L of TBS containing biotin-labeled CD3 epsilon peptide, biotin labeled human CD137-Fc or biotin labeled cyno CD137-Fc at room temperature for one or more hours. After removing biotin-labeled antigen that are not bound to the plate by washing each well of the plate with TBST, the wells were blocked with 20 micro L of Blocking Buffer (2% skim milk/TBS) for one or more hours. Blocking Buffer was removed from each well. 20 micro L each of the 10 ng/micro L IgG containing mammalian cell supernatant twice diluted with 1% Skim milk/TBS were added to the wells, and the plate was allowed to stand at room temperature for one hour to allow each IgG to bind to biotin-labeled antigen in each well. After that each well was washed with TBST. Goat anti-human kappa Light chain alkaline phosphatase conjugate (BETHYL, A80-115AP) diluted with TBS was added to each well. The plate was incubated for one hour. After washing with TBST, the chromogenic reaction of the solution in each well added with Blue Phos Microwell Phosphatase Substrate System (KPL) was terminated by adding Blue Phos Stop Solution (KPL). Then, the color development was measured by absorbance at 615 nm. The measurement results are shown in FIG. 27.

Many IgG clones which showed binding to both CD3 epsilon, human CD137 and cyno CD137 were obtained from each panning procedure. Ninety-six clones which showed better binding were selected and evaluated further.

(9-4) Evaluation of Binding of IgG Having Obtained Fab Domain to CD3 Epsilon and Human CD137 at Same Time Ninety-six antibodies which showed obvious binding to both CD3 epsilon, human CD137 and cyno CD137 in Example 9-3 were selected to evaluate further. Purified antibodies were subjected to ELISA to evaluate their binding capacity to CD3 epsilon and human CD137 at same time.

First, 20 micro g of Streptavidin-coated magnetic beads MyOne-T1 beads was washed three-times with blocking buffer including 0.5× block Ace, 0.02% Tween and 0.05% ProClin 300 and then blocked with this blocking buffer at room temperature for 60 minutes or more. After washing once with TBST, magnetic beads were applied to each well of black round bottom PS plate (Corning, 3792). 0.625 pmol of biotin-labeled human CD137-Fc was added and incubated at room temperature for 10 minute. After that magnetic beads were washed by TBS once. 250 ng of purified IgG was mixed with 62.5, 6.25 or 0.625 pmol of free CD3 epsilon or 62.5 pmol of free human IgG1 Fc domain and then added to the magnetic beads in each well, and the plate was allowed to stand at room temperature for one hour to allow each IgG to bind to biotin-labeled antigen in each well. After that each well was washed with TBST. Goat anti-human kappa Light chain alkaline phosphatase conjugate (BETHYL, A80-115AP) diluted with TBS was added to each well. The plate was incubated for 10 minutes. After washing with TBST, APS-5 (Lumigen) was added to each well. 2 minutes later the fluorescence of each well was detected. The measurement results are shown in FIG. 28 and Table 19. The binding to human CD137 of most tested clones was inhibited by excess amount of free CD3 epsilon peptide, it demonstrated that obtained antibodies with dual Fab library did not bind to CD3 epsilon and human CD137 at same time.

TABLE 19

|  | biotin-human CD137-Fc | | |
|---|---|---|---|
|  | Free CD3e 62.5 pmol | Free Fc 62.5 pmol | Signal decrease |
| dBBDu183/L057 | 2732 | 9025 | 69.73% |
| dBBDu183/L058 | 2225 | 11115 | 79.98% |
| dBBDu183/L059 | 2134 | 100126 | 97.87% |
| dBBDu183/L060 | 2169 | 37723 | 94.25% |
| dBBDu183/L061 | 2118 | 2723 | 22.22% |
| dBBDu183/L062 | 2777 | 27880 | 90.04% |
| dBBDu183/L063 | 2943 | 28858 | 89.80% |
| dBBDu183/L064 | 2206 | 13474 | 83.63% |
| dBBDu183/L065 | 2725 | 6024 | 54.76% |
| dBBDu183/L066 | 2325 | 34020 | 93.17% |
| dBBDu183/L067 | 2936 | 19722 | 85.11% |
| dBBDu197/L068 | 2786 | 105219 | 97.35% |
| dBBDu183/L069 | 2463 | 31769 | 92.25% |
| dBBDu183/L070 | 3267 | 92395 | 96.46% |
| dBBDu183/L071 | 2297 | 8670 | 73.51% |
| dBBDu183/L072 | 2840 | 54764 | 94.81% |
| dBBDu183/L073 | 2876 | 6724 | 57.23% |
| dBBDu196/L074 | 2724 | 12891 | 78.87% |
| dBBDu183/L075 | 2568 | 8029 | 68.02% |
| dBBDu196/L076 | 2188 | 5037 | 56.56% |
| dBBDu179/L077 | 3147 | 8018 | 60.75% |
| dBBDu167/L078 | 2378 | 27120 | 91.23% |
| dBBDu167/L079 | 2269 | 5869 | 61.34% |
| dBBDu167/L080 | 2236 | 95870 | 97.67% |
| dBBDu167/L081 | 2508 | 44240 | 94.33% |
| dBBDu167/L082 | 2398 | 177750 | 98.65% |
| dBBDu167/L083 | 2164 | 78935 | 97.26% |
| dBBDu167/L084 | 2182 | 18392 | 88.14% |
| dBBDu167/L085 | 2202 | 8724 | 74.76% |
| dBBDu167/L086 | 2627 | 135762 | 98.06% |
| dBBDu167/L087 | 2168 | 106703 | 97.97% |
| dBBDu167/L088 | 2040 | 2163 | 5.69% |
| dBBDu167/L089 | 2424 | 10161 | 76.14% |
| dBBDu167/L090 | 2595 | 181795 | 98.57% |
| dBBDu167/L091 | 11345 | 124409 | 90.88% |
| dBBDu167/L092 | 2924 | 123122 | 97.63% |
| dBBDu167/L093 | 4934 | 139388 | 96.46% |
| dBBDu167/L094 | 4374 | 140938 | 96.90% |
| dBBDu167/L095 | 2207 | 112225 | 98.03% |
| dBBDu186/L096 | 37273 | 84887 | 56.09% |
| dBBDu186/L097 | 9006 | 114399 | 92.13% |
| dBBDu186/L098 | 15908 | 114905 | 86.16% |
| dBBDu186/L099 | 2367 | 19583 | 87.91% |
| dBBDu186/L100 | 88856 | 102097 | 12.97% |
| dBBDu186/L101 | 2340 | 37392 | 93.74% |
| dBBDu186/L102 | 2427 | 2685 | 9.61% |
| dBBDu186/L103 | 21977 | 74203 | 70.38% |
| dBBDu186/L104 | 2165 | 2145 | −0.93% |
| dBBDu186/L105 | 13426 | 89231 | 84.95% |
| dBBDu186/L106 | 3088 | 9857 | 68.67% |
| dBBDu186/L107 | 2104 | 2047 | −2.78% |
| dBBDu186/L108 | 50796 | 83558 | 39.21% |
| dBBDu189/L109 | 3000 | 76770 | 96.09% |
| dBBDu189/L110 | 3836 | 119618 | 96.79% |
| dBBDu189/L111 | 2568 | 49623 | 94.82% |
| dBBDu189/L112 | 4768 | 91051 | 94.76% |
| dBBDu189/L113 | 3357 | 89648 | 96.26% |
| dBBDu189/L114 | 2158 | 2512 | 14.09% |
| dBBDu189/L115 | 4058 | 141183 | 97.13% |
| dBBDu189/L116 | 3149 | 109316 | 97.12% |
| dBBDu189/L117 | 2625 | 102489 | 97.44% |
| dBBDu189/L118 | 2446 | 19372 | 87.37% |
| dBBDu189/L119 | 20377 | 88058 | 76.86% |
| dBBDu189/L120 | 3778 | 113755 | 96.68% |
| dBBDu189/L121 | 3300 | 37197 | 91.13% |
| dBBDu189/L122 | 3949 | 141349 | 97.21% |
| dBBDu189/L123 | 4950 | 22574 | 78.07% |
| dBBDu189/L124 | 3282 | 111075 | 97.05% |
| dBBDu189/L125 | 6494 | 121498 | 94.66% |
| dBBDu189/L126 | 9750 | 75082 | 87.01% |

TABLE 19-continued

|  | biotin-human CD137-Fc | | |
|---|---|---|---|
|  | Free CD3e 62.5 pmol | Free Fc 62.5 pmol | Signal decrease |
| dBBDu193/L127 | 2471 | 6084 | 59.39% |
| dBBDu193/L128 | 3197 | 120777 | 97.35% |
| dBBDu193/L129 | 2773 | 5310 | 47.78% |
| dBBDu193/L130 | 3055 | 124130 | 97.54% |
| dBBDu193/L131 | 15481 | 109233 | 85.83% |
| dBBDu193/L132 | 10414 | 115982 | 91.02% |
| dBBDu193/L133 | 2388 | 33076 | 92.78% |
| dBBDu193/L134 | 3046 | 109154 | 97.21% |
| dBBDu193/L135 | 2284 | 54304 | 95.79% |
| dBBDu193/L136 | 2092 | 113254 | 98.15% |
| dBBDu193/L137 | 2458 | 6602 | 62.77% |
| dBBDu193/L138 | 8165 | 100690 | 91.89% |
| dBBDu193/L139 | 2077 | 2190 | 5.16% |
| dBBDu222/L140 | 2721 | 22972 | 88.16% |
| dBBDu193/L141 | 2166 | 5582 | 61.20% |
| dBBDu193/L142 | 12085 | 103522 | 88.33% |
| dBBDu193/L143 | 2338 | 50082 | 95.33% |
| dBBDu193/L144 | 1952 | 2366 | 17.50% |
| dBBDu193/L145 | 2739 | 2820 | 2.87% |

(9-5) Evaluation of Affinity of IgG Having Obtained Fab Domain to CD3 Epsilon, Human CD137 and Cyno CD137

The binding of each IgG obtained in the Example 9-4 to human CD3ed, human CD137 and cyno CD137 was confirmed using Biacore T200. Sixteen antibodies were selected by the results in Example 9-4. Sensor chip CM3 (GE Healthcare) was immobilized with an appropriate amount of sure protein A (GE Healthcare) by amine coupling. The selected antibodies were captured by the chip to allow interaction to human CD3ed, human CD137 and cyno CD137 as an antigen. The running buffer used was 20 mmol/l ACES, 150 mmol/l NaCl, 0.05% (w/v) Tween20, pH 7.4. All measurements were carried out at 25 degrees C. The antigens were diluted using the running buffer.

Regarding human CD137, the selected antibodies were assessed for its binding at antigen concentrations of 4000, 1000, 250, 62.5, and 15.6 nM. Diluted antigen solutions and the running buffer which is the blank were loaded at a flow rate of 30 micro L/min for 180 seconds to allow each concentration of the antigen to interact with the antibody captured on the sensor chip. Then, running buffer was run at a flow rate of 30 micro L/min for 300 seconds and dissociation of the antigen from the antibody was observed. Next, to regenerate the sensor chip, 10 mmol/L glycine-HCl, pH 1.5 was loaded at a flow rate of 30 micro L/min for 10 seconds and 50 mmol/L NaOH was loaded at a flow rate 30 micro L/min for 10 seconds.

Regarding cyno CD137, the selected antibodies were assessed for its binding at antigen concentrations of 4000, 1000 and 250 nM. Diluted antigen solutions and the running buffer which is the blank were loaded at a flow rate of 30 micro L/min for 180 seconds to allow each of the antigens to interact with the antibody captured on the sensor chip. Then, running buffer was run at a flow rate of 30 micro L/min for 300 seconds and dissociation of the antigen from the antibody was observed. Next, to regenerate the sensor chip, 10 mmol/L glycine-HCl, pH 1.5 was loaded at a flow rate of 30 micro L/min for 10 seconds and 50 mmol/L NaOH was loaded at a flow rate 30 micro L/min for 10 seconds.

Regarding human CD3ed, the selected antibodies were assessed for its binding at antigen concentrations of 1000, 250, and 62.5 nM. Diluted antigen solutions and the running buffer which is the blank were loaded at a flow rate of 30 micro L/min for 120 seconds to allow each of the antigens to interact with the antibody captured on the sensor chip. Then, running buffer was run at a flow rate of 30 micro L/min for 180 seconds and dissociation of the antigen from the antibody was observed. Next, to regenerate the sensor chip, 10 mmol/L glycine-HCl, pH 1.5 was loaded at a flow rate of 30 micro L/min for 30 seconds and 50 mmol/L NaOH was loaded at a flow rate 30 micro L/min for 30 seconds.

Kinetic parameters such as the association rate constant ka (1/Ms) and the dissociation rate constant kd (1/s) were calculated based on the sensorgrams obtained by the measurements. The dissociation constant KD (M) was calculated from these constants. Each parameter was calculated using the Biacore T200 Evaluation Software (GE Healthcare). The results are shown in Table 20.

TABLE 20

| | | | human CD137 | | |
|---|---|---|---|---|---|
| Hch Name | Lch name | SEQ ID NO | ka (1/Ms) | kd (1/s) | KD (M) |
| dBBDu_183 | dBBDu_L063 | 50 | 2.05E+03 | 3.58E−03 | 1.74E−06 |
| dBBDu_183 | dBBDu_L072 | 51 | 1.76E+03 | 4.25E−03 | 2.41E−06 |
| dBBDu_167 | dBBDu_L091 | 52 | 2.72E+03 | 1.85E−02 | 6.79E−06 |
| dBBDu_186 | dBBDu_L096 | 53 | 2.46E+02 | 5.58E−04 | 2.27E−06 |
| dBBDu_186 | dBBDu_L098 | 54 | 2.31E+02 | 5.34E−04 | 2.31E−06 |
| dBBDu_186 | dBBDu_L106 | 55 | 1.30E+02 | 4.47E−04 | 3.44E−06 |
| dBBDu_189 | dBBDu_L116 | 56 | 7.07E+02 | 2.91E−03 | 4.12E−06 |
| dBBDu_189 | dBBDu_L119 | 57 | 1.48E+02 | 4.02E−04 | 2.71E−06 |
| dBBDu_183 | dBBDu_L067 | 58 | 1.38E+03 | 4.51E−03 | 3.26E−06 |
| dBBDu_186 | dBBDu_L100 | 59 | 3.91E+02 | 7.46E−04 | 1.91E−06 |
| dBBDu_186 | dBBDu_L108 | 60 | 3.35E+02 | 8.10E−04 | 2.41E−06 |
| dBBDu_189 | dBBDu_L112 | 61 | 1.18E+03 | 3.13E−03 | 2.66E−06 |
| dBBDu_189 | dBBDu_L126 | 62 | 1.34E+03 | 6.88E−04 | 5.13E−07 |
| dBBDu_167 | dBBDu.L094 | 63 | 1.21E+03 | 1.02E−02 | 8.43E−06 |
| dBBDu_193 | dBBDu.L127 | 64 | 4.40E+02 | 1.45E−03 | 3.30E−06 |
| dBBDu_193 | dBBDu.L132 | 65 | 4.71E+02 | 2.11E−03 | 4.48E−06 |
| dBBDu_183 | dBBDu_L063 | 50 | 1.47E+03 | 4.57E−03 | 3.12E−06 |
| dBBDu_183 | dBBDu_L072 | 51 | 1.22E+03 | 5.93E−03 | 4.87E−06 |
| dBBDu_167 | dBBDu_L091 | 52 | 2.43E+03 | 1.01E−02 | 4.17E−06 |
| dBBDu_186 | dBBDu_L096 | 53 | 1.09E+01 | 2.23E−03 | 2.05E−04 |
| dBBDu_186 | dBBDu_L098 | 54 | 8.84E+00 | 1.19E−03 | 1.34E−04 |
| dBBDu_186 | dBBDu_L106 | 55 | 2.05E+01 | 1.26E−03 | 6.13E−05 |
| dBBDu_189 | dBBDu_L116 | 56 | 7.44E+02 | 8.23E−03 | 1.11E−05 |
| dBBDu_189 | dBBDu_L119 | 57 | 3.42E+01 | 1.22E−03 | 3.57E−05 |
| dBBDu_183 | dBBDu_L067 | 58 | 1.31E+03 | 8.13E−03 | 6.20E−06 |
| dBBDu_186 | dBBDu_L100 | 59 | 2.95E+01 | 2.08E−03 | 7.04E−05 |
| dBBDu_186 | dBBDu_L108 | 60 | 2.25E+02 | 3.61E−03 | 1.61E−05 |
| dBBDu_189 | dBBDu_L112 | 61 | 4.98E+03 | 2.86E−02 | 5.76E−06 |
| dBBDu_189 | dBBDu_L126 | 62 | 8.07E+02 | 2.47E−03 | 3.06E−06 |
| dBBDu_167 | dBBDu.L094 | 63 | 1.08E+04 | 7.48E−02 | 6.92E−06 |
| dBBDu_193 | dBBDu.L127 | 64 | 1.12E+02 | 3.16E−03 | 2.81E−05 |
| dBBDu_193 | dBBDu.L132 | 65 | 8.06E+00 | 6.10E−03 | 7.57E−04 |
| dBBDu_183 | dBBDu_L063 | 50 | 5.69E+04 | 1.57E−02 | 2.76E−07 |
| dBBDu_183 | dBBDu_L072 | 51 | 3.61E+04 | 7.85E−03 | 2.17E−07 |
| dBBDu_167 | dBBDu_L091 | 52 | 5.24E+04 | 2.16E−02 | 4.13E−07 |
| dBBDu_186 | dBBDu_L096 | 53 | 1.12E+04 | 1.02E−01 | 9.11E−06 |
| dBBDu_186 | dBBDu_L098 | 54 | 1.11E+04 | 2.09E−02 | 1.88E−06 |
| dBBDu_186 | dBBDu_L106 | 55 | 1.03E+04 | 3.18E−02 | 3.09E−06 |
| dBBDu_189 | dBBDu_L116 | 56 | 2.08E+04 | 4.34E−03 | 2.09E−07 |
| dBBDu_189 | dBBDu_L119 | 57 | 1.25E+04 | 2.58E−02 | 2.06E−06 |
| dBBDu_183 | dBBDu_L067 | 58 | 8.89E+04 | 1.93E−02 | 2.17E−07 |
| dBBDu_186 | dBBDu_L100 | 59 | 1.62E+04 | 5.46E−02 | 3.36E−06 |
| dBBDu_186 | dBBDu_L108 | 60 | 1.36E+04 | 4.08E−02 | 3.01E−06 |
| dBBDu_189 | dBBDu_L112 | 61 | 3.03E+04 | 1.00E−02 | 3.31E−07 |
| dBBDu_189 | dBBDu_L126 | 62 | 1.09E+04 | 2.81E−02 | 2.57E−06 |
| dBBDu_167 | dBBDu.L094 | 63 | 6.02E+04 | 2.10E−02 | 3.49E−07 |
| dBBDu_193 | dBBDu.L127 | 64 | 1.26E+04 | 1.91E−02 | 1.51E−06 |
| dBBDu_193 | dBBDu.L132 | 65 | 9.89E+03 | 2.01E−02 | 2.03E−06 |

[Example 10] Preparation of Anti-Human GPC3/Dual-Fab Trispecific Antibodies and Assessment of their Human CD137 Agonist Activities (10-1) Preparation of Anti-Human GPC3/Anti-Human CD137 Bispecific Antibodies and Anti-Human GPC3/Dual-Fab Trispecific Antibodies The anti-human GPC3/anti-human CD137 bispecific antibodies and the anti-human GPC3/Dual-Fab Trispecific antibodies carrying human IgG1 constant regions were produced by the following procedure. Genes encoding an anti-human CD137 antibody (SEQ ID NO: 19 for the H chain, and SEQ ID NO: 20 for the L-chain) described in WO2005/035584A (abbreviated as B) was used as a control antibody. The anti-human GPC3 side of the antibodies shared the heavy-chain variable region H0000 (SEQ ID NO: 66) and light-chain variable region GL4 (SEQ ID NO: 67). Sixteen dual-Ig Fab described in Example 9 and Table 20 was used as candidate dual-Ig antibody. For these molecules, the CrossMab technique reported by Schaefer et al. (Schaefer, Proc. Natl. Acad. Sci., 2011, 108, 11187-11192) was used to regulate the association between the H and L-chains of bispecific antibodies. More specifically, these molecules were produced by exchanging the VH and VL domains of Fab against human GPC3. For promotion of heterologous association, the Knobs-into-Holes technology was used for the constant region of the antibody H chain. The Knobs-into-Holes technology is a technique that enables preparation of heterodimerized antibodies of interest through promotion of the heterodimerization of H chains by substituting an amino acid side chain present in the CH3 region of one of the H chains with a larger side chain (Knob) and substituting an amino acid side chain in the CH3 region of the other H chain with a smaller side chains (Hole) so that the knob will be placed into the hole (Burmeister, Nature, 1994, 372, 379-383). Hereinafter, the constant region into which the Knob modification has been introduced will be indicated as Kn, and the constant region into which the Hole modification has been introduced will be indicated as Hl. Furthermore, the modifications described in WO2011/108714 were used to reduce the Fc gamma binding. Specifically, modifications of substituting Ala for the amino acids at positions 234, 235, and 297 (EU numbering) were introduced. Gly at position 446 and Lys at position 447 (EU numbering) were removed from the C termini of the antibody H chains. A histidine tag was added to the C terminus of the Kn Fc region, and a FLAG tag was added to the C terminus of Hl Fc region. The anti-human GPC3 H chains prepared by introducing the above-mentioned modifications were GC33(2)H-G1dKnHS (SEQ ID NO: 68). The anti-human CD137 H chains prepared were BVH-G1dHlFS(SEQ ID NO: 69). The antibody L chains GC33(2)L-k0 (SEQ ID NO: 70) and BVL-k0 (SEQ ID NO: 71) were commonly used on the anti-human GPC3 side and the anti-CD137 side, respectively. The H chains and L chains of Dual antibodies are also shown in Table 20. The VH of each dual antibody clones were fused to G1dHlFS (SEQ ID NO: 83) CH region and the VL of each dual antibody clones were fused to k0 (SEQ ID NO: 84) CL region, respectively, as same as BVH-G1dHlFS and BVL-k0. The antibodies having the combinations shown in Table 22 were expressed to obtain the bispecific antibodies of interest. An antibody having received irrelevant was used as control (abbreviated as Ctrl). These antibodies were expressed by transient expression in FreeStyle293 cells (Invitrogen) and purified according to "Reference Example 1".

(10-2). Assessment of the In Vitro GPC3-Dependent CD137 Agonist Effect of Anti-Human GPC3/Dual-Fab Trispecific Antibodies The agonistic activity for human CD137 was evaluated on the basis of the cytokine production using ELISA kit (R&D systems, DY206). In order to avoid the effect of CD3 epsilon binding domain of the anti-human GPC3/Dual-Fab antibodies, the B cell strain HDLM-2 was used, which did not express the CD3 epsilon neither GPC3, but express CD137 constitutively. The HDLM-2 was suspended in 20% FBS-containing RPMI-1640 medium at a density of $8 \times 10^5$ cells/ml. The mouse cancer cell strain CT26-GPC3 which expressed GPC3 (Reference Example 5) was suspended in the same medium at a density of $4 \times 10^5$ cells/ml. The same volume of each cell suspension was mixed, the mixed cell suspension was seeded into the 96-well plate at a volume of 200 ul/well. The anti-GPC3/Ctrl antibodies, the anti-GPC3/anti-CD137 antibodies, and eight anti-GPC3/Dual-Fab antibodies prepared in Example 10-1 were added at 30 micro g/ml, 6 micro g/ml, 1.2 micro g/ml, 0.24 micro g/ml each. The cells were cultured under the condition of 37 degrees C. and 5% C02 for 3 days. The culture supernatant was collected, and the concentration of human IL-6 contained in the supernatant was measured with Human IL-6 DuoSet ELISA (R&D systems, DY206) to assess the HDLM-2 activation. ELISA was performed by following the instructions provided by the kit manufacturer (R&D systems).

As a result (FIG. 29 and Table 21), seven of eight anti-GPC3/Dual-Fab antibodies showed the activation of IL-6 production of HDLM-2 as well as anti-GPC3/anti-CD137 antibodies depending on antibody concentration. In Table 21, agonistic activity compared to Ctrl means the increase level of hIL-6 secretion beyond the background level in the presence of Ctrl. Based on this result, it was thought that these Dual-Fab antibodies have the agonistic activity on human CD137.

TABLE 21

| Antibody | hIL-6 (pg/mL) | | Agonistic activity compared to B | | Agonistic activity compared to Ctrl | |
|---|---|---|---|---|---|---|
| (μg/mL) | 30 | 6 | 30 | 6 | 30 | 6 |
| Ctrl | 906.060814 | 1012.42048 | | | 0.00% | 0.00% |
| B | 4344.80386 | 4524.76696 | 100.00% | 100.00% | 379.53% | 346.93% |
| L063 | 1129.89262 | 967.744207 | 6.51% | −1.27% | 24.70% | −4.41% |
| L072 | 1447.54151 | 1125.01544 | 15.75% | 3.21% | 59.76% | 11.12% |
| L091 | 944.057133 | 934.684418 | 1.10% | −2.21% | 4.19% | −7.68% |
| L096 | 1736.82678 | 1681.25602 | 24.16% | 19.04% | 91.69% | 66.06% |
| L098 | 1753.61596 | 1501.11166 | 24.65% | 13.91% | 93.54% | 48.27% |
| L106 | 1573.01967 | 1476.44391 | 19.40% | 13.21% | 73.61% | 45.83% |
| L116 | 1566.84383 | 1303.26238 | 19.22% | 8.28% | 72.93% | 28.73% |
| L119 | 1606.92382 | 1255.50299 | 20.38% | 6.92% | 77.35% | 24.01% |

[Example 11] Assessment of the Human CD3 Epsilon Agonist Activities of Anti-human GPC3/Dual-Fab Trispecific Antibodies (11-1) Preparation of Anti-Human GPC3/Anti-Human CD3 Epsilon Bispecific Antibodies and Anti-Human GPC3/Dual-Fab Trispecific Antibodies The anti-human GPC3/Ctrl bispecific antibodies and the anti-human GPC3/Dual-Fab Trispecific antibodies carrying human IgG1 constant regions were produced in Example 10-1, and the anti-human GPC3/anti-human CD3 epsilon bispecific antibody was also prepared as same construct. CE115 VH(SEQ ID NO:72) and CE115 VL (SEQ ID NO:73) produced in Reference Example 2 was used for anti-human CD3 epsilon antibody Heavy chain and Light chain. The antibodies having the combinations shown in Table 22. These antibodies were expressed by transient expression in FreeStyle293 cells (Invitrogen) and purified according to "Reference Example 1".

TABLE 22

| Antibody name | Hch gene1 | Lch gene1 | Hch gene1 | Lch gene1 |
| --- | --- | --- | --- | --- |
| GPC3 ERY22-B | GC33(2)H-G1dKnHS | GC33(2)L-k0 | BVH-G1dHIFS | BVL-k0 |
| GPC3 ERY22-dBBDu_183/L063 | GC33(2)H-G1dKnHS | GC33(2)L-k0 | dBBDu_183VH-G1dHIFS | L063VL-k0 |
| GPC3 ERY22-dBBDu_183/L072 | GC33(2)H-G1dKnHS | GC33(2)L-k0 | dBBDu_183VH-G1dHIFS | L072VL-k0 |
| GPC3 ERY22-dBBDu_167/L091 | GC33(2)H-G1dKnHS | GC33(2)L-k0 | dBBDu_167VH-G1dHIFS | L091VL-k0 |
| GPC3 ERY22-dBBDu_186/L096 | GC33(2)H-G1dKnHS | GC33(2)L-k0 | dBBDu_186VH-G1dHIFS | L096VL-k0 |
| GPC3 ERY22-dBBDu_186/L098 | GC33(2)H-G1dKnHS | GC33(2)L-k0 | dBBDu_186VH-G1dHIFS | L098VL-k0 |
| GPC3 ERY22-dBBDu_186/L106 | GC33(2)H-G1dKnHS | GC33(2)L-k0 | dBBDu_186VH-G1dHIFS | L106VL-k0 |
| GPC3 ERY22-dBBDu_189/L116 | GC33(2)H-G1dKnHS | GC33(2)L-k0 | dBBDu_189VH-G1dHIFS | L116VL-k0 |
| GPC3 ERY22-dBBDu_189/L119 | GC33(2)H-G1dKnHS | GC33(2)L-k0 | dBBDu_189VH-G1dHIFS | L119VL-k0 |
| GPC3 ERY22-dBBDu_183/L067 | GC33(2)H-G1dKnHS | GC33(2)L-k0 | dBBDu_183VH-G1dHIFS | L067VL-k0 |
| GPC3 ERY22-dBBDu_186/L100 | GC33(2)H-G1dKnHS | GC33(2)L-k0 | dBBDu_186VH-G1dHIFS | L100VL-k0 |
| GPC3 ERY22-dBBDu_186/L108 | GC33(2)H-G1dKnHS | GC33(2)L-k0 | dBBDu_186VH-G1dHIFS | L108VL-k0 |
| GPC3 ERY22-dBBDu_189/L112 | GC33(2)H-G1dKnHS | GC33(2)L-k0 | dBBDu_189VH-G1dHIFS | L112VL-k0 |
| GPC3 ERY22-dBBDu_189/L126 | GC33(2)H-G1dKnHS | GC33(2)L-k0 | dBBDu_189VH-G1dHIFS | L126VL-k0 |
| GPC3 ERY22-dBBDu_167/L094 | GC33(2)H-G1dKnHS | GC33(2)L-k0 | dBBDu_167VH-G1dHIFS | L094VL-k0 |
| GPC3 ERY22-dBBDu_193/L127 | GC33(2)H-G1dKnHS | GC33(2)L-k0 | dBBDu_193VH-G1dHIFS | L127VL-k0 |
| GPC3 ERY22-dBBDu_193/L132 | GC33(2)H-G1dKnHS | GC33(2)L-k0 | dBBDu_193VH-G1dHIFS | L132VL-k0 |
| GPC3 ERY22-CE115 | GC33(2)H-G1dKnHS | GC33(2)L-k0 | CE115VH-G1dHIFS | CE115VL-k0 |
| GPC3 ERY22-Ctrl | GC33(2)H-G1dKnHS | GC33(2)L-k0 | CtrlVH-G1dHIFS | CtrlVL-k0 |

(11-2) Assessment of the In Vitro GPC3-Dependent CD3 Agonist Effect of Anti-Human GPC3/Dual-Fab Trispecific Antibodies The agonistic activity to human CD3 was evaluated by using GoResponse™ NFAT-luc2 Jurkat Cell Line (Promega, CS #176401) as effector cell. Jurkat cell is an immortalized cell line of human T lymphocyte cells derived from human acute T cell leukemia and it expresses human CD3 on itself. In NFAT luc2_jurkat cell, the expression of Luciferase was induced by the signal from CD3 activation. SK-pca60 cell line which express human GPC3 on the cell membrane (Reference Example 5) was used as target cell.

Both 5.00E+03 SK-pca69 cells (target cells) and 3.00E+04 NFAT-luc2 Jurkat Cells (Effector cells) were added on the each well of white-bottomed, 96-well assay plate (Costar, 3917), and then 10 micro L of each antibodies with 0.1, 1 or 10 mg/L concentration were added on each well and incubated in the presence of 5% C02 at 37 degrees Celsius for 24 hours. The expressed Luciferase was detected with Bio-Glo luciferase assay system (Promega, G7940) in accordance with the attached instruction. 2104 EnVIsion was used for detection. The result was shown in FIG. 30.

Most Dual Fab clones showed obvious CD3 epsilon agonist activity and some of them showed equal level of activity with CE115 anti-human CD3 epsilon antibody. It demonstrated that addition of CD137 binding activity to Dual-Fab domain did not induce loss of CD3 epsilon agonist activity and that Dual-Fab domain showed not only binding to two different antigen, human CD3 epsilon and CD137 but also the agonist activity of both human CD3 epsilon and CD137 by only one domain.

Some Dual-Fab domain with Heavy chain dBBDu_186 showed weaker CD3 epsilon agonist activity than others. These antibodies also showed weaker affinity to human CD3 epsilon in biacore analysis in Example 9-5. It demonstrates that the CD3 epsilon agonist activity of Dual-Fab from this Dual Fab library only depends on its affinity to human CD3 epsilon, it means the CD3 epsilon agonist activity was retained in this library design.

[Example 12] Assessment of the Human CD3 Epsilon/Human CD137 Synergistic Activities of Dual-Fab Antibodies in PBMC T Cell Cytokine Release Assay (12-1) Antibody Preparation Anti-CD137 antibodies described in WO2005/035584A1 (abbreviated as B), Ctrl antibodies described in Example 10-1 and anti-CD3 epsilon CE115 antibody, described in Example 12 were used as single antigen specific controls. Dual-Fab, H183L072 (Heavy chain: SEQ ID NO 30, Light chain: SEQ ID NO 51) described in Table 20 was selected for further evaluation and was expressed by transient expression in FreeStyle293 cells (Invitrogen) and purified according to "Reference Example 1".

(12-2) PBMC T Cell Assay

In order to investigate the synergistic effect of Dual-Fab antibody on CD3 epsilon and CD137 activation, total cytokine release was evaluated using cytometric bead array (CBA) Human Th1/T2 Cytokine kit II (BD Biosciences #551809). Relevant to CD137 activation, IL-2 (Interleukin-2), IFN gamma (Interferon gamma) and TNF alpha (Tumor Necrosis Factor-alpha) were evaluated from T cells were isolated from frozen human peripheral blood mononuclear cells (PBMC) purchased frozen (STEMCELL).

(12-2-1) Preparation of Frozen Human PBMC and Isolation of T Cells

Cryovials containing PBMCs were placed in the water bath at 37 degrees C. to thaw cells. Cells were then dispensed into a 15 mL falcon tube containing 9 mL of media (media used to culture target cells). Cell suspension was then subjected to centrifugation at 1,200 rpm for 5 minutes at room temperature. The supernatant was aspirated gently and fresh warmed medium was added for resuspension and used as the human PBMC solution. T cells were isolated using Dynabeads Untouched Human T cell kit (Invitrogen #11344D) following manufacturer's instructions.

(12-2-2) Cytokine Release Assay 30 micro g/mL and 10 micro g/mL of antibodies prepared in Example 12-1 were coated on maxisorp 96-well plate (Thermofisher #442404) overnight. 1.00E+05 T cells were added to each well containing antibodies and incubated at 37 degrees C. for 72 hours. Plates were centrifuged at 1,200 rpm for 5 minutes and supernatant was collected. CBA was performed according to manufacturer's instructions and the results are shown in FIG. 31.

Only dual-Fab, H183L72 antibody showed IL-2 secretion by T cells. Neither anti-CD137(B) not anti-CD3 epsilon antibody (CE115) alone could result in induction of IL-2 from T cells. In addition, anti-CD137 antibody alone did not result in detection of any cytokine. As compared to anti-CD3 epsilon antibody, Dual-Fab antibody resulted in increased levels of TNF alpha and similar secretion of IFN gamma. These results suggest that dual-Fab antibody could elicit synergistic activation of both CD3 epsilon and CD137 for functional activation of T cells.

[Example 13] Assessment of the Cytotoxicity of Anti-GPC3/Dual-Fab Trispecific Antibodies (13-1) Anti-GPC3/Dual-Fab and Anti-GPC3/CD137 Bi-Specific Antibody Preparation Anti-GPC3 or Ctrl antibodies described in Example 11 and Dual-Fab (H183L072) or anti-CD137 antibodies were used to generate four antibodies, Anti-GPC3/dual-Fab, anti-GPC3/CD137, Ctrl/H183L072, and Ctrl/CD137 antibodies using Fab-arm exchange (FAE) according to a method described in (Proc Natl Acad Sci USA. 2013 Mar. 26; 110(13): 5145-5150). The molecular format of all four antibodies is the same format as a conventional IgG. Anti-GPC3/H183L072 is tri-specific antibody that is able to bind GPC3, CD3, and CD137, anti-GPC3/CD137 is bi-specific antibody that is able to bind GPC3 and CD137, and Ctrl/H183L072, and Ctrl/CD137 were used as control. All four antibodies generated consist of a silent Fc with attenuated affinity for Fc gamma receptor (L235R,G236R,S239K) and deglycosylated (N297A).

(13-2) T-Cell Dependent Cellular Cytotoxicity (TDCC) Assay

Cytotoxic activity was assessed by the rate of cell growth inhibition using xCELLigence Real-Time Cell Analyzer (Roche Diagnostics) as described in Reference Example (2-5-2). 1.00E+04 SK-pca60 or SK-pca13a, both transfectant cell lines expressing GPC3 were used as target (abbreviated as T) cells (Reference Examples 5 and 2 respectively) and co-cultured with 5.00E+04 frozen human PBMCs effector (abbreviated as E) cells that were prepared as described in Example (12-2-1). It means 5-fold amount of effector cells were added on tumor cells, so it is described here as ET 5. Anti-GPC3/H183L072 antibodies and GPC3/CD137 antibodies were added at 0.4, 5 and 10 nM while Ctrl/H183L072 antibodies and Ctrl/CD137 antibodies were added at 10 nM each well. Measurement of cytotoxic activity was conducted similarly as described in Reference Example 2-5-2. The reaction was carried out under the conditions of 5% carbon dioxide gas at 37 degrees C. 72 hours after the addition of PBMCs, Cell Growth Inhibition (CGI) rate (%) was determined using the equation described in Reference Example 2-5-2 and plotted in the graph as shown in FIG. 32. Anti-GPC3/H183L72 dual-Fab antibody which showed CD3 activation on Jurkat cells in Example 11-2 but not Control/H183L072 dual-Fab antibody which did not show CD3 activation and anti-GPC3/CD137 antibody resulted in strong cytotoxic activity of GPC3-expressing cells at all concentrations in both target cell lines, suggesting that Dual-Fab tri-specific antibodies can result in cytotoxic activity.

[Example 14] Assessment of the Off-Target Cytotoxicity of Anti-GPC3/CD3/Human CD137 Trispecific Antibodies and Anti-GPC3/Dual-Fab Antibodies (14-1) Preparation of Anti-GPC3/CD3/Human CD137 Trispecific Antibodies To investigate target independent cytotoxicity and cytokine release, trispecific antibodies were generated by utilizing CrossMab and FAE technology (FIG. 33). Tetravalent IgG-like molecule, Antibody A (mAb A) which of each arm has two binding domains resulting in four binding domains in one molecular was generated with CrossMab as mentioned above. Bivalent IgG, Antibody B (mAb B) is the same format as a conventional IgG. Fc region of both mAb A and mAb B was a Fc gamma R silent with attenuated affinity for Fc gamma receptor (L235R,G236R,S239K) and deglycosylated (N297A) and applicable for FAE. Six trispecific antibodies were constructed. The target antigen of each Fv region in six trispecific antibodies was shown in Table 23. The naming rule of each of binding domain of mAb A, mAb B, and mAb AB are shown in FIG. 34. The pair of mAb A and mAb B to generate each of six trispecific antibodies, mAb AB, and their SEQ ID NOs were shown in Table xx19 and Table xx20, respectively. Antibody CD3D(2)_il21 which was described in WO2005/035584A1 (abbreviated as AN121) was used as anti-CD3 epsilon antibody. All six trispecific antibodies were expressed and purified by the method described above.

TABLE 23

Target of each arm of antibodies

| Name of mAb AB | Fv A1 | Fv A2 | Fv B |
|---|---|---|---|
| GPC3/CD137 × CD3 | Anti-CD137 | Anti-CD3ε | Anti-GPC3 |
| GPC3/CD137 × Ctrl | Anti-CD137 | Ctrl | Anti-GPC3 |
| GPC3/Ctrl × CD3 | Ctrl | Anti-CD3ε | Anti-GPC3 |
| Ctrl/CD137 × CD3 | Anti-CD137 | Anti-CD3ε | Ctrl |
| Ctrl/CD137 × Ctrl | Anti-CD137 | Ctrl | Ctrl |
| Ctrl/Ctrl × CD3 | Ctrl | Anti-CD3ε | Ctrl |

TABLE 24

| Name of mAb | Name of mAb A to generate mAb AB | VHA1 (SEQ ID NO) | VLA1 (SEQ ID NO) | VHA2 (SEQ ID NO) | VLA2 (SEQ ID NO) | Name of mAb B to generate mAb AB | VHB (SEQ ID NO) | VLB (SEQ ID NO) |
|---|---|---|---|---|---|---|---|---|
| GPC3/CD137xCD3 | CD137xCD3 | 85 | 86 | 87 | 88 | GPC3 | 89 | 90 |
| GPC3/CD137xCtrl | CD137xCtrl | 85 | 86 | Ctrl | Ctrl | GPC3 | 89 | 90 |
| GPC3/CtrlxCD3 | CtrlxCD3 | Ctrl | Ctrl | 87 | 88 | GPC3 | 89 | 90 |
| Ctrl/CD137xCD3 | CD137xCD3 | 85 | 86 | 87 | 88 | Ctrl | Ctrl | Ctrl |
| Ctrl/CD137xCtrl | CD137xCtrl | 85 | 86 | Ctrl | Ctrl | Ctrl | Ctrl | Ctrl |
| Ctrl/CtrlxCD3 | CtrlxCD3 | Ctrl | Ctrl | 87 | 88 | Ctrl | Ctrl | Ctrl |

TABLE 25

| Name of VH or VL | SEQ ID NO | Amino acid sequence |
|---|---|---|
| CD137 VHA1 | 85 | QVQLQQWGAGLLKPSETLSLTCAVYGGSFSGYYWS WIRQSPEKGLEWIGEINHG- GYVTYNPSLESRVTISVD TSKNQFSLKLSSVTAADTAVYYCARDYGPGNYDWY FDLWGRGTLVTVSS |
| CD137 VLA1 | 86 | EIVLTQSPATLSLSPGERATLSCRASQSVSSYLAWY QQKPGQAPRLLIYDASNRATGIPARFSGSGSGTDFT LTISSLEPEDFAVYYCQQRSNWPPAL- TFGGGTKVEIK |
| CD3 VHA2 | 87 | QVQLVESGGGLVQPGRSLRLSCAASGFTFSNAWMH WVRQAPGKGLEVVVAQI KDRANSYNTYY- AESVKGRF TISRDDSKNSIYLQMNSLKTEDTAVYYCRYVHYT- TYA GSSFSYGVDAWGQGTTVTVSS |
| CD3 VLA2 | 88 | DIVMTQSPLSLPVTPGEPASIS- CRSSQPLVHSNRNTY LHWYQQKPGQAPRLLIYKVSNRFSGVPDRFSGSGS GTDFTLKISRVEAEDVGVYYCGQGTQVPYTFGQGTK LEIK |
| GPC3 VHB | 89 | QVQLVQSGAEVKKPGASVTVSCKASGYTFTDYEMH WIRQPPGEGLEWIGAIDGPTPDTAYSEKFKGRVTLT ADKSTSTAYMELSSLTSEDTAVYYCTRFY- SYTYVVGQ GTLVTVSS |
| GPC3 VLB | 90 | DIVMTQSPLSLPVTPGEPASIS- CRSSQPLVHSNRNTY LHWYQQKPGQAPRLLIYKVSNRFSGVPDRFSGSGS GTDFTLKISRVEAEDVGVYYCGQGTQVPYTFGQGTK LEIK |

(14-2) Evaluation of the Binding of GPC3/CD3/Human CD137 Trispecific Antibodies

Binding affinity of trispecific antibodies to human CD3 and CD137 were assessed at 37 degrees C. using Biacore T200 instrument (GE Healthcare). Anti-human Fc antibody (GE Healthcare) was immobilized onto all flow cells of a CM4 sensor chip using amine coupling kit (GE Healthcare). Antibodies were captured onto the anti-Fc sensor surfaces, then recombinant human CD3 or CD137 was injected over the flow cell. All antibodies and analytes were prepared in ACES pH 7.4 containing 20 mM ACES, 150 mM NaCl, 0.05% Tween 20, 0.005% NaN3. Sensor surface was regenerated each cycle with 3M MgCl2. Binding affinity were determined by processing and fitting the data to 1:1 binding model using Biacore T200 Evaluation software, version 2.0 (GE Healthcare).

Binding affinity of trispecific antibodies to recombinant human CD3 and CD137 are shown in Table 26.

TABLE 26

| | CD137 | | | CD3 | | |
|---|---|---|---|---|---|---|
| Ab name | ka ($M^{-1}s^{-1}$) | kd ($s^{-1}$) | KD (M) | ka ($M^{-1}s^{-1}$) | kd ($s^{-1}$) | KD (M) |
| GPC3/CD137xCD3 | 5.47E+05 | 2.06E−02 | 3.77E−08 | 8.18E+04 | 1.61E−03 | 1.97E−08 |
| GPC3/CD137xCtrl | 5.72E+05 | 2.04E−02 | 3.57E−08 | | no binding | |
| GPC3/CtrlxCD3 | | no binding | | 8.50E+04 | 1.51E−03 | 1.78E−08 |
| Ctrl/CD137xCD3 | 5.48E+05 | 1.82E−02 | 3.31E−08 | 8.24E+04 | 1.52E−03 | 1.85E−08 |
| Ctrl/CD137xCtrl | 5.59E+05 | 1.79E−02 | 3.21E−08 | | no binding | |
| Ctrl/CtrlxCD3 | | no binding | | 8.37E+04 | 1.47E−03 | 1.75E−08 |

(14-3) Evaluation of the Simultaneous Binding of GPC3/CD137×CD3 Trispecific Antibodies and Anti-GPC3/Dual-Fab to Human CD137 and CD3

Biacore in-tandem blocking assay was performed to characterize simultaneous binding of Trispecific antibodies or Dual-Fab antibodies for both CD3 and CD137. The assay was performed on Biacore T200 instrument (GE Healthcare) at 25 degrees C. in ACES pH 7.4 buffer containing 20 mM ACES, 150 mM NaCl, 0.05% Tween 20, 0.005% NaN3. Anti-human Fc antibody (GE Healthcare) was immobilized onto all flow cells of a CM4 sensor chip using amine coupling kit (GE Healthcare). Antibodies were captured onto the anti-Fc sensor surfaces, then 8 micro M CD3 was injected over the flow cell followed by an identical injection of 8 micro M CD137 in the presence of 8 micro M CD3. An increased of binding response for second injection was indicative of binding to different paratopes therefore a simultaneous binding interactions; whereas no enhancement or decreased of binding response for the 2nd injection was indicative of binding to the same or overlapping or adjacent paratopes, therefore a non-simultaneous binding interactions.

Results of this assay are shown in FIG. 35 where GPC3/CD137×CD3 Trispecific antibody but not anti-GPC3/Dual-Fab antibody showed simultaneous binding characteristics to CD3 and CD137.

(14-4) Evaluation of the Binding of GPC3/CD137×CD3 Trispecific Antibodies and Anti-GPC3/Dual-Fab Antibodies to Human CD137 Expressing CHO Cells or Jurkat Cells FIG. 36 show binding of tri-specific antibodies and Dual-Fab antibodies to hCD137 transfectant, parental CHO cells generated in Reference Example 5 or binding to hCD3 expressed on Jurkat cells (reference Example 11-2) determined by FACS analysis. Briefly, tri-specific antibodies and Dual-Fab antibodies were incubated with each cell line for 2 hours at room temperature and washed with FACS buffer (2% FBS, 2 mM EDTA in PBS). Goat F(ab')2 anti-Human IgG, Mouse ads-PE (Southern Biotech, Cat. 2043-09) was then added and incubated for 30 minutes at 4 degrees C. and washed with FACS buffer. Data acquisition was performed on an FACS Verse (Becton Dickinson), followed by analysis using the FlowJo software (Tree Star).

FIG. 36 shows that 50 nM of anti-GPC3/H183L072 (black line) antibody binds hCD137 specifically on hCD137 transfectant (FIG. 36a) but no binding is observed for CHO parental cells (FIG. 36b), relative to Ctrl antibody (grey filled). Similarly, 2 nM of anti-GPC3/CD137×CD3 (dark grey filled) and anti-GPC3/CD137×Ctrl (black line) tri-specific antibodies showed specific binding to hCD137 on transfectant cells (FIG. 36c) relative to Ctrl/Ctrl×CD3 tri-specific control antibody (light grey, filled). No non-specific binding was observed in CHO parental cells (FIG. 36d).

50 nM of both anti-GPC3/H183L072 (black line) antibodies in FIG. 36e and GPC3/CD137×CD3 (dark grey filled) or GPC3/CD137×Ctrl (black line) trispecific antibodies in FIG. 36f was shown to bind CD3 expressed on Jurkat cells relative to their respective controls (light grey filled).

(14-5) Assessment of CD3 Activation on T Cell to Human GPC3 Expression Cells of GPC3/CD137×CD3 Tri-Specific Antibodies and Anti-GPC3/Dual-Fab Tri-Specific Antibodies.

To investigate if both formats of tri-specific antibodies and anti-GPC3/Dual-Fab antibodies can activate effector cells in a target-dependent manner, NFAT-luc2 Jurkat luciferase assay was conducted as described in Example 11-2. 5.00E+03 SK-pca60 cells (reference Example 5) were used as target cells and co-cultured with 2.50E+04 NFAT-luc2 Jurkat cells for 24 hours in the presence of 0.1, 1 and 10 nM of tri-specific antibodies or Dual-Fab antibodies. 24 hours later, luciferase activity was detected with Bio-Glo luciferase assay system (Promega, G7940) according to manufacturer's instructions. Luminescence (units) was detected using GloMax(registered trademark) Explorer System (Promega #GM3500) and captured values were plotted using Graphpad Prism 7. As shown in FIG. 37, only tri-specific antibodies which comprised of both anti-GPC3 and anti-CD3 binding such as GPC3/CD137×CD3, GPC3/Ctrl×CD3 or anti-GPC3/H183L072 resulted in dose-dependent activation of Jurkat cells in the presence of target cells. Of note, anti-GPC3/H183L72 antibodies could elicit similar extent of Jurkat activation as GPC3/CD137×CD3 or GPC3/Ctrl×CD3 antibodies even though binding of anti-GPC3/H183L072 antibodies on Jurkat cells by FACS analysis in Example (14-4) is weaker. Altogether, both tri-specific antibodies and anti-GPC3/Dual-Fab antibodies can result in target dependent activation of effector cells.

(14-6) Assessment of CD3 Activation on T Cell to Human CD137 Expression Cells of GPC3/CD137×CD3 Tri-Specific Antibodies and Anti-GPC3/Dual-Fab Antibodies.

To investigate if both tri-specific antibody formats and anti-GPC3/Dual-Fab antibodies can result in cross-linking of hCD137 expressing cells to hCD3 expressing effector cells, 5.00E+03 hCD137 expressing CHO was co-cultured with 2.50E+04 NFAT-luc2 Jurkat cells for 24 hours in the presence of 0.1, 1 and 10 nM of tri-specific antibodies as described in Example (14-5). FIG. 38 showed no non-specific activation of Jurkat cells by all tri-specific antibodies when co-cultured with parental CHO cells. However, it was observed that both GPC3/CD137×CD3 and Ctrl/CD137×CD3 trispecific antibodies can activate Jurkat cells in the presence of hCD137 expressing CHO cells. Anti-GPC3/H183L072 antibodies did not result in activation of Jurkat cells when co-cultured with hCD137 expressing CHO cells. Anti-GPC3/H183L072 antibody with 10 nM showed about 0.96% Luminescense of that of GPC3/CD137×CD3 trispecific antibody with 10 nM and anti-GPC3/H183L072 antibody with 1 nM showed about 1.93% Luminescence of that of GPC3/CD137×CD3 trispecific antibody with 1 nM. When it compared with the CD3 activation against GPC3 positive cells evaluated in Example 14-5, about 1.36% or 1.89% Luminescence were detected against CD137 positive cells when 10 nM or 1 nM of anti-GPC3/H183L072 antibodies were used although GPC3/CD137×CD3 trispecific antibody with 10 and 1 nM showed about 127.77% and 107.22% Luminescence against CD137 positive cells compared to that against GPC3 positive cells respectively. Taken together, this suggests that tri-specific format anti-GPC3/CD137×CD3, which binds to CD3 and CD137 at the same time, can result in Jurkat cell activation against hCD137 expressing cells independent of target or tumor antigen binding, giving rise to off-target cytotoxicity unlike that of anti-GPC3/Dual-Fab format which does not bind to CD3 and CD137 at the same time. Those results shown in Example 13, 14-5 and 14-6 prove that only antibodies which does not bind to CD3 and CD137 at the same time can kill target antigen expressing cells specifically.

(14-7) Assessment of Off Target Cytokine Release of Ctrl/CD137×CD3 Tri-Specific Antibodies and Ctrl/Dual-Fab Antibodies from PBMCs Comparison of tri-specific antibody formats and Dual-Fab antibodies for off-target toxicity was also assessed using human PBMC solution. Briefly, 2.00E+05 PBMCs prepared as described in Example (12-2-1) were incubated with 80, 16 and 3.2 nM of tri-specific antibodies or Dual-Fab antibodies in the absence of target cells for 48 hours. IL-2, IFN gamma and TNF alpha in the supernatant was measured using cytokine release assay as described in Example (12-2-2). As shown in FIG. 39, Ctrl/CD137×CD3 trispecific antibodies but Ctrl/Dual-Fab antibodies can result in IL-2, IFN gamma and TNF alpha release from PBMCs. 80 nM Ctrl/Dual-Fab antibodies showed about 50% IL-2 concentration of that of 80 nM Ctrl/CD137×CD3 trispecific antibodies and less than 10% IL-2 concentration was observed when 16 nM antibodies were used. As for IFN gamma and TNF alpha, Ctrl/Dual-Fab antibodies showed less than 10% IL2 concentration of that with Ctrl/CD137×CD3 trispecific antibodies in each antibody concentration.

These results suggest that Ctrl/CD137×CD3 tri-specific format resulted in non-specific activation of PBMCs in the absence of target cells. Finally, the data showed that Dual-Fab format can confer target-specific effector cell activation without off-target toxicity.

REFERENCE EXAMPLES

[Reference Example 1] Preparation of Antibody Expression Vector and Expression and Purification of Antibody Amino acid substitution or IgG conversion was carried out by a method generally known to those skilled in the art using QuikChange Site-Directed Mutagenesis Kit (Stratagene Corp.), PCR, or In fusion Advantage PCR cloning kit (Takara Bio Inc.), etc., to construct expression vectors. The obtained expression vectors were sequenced by a method generally known to those skilled in the art. The prepared plasmids were transiently transferred to human embryonic kidney cancer cell-derived HEK293H line (Invitrogen Corp.) or FreeStyle 293 cells (Invitrogen Corp.) to express antibodies. Each antibody was purified from the obtained culture supernatant by a method generally known to those skilled in the art using rProtein A Sepharose™ Fast Flow (GE Healthcare Japan Corp.). As for the concentration of the purified antibody, the absorbance was measured at 280 nm using a spectrophotometer, and the antibody concentration was calculated by use of an extinction coefficient calculated from the obtained value by PACE (Protein Science 1995; 4: 2411-2423).

[Reference Example 2] Preparation of Anti-Human and Anti-Cynomolgus Monkey CD3 Epsilon Antibody CE115

(2-1) Preparation of Hybridoma Using Rat Immunized with Cell Expressing Human CD3 and Cell Expressing Cynomolgus Monkey CD3

Each SD rat (female, 6 weeks old at the start of immunization, Charles River Laboratories Japan, Inc.) was immunized with Ba/F3 cells expressing human CD3 epsilon gamma or cynomolgus monkey CD3 epsilon gamma as follows: at day 0 (the priming date was defined as day 0), $5\times10^7$ Ba/F3 cells expressing human CD3 epsilon gamma were intraperitoneally administered together with a Freund complete adjuvant (Difco Laboratories, Inc.) to the rat. At day 14, $5\times10^7$ Ba/F3 cells expressing cynomolgus monkey CD3 epsilon gamma were intraperitoneally administered thereto together with a Freund incomplete adjuvant (Difco Laboratories, Inc.). Then, $5\times10^7$ Ba/F3 cells expressing human CD3 epsilon gamma and Ba/F3 cells expressing cynomolgus monkey CD3 epsilon gamma were intraperitoneally administered thereto a total of four times every other week in an alternate manner. One week after (at day 49) the final administration of CD3 epsilon gamma, Ba/F3 cells expressing human CD3 epsilon gamma were intravenously administered thereto as a booster. Three days thereafter, the spleen cells of the rat were fused with mouse myeloma cells SP2/0 according to a routine method using PEG1500 (Roche Diagnostics K.K.). Fusion cells, i.e., hybridomas, were cultured in an RPMI1640 medium containing 10% FBS (hereinafter, referred to as 10% FBS/RPMI1640).

On the day after the fusion, (1) the fusion cells were suspended in a semi-fluid medium (Stemcell Technologies, Inc.). The hybridomas were selectively cultured and also colonized.

Nine or ten days after the fusion, hybridoma colonies were picked up and inoculated at 1 colony/well to a 96-well plate containing a HAT selective medium (10% FBS/RPMI1640, 2 vol % HAT 50× concentrate (Sumitomo Dainippon Pharma Co., Ltd.), and 5 vol % BM-Condimed H1 (Roche Diagnostics K.K.)). After 3- to 4-day culture, the culture supernatant in each well was recovered, and the rat IgG concentration in the culture supernatant was measured. The culture supernatant confirmed to contain rat IgG was screened for a clone producing an antibody specifically binding to human CD3 epsilon gamma by cell-ELISA using attached Ba/F3 cells expressing human CD3 epsilon gamma or attached Ba/F3 cells expressing no human CD3 epsilon gamma (FIG. 40). The clone was also evaluated for cross reactivity with monkey CD3 epsilon gamma by cell-ELISA using attached Ba/F3 cells expressing cynomolgus monkey CD3 epsilon gamma (FIG. 40).

(2-2) Preparation of Anti-Human and Anti-Monkey CD3 Epsilon Chimeric Antibody

Total RNA was extracted from each hybridoma cell using RNeasy Mini Kits (Qiagen N.V.), and cDNA was synthesized using SMART RACE cDNA Amplification Kit (BD Biosciences). The prepared cDNA was used in PCR to insert the antibody variable region gene to a cloning vector. The nucleotide sequence of each DNA fragment was determined using BigDye Terminator Cycle Sequencing Kit (Applied Biosystems, Inc.) and a DNA sequencer ABI PRISM 3700 DNA Sequencer (Applied Biosystems, Inc.) according to the method described in the instruction manual included therein. CDRs and FRs of the CE115 H chain variable domain (SEQ ID NO: 113) and the CE115 L chain variable domain (SEQ ID NO: 114) were determined according to the Kabat numbering.

A gene encoding a chimeric antibody H chain containing the rat antibody H chain variable domain linked to a human antibody IgG1 chain constant domain, and a gene encoding a chimeric antibody L chain containing the rat antibody L chain variable domain linked to a human antibody kappa chain constant domain were integrated to expression vectors for animal cells. The prepared expression vectors were used for the expression and purification of the CE115 chimeric antibody (Reference Example 1).

(2-3) Preparation of EGFR_ERY22_CE115

Next, IgG against a cancer antigen (EGFR) was used as a backbone to prepare a molecule in a form with one Fab replaced with CD3 epsilon-binding domains. In this operation, silent Fc having attenuated binding activity against FcgR (Fc gamma receptor) was used, as in the case mentioned above, as Fc of the backbone IgG. Cetuximab-VH (SEQ ID NO: 115) and Cetuximab-VL (SEQ ID NO: 116) constituting the variable region of cetuximab were used as EGFR-binding domains. G1d derived from IgG1 by the deletion of C-terminal Gly and Lys, A5 derived from G1d by the introduction of D356K and H435R mutations, and B3 derived from G1d by the introduction of a K439E mutation were used as antibody H chain constant domains and each combined with Cetuximab-VH to prepare Cetuximab-VH-G1d (SEQ ID NO: 117), Cetuximab-VH-A5 (SEQ ID NO: 118), and Cetuximab-VH-B3 (SEQ ID NO: 119) according to the method of Reference Example 1. When the antibody H chain constant domain was designated as H1, the sequence corresponding to the antibody H chain having Cetuximab-VH as a variable domain was represented by Cetuximab-VH-H1.

In this context, the alteration of an amino acid is represented by, for example, D356K. The first alphabet (which corresponds to D in D356K) means an alphabet that represents the one-letter code of the amino acid residue before the alteration. The number (which corresponds to 356 in D356K) following the alphabet means the EU numbering position of this altered residue. The last alphabet (which corresponds to K in D356K) means an alphabet that represents the one-letter code of an amino acid residue after the alteration.

EGFR_ERY22_CE115 (FIG. 41) was prepared by the exchange between the VH domain and the VL domain of Fab against EGFR. Specifically, a series of expression vectors having an insert of each polynucleotide encoding EGFR ERY22_Hk (SEQ ID NO: 120), EGFR ERY22_L (SEQ ID NO: 121), CE115_ERY22_Hh (SEQ ID NO: 122), or CE115_ERY22_L (SEQ ID NO: 123) was prepared by a method generally known to those skilled in the art, such as PCR, using primers with an appropriate sequence added in the same way as the aforementioned method.

The expression vectors were transferred in the following combination to FreeStyle 293-F cells where each molecule of interest was transiently expressed:

Molecule of interest: EGFR_ERY22_CE115

Polypeptides encoded by the polynucleotides inserted in the expression vectors: EGFR ERY22_Hk, EGFR ERY22_L, CE115_ERY22_Hh, and CE115_ERY22_L (2-4) Purification of EGFR_ERY22_CE115

The obtained culture supernatant was added to Anti FLAG M2 column (Sigma-Aldrich Corp.), and the column was washed, followed by elution with 0.1 mg/mL FLAG peptide (Sigma-Aldrich Corp.). The fraction containing the molecule of interest was added to HisTrap HP column (GE Healthcare Japan Corp.), and the column was washed, followed by elution with the concentration gradient of imidazole. The fraction containing the molecule of interest was concentrated by ultrafiltration. Then, this fraction was added to Superdex 200 column (GE Healthcare Japan Corp.). Only a monomer fraction was recovered from the eluate to obtain each purified molecule of interest.

(2-5) Measurement of Cytotoxic Activity Using Human Peripheral Blood Mononuclear Cell (2-5-1) Preparation of Human Peripheral Blood Mononuclear Cell (PBMC) Solution 50 mL of peripheral blood was collected from each healthy volunteer (adult) using a syringe pre-filled with 100 micro L of 1,000 units/mL of a heparin solution (Novo-Heparin 5,000 units for Injection, Novo Nordisk A/S). The peripheral blood was diluted 2-fold with PBS(−) and then divided into four equal parts, which were then added to Leucosep lymphocyte separation tubes (Cat. No. 227290, Greiner Bio-One GmbH) pre-filled with 15 mL of Ficoll-Paque PLUS and centrifuged in advance. After centrifugation (2,150 rpm, 10 minutes, room temperature) of the separation tubes, a mononuclear cell fraction layer was separated. The cells in the mononuclear cell fraction were washed once with Dulbecco's Modified Eagle's Medium containing 10% FBS (Sigma-Aldrich Corp.; hereinafter, referred to as 10% FBS/D-MEM). Then, the cells were adjusted to a cell density of $4\times10^6$ cells/mL with 10% FBS/D-MEM. The cell solution thus prepared was used as a human PBMC solution in the subsequent test.

(2-5-2) Measurement of Cytotoxic Activity

The cytotoxic activity was evaluated on the basis of the rate of cell growth inhibition using xCELLigence real-time cell analyzer (Roche Diagnostics). The target cells used were an SK-pca13a cell line established by forcing an SK-HEP-1 cell line to express human EGFR. SK-pca13a was dissociated from the dish and inoculated at 100 micro L/well ($1\times10^4$ cells/well) to an E-Plate 96 plate (Roche Diagnostics) to start the assay of live cells using the xCELLigence real-time cell analyzer. On the next day, the plate was taken out of the xCELLigence real-time cell analyzer, and 50 micro L of each antibody adjusted to each concentration (0.004, 0.04, 0.4, and 4 nM) was added to the plate. After reaction at room temperature for 15 minutes, 50 micro L ($2\times10^5$ cells/well) of the human PBMC solution prepared in the preceding paragraph (2-5-1) was added thereto. This plate was reloaded to the xCELLigence real-time cell analyzer to start the assay of live cells. The reaction was carried out under conditions of 5% $CO_2$ and 37 degrees C. 72 hours after the addition of human PBMC. The rate of cell growth inhibition (%) was determined from the cell index value according to the expression given below. A numeric value after normalization against the cell index value immediately before the addition of the antibody defined as 1 was used as the cell index value in this calculation.

Rate of cell growth inhibition (%)=$(A-B)\times100/(A-1)$, wherein

A represents the average cell index value of wells non-supplemented with the antibody (only the target cells and human PBMC), and B represents the average cell index value of the wells supplemented with each antibody. The test was conducted in triplicate.

The cytotoxic activity of EGFR_ERY22_CE115 containing CE115 was measured with PBMC prepared from human blood as effector cells. As a result, very strong activity was confirmed (FIG. 42).

[Reference Example 3] Antibody Alteration for Preparation of Antibody Binding to CD3 and Second Antigen (3-1) Study on Insertion Site and Length of Peptide Capable of Binding to Second Antigen A study was conducted to obtain a dual binding Fab molecule capable of binding to a cancer antigen through one variable region (Fab) and binding to the first antigen CD3 and the second antigen through the other variable region, but not capable of binding to CD3 and the second antigen at the same time. A GGS peptide was inserted to the heavy chain loop of the CD3 epsilon-binding antibody CE115 to prepare each heterodimerized antibody having EGFR-binding domains in one Fab and CD3-binding domains in the other Fab according to Reference Example 1.

Specifically, EGFR ERY22_Hk/EGFR ERY22_L/ CE115_CE31 ERY22_Hh/CE115_ERY22_L ((SEQ ID NO: 120/121/124/123) with GGS inserted between K52B and S52c in CDR2, EGFR ERY22_Hk/EGFR ERY22_L/ CE115_CE32 ERY22_Hh/CE115_ERY22_L ((SEQ ID NO: 120/121/125/123) with a GGSGGS peptide (SEQ ID NO: 126) inserted at this position, and EGFR ERY22_Hk/EGFR ERY22_L/CE115_CE33 ERY22_Hh/CE115_ERY22_L ((SEQ ID NO: 120/121/127/123) with a GGSGGSGGS peptide (SEQ ID NO: 128) inserted at this position were prepared. Likewise, EGFR ERY22_Hk/EGFR ERY22_L/CE115_CE34 ERY22_Hh/CE115_ERY22_L ((SEQ ID NO: 120/121/129/123) with GGS inserted between D72 and D73 (loop) in FR3, EGFR ERY22_Hk/EGFR ERY22_L/CE115_CE35 ERY22_Hh/CE115_ERY22_L ((SEQ ID NO: 120/121/130/123) with a GGSGGS peptide (SEQ ID NO: 126) inserted at this position, and EGFR ERY22_Hk/EGFR ERY22_L/CE115_CE36 ERY22_Hh/CE115_ERY22_L ((SEQ ID NO: 120/121/131/123) with a GGSGGSGGS peptide (SEQ ID NO: 128) inserted at this position were prepared. In addition, EGFR ERY22_Hk/EGFR ERY22_L/CE115_CE37 ERY22_Hh/CE115_ERY22_L ((SEQ ID NO: 120/121/132/123) with GGS inserted between A99 and Y100 in CDR3, EGFR ERY22_Hk/EGFR ERY22_L/CE115_CE38 ERY22_Hh/CE115_ERY22_L ((SEQ ID NO: 120/121/133/123) with a GGSGGS peptide inserted at this position, and EGFR ERY22_Hk/EGFR ERY22_L/CE115_CE39 ERY22_Hh/CE115_ERY22_L ((SEQ ID NO: 120/121/134/123) with a GGSGGSGGS peptide inserted at this position were prepared.

(3-2) Confirmation of Binding of GGS Peptide-Inserted CE115 Antibody to CD3 Epsilon The binding activity of each prepared antibody against CD3 epsilon was confirmed using Biacore T100. A biotinylated CD3 epsilon epitope peptide was immobilized to a CM5 chip via streptavidin, and the prepared antibody was injected thereto as an analyte and analyzed for its binding affinity.

The results are shown in Table 27. The binding affinity of CE35, CE36, CE37, CE38, and CE39 for CD3 epsilon was equivalent to the parent antibody CE115. This indicated that a peptide binding to the second antigen can be inserted into their loops. The binding affinity was not reduced in GGSGGSGGS-inserted CE36 or CE39. This indicated that the insertion of a peptide up to at least 9 amino acids to these sites does not influence the binding activity against CD3 epsilon.

TABLE 27

| Sample | ka | kd | KD | Insertion position | Linker |
|---|---|---|---|---|---|
| CE115_M | 1.5E+05 | 9.8E−03 | 6.7E−08 | | |
| CE31 | 2.3E+05 | 3.5E−02 | 1.5E−07 | K52b-S52c | GS3 |
| GE32 | 8.5E+04 | 1.8E−02 | 2.1E−07 | K52b-S52c | GS6 |
| CE33 | 4.9E+05 | 1.1E−01 | 2.3E−07 | K52b-S52c | GS9 |
| CE34 | 1.1E+05 | 1.3E−02 | 1.2E−07 | D72-D73 | GS3 |
| CE35 | 1.3E+05 | 1.1E−02 | 8.7E−08 | D72-D73 | GS6 |
| CE36 | 1.2E+05 | 1.2E−02 | 9.9E−08 | D72-D73 | GS9 |
| CE37 | 2.2E+05 | 2.0E−02 | 9.4E−08 | A99-Y100 | GS3 |
| CE38 | 2.0E+05 | 1.7E−02 | 8.7E−08 | A99-Y100 | GS6 |
| CE39 | 1.6E+05 | 1.4E−02 | 9.1E−08 | A99-Y100 | GS9 |

These results indicated that the antibody capable of binding to CD3 and the second antigen, but does not bind to these antigens at the same time can be prepared by obtaining an antibody binding to the second antigen using such peptide-inserted CE115.

In this context, a library can be prepared by altering at random the amino acid sequence of the peptide for use in insertion or substitution according to a method known in the art such as site-directed mutagenesis (Kunkel et al., Proc. Natl. Acad. Sci. U.S.A. (1985) 82, 488-492) or overlap extension PCR, and comparing the binding activity, etc., of each altered form according to the aforementioned method to determine an insertion or substitution site that permits exertion of the activity of interest even after alteration of the amino acid sequence, and the types and length of amino acids of this site.

[Reference Example 4] Library Design for Obtaining Antibody Binding to CD3 and Second Antigen (4-1) Antibody Library for Obtaining Antibody Binding to CD3 and Second Antigen (Also Referred to as Dual Fab Library)

In the case of selecting CD3 (CD3 epsilon) as the first antigen, examples of a method for obtaining an antibody binding to CD3 (CD3 epsilon) and an arbitrary second antigen include the following 6 methods:

1. a method which involves inserting a peptide or a polypeptide binding to the second antigen to a Fab domain binding to the first antigen (this method includes the peptide insertion shown in Example 3 or 4 in WO2016076345A1 as well as a G-CSF insertion method illustrated in Angew Chem Int Ed Engl. 2013 Aug. 5; 52 (32): 8295-8), wherein the binding peptide or polypeptide may be obtained from a peptide- or polypeptide-displaying library, or the whole or a portion of a naturally occurring protein may be used;

2. a method which involves preparing an antibody library such that various amino acids appear positions that permit alteration to a larger length (extension) of Fab loops as shown in Example 5 in WO2016076345A1, and obtaining Fab having binding activity against an arbitrary second antigen from the antibody library by using the binding activity against the antigen as an index;

3. a method which involves identifying amino acids that maintain binding activity against CD3 by use of an antibody prepared by site-directed mutagenesis from a Fab domain previously known to bind to CD3, and obtaining Fab having binding activity against an arbitrary second antigen from an antibody library in which the identified amino acids appear by using the binding activity against the antigen as an index;

4. the method 3 which further involves preparing an antibody library such that various amino acids appear positions that permit alteration to a larger length (extension) of Fab loops, and obtaining Fab having binding activity against an arbitrary second antigen from the antibody library by using the binding activity against the antigen as an index;

5. the method 1, 2, 3, or 4 which further involves altering the antibodies such that glycosylation sequences (e.g., NxS and NxT wherein x is an amino acid other than P) appear to add thereto sugar chains that are recognized by sugar chain receptors (e.g., high-mannose-type sugar chains are added thereto and thereby recognized by high-mannose receptors; it is known that the high-mannose-type sugar chains are obtained by the addition of kifunensine at the time of antibody expression (mAbs. 2012 July-August; 4 (4): 475-87)); and 6. the method 1, 2, 3, or 4 which further involves adding thereto domains (polypeptides, sugar chains, and nucleic acids typified by TLR agonists) each binding to the second antigen through a covalent bond by inserting Cys, Lys, or a non-natural amino acid to loops or sites found to be alterable to various amino acids or substituting these sites with Cys, Lys, or a non-natural amino acid (this method is typified by antibody drug conjugates and is a method for conjugation to Cys, Lys, or a non-natural amino acid through a covalent bond (described in mAbs 6: 1, 34-45; January/February 2014; WO2009/134891 A2; and Bioconjug Chem. 2014 Feb. 19; 25 (2): 351-61)). The dual binding Fab that binds to the first antigen and the second antigen, but does not bind to these antigens at the same time is obtained by use of any of these methods, and can be combined with domains (referred to as the other variable region, which is described in Example 1) binding to an arbitrary third antigen by a method generally known to those skilled in the art, for example, common L chains, CrossMab, or Fab arm exchange.

(4-2) Preparation of One-Amino Acid Alteration Antibody of CD3 (CD3 Epsilon)-Binding Antibody Using Site-Directed Mutagenesis A VH domain CE115HA000 (SEQ ID NO: 135) and a VL domain GLS3000 (SEQ ID NO: 136) were selected as template sequences for a CD3 (CD3 epsilon)-binding antibody. Each domain was subjected to amino acid alteration at a site presumed to participate in antigen binding according to Reference Example 1. Also, pE22Hh (sequence derived from natural IgG1 CH1 and subsequent sequences by the alteration of L234A, L235A, N297A, D356C, T366S, L368A, and Y407V, the deletion of a C-terminal GK sequence, and the addition of a DYKDDDDK sequence (SEQ ID NO: 161); SEQ ID NO: 137) was used as an H chain constant domain, and a kappa chain (SEQ ID NO: 138) was used as an L chain constant domain. The alteration sites are shown in Table 28. For CD3 (CD3 epsilon)-binding activity evaluation, each one-amino acid alteration antibody was obtained as a one-arm antibody (naturally occurring IgG antibody lacking one of the Fab domains). Specifically, in the case of H chain alteration, the altered H chain linked to the constant domain pE22Hh, and Kn010G3 (naturally occurring IgG1 amino acid sequence from position 216 to the C terminus having C220S, Y349C, T366W, and H435R alterations; SEQ ID NO: 139) were used as H chains, and GLS3000 linked at the 3' side to the kappa chain was used as an L chain. In the case of L chain alteration, the altered L chain linked at the 3' side to the kappa chain was used as an L chain, and CE115HA000 linked at the 3' side to pE22Hh, and Kn010G3 were used as H chains. These sequences were expressed and purified in FreeStyle 293 cells (which employed the method of Reference Example 1).

TABLE 28

H chain alteration site

| Domain | FR1 | | | | | CDR1 | | | FR2 | | | | | CDR2 | | | | | |
|---|---|---|---|---|---|---|---|---|---|---|---|---|---|---|---|---|---|---|---|
| Kabat numbering | 11 | 16 | 19 | 28 | 29 | 30 | 31 | 32 | 33 | 35 | 43 | 50 | 51 | 52 | 52a | 52b | 52c | 53 | 54 | 55 |
| Amino acid before substitution | V | R | R | T | F | S | N | A | W | H | K | Q | I | K | A | K | S | N | N | Y |

| Domain | CDR2 | | | | | | | | |
|---|---|---|---|---|---|---|---|---|---|
| Kabat numbering | 56 | 57 | 58 | 59 | 60 | 61 | 62 | 64 | 65 |
| Amino acid before substitution | A | T | Y | Y | A | E | S | K | G |

| Domain | FR3 | | | | | | | | CDR3 | | | | | | | | | FR4 |
|---|---|---|---|---|---|---|---|---|---|---|---|---|---|---|---|---|---|---|
| Kabat numbering | 72 | 73 | 74 | 75 | 76 | 77 | 78 | 82a | 95 | 96 | 97 | 98 | 99 | 100 | 100a | 100b | 100c | 101 | 102 | 105 |
| Amino acid before substitution | D | D | S | K | N | S | L | N | V | H | Y | G | A | Y | Y | G | V | D | A | Q |

L chain alteration site

| Domain | CDR1 | | | | | | | | | | | | | FR2 | |
|---|---|---|---|---|---|---|---|---|---|---|---|---|---|---|---|
| Kabat numbering | 24 | 25 | 26 | 27 | 27a | 27b | 27c | 27d | 27e | 28 | 29 | 30 | 31 | 32 | 33 | 34 | 35 |
| Amino acid before substitution | R | S | S | Q | S | L | V | H | S | N | R | N | T | Y | L | H | Q |

| Domain | CDR2 | | | | | | FR3 | | CDR3 | | | | | | FR4 | |
|---|---|---|---|---|---|---|---|---|---|---|---|---|---|---|---|---|
| Kabat numbering | 50 | 51 | 52 | 53 | 54 | 55 | 56 | 74 | 77 | 89 | 90 | 91 | 92 | 93 | 94 | 95 | 96 | 97 | 107 |
| Amino acid before substitution | K | V | S | N | R | F | S | K | R | G | Q | G | T | Q | V | P | Y | T | K |

(4-3) Evaluation of Binding of One-Amino Acid Alteration Antibody to CD3

Each one-amino acid altered form constructed, expressed, and purified in the paragraph (Reference Example 4-2) was evaluated using Biacore T200 (GE Healthcare Japan Corp.). An appropriate amount of CD3 epsilon homodimer protein was immobilized onto Sensor chip CM4 (GE Healthcare Japan Corp.) by the amine coupling method. Then, the antibody having an appropriate concentration was injected thereto as an analyte and allowed to interact with the CD3 epsilon homodimer protein on the sensor chip. Then, the sensor chip was regenerated by the injection of 10 mmol/L glycine-HCl (pH 1.5). The assay was conducted at 25 degrees C., and HBS-EP+ (GE Healthcare Japan Corp.) was used as a running buffer. From the assay results, the dissociation constant $K_D$ (M) was calculated using single-cycle kinetics model (1:1 binding RI=0) for the amount bound and the sensorgram obtained in the assay. Each parameter was calculated using Biacore T200 Evaluation Software (GE Healthcare Japan Corp.).

(4-3-1) Alteration of H Chain

Table 29 shows the results of the ratio of the amount of each H chain altered form bound to the amount of the corresponding unaltered antibody CE115HA000 bound. Specifically, when the amount of the antibody comprising CE115HA000 bound was defined as X and the amount of the H chain one-amino acid altered form bound was defined as Y, a value of Z (ratio of amounts bound)=Y/X was used. As shown in FIG. 43, a very small amount bound was observed in the sensorgram for Z of less than 0.8, suggesting the possibility that the dissociation constant $K_D$ (M) cannot be calculated correctly. Table 30 shows the dissociation constant $K_D$ (M) ratio of each H chain altered form to CE115HA000 (=KD value of CE115HA000/KD value of the altered form).

When Z shown in Table 29 is 0.8 or more, the altered form is considered to maintain the binding relative to the corresponding unaltered antibody CE15HA000. Therefore, an antibody library designed such that these amino acids appear can serve as a dual Fab library.

TABLE 29

| | Domain | | | | | | | | | | | | | | | | |
|---|---|---|---|---|---|---|---|---|---|---|---|---|---|---|---|---|---|
| | FR1 | | | | | | CDR1 | | | FR2 | | | CDR2 | | | | |
| | Kabat numbering | | | | | | | | | | | | | | | | |
| | 11 | 16 | 19 | 28 | 29 | 30 | 31 | 32 | 33 | 35 | 43 | 50 | 51 | 52 | 52a | 52b | 52c |
| | Amino acid before substitution (wt) | | | | | | | | | | | | | | | | |
| | V | R | R | T | F | S | N | A | W | H | K | Q | I | K | A | K | S |
| A | | | | | | | 0.5 | | 0.1 | 0.17 | | 0.24 | | | | 0.67 | 0.96 |
| D | | | 0.56 | | | 0.86 | 0.37 | | 0.1 | 0.2 | | 0.27 | 0.29 | 0.25 | 1.34 | 0.27 | 0.6 |
| E | | 0.88 | | | | | | | | 0.19 | 0.9 | 0.26 | 0.55 | 0.26 | 0.57 | | |
| F | | | | | | | 0.62 | | 0.65 | 0.21 | | | | 0.17 | | | 1.13 |
| G | | | | | 1.01 | | 0.39 | | | 0.22 | | | | | 0.81 | | 0.97 |
| H | | | | | | | 0.68 | | 0.13 | | | | | 0.22 | | | |
| I | | | | | | | 0.81 | | | 0.12 | | 0.4 | | 0.33 | | | |
| K | | | | | | | 1.01 | | | 0.15 | | 0.33 | | | | | 1.19 |
| L | 1 | | | | | | | | 0.1 | 0.11 | | 0.23 | | | | 0.61 | 0.98 |
| M | | | | | | | | | | 0.29 | | | | | | | |
| N | | | | | | | | | | 0.35 | | 0.17 | | 0.34 | | 0.27 | |
| P | | | | | | | | | | | | | | | 0.15 | | |
| Q | | 0.9 | | | | | 0.49 | | | 0.13 | 0.99 | | | | | 0.6 | 1.04 |
| R | | | | | | | 1.14 | | | 0.14 | | | | 0.91 | | 1.11 | |
| S | | | | 0.91 | | | 0.81 | | | 0.23 | | 0.24 | | 0.28 | 1.05 | 0.68 | |
| T | | | 0.8 | | | | | | | 0.26 | | | | | | | |
| V | | | | | 0.36 | | | | | 0.22 | | | | 0.52 | | | 0.93 |
| W | | | | | | | 0.63 | | | 0.22 | | | 0.22 | | | | |
| Y | | | | | | | 0.64 | 0.33 | 0.66 | 0.16 | | 0.25 | | 0.18 | 0.31 | 0.74 | 1.11 |

| | Domain | | | | | | | | | | | | | | | |
|---|---|---|---|---|---|---|---|---|---|---|---|---|---|---|---|---|
| | CDR2 | | | | | | | | | | | | FR3 | | | |
| | Kabat numbering | | | | | | | | | | | | | | | |
| | 53 | 54 | 55 | 56 | 57 | 58 | 59 | 60 | 61 | 62 | 64 | 65 | 72 | 73 | 74 | 75 | 76 |
| | Amino acid before substitution (wt) | | | | | | | | | | | | | | | |
| | N | N | Y | A | T | Y | Y | A | E | S | K | G | D | D | S | K | N |
| A | 0.7 | 0.85 | | | 0.98 | 0.22 | 0.85 | | 1.09 | | 0.82 | | 1.41 | 0.83 | 1.05 | | |
| D | 0.39 | 0.62 | 0.45 | 0.51 | | 0.11 | 0.7 | 0.99 | 0.91 | 0.92 | 0.72 | 0.76 | | | | | |
| E | | | | | | | 0.66 | 0.94 | | 0.92 | 0.74 | 0.78 | 1.05 | 0.73 | | | |
| F | | 1.12 | | | | | | | | | | | | | | | |
| G | 0.5 | 0.98 | 0.55 | 0.61 | | | | | | | | | | 1.07 | | | |
| H | 0.76 | | | | | | | | | | | | | | | | |
| I | 0.68 | | | 0.61 | | | | | | | | | | | | | |
| K | 0.78 | 1.2 | | 1.35 | 1.32 | 0.3 | | | | 1.19 | | | | 0.87 | | | |
| L | | 0.94 | | 0.8 | | 0.27 | | | | | | | | | | | |
| M | | | | | | | | | | | | | | | | | |
| N | | | | 0.87 | 0.97 | 0.33 | | | | | | | | 0.94 | | | |
| P | | | | | | | | 1.07 | 1 | | | | | 0.91 | | | |
| Q | 1.1 | 0.84 | | 0.76 | | 0.19 | | | 1.07 | | 0.89 | | | | | | |
| R | | | | | | | | | | | | | | 1.04 | | 1.01 | |

TABLE 29-continued

| | | | | | | | | | | | | | | |
|---|---|---|---|---|---|---|---|---|---|---|---|---|---|---|
| S | 0.83 | 0.84 | 0.26 | | 0.18 | 0.94 | | 0.84 | | | | | | 0.92 |
| T | | | | | | | | | | | 0.63 | 0.84 | | |
| V | | | | | | | | | | 1.43 | | | | |
| W | 0.88 | | | | | | | | | | | | | |
| Y | 0.63 | 1.09 | | 0.66 | | | | | | | | | | |

| Domain | | | | | | | | | | | | | | |
|---|---|---|---|---|---|---|---|---|---|---|---|---|---|---|
| FR3 | | | CDR3 | | | | | | | | | | | FR4 |
| | | | | | | Kabat numbering | | | | | | | | |
| 77 | 78 | 82a | 95 | 96 | 97 | 98 | 99 | 100 | 100a | 100b | 100c | 101 | 102 | 105 |
| | | | | | | Amino acid before substitution (wt) | | | | | | | | |
| S | L | N | V | H | Y | G | A | Y | Y | G | V | D | A | Q |

| | 77 | 78 | 82a | 95 | 96 | 97 | 98 | 99 | 100 | 100a | 100b | 100c | 101 | 102 | 105 |
|---|---|---|---|---|---|---|---|---|---|---|---|---|---|---|---|
| A | | | | | 0.11 | 0.35 | 0.16 | 1.1 | | 0.9 | 0.62 | | 1.26 | | |
| D | | | 0.73 | 0.24 | 0.09 | 0.24 | 0.26 | 0.28 | 0.52 | 0.31 | 0.27 | 0.44 | | | |
| E | | | | 0.24 | | | | | | | 0.26 | 0.46 | | | 0.94 |
| F | | | | | | | | 1.43 | | 0.87 | 0.3 | | 0.75 | | |
| G | | | | 0.19 | 0.43 | 0.18 | | | 1.07 | 1.23 | | | 1.38 | | |
| H | | | | | | | 1.58 | | | | | | 1.21 | | |
| I | | 1.34 | | | | | | | | | | | 1.18 | 1.48 | |
| K | | | | 0.64 | 0.35 | | 2.83 | 1.48 | 1.07 | 0.9 | | | 0.63 | | |
| L | | | | | 0.14 | | | 1.13 | 0.7 | 0.48 | | 0.27 | 0.62 | | |
| M | | | | | | | | | | | | | 1.2 | | |
| N | | | | | | | | | | | | | 2.02 | | |
| P | | | | 0.12 | 0.11 | 1.02 | | 0.48 | | | | 0.2 | 0.2 | 0.14 | |
| Q | | | | 0.42 | | | 1.22 | 0.91 | 0.8 | 0.56 | | | 2.35 | | |
| R | | | | 0.46 | 0.27 | 2.96 | | | | | | | 0.24 | | |
| S | | | 0.22 | 0.44 | 0.18 | 1.01 | 0.82 | 0.81 | 0.64 | 0.52 | | | 1.16 | | |
| T | 0.9 | | | | | | 1.05 | 0.84 | | | | | 0.79 | | |
| V | | | | | | | | | 0.6 | | | | 1.33 | 1.43 | |
| W | | | | | | | | 1.03 | | | | | | | |
| Y | | | | | 0.17 | 2.22 | 1.59 | | | | 0.23 | | 0.49 | 0.91 | |

TABLE 30

| Domain | | | | | | | | | | | | | |
|---|---|---|---|---|---|---|---|---|---|---|---|---|---|
| FR1 | | | | | | CDR1 | | | | FR2 | | CDR2 | |
| | | | | | | Kabat numbering | | | | | | | |
| 11 | 16 | 19 | 28 | 29 | 30 | 31 | 32 | 33 | 35 | 43 | 50 | | 51 |
| | | | | | | Amino acid before substitution (wt) | | | | | | | |
| V | R | R | T | F | S | N | A | W | H | K | Q | | I |

| | 11 | 16 | 19 | 28 | 29 | 30 | 31 | 32 | 33 | 35 | 43 | 50 | 51 |
|---|---|---|---|---|---|---|---|---|---|---|---|---|---|
| A | | | | | | | 0.96 | | 29.99 | 25.04 | | 22.63 | |
| D | | | | 0.93 | | 0.79 | 1.14 | | 1693.03 | 68.99 | | 75.37 | 6.37 |
| E | | 0.74 | | | | | | | | 70.35 | 0.88 | 16738.09 | 0.84 |
| F | | | | | | | 1.24 | | 0.66 | 53.59 | | | |
| G | | | | | | 0.93 | 1.37 | | | 45.77 | | | |
| H | | | | | | | 0.96 | | 4.96 | | | | |
| I | | | | | | | 0.62 | | | 7.23 | | 1.21 | |
| K | | | | | | | 0.97 | | | 14.45 | | 0.71 | |
| L | 0.83 | | | | | | | | 56573.23 | 4.8 | | 1.41 | |
| M | | | | | | | | | | 3.98 | | | |
| N | | | | | | | | | | 2.88 | | 1.48 | |
| P | | | | | | | | | | | | | |
| Q | | 0.87 | | | | | 0.94 | | | 4.8 | 0.89 | | |
| R | | | | | | | 0.98 | | | 15429.77 | | | |
| S | | | | 0.79 | | | 0.67 | | | 2.93 | | 47.38 | |
| T | | | 0.81 | | | | | | | 4.4 | | | |
| V | | | | | 2.94 | | | | | 28.08 | | | |
| W | | | | | | | 1.07 | | | 50.42 | | | |
| Y | | | | | | | 1.1 | 2.11 | 0.69 | 119458.13 | | 49.09 | |

TABLE 30-continued

| Domain | | | | | | | | | | | | |
|---|---|---|---|---|---|---|---|---|---|---|---|---|
| CDR2 Kabat numbering | | | | | | | | | | | | |
| 52 | 52a | 52b | 52c | 53 | 54 | 55 | 56 | 57 | 58 | 59 | 60 | 61 |
| Amino acid before substitution (wt) | | | | | | | | | | | | |
| K | A | K | S | N | N | Y | A | T | Y | Y | A | E |

| | 52 | 52a | 52b | 52c | 53 | 54 | 55 | 56 | 57 | 58 | 59 | 60 | 61 |
|---|---|---|---|---|---|---|---|---|---|---|---|---|---|
| A | | | 0.58 | 0.67 | 0.55 | 0.58 | | | 0.87 | 1.06 | 0.74 | | 0.94 |
| D | 166.47 | 1.35 | 0.56 | 0.55 | 0.55 | 0.59 | 0.89 | 0.71 | | 4.81 | 0.66 | 0.94 | 0.9 |
| E | 19.38 | 0.89 | | | | | | | | | 0.61 | 0.88 | |
| F | 4.04 | | | 0.93 | | 0.97 | | | | | | | |
| G | | 0.61 | | 0.81 | 0.95 | 0.84 | 0.99 | 0.59 | | | | | |
| H | 2.65 | | | | 0.55 | | | | | | | | |
| I | 3.54 | | | | 0.57 | | | | 0.81 | | | | |
| K | | | | 0.88 | 0.79 | 0.82 | | | 1.32 | 1.22 | 0.66 | | |
| L | | | 0.61 | 0.94 | | 0.91 | | | 0.77 | 1.21 | | | |
| M | | | | | | | | | | | | | |
| N | 3.29 | | 0.43 | | | | | | 0.84 | 0.9 | 1.86 | | |
| P | | 5 | | | | | | | | | | | 0.82 |
| Q | | | 0.62 | 0.97 | 1.05 | 0.8 | | | 0.74 | 1.24 | | | 0.85 |
| R | 0.8 | | 0.91 | | | | | | | | | | |
| S | 92.1 | 0.82 | 0.58 | | 0.59 | 0.57 | 5.65 | | | 1.22 | 0.79 | | |
| T | | | | | | | | | | | | | |
| V | | 0.95 | | 0.82 | | | | | | | | | |
| W | 2.69 | | | | 0.69 | | | | | | | | |
| Y | 6.47 | 7.71 | 0.61 | 0.87 | 0.94 | 1.03 | | 0.63 | | | | | |

| Domain | | | | | | | | | | | | |
|---|---|---|---|---|---|---|---|---|---|---|---|---|
| CDR2 | | | FR3 Kabat numbering | | | | | | | | CDR3 | |
| 62 | 64 | 65 | 72 | 73 | 74 | 75 | 76 | 77 | 78 | 82a | 95 | 96 |
| Amino acid before substitution (wt) | | | | | | | | | | | | |
| S | K | G | D | D | S | K | N | S | L | N | V | H |

| | 62 | 64 | 65 | 72 | 73 | 74 | 75 | 76 | 77 | 78 | 82a | 95 | 96 |
|---|---|---|---|---|---|---|---|---|---|---|---|---|---|
| A | | 0.81 | | 1.19 | 0.73 | 0.77 | | | | | | 3.15 | 1 |
| D | 0.87 | 0.76 | 0.61 | | | | | | | | 0.56 | 108.01 | 7.27 |
| E | 0.82 | 0.84 | 0.61 | 0.73 | 0.56 | | | | | | | 50.46 | |
| F | | | | | | | | | | | | | |
| G | | | | | 0.78 | | | | | | | 78256.33 | 0.8 |
| H | | | | | | | | | | | | | |
| I | | | | | | | | | | 1.08 | | | |
| K | 0.99 | | | | 0.74 | | | | | | | 1.15 | 1.56 |
| L | | | | | | | | | | | | | 3.14 |
| M | | | | | | | | | | | | | |
| N | | | | 0.7 | | | | | | | | | |
| P | 0.77 | | | | 0.7 | | | | | | | | 87044.4 |
| Q | | 0.87 | | | | | | | | | | | 1.36 |
| R | | | | 0.79 | | 0.88 | | | | | | | 1.59 |
| S | | 0.85 | | | | | 0.84 | | | | | 4.61 | 1.15 |
| T | | | | 0.78 | | 0.75 | | 0.83 | | | | | |
| V | | | | 1.17 | | | | | | | | | |
| W | | | | | | | | | | | | | |
| Y | | | | | | | | | | | | | 6.67 |

| Domain | | | | | | | | | | |
|---|---|---|---|---|---|---|---|---|---|---|
| CDR3 Kabat numbering | | | | | | | | | | FR4 |
| 97 | 98 | 99 | 100 | 100a | 100b | 100c | 101 | 102 | 105 | |
| Amino acid before substitution (wt) | | | | | | | | | | |
| Y | G | A | Y | Y | G | V | D | A | Q | |

| | 97 | 98 | 99 | 100 | 100a | 100b | 100c | 101 | 102 | 105 |
|---|---|---|---|---|---|---|---|---|---|---|
| A | 41309 | 0.98 | | 0.92 | 0.66 | | | 0.86 | | |
| D | 64.7 | 2.36 | 1.03 | 0.63 | 1.2 | 6.25 | 1.64 | | | |
| E | | | | | | 7.29 | 1.31 | | | 0.89 |
| F | | | 1.15 | | 0.98 | 4.37 | | 0.73 | | |
| G | 47213 | | | 0.97 | 1.01 | | | 3.16 | | |
| H | | 1.14 | | | | | | 0.91 | | |
| I | | | | | | | | 1.73 | 1.29 | |
| K | | 4.85 | 1.4 | 0.93 | 0.79 | | | 4.37 | | |
| L | | | 1 | 0.67 | 0.57 | 5.84 | | 0.71 | | |
| M | | | | | | | | 1.94 | | |

TABLE 30-continued

| | | | | | | | | | | |
|---|---|---|---|---|---|---|---|---|---|---|
| N | | | | | | | | 2.28 | | |
| P | 12429 | 0.88 | | 1.3 | | | 0.97 | 43.42 | 3.51 | |
| Q | | 1.04 | 0.85 | 0.77 | 0.51 | | | 3.55 | | |
| R | 23180 | 4.69 | | | | | | 5.66 | | |
| S | 1178 | 0.98 | 0.76 | 0.7 | 0.59 | 1.25 | | 0.91 | | |
| T | | 0.93 | 0.93 | | | | | 0.62 | | |
| V | | | | 0.92 | | | | 1.18 | 1.27 | |
| W | | | | 0.96 | | | | | | |
| Y | | 2.75 | 1.25 | | | 51.41 | | 0.97 | 1 | |

Table 31 shows the results of the ratio of the amount of each L chain altered form bound to the amount of the corresponding unaltered antibody GLS3000 bound. Specifically, when the amount of the GLS3000-containing antibody bound was defined as X and the amount of the L chain one-amino acid altered form bound was defined as Y, a value of Z (ratio of amounts bound)=Y/X was used. As shown in FIG. 43, a very small amount bound was observed in the sensorgram for Z of less than 0.8, suggesting the possibility that the dissociation constant $K_D$ (M) cannot be calculated correctly. Table 32 shows the dissociation constant $K_D$ (M) ratio of each L chain altered form to GLS3000.

When Z shown in Table 31 is 0.8 or more, the altered form is considered to maintain the binding relative to the corresponding unaltered antibody GLS3000. Therefore, an antibody library designed such that these amino acids appear can serve as a dual Fab library.

TABLE 31

| Domain | | | | | | | | | | | |
|---|---|---|---|---|---|---|---|---|---|---|---|
| CDR1 | | | | | | | | | | | |
| Kabat numbering | | | | | | | | | | | |
| | 24 | 25 | 26 | 27 | 27a | 27b | 27c | 27d | 27e | 28 | 29 | 30 |
| Amino acid before substitution | | | | | | | | | | | |
| | R | S | S | Q | S | L | V | H | S | N | R | N |
| A | 0.86 | 0.92 | | | | | | 0.48 | 1.03 | 0.25 | 0.63 | 0.5 |
| D | 0.75 | 0.18 | 0.86 | 0.85 | 0.79 | 0.17 | 0.32 | 0.22 | 0.69 | 0.19 | 0.41 | 0.34 |
| E | 0.83 | 0.21 | 0.74 | 0.88 | 0.81 | 0.17 | 0.61 | 0.23 | 0.76 | 0.4 | | 0.44 |
| F | | | | | | 0.42 | | 0.63 | 1.32 | 0.46 | | 1.1 |
| G | 0.89 | | | | 1.03 | | | 0.3 | 1.04 | 0.46 | 0.67 | 0.47 |
| H | | | | | | | | | 1.23 | 0.42 | | 0.98 |
| I | | 0.53 | | | 1 | 1.19 | 0.96 | 0.26 | 1.07 | 0.44 | 0.37 | 0.61 |
| K | | | | | | | | 0.29 | 1.59 | 0.44 | | 1.65 |
| L | | 0.24 | | 0.92 | | | 0.84 | 0.3 | 1.17 | 0.39 | 0.56 | 0.7 |
| M | | 0.31 | | | | 0.71 | | 0.3 | 1.23 | 0.39 | | 0.8 |
| N | | | | | 1.1 | | | 0.3 | 1.16 | | | |
| P | 0.7 | 1.01 | 0.78 | 0.29 | 0.99 | 0.91 | 0.3 | 0.24 | 1.26 | 0.36 | 0.31 | 0.31 |
| Q | 0.9 | | | | | | | 0.25 | 1.1 | 0.37 | | 0.87 |
| R | | | | 1.19 | | | | 0.31 | 1.58 | | | 1.86 |
| S | 0.89 | | | | | 0.71 | 0.51 | 0.32 | | 0.32 | 0.68 | 0.29 |
| T | 0.88 | 0.83 | | | | | | 0.29 | 0.97 | 0.45 | 0.63 | 0.29 |
| V | | 0.73 | | | | 1.12 | | 0.3 | 1.08 | 0.36 | 0.34 | 0.61 |
| W | | | | | | 0.26 | | | 0.39 | 1.55 | 0.41 | | 0.99 |
| Y | 0.87 | | | | 1.1 | 0.25 | 0.77 | 0.64 | 1.2 | 0.26 | 0.69 | 1.04 |

| Domain | | | | | | | | | | | |
|---|---|---|---|---|---|---|---|---|---|---|---|
| | CDR1 | | | | FR2 | | | | CDR2 | | | |
| Kabat numbering | | | | | | | | | | | |
| | 31 | 32 | 33 | 34 | 45 | 50 | 51 | 52 | 53 | 54 | 55 | 56 |
| Amino acid before substitution | | | | | | | | | | | |
| | T | Y | L | H | Q | K | V | S | N | R | F | S |
| A | | 0.24 | 0.85 | 1.06 | | 0.23 | | 0.93 | 0.61 | 0.69 | 1.13 | 1.16 |
| D | 0.23 | 0.23 | 0.17 | 0.22 | 0.77 | 0.22 | 0.33 | 0.63 | 0.34 | 0.36 | 0.65 | 0.77 |
| E | 0.49 | | 0.72 | 0.23 | 0.75 | 0.24 | 0.64 | | 0.54 | 0.58 | 0.72 | 0.71 |
| F | | 0.29 | 0.78 | 0.27 | | | | | 0.69 | | | 1.32 |
| G | | | | 1.02 | | 0.16 | 0.84 | | 0.76 | 0.67 | 1.31 | 0.92 |
| H | | | | | | | | | 1.18 | | 0.94 | 1.05 |
| I | 0.97 | | 0.83 | 0.65 | | | 0.81 | | 0.5 | | 0.82 | 0.99 |
| K | 1.04 | | | 2.17 | | | | | 1.08 | | 1.33 | 1.46 |
| L | | | | 0.59 | | 0.24 | | | 0.56 | | 0.76 | 1.02 |
| M | | | 0.93 | 0.35 | | | | | 0.62 | | 0.8 | 1.05 |
| N | 0.32 | | | 0.65 | | | | | | | 0.98 | 0.92 |
| P | 0.31 | 0.24 | 0.3 | 0.34 | | 0.3 | 0.32 | 0.33 | 0.81 | 0.84 | 1.16 | 0.95 |
| Q | | | | 0.25 | 0.86 | 0.18 | | 1.05 | 0.77 | 0.68 | 0.91 | 1.04 |
| R | | | | 0.2 | | 0.5 | | | 1.58 | | 1.31 | 1.36 |
| S | | | | 0.78 | | 0.23 | | | 0.69 | 0.79 | 0.69 | |

TABLE 31-continued

| | | | | | | | | | | |
|---|---|---|---|---|---|---|---|---|---|---|
| T | | | 0.89 | | 0.19 | | | 0.56 | 0.65 | 0.41 | 0.97 |
| V | | 1.05 | 0.85 | | | | | 0.56 | | 0.71 | 0.95 |
| W | | | 0.24 | | | | | 0.81 | 0.78 | 0.69 | 1.38 |
| Y | | | 0.59 | | 0.24 | | 1.12 | 0.67 | | 0.92 | 1.46 |

| Domain | | | | | | | | | | |
|---|---|---|---|---|---|---|---|---|---|---|
| FR3 | | | | CDR3 | | | | | | FR4 |
| | | | | Kabat numbering | | | | | | |
| 74 | 77 | 89 | 90 | 91 | 92 | 93 | 94 | 95 | 96 | 97 | 107 |
| | | | | Amino acid before substitution | | | | | | |
| K | R | G | Q | G | T | Q | V | P | Y | T | K |

| | 74 | 77 | 89 | 90 | 91 | 92 | 93 | 94 | 95 | 96 | 97 | 107 |
|---|---|---|---|---|---|---|---|---|---|---|---|---|
| A | | | 1.13 | 0.5 | 0.27 | 0.63 | 0.85 | 1.05 | 0.63 | | | |
| D | | | 0.33 | 0.19 | 0.16 | 0.18 | 0.72 | 0.89 | 0.24 | 0.17 | | |
| E | | | 0.26 | 0.86 | 0.16 | 0.17 | 0.75 | 0.5 | 0.39 | 0.17 | | 0.94 |
| F | | | 1.09 | | | | | 0.71 | | 1.17 | | |
| G | | | | | | | | 0.48 | 0.37 | | | |
| H | | | 0.7 | | | | | 0.78 | | 0.23 | | |
| I | | | 1.07 | | | 0.34 | | 0.66 | | | | |
| K | | | 0.4 | | | | | 0.57 | | | | |
| L | | | 0.94 | | | 0.42 | | 0.44 | | 0.24 | 0.32 | |
| M | | | 0.52 | | | | | 0.44 | | | | |
| N | | | 0.8 | | | | | 1.05 | | | | |
| P | | | 0.35 | 0.27 | 0.27 | 0.26 | 0.25 | 1.26 | | | 0.31 | |
| Q | | | 0.38 | | | | | 0.76 | | | | |
| R | | | 0.19 | | | | 1.13 | 0.66 | | | | |
| S | | 0.92 | | 0.73 | 0.26 | 0.96 | 0.96 | 0.93 | 0.43 | | | |
| T | 0.84 | | 1.03 | | 0.26 | | | 0.93 | | | | |
| V | | | 1.63 | | | | | | | | | |
| W | | | 0.5 | | | | | 0.58 | | | | |
| Y | | | 1.19 | 0.17 | 0.17 | 0.33 | 0.87 | 0.63 | | | | |

TABLE 32

| Domain | | | | | | | | | | | |
|---|---|---|---|---|---|---|---|---|---|---|---|
| CDR1 | | | | | | | | | | | |
| Kabat numbering | | | | | | | | | | | |
| 24 | 25 | 26 | 27 | 27a | 27b | 27c | 27d | 27e | 28 | 29 | 30 |
| Amino acid before substitution | | | | | | | | | | | |
| R | S | S | Q | S | L | V | H | S | N | R | N |
| Affinity up | | | | | | | | | | | |

| | 24 | 25 | 26 | 27 | 27a | 27b | 27c | 27d | 27e | 28 | 29 | 30 |
|---|---|---|---|---|---|---|---|---|---|---|---|---|
| A | 1 | 0.73 | | | | | | 2.57 | 1.01 | 4.18 | 1.15 | 1.16 |
| D | 0.83 | 8.86 | 1.06 | 0.89 | 0.94 | 25.07 | 3.21 | 13641 | 1.23 | 4455.11 | 1.58 | 3.82 |
| E | 0.89 | 6.54 | 0.9 | 0.99 | 0.94 | 26.75 | 1.1 | 42.28 | 1.04 | 5.47 | | 2.83 |
| F | | | | | | 2.67 | | 2.05 | 1.16 | 2.59 | | f |
| G | 0.92 | | | | 0.8 | | | 3.51 | 1.03 | 2.41 | 0.62 | 2.1 |
| H | | | | | | | | | 1.09 | 3 | | 1.08 |
| I | | 0.67 | | | 0.87 | 1.17 | 1.03 | 7.77 | 1.05 | 2.81 | 1.6 | 1.24 |
| K | | | | | | | | 3.8 | 1.32 | 2.34 | | 1.35 |
| L | | 4.93 | | 0.86 | | | 0.81 | 3.37 | 1.06 | 3.34 | 0.9 | 1.19 |
| M | | 1.6 | | | | 1.31 | | 3.43 | 1.11 | 3.29 | | 1.2 |
| N | | | | | 0.98 | | | 3.43 | 1.01 | | | |
| P | 0.34 | 0.79 | 0.67 | 2.16 | 1.01 | 0.96 | 3.71 | 9.21 | 1.06 | 4.18 | 14.01 | 12.14 |
| Q | 0.87 | | | | | | | 7.48 | 1.08 | 3.48 | | 1 |
| R | | | | 1.06 | | | | 2.35 | 1.35 | | | 1.73 |
| S | 0.97 | | | | | 0.9 | 3.04 | 3.05 | | 4.3 | 1.05 | 10.64 |
| T | 1.03 | 0.75 | | | | | | 12973 | 0.98 | 2.67 | 1.02 | 12.72 |
| V | | 0.74 | | | | 1.11 | | 353.86 | 0.95 | 3.73 | 2.25 | 2.62 |
| W | | | | | | 23.6 | | 1.86 | 1.32 | 3.17 | | 0.97 |
| Y | 0.94 | | | | 0.93 | 22.2 | 1.25 | 1.98 | 1.1 | 3.89 | 1.08 | 1.03 |

TABLE 32-continued

| | Domain | | | | | | | | | | | |
|---|---|---|---|---|---|---|---|---|---|---|---|---|
| | CDR1 | | | | FR2 | | | | CDR2 | | | |
| | Kabat numbering | | | | | | | | | | | |
| | 31 | 32 | 33 | 34 | 45 | 50 | 51 | 52 | 53 | 54 | 55 | 56 |
| | Amino acid before substitution | | | | | | | | | | | |
| | T | Y | L | H | Q | K | V | S | N | R | F | S |
| | Affinity up | | | | | | | | | | | |
| | 31 | 32 | 33 | 34 | 45 | 50 | 51 | 52 | 53 | 54 | 55 | 56 |
| A | | 66.77 | 0.82 | 1.18 | | 59.5 | | 0.9 | 0.82 | 0.85 | 1.16 | 1.18 |
| D | 30.86 | 25.92 | 37.53 | 2100 | 0.86 | 114 | 1.5 | 0.94 | 2.8 | 1.8 | 1.02 | 1.11 |
| E | 1.59 | | 0.83 | 8.03 | 1.01 | 57.2 | 0.88 | | 2.47 | 0.84 | 0.92 | 0.91 |
| F | | 4.51 | 0.65 | 3.5 | | | | | 0.96 | | | 1.12 |
| G | | | | 1.08 | | 42.4 | 0.83 | | 1.33 | 0.88 | 1.15 | 0.99 |
| H | | | | | | | | | 1.31 | | 1.02 | 0.96 |
| I | 1.1 | | 0.86 | 0.89 | | | 0.69 | | 2.69 | | 1.28 | 1.01 |
| K | 0.88 | | | 4.1 | | | | | 1.05 | | 1.22 | 1.21 |
| L | | | 1.03 | | | 36.4 | | | 1.62 | | 1.43 | 1.03 |
| M | | | 0.9 | 3.16 | | | | | 1.21 | | 1.29 | 0.93 |
| N | 4.46 | | | 2.84 | | | | | | | 0.91 | 0.9 |
| P | 10.82 | 61.98 | 32.66 | 1.22 | | 27.7 | 6 | 7.38 | 0.98 | 1.05 | 1.15 | 0.98 |
| Q | | | | 4.6 | 0.98 | 8.13 | | 1.01 | 1.28 | 1.04 | 1.09 | 0.97 |
| R | | | | 85764 | | 1.83 | | | 1.56 | | 1.27 | 1.15 |
| S | | | | 1.24 | | 45.3 | | | 0.88 | 0.78 | 1.15 | |
| T | | | | 1.1 | | 25.1 | | | 2.68 | 0.89 | 2.42 | 1.01 |
| V | | | 1.26 | 1.04 | | | | | 2.14 | | 1.12 | 0.94 |
| W | | | | 8.45 | | | | | 1.01 | 0.65 | 1.72 | 1.12 |
| Y | | | | 2.44 | | 195 | | 1.02 | 0.99 | | 1.13 | 1.1 |

| | Domain | | | | | | | | | | |
|---|---|---|---|---|---|---|---|---|---|---|---|
| | FR3 | | | CDR3 | | | | | | | FR4 |
| | Kabat numbering | | | | | | | | | | |
| | 74 | 77 | 89 | 90 | 91 | 92 | 93 | 94 | 95 | 96 | 97 | 107 |
| | Amino acid before substitution | | | | | | | | | | |
| | K | R | G | Q | G | T | Q | V | P | Y | T | K |
| | Affinity up | | | | | | | | | | |
| | 74 | 77 | 89 | 90 | 91 | 92 | 93 | 94 | 95 | 96 | 97 | 107 |
| A | | | 1.1 | 0.89 | 28.14 | 1.35 | 0.65 | 1.05 | 0.87 | | | |
| D | | | 1.96 | 11.13 | 44.76 | 11.19 | 0.72 | 1.05 | 2.37 | 40.88 | | |
| E | | | 34.63 | 0.91 | 48.54 | 19.56 | 1.05 | 1.18 | 1.01 | 46.81 | | 0.95 |
| F | | | 3.34 | | | | | 1.75 | | 0.86 | | |
| G | | | | | | | | 2.59 | 1.94 | | | |
| H | | | 1.44 | | | | | 1.16 | | 80.34 | | |
| I | | | 1.11 | | | 1.91 | | 1.46 | | | | |
| K | | | 1.8 | | | | | 0.91 | | | | |
| L | | | 2.38 | | | 1.61 | | 3.06 | 11.66 | 1.84 | | |
| M | | | 1.96 | | | | | 2.74 | | | | |
| N | | | 1.2 | | | | | 0.96 | | | | |
| P | | | 1.8 | 15.86 | 23.05 | 26.71 | 39.54 | 1.1 | | | 3.35 | |
| Q | | | 2.11 | | | | | 1.1 | | | | |
| R | | | 4127.4 | | | | | 0.79 | 1.11 | | | |
| S | | 0.94 | | | 0.96 | 72076 | 0.81 | 0.75 | 0.81 | 1.19 | | |
| T | 0.85 | | 1.1 | | | 39.87 | | 1.06 | | | | |
| V | | | 1.4 | | | | | | | | | |
| W | | | 2.2 | | | | | 1.81 | | | | |
| Y | | | 1.12 | | 36.29 | 33.84 | 2.55 | 0.76 | 2.45 | | | |

Each antibody was obtained as an H chain or L chain altered form by the method described in the paragraph (Reference Example 4-2). Next, its ECM binding was evaluated according to the method of Reference Example 6. The ECM binding value (ECL reaction) of each altered form was divided by the ECM binding value of the antibody MRA (H chain: SEQ ID NO: 140, L chain: SEQ ID NO: 141) obtained in the same plate or at the same execution date, and the resulting value is shown in Tables 33 (H chain) and 34 (L chain). As shown in Tables 33 and 34, some alterations were confirmed to have tendency to enhance ECM binding.

Of the values shown in Tables 33 (H chain) and 34 (L chain), an effective value up to 10 times was adopted to the dual Fab library in consideration of the effect of enhancing ECM binding by a plurality of alterations.

TABLE 33

| Domain | | | | | | | | | | | | | | | | |
|---|---|---|---|---|---|---|---|---|---|---|---|---|---|---|---|---|
| FR1 | | | | | | | CDR1 | | | FR2 | | CDR2 | | | | |
| Kabat numbering | | | | | | | | | | | | | | | | |
| 11 | 16 | 19 | 28 | 29 | 30 | 31 | 32 | 33 | 35 | 43 | 50 | 51 | 52 | 52 | 52b | 52c |
| Amino acid before substitution | | | | | | | | | | | | | | | | |
| V | R | R | T | F | S | N | A | W | H | K | Q | I | K | A | K | S |
| A | | | | | | | | | | | | | | | | 2.95 |
| D | | 1.14 | | 0.91 | | 1.11 | | | 1.1 | | 1.06 | 4.75 | 1.07 | 1.66 | | |
| E | | 1.14 | | | | | | | 1.04 | 1.8 | 1.08 | 4.55 | 1.18 | 1.19 | | |
| F | | | | | | | | | 2.62 | | | | | | | 10.46 |
| G | | | | | 3.32 | | | | 8.82 | | | | | 4.72 | | 5.41 |
| H | | | | | | | | | | | | | | | | |
| I | | | | | | 2.51 | | | | | | | | | | |
| K | | | | | | 41.37 | | | | | | | | | | 58.7 |
| L | 3.41 | | | | | | | | | | | | | | | 4.07 |
| M | | | | | | | | | 4.69 | | | | | | | |
| N | | | | | | | | | 3.06 | | | | | | | |
| P | | | | | | | | | 51.18 | | | | | | | |
| Q | | 1.55 | | | | | | | | | 2 | | | | | 4.99 |
| R | | | | | | 71.66 | | | | | | | 11.19 | | 7.28 | |
| S | | | 2.32 | | | 0.95 | | | | | | | | 3.34 | | |
| T | | | 1.17 | | | | | | 3.49 | | | | | | | |
| V | | | | 17.13 | | | | | 7.32 | | | | | | | 3.23 |
| W | | | | | | | | | 8.8 | | | | | | | |
| Y | | | | | | | | | | | | | | | | 19.56 |

| Domain | | | | | | | | | | | | | | | | |
|---|---|---|---|---|---|---|---|---|---|---|---|---|---|---|---|---|
| CDR2 | | | | | | | | | | | FR3 | | | | | |
| Kabat numbering | | | | | | | | | | | | | | | | |
| 53 | 54 | 55 | 56 | 57 | 58 | 59 | 60 | 61 | 62 | 64 | 65 | 72 | 73 | 74 | 75 | 76 |
| Amino acid before substitution | | | | | | | | | | | | | | | | |
| N | N | Y | A | T | Y | Y | A | E | S | K | G | D | D | S | K | N |
| A | | 4.5 | | 4.67 | | 5.82 | | 7.23 | | 2.08 | | 22.3 | | | | |
| D | | | | | | 2.77 | 4.02 | 3.23 | 4.4 | 1.23 | 0.91 | | | | | |
| E | | | | | | 2.33 | 4.36 | | 2.75 | 1.33 | 2.13 | | | | | |
| F | | 15.16 | | | | | | | | | | | | | | |
| G | | 4.43 | | | | | | | | | | | | | | |
| H | | | | | | | | | | | | | | | | |
| I | | | | | | | | | | | | | | | | |
| K | | 85.86 | | 32.07 | 16.29 | | | | | 4.07 | | | | | | |
| L | | 6.02 | | 3.56 | | | | | | | | | | | | |
| M | | | | | | | | | | | | | | | | |
| N | | | | 4.07 | 4.49 | | | | | | | | | | | |
| P | | | | | | | | | 9.99 | 3.83 | | | | | | |
| Q | 3.18 | 3.23 | | | | | | | 9.29 | | 1.91 | | | | | |
| R | | | | | | | | | | | | | | | 2.92 | |
| S | 3.71 | 4.33 | | | | 6.58 | | | | 1.89 | | | | | | 1.93 |
| T | | | | | | | | | | | | | | | 1.2 | |
| V | | | | | | | | | | | | | | | | |
| W | 23.56 | | | | | | | | | | | | | | | |
| Y | | 17.47 | | | | | | | | | | | | | | |

TABLE 33-continued

| | | | FR3 | | | | | | CDR3 | | | | | | FR4 |
|---|---|---|---|---|---|---|---|---|---|---|---|---|---|---|---|
| | | | | | | Kabat numbering | | | | | | | | | |
| | 77 | 78 | 82a | 95 | 96 | 97 | 98 | 99 | 100 | 100a | 100b | 100c | 101 | 102 | 105 |
| | | | | | | | Amino acid before substitution | | | | | | | | |
| | S | L | N | V | H | Y | G | A | Y | Y | G | V | D | A | Q |
| A | | | | | | | 2.7 | | 1.46 | | | | 66.85 | | |
| D | | | | 1.12 | 0.96 | | 0.65 | | | | 0.98 | 1.18 | | | |
| E | | | | | 0.76 | | | | | | 1.2 | 1.3 | | | 1.33 |
| F | | | | | | | | | 16.97 | 2.81 | | | | | |
| G | | | | | | | | | 1 | 2.61 | | | 56.66 | | |
| H | | | | | | | 2.12 | | | | | | 16.16 | | |
| I | | | | | | | | | | | | | 63.16 | 6.63 | |
| K | | | | | | | 32.29 | 57.13 | 8.2 | 10.3 | | | 38.94 | | |
| L | | | | | | | | 6.94 | | | | | | | |
| M | | | | | | | | | | | | | 123.87 | | |
| N | | | | | | | | | | | | | 90.66 | | |
| P | | | | | | | 3 | | | | | | | | |
| Q | | | | | | | 2.99 | 2.12 | 0.94 | | | | 130.29 | | |
| R | | | | | | | 48.83 | | | | | | | | |
| S | | | | | | | 2.41 | 3.34 | 1 | | | | 58.7 | | |
| T | 2.31 | | | | | | 1.6 | 2.54 | | | | | | | |
| V | | | | | | | | | | | | | 48.47 | 6.29 | |
| W | | | | | | | | | | 10.83 | | | | | |
| Y | | | | | | | 27.01 | 30.37 | | | | | | 2.82 | |

TABLE 34

| | | | | | | | CDR1 | | | | | | | | | | FR2 |
|---|---|---|---|---|---|---|---|---|---|---|---|---|---|---|---|---|---|
| | | | | | | | Kabat numbering | | | | | | | | | | |
| | 24 | 25 | 26 | 27 | 27a | 27b | 27c | 27d | 27e | 28 | 29 | 30 | 31 | 32 | 33 | 34 | 45 |
| | | | | | | | Amino acid before substitution | | | | | | | | | | |
| | R | S | S | Q | S | L | V | H | S | N | R | N | T | Y | L | H | Q |
| A | 2.62 | 2.28 | | | | | | 3.25 | | | 0.87 | | | 2.21 | 5.92 | 2.61 | |
| D | 1.86 | 1.01 | 1.31 | 1.3 | 1.03 | 1.16 | 0.76 | | | | 0.64 | | 0.66 | 0.98 | 0.6 | | 0.99 |
| E | 2.02 | 1.16 | 1.22 | 1.24 | 1.12 | 1.04 | 0.72 | 1.19 | | | | 0.79 | | | 1.45 | | 1.15 |
| F | | | | | | | | 16.43 | | | | 5.79 | | 1.55 | | | |
| G | 1.53 | | | | 10.04 | | | 5.42 | | | | | | | | 3.9 | |
| H | | | | | | | | 13.64 | | | | 8.6 | | | | | |
| I | | | | 11.11 | 2.68 | | 56.75 | 4.28 | | | | | | 2.87 | | 4.74 | |
| K | | | | | | | | 34.74 | | | | | 31.93 | 59.62 | | 84.66 | |
| L | | | | 11.8 | | | 3.16 | 5.89 | | | | | | | | | |
| M | | | | | | | | 6.53 | | | | | 3.32 | | 19.8 | | |
| N | | | | | 48.45 | | | 4.63 | | | | | | | | | |
| P | | 2.83 | | | 2.3 | 2.7 | | 7.26 | | | | | | | | | |
| Q | 1.26 | | | | | | | 2.58 | | | | 3.45 | | | | | 2.31 |
| R | | | 18.19 | | | | | 74.03 | | | | 69.62 | | | | | |
| S | 2.65 | | | | | 3.3 | | | | | | | | | 2.17 | | |
| T | 1.8 | 2.7 | | | | | | 2.32 | | | 0.63 | | | | 4.51 | | |
| V | | | | | | 2.82 | | 2.31 | | | | | | | 2.68 | 6.43 | |
| W | | | | | | | | 46.73 | | | | 11.21 | | | | | |
| Y | 1.89 | | | | 42.7 | | | 30.66 | | | | 3.08 | | | | | |

| | | | CDR2 | | | | | FR3 | | | | | CDR3 | | | | | FR4 |
|---|---|---|---|---|---|---|---|---|---|---|---|---|---|---|---|---|---|---|
| | | | | | | | | Kabat numbering | | | | | | | | | | |
| | 50 | 51 | 52 | 53 | 54 | 55 | 56 | 74 | 77 | 89 | 90 | 91 | 92 | 93 | 94 | 95 | 96 | 97 | 107 |
| | | | | | | | | Amino acid before substitution | | | | | | | | | | |
| | K | V | S | N | R | F | S | K | R | G | Q | G | T | Q | V | P | Y | T | K |
| A | 0.83 | | 3.65 | | 1.78 | 2.41 | 16.89 | | 8.43 | 3.14 | | 3.11 | 3.34 | 3.22 | | | | | |
| D | 0.64 | 1.01 | | | 1.44 | | | | | 1.37 | 0.8 | 0.84 | | 0.88 | 4.38 | 0.66 | | | |
| E | | 0.95 | | | 0.94 | | | | | 2.55 | 1 | 0.67 | 0.85 | | 3.71 | 0.59 | | | 2.96 |
| F | | | | | | | 10.25 | | 31.93 | | | | | | 3.44 | | | | |

TABLE 34-continued

| | | | | | | | | | | | | |
|---|---|---|---|---|---|---|---|---|---|---|---|---|
| G | 0.67 | 3.5 | | 1.19 | 6.49 | 3.26 | | | | | | |
| H | | | 4.88 | | 7.39 | 6.83 | | | | | | |
| I | | 2.11 | | | 23.25 | 5.1 | | 14.58 | | | | |
| K | | | 19.31 | | 5.18 | 31.33 | | | | | | |
| L | | | | | | 5.65 | | 18.53 | | | | |
| M | | | | | 12.14 | 5.15 | | | | | | |
| N | | | | | 7.83 | 3.96 | | 4.96 | | | | 3.01 |
| P | | | 4.72 | 5.49 | 5.16 | 6 | | | | | | 10.7 |
| Q | 0.76 | | 2.37 | | 1.33 | 35.06 | 2.96 | | | | | |
| R | | | | 34.13 | | 16.5 | 19.76 | | | | 44.29 | |
| S | 0.84 | | | | | | | 2.37 | | 4.37 | 3.12 | 3.82 | 3.78 |
| T | 1.03 | | | | 1.39 | | 2.48 | 2.05 | 6.79 | | | 2.63 |
| V | | | | | | | 4 | | 26.88 | | | |
| W | | | | 2.19 | | | 26.63 | | | | | |
| Y | 0.88 | | 6.28 | | | 6.18 | 3.87 | | 28.25 | 3.75 | 3.26 | 2.96 | 14.49 |

(4-5) Study on Insertion Site and Length of Peptide for Enhancing Diversity of Library Reference Example 3 showed that a peptide can be inserted to each site using a GGS sequence without canceling binding to CD3 (CD3 epsilon). If loop extension is possible for the dual Fab library, the resulting library might include more types of molecules (or have larger diversity) and permit obtainment of Fab domains binding to diverse second antigens. Thus, in view of presumed reduction in binding activity caused by peptide insertion, V11L/D72A/L78I/D101Q alteration to enhance binding activity against CD3 epsilon was added to the CE115HA000 sequence, which was further linked to pE22Hh. A molecule was prepared by the insertion of the GGS linker to this sequence, as in Reference Example 3, and evaluated for its CD3 binding. The GGS sequence was inserted between Kabat numbering positions 99 and 100. The antibody molecule was expressed as a one-arm antibody. Specifically, the GGS linker-containing H chain mentioned above and Kn010G3 (SEQ ID NO: 139) were used as H chains, and GLS3000 (SEQ ID NO: 136) linked to the kappa sequence (SEQ ID NO: 138) was adopted as an L chain. These sequences were expressed and purified according to Reference Example 1.

(4-6) Confirmation of Binding of GGS Peptide-Inserted CE115 Antibody to CD3

The binding of the GGS peptide-inserted altered antibody to CD3 epsilon was confirmed using Biacore by the method described in Reference Example 3. As shown in Table 35, the results demonstrated that the GGS linker can be inserted to loops. Particularly, the GGS linker was able to be inserted to the H chain CDR3 region, which is important for antigen binding, and the binding to CD3 epsilon was maintained as a result of any of the 3-, 6-, and 9-amino acid insertions. Although this study was conducted using the GGS linker, an antibody library in which various amino acids other than GGS appear may be acceptable.

TABLE 35

| Inserted amino acid sequence (99-100) | CD3_KD[M] |
|---|---|
| GGS | 6.31E-08 |
| GGSGGS (SEQ ID NO:126) | 3.46E-08 |
| GGSGGS (SEQ ID NO:126) | 3.105E-08 |
| GGSGGGS (SEQ ID NO:142) | 4.352E-08 |
| GGSGGGS (SEQ ID NO:142) | 3.429E-08 |
| GGGSGGGS (SEQ ID NO:143) | 4.129E-08 |
| GGGSGGGS (SEQ ID NO:143) | 3.753E-08 |
| GGSGGSGGS (SEQ ID NO:128) | 4.39E-08 |
| GGSGGSGGS (SEQ ID NO:128) | 3.537E-08 |
| No insertion | 6.961E-09 |
| CE115HA000 | 1.097E-07 |

(4-7) Study on Insertion for Library to H Chain CDR3 Using NNS Nucleotide Sequence The paragraph (Reference Example 4-6) showed that the 3, 6, or 9 amino acids can be inserted using the GGS linker, and inferred that a library having the 3-, 6-, or 9-amino acid insertion can be prepared to obtain an antibody binding to the second antigen by use of a usual antibody obtainment method typified by the phage display method. Thus, a study was conducted on whether the 6-amino acid insertion to CDR3 could maintain binding to CD3 even if various amino acids appeared at the 6-amino acid insertion site using an NNS nucleotide sequence (which allows every type of amino acid to appear). In view of presumed reduction in binding activity, primers were designed using the NNS nucleotide sequence such that 6 amino acids were inserted between positions 99 and 100 (Kabat numbering) in CDR3 of a CE115HA340 sequence (SEQ ID NO: 144) having higher CD3 epsilon-binding activity than that of CE115HA000. The antibody molecule was expressed as a one-arm antibody. Specifically, the altered H chain mentioned above and Kn010G3 (SEQ ID NO: 139) were used as H chains, and GLS3000 (SEQ ID NO: 136) linked to the kappa sequence (SEQ ID NO: 138) was adopted as an L chain. These sequences were expressed and purified according to Reference Example 1. The obtained altered antibody was evaluated for its binding by the method described in the paragraph (Reference Example 4-6). The results are shown in Table 36. The results demonstrated that the binding activity against CD3 (CD3 epsilon) is maintained even if various amino acids appear at the site extended with the amino acids. Table 37 shows results of further evaluating the presence or absence of enhancement in nonspecific binding by the method described in Reference Example 6. As a result, the binding to ECM was enhanced if the extended loop of CDR3 was rich in amino acids having a positively charged side chain. Therefore, it was desired that three or more amino acids having a positively charged side chain should not appear in the loop.

TABLE 36

| | | CDR 3 | |
|---|---|---|---|
| VH | CD3_KD[M] | 9 | 1 0 |
| CE115HA340 | 2.0E-08 | 5 6 7 8 9 0 a b c d e f g h i k 1 1 2 |
| CE115HA340 | 2.7E-08 | V H Y A A X X X X X X Y Y G V - - D A |
| NHS6f17 | 7.4E-08 | . . . . . W G E G V V . . . . . . . . |
| NNS6f27 | 3.8E-08 | . . . . . V W G S V W . . . . . . . . |
| NHS6f29 | 9.0E-08 | . . . . . I Y Y P T N . . . . . . . . |
| NNS6f47 | 3.1E.08 | . . . . . H F M W W G . . . . . . . . |

TABLE 36 -continued

| VH | CD3 KD[M] | CDR 3 |
|---|---|---|
| | | 9　　　　　　　　　　1 0　　　　　　　　5 |
| NHS6f50 | 7.1E-08 | . . . . . L T G G L G . . . . . . . . |
| NNS6f51 | 3.1E-08 | . . . . . G F L V L W . . . . . . . . |
| NHS6f52 | 5.2E-08 | . . . . . Y M L G L G . . . . . . . . |
| NNS6f54 | 2.9E-08 | . . . . . F E W V G W . . . . . . . . |
| NNS6f55 | 3.1E-08 | . . . . . A G R W L A . . . . . . . . |
| NNS6f56 | 2.1E-08 | . . . . . R E A T R W . . . . . . . . |
| NNS6f58 | 4.4E-08 | . . . . . S W Q V S R . . . . . . . . |
| NNS6f59 | 2.0E-07 | . . . . . L L V Q E G . . . . . . . . |
| NNS6f62 | 6.1E-08 | . . . . . N G G T R H . . . . . . . . |
| NNS6f63 | 6.9E-08 | . . . . . G G G G W V . . . . . . . . |
| NNS6f64 | 7.8E-08 | . . . . . L V S L T V . . . . . . . . |
| NNS6f67 | 3.6E-08 | . . . . . G L L R A A . . . . . . . . |
| NNS6f68 | 4.5E-08 | . . . . . V E W G R W . . . . . . . . |
| NNS6f71 | 5.1E-08 | . . . . . G W V L G S . . . . . . . . |
| NNS6f72 | 1.5E-07 | . . . . . E G I W W G . . . . . . . . |
| NNS6f73 | 2.6E-08 | . . . . . W V V G V R . . . . . . . . |

TABLE 37

| H chain | ECL reaction | | | CDR 3 |
|---|---|---|---|---|
| | ECM 3 µg/ml | MRA | Ratio ECM vs MRA | 9　　　　　　　　1 0<br>5 6 7 8 9 0 a b c d e f g h i k 1 1 2 |
| CE115HA340 | 394 | 448 | 0.9 | V H Y A A X X X X X X Y Y G V - - D A |
| NHS6f17 | 409 | 448 | 0.9 | . . . . . W G E G V V . . . . . . . . |
| NNS6f27 | 3444 | 448 | 7.7 | . . . . . V W G S V W . . . . . . . . |
| NHS6f29 | 481 | 448 | 1.1 | . . . . . I Y Y P T N . . . . . . . . |
| NNS6f47 | 94137 | 448 | 210.3 | . . . . . H F M W W G . . . . . . . . |
| NHS6f50 | 385 | 564 | 0.7 | . . . . . L T G G L G . . . . . . . . |
| NNS6f51 | 20148 | 564 | 35.7 | . . . . . G F L V L W . . . . . . . . |
| NHS6f52 | 790 | 564 | 1.4 | . . . . . Y M L G L G . . . . . . . . |
| NNS6f54 | 1824 | 564 | 3.2 | . . . . . F E W V G W . . . . . . . . |
| NNS6f55 | 14183 | 564 | 25.1 | . . . . . A G R W L A . . . . . . . . |
| NNS6f56 | 6534 | 564 | 11.6 | . . . . . R E A T R W . . . . . . . . |
| NNS6f58 | 2700 | 564 | 4.8 | . . . . . S W Q V S R . . . . . . . . |
| NNS6f59 | 388 | 564 | 0.7 | . . . . . L L V Q E G . . . . . . . . |
| NNS6f62 | 554 | 564 | 1.0 | . . . . . N G G T R H . . . . . . . . |
| NNS6f63 | 624 | 564 | 1.1 | . . . . . G G G G W V . . . . . . . . |
| NNS6f64 | 603 | 564 | 1.1 | . . . . . L V S L T V . . . . . . . . |
| NNS6f67 | 1292 | 564 | 2.3 | . . . . . G L L R A A . . . . . . . . |
| NNS6f68 | 2789 | 564 | 4.9 | . . . . . V E W G R W . . . . . . . . |
| NNS6f71 | 618 | 564 | 1.1 | . . . . . G W V L G S . . . . . . . . |
| NNS6f72 | 536 | 564 | 0.9 | . . . . . E G I W W G . . . . . . . . |
| NNS6f73 | 2193 | 564 | 3.9 | . . . . . W V V G V R . . . . . . . . |

(4-7) Design and Construction of Dual Fab Library

On the basis of the study described in Reference Example 4, an antibody library (dual Fab library) for obtaining an antibody binding to CD3 and the second antigen was designed as follows:

step 1: selecting amino acids that maintain the ability to bind to CD3 (CD3 epsilon) (to secure 80% or more of the amount of CE15HA000 bound to CD3);

step 2: selecting amino acids that keep ECM binding within 10 times that of MRA compared with before alteration; and step 3: inserting 6 amino acids to between positions 99 and 100 (Kabat numbering) in H chain CDR3.

The antigen-binding site of Fab can be diversified by merely performing the step 1. The resulting library can therefore be used for identifying an antigen-binding molecule binding to the second antigen. The antigen-binding site of Fab can be diversified by merely performing the steps 1 and 3. The resulting library can therefore be used for identifying an antigen-binding molecule binding to the second antigen. Even library design without the step 2 allows an obtained molecule to be assayed and evaluated for ECM binding.

Thus, for the dual Fab library, sequences derived from CE15HA000 by adding the V11L/L78I mutation to FR (framework) and further diversifying CDRs as shown in Table 38 were used as H chains, and sequences derived from GLS3000 by diversifying CDRs as shown in Table 39 were used as L chains. These antibody library fragments can be synthesized by a DNA synthesis method generally known to those skilled in the art. The dual Fab library may be prepared as (1) a library in which H chains are diversified as shown in Table 38 while L chains are fixed to the original sequence GLS3000 or the L chain having enhanced CD3 epsilon binding described in Reference Example 4, (2) a library in which H chains are fixed to the original sequence (CE115HA000) or the H chain having enhanced CD3 epsilon binding described in Reference Example 4 while L chains are diversified as shown in Table 39, and (3) a library in which H chains are diversified as shown in Table 38 while L chains are diversified as shown in Table 39. The H chain library sequences derived from CE115HA000 by adding the V11L/L78I mutation to FR (framework) and further diversifying CDRs as shown in Table 38 were entrusted to the DNA synthesizing company DNA2.0, Inc. to obtain antibody library fragments (DNA fragments). The obtained antibody library fragments were inserted to phagemids for phage display amplified by PCR. GLS3000 was selected as L chains. The constructed phagemids for phage display were transferred to *E. coli* by electroporation to prepare *E. coli* harboring the antibody library fragments.

Based on Table 39 we designed the new diversified library for GLS3000 as shown in Table 40. The L chain library sequences was derived from GLS3000 and diversified as shown in Table 40 (DNA library). The DNA library was constructed by DNA synthesizing company. Then the L chain library containing various GLS3000 derived sequences and the H chain library containing various CE115HA000 derived sequences were inserted into phagemid to construct phage display library.

TABLE 38

| | CDR 1 | CDR 2 | CDR 3 |
|---|---|---|---|
| Kabat numbering | 3    5 5<br>1 2 3 4 5 0 1 2 a b c | 6<br>3 4 5 6 7 8 9 0 1 2 3 4 5 | 9        1 0<br>5 6 7 8 9 0 a b c d e f g h i 1 2 |
| Before substitution | N A W M H Q I K A K S | N N Y A T Y Y A E S V K G V H | Y G A x x x x x x Y Y G V D A |
| Library | I A W M H Q I K D R A<br>N<br>S | Q A Y L A Y Y A P S V K G V H<br>K G S G    N N         E<br>L N L    A T<br>Q    Q<br>V    S<br>S    N | Y A A A A G A L P A Y G V D A<br>G L V V S V G G S F<br>P S G G T L S S Q G<br>S Q S S Y G Y Y K<br>T T T T F S F F Y<br>Q    Y Y D Y       G<br>H    F F    F<br>D |

TABLE 39

| Domain | CDR1 | FR2 | CDR2 | FR3 | CDR3 | FR4 |
|---|---|---|---|---|---|---|
| Kabat numbering | 2                     3<br>4 5 6 7 a b c d e 8 9 0 1 2 3 4 | 4<br>5 | 5<br>0 1 2 3 4 | 5 6 4 | 7        9<br>7 9 0 1 2 3 | 10<br>4 5 6 7    7 |
| Before substitution | R S S Q S L V H S N R N T Y L H | Q | K V S N R | F S K R | G Q G T Q V P Y T | K |
| Library | R S S Q S L V H S N R N T Y L H<br>A A D D E I L    A    F I<br>E P    E P P    G    H<br>G T       V    I    M<br>Q             L    Q<br>S             M<br>T             N<br>Y             P<br>              Q<br>              T<br>              V | Q | K V S N R<br>A A<br>I G<br>V T<br>V | F S K R<br>G A P P<br>I Q W<br>Y | G Q G T Q V P Y T<br>A G T S A E<br>G H    N<br>H I    T<br>K L<br>N M<br>P N<br>Y P<br>Q<br>T<br>V<br>Y | K<br>E |
| | | | | | S A A    F<br>S D<br>N<br>S<br>T | |

TABLE 40

| Region | CDR1 | CDR2 | CDR3 |
|---|---|---|---|
| Kabat numbering | 2                     3<br>4 5 6 7 a b c d e 8 9 0 1 2 3 4 | 5<br>0 1 2 3 4 5 6 9 | 9<br>0 1 2 3 4 5 6 7 |
| Original | R S S Q S L V H S N R N T Y L H | K V S N R F S | G Q G T Q V P Y T |
| Library | R S S Q S L V H S N R N T Y L H<br>A A D    E    L    A    F I<br>E T       E          G    H<br>G                   I    M<br>Q                   L    Q<br>S                   M<br>T                   N<br>Y | K V S N R F S<br>A             A<br>G             Q<br>M             T<br>Q             V<br>Y | G Q G T Q V P Y T<br>G A E    S A A    F<br>H N       S D<br>I T          N<br>L             S<br>M             T<br>N |

TABLE 40-continued

| Region | CDR1 | CDR2 | CDR3 |
|--------|------|------|------|
|        | Q<br>T<br>V | Q<br>T<br>V<br>Y |  |

[Reference Example 5] Experimental Cell Lines

The human GPC3 gene was integrated into the chromosome of the mouse colorectal cancer cell line CT-26 (ATCC No. CRL-2638) by a method well known to those skilled in the art to obtain the high expression CT26-GPC3 cell line. The expression level of human GPC3 ($2.3 \times 10^5$/cell) was determined using the QIFI kit (Dako) by the manufacturer's recommended method. To maintain the human GPC3 gene, these recombinant cell lines were cultured in ATCC-recommended media by adding Geneticin (GIBCO) at 200 micro g/ml for CT26-GPC3. After culturing, these cells were detached using 2.5 g/L trypsin-1 mM EDTA (nacalai tesque), and then used for each of the experiments The human CD137 gene was integrated into the chromosome of the Chinese Hamster Ovary cell line CHO-DG44 by a method well known to those skilled in the art to obtain the high expression CHO-hCD137 cell line. The expression level of human CD137 was determined by FACS analysis using the PE anti-human CD137 (4-1BB) Antibody (BioLegend, Cat. No. 309803) by the manufacturer's recommended method.

[Reference Example 6] Evaluation of Binding of Antibody to ECM (Extracellular Matrix)

The binding of each antibody to ECM (extracellular matrix) was evaluated by the following procedures with reference to WO2012093704 A1: ECM Phenol red free (BD Matrigel #356237) was diluted to 2 mg/mL with TBS and added dropwise at 5 micro L/well to the center of each well of a plate for ECL assay (L15XB-3, MSD K.K., high bind) cooled on ice. Then, the plate was capped with a plate seal and left standing overnight at 4 degrees C. The ECM-immobilized plate was brought to room temperature. An ECL blocking buffer (PBS supplemented with 0.5% BSA and 0.05% Tween 20) was added thereto at 150 micro L/well, and the plate was left standing at room temperature for 2 hours or longer or overnight at 4 degrees C. Next, each antibody sample was diluted to 9 micro g/mL with PBS-T (PBS supplemented with 0.05% Tween 20). A secondary antibody was diluted to 2 micro g/mL with ECLDB (PBS supplemented with 0.1% BSA and 0.01% Tween 20). 20 micro L of the antibody solution and 30 micro L of the secondary antibody solution were added to each well of a round-bottomed plate containing ECLDB dispensed at 10 micro L/well and stirred at room temperature for 1 hour while shielded from light. The ECL blocking buffer was removed by inverting the ECM plate containing the ECL blocking buffer. To this plate, a mixed solution of the aforementioned antibody and secondary antibody was added at 50 micro L/well. Then, the plate was left standing at room temperature for 1 hour while shielded from light. The sample was removed by inverting the plate, and READ buffer (MSD K.K.) was then added thereto at 150 micro L/well, followed by the detection of the luminescence signal of the sulfo-tag using Sector Imager 2400 (MSD K.K.).

INDUSTRIAL APPLICABILITY

The present invention provides antigen-binding domains that are capable of binding to CD3 and CD137 but do not bind to CD3 and CD137 at the same time and methods of using the same. Antibody-binding molecules comprising such an antigen-binding domain according to the present invention may be useful as a medicament, in particular, for treating various types of cancer.

The invention claimed is:

1. A tri-specific IgG antibody comprising:
a dual-binding Fab comprising a first variable region that binds to human CD3 epsilon and human CD137, but does not bind to human CD3 epsilon and human CD137 at the same time;
a second Fab comprising a second variable region that binds to a third antigen different from human CD3 epsilon and human CD137, wherein the third antigen is a cancer antigen; and
an Fc region,
wherein the first variable region comprises a heavy chain variable domain (VH) and a light chain variable domain (VL) selected from the VH and VL of (a) to (e) below:
(a) a VH comprising the amino acid sequence of SEQ ID NO: 30 and a VL comprising the amino acid sequence of SEQ ID NO: 51,
(b) a VH comprising the amino acid sequence of SEQ ID NO: 46 and a VL comprising the amino acid sequence of SEQ ID NO: 53,
(c) a VH comprising the amino acid sequence of SEQ ID NO: 40 and a VL comprising the amino acid sequence of SEQ ID NO: 56,
(d) a VH comprising the amino acid sequence of SEQ ID NO: 30 and a VL comprising the amino acid sequence of SEQ ID NO: 58, and
(e) a VH comprising the amino acid sequence of SEQ ID NO: 40 and a VL comprising the amino acid sequence of SEQ ID NO: 61.

2. The tri-specific antibody of claim 1, wherein
(a) the tri-specific antibody has an agonistic activity against human CD137, or
(b) the tri-specific antibody does not induce a cytokine release from peripheral blood mononuclear cells (PBMC) in the absence of a cell expressing the third antigen, or
(c) both (a) and (b).

3. The tri-specific antibody of claim 1, wherein the Fc region has reduced binding activity, as compared to a naturally occurring human IgG1 Fc region, against a human Fc gamma receptor isoform selected from Fc gamma receptor Ia, Fc gamma receptor IIa, Fc gamma receptor IIb, Fc gamma receptor IIIa, or Fc gamma receptor IIIb.

4. The tri-specific antibody of claim 1, wherein the tri-specific antibody has one or both of the following characteristics:
(1) the first variable region binds to an extracellular domain of human CD3 epsilon comprising the amino acid sequence of SEQ ID NO: 91; or
(2) the tri-specific antibody induces CD3 activation of a T cell against a cell expressing the third antigen, but does not induce CD3 activation of a T cell against a cell expressing human CD137.

5. A pharmaceutical composition comprising the tri-specific antibody according to claim 1 and a pharmaceutically acceptable carrier.

6. A tri-specific IgG antibody comprising:
a dual-binding Fab comprising a first variable region that binds to human CD3 epsilon and human CD137, but does not bind to human CD3 epsilon and human CD137 at the same time;
a second Fab comprising a second variable region that binds to a third antigen different from human CD3 epsilon and human CD137, wherein the third antigen is a cancer antigen; and
an Fc region,
wherein:
the first variable region comprises a VH and a VL;
the amino acid sequence of the VH has at least 95% sequence identity to the amino acid sequence of SEQ ID NO: 41, 30, 46, or 40; and
the amino acid sequence of the VL has at least 95% sequence identity to the amino acid sequence of SEQ ID NO: 51, 52, 53, 54, 55, 56, or 57.

7. The tri-specific antibody of claim 6, wherein:
(a) the tri-specific antibody has an agonistic activity against human CD137, or
(b) the tri-specific antibody does not induce a cytokine release from PBMCs in the absence of a cell expressing the third antigen, or
(c) both (a) and (b).

8. The tri-specific antibody of claim 6, wherein the Fc region has reduced binding activity, as compared to a naturally occurring IgG1 Fc region, against a human Fc gamma receptor isoform selected from Fc gamma receptor Ia, Fc gamma receptor IIa, Fc gamma receptor IIb, Fc gamma receptor IIIa, or Fc gamma receptor IIIb.

9. The tri-specific antibody of claim 6, wherein the tri-specific antibody has one or both of the following characteristics:
(1) the first variable region binds to an extracellular domain of human CD3 epsilon consisting of the amino acid sequence of SEQ ID NO: 91; or
(2) the tri-specific antibody induces CD3 activation of a T cell against a cell expressing the third antigen, but does not induce CD3 activation of a T cell against a cell expressing human CD137.

10. A pharmaceutical composition comprising the tri-specific antibody according to claim 6 and a pharmaceutically acceptable carrier.

11. The tri-specific IgG antibody of claim 6, wherein the amino acid sequence of the VH comprises the amino acid sequence of SEQ ID NO: 41, 30, 46, or 40, with just one or no substitution, and the amino acid sequence of the VL comprises the amino acid sequence of SEQ ID NO: 51, 52, 53, 54, 55, 56, or 57, with just one or no substitution.

12. The tri-specific IgG antibody of claim 6, wherein the amino acid sequence of the VH comprises the amino acid sequence of SEQ ID NO: 41, 30, 46, or 40, and the amino acid sequence of the VL comprises the amino acid sequence of SEQ ID NO: 51, 52, 53, 54, 55, 56, or 57.

13. A tri-specific IgG antibody comprising:
 a dual-binding Fab comprising a first variable region that binds to human CD3 epsilon and human CD137, but does not bind to human CD3 epsilon and human CD137 at the same time;
 a second Fab comprising a second variable region that binds to a third antigen different from human CD3 epsilon and human CD137, wherein the third antigen is a cancer antigen; and
 an Fc region,
wherein the first variable region comprises:
 (1) a VL having at least 95% sequence identity to the amino acid sequence of SEQ ID NO: 51, 52, 53, 54, 55, 56, or 57, and
 (2) a VH that comprises an amino acid sequence comprising SEQ ID NO: 135 with a substitution at 2 to 10 positions, and wherein the VH comprises, at one or more positions selected from the following Kabat numbering positions, one of the amino acids indicated for that position:
 Ile, Asn, or Ser at position 31;
 Arg or Lys at position 52b;
 Ala, Gly, Leu, Gln, Val, or Ser at position 52c;
 Gln, Ser, or Asn at position 53;
 Ala, Gly, Leu, Gln, Ser, or Asn at position 54;
 Leu, Asn, or Ala at position 56;
 Ala, Asn, or Thr at position 57;
 Pro or Glu at position 61;
 Ala, Gly, Pro, Ser, Thr, Gln, or His at position 98;
 Ala, Leu, Ser, Gln, or Thr at position 99;
 Ala, Val, Gly, Ser, Thr, Tyr, or Phe at position 100;
 Ala, Val, Gly, Ser, Thr, Tyr, Phe, or Asp at position 100a;
 Gly, Ser, Thr, Tyr, Phe, or Asp at position 100b;
 Ala, Val, Leu, Gly, Ser, Tyr, or Phe at position 100c;
 Leu, Gly, Ser, Tyr, or Phe at position 100d;
 Pro, Gly, Ser, Tyr, or Phe at position 100e;
 Ala, Ser, Gln, Lys, Tyr, or Gly at position 100f;
 Tyr, Phe, or Gly at position 100g.

14. The tri-specific IgG antibody of claim 6, wherein the amino acid sequence of the VH has at least 95% sequence identity to the amino acid sequence of SEQ ID NO: 30.

15. The tri-specific IgG antibody of claim 6, wherein the amino acid sequence of the VL has at least 95% sequence identity to the amino acid sequence of SEQ ID NO: 51.

* * * * *

UNITED STATES PATENT AND TRADEMARK OFFICE
CERTIFICATE OF CORRECTION

| | |
|---|---|
| PATENT NO. | : 11,952,422 B2 |
| APPLICATION NO. | : 16/769299 |
| DATED | : April 9, 2024 |
| INVENTOR(S) | : Shun Shimizu et al. |

It is certified that error appears in the above-identified patent and that said Letters Patent is hereby corrected as shown below:

In the Specification

At Column 135, prior to Line 12, insert -- (4-3-2) Alteration of L chain --.

At Column 141, prior to Line 1, insert
-- (4-4) Evaluation of binding of one-amino acid alteration antibody to ECM (extracellular matrix) ECM (extracellular matrix) is an extracellular constituent and resides at various sites in vivo. Therefore, an antibody strongly binding to ECM is known to have poorer kinetics in blood (shorter half-life) (WO2012093704 A1). Thus, amino acids that do not enhance ECM binding are preferably selected as the amino acids that appear in the antibody library. --.

Signed and Sealed this
Sixth Day of August, 2024

Katherine Kelly Vidal
*Director of the United States Patent and Trademark Office*

SEQUENCE LISTING

```
<160> NUMBER OF SEQ ID NOS: 175

<210> SEQ ID NO 1
<211> LENGTH: 112
<212> TYPE: PRT
<213> ORGANISM: Artificial Sequence
<220> FEATURE:
<223> OTHER INFORMATION: an artificially synthesized sequence

<400> SEQUENCE: 1

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Arg Asn Thr Tyr Leu His Trp Tyr Gln Gln Lys Pro Gly Gln Ala
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80
```

```
Ser Arg Val Glu Ala Glu Asp Val Gly Val Tyr Tyr Cys Gly Gln Gly
                85                  90                  95

Thr Gln Val Pro Tyr Thr Phe Gly Gln Gly Thr Lys Leu Glu Ile Lys
            100                 105                 110

<210> SEQ ID NO 2
<211> LENGTH: 169
<212> TYPE: PRT
<213> ORGANISM: Artificial Sequence
<220> FEATURE:
<223> OTHER INFORMATION: an artificially synthesized sequence

<400> SEQUENCE: 2

Thr Ala Thr Ala Pro Gly Gly Leu Ser Ala Lys Ala Pro Ala Met Thr
1               5                   10                  15

Pro Leu Met Leu Asp Thr Ser Ser Arg Lys Leu Val Ala Trp Asp Gly
            20                  25                  30

Thr Thr Asp Gly Ala Ala Val Gly Ile Leu Ala Val Ala Ala Asp Gln
        35                  40                  45

Thr Ser Thr Thr Leu Thr Phe Tyr Lys Ser Gly Thr Phe Arg Tyr Glu
    50                  55                  60

Asp Val Leu Trp Pro Glu Ala Ala Ser Asp Glu Thr Lys Lys Arg Thr
65                  70                  75                  80

Ala Phe Ala Gly Thr Ala Ile Ser Ile Val Gly Gly Ser Glu Gly
                85                  90                  95

Gly Gly Ser Glu Gly Gly Gly Ser Glu Gly Gly Gly Ser Glu Gly Gly
            100                 105                 110

Gly Ser Gly Ser Phe Ser Thr Pro Val Trp Ile Ser Gln Ala Gln Gly
        115                 120                 125

Ile Arg Ala Gly Pro Gln Arg Leu Thr Gly Ser Ala Ala Phe Ser Thr
    130                 135                 140

Pro Val Trp Ile Ser Gln Ala Gln Gly Ile Arg Ala Gly Pro Gln Arg
145                 150                 155                 160

Leu Thr Val Lys Ala Arg Gly Thr Ser
                165

<210> SEQ ID NO 3
<211> LENGTH: 141
<212> TYPE: PRT
<213> ORGANISM: Artificial Sequence
<220> FEATURE:
<223> OTHER INFORMATION: an artificially synthesized sequence

<400> SEQUENCE: 3

Ser Ser Gly Gly Gly Ser Gly Gly Gly Ser Gly Gly Ser Ala Asp Ile
1               5                   10                  15

Val Met Thr Gln Ser Pro Leu Ser Leu Pro Val Thr Pro Gly Glu Pro
            20                  25                  30

Ala Ser Ile Ser Cys Arg Ser Gln Ser Leu Val His Ser Asn Arg
        35                  40                  45

Asn Thr Tyr Leu His Trp Tyr Gln Gln Lys Pro Gly Gln Ala Pro Arg
    50                  55                  60

Leu Leu Ile Tyr Lys Val Ser Asn Arg Phe Ser Gly Val Pro Asp Arg
65                  70                  75                  80

Phe Ser Gly Ser Gly Ser Gly Thr Asp Phe Thr Leu Lys Ile Ser Arg
                85                  90                  95

Val Glu Ala Glu Asp Val Gly Val Tyr Tyr Cys Gly Gln Gly Thr Gln
```

```
                   100                 105                 110

Val Pro Tyr Thr Phe Gly Gln Gly Thr Lys Leu Glu Ile Lys Ala Ala
            115                 120                 125

Ser Gly Ala Gly Gly Ser Gly Gly Gly Ser Gly Ser
        130                 135                 140
```

<210> SEQ ID NO 4
<211> LENGTH: 89
<212> TYPE: DNA
<213> ORGANISM: Artificial Sequence
<220> FEATURE:
<223> OTHER INFORMATION: an artificially synthesized sequence

<400> SEQUENCE: 4

```
atacgaaatt aatacgactc actataggga gaccacaacg gtttccctct agaaataatt    60
ttgtttaact ttaagaagga gatatatcc                                     89
```

<210> SEQ ID NO 5
<211> LENGTH: 129
<212> TYPE: PRT
<213> ORGANISM: Artificial Sequence
<220> FEATURE:
<223> OTHER INFORMATION: an artificially synthesized sequence

<400> SEQUENCE: 5

```
Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Ser Asn Ala
            20                  25                  30

Trp Met His Trp Val Arg Gln Ala Pro Gly Lys Gly Leu Glu Trp Val
        35                  40                  45

Ala Gln Ile Lys Asp Lys Ser Ser Leu Tyr Asn Thr Tyr Tyr Ala Pro
    50                  55                  60

Ser Val Lys Gly Arg Phe Thr Ile Ser Arg Asp Asp Ser Lys Asn Ser
65                  70                  75                  80

Ile Tyr Leu Gln Met Asn Ser Leu Lys Thr Glu Asp Thr Ala Val Tyr
                85                  90                  95

Tyr Cys Arg Tyr Val His Tyr Gly Ala Ser Tyr Gly Phe Leu Phe Ala
            100                 105                 110

Gly Tyr Gly Val Asp Ala Trp Gly Gln Gly Thr Thr Val Thr Val Ser
        115                 120                 125

Ser
```

<210> SEQ ID NO 6
<211> LENGTH: 15
<212> TYPE: PRT
<213> ORGANISM: Homo sapiens

<400> SEQUENCE: 6

```
Gln Asp Gly Asn Glu Glu Met Gly Gly Ile Thr Gln Thr Pro Tyr
1               5                   10                  15
```

<210> SEQ ID NO 7
<211> LENGTH: 129
<212> TYPE: PRT
<213> ORGANISM: Artificial Sequence
<220> FEATURE:
<223> OTHER INFORMATION: an artificially synthesized sequence

<400> SEQUENCE: 7

```
Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Ser Asn Ala
            20                  25                  30

Trp Met His Trp Val Arg Gln Ala Pro Gly Lys Gly Leu Glu Trp Val
            35                  40                  45

Ala Gln Ile Lys Asp Lys Ala Asn Ser Tyr Asn Thr Tyr Tyr Ala Pro
        50                  55                  60

Ser Val Lys Gly Arg Phe Thr Ile Ser Arg Asp Asp Ser Lys Asn Ser
65                  70                  75                  80

Ile Tyr Leu Gln Met Asn Ser Leu Lys Thr Glu Asp Thr Ala Val Tyr
                85                  90                  95

Tyr Cys Arg Tyr Val His Tyr Gly Ser Ser Tyr Gly Phe Leu Phe Ala
            100                 105                 110

Gly Tyr Gly Val Asp Ala Trp Gly Gln Gly Thr Thr Val Thr Val Ser
            115                 120                 125

Ser
```

<210> SEQ ID NO 8
<211> LENGTH: 306
<212> TYPE: PRT
<213> ORGANISM: Artificial Sequence
<220> FEATURE:
<223> OTHER INFORMATION: an artificially synthesized sequence

<400> SEQUENCE: 8

```
Ser Ser Gly Gly Gly Ser Gly Gly Gly Ser Gly Gly Ser Ala Gln Val
1               5                   10                  15

Gln Leu Val Glu Ser Gly Gly Gly Leu Val Gln Pro Gly Arg Ser Leu
            20                  25                  30

Arg Leu Ser Cys Ala Ala Ser Gly Phe Thr Phe Ser Asn Ala Trp Met
            35                  40                  45

His Trp Val Arg Gln Ala Pro Gly Lys Gly Leu Glu Trp Val Ala Gln
        50                  55                  60

Ile Lys Asp Lys Ala Asn Ser Tyr Asn Thr Tyr Tyr Ala Pro Ser Val
65                  70                  75                  80

Lys Gly Arg Phe Thr Ile Ser Arg Asp Asp Ser Lys Asn Ser Ile Tyr
                85                  90                  95

Leu Gln Met Asn Ser Leu Lys Thr Glu Asp Thr Ala Val Tyr Tyr Cys
            100                 105                 110

Arg Tyr Val His Tyr Gly Ser Ser Tyr Gly Phe Leu Phe Ala Gly Tyr
            115                 120                 125

Gly Val Asp Ala Trp Gly Gln Gly Thr Thr Val Thr Val Ser Ser Ser
        130                 135                 140

Ala Ala Ser Gly Ala Gly Gly Ser Gly Gly Gly Ser Gly Ser Ser Thr
145                 150                 155                 160

Ala Thr Ala Pro Gly Gly Leu Ser Ala Lys Pro Ala Met Thr Pro Leu
                165                 170                 175

Leu Met Leu Asp Thr Ser Ser Arg Lys Leu Val Ala Trp Asp Gly Thr
            180                 185                 190

Thr Asp Gly Ala Ala Val Gly Ile Leu Ala Val Ala Asp Gln Thr Ser
            195                 200                 205

Ser Thr Thr Leu Thr Phe Tyr Lys Ser Gly Thr Phe Arg Tyr Glu Asp
        210                 215                 220

Val Leu Trp Pro Glu Ala Ala Ser Asp Glu Thr Lys Lys Arg Thr Ala
```

```
                            225                 230                 235                 240

Phe Ala Gly Thr Ala Ile Ser Ile Val Gly Ser Gly Ser Phe Ser Thr
                            245                 250                 255

Pro Val Trp Ile Ser Gln Ala Gln Gly Ile Arg Ala Gly Pro Gln Arg
                            260                 265                 270

Leu Thr Gly Ser Ala Ala Phe Ser Thr Pro Val Trp Ile Ser Gln Ala
                            275                 280                 285

Gln Gly Ile Arg Ala Gly Pro Gln Arg Leu Thr Val Lys Ala Arg Gly
                            290                 295                 300

Thr Ser
          305

<210> SEQ ID NO 9
<211> LENGTH: 268
<212> TYPE: PRT
<213> ORGANISM: Artificial Sequence
<220> FEATURE:
<223> OTHER INFORMATION: an artificially synthesized sequence

<400> SEQUENCE: 9

Arg Thr Val Ala Ala Pro Ser Val Phe Ile Phe Pro Pro Ser Asp Glu
          1               5                   10                  15

Gln Leu Lys Ser Gly Thr Ala Ser Val Val Cys Leu Leu Asn Asn Phe
                          20                  25                  30

Tyr Pro Arg Glu Ala Lys Val Gln Trp Lys Val Asp Asn Ala Leu Gln
                      35                  40                  45

Ser Gly Asn Ser Gln Glu Ser Val Thr Glu Gln Asp Ser Lys Asp Ser
          50                  55                  60

Thr Tyr Ser Leu Ser Ser Thr Leu Thr Leu Ser Lys Ala Asp Tyr Glu
          65                  70                  75                  80

Lys His Lys Val Tyr Ala Cys Glu Val Thr His Gln Gly Leu Ser Ser
                          85                  90                  95

Pro Val Thr Lys Ser Phe Asn Arg Gly Glu Ala Ala Ser Gly Ala Gly
                      100                 105                 110

Gly Gly Ser Gly Gly Gly Ser Gly Ser Thr Ala Thr Ala Pro Gly Gly
                      115                 120                 125

Leu Ser Ala Lys Ala Pro Ala Met Thr Pro Leu Met Leu Asp Thr Ser
                  130                 135                 140

Ser Arg Lys Leu Val Ala Trp Asp Gly Thr Thr Asp Gly Ala Ala Val
          145                 150                 155                 160

Gly Ile Leu Ala Val Ala Ala Asp Gln Thr Ser Thr Thr Leu Thr Phe
                          165                 170                 175

Tyr Lys Ser Gly Thr Phe Arg Tyr Glu Asp Val Leu Trp Pro Glu Ala
                      180                 185                 190

Ala Ser Asp Glu Thr Lys Lys Arg Thr Ala Phe Ala Gly Thr Ala Ile
                  195                 200                 205

Ser Ile Val Gly Ser Gly Ser Phe Ser Thr Pro Val Trp Ile Ser Gln
                  210                 215                 220

Ala Gln Gly Ile Arg Ala Gly Pro Gln Arg Leu Thr Gly Ser Ala Ala
          225                 230                 235                 240

Phe Ser Thr Pro Val Trp Ile Ser Gln Ala Gln Gly Ile Arg Ala Gly
                          245                 250                 255

Pro Gln Arg Leu Thr Val Lys Ala Arg Gly Thr Ser
                      260                 265
```

```
<210> SEQ ID NO 10
<211> LENGTH: 98
<212> TYPE: PRT
<213> ORGANISM: Artificial Sequence
<220> FEATURE:
<223> OTHER INFORMATION: an artificially synthesized sequence

<400> SEQUENCE: 10

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Ala

<210> SEQ ID NO 11
<211> LENGTH: 112
<212> TYPE: PRT
<213> ORGANISM: Artificial Sequence
<220> FEATURE:
<223> OTHER INFORMATION: an artificially synthesized sequence

<400> SEQUENCE: 11

Asp Ile Val Met Thr Gln Ser Pro Leu Ser Leu Pro Val Thr Pro Gly
1               5                   10                  15

Glu Pro Ala Ser Ile Ser Cys Gln Ser Ser Glu Leu Leu His Ala
            20                  25                  30

Asn Arg Lys Thr Tyr Leu His Trp Tyr Gln Gln Lys Pro Gly Gln Ala
        35                  40                  45

Pro Arg Leu Leu Ile Tyr Lys Val Gln Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Gly
                85                  90                  95

Thr Ala Thr Pro Phe Thr Phe Gly Gln Gly Thr Lys Leu Glu Ile Lys
            100                 105                 110

<210> SEQ ID NO 12
<211> LENGTH: 112
<212> TYPE: PRT
<213> ORGANISM: Artificial Sequence
<220> FEATURE:
<223> OTHER INFORMATION: an artificially synthesized sequence

<400> SEQUENCE: 12

Asp Ile Val Met Thr Gln Ser Pro Leu Ser Leu Pro Val Thr Pro Gly
1               5                   10                  15

Glu Pro Ala Ser Ile Ser Cys Thr Ser Ser Gln Ser Leu Leu His Gln
            20                  25                  30

Asn Arg Asn Thr Tyr Leu His Trp Tyr Gln Gln Lys Pro Gly Gln Ala
        35                  40                  45
```

-continued

Pro Arg Leu Leu Ile Tyr Lys Val Ser Asn Arg Phe Asn Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Gly
                85                  90                  95

Thr Ala Asn Pro Phe Thr Phe Gly Gln Gly Thr Lys Leu Glu Ile Lys
            100                 105                 110

<210> SEQ ID NO 13
<211> LENGTH: 112
<212> TYPE: PRT
<213> ORGANISM: Artificial Sequence
<220> FEATURE:
<223> OTHER INFORMATION: an artificially synthesized sequence

<400> SEQUENCE: 13

Asp Ile Val Met Thr Gln Ser Pro Met Ser Leu Pro Val Thr Pro Gly
1               5                   10                  15

Glu Pro Ala Ser Ile Ser Cys Gln Ser Ser Glu Ser Leu Leu His Ala
            20                  25                  30

Asn Arg Asn Thr Tyr Leu His Trp Tyr Gln Gln Lys Pro Gly Gln Ala
        35                  40                  45

Pro Arg Leu Leu Ile Tyr Lys Val Ser Asn Arg Phe Asn Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Gly
                85                  90                  95

Thr Ala Asn Pro Tyr Thr Phe Gly Gln Gly Thr Lys Leu Glu Ile Lys
            100                 105                 110

<210> SEQ ID NO 14
<211> LENGTH: 112
<212> TYPE: PRT
<213> ORGANISM: Artificial Sequence
<220> FEATURE:
<223> OTHER INFORMATION: an artificially synthesized sequence

<400> SEQUENCE: 14

Asp Ile Val Met Thr Gln Ser Pro Leu Ser Leu Pro Val Thr Pro Gly
1               5                   10                  15

Glu Pro Ala Ser Ile Ser Cys Ala Ala Ser Glu Ser Leu Leu His Thr
            20                  25                  30

Asn Arg Asn Thr Tyr Leu His Trp Tyr Gln Gln Lys Pro Gly Gln Ala
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Gly
                85                  90                  95

Thr Gln Ser Pro Phe Thr Phe Gly Gln Gly Thr Lys Leu Glu Ile Lys
            100                 105                 110

<210> SEQ ID NO 15
<211> LENGTH: 112
<212> TYPE: PRT
<213> ORGANISM: Artificial Sequence
<220> FEATURE:
<223> OTHER INFORMATION: an artificially synthesized sequence

<400> SEQUENCE: 15

Asp Ile Val Met Thr Gln Ser Pro Leu Ser Leu Pro Val Thr Pro Gly
1               5                   10                  15

Glu Pro Ala Ser Ile Ser Cys Thr Ser Ser Gln Ser Leu Leu His Ala
            20                  25                  30

Asn Arg Asn Thr Tyr Leu His Trp Tyr Gln Gln Lys Pro Gly Gln Ala
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Gly
                85                  90                  95

Thr Ser Ala Pro Phe Thr Phe Gly Gln Gly Thr Lys Leu Glu Ile Lys
            100                 105                 110

<210> SEQ ID NO 16
<211> LENGTH: 399
<212> TYPE: PRT
<213> ORGANISM: Homo sapiens

<400> SEQUENCE: 16

Leu Gln Asp Pro Cys Ser Asn Cys Pro Ala Gly Thr Phe Cys Asp Asn
1               5                   10                  15

Asn Arg Asn Gln Ile Cys Ser Pro Cys Pro Pro Asn Ser Phe Ser Ser
            20                  25                  30

Ala Gly Gly Gln Arg Thr Cys Asp Ile Cys Arg Gln Cys Lys Gly Val
        35                  40                  45

Phe Arg Thr Arg Lys Glu Cys Ser Ser Thr Ser Asn Ala Glu Cys Asp
    50                  55                  60

Cys Thr Pro Gly Phe His Cys Leu Gly Ala Gly Cys Ser Met Cys Glu
65                  70                  75                  80

Gln Asp Cys Lys Gln Gly Gln Glu Leu Thr Lys Lys Gly Cys Lys Asp
                85                  90                  95

Cys Cys Phe Gly Thr Phe Asn Asp Gln Lys Arg Gly Ile Cys Arg Pro
            100                 105                 110

Trp Thr Asn Cys Ser Leu Asp Gly Lys Ser Val Leu Val Asn Gly Thr
        115                 120                 125

Lys Glu Arg Asp Val Val Cys Gly Pro Ser Pro Ala Asp Leu Ser Pro
    130                 135                 140

Gly Ala Ser Ser Val Thr Pro Pro Ala Pro Ala Arg Glu Pro Gly His
145                 150                 155                 160

Ser Pro Gln Asp Ile Glu Gly Arg Met Asp Pro Lys Ser Cys Asp Lys
                165                 170                 175

Thr His Thr Cys Pro Pro Cys Pro Ala Pro Glu Leu Leu Gly Gly Pro
            180                 185                 190

Ser Val Phe Leu Phe Pro Pro Lys Pro Lys Asp Thr Leu Met Ile Ser
        195                 200                 205

Arg Thr Pro Glu Val Thr Cys Val Val Val Asp Val Ser His Glu Asp
    210                 215                 220

Pro Glu Val Lys Phe Asn Trp Tyr Val Asp Gly Val Glu Val His Asn
225                 230                 235                 240

```
Ala Lys Thr Lys Pro Arg Glu Glu Gln Tyr Asn Ser Thr Tyr Arg Val
                245                 250                 255

Val Ser Val Leu Thr Val Leu His Gln Asp Trp Leu Asn Gly Lys Glu
            260                 265                 270

Tyr Lys Cys Lys Val Ser Asn Lys Ala Leu Pro Ala Pro Ile Glu Lys
        275                 280                 285

Thr Ile Ser Lys Ala Lys Gly Gln Pro Arg Glu Pro Gln Val Tyr Thr
    290                 295                 300

Leu Pro Pro Ser Arg Asp Glu Leu Thr Lys Asn Gln Val Ser Leu Thr
305                 310                 315                 320

Cys Leu Val Lys Gly Phe Tyr Pro Ser Asp Ile Ala Val Glu Trp Glu
                325                 330                 335

Ser Asn Gly Gln Pro Glu Asn Asn Tyr Lys Thr Thr Pro Pro Val Leu
            340                 345                 350

Asp Ser Asp Gly Ser Phe Phe Leu Tyr Ser Lys Leu Thr Val Asp Lys
        355                 360                 365

Ser Arg Trp Gln Gln Gly Asn Val Phe Ser Cys Ser Val Met His Glu
    370                 375                 380

Ala Leu His Asn His Tyr Thr Gln Lys Ser Leu Ser Leu Ser Pro
385                 390                 395

<210> SEQ ID NO 17
<211> LENGTH: 270
<212> TYPE: PRT
<213> ORGANISM: Artificial Sequence
<220> FEATURE:
<223> OTHER INFORMATION: an artificially synthesized sequence

<400> SEQUENCE: 17

Met Lys Ser Leu Phe Lys Val Thr Leu Leu Ala Thr Thr Met Ala Val
1               5                   10                  15

Ala Leu His Ala Pro Ile Thr Phe Ala Ala Glu Ala Ala Lys Pro Ala
                20                  25                  30

Thr Ala Ala Asp Ser Lys Ala Ala Phe Lys Asn Asp Asp Gln Lys Ser
            35                  40                  45

Ala Tyr Ala Leu Gly Ala Ser Leu Gly Arg Tyr Met Glu Asn Ser Leu
        50                  55                  60

Lys Glu Gln Glu Lys Leu Gly Ile Lys Leu Asp Lys Asp Gln Leu Ile
65                  70                  75                  80

Ala Gly Val Gln Asp Ala Phe Ala Asp Lys Ser Lys Leu Ser Asp Gln
                85                  90                  95

Glu Ile Glu Gln Thr Leu Gln Ala Phe Glu Ala Arg Val Lys Ser Ser
            100                 105                 110

Ala Gln Ala Lys Met Glu Lys Asp Ala Ala Asp Asn Glu Ala Lys Gly
        115                 120                 125

Lys Glu Tyr Arg Glu Lys Phe Ala Lys Glu Lys Gly Val Lys Thr Ser
    130                 135                 140

Ser Thr Gly Leu Val Tyr Gln Val Val Glu Ala Gly Lys Gly Glu Ala
145                 150                 155                 160

Pro Lys Asp Ser Asp Thr Val Val Val Asn Tyr Lys Gly Thr Leu Ile
                165                 170                 175

Asp Gly Lys Glu Phe Asp Asn Ser Tyr Thr Arg Gly Glu Pro Leu Ser
            180                 185                 190

Phe Arg Leu Asp Gly Val Ile Pro Gly Trp Thr Glu Gly Leu Lys Asn
        195                 200                 205
```

```
Ile Lys Lys Gly Gly Lys Ile Lys Leu Val Ile Pro Pro Glu Leu Ala
    210                 215                 220

Tyr Gly Lys Ala Gly Val Pro Gly Ile Pro Pro Asn Ser Thr Leu Val
225                 230                 235                 240

Phe Asp Val Glu Leu Leu Asp Val Lys Pro Ala Pro Lys Ala Asp Ala
                245                 250                 255

Lys Pro Glu Ala Asp Ala Lys Ala Ala Asp Ser Ala Lys Lys
        260                 265                 270

<210> SEQ ID NO 18
<211> LENGTH: 163
<212> TYPE: PRT
<213> ORGANISM: Macaca fascicularis

<400> SEQUENCE: 18

Leu Gln Asp Leu Cys Ser Asn Cys Pro Ala Gly Thr Phe Cys Asp Asn
1               5                   10                  15

Asn Arg Ser Gln Ile Cys Ser Pro Cys Pro Pro Asn Ser Phe Ser Ser
            20                  25                  30

Ala Gly Gly Gln Arg Thr Cys Asp Ile Cys Arg Gln Cys Lys Gly Val
        35                  40                  45

Phe Lys Thr Arg Lys Glu Cys Ser Ser Thr Ser Asn Ala Glu Cys Asp
50                  55                  60

Cys Ile Ser Gly Tyr His Cys Leu Gly Ala Glu Cys Ser Met Cys Glu
65                  70                  75                  80

Gln Asp Cys Lys Gln Gly Gln Glu Leu Thr Lys Lys Gly Cys Lys Asp
                85                  90                  95

Cys Cys Phe Gly Thr Phe Asn Asp Gln Lys Arg Gly Ile Cys Arg Pro
            100                 105                 110

Trp Thr Asn Cys Ser Leu Asp Gly Lys Ser Val Leu Val Asn Gly Thr
        115                 120                 125

Lys Glu Arg Asp Val Val Cys Gly Pro Ser Pro Ala Asp Leu Ser Pro
130                 135                 140

Gly Ala Ser Ser Ala Thr Pro Pro Ala Pro Ala Arg Glu Pro Gly His
145                 150                 155                 160

Ser Pro Gln

<210> SEQ ID NO 19
<211> LENGTH: 121
<212> TYPE: PRT
<213> ORGANISM: Artificial Sequence
<220> FEATURE:
<223> OTHER INFORMATION: an artificially synthesized sequence

<400> SEQUENCE: 19

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Ser Pro Glu Lys Gly Leu Glu Trp Ile
        35                  40                  45

Gly Glu Ile Asn His Gly Gly Tyr Val Thr Tyr Asn Pro Ser Leu Glu
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95
```

Arg Asp Tyr Gly Pro Gly Asn Tyr Asp Trp Tyr Phe Asp Leu Trp Gly
              100                 105                 110

Arg Gly Thr Leu Val Thr Val Ser Ser
              115                 120

<210> SEQ ID NO 20
<211> LENGTH: 109
<212> TYPE: PRT
<213> ORGANISM: Artificial Sequence
<220> FEATURE:
<223> OTHER INFORMATION: an artificially synthesized sequence

<400> SEQUENCE: 20

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Ala Leu Thr Phe Gly Gly Gly Thr Lys Val Glu Ile Lys
            100                 105

<210> SEQ ID NO 21
<211> LENGTH: 373
<212> TYPE: PRT
<213> ORGANISM: Artificial Sequence
<220> FEATURE:
<223> OTHER INFORMATION: an artificially synthesized sequence

<400> SEQUENCE: 21

Gln Asp Gly Asn Glu Glu Met Gly Gly Ile Thr Gln Thr Pro Tyr Lys
1               5                   10                  15

Val Ser Ile Ser Gly Thr Thr Val Ile Leu Thr Cys Pro Gln Tyr Pro
            20                  25                  30

Gly Ser Glu Ile Leu Trp Gln His Asn Asp Lys Asn Ile Gly Gly Asp
        35                  40                  45

Glu Asp Asp Lys Asn Ile Gly Ser Asp Glu Asp His Leu Ser Leu Lys
    50                  55                  60

Glu Phe Ser Glu Leu Glu Gln Ser Gly Tyr Tyr Val Cys Tyr Pro Arg
65                  70                  75                  80

Gly Ser Lys Pro Glu Asp Ala Asn Phe Tyr Leu Tyr Leu Arg Ala Arg
                85                  90                  95

Val Cys Glu Asn Cys Met Glu Met Asp Asp Ile Glu Gly Arg Met Asp
            100                 105                 110

Pro Lys Ser Cys Asp Lys Thr His Thr Cys Pro Pro Cys Pro Ala Pro
        115                 120                 125

Glu Leu Leu Gly Gly Pro Ser Val Phe Leu Phe Pro Pro Lys Pro Lys
    130                 135                 140

Asp Thr Leu Met Ile Ser Arg Thr Pro Glu Val Thr Cys Val Val Val
145                 150                 155                 160

Asp Val Ser His Glu Asp Pro Glu Val Lys Phe Asn Trp Tyr Val Asp

```
                165                 170                 175
Gly Val Glu Val His Asn Ala Lys Thr Lys Pro Arg Glu Glu Gln Tyr
            180                 185                 190

Asn Ser Thr Tyr Arg Val Val Ser Val Leu Thr Val Leu His Gln Asp
            195                 200                 205

Trp Leu Asn Gly Lys Glu Tyr Lys Cys Lys Val Ser Asn Lys Ala Leu
    210                 215                 220

Pro Ala Pro Ile Glu Lys Thr Ile Ser Lys Ala Lys Gly Gln Pro Arg
225                 230                 235                 240

Glu Pro Gln Val Cys Thr Leu Pro Pro Ser Arg Asp Glu Leu Thr Lys
                245                 250                 255

Asn Gln Val Ser Leu Trp Cys Leu Val Lys Gly Phe Tyr Pro Ser Asp
            260                 265                 270

Ile Ala Val Glu Trp Glu Ser Asn Gly Gln Pro Glu Asn Asn Tyr Lys
            275                 280                 285

Thr Thr Pro Pro Val Leu Asp Ser Asp Gly Ser Phe Phe Leu Tyr Ser
            290                 295                 300

Lys Leu Thr Val Asp Lys Ser Arg Trp Gln Gln Gly Asn Val Phe Ser
305                 310                 315                 320

Cys Ser Val Met His Glu Ala Leu His Asn His Tyr Thr Gln Lys Ser
                325                 330                 335

Leu Ser Leu Ser Pro Gly Gly Ser Gly Gly Ser Gly Asn Leu Tyr
            340                 345                 350

Phe Gln Gly Ser Gly Gly Gly Leu Asn Asp Ile Phe Glu Ala Gln Lys
            355                 360                 365

Ile Glu Trp His Glu
    370

<210> SEQ ID NO 22
<211> LENGTH: 323
<212> TYPE: PRT
<213> ORGANISM: Artificial Sequence
<220> FEATURE:
<223> OTHER INFORMATION: an artificially synthesized sequence

<400> SEQUENCE: 22

Phe Lys Ile Pro Ile Glu Glu Leu Glu Asp Arg Val Phe Val Asn Cys
1               5                   10                  15

Asn Thr Ser Ile Thr Trp Val Glu Gly Thr Val Gly Thr Leu Leu Ser
            20                  25                  30

Asp Ile Thr Arg Leu Asp Leu Gly Lys Arg Ile Leu Asp Pro Arg Gly
        35                  40                  45

Ile Tyr Arg Cys Asn Gly Thr Asp Ile Tyr Lys Asp Lys Glu Ser Thr
    50                  55                  60

Val Gln Val His Tyr Arg Met Cys Gln Ser Cys Val Glu Leu Asp Asp
65                  70                  75                  80

Ile Glu Gly Arg Met Asp Pro Lys Ser Cys Asp Lys Thr His Thr Cys
                85                  90                  95

Pro Pro Cys Pro Ala Pro Glu Leu Leu Gly Gly Pro Ser Val Phe Leu
            100                 105                 110

Phe Pro Pro Lys Pro Lys Asp Thr Leu Met Ile Ser Arg Thr Pro Glu
            115                 120                 125

Val Thr Cys Val Val Val Asp Val Ser His Glu Asp Pro Glu Val Lys
        130                 135                 140

Phe Asn Trp Tyr Val Asp Gly Val Glu Val His Asn Ala Lys Thr Lys
```

```
                145                 150                 155                 160
Pro Arg Glu Glu Gln Tyr Asn Ser Thr Tyr Arg Val Ser Val Leu
                    165                 170                 175

Thr Val Leu His Gln Asp Trp Leu Asn Gly Lys Glu Tyr Lys Cys Lys
                180                 185                 190

Val Ser Asn Lys Ala Leu Pro Ala Pro Ile Glu Lys Thr Ile Ser Lys
            195                 200                 205

Ala Lys Gly Gln Pro Arg Glu Pro Gln Val Tyr Thr Leu Pro Pro Ser
        210                 215                 220

Arg Cys Glu Leu Thr Lys Asn Gln Val Ser Leu Ser Cys Ala Val Lys
225                 230                 235                 240

Gly Phe Tyr Pro Ser Asp Ile Ala Val Glu Trp Glu Ser Asn Gly Gln
                245                 250                 255

Pro Glu Asn Asn Tyr Lys Thr Thr Pro Pro Val Leu Asp Ser Asp Gly
                260                 265                 270

Ser Phe Phe Leu Val Ser Lys Leu Thr Val Asp Lys Ser Arg Trp Gln
            275                 280                 285

Gln Gly Asn Val Phe Ser Cys Ser Val Met His Glu Ala Leu His Asn
        290                 295                 300

His Tyr Thr Gln Lys Ser Leu Ser Leu Ser Pro Asp Tyr Lys Asp Asp
305                 310                 315                 320

Asp Asp Lys

<210> SEQ ID NO 23
<211> LENGTH: 128
<212> TYPE: PRT
<213> ORGANISM: Artificial Sequence
<220> FEATURE:
<223> OTHER INFORMATION: an artificially synthesized sequence

<400> SEQUENCE: 23

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Ser Asn Ala
            20                  25                  30

Trp Met His Trp Val Arg Gln Ala Pro Gly Lys Gly Leu Glu Trp Val
        35                  40                  45

Ala Gln Ile Lys Asp Lys Gly Asn Ala Tyr Ala Ala Tyr Tyr Ala Pro
    50                  55                  60

Ser Val Lys Gly Arg Phe Thr Ile Ser Arg Asp Asp Ser Lys Asn Ser
65                  70                  75                  80

Ile Tyr Leu Gln Met Asn Ser Leu Lys Thr Glu Asp Thr Ala Val Tyr
                85                  90                  95

Tyr Cys His Tyr Val His Tyr Ala Ser Ala Ala Gly Gly Leu Pro Gly
            100                 105                 110

Phe Gly Val Asp Ala Trp Gly Gln Gly Thr Thr Val Thr Val Ser Ser
        115                 120                 125

<210> SEQ ID NO 24
<211> LENGTH: 128
<212> TYPE: PRT
<213> ORGANISM: Artificial Sequence
<220> FEATURE:
<223> OTHER INFORMATION: an artificially synthesized sequence

<400> SEQUENCE: 24

Gln Val Gln Leu Val Glu Ser Gly Gly Gly Leu Val Gln Pro Gly Arg
```

```
                1               5                   10                  15
            Ser Leu Arg Leu Ser Cys Ala Ala Ser Gly Phe Thr Phe Ser Asn Ala
                            20                  25                  30

Trp Met His Trp Val Arg Gln Ala Pro Gly Lys Gly Leu Glu Trp Val
                        35                  40                  45

Ala Gln Ile Lys Asp Arg Ser Gln Leu Tyr Ala Tyr Tyr Ala Pro
                50                  55                  60

Ser Val Lys Gly Arg Phe Thr Ile Ser Arg Asp Asp Ser Lys Asn Ser
            65                  70                  75                  80

Ile Tyr Leu Gln Met Asn Ser Leu Lys Thr Glu Asp Thr Ala Val Tyr
                            85                  90                  95

Tyr Cys His Tyr Val His Tyr Ala Ser Ala Ser Thr Val Leu Gly Ala
                            100                 105                 110

Tyr Gly Val Asp Ala Trp Gly Gln Gly Thr Thr Val Thr Val Ser Ser
                            115                 120                 125
```

<210> SEQ ID NO 25
<211> LENGTH: 128
<212> TYPE: PRT
<213> ORGANISM: Artificial Sequence
<220> FEATURE:
<223> OTHER INFORMATION: an artificially synthesized sequence

<400> SEQUENCE: 25

```
            Gln Val Gln Leu Val Glu Ser Gly Gly Gly Leu Val Gln Pro Gly Arg
            1               5                   10                  15

Ser Leu Arg Leu Ser Cys Ala Ala Ser Gly Phe Thr Phe Ser Asn Ala
                            20                  25                  30

Trp Met His Trp Val Arg Gln Ala Pro Gly Lys Gly Leu Glu Trp Val
                        35                  40                  45

Ala Gln Ile Lys Asp Arg Ala Asn Ser Tyr Asn Ala Tyr Tyr Ala Pro
                50                  55                  60

Ser Val Lys Gly Arg Phe Thr Ile Ser Arg Asp Asp Ser Lys Asn Ser
            65                  70                  75                  80

Ile Tyr Leu Gln Met Asn Ser Leu Lys Thr Glu Asp Thr Ala Val Tyr
                            85                  90                  95

Tyr Cys His Tyr Val His Tyr Ser Ala Ala Ser Thr Leu Leu Pro Ser
                            100                 105                 110

Phe Gly Val Asp Ala Trp Gly Gln Gly Thr Thr Val Thr Val Ser Ser
                            115                 120                 125
```

<210> SEQ ID NO 26
<211> LENGTH: 128
<212> TYPE: PRT
<213> ORGANISM: Artificial Sequence
<220> FEATURE:
<223> OTHER INFORMATION: an artificially synthesized sequence

<400> SEQUENCE: 26

```
            Gln Val Gln Leu Val Glu Ser Gly Gly Gly Leu Val Gln Pro Gly Arg
            1               5                   10                  15

Ser Leu Arg Leu Ser Cys Ala Ala Ser Gly Phe Thr Phe Ser Asn Ala
                            20                  25                  30

Trp Met His Trp Val Arg Gln Ala Pro Gly Lys Gly Leu Glu Trp Val
                        35                  40                  45

Ala Gln Ile Lys Asp Lys Gln Asn Leu Tyr Asn Ala Tyr Tyr Ala Glu
                50                  55                  60
```

```
Ser Val Lys Gly Arg Phe Thr Ile Ser Arg Asp Asp Ser Lys Asn Ser
 65                  70                  75                  80

Ile Tyr Leu Gln Met Asn Ser Leu Lys Thr Glu Asp Thr Ala Val Tyr
                 85                  90                  95

Tyr Cys His Tyr Val His Tyr Ala Ser Ala Ser Thr Val Leu Pro Ala
            100                 105                 110

Phe Gly Val Asp Ala Trp Gly Gln Gly Thr Thr Val Thr Val Ser Ser
        115                 120                 125

<210> SEQ ID NO 27
<211> LENGTH: 128
<212> TYPE: PRT
<213> ORGANISM: Artificial Sequence
<220> FEATURE:
<223> OTHER INFORMATION: an artificially synthesized sequence

<400> SEQUENCE: 27

Gln Val Gln Leu Val Glu Ser Gly Gly Gly Leu Val Gln Pro Gly Arg
  1               5                  10                  15

Ser Leu Arg Leu Ser Cys Ala Ala Ser Gly Phe Thr Phe Ser Ile Ala
                 20                  25                  30

Trp Met His Trp Val Arg Gln Ala Pro Gly Lys Gly Leu Glu Trp Val
             35                  40                  45

Ala Gln Ile Lys Asp Lys Val Asn Gly Tyr Thr Ala Tyr Tyr Ala Glu
 50                  55                  60

Ser Val Lys Gly Arg Phe Thr Ile Ser Arg Asp Asp Ser Lys Asn Ser
 65                  70                  75                  80

Ile Tyr Leu Gln Met Asn Ser Leu Lys Thr Glu Asp Thr Ala Val Tyr
                 85                  90                  95

Tyr Cys Arg Tyr Val His Tyr Ala Ala Tyr Tyr Asp Val Leu Gly Tyr
            100                 105                 110

Gly Gly Val Asp Ala Trp Gly Gln Gly Thr Thr Val Thr Val Ser Ser
        115                 120                 125

<210> SEQ ID NO 28
<211> LENGTH: 128
<212> TYPE: PRT
<213> ORGANISM: Artificial Sequence
<220> FEATURE:
<223> OTHER INFORMATION: an artificially synthesized sequence

<400> SEQUENCE: 28

Gln Val Gln Leu Val Glu Ser Gly Gly Gly Leu Val Gln Pro Gly Arg
  1               5                  10                  15

Ser Leu Arg Leu Ser Cys Ala Ala Ser Gly Phe Thr Phe Ser Ile Ala
                 20                  25                  30

Trp Met His Trp Val Arg Gln Ala Pro Gly Lys Gly Leu Glu Trp Val
             35                  40                  45

Ala Gln Ile Lys Asp Arg Val Asn Ala Tyr Glu Ala Tyr Tyr Ala Pro
 50                  55                  60

Ser Val Lys Gly Arg Phe Thr Ile Ser Arg Asp Asp Ser Lys Asn Ser
 65                  70                  75                  80

Ile Tyr Leu Gln Met Asn Ser Leu Lys Thr Glu Asp Thr Ala Val Tyr
                 85                  90                  95

Tyr Cys Arg Tyr Val His Tyr Ala Ser Tyr Tyr Asp Leu Leu Gly Tyr
            100                 105                 110

Gly Gly Val Asp Ala Trp Gly Gln Gly Thr Thr Val Thr Val Ser Ser
        115                 120                 125
```

<210> SEQ ID NO 29
<211> LENGTH: 128
<212> TYPE: PRT
<213> ORGANISM: Artificial Sequence
<220> FEATURE:
<223> OTHER INFORMATION: an artificially synthesized sequence

<400> SEQUENCE: 29

```
Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Ser Asn Ala
                20                  25                  30

Trp Met His Trp Val Arg Gln Ala Pro Gly Lys Gly Leu Glu Trp Val
            35                  40                  45

Ala Gln Ile Lys Asp Arg Gly Gln Gln Tyr Asn Ala Tyr Tyr Ala Pro
        50                  55                  60

Ser Val Lys Gly Arg Phe Thr Ile Ser Arg Asp Asp Ser Lys Asn Ser
65                  70                  75                  80

Ile Tyr Leu Gln Met Asn Ser Leu Lys Thr Glu Asp Thr Ala Val Tyr
                85                  90                  95

Tyr Cys His Tyr Val His Tyr Ala Ser Ala Ser Ser Val Leu Pro Gly
            100                 105                 110

Tyr Gly Val Asp Ala Trp Gly Gln Gly Thr Thr Val Thr Val Ser Ser
        115                 120                 125
```

<210> SEQ ID NO 30
<211> LENGTH: 128
<212> TYPE: PRT
<213> ORGANISM: Artificial Sequence
<220> FEATURE:
<223> OTHER INFORMATION: an artificially synthesized sequence

<400> SEQUENCE: 30

```
Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Ser Asn Ala
                20                  25                  30

Trp Met His Trp Val Arg Gln Ala Pro Gly Lys Gly Leu Glu Trp Val
            35                  40                  45

Ala Gln Ile Lys Asp Lys Gly Asn Ala Tyr Ala Tyr Tyr Ala Pro
        50                  55                  60

Ser Val Lys Gly Arg Phe Thr Ile Ser Arg Asp Asp Ser Lys Asn Ser
65                  70                  75                  80

Ile Tyr Leu Gln Met Asn Ser Leu Lys Thr Glu Asp Thr Ala Val Tyr
                85                  90                  95

Tyr Cys His Tyr Val His Tyr Ala Ser Ala Ser Thr Val Leu Pro Ala
            100                 105                 110

Phe Gly Val Asp Ala Trp Gly Gln Gly Thr Thr Val Thr Val Ser Ser
        115                 120                 125
```

<210> SEQ ID NO 31
<211> LENGTH: 128
<212> TYPE: PRT
<213> ORGANISM: Artificial Sequence
<220> FEATURE:
<223> OTHER INFORMATION: an artificially synthesized sequence

<400> SEQUENCE: 31

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Ser Asn Ala
            20                  25                  30

Trp Met His Trp Val Arg Gln Ala Pro Gly Lys Gly Leu Glu Trp Val
        35                  40                  45

Ala Gln Ile Lys Asp Arg Ser Asn Gln Tyr Ala Thr Tyr Tyr Ala Pro
    50                  55                  60

Ser Val Lys Gly Arg Phe Thr Ile Ser Arg Asp Asp Ser Lys Asn Ser
65                  70                  75                  80

Ile Tyr Leu Gln Met Asn Ser Leu Lys Thr Glu Asp Thr Ala Val Tyr
                85                  90                  95

Tyr Cys His Tyr Val His Tyr Ala Ser Ala Ser Thr Val Leu Pro Ala
            100                 105                 110

Phe Gly Val Asp Ala Trp Gly Gln Gly Thr Thr Val Thr Val Ser Ser
            115                 120                 125

<210> SEQ ID NO 32
<211> LENGTH: 128
<212> TYPE: PRT
<213> ORGANISM: Artificial Sequence
<220> FEATURE:
<223> OTHER INFORMATION: an artificially synthesized sequence

<400> SEQUENCE: 32

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Ser Asn Ala
            20                  25                  30

Trp Met His Trp Val Arg Gln Ala Pro Gly Lys Gly Leu Glu Trp Val
        35                  40                  45

Ala Gln Ile Lys Asp Arg Gly Asn Ala Tyr Asn Ala Tyr Tyr Ala Glu
    50                  55                  60

Ser Val Lys Gly Arg Phe Thr Ile Ser Arg Asp Asp Ser Lys Asn Ser
65                  70                  75                  80

Ile Tyr Leu Gln Met Asn Ser Leu Lys Thr Glu Asp Thr Ala Val Tyr
                85                  90                  95

Tyr Cys His Tyr Val His Tyr Ala Ser Ala Ser Thr Val Leu Pro Ala
            100                 105                 110

Phe Gly Val Asp Ala Trp Gly Gln Gly Thr Thr Val Thr Val Ser Ser
            115                 120                 125

<210> SEQ ID NO 33
<211> LENGTH: 128
<212> TYPE: PRT
<213> ORGANISM: Artificial Sequence
<220> FEATURE:
<223> OTHER INFORMATION: an artificially synthesized sequence

<400> SEQUENCE: 33

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Ser Asn Ala
            20                  25                  30

Trp Met His Trp Val Arg Gln Ala Pro Gly Lys Gly Leu Glu Trp Val
        35                  40                  45

Ala Gln Ile Lys Asp Arg Ser Asn Ala Tyr Ala Ala Tyr Tyr Ala Pro
    50                  55                  60

```
Ser Val Lys Gly Arg Phe Thr Ile Ser Arg Asp Asp Ser Lys Asn Ser
65                  70                  75                  80

Ile Tyr Leu Gln Met Asn Ser Leu Lys Thr Glu Asp Thr Ala Val Tyr
                85                  90                  95

Tyr Cys His Tyr Val His Tyr Ala Ser Ala Ser Thr Val Leu Pro Ala
            100                 105                 110

Phe Gly Val Asp Ala Trp Gly Gln Gly Thr Thr Val Thr Val Ser Ser
        115                 120                 125

<210> SEQ ID NO 34
<211> LENGTH: 128
<212> TYPE: PRT
<213> ORGANISM: Artificial Sequence
<220> FEATURE:
<223> OTHER INFORMATION: an artificially synthesized sequence

<400> SEQUENCE: 34

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Ser Asn Ala
                20                  25                  30

Trp Met His Trp Val Arg Gln Ala Pro Gly Lys Gly Leu Glu Trp Val
            35                  40                  45

Ala Gln Ile Lys Asp Lys Gln Ser Gly Tyr Asn Thr Tyr Tyr Ala Pro
        50                  55                  60

Ser Val Lys Gly Arg Phe Thr Ile Ser Arg Asp Asp Ser Lys Asn Ser
65                  70                  75                  80

Ile Tyr Leu Gln Met Asn Ser Leu Lys Thr Glu Asp Thr Ala Val Tyr
                85                  90                  95

Tyr Cys His Tyr Val His Tyr Ala Ser Ala Ser Thr Val Leu Pro Ala
            100                 105                 110

Phe Gly Val Asp Ala Trp Gly Gln Gly Thr Thr Val Thr Val Ser Ser
        115                 120                 125

<210> SEQ ID NO 35
<211> LENGTH: 128
<212> TYPE: PRT
<213> ORGANISM: Artificial Sequence
<220> FEATURE:
<223> OTHER INFORMATION: an artificially synthesized sequence

<400> SEQUENCE: 35

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Ser Asn Ala
                20                  25                  30

Trp Met His Trp Val Arg Gln Ala Pro Gly Lys Gly Leu Glu Trp Val
            35                  40                  45

Ala Gln Ile Lys Asp Arg Ser Asn Asn Tyr Ala Thr Tyr Tyr Ala Glu
        50                  55                  60

Ser Val Lys Gly Arg Phe Thr Ile Ser Arg Asp Asp Ser Lys Asn Ser
65                  70                  75                  80

Ile Tyr Leu Gln Met Asn Ser Leu Lys Thr Glu Asp Thr Ala Val Tyr
                85                  90                  95

Tyr Cys His Tyr Val His Tyr Ala Ser Ala Ser Thr Val Leu Pro Ala
            100                 105                 110

Phe Gly Val Asp Ala Trp Gly Gln Gly Thr Thr Val Thr Val Ser Ser
```

-continued 115                  120                  125

```
<210> SEQ ID NO 36
<211> LENGTH: 128
<212> TYPE: PRT
<213> ORGANISM: Artificial Sequence
<220> FEATURE:
<223> OTHER INFORMATION: an artificially synthesized sequence

<400> SEQUENCE: 36
```

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Ser Asn Ala
            20                  25                  30

Trp Met His Trp Val Arg Gln Ala Pro Gly Lys Gly Leu Glu Trp Val
        35                  40                  45

Ala Gln Ile Lys Asp Arg Ser Gln Leu Tyr Ala Ala Tyr Tyr Ala Pro
    50                  55                  60

Ser Val Lys Gly Arg Phe Thr Ile Ser Arg Asp Asp Ser Lys Asn Ser
65                  70                  75                  80

Ile Tyr Leu Gln Met Asn Ser Leu Lys Thr Glu Asp Thr Ala Val Tyr
                85                  90                  95

Tyr Cys His Tyr Val His Tyr Ala Ser Ala Ser Thr Val Leu Pro Ala
            100                 105                 110

Phe Gly Val Asp Ala Trp Gly Gln Gly Thr Thr Val Thr Val Ser Ser
            115                 120                 125

```
<210> SEQ ID NO 37
<211> LENGTH: 128
<212> TYPE: PRT
<213> ORGANISM: Artificial Sequence
<220> FEATURE:
<223> OTHER INFORMATION: an artificially synthesized sequence

<400> SEQUENCE: 37
```

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Ser Asn Ala
            20                  25                  30

Trp Met His Trp Val Arg Gln Ala Pro Gly Lys Gly Leu Glu Trp Val
        35                  40                  45

Ala Gln Ile Lys Asp Arg Ser Asn Gln Tyr Ala Thr Tyr Tyr Ala Pro
    50                  55                  60

Ser Val Lys Gly Arg Phe Thr Ile Ser Arg Asp Asp Ser Lys Asn Ser
65                  70                  75                  80

Ile Tyr Leu Gln Met Asn Ser Leu Lys Thr Glu Asp Thr Ala Val Tyr
                85                  90                  95

Tyr Cys His Tyr Val His Tyr Ser Ala Ala Ser Thr Leu Leu Pro Ser
            100                 105                 110

Phe Gly Val Asp Ala Trp Gly Gln Gly Thr Thr Val Thr Val Ser Ser
            115                 120                 125

```
<210> SEQ ID NO 38
<211> LENGTH: 126
<212> TYPE: PRT
<213> ORGANISM: Artificial Sequence
<220> FEATURE:
<223> OTHER INFORMATION: an artificially synthesized sequence

<400> SEQUENCE: 38
```

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Ser Asn Ala
            20                  25                  30

Trp Met His Trp Val Arg Gln Ala Pro Gly Lys Gly Leu Glu Trp Val
        35                  40                  45

Ala Gln Ile Lys Asp Arg Gln Gln Gly Tyr Ala Thr Tyr Tyr Ala Pro
    50                  55                  60

Ser Val Lys Gly Arg Phe Thr Ile Ser Arg Asp Asp Ser Lys Asn Ser
65                  70                  75                  80

Ile Tyr Leu Gln Met Asn Ser Leu Lys Thr Glu Asp Thr Ala Val Tyr
            85                  90                  95

Tyr Cys Arg Phe Val His Tyr His Leu Ala Gly Tyr Gly Tyr Tyr Gly
            100                 105                 110

Val Asp Ala Trp Gly Gln Gly Thr Thr Val Thr Val Ser Ser
            115                 120                 125

<210> SEQ ID NO 39
<211> LENGTH: 127
<212> TYPE: PRT
<213> ORGANISM: Artificial Sequence
<220> FEATURE:
<223> OTHER INFORMATION: an artificially synthesized sequence

<400> SEQUENCE: 39

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Ser Asn Ala
            20                  25                  30

Trp Met His Trp Val Arg Gln Ala Pro Gly Lys Gly Leu Glu Trp Val
        35                  40                  45

Ala Gln Ile Lys Asp Arg Gly Asn Ala Tyr Asn Ala Tyr Tyr Ala Glu
    50                  55                  60

Ser Val Lys Gly Arg Phe Thr Ile Ser Arg Asp Asp Ser Lys Asn Ser
65                  70                  75                  80

Ile Tyr Leu Gln Met Asn Ser Leu Lys Thr Glu Asp Thr Ala Val Tyr
            85                  90                  95

Tyr Cys Arg Phe Val His Tyr Arg His Pro Leu Leu His Ile Gln Tyr
            100                 105                 110

Gly Val Asp Ala Trp Gly Gln Gly Thr Thr Val Thr Val Ser Ser
            115                 120                 125

<210> SEQ ID NO 40
<211> LENGTH: 128
<212> TYPE: PRT
<213> ORGANISM: Artificial Sequence
<220> FEATURE:
<223> OTHER INFORMATION: an artificially synthesized sequence

<400> SEQUENCE: 40

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Ser Asn Ala
            20                  25                  30

Trp Met His Trp Val Arg Gln Ala Pro Gly Lys Gly Leu Glu Trp Ile
        35                  40                  45

Ala Gln Ile Lys Asp Arg Ser Asn Gln Tyr Ala Thr Tyr Tyr Ala Pro

```
                  50                  55                  60

Ser Val Lys Gly Arg Phe Thr Ile Ser Arg Asp Asp Ser Lys Asn Ser
 65                  70                  75                  80

Ile Tyr Leu Gln Met Asn Ser Leu Lys Thr Glu Asp Thr Ala Val Tyr
                     85                  90                  95

Tyr Cys His Tyr Val His Tyr Ala Gln Ala Ser Ser Leu Leu Pro Ser
                    100                 105                 110

Phe Gly Val Asp Ala Trp Gly Gln Gly Thr Thr Val Thr Val Ser Ser
                    115                 120                 125
```

<210> SEQ ID NO 41
<211> LENGTH: 128
<212> TYPE: PRT
<213> ORGANISM: Artificial Sequence
<220> FEATURE:
<223> OTHER INFORMATION: an artificially synthesized sequence

<400> SEQUENCE: 41

```
Gln Val Gln Leu Val Glu Ser Gly Gly Gly Leu Val Gln Pro Gly Arg
  1               5                  10                  15

Ser Leu Arg Leu Ser Cys Ala Ala Ser Gly Phe Thr Phe Ser Asn Ala
                 20                  25                  30

Trp Met His Trp Val Arg Gln Ala Pro Gly Lys Gly Leu Glu Trp Val
             35                  40                  45

Ala Gln Ile Lys Asp Lys Gly Asn Leu Tyr Ala Ala Tyr Tyr Ala Pro
         50                  55                  60

Ser Val Lys Gly Arg Phe Thr Ile Ser Arg Asp Asp Ser Lys Asn Ser
 65                  70                  75                  80

Ile Tyr Leu Gln Met Asn Ser Leu Lys Thr Glu Asp Thr Ala Val Tyr
                     85                  90                  95

Tyr Cys His Tyr Val His Tyr Ala Ser Ala Gly Gly Gly Leu Pro Gly
                    100                 105                 110

Phe Gly Val Asp Ala Trp Gly Gln Gly Thr Thr Val Thr Val Ser Ser
                    115                 120                 125
```

<210> SEQ ID NO 42
<211> LENGTH: 129
<212> TYPE: PRT
<213> ORGANISM: Artificial Sequence
<220> FEATURE:
<223> OTHER INFORMATION: an artificially synthesized sequence

<400> SEQUENCE: 42

```
Gln Val Gln Leu Val Glu Ser Gly Gly Gly Leu Val Gln Pro Gly Ser
  1               5                  10                  15

Ser Leu Arg Leu Ser Cys Ala Ala Ser Gly Phe Thr Phe Ser Ser Ala
                 20                  25                  30

Trp Met His Trp Val Arg Gln Ala Pro Gly Lys Gly Leu Glu Trp Val
             35                  40                  45

Ala Gln Ile Lys Asp Arg Gly Asn Gln Tyr Ala Thr Tyr Tyr Ala Glu
         50                  55                  60

Ser Val Lys Gly Arg Phe Thr Ile Ser Arg Asp Asp Ser Lys Asn Ser
 65                  70                  75                  80

Ile Tyr Leu Gln Met Asn Ser Leu Lys Lys Leu Lys Thr Pro Pro Phe
                     85                  90                  95

Thr Ile Ala Arg Tyr Val His Tyr Thr Ser Phe Ser Tyr Ala Tyr Phe
                    100                 105                 110
```

Lys Phe Gly Val Asp Ala Trp Gly Gln Gly Thr Thr Val Thr Val Ser
            115                 120                 125

Ser

<210> SEQ ID NO 43
<211> LENGTH: 128
<212> TYPE: PRT
<213> ORGANISM: Artificial Sequence
<220> FEATURE:
<223> OTHER INFORMATION: an artificially synthesized sequence

<400> SEQUENCE: 43

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Ser Asn Ala
                20                  25                  30

Trp Met His Trp Val Arg Gln Ala Pro Gly Lys Gly Leu Glu Trp Val
            35                  40                  45

Ala Gln Ile Lys Asp Lys Gly Asn Leu Tyr Ala Ala Tyr Tyr Ala Pro
        50                  55                  60

Ser Val Lys Gly Arg Phe Thr Ile Ser Arg Asp Asp Ser Lys Asn Ser
65                  70                  75                  80

Ile Tyr Leu Gln Met Asn Ser Leu Lys Thr Glu Asp Thr Ala Val Tyr
                85                  90                  95

Tyr Cys His Tyr Val His Tyr Ala Ser Ala Gly Gly Leu Ser Ala
            100                 105                 110

Tyr Gly Val Asp Ala Trp Gly Gln Gly Thr Thr Val Thr Val Ser Ser
            115                 120                 125

<210> SEQ ID NO 44
<211> LENGTH: 128
<212> TYPE: PRT
<213> ORGANISM: Artificial Sequence
<220> FEATURE:
<223> OTHER INFORMATION: an artificially synthesized sequence

<400> SEQUENCE: 44

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Ser Ser Ala
                20                  25                  30

Trp Met His Trp Val Arg Gln Ala Pro Gly Lys Gly Leu Glu Trp Val
            35                  40                  45

Ala Gln Ile Lys Asp Arg Ala Ser Ala Tyr Asn Ala Tyr Tyr Ala Glu
        50                  55                  60

Ser Val Lys Gly Arg Phe Thr Ile Ser Arg Asp Asp Ser Lys Asn Ser
65                  70                  75                  80

Ile Tyr Leu Gln Met Asn Ser Leu Lys Thr Glu Asp Thr Ala Val Tyr
                85                  90                  95

Tyr Cys Arg Tyr Val His Tyr Pro Ser Tyr Val Ser Phe Leu Pro Tyr
            100                 105                 110

Tyr Gly Val Asp Ala Trp Gly Gln Gly Thr Thr Val Thr Val Ser Ser
            115                 120                 125

<210> SEQ ID NO 45
<211> LENGTH: 128
<212> TYPE: PRT
<213> ORGANISM: Artificial Sequence
<220> FEATURE:

<223> OTHER INFORMATION: an artificially synthesized sequence

<400> SEQUENCE: 45

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Ser Asn Ala
            20                  25                  30

Trp Met His Trp Val Arg Gln Ala Pro Gly Lys Gly Leu Glu Trp Ile
        35                  40                  45

Ala Gln Ile Lys Asp Arg Gly Asn Asn Tyr Asn Asn Tyr Tyr Ala Pro
    50                  55                  60

Ser Val Lys Gly Arg Phe Thr Ile Ser Arg Asp Asp Ser Lys Asn Ser
65                  70                  75                  80

Ile Tyr Leu Gln Met Asn Ser Leu Lys Thr Glu Asp Thr Ala Val Tyr
                85                  90                  95

Tyr Cys His Tyr Val His Tyr Ala Thr Ala Ser Thr Leu Leu Gly Ala
            100                 105                 110

Tyr Gly Val Asp Ala Trp Gly Gln Gly Thr Thr Val Thr Val Ser Ser
        115                 120                 125

<210> SEQ ID NO 46
<211> LENGTH: 128
<212> TYPE: PRT
<213> ORGANISM: Artificial Sequence
<220> FEATURE:
<223> OTHER INFORMATION: an artificially synthesized sequence

<400> SEQUENCE: 46

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Ser Asn Ala
            20                  25                  30

Trp Met His Trp Val Arg Gln Ala Pro Gly Lys Gly Leu Glu Trp Val
        35                  40                  45

Ala Gln Ile Lys Asp Arg Ser Asn Gln Tyr Ala Thr Tyr Tyr Ala Pro
    50                  55                  60

Ser Val Lys Gly Arg Phe Thr Ile Ser Arg Asp Asp Ser Lys Asn Ser
65                  70                  75                  80

Ile Tyr Leu Gln Met Asn Ser Leu Lys Thr Glu Asp Thr Ala Val Tyr
                85                  90                  95

Tyr Cys His Tyr Val His Tyr Ala Gln Ala Ser Thr Val Leu Pro Ala
            100                 105                 110

Phe Gly Val Asp Ala Trp Gly Gln Gly Thr Thr Val Thr Val Ser Ser
        115                 120                 125

<210> SEQ ID NO 47
<211> LENGTH: 128
<212> TYPE: PRT
<213> ORGANISM: Artificial Sequence
<220> FEATURE:
<223> OTHER INFORMATION: an artificially synthesized sequence

<400> SEQUENCE: 47

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Ser Asn Ala
            20                  25                  30

Trp Met His Trp Val Arg Gln Ala Pro Gly Lys Gly Leu Glu Trp Val

```
                    35                  40                  45

Ala Gln Ile Lys Asp Arg Ser Ser Tyr Leu Thr Tyr Tyr Ala Glu
 50                  55                  60

Ser Val Lys Gly Arg Phe Thr Ile Ser Arg Asp Asp Ser Lys Asn Ser
 65                  70                  75                  80

Ile Tyr Leu Gln Met Asn Ser Leu Lys Thr Glu Asp Thr Ala Val Tyr
                     85                  90                  95

Tyr Cys His Tyr Val His Tyr Ala Ser Ser Thr Leu Leu Pro Ser
                    100                 105                 110

Phe Gly Val Asp Ala Trp Gly Gln Gly Thr Thr Val Thr Val Ser Ser
                115                 120                 125

<210> SEQ ID NO 48
<211> LENGTH: 128
<212> TYPE: PRT
<213> ORGANISM: Artificial Sequence
<220> FEATURE:
<223> OTHER INFORMATION: an artificially synthesized sequence

<400> SEQUENCE: 48

Gln Val Gln Leu Val Glu Ser Gly Gly Gly Leu Val Gln Pro Gly Arg
 1               5                  10                  15

Ser Leu Arg Leu Ser Cys Ala Ala Ser Gly Phe Thr Phe Ser Asn Ala
                20                  25                  30

Trp Met His Trp Val Arg Gln Ala Pro Gly Lys Gly Leu Glu Trp Val
                35                  40                  45

Ala Gln Ile Lys Asp Lys Gly Asn Ala Tyr Ala Ala Tyr Tyr Ala Pro
 50                  55                  60

Ser Val Lys Gly Arg Phe Thr Ile Ser Arg Asp Asp Ser Lys Asn Ser
 65                  70                  75                  80

Ile Tyr Leu Gln Met Asn Ser Leu Lys Thr Glu Asp Thr Ala Val Tyr
                     85                  90                  95

Tyr Cys His Tyr Val His Tyr Ser Ala Ser Thr Val Leu Pro Ala
                    100                 105                 110

Phe Gly Val Asp Ala Trp Gly Gln Gly Thr Thr Val Thr Val Ser Ser
                115                 120                 125

<210> SEQ ID NO 49
<211> LENGTH: 128
<212> TYPE: PRT
<213> ORGANISM: Artificial Sequence
<220> FEATURE:
<223> OTHER INFORMATION: an artificially synthesized sequence

<400> SEQUENCE: 49

Gln Val Gln Leu Val Glu Ser Gly Gly Gly Leu Val Gln Pro Gly Arg
 1               5                  10                  15

Ser Leu Arg Leu Ser Cys Ala Ala Ser Gly Phe Thr Ile Ser Ser Ala
                20                  25                  30

Trp Met His Trp Val Arg Gln Ala Pro Gly Lys Gly Leu Glu Trp Val
                35                  40                  45

Ala Gln Ile Lys Asp Arg Ala Asn Gly Tyr Ala Ala Tyr Tyr Ala Pro
 50                  55                  60

Ser Val Lys Gly Arg Phe Thr Ile Ser Arg Asp Asp Ser Lys Asn Ser
 65                  70                  75                  80

Ile Tyr Leu Gln Met Asn Ser Leu Lys Thr Glu Asp Thr Ala Val Tyr
                     85                  90                  95
```

```
Tyr Cys Arg Tyr Val His Tyr Ala Thr Ala Tyr Asp Gly Phe Tyr Gly
            100                 105                 110

Phe Gly Val Asp Ala Trp Gly Gln Gly Thr Thr Val Thr Val Ser Ser
        115                 120                 125
```

<210> SEQ ID NO 50
<211> LENGTH: 112
<212> TYPE: PRT
<213> ORGANISM: Artificial Sequence
<220> FEATURE:
<223> OTHER INFORMATION: an artificially synthesized sequence

<400> SEQUENCE: 50

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Glu Leu Val His Thr
            20                  25                  30

Asn Arg His Thr Tyr Leu His Trp Tyr Gln Gln Lys Pro Gly Gln Ala
        35                  40                  45

Pro Arg Leu Leu Ile Tyr Lys Val Ser Asn Arg Phe Pro Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Gly
                85                  90                  95

Thr Gln Val Pro Phe Thr Phe Gly Gln Gly Thr Lys Leu Glu Ile Lys
            100                 105                 110
```

<210> SEQ ID NO 51
<211> LENGTH: 112
<212> TYPE: PRT
<213> ORGANISM: Artificial Sequence
<220> FEATURE:
<223> OTHER INFORMATION: an artificially synthesized sequence

<400> SEQUENCE: 51

```
Asp Ile Val Met Thr Gln Ser Pro Leu Ser Leu Pro Val Thr Pro Gly
1               5                   10                  15

Glu Pro Ala Ser Ile Ser Cys Gln Ala Ser Gln Glu Leu Val His Met
            20                  25                  30

Asn Arg Asn Thr Tyr Leu His Trp Tyr Gln Gln Lys Pro Gly Gln Ala
        35                  40                  45

Pro Arg Leu Leu Ile Tyr Lys Val Ser Asn Arg Phe Pro Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Gly
                85                  90                  95

Thr Ser Val Pro Phe Thr Phe Gly Gln Gly Thr Lys Leu Glu Ile Lys
            100                 105                 110
```

<210> SEQ ID NO 52
<211> LENGTH: 112
<212> TYPE: PRT
<213> ORGANISM: Artificial Sequence
<220> FEATURE:
<223> OTHER INFORMATION: an artificially synthesized sequence

<400> SEQUENCE: 52

```
Asp Ile Val Met Thr Gln Ser Pro Leu Ser Leu Pro Val Thr Pro Gly
```

```
                1               5                   10                  15
                Glu Pro Ala Ser Ile Ser Cys Ser Ala Ser Glu Ser Leu Leu His Asn
                                20                  25                  30

Asn Arg His Thr Tyr Leu His Trp Tyr Gln Gln Lys Pro Gly Gln Ala
                            35                  40                  45

Pro Arg Leu Leu Ile Tyr Arg Val Ser Asn Arg Phe Asn Gly Val Pro
                        50                  55                  60

Asp Arg Phe Ser Gly Ser Gly Ser Gly Thr Asp Phe Thr Leu Lys Ile
                65                  70                  75                  80

Ser Arg Val Glu Ala Glu Asp Val Gly Val Tyr Tyr Cys Gln Gly Gly
                                85                  90                  95

Thr Gln Val Pro Phe Thr Phe Gly Gln Gly Thr Lys Leu Glu Ile Lys
                            100                 105                 110

<210> SEQ ID NO 53
<211> LENGTH: 112
<212> TYPE: PRT
<213> ORGANISM: Artificial Sequence
<220> FEATURE:
<223> OTHER INFORMATION: an artificially synthesized sequence

<400> SEQUENCE: 53

Asp Ile Val Met Thr Gln Ser Pro Leu Ser Leu Pro Val Thr Pro Gly
1               5                   10                  15

Glu Pro Ala Ser Ile Ser Cys Arg Thr Ser Gln Glu Leu Val His Ile
                20                  25                  30

Asn Arg Tyr Ile Phe Leu His Trp Tyr Gln Gln Lys Pro Gly Gln Ala
            35                  40                  45

Pro Arg Leu Leu Ile Tyr Lys Val Tyr Asn Arg Phe Gln Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Gly
                85                  90                  95

Thr Ser Val Pro Tyr Thr Phe Gly Gln Gly Thr Lys Leu Glu Ile Lys
            100                 105                 110

<210> SEQ ID NO 54
<211> LENGTH: 112
<212> TYPE: PRT
<213> ORGANISM: Artificial Sequence
<220> FEATURE:
<223> OTHER INFORMATION: an artificially synthesized sequence

<400> SEQUENCE: 54

Asp Ile Val Met Thr Gln Ser Pro Leu Ser Leu Pro Val Thr Pro Gly
1               5                   10                  15

Glu Pro Ala Ser Ile Ser Cys Ala Ala Ser Glu Glu Leu Val His Ile
                20                  25                  30

Asn Arg Tyr Ile Phe Leu His Trp Tyr Gln Gln Lys Pro Gly Gln Ala
            35                  40                  45

Pro Arg Leu Leu Ile Tyr Lys Val Ser Asn Arg Phe Ile Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Gly
                85                  90                  95
```

```
Ser Gln Val Pro Phe Thr Phe Gly Gln Gly Thr Lys Leu Glu Ile Lys
        100                 105                 110
```

<210> SEQ ID NO 55
<211> LENGTH: 112
<212> TYPE: PRT
<213> ORGANISM: Artificial Sequence
<220> FEATURE:
<223> OTHER INFORMATION: an artificially synthesized sequence

<400> SEQUENCE: 55

```
Asp Ile Val Met Thr Gln Ser Pro Leu Ser Leu Pro Val Thr Pro Gly
1               5                   10                  15

Glu Pro Ala Ser Ile Ser Cys Ser Thr Ser Glu Glu Leu Leu His Ile
            20                  25                  30

Asn Arg Phe Ile Phe Leu His Trp Tyr Gln Gln Lys Pro Gly Gln Ala
        35                  40                  45

Pro Arg Leu Leu Ile Tyr Lys Val Ala Asn Arg Phe Met Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Gly
                85                  90                  95

Ser Gln Val Pro Phe Thr Phe Gly Gln Gly Thr Lys Leu Glu Ile Lys
        100                 105                 110
```

<210> SEQ ID NO 56
<211> LENGTH: 112
<212> TYPE: PRT
<213> ORGANISM: Artificial Sequence
<220> FEATURE:
<223> OTHER INFORMATION: an artificially synthesized sequence

<400> SEQUENCE: 56

```
Asp Ile Val Met Thr Gln Ser Pro Leu Ser Leu Pro Val Thr Pro Gly
1               5                   10                  15

Glu Pro Ala Ser Ile Ser Cys Ser Ser Ser Gln Glu Leu Val His Ala
            20                  25                  30

Asn Arg Gln Ile Tyr Leu His Trp Tyr Gln Gln Lys Pro Gly Gln Ala
        35                  40                  45

Pro Arg Leu Leu Ile Tyr Lys Val Ala Asn Arg Phe Pro Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Gly
                85                  90                  95

Thr Gln Val Pro Phe Thr Phe Gly Gln Gly Thr Lys Leu Glu Ile Lys
        100                 105                 110
```

<210> SEQ ID NO 57
<211> LENGTH: 112
<212> TYPE: PRT
<213> ORGANISM: Artificial Sequence
<220> FEATURE:
<223> OTHER INFORMATION: an artificially synthesized sequence

<400> SEQUENCE: 57

```
Asp Ile Val Met Thr Gln Ser Pro Leu Ser Leu Pro Val Thr Pro Gly
1               5                   10                  15

Glu Pro Ala Ser Ile Ser Cys Thr Ala Ser Gln Glu Leu Val His Ile
```

```
            20                  25                  30

Asn Arg Phe Ile Phe Leu His Trp Tyr Gln Gln Lys Pro Gly Gln Ala
            35                  40                  45

Pro Arg Leu Leu Ile Tyr Lys Val Ser Asn Arg Phe Ile Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Gly
                85                  90                  95

Ser Gln Val Pro Phe Thr Phe Gly Gln Gly Thr Lys Leu Glu Ile Lys
            100                 105                 110

<210> SEQ ID NO 58
<211> LENGTH: 112
<212> TYPE: PRT
<213> ORGANISM: Artificial Sequence
<220> FEATURE:
<223> OTHER INFORMATION: an artificially synthesized sequence

<400> SEQUENCE: 58

Asp Ile Val Met Thr Gln Ser Pro Leu Ser Leu Pro Val Thr Pro Gly
1               5                   10                  15

Glu Pro Ala Ser Ile Ser Cys Gln Ser Ser Glu Ser Leu Val His Val
            20                  25                  30

Asn Arg His Thr Tyr Leu His Trp Tyr Gln Gln Lys Pro Gly Gln Ala
            35                  40                  45

Pro Arg Leu Leu Ile Tyr Lys Val Tyr Asn Arg Phe Pro Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Gly
                85                  90                  95

Thr Ser Val Pro Phe Thr Phe Gly Gln Gly Thr Lys Leu Glu Ile Lys
            100                 105                 110

<210> SEQ ID NO 59
<211> LENGTH: 112
<212> TYPE: PRT
<213> ORGANISM: Artificial Sequence
<220> FEATURE:
<223> OTHER INFORMATION: an artificially synthesized sequence

<400> SEQUENCE: 59

Asp Ile Val Met Thr Gln Ser Pro Leu Ser Leu Pro Val Thr Pro Gly
1               5                   10                  15

Glu Pro Ala Ser Ile Ser Cys Ser Ala Ser Glu Glu Leu Val His Ile
            20                  25                  30

Asn Arg Tyr Ile Phe Leu His Trp Tyr Gln Gln Lys Pro Gly Gln Ala
            35                  40                  45

Pro Arg Leu Leu Ile Tyr Lys Val Tyr Asn Arg Phe Met Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Gly Gln Gly
                85                  90                  95

Ser Ser Val Pro Phe Thr Phe Gly Gln Gly Thr Lys Leu Glu Ile Lys
            100                 105                 110
```

-continued

```
<210> SEQ ID NO 60
<211> LENGTH: 112
<212> TYPE: PRT
<213> ORGANISM: Artificial Sequence
<220> FEATURE:
<223> OTHER INFORMATION: an artificially synthesized sequence

<400> SEQUENCE: 60

Asp Ile Val Met Thr Gln Ser Pro Leu Ser Leu Pro Val Thr Pro Gly
1               5                   10                  15

Glu Pro Ala Ser Ile Ser Cys Arg Thr Ser Glu Glu Leu Leu His Ile
            20                  25                  30

Asn Arg Phe Thr Phe Leu His Trp Tyr Gln Gln Lys Pro Gly Gln Ala
        35                  40                  45

Pro Arg Leu Leu Ile Tyr Lys Val Ser Asn Arg Phe Met Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Gly
                85                  90                  95

Ser Ala Val Pro Phe Thr Phe Gly Gln Gly Thr Lys Leu Glu Ile Lys
            100                 105                 110

<210> SEQ ID NO 61
<211> LENGTH: 112
<212> TYPE: PRT
<213> ORGANISM: Artificial Sequence
<220> FEATURE:
<223> OTHER INFORMATION: an artificially synthesized sequence

<400> SEQUENCE: 61

Asp Ile Val Met Thr Gln Ser Pro Leu Ser Leu Pro Val Thr Pro Gly
1               5                   10                  15

Glu Pro Ala Ser Ile Ser Cys Thr Ser Asp Gln Glu Leu Val His Met
            20                  25                  30

Asn Arg His Thr Tyr Leu His Trp Tyr Gln Gln Lys Pro Gly Gln Ala
        35                  40                  45

Pro Arg Leu Leu Ile Tyr Lys Val Tyr Asn Arg Phe Pro Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Gly
                85                  90                  95

Thr Ser Val Pro Phe Thr Phe Gly Gln Gly Thr Lys Leu Glu Ile Lys
            100                 105                 110

<210> SEQ ID NO 62
<211> LENGTH: 112
<212> TYPE: PRT
<213> ORGANISM: Artificial Sequence
<220> FEATURE:
<223> OTHER INFORMATION: an artificially synthesized sequence

<400> SEQUENCE: 62

Asp Ile Val Met Thr Gln Ser Pro Leu Ser Leu Pro Val Thr Pro Gly
1               5                   10                  15

Glu Pro Ala Ser Ile Ser Cys Arg Thr Ser Glu Glu Leu Leu His Ile
            20                  25                  30

Asn Arg Tyr Ile Phe Leu His Trp Tyr Gln Gln Lys Pro Gly Gln Ala
```

```
              35                  40                  45
Pro Arg Leu Leu Ile Tyr Lys Val Gln Asn Arg Phe Ser Gly Val Pro
        50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ala Gln Gly
                85                  90                  95

Ser Ala Val Pro Phe Thr Phe Gly Gln Gly Thr Lys Leu Glu Ile Lys
               100                 105                 110
```

<210> SEQ ID NO 63
<211> LENGTH: 112
<212> TYPE: PRT
<213> ORGANISM: Artificial Sequence
<220> FEATURE:
<223> OTHER INFORMATION: an artificially synthesized sequence

<400> SEQUENCE: 63

```
Asp Ile Val Met Thr Gln Ser Pro Leu Ser Leu Pro Val Thr Pro Gly
 1               5                  10                  15

Glu Pro Ala Ser Ile Ser Cys Tyr Ala Ser Glu Glu Leu Leu His Ile
                20                  25                  30

Asn Arg His Ile Tyr Leu His Trp Tyr Gln Gln Lys Pro Gly Gln Ala
            35                  40                  45

Pro Arg Leu Leu Ile Tyr Lys Val Tyr Asn Arg Phe Asn Gly Val Pro
        50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ala Gln Gly
                85                  90                  95

Ser Ser Val Pro Phe Thr Phe Gly Gln Gly Thr Lys Leu Glu Ile Lys
               100                 105                 110
```

<210> SEQ ID NO 64
<211> LENGTH: 112
<212> TYPE: PRT
<213> ORGANISM: Artificial Sequence
<220> FEATURE:
<223> OTHER INFORMATION: an artificially synthesized sequence

<400> SEQUENCE: 64

```
Asp Ile Val Met Thr Gln Ser Pro Leu Ser Leu Pro Val Thr Pro Gly
 1               5                  10                  15

Glu Pro Ala Ser Ile Ser Cys Arg Ala Ser Glu Glu Leu Leu His Ile
                20                  25                  30

Asn Arg His Ile Phe Leu His Trp Tyr Gln Gln Lys Pro Gly Gln Ala
            35                  40                  45

Pro Arg Leu Leu Ile Tyr Lys Val Tyr Asn Arg Phe Thr Gly Val Pro
        50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ala Gln Gly
                85                  90                  95

Thr Ser Val Pro Phe Thr Phe Gly Gln Gly Thr Lys Leu Glu Ile Lys
               100                 105                 110
```

<210> SEQ ID NO 65
<211> LENGTH: 112

```
<212> TYPE: PRT
<213> ORGANISM: Artificial Sequence
<220> FEATURE:
<223> OTHER INFORMATION: an artificially synthesized sequence

<400> SEQUENCE: 65

Asp Ile Val Met Thr Gln Ser Pro Leu Ser Leu Pro Val Thr Pro Gly
1               5                   10                  15

Glu Pro Ala Ser Ile Ser Cys Gln Thr Ser Glu Glu Leu Val His Ile
            20                  25                  30

Asn Arg Phe Ile Phe Leu His Trp Tyr Gln Gln Lys Pro Gly Gln Ala
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Gly
                85                  90                  95

Thr Ser Val Pro Phe Thr Phe Gly Gln Gly Thr Lys Leu Glu Ile Lys
            100                 105                 110

<210> SEQ ID NO 66
<211> LENGTH: 115
<212> TYPE: PRT
<213> ORGANISM: Artificial Sequence
<220> FEATURE:
<223> OTHER INFORMATION: an artificially synthesized sequence

<400> SEQUENCE: 66

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Glu Met His Trp Ile Arg Gln Pro Pro Gly Gln Gly Leu Glu Trp Ile
        35                  40                  45

Gly Ala Ile Asp Pro Lys Thr Gly Asp Thr Ala Tyr Ser Gln Lys Phe
    50                  55                  60

Lys Gly Arg Val Thr Leu Thr Ala Asp Lys Ser Thr Ser Thr Ala Tyr
65                  70                  75                  80

Met Glu Leu Ser Ser Leu Thr Ser Glu Asp Thr Ala Val Tyr Tyr Cys
                85                  90                  95

Thr Arg Phe Tyr Ser Tyr Thr Tyr Trp Gly Gln Gly Thr Leu Val Thr
            100                 105                 110

Val Ser Ser
        115

<210> SEQ ID NO 67
<211> LENGTH: 112
<212> TYPE: PRT
<213> ORGANISM: Artificial Sequence
<220> FEATURE:
<223> OTHER INFORMATION: an artificially synthesized sequence

<400> SEQUENCE: 67

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Arg Asn Thr Tyr Leu His Trp Tyr Gln Gln Lys Pro Gly Gln Ala
```

```
            35                  40                  45

Pro Arg Leu Leu Ile Tyr Lys Val Ser Asn Arg Phe Ser Gly Val Pro
            50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Leu Glu Ile Lys
            100                 105                 110

<210> SEQ ID NO 68
<211> LENGTH: 450
<212> TYPE: PRT
<213> ORGANISM: Artificial Sequence
<220> FEATURE:
<223> OTHER INFORMATION: an artificially synthesized sequence

<400> SEQUENCE: 68

Asp Ile Val Met Thr Gln Ser Pro Leu Ser Leu Pro Val Thr Pro Gly
 1                   5                  10                  15

Glu Pro Ala Ser Ile Ser Cys Arg Ser Ser Gln Ser Leu Val His Ser
            20                  25                  30

Asn Arg Asn Thr Tyr Leu His Trp Tyr Gln Gln Lys Pro Gly Gln Ala
            35                  40                  45

Pro Arg Leu Leu Ile Tyr Lys Val Ser Asn Arg Phe Ser Gly Val Pro
            50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Leu Glu Ile Lys
            100                 105                 110

Ser Ser Ala Ser Thr Lys Gly Pro Ser Val Phe Pro Leu Ala Pro Ser
            115                 120                 125

Ser Lys Ser Thr Ser Gly Gly Thr Ala Ala Leu Gly Cys Leu Val Lys
        130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
            195                 200                 205

Asp Lys Lys Val Glu Pro Lys Ser Cys Asp Lys Thr His Thr Cys Pro
        210                 215                 220

Pro Cys Pro Ala Pro Glu Ala Ala Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Lys Phe
            260                 265                 270

Asn Trp Tyr Val Asp Gly Val Glu Val His Asn Ala Lys Thr Lys Pro
            275                 280                 285

Arg Glu Glu Gln Tyr Ala Ser Thr Tyr Arg Val Val Ser Val Leu Thr
```

```
                290                 295                 300

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
                325                 330                 335

Lys Gly Gln Pro Arg Glu Pro Gln Val Cys Thr Leu Pro Pro Ser Arg
                340                 345                 350

Asp Glu Leu Thr Lys Asn Gln Val Ser Leu Trp Cys Leu Val Lys Gly
                355                 360                 365

Phe Tyr Pro Ser Asp Ile Ala Val Glu Trp Glu Ser Asn Gly Gln Pro
                370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
                420                 425                 430

Tyr Thr Gln Lys Ser Leu Ser Leu Ser Pro His His His His His His
                435                 440                 445

His His
    450

<210> SEQ ID NO 69
<211> LENGTH: 449
<212> TYPE: PRT
<213> ORGANISM: Artificial Sequence
<220> FEATURE:
<223> OTHER INFORMATION: an artificially synthesized sequence

<400> SEQUENCE: 69

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
                20                  25                  30

Tyr Trp Ser Trp Ile Arg Gln Ser Pro Glu Lys Gly Leu Glu Trp Ile
                35                  40                  45

Gly Glu Ile Asn His Gly Gly Tyr Val Thr Tyr Asn Pro Ser Leu Glu
        50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Tyr Gly Pro Gly Asn Tyr Asp Trp Tyr Phe Asp Leu Trp Gly
                100                 105                 110

Arg Gly Thr Leu Val Thr Val Ser Ser Ala Ser Thr Lys Gly Pro Ser
                115                 120                 125

Val Phe Pro Leu Ala Pro Ser Ser Lys Ser Thr Ser Gly Gly Thr Ala
                130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
```

```
                195                 200                 205
Lys Pro Ser Asn Thr Lys Val Asp Lys Lys Val Glu Pro Lys Ser Cys
        210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Ala Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Cys Glu Leu Thr Lys Asn Gln Val Ser
        355                 360                 365

Leu Ser Cys Ala Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Val Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro

<210> SEQ ID NO 70
<211> LENGTH: 222
<212> TYPE: PRT
<213> ORGANISM: Artificial Sequence
<220> FEATURE:
<223> OTHER INFORMATION: an artificially synthesized sequence

<400> SEQUENCE: 70

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Glu Met His Trp Ile Arg Gln Pro Pro Gly Gln Gly Leu Glu Trp Ile
        35                  40                  45

Gly Ala Ile Asp Pro Lys Thr Gly Asp Thr Ala Tyr Ser Gln Lys Phe
    50                  55                  60

Lys Gly Arg Val Thr Leu Thr Ala Asp Lys Ser Thr Ser Thr Ala Tyr
65                  70                  75                  80

Met Glu Leu Ser Ser Leu Thr Ser Glu Asp Thr Ala Val Tyr Tyr Cys
                85                  90                  95

Thr Arg Phe Tyr Ser Tyr Thr Tyr Trp Gly Gln Gly Thr Leu Val Thr
            100                 105                 110
```

Val Ser Ser Ala Ser Val Ala Ala Pro Ser Val Phe Ile Phe Pro Pro
        115                 120                 125

Ser Asp Glu Gln Leu Lys Ser Gly Thr Ala Ser Val Val Cys Leu Leu
130                 135                 140

Asn Asn Phe Tyr Pro Arg Glu Ala Lys Val Gln Trp Lys Val Asp Asn
145                 150                 155                 160

Ala Leu Gln Ser Gly Asn Ser Gln Glu Ser Val Thr Glu Gln Asp Ser
                165                 170                 175

Lys Asp Ser Thr Tyr Ser Leu Ser Ser Thr Leu Thr Leu Ser Lys Ala
            180                 185                 190

Asp Tyr Glu Lys His Lys Val Tyr Ala Cys Glu Val Thr His Gln Gly
        195                 200                 205

Leu Ser Ser Pro Val Thr Lys Ser Phe Asn Arg Gly Glu Cys
    210                 215                 220

<210> SEQ ID NO 71
<211> LENGTH: 216
<212> TYPE: PRT
<213> ORGANISM: Artificial Sequence
<220> FEATURE:
<223> OTHER INFORMATION: an artificially synthesized sequence

<400> SEQUENCE: 71

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Ala Leu Thr Phe Gly Gly Gly Thr Lys Val Glu Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215

<210> SEQ ID NO 72
<211> LENGTH: 122
<212> TYPE: PRT
<213> ORGANISM: Artificial Sequence
<220> FEATURE:
<223> OTHER INFORMATION: an artificially synthesized sequence

<400> SEQUENCE: 72

Glu Val Gln Leu Val Glu Thr Gly Gly Ser Leu Val Gln Pro Gly Lys
1               5                   10                  15

Ser Leu Lys Leu Thr Cys Ala Thr Ser Gly Phe Thr Phe Ser Asn Ala
            20                  25                  30

Trp Met His Trp Val Arg Gln Ser Pro Glu Lys Gln Leu Glu Trp Val
        35                  40                  45

Ala Gln Ile Lys Ala Lys Ser Asn Asn Tyr Ala Thr Tyr Tyr Ala Glu
    50                  55                  60

Ser Val Lys Gly Arg Phe Thr Ile Ser Arg Asp Asp Ser Lys Ser Asn
65                  70                  75                  80

Ile Tyr Leu Gln Met Asn Ser Leu Lys Glu Asp Thr Ala Val Tyr
                85                  90                  95

Tyr Cys Arg Tyr Val His Tyr Gly Ala Tyr Tyr Gly Val Asp Ala Trp
            100                 105                 110

Gly Gln Gly Thr Ser Val Thr Val Ser Ser
        115                 120

<210> SEQ ID NO 73
<211> LENGTH: 112
<212> TYPE: PRT
<213> ORGANISM: Artificial Sequence
<220> FEATURE:
<223> OTHER INFORMATION: an artificially synthesized sequence

<400> SEQUENCE: 73

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Arg Asn Thr Tyr Leu His Trp Tyr Gln Gln Lys Pro Gly Gln Ala
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Gly Gln Gly
                85                  90                  95

Thr Gln Val Pro Tyr Thr Phe Gly Gln Gly Thr Lys Leu Glu Ile Lys
            100                 105                 110

<210> SEQ ID NO 74
<211> LENGTH: 22
<212> TYPE: PRT
<213> ORGANISM: Homo sapiens

<400> SEQUENCE: 74

Leu Gln Asp Pro Cys Ser Asn Cys Pro Ala Gly Thr Phe Cys Asp Asn
1               5                   10                  15

Asn Arg Asn Gln Ile Cys
            20

<210> SEQ ID NO 75
<211> LENGTH: 41
<212> TYPE: PRT
<213> ORGANISM: Homo sapiens

<400> SEQUENCE: 75

Ser Pro Cys Pro Pro Asn Ser Phe Ser Ser Ala Gly Gly Gln Arg Thr
1               5                   10                  15

Cys Asp Ile Cys Arg Gln Cys Lys Gly Val Phe Arg Thr Arg Lys Glu
            20                  25                  30

Cys Ser Ser Thr Ser Asn Ala Glu Cys
            35                  40

<210> SEQ ID NO 76
<211> LENGTH: 31
<212> TYPE: PRT
<213> ORGANISM: Homo sapiens

<400> SEQUENCE: 76

Asp Cys Thr Pro Gly Phe His Cys Leu Gly Ala Gly Cys Ser Met Cys
1               5                   10                  15

Glu Gln Asp Cys Lys Gln Gly Gln Glu Leu Thr Lys Lys Gly Cys
            20                  25                  30

<210> SEQ ID NO 77
<211> LENGTH: 69
<212> TYPE: PRT
<213> ORGANISM: Homo sapiens

<400> SEQUENCE: 77

Lys Asp Cys Cys Phe Gly Thr Phe Asn Asp Gln Lys Arg Gly Ile Cys
1               5                   10                  15

Arg Pro Trp Thr Asn Cys Ser Leu Asp Gly Lys Ser Val Leu Val Asn
            20                  25                  30

Gly Thr Lys Glu Arg Asp Val Val Cys Gly Pro Ser Pro Ala Asp Leu
        35                  40                  45

Ser Pro Gly Ala Ser Ser Val Thr Pro Pro Ala Pro Ala Arg Glu Pro
    50                  55                  60

Gly His Ser Pro Gln
65

<210> SEQ ID NO 78
<211> LENGTH: 94
<212> TYPE: PRT
<213> ORGANISM: Homo sapiens

<400> SEQUENCE: 78

Leu Gln Asp Pro Cys Ser Asn Cys Pro Ala Gly Thr Phe Cys Asp Asn
1               5                   10                  15

Asn Arg Asn Gln Ile Cys Ser Pro Cys Pro Pro Asn Ser Phe Ser Ser
            20                  25                  30

Ala Gly Gly Gln Arg Thr Cys Asp Ile Cys Arg Gln Cys Lys Gly Val
        35                  40                  45

Phe Arg Thr Arg Lys Glu Cys Ser Ser Thr Ser Asn Ala Glu Cys Asp
    50                  55                  60

Cys Thr Pro Gly Phe His Cys Leu Gly Ala Gly Cys Ser Met Cys Glu
65                  70                  75                  80

Gln Asp Cys Lys Gln Gly Gln Glu Leu Thr Lys Lys Gly Cys
            85                  90

<210> SEQ ID NO 79
<211> LENGTH: 63
<212> TYPE: PRT

<213> ORGANISM: Homo sapiens

<400> SEQUENCE: 79

Leu Gln Asp Pro Cys Ser Asn Cys Pro Ala Gly Thr Phe Cys Asp Asn
1               5                   10                  15

Asn Arg Asn Gln Ile Cys Ser Pro Cys Pro Pro Asn Ser Phe Ser Ser
            20                  25                  30

Ala Gly Gly Gln Arg Thr Cys Asp Ile Cys Arg Gln Cys Lys Gly Val
        35                  40                  45

Phe Arg Thr Arg Lys Glu Cys Ser Ser Thr Ser Asn Ala Glu Cys
50                  55                  60

<210> SEQ ID NO 80
<211> LENGTH: 141
<212> TYPE: PRT
<213> ORGANISM: Homo sapiens

<400> SEQUENCE: 80

Ser Pro Cys Pro Pro Asn Ser Phe Ser Ser Ala Gly Gly Gln Arg Thr
1               5                   10                  15

Cys Asp Ile Cys Arg Gln Cys Lys Gly Val Phe Arg Thr Arg Lys Glu
            20                  25                  30

Cys Ser Ser Thr Ser Asn Ala Glu Cys Asp Cys Thr Pro Gly Phe His
        35                  40                  45

Cys Leu Gly Ala Gly Cys Ser Met Cys Glu Gln Asp Cys Lys Gln Gly
    50                  55                  60

Gln Glu Leu Thr Lys Lys Gly Cys Lys Asp Cys Cys Phe Gly Thr Phe
65                  70                  75                  80

Asn Asp Gln Lys Arg Gly Ile Cys Arg Pro Trp Thr Asn Cys Ser Leu
                85                  90                  95

Asp Gly Lys Ser Val Leu Val Asn Gly Thr Lys Glu Arg Asp Val Val
            100                 105                 110

Cys Gly Pro Ser Pro Ala Asp Leu Ser Pro Gly Ala Ser Ser Val Thr
        115                 120                 125

Pro Pro Ala Pro Ala Arg Glu Pro Gly His Ser Pro Gln
    130                 135                 140

<210> SEQ ID NO 81
<211> LENGTH: 72
<212> TYPE: PRT
<213> ORGANISM: Homo sapiens

<400> SEQUENCE: 81

Ser Pro Cys Pro Pro Asn Ser Phe Ser Ser Ala Gly Gly Gln Arg Thr
1               5                   10                  15

Cys Asp Ile Cys Arg Gln Cys Lys Gly Val Phe Arg Thr Arg Lys Glu
            20                  25                  30

Cys Ser Ser Thr Ser Asn Ala Glu Cys Asp Cys Thr Pro Gly Phe His
        35                  40                  45

Cys Leu Gly Ala Gly Cys Ser Met Cys Glu Gln Asp Cys Lys Gln Gly
    50                  55                  60

Gln Glu Leu Thr Lys Lys Gly Cys
65                  70

<210> SEQ ID NO 82
<211> LENGTH: 100
<212> TYPE: PRT
<213> ORGANISM: Homo sapiens

<400> SEQUENCE: 82

```
Asp Cys Thr Pro Gly Phe His Cys Leu Gly Ala Gly Cys Ser Met Cys
1               5                   10                  15

Glu Gln Asp Cys Lys Gln Gly Gln Glu Leu Thr Lys Lys Gly Cys Lys
            20                  25                  30

Asp Cys Cys Phe Gly Thr Phe Asn Asp Gln Lys Arg Gly Ile Cys Arg
        35                  40                  45

Pro Trp Thr Asn Cys Ser Leu Asp Gly Lys Ser Val Leu Val Asn Gly
50                  55                  60

Thr Lys Glu Arg Asp Val Val Cys Gly Pro Ser Pro Ala Asp Leu Ser
65                  70                  75                  80

Pro Gly Ala Ser Ser Val Thr Pro Pro Ala Pro Ala Arg Glu Pro Gly
                85                  90                  95

His Ser Pro Gln
            100
```

<210> SEQ ID NO 83
<211> LENGTH: 336
<212> TYPE: PRT
<213> ORGANISM: Artificial Sequence
<220> FEATURE:
<223> OTHER INFORMATION: an artificially synthesized sequence

<400> SEQUENCE: 83

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Cys Glu
225                 230                 235                 240
```

```
Leu Thr Lys Asn Gln Val Ser Leu Ser Cys Ala Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Val Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Asp Tyr Lys Asp Asp Asp Asp Lys
                325                 330                 335

<210> SEQ ID NO 84
<211> LENGTH: 107
<212> TYPE: PRT
<213> ORGANISM: Artificial Sequence
<220> FEATURE:
<223> OTHER INFORMATION: an artificially synthesized sequence

<400> SEQUENCE: 84

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 85
<211> LENGTH: 121
<212> TYPE: PRT
<213> ORGANISM: Artificial Sequence
<220> FEATURE:
<223> OTHER INFORMATION: an artificially synthesized sequence

<400> SEQUENCE: 85

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Ser Pro Glu Lys Gly Leu Glu Trp Ile
        35                  40                  45

Gly Glu Ile Asn His Gly Gly Tyr Val Thr Tyr Asn Pro Ser Leu Glu
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Tyr Gly Pro Gly Asn Tyr Asp Trp Tyr Phe Asp Leu Trp Gly
            100                 105                 110
```

Arg Gly Thr Leu Val Thr Val Ser Ser
        115                 120

<210> SEQ ID NO 86
<211> LENGTH: 109
<212> TYPE: PRT
<213> ORGANISM: Artificial Sequence
<220> FEATURE:
<223> OTHER INFORMATION: an artificially synthesized sequence

<400> SEQUENCE: 86

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Ala Leu Thr Phe Gly Gly Gly Thr Lys Val Glu Ile Lys
            100                 105

<210> SEQ ID NO 87
<211> LENGTH: 128
<212> TYPE: PRT
<213> ORGANISM: Artificial Sequence
<220> FEATURE:
<223> OTHER INFORMATION: an artificially synthesized sequence

<400> SEQUENCE: 87

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Ser Asn Ala
            20                  25                  30

Trp Met His Trp Val Arg Gln Ala Pro Gly Lys Gly Leu Glu Trp Val
        35                  40                  45

Ala Gln Ile Lys Asp Arg Ala Asn Ser Tyr Asn Thr Tyr Tyr Ala Glu
    50                  55                  60

Ser Val Lys Gly Arg Phe Thr Ile Ser Arg Asp Asp Ser Lys Asn Ser
65                  70                  75                  80

Ile Tyr Leu Gln Met Asn Ser Leu Lys Thr Glu Asp Thr Ala Val Tyr
                85                  90                  95

Tyr Cys Arg Tyr Val His Tyr Thr Thr Tyr Ala Gly Ser Ser Phe Ser
            100                 105                 110

Tyr Gly Val Asp Ala Trp Gly Gln Gly Thr Thr Val Thr Val Ser Ser
        115                 120                 125

<210> SEQ ID NO 88
<211> LENGTH: 112
<212> TYPE: PRT
<213> ORGANISM: Artificial Sequence
<220> FEATURE:
<223> OTHER INFORMATION: an artificially synthesized sequence

<400> SEQUENCE: 88

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Pro Leu Val His Ser
            20                  25                  30

Asn Arg Asn Thr Tyr Leu His Trp Tyr Gln Gln Lys Pro Gly Gln Ala
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Gln Gly Gly
                85                  90                  95

Thr Gln Val Pro Tyr Thr Phe Gly Gln Gly Thr Lys Leu Glu Ile Lys
            100                 105                 110
```

<210> SEQ ID NO 89
<211> LENGTH: 115
<212> TYPE: PRT
<213> ORGANISM: Artificial Sequence
<220> FEATURE:
<223> OTHER INFORMATION: an artificially synthesized sequence

<400> SEQUENCE: 89

```
Gln Val Gln Leu Val Gln Ser Gly Ala Glu Val Lys Lys Pro Gly Ala
1               5                   10                  15

Ser Val Thr Val Ser Cys Lys Ala Ser Gly Tyr Thr Phe Thr Asp Tyr
            20                  25                  30

Glu Met His Trp Ile Arg Gln Pro Pro Gly Gln Gly Leu Glu Trp Ile
        35                  40                  45

Gly Ala Ile Asp Gly Pro Thr Pro Asp Thr Ala Tyr Ser Glu Lys Phe
    50                  55                  60

Lys Gly Arg Val Thr Leu Thr Ala Asp Lys Ser Thr Ser Thr Ala Tyr
65                  70                  75                  80

Met Glu Leu Ser Ser Leu Thr Ser Glu Asp Thr Ala Val Tyr Tyr Cys
                85                  90                  95

Thr Arg Phe Tyr Ser Tyr Thr Tyr Trp Gly Gln Gly Thr Leu Val Thr
            100                 105                 110

Val Ser Ser
        115
```

<210> SEQ ID NO 90
<211> LENGTH: 112
<212> TYPE: PRT
<213> ORGANISM: Artificial Sequence
<220> FEATURE:
<223> OTHER INFORMATION: an artificially synthesized sequence

<400> SEQUENCE: 90

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Pro Leu Val His Ser
            20                  25                  30

Asn Arg Asn Thr Tyr Leu His Trp Tyr Gln Gln Lys Pro Gly Gln Ala
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80
```

```
Ser Arg Val Glu Ala Glu Asp Val Gly Val Tyr Tyr Cys Gly Gln Gly
            85                  90                  95

Thr Gln Val Pro Tyr Thr Phe Gly Gln Gly Thr Lys Leu Glu Ile Lys
            100                 105                 110
```

<210> SEQ ID NO 91
<211> LENGTH: 15
<212> TYPE: PRT
<213> ORGANISM: Homo sapiens

<400> SEQUENCE: 91

```
Gln Asp Gly Asn Glu Glu Met Gly Gly Ile Thr Gln Thr Pro Tyr
1               5                   10                  15
```

<210> SEQ ID NO 92
<211> LENGTH: 128
<212> TYPE: PRT
<213> ORGANISM: Artificial Sequence
<220> FEATURE:
<223> OTHER INFORMATION: an artificially synthesized sequence

<400> SEQUENCE: 92

```
Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Ser Asn Ala
            20                  25                  30

Trp Met His Trp Val Arg Gln Ala Pro Gly Lys Gly Leu Glu Trp Val
            35                  40                  45

Ala Gln Ile Lys Asp Lys Ser Asn Asn Tyr Ala Thr Tyr Tyr Ala Glu
    50                  55                  60

Ser Val Lys Gly Arg Phe Thr Ile Ser Arg Asp Asp Ser Lys Asn Ser
65                  70                  75                  80

Ile Tyr Leu Gln Met Asn Ser Leu Lys Thr Glu Asp Thr Ala Val Tyr
            85                  90                  95

Tyr Cys Arg Tyr Val His Tyr Gly Ala Gly Ser Gly Gly Ser Tyr
            100                 105                 110

Tyr Gly Val Asp Ala Trp Gly Gln Gly Thr Thr Val Thr Val Ser Ser
            115                 120                 125
```

<210> SEQ ID NO 93
<211> LENGTH: 112
<212> TYPE: PRT
<213> ORGANISM: Artificial Sequence
<220> FEATURE:
<223> OTHER INFORMATION: an artificially synthesized sequence

<400> SEQUENCE: 93

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Arg Asn Thr Tyr Leu His Trp Tyr Gln Gln Lys Pro Gly Gln Ala
            35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Gly Gln Gly
            85                  90                  95
```

```
Thr Gln Val Pro Tyr Thr Phe Gly Gln Gly Thr Lys Leu Glu Ile Lys
                100                 105                 110
```

<210> SEQ ID NO 94
<211> LENGTH: 330
<212> TYPE: PRT
<213> ORGANISM: Homo sapiens

<400> SEQUENCE: 94

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 95
<211> LENGTH: 326
<212> TYPE: PRT

<213> ORGANISM: Homo sapiens

<400> SEQUENCE: 95

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325
```

<210> SEQ ID NO 96
<211> LENGTH: 377
<212> TYPE: PRT
<213> ORGANISM: Homo sapiens

<400> SEQUENCE: 96

```
Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
```

```
            20                  25                  30
Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Pro Cys Pro Arg
            115                 120                 125

Cys Pro Glu Pro Lys Ser Cys Asp Thr Pro Pro Pro Cys Pro Arg Cys
        130                 135                 140

Pro Glu Pro Lys Ser Cys Asp Thr Pro Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
            195                 200                 205

Val Asp Gly Val Glu Val His Asn Ala Lys Thr Lys Pro Arg Glu Glu
        210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
            275                 280                 285

Thr Lys Asn Gln Val Ser Leu Thr Cys Leu Val Lys Gly Phe Tyr Pro
        290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Phe Thr Gln
        355                 360                 365

Lys Ser Leu Ser Leu Ser Pro Gly Lys
    370                 375

<210> SEQ ID NO 97
<211> LENGTH: 327
<212> TYPE: PRT
<213> ORGANISM: Homo sapiens

<400> SEQUENCE: 97

Ala Ser Thr Lys Gly Pro Ser Val Phe Pro Leu Ala Pro Cys Ser Arg
1               5                   10                  15
```

```
Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 98
<211> LENGTH: 119
<212> TYPE: PRT
<213> ORGANISM: Artificial Sequence
<220> FEATURE:
<223> OTHER INFORMATION: an artificially synthesized sequence

<400> SEQUENCE: 98

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45
```

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Tyr Ser Tyr Met Leu Arg Met Asp Tyr Trp Gly Gln Gly
            100                 105                 110

Thr Leu Val Thr Val Ser Ser
            115

<210> SEQ ID NO 99
<211> LENGTH: 107
<212> TYPE: PRT
<213> ORGANISM: Artificial Sequence
<220> FEATURE:
<223> OTHER INFORMATION: an artificially synthesized sequence

<400> SEQUENCE: 99

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe His Ser Phe Pro Leu
                85                  90                  95

Thr Phe Gly Gly Gly Thr Lys Val Glu Ile Lys
            100                 105

<210> SEQ ID NO 100
<211> LENGTH: 120
<212> TYPE: PRT
<213> ORGANISM: Artificial Sequence
<220> FEATURE:
<223> OTHER INFORMATION: an artificially synthesized sequence

<400> SEQUENCE: 100

Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Ala Met Tyr His Pro Ser Phe Asn Tyr Trp Gly Gln
            100                 105                 110

Gly Thr Leu Val Thr Val Ser Ser
            115                 120

```
<210> SEQ ID NO 101
<211> LENGTH: 107
<212> TYPE: PRT
<213> ORGANISM: Artificial Sequence
<220> FEATURE:
<223> OTHER INFORMATION: an artificially synthesized sequence

<400> SEQUENCE: 101

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gly Gly Thr Lys Val Glu Ile Lys
            100                 105

<210> SEQ ID NO 102
<211> LENGTH: 118
<212> TYPE: PRT
<213> ORGANISM: Artificial Sequence
<220> FEATURE:
<223> OTHER INFORMATION: an artificially synthesized sequence

<400> SEQUENCE: 102

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Met Asp Tyr Trp Met Leu Pro Asp Val Trp Gly Gln Gly Thr
            100                 105                 110

Leu Val Thr Val Ser Ser
        115

<210> SEQ ID NO 103
<211> LENGTH: 107
<212> TYPE: PRT
<213> ORGANISM: Artificial Sequence
<220> FEATURE:
<223> OTHER INFORMATION: an artificially synthesized sequence

<400> SEQUENCE: 103

Asp Ile Gln Met Thr Gln Ser Pro Ser Ser Leu Ser Ala Ser Val Gly
1               5                   10                  15
```

```
Asp Arg Val Thr Ile Thr Cys Arg Ala Ser Gln Ser Ile Ser Ser Tyr
             20                  25                  30

Leu Asn Trp Tyr Gln Gln Lys Pro Gly Lys Ala Pro Lys Leu Leu Ile
         35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asp Asn Phe Pro Leu
                 85                  90                  95

Thr Phe Gly Gly Gly Thr Lys Val Glu Ile Lys
            100                 105
```

<210> SEQ ID NO 104
<211> LENGTH: 119
<212> TYPE: PRT
<213> ORGANISM: Artificial Sequence
<220> FEATURE:
<223> OTHER INFORMATION: an artificially synthesized sequence

<400> SEQUENCE: 104

```
Glu Val Gln Leu Leu Glu Ser Gly Gly Gly Leu Val Gln Pro Gly Gly
1               5                  10                  15

Ser Leu Arg Leu Ser Cys Ala Ala Ser Gly Phe Thr Phe Ser Ser Tyr
             20                  25                  30

Ala Met Ser Trp Val Arg Gln Ala Pro Gly Lys Gly Leu Glu Trp Val
         35                  40                  45

Ser Ala Ile Ser Gly Ser Gly Gly Ser Thr Tyr Tyr Ala Asp Ser Val
 50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                 85                  90                  95

Ala Arg Gln Pro Ser Tyr Tyr Pro Trp Met Asp Tyr Trp Gly Gln Gly
            100                 105                 110

Thr Leu Val Thr Val Ser Ser
        115
```

<210> SEQ ID NO 105
<211> LENGTH: 107
<212> TYPE: PRT
<213> ORGANISM: Artificial Sequence
<220> FEATURE:
<223> OTHER INFORMATION: an artificially synthesized sequence

<400> SEQUENCE: 105

```
Asp Ile Gln Met Thr Gln Ser Pro Ser Ser Leu Ser Ala Ser Val Gly
1               5                  10                  15

Asp Arg Val Thr Ile Thr Cys Arg Ala Ser Gln Ser Ile Ser Ser Tyr
             20                  25                  30

Leu Asn Trp Tyr Gln Gln Lys Pro Gly Lys Ala Pro Lys Leu Leu Ile
         35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Asn Tyr Pro Leu
                 85                  90                  95
```

```
                   Thr Phe Gly Gly Gly Thr Lys Val Glu Ile Lys
                                   100                 105

<210> SEQ ID NO 106
<211> LENGTH: 118
<212> TYPE: PRT
<213> ORGANISM: Artificial Sequence
<220> FEATURE:
<223> OTHER INFORMATION: an artificially synthesized sequence

<400> SEQUENCE: 106

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Gly Leu Glu Trp Met
            35                  40                  45

Gly Trp Ile Asn Pro Asn Ser Gly Gly Thr Asn Tyr Ala Gln Lys Phe
        50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Asn Tyr Tyr Met Phe Met Asp Leu Trp Gly Gln Gly Thr
                100                 105                 110

Leu Val Thr Val Tyr Ser
            115

<210> SEQ ID NO 107
<211> LENGTH: 107
<212> TYPE: PRT
<213> ORGANISM: Artificial Sequence
<220> FEATURE:
<223> OTHER INFORMATION: an artificially synthesized sequence

<400> SEQUENCE: 107

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Phe Thr Ser Phe Pro Leu
                85                  90                  95

Thr Phe Gly Gly Gly Thr Lys Val Glu Ile Lys
                100                 105

<210> SEQ ID NO 108
<211> LENGTH: 119
<212> TYPE: PRT
<213> ORGANISM: Artificial Sequence
<220> FEATURE:
<223> OTHER INFORMATION: an artificially synthesized sequence

<400> SEQUENCE: 108
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Asp Arg Tyr Gly Leu His Met Phe Asp Tyr Trp Gly Gln Gly
            100                 105                 110

Thr Leu Val Thr Val Ser Ser
            115

<210> SEQ ID NO 109
<211> LENGTH: 107
<212> TYPE: PRT
<213> ORGANISM: Artificial Sequence
<220> FEATURE:
<223> OTHER INFORMATION: an artificially synthesized sequence

<400> SEQUENCE: 109

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Phe Asn Ser Phe Pro Leu
            85                  90                  95

Thr Phe Gly Gly Gly Thr Lys Val Glu Ile Lys
            100                 105

<210> SEQ ID NO 110
<211> LENGTH: 328
<212> TYPE: PRT
<213> ORGANISM: Artificial Sequence
<220> FEATURE:
<223> OTHER INFORMATION: an artificially synthesized sequence

<400> SEQUENCE: 110

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

```
Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Glu His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Phe Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro
                325

<210> SEQ ID NO 111
<211> LENGTH: 107
<212> TYPE: PRT
<213> ORGANISM: Artificial Sequence
<220> FEATURE:
<223> OTHER INFORMATION: an artificially synthesized sequence

<400> SEQUENCE: 111

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 112
<211> LENGTH: 106
<212> TYPE: PRT
<213> ORGANISM: Artificial Sequence
<220> FEATURE:
<223> OTHER INFORMATION: an artificially synthesized sequence

<400> SEQUENCE: 112

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 113
<211> LENGTH: 122
<212> TYPE: PRT
<213> ORGANISM: Rattus norvegicus

<400> SEQUENCE: 113

Glu Val Gln Leu Val Glu Thr Gly Gly Ser Leu Val Gln Pro Gly Lys
1               5                   10                  15

Ser Leu Lys Leu Thr Cys Ala Thr Ser Gly Phe Thr Phe Ser Asn Ala
            20                  25                  30

Trp Met His Trp Val Arg Gln Ser Pro Glu Lys Gln Leu Glu Trp Val
        35                  40                  45

Ala Gln Ile Lys Ala Lys Ser Asn Asn Tyr Ala Thr Tyr Tyr Ala Glu
    50                  55                  60

Ser Val Lys Gly Arg Phe Thr Ile Ser Arg Asp Asp Ser Lys Ser Asn
65                  70                  75                  80

Ile Tyr Leu Gln Met Asn Ser Leu Lys Glu Glu Asp Thr Ala Val Tyr
                85                  90                  95

Tyr Cys Arg Tyr Val His Tyr Gly Ala Tyr Tyr Gly Val Asp Ala Trp
            100                 105                 110

Gly Gln Gly Thr Ser Val Thr Val Ser Ser
        115                 120

<210> SEQ ID NO 114
<211> LENGTH: 112
<212> TYPE: PRT
<213> ORGANISM: Rattus norvegicus

<400> SEQUENCE: 114

Asp Val Val Met Thr Gln Thr Pro Val Ser Met Ser Val Ser Leu Gly
1               5                   10                  15

Gly Gln Val Ser Ile Ser Cys Arg Ser Ser Gln Ser Leu Val His Asn
            20                  25                  30

Asn Gly Asn Thr Tyr Val Ser Trp Tyr Ile Gln Lys Pro Ser Gln Ser

```
            35                  40                  45
Pro Gln Leu Leu Ile Tyr Lys Val Ser Asn Arg Phe Ser Gly Ile Ser
     50                  55                  60

Asp Arg Phe Ser Gly Ser Gly Ser Gly Thr Asp Phe Thr Leu Lys Ile
 65                  70                  75                  80

Ser Arg Val Glu Pro Asp Asp Leu Gly Val Tyr Tyr Cys Gly Gln Gly
                 85                  90                  95

Thr Gln Asp Pro Tyr Thr Phe Gly Ala Gly Thr Lys Leu Glu Leu Lys
            100                 105                 110

<210> SEQ ID NO 115
<211> LENGTH: 119
<212> TYPE: PRT
<213> ORGANISM: Mus musculus

<400> SEQUENCE: 115

Gln Val Gln Leu Lys Gln Ser Gly Pro Gly Leu Val Gln Pro Ser Gln
 1               5                  10                  15

Ser Leu Ser Ile Thr Cys Thr Val Ser Gly Phe Ser Leu Thr Asn Tyr
                 20                  25                  30

Gly Val His Trp Val Arg Gln Ser Pro Gly Lys Gly Leu Glu Trp Leu
            35                  40                  45

Gly Val Ile Trp Ser Gly Gly Asn Thr Asp Tyr Asn Thr Pro Phe Thr
     50                  55                  60

Ser Arg Leu Ser Ile Asn Lys Asp Asn Ser Lys Ser Gln Val Phe Phe
 65                  70                  75                  80

Lys Met Asn Ser Leu Gln Ser Asn Asp Thr Ala Ile Tyr Tyr Cys Ala
                 85                  90                  95

Arg Ala Leu Thr Tyr Tyr Asp Tyr Glu Phe Ala Tyr Trp Gly Gln Gly
            100                 105                 110

Thr Leu Val Thr Val Ser Ala
        115

<210> SEQ ID NO 116
<211> LENGTH: 107
<212> TYPE: PRT
<213> ORGANISM: Mus musculus

<400> SEQUENCE: 116

Asp Ile Leu Leu Thr Gln Ser Pro Val Ile Leu Ser Val Ser Pro Gly
 1               5                  10                  15

Glu Arg Val Ser Phe Ser Cys Arg Ala Ser Gln Ser Ile Gly Thr Asn
                 20                  25                  30

Ile His Trp Tyr Gln Gln Arg Thr Asn Gly Ser Pro Arg Leu Leu Ile
            35                  40                  45

Lys Tyr Ala Ser Glu Ser Ile Ser Gly Ile Pro Ser Arg Phe Ser Gly
     50                  55                  60

Ser Gly Ser Gly Thr Asp Phe Thr Leu Ser Ile Asn Ser Val Glu Ser
 65                  70                  75                  80

Glu Asp Ile Ala Asp Tyr Tyr Cys Gln Gln Asn Asn Asn Trp Pro Thr
                 85                  90                  95

Thr Phe Gly Ala Gly Thr Lys Leu Glu Leu Lys
            100                 105

<210> SEQ ID NO 117
<211> LENGTH: 447
<212> TYPE: PRT
```

<213> ORGANISM: Artificial Sequence
<220> FEATURE:
<223> OTHER INFORMATION: an artificially synthesized sequence

<400> SEQUENCE: 117

```
Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
```

-continued

```
                385                 390                 395                 400
Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro
            435                 440                 445
```

<210> SEQ ID NO 118
<211> LENGTH: 447
<212> TYPE: PRT
<213> ORGANISM: Artificial Sequence
<220> FEATURE:
<223> OTHER INFORMATION: an artificially synthesized sequence

<400> SEQUENCE: 118

```
Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
```

```
                    305                 310                 315                 320
Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Lys Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn Arg Tyr Thr Gln Lys Ser Leu Ser Leu Ser Pro
        435                 440                 445

<210> SEQ ID NO 119
<211> LENGTH: 447
<212> TYPE: PRT
<213> ORGANISM: Artificial Sequence
<220> FEATURE:
<223> OTHER INFORMATION: an artificially synthesized sequence

<400> SEQUENCE: 119

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
```

-continued

```
            225                 230                 235                 240

Ser Val Phe Leu Phe Pro Pro Lys Pro Lys Asp Thr Leu Met Ile Ser
                        245                 250                 255

Arg Thr Pro Glu Val Thr Cys Val Val Val Asp Val Ser His Glu Asp
                        260                 265                 270

Pro Glu Val Lys Phe Asn Trp Tyr Val Asp Gly Val Glu Val His Asn
                        275                 280                 285

Ala Lys Thr Lys Pro Arg Glu Glu Gln Tyr Asn Ser Thr Tyr Arg Val
                    290                 295                 300

Val Ser Val Leu Thr Val Leu His Gln Asp Trp Leu Asn Gly Lys Glu
        305                 310                 315                 320

Tyr Lys Cys Lys Val Ser Asn Lys Ala Leu Pro Ala Pro Ile Glu Lys
                        325                 330                 335

Thr Ile Ser Lys Ala Lys Gly Gln Pro Arg Glu Pro Gln Val Tyr Thr
                        340                 345                 350

Leu Pro Pro Ser Arg Asp Glu Leu Thr Lys Asn Gln Val Ser Leu Thr
                        355                 360                 365

Cys Leu Val Lys Gly Phe Tyr Pro Ser Asp Ile Ala Val Glu Trp Glu
                    370                 375                 380

Ser Asn Gly Gln Pro Glu Asn Asn Tyr Lys Thr Thr Pro Pro Val Leu
        385                 390                 395                 400

Asp Ser Asp Gly Ser Phe Phe Leu Tyr Ser Lys Leu Thr Val Asp Lys
                        405                 410                 415

Ser Arg Trp Gln Gln Gly Asn Val Phe Ser Cys Ser Val Met His Glu
                        420                 425                 430

Ala Leu His Asn His Tyr Thr Gln Glu Ser Leu Ser Leu Ser Pro
                    435                 440                 445

<210> SEQ ID NO 120
<211> LENGTH: 445
<212> TYPE: PRT
<213> ORGANISM: Artificial Sequence
<220> FEATURE:
<223> OTHER INFORMATION: an artificially synthesized sequence

<400> SEQUENCE: 120

Asp Ile Leu Leu Thr Gln Ser Pro Val Ile Leu Ser Val Ser Pro Gly
        1               5                   10                  15

Glu Arg Val Ser Phe Ser Cys Arg Ala Ser Gln Ser Ile Gly Thr Asn
                        20                  25                  30

Ile His Trp Tyr Gln Gln Arg Thr Asn Gly Ser Pro Arg Leu Leu Ile
                    35                  40                  45

Lys Tyr Ala Ser Glu Ser Ile Ser Gly Ile Pro Ser Arg Phe Ser Gly
            50                  55                  60

Ser Gly Ser Gly Thr Asp Phe Thr Leu Ser Ile Asn Ser Val Glu Ser
        65                  70                  75                  80

Glu Asp Ile Ala Asp Tyr Tyr Cys Gln Gln Asn Asn Asn Trp Pro Thr
                        85                  90                  95

Thr Phe Gly Ala Gly Thr Lys Leu Glu Leu Lys Ser Ser Ala Ser Thr
                        100                 105                 110

Lys Gly Pro Ser Val Phe Pro Leu Ala Pro Ser Ser Lys Ser Thr Ser
                    115                 120                 125

Gly Gly Thr Ala Ala Leu Gly Cys Leu Val Lys Asp Tyr Phe Pro Glu
            130                 135                 140

Pro Val Thr Val Ser Trp Asn Ser Gly Ala Leu Thr Ser Gly Val His
```

```
                145                 150                 155                 160
Thr Phe Pro Ala Val Leu Gln Ser Ser Gly Leu Tyr Ser Leu Ser Ser
                    165                 170                 175

Val Val Thr Val Pro Ser Ser Leu Gly Thr Gln Thr Tyr Ile Cys
                180                 185                 190

Asn Val Asn His Lys Pro Ser Asn Thr Lys Val Asp Lys Val Glu
                195                 200                 205

Pro Lys Ser Cys Asp Lys Thr His Thr Cys Pro Pro Cys Pro Ala Pro
210                 215                 220

Glu Ala Ala Gly Gly Pro Ser Val Phe Leu Phe Pro Pro Lys Pro Lys
225                 230                 235                 240

Asp Thr Leu Met Ile Ser Arg Thr Pro Glu Val Thr Cys Val Val Val
                    245                 250                 255

Asp Val Ser His Glu Asp Pro Glu Val Lys Phe Asn Trp Tyr Val Asp
                260                 265                 270

Gly Val Glu Val His Asn Ala Lys Thr Lys Pro Arg Glu Glu Gln Tyr
                275                 280                 285

Ala Ser Thr Tyr Arg Val Val Ser Val Leu Thr Val Leu His Gln Asp
290                 295                 300

Trp Leu Asn Gly Lys Glu Tyr Lys Cys Lys Val Ser Asn Lys Ala Leu
305                 310                 315                 320

Pro Ala Pro Ile Glu Lys Thr Ile Ser Lys Ala Lys Gly Gln Pro Arg
                    325                 330                 335

Glu Pro Gln Val Cys Thr Leu Pro Pro Ser Arg Asp Glu Leu Thr Lys
                340                 345                 350

Asn Gln Val Ser Leu Trp Cys Leu Val Lys Gly Phe Tyr Pro Ser Asp
                355                 360                 365

Ile Ala Val Glu Trp Glu Ser Asn Gly Gln Pro Glu Asn Asn Tyr Lys
                370                 375                 380

Thr Thr Pro Pro Val Leu Asp Ser Asp Gly Ser Phe Phe Leu Tyr Ser
385                 390                 395                 400

Lys Leu Thr Val Asp Lys Ser Arg Trp Gln Gln Gly Asn Val Phe Ser
                    405                 410                 415

Cys Ser Val Met His Glu Ala Leu His Asn Arg Tyr Thr Gln Lys Ser
                420                 425                 430

Leu Ser Leu Ser Pro His His His His His His
                    435                 440                 445

<210> SEQ ID NO 121
<211> LENGTH: 226
<212> TYPE: PRT
<213> ORGANISM: Artificial Sequence
<220> FEATURE:
<223> OTHER INFORMATION: an artificially synthesized sequence

<400> SEQUENCE: 121

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
                20                  25                  30

Gly Val His Trp Val Arg Gln Ser Pro Gly Lys Gly Leu Glu Trp Leu
            35                  40                  45

Gly Val Ile Trp Ser Gly Gly Asn Thr Asp Tyr Asn Thr Pro Phe Thr
        50                  55                  60

Ser Arg Leu Ser Ile Asn Lys Asp Asn Ser Lys Ser Gln Val Phe Phe
```

```
                65                  70                  75                  80
Lys Met Asn Ser Leu Gln Ser Asn Asp Thr Ala Ile Tyr Tyr Cys Ala
                    85                  90                  95
Arg Ala Leu Thr Tyr Tyr Asp Tyr Glu Phe Ala Tyr Trp Gly Gln Gly
                   100                 105                 110
Thr Leu Val Thr Val Ser Ala Arg Thr Val Ala Ala Pro Ser Val Phe
                   115                 120                 125
Ile Phe Pro Pro Ser Asp Glu Gln Leu Lys Ser Gly Thr Ala Ser Val
    130                 135                 140
Val Cys Leu Leu Asn Asn Phe Tyr Pro Arg Glu Ala Lys Val Gln Trp
145                 150                 155                 160
Lys Val Asp Asn Ala Leu Gln Ser Gly Asn Ser Gln Glu Ser Val Thr
                    165                 170                 175
Glu Gln Asp Ser Lys Asp Ser Thr Tyr Ser Leu Ser Ser Thr Leu Thr
                180                 185                 190
Leu Ser Lys Ala Asp Tyr Glu Lys His Lys Val Tyr Ala Cys Glu Val
                195                 200                 205
Thr His Gln Gly Leu Ser Ser Pro Val Thr Lys Ser Phe Asn Arg Gly
    210                 215                 220
Glu Cys
225

<210> SEQ ID NO 122
<211> LENGTH: 458
<212> TYPE: PRT
<213> ORGANISM: Artificial Sequence
<220> FEATURE:
<223> OTHER INFORMATION: an artificially synthesized sequence

<400> SEQUENCE: 122

Glu Val Gln Leu Val Glu Thr Gly Gly Ser Leu Val Gln Pro Gly Lys
1               5                   10                  15
Ser Leu Lys Leu Thr Cys Ala Thr Ser Gly Phe Thr Phe Ser Asn Ala
                20                  25                  30
Trp Met His Trp Val Arg Gln Ser Pro Glu Lys Gln Leu Glu Trp Val
            35                  40                  45
Ala Gln Ile Lys Ala Lys Ser Asn Asn Tyr Ala Thr Tyr Tyr Ala Glu
        50                  55                  60
Ser Val Lys Gly Arg Phe Thr Ile Ser Arg Asp Asp Ser Lys Ser Asn
65                  70                  75                  80
Ile Tyr Leu Gln Met Asn Ser Leu Lys Glu Glu Asp Thr Ala Val Tyr
                85                  90                  95
Tyr Cys Arg Tyr Val His Tyr Gly Ala Tyr Tyr Gly Val Asp Ala Trp
                100                 105                 110
Gly Gln Gly Thr Ser Val Thr Val Ser Ser Ala Ser Thr Lys Gly Pro
            115                 120                 125
Ser Val Phe Pro Leu Ala Pro Ser Ser Lys Ser Thr Ser Gly Gly Thr
    130                 135                 140
Ala Ala Leu Gly Cys Leu Val Lys Asp Tyr Phe Pro Glu Pro Val Thr
145                 150                 155                 160
Val Ser Trp Asn Ser Gly Ala Leu Thr Ser Gly Val His Thr Phe Pro
                165                 170                 175
Ala Val Leu Gln Ser Ser Gly Leu Tyr Ser Leu Ser Ser Val Val Thr
                180                 185                 190
Val Pro Ser Ser Ser Leu Gly Thr Gln Thr Tyr Ile Cys Asn Val Asn
```

```
                195                 200                 205
His Lys Pro Ser Asn Thr Lys Val Asp Lys Val Glu Pro Lys Ser
    210                 215                 220

Cys Asp Lys Thr His Thr Cys Pro Pro Cys Pro Ala Pro Glu Ala Ala
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Ala Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Cys Glu Leu Thr Lys Asn Gln Val
        355                 360                 365

Ser Leu Ser Cys Ala Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Val Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Asp Tyr Lys Asp Asp Asp Lys
    450                 455

<210> SEQ ID NO 123
<211> LENGTH: 219
<212> TYPE: PRT
<213> ORGANISM: Artificial Sequence
<220> FEATURE:
<223> OTHER INFORMATION: an artificially synthesized sequence

<400> SEQUENCE: 123

Asp Val Val Met Thr Gln Thr Pro Val Ser Met Ser Val Ser Leu Gly
1               5                   10                  15

Gly Gln Val Ser Ile Ser Cys Arg Ser Ser Gln Ser Leu Val His Asn
            20                  25                  30

Asn Gly Asn Thr Tyr Val Ser Trp Tyr Ile Gln Lys Pro Ser Gln Ser
        35                  40                  45

Pro Gln Leu Leu Ile Tyr Lys Val Ser Asn Arg Phe Ser Gly Ile Ser
    50                  55                  60

Asp Arg Phe Ser Gly Ser Gly Ser Gly Thr Asp Phe Thr Leu Lys Ile
65                  70                  75                  80

Ser Arg Val Glu Pro Asp Asp Leu Gly Val Tyr Tyr Cys Gly Gln Gly
                85                  90                  95

Thr Gln Asp Pro Tyr Thr Phe Gly Ala Gly Thr Lys Leu Glu Leu Lys
```

```
                    100                 105                 110
Arg Thr Val Ala Ala Pro Ser Val Phe Ile Phe Pro Pro Ser Asp Glu
                115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
        180                 185                 190

Lys His Lys Val Tyr Ala Cys Glu Val Thr His Gln Gly Leu Ser Ser
                195                 200                 205

Pro Val Thr Lys Ser Phe Asn Arg Gly Glu Cys
        210                 215

<210> SEQ ID NO 124
<211> LENGTH: 461
<212> TYPE: PRT
<213> ORGANISM: Artificial Sequence
<220> FEATURE:
<223> OTHER INFORMATION: an artificially synthesized sequence

<400> SEQUENCE: 124

Glu Val Gln Leu Val Glu Thr Gly Gly Ser Leu Val Gln Pro Gly Lys
1               5                   10                  15

Ser Leu Lys Leu Thr Cys Ala Thr Ser Gly Phe Thr Phe Ser Asn Ala
                20                  25                  30

Trp Met His Trp Val Arg Gln Ser Pro Glu Lys Gln Leu Glu Trp Val
            35                  40                  45

Ala Gln Ile Lys Ala Lys Gly Gly Ser Ser Asn Asn Tyr Ala Thr Tyr
        50                  55                  60

Tyr Ala Glu Ser Val Lys Gly Arg Phe Thr Ile Ser Arg Asp Asp Ser
65                  70                  75                  80

Lys Ser Asn Ile Tyr Leu Gln Met Asn Ser Leu Lys Glu Glu Asp Thr
                85                  90                  95

Ala Val Tyr Tyr Cys Arg Tyr Val His Tyr Gly Ala Tyr Tyr Gly Val
                100                 105                 110

Asp Ala Trp Gly Gln Gly Thr Ser Val Thr Val Ser Ser Ala Ser Thr
            115                 120                 125

Lys Gly Pro Ser Val Phe Pro Leu Ala Pro Ser Ser Lys Ser Thr Ser
        130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
                210                 215                 220

Pro Lys Ser Cys Asp Lys Thr His Thr Cys Pro Pro Cys Pro Ala Pro
225                 230                 235                 240

Glu Ala Ala Gly Gly Pro Ser Val Phe Leu Phe Pro Pro Lys Pro Lys
```

```
                    245                 250                 255
Asp Thr Leu Met Ile Ser Arg Thr Pro Glu Val Thr Cys Val Val Val
                260                 265                 270

Asp Val Ser His Glu Asp Pro Glu Val Lys Phe Asn Trp Tyr Val Asp
            275                 280                 285

Gly Val Glu Val His Asn Ala Lys Thr Lys Pro Arg Glu Glu Gln Tyr
        290                 295                 300

Ala Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Cys Glu Leu Thr Lys
        355                 360                 365

Asn Gln Val Ser Leu Ser Cys Ala Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Val Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Asp Tyr Lys Asp Asp Asp Lys
    450                 455                 460

<210> SEQ ID NO 125
<211> LENGTH: 464
<212> TYPE: PRT
<213> ORGANISM: Artificial Sequence
<220> FEATURE:
<223> OTHER INFORMATION: an artificially synthesized sequence

<400> SEQUENCE: 125

Glu Val Gln Leu Val Glu Thr Gly Gly Ser Leu Val Gln Pro Gly Lys
1               5                   10                  15

Ser Leu Lys Leu Thr Cys Ala Thr Ser Gly Phe Thr Phe Ser Asn Ala
            20                  25                  30

Trp Met His Trp Val Arg Gln Ser Pro Glu Lys Gln Leu Glu Trp Val
        35                  40                  45

Ala Gln Ile Lys Ala Lys Gly Gly Ser Gly Ser Ser Asn Asn Tyr
    50                  55                  60

Ala Thr Tyr Tyr Ala Glu Ser Val Lys Gly Arg Phe Thr Ile Ser Arg
65                  70                  75                  80

Asp Asp Ser Lys Ser Asn Ile Tyr Leu Gln Met Asn Ser Leu Lys Glu
                85                  90                  95

Glu Asp Thr Ala Val Tyr Tyr Cys Arg Tyr Val His Tyr Gly Ala Tyr
            100                 105                 110

Tyr Gly Val Asp Ala Trp Gly Gln Gly Thr Ser Val Thr Val Ser Ser
        115                 120                 125

Ala Ser Thr Lys Gly Pro Ser Val Phe Pro Leu Ala Pro Ser Ser Lys
    130                 135                 140

Ser Thr Ser Gly Gly Thr Ala Ala Leu Gly Cys Leu Val Lys Asp Tyr
```

```
            145                 150                 155                 160
        Phe Pro Glu Pro Val Thr Val Ser Trp Asn Ser Gly Ala Leu Thr Ser
                        165                 170                 175

Gly Val His Thr Phe Pro Ala Val Leu Gln Ser Ser Gly Leu Tyr Ser
                        180                 185                 190

Leu Ser Ser Val Val Thr Val Pro Ser Ser Ser Leu Gly Thr Gln Thr
                        195                 200                 205

Tyr Ile Cys Asn Val Asn His Lys Pro Ser Asn Thr Lys Val Asp Lys
                        210                 215                 220

Lys Val Glu Pro Lys Ser Cys Asp Lys Thr His Thr Cys Pro Pro Cys
        225                 230                 235                 240

Pro Ala Pro Glu Ala Ala Gly Gly Pro Ser Val Phe Leu Phe Pro Pro
                        245                 250                 255

Lys Pro Lys Asp Thr Leu Met Ile Ser Arg Thr Pro Glu Val Thr Cys
                        260                 265                 270

Val Val Val Asp Val Ser His Glu Asp Pro Glu Val Lys Phe Asn Trp
                        275                 280                 285

Tyr Val Asp Gly Val Glu Val His Asn Ala Lys Thr Lys Pro Arg Glu
                        290                 295                 300

Glu Gln Tyr Ala Ser Thr Tyr Arg Val Val Ser Val Leu Thr Val Leu
        305                 310                 315                 320

His Gln Asp Trp Leu Asn Gly Lys Glu Tyr Lys Cys Lys Val Ser Asn
                        325                 330                 335

Lys Ala Leu Pro Ala Pro Ile Glu Lys Thr Ile Ser Lys Ala Lys Gly
                        340                 345                 350

Gln Pro Arg Glu Pro Gln Val Tyr Thr Leu Pro Pro Ser Arg Cys Glu
                        355                 360                 365

Leu Thr Lys Asn Gln Val Ser Leu Ser Cys Ala Val Lys Gly Phe Tyr
                        370                 375                 380

Pro Ser Asp Ile Ala Val Glu Trp Glu Ser Asn Gly Gln Pro Glu Asn
        385                 390                 395                 400

Asn Tyr Lys Thr Thr Pro Pro Val Leu Asp Ser Asp Gly Ser Phe Phe
                        405                 410                 415

Leu Val Ser Lys Leu Thr Val Asp Lys Ser Arg Trp Gln Gln Gly Asn
                        420                 425                 430

Val Phe Ser Cys Ser Val Met His Glu Ala Leu His Asn His Tyr Thr
                        435                 440                 445

Gln Lys Ser Leu Ser Leu Ser Pro Asp Tyr Lys Asp Asp Asp Asp Lys
        450                 455                 460

<210> SEQ ID NO 126
<211> LENGTH: 6
<212> TYPE: PRT
<213> ORGANISM: Artificial Sequence
<220> FEATURE:
<223> OTHER INFORMATION: an artificially synthesized sequence

<400> SEQUENCE: 126

Gly Gly Ser Gly Gly Ser
1               5

<210> SEQ ID NO 127
<211> LENGTH: 467
<212> TYPE: PRT
<213> ORGANISM: Artificial Sequence
<220> FEATURE:
<223> OTHER INFORMATION: an artificially synthesized sequence
```

<400> SEQUENCE: 127

Glu Val Gln Leu Val Glu Thr Gly Gly Ser Leu Val Gln Pro Gly Lys
1               5                   10                  15

Ser Leu Lys Leu Thr Cys Ala Thr Ser Gly Phe Thr Phe Ser Asn Ala
            20                  25                  30

Trp Met His Trp Val Arg Gln Ser Pro Glu Lys Gln Leu Glu Trp Val
        35                  40                  45

Ala Gln Ile Lys Ala Lys Gly Ser Gly Gly Ser Gly Gly Ser Ser
    50                  55                  60

Asn Asn Tyr Ala Thr Tyr Tyr Ala Glu Ser Val Lys Gly Arg Phe Thr
65                  70                  75                  80

Ile Ser Arg Asp Asp Ser Lys Ser Asn Ile Tyr Leu Gln Met Asn Ser
                85                  90                  95

Leu Lys Glu Glu Asp Thr Ala Val Tyr Tyr Cys Arg Tyr Val His Tyr
            100                 105                 110

Gly Ala Tyr Tyr Gly Val Asp Ala Trp Gly Gln Gly Thr Ser Val Thr
        115                 120                 125

Val Ser Ser Ala Ser Thr Lys Gly Pro Ser Val Phe Pro Leu Ala Pro
130                 135                 140

Ser Ser Lys Ser Thr Ser Gly Gly Thr Ala Ala Leu Gly Cys Leu Val
145                 150                 155                 160

Lys Asp Tyr Phe Pro Glu Pro Val Thr Val Ser Trp Asn Ser Gly Ala
                165                 170                 175

Leu Thr Ser Gly Val His Thr Phe Pro Ala Val Leu Gln Ser Ser Gly
            180                 185                 190

Leu Tyr Ser Leu Ser Ser Val Val Thr Val Pro Ser Ser Ser Leu Gly
        195                 200                 205

Thr Gln Thr Tyr Ile Cys Asn Val Asn His Lys Pro Ser Asn Thr Lys
    210                 215                 220

Val Asp Lys Lys Val Glu Pro Lys Ser Cys Asp Lys Thr His Thr Cys
225                 230                 235                 240

Pro Pro Cys Pro Ala Pro Glu Ala Ala Gly Gly Pro Ser Val Phe Leu
                245                 250                 255

Phe Pro Pro Lys Pro Lys Asp Thr Leu Met Ile Ser Arg Thr Pro Glu
            260                 265                 270

Val Thr Cys Val Val Asp Val Ser His Glu Asp Pro Glu Val Lys
        275                 280                 285

Phe Asn Trp Tyr Val Asp Gly Val Glu Val His Asn Ala Lys Thr Lys
    290                 295                 300

Pro Arg Glu Glu Gln Tyr Ala Ser Thr Tyr Arg Val Val Ser Val Leu
305                 310                 315                 320

Thr Val Leu His Gln Asp Trp Leu Asn Gly Lys Glu Tyr Lys Cys Lys
                325                 330                 335

Val Ser Asn Lys Ala Leu Pro Ala Pro Ile Glu Lys Thr Ile Ser Lys
            340                 345                 350

Ala Lys Gly Gln Pro Arg Glu Pro Gln Val Tyr Thr Leu Pro Pro Ser
        355                 360                 365

Arg Cys Glu Leu Thr Lys Asn Gln Val Ser Leu Ser Cys Ala Val Lys
    370                 375                 380

Gly Phe Tyr Pro Ser Asp Ile Ala Val Glu Trp Glu Ser Asn Gly Gln
385                 390                 395                 400

Pro Glu Asn Asn Tyr Lys Thr Thr Pro Pro Val Leu Asp Ser Asp Gly

```
                    405                 410                 415
Ser Phe Phe Leu Val Ser Lys Leu Thr Val Asp Lys Ser Arg Trp Gln
                420                 425                 430

Gln Gly Asn Val Phe Ser Cys Ser Val Met His Glu Ala Leu His Asn
            435                 440                 445

His Tyr Thr Gln Lys Ser Leu Ser Leu Ser Pro Asp Tyr Lys Asp Asp
        450                 455                 460

Asp Asp Lys
465

<210> SEQ ID NO 128
<211> LENGTH: 9
<212> TYPE: PRT
<213> ORGANISM: Artificial Sequence
<220> FEATURE:
<223> OTHER INFORMATION: an artificially synthesized sequence

<400> SEQUENCE: 128

Gly Gly Ser Gly Gly Ser Gly Gly Ser
1               5

<210> SEQ ID NO 129
<211> LENGTH: 461
<212> TYPE: PRT
<213> ORGANISM: Artificial Sequence
<220> FEATURE:
<223> OTHER INFORMATION: an artificially synthesized sequence

<400> SEQUENCE: 129

Glu Val Gln Leu Val Glu Thr Gly Gly Ser Leu Val Gln Pro Gly Lys
1               5                   10                  15

Ser Leu Lys Leu Thr Cys Ala Thr Ser Gly Phe Thr Phe Ser Asn Ala
            20                  25                  30

Trp Met His Trp Val Arg Gln Ser Pro Glu Lys Gln Leu Glu Trp Val
        35                  40                  45

Ala Gln Ile Lys Ala Lys Ser Asn Asn Tyr Ala Thr Tyr Tyr Ala Glu
    50                  55                  60

Ser Val Lys Gly Arg Phe Thr Ile Ser Arg Asp Gly Gly Ser Asp Ser
65                  70                  75                  80

Lys Ser Asn Ile Tyr Leu Gln Met Asn Ser Leu Lys Glu Glu Asp Thr
                85                  90                  95

Ala Val Tyr Tyr Cys Arg Tyr Val His Tyr Gly Ala Tyr Tyr Gly Val
            100                 105                 110

Asp Ala Trp Gly Gln Gly Thr Ser Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220
```

```
Pro Lys Ser Cys Asp Lys Thr His Thr Cys Pro Cys Pro Ala Pro
225                 230                 235                 240

Glu Ala Ala Gly Gly Pro Ser Val Phe Leu Phe Pro Pro Lys Pro Lys
            245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Ala Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
                340                 345                 350

Glu Pro Gln Val Tyr Thr Leu Pro Pro Ser Arg Cys Glu Leu Thr Lys
            355                 360                 365

Asn Gln Val Ser Leu Ser Cys Ala Val Lys Gly Phe Tyr Pro Ser Asp
370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Val Ser
                405                 410                 415

Lys Leu Thr Val Asp Lys Ser Arg Trp Gln Gln Gly Asn Val Phe Ser
                420                 425                 430

Cys Ser Val Met His Glu Ala Leu His Asn His Tyr Thr Gln Lys Ser
            435                 440                 445

Leu Ser Leu Ser Pro Asp Tyr Lys Asp Asp Asp Asp Lys
            450                 455                 460

<210> SEQ ID NO 130
<211> LENGTH: 464
<212> TYPE: PRT
<213> ORGANISM: Artificial Sequence
<220> FEATURE:
<223> OTHER INFORMATION: an artificially synthesized sequence

<400> SEQUENCE: 130

Glu Val Gln Leu Val Glu Thr Gly Gly Ser Leu Val Gln Pro Gly Lys
1               5                   10                  15

Ser Leu Lys Leu Thr Cys Ala Thr Ser Gly Phe Thr Phe Ser Asn Ala
            20                  25                  30

Trp Met His Trp Val Arg Gln Ser Pro Glu Lys Gln Leu Glu Trp Val
        35                  40                  45

Ala Gln Ile Lys Ala Lys Ser Asn Asn Tyr Ala Thr Tyr Ala Glu
50                  55                  60

Ser Val Lys Gly Arg Phe Thr Ile Ser Arg Asp Gly Ser Gly Gly
65                  70                  75                  80

Ser Asp Ser Lys Ser Asn Ile Tyr Leu Gln Met Asn Ser Leu Lys Glu
            85                  90                  95

Glu Asp Thr Ala Val Tyr Tyr Cys Arg Tyr Val His Tyr Gly Ala Tyr
            100                 105                 110

Tyr Gly Val Asp Ala Trp Gly Gln Gly Thr Ser Val Thr Val Ser Ser
            115                 120                 125
```

```
Ala Ser Thr Lys Gly Pro Ser Val Phe Pro Leu Ala Pro Ser Ser Lys
            130                 135                 140

Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Leu Gly Thr Gln Thr
        195                 200                 205

Tyr Ile Cys Asn Val Asn His Lys Pro Ser Asn Thr Lys Val Asp Lys
        210                 215                 220

Lys Val Glu Pro Lys Ser Cys Asp Lys Thr His Thr Cys Pro Pro Cys
225                 230                 235                 240

Pro Ala Pro Glu Ala Ala Gly Gly Pro Ser Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
        275                 280                 285

Tyr Val Asp Gly Val Glu Val His Asn Ala Lys Thr Lys Pro Arg Glu
        290                 295                 300

Glu Gln Tyr Ala Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Pro Ala Pro Ile Glu Lys Thr Ile Ser Lys Ala Lys Gly
            340                 345                 350

Gln Pro Arg Glu Pro Gln Val Tyr Thr Leu Pro Pro Ser Arg Cys Glu
        355                 360                 365

Leu Thr Lys Asn Gln Val Ser Leu Ser Cys Ala Val Lys Gly Phe Tyr
        370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Val Ser Lys Leu Thr Val Asp Lys Ser Arg Trp Gln Gln Gly Asn
            420                 425                 430

Val Phe Ser Cys Ser Val Met His Glu Ala Leu His Asn His Tyr Thr
        435                 440                 445

Gln Lys Ser Leu Ser Leu Ser Pro Asp Tyr Lys Asp Asp Asp Asp Lys
        450                 455                 460

<210> SEQ ID NO 131
<211> LENGTH: 467
<212> TYPE: PRT
<213> ORGANISM: Artificial Sequence
<220> FEATURE:
<223> OTHER INFORMATION: an artificially synthesized sequence

<400> SEQUENCE: 131

Glu Val Gln Leu Val Glu Thr Gly Gly Ser Leu Val Gln Pro Gly Lys
1               5                   10                  15

Ser Leu Lys Leu Thr Cys Ala Thr Ser Gly Phe Thr Phe Ser Asn Ala
            20                  25                  30
```

-continued

Trp Met His Trp Val Arg Gln Ser Pro Glu Lys Gln Leu Glu Trp Val
    35                  40                  45
Ala Gln Ile Lys Ala Lys Ser Asn Asn Tyr Ala Thr Tyr Tyr Ala Glu
 50                  55                  60
Ser Val Lys Gly Arg Phe Thr Ile Ser Arg Asp Gly Ser Gly Gly
65                  70                  75                  80
Ser Gly Gly Ser Asp Ser Lys Ser Asn Ile Tyr Leu Gln Met Asn Ser
            85                  90                  95
Leu Lys Glu Glu Asp Thr Ala Val Tyr Tyr Cys Arg Tyr Val His Tyr
            100                 105                 110
Gly Ala Tyr Tyr Gly Val Asp Ala Trp Gly Gln Gly Thr Ser Val Thr
        115                 120                 125
Val Ser Ser Ala Ser Thr Lys Gly Pro Ser Val Phe Pro Leu Ala Pro
    130                 135                 140
Ser Ser Lys Ser Thr Ser Gly Gly Thr Ala Ala Leu Gly Cys Leu Val
145                 150                 155                 160
Lys Asp Tyr Phe Pro Glu Pro Val Thr Val Ser Trp Asn Ser Gly Ala
                165                 170                 175
Leu Thr Ser Gly Val His Thr Phe Pro Ala Val Leu Gln Ser Ser Gly
            180                 185                 190
Leu Tyr Ser Leu Ser Ser Val Val Thr Val Pro Ser Ser Ser Leu Gly
        195                 200                 205
Thr Gln Thr Tyr Ile Cys Asn Val Asn His Lys Pro Ser Asn Thr Lys
    210                 215                 220
Val Asp Lys Lys Val Glu Pro Lys Ser Cys Asp Lys Thr His Thr Cys
225                 230                 235                 240
Pro Pro Cys Pro Ala Pro Glu Ala Ala Gly Gly Pro Ser Val Phe Leu
                245                 250                 255
Phe Pro Pro Lys Pro Lys Asp Thr Leu Met Ile Ser Arg Thr Pro Glu
            260                 265                 270
Val Thr Cys Val Val Val Asp Val Ser His Glu Asp Pro Glu Val Lys
        275                 280                 285
Phe Asn Trp Tyr Val Asp Gly Val Glu Val His Asn Ala Lys Thr Lys
    290                 295                 300
Pro Arg Glu Glu Gln Tyr Ala Ser Thr Tyr Arg Val Val Ser Val Leu
305                 310                 315                 320
Thr Val Leu His Gln Asp Trp Leu Asn Gly Lys Glu Tyr Lys Cys Lys
                325                 330                 335
Val Ser Asn Lys Ala Leu Pro Ala Pro Ile Glu Lys Thr Ile Ser Lys
            340                 345                 350
Ala Lys Gly Gln Pro Arg Glu Pro Gln Val Tyr Thr Leu Pro Pro Ser
        355                 360                 365
Arg Cys Glu Leu Thr Lys Asn Gln Val Ser Leu Ser Cys Ala Val Lys
    370                 375                 380
Gly Phe Tyr Pro Ser Asp Ile Ala Val Glu Trp Glu Ser Asn Gly Gln
385                 390                 395                 400
Pro Glu Asn Asn Tyr Lys Thr Thr Pro Pro Val Leu Asp Ser Asp Gly
                405                 410                 415
Ser Phe Phe Leu Val Ser Lys Leu Thr Val Asp Lys Ser Arg Trp Gln
            420                 425                 430
Gln Gly Asn Val Phe Ser Cys Ser Val Met His Glu Ala Leu His Asn
        435                 440                 445
His Tyr Thr Gln Lys Ser Leu Ser Leu Ser Pro Asp Tyr Lys Asp Asp

Asp Asp Lys
465

<210> SEQ ID NO 132
<211> LENGTH: 461
<212> TYPE: PRT
<213> ORGANISM: Artificial Sequence
<220> FEATURE:
<223> OTHER INFORMATION: an artificially synthesized sequence

<400> SEQUENCE: 132

Glu Val Gln Leu Val Glu Thr Gly Gly Ser Leu Val Gln Pro Gly Lys
1               5                   10                  15

Ser Leu Lys Leu Thr Cys Ala Thr Ser Gly Phe Thr Phe Ser Asn Ala
            20                  25                  30

Trp Met His Trp Val Arg Gln Ser Pro Glu Lys Gln Leu Glu Trp Val
        35                  40                  45

Ala Gln Ile Lys Ala Lys Ser Asn Asn Tyr Ala Thr Tyr Tyr Ala Glu
    50                  55                  60

Ser Val Lys Gly Arg Phe Thr Ile Ser Arg Asp Asp Ser Lys Ser Asn
65                  70                  75                  80

Ile Tyr Leu Gln Met Asn Ser Leu Lys Glu Glu Asp Thr Ala Val Tyr
                85                  90                  95

Tyr Cys Arg Tyr Val His Tyr Gly Ala Gly Ser Tyr Tyr Gly Val
            100                 105                 110

Asp Ala Trp Gly Gln Gly Thr Ser Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Ala Ala Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Ala Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg

```
            340                 345                 350
Glu Pro Gln Val Tyr Thr Leu Pro Pro Ser Arg Cys Glu Leu Thr Lys
            355                 360                 365

Asn Gln Val Ser Leu Ser Cys Ala Val Lys Gly Phe Tyr Pro Ser Asp
            370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Val Ser
                    405                 410                 415

Lys Leu Thr Val Asp Lys Ser Arg Trp Gln Gln Gly Asn Val Phe Ser
                    420                 425                 430

Cys Ser Val Met His Glu Ala Leu His Asn His Tyr Thr Gln Lys Ser
                    435                 440                 445

Leu Ser Leu Ser Pro Asp Tyr Lys Asp Asp Asp Lys
                    450                 455                 460

<210> SEQ ID NO 133
<211> LENGTH: 464
<212> TYPE: PRT
<213> ORGANISM: Artificial Sequence
<220> FEATURE:
<223> OTHER INFORMATION: an artificially synthesized sequence

<400> SEQUENCE: 133

Glu Val Gln Leu Val Glu Thr Gly Gly Ser Leu Val Gln Pro Gly Lys
1               5                   10                  15

Ser Leu Lys Leu Thr Cys Ala Thr Ser Gly Phe Thr Phe Ser Asn Ala
                20                  25                  30

Trp Met His Trp Val Arg Gln Ser Pro Glu Lys Gln Leu Glu Trp Val
            35                  40                  45

Ala Gln Ile Lys Ala Lys Ser Asn Asn Tyr Ala Thr Tyr Tyr Ala Glu
        50                  55                  60

Ser Val Lys Gly Arg Phe Thr Ile Ser Arg Asp Asp Ser Lys Ser Asn
65                  70                  75                  80

Ile Tyr Leu Gln Met Asn Ser Leu Lys Glu Glu Asp Thr Ala Val Tyr
                85                  90                  95

Tyr Cys Arg Tyr Val His Tyr Gly Ala Gly Gly Ser Gly Ser Tyr
            100                 105                 110

Tyr Gly Val Asp Ala Trp Gly Gln Gly Thr Ser Val Thr Val Ser Ser
            115                 120                 125

Ala Ser Thr Lys Gly Pro Ser Val Phe Pro Leu Ala Pro Ser Ser Lys
        130                 135                 140

Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                    165                 170                 175

Gly Val His Thr Phe Pro Ala Val Leu Gln Ser Ser Gly Leu Tyr Ser
                180                 185                 190

Leu Ser Ser Val Val Thr Val Pro Ser Ser Ser Leu Gly Thr Gln Thr
            195                 200                 205

Tyr Ile Cys Asn Val Asn His Lys Pro Ser Asn Thr Lys Val Asp Lys
        210                 215                 220

Lys Val Glu Pro Lys Ser Cys Asp Lys Thr His Thr Cys Pro Pro Cys
225                 230                 235                 240

Pro Ala Pro Glu Ala Ala Gly Gly Pro Ser Val Phe Leu Phe Pro Pro
```

```
              245                 250                 255
Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
            275                 280                 285

Tyr Val Asp Gly Val Glu Val His Asn Ala Lys Thr Lys Pro Arg Glu
            290                 295                 300

Glu Gln Tyr Ala Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Pro Ala Pro Ile Glu Lys Thr Ile Ser Lys Ala Lys Gly
                340                 345                 350

Gln Pro Arg Glu Pro Gln Val Tyr Thr Leu Pro Pro Ser Arg Cys Glu
                355                 360                 365

Leu Thr Lys Asn Gln Val Ser Leu Ser Cys Ala Val Lys Gly Phe Tyr
            370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Val Ser Lys Leu Thr Val Asp Lys Ser Arg Trp Gln Gln Gly Asn
                420                 425                 430

Val Phe Ser Cys Ser Val Met His Glu Ala Leu His Asn His Tyr Thr
            435                 440                 445

Gln Lys Ser Leu Ser Leu Ser Pro Asp Tyr Lys Asp Asp Asp Asp Lys
            450                 455                 460

<210> SEQ ID NO 134
<211> LENGTH: 467
<212> TYPE: PRT
<213> ORGANISM: Artificial Sequence
<220> FEATURE:
<223> OTHER INFORMATION: an artificially synthesized sequence

<400> SEQUENCE: 134

Glu Val Gln Leu Val Glu Thr Gly Gly Ser Leu Val Gln Pro Gly Lys
1               5                   10                  15

Ser Leu Lys Leu Thr Cys Ala Thr Ser Gly Phe Thr Phe Ser Asn Ala
            20                  25                  30

Trp Met His Trp Val Arg Gln Ser Pro Glu Lys Gln Leu Glu Trp Val
        35                  40                  45

Ala Gln Ile Lys Ala Lys Ser Asn Asn Tyr Ala Thr Tyr Tyr Ala Glu
    50                  55                  60

Ser Val Lys Gly Arg Phe Thr Ile Ser Arg Asp Asp Ser Lys Ser Asn
65                  70                  75                  80

Ile Tyr Leu Gln Met Asn Ser Leu Lys Glu Glu Asp Thr Ala Val Tyr
                85                  90                  95

Tyr Cys Arg Tyr Val His Tyr Gly Ala Gly Ser Gly Ser Gly Ser Gly
            100                 105                 110

Gly Ser Tyr Tyr Gly Val Asp Ala Trp Gly Gln Gly Thr Ser Val Thr
        115                 120                 125

Val Ser Ser Ala Ser Thr Lys Gly Pro Ser Val Phe Pro Leu Ala Pro
    130                 135                 140

Ser Ser Lys Ser Thr Ser Gly Gly Thr Ala Ala Leu Gly Cys Leu Val
```

-continued

```
            145                 150                 155                 160
Lys Asp Tyr Phe Pro Glu Pro Val Thr Val Ser Trp Asn Ser Gly Ala
                165                 170                 175

Leu Thr Ser Gly Val His Thr Phe Pro Ala Val Leu Gln Ser Ser Gly
            180                 185                 190

Leu Tyr Ser Leu Ser Ser Val Val Thr Val Pro Ser Ser Ser Leu Gly
                195                 200                 205

Thr Gln Thr Tyr Ile Cys Asn Val Asn His Lys Pro Ser Asn Thr Lys
            210                 215                 220

Val Asp Lys Lys Val Glu Pro Lys Ser Cys Asp Lys Thr His Thr Cys
225                 230                 235                 240

Pro Pro Cys Pro Ala Pro Glu Ala Ala Gly Gly Pro Ser Val Phe Leu
                245                 250                 255

Phe Pro Pro Lys Pro Lys Asp Thr Leu Met Ile Ser Arg Thr Pro Glu
                260                 265                 270

Val Thr Cys Val Val Val Asp Val Ser His Glu Asp Pro Glu Val Lys
            275                 280                 285

Phe Asn Trp Tyr Val Asp Gly Val Glu Val His Asn Ala Lys Thr Lys
            290                 295                 300

Pro Arg Glu Glu Gln Tyr Ala Ser Thr Tyr Arg Val Val Ser Val Leu
305                 310                 315                 320

Thr Val Leu His Gln Asp Trp Leu Asn Gly Lys Glu Tyr Lys Cys Lys
                325                 330                 335

Val Ser Asn Lys Ala Leu Pro Ala Pro Ile Glu Lys Thr Ile Ser Lys
            340                 345                 350

Ala Lys Gly Gln Pro Arg Glu Pro Gln Val Tyr Thr Leu Pro Pro Ser
            355                 360                 365

Arg Cys Glu Leu Thr Lys Asn Gln Val Ser Leu Ser Cys Ala Val Lys
370                 375                 380

Gly Phe Tyr Pro Ser Asp Ile Ala Val Glu Trp Glu Ser Asn Gly Gln
385                 390                 395                 400

Pro Glu Asn Asn Tyr Lys Thr Thr Pro Pro Val Leu Asp Ser Asp Gly
                405                 410                 415

Ser Phe Phe Leu Val Ser Lys Leu Thr Val Asp Lys Ser Arg Trp Gln
            420                 425                 430

Gln Gly Asn Val Phe Ser Cys Ser Val Met His Glu Ala Leu His Asn
            435                 440                 445

His Tyr Thr Gln Lys Ser Leu Ser Leu Ser Pro Asp Tyr Lys Asp Asp
            450                 455                 460

Asp Asp Lys
465

<210> SEQ ID NO 135
<211> LENGTH: 122
<212> TYPE: PRT
<213> ORGANISM: Artificial Sequence
<220> FEATURE:
<223> OTHER INFORMATION: an artificially synthesized sequence

<400> SEQUENCE: 135

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Ala
            20                  25                  30

Trp Met His Trp Val Arg Gln Ala Pro Gly Lys Gly Leu Glu Trp Val
```

```
                35                  40                  45
Ala Gln Ile Lys Ala Lys Ser Asn Asn Tyr Ala Thr Tyr Tyr Ala Glu
            50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Arg Tyr Val His Tyr Gly Ala Tyr Tyr Gly Val Asp Ala Trp
            100                 105                 110

Gly Gln Gly Thr Thr Val Thr Val Ser Ser
            115                 120

<210> SEQ ID NO 136
<211> LENGTH: 112
<212> TYPE: PRT
<213> ORGANISM: Artificial Sequence
<220> FEATURE:
<223> OTHER INFORMATION: an artificially synthesized sequence

<400> SEQUENCE: 136

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
                20                  25                  30

Asn Arg Asn Thr Tyr Leu His Trp Tyr Gln Gln Lys Pro Gly Gln Ala
            35                  40                  45

Pro Arg Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Gly
                85                  90                  95

Thr Gln Val Pro Tyr Thr Phe Gly Gln Gly Thr Lys Leu Glu Ile Lys
            100                 105                 110

<210> SEQ ID NO 137
<211> LENGTH: 336
<212> TYPE: PRT
<213> ORGANISM: Artificial Sequence
<220> FEATURE:
<223> OTHER INFORMATION: an artificially synthesized sequence

<400> SEQUENCE: 137

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110
```

```
Pro Ala Pro Glu Ala Ala Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Cys Glu
225                 230                 235                 240

Leu Thr Lys Asn Gln Val Ser Leu Ser Cys Ala Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Val Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Asp Tyr Lys Asp Asp Asp Asp Lys
                325                 330                 335

<210> SEQ ID NO 138
<211> LENGTH: 107
<212> TYPE: PRT
<213> ORGANISM: Artificial Sequence
<220> FEATURE:
<223> OTHER INFORMATION: an artificially synthesized sequence

<400> SEQUENCE: 138

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 139
<211> LENGTH: 230
<212> TYPE: PRT
<213> ORGANISM: Artificial Sequence
<220> FEATURE:
```

<223> OTHER INFORMATION: an artificially synthesized sequence

<400> SEQUENCE: 139

```
Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Cys Thr Leu Pro Pro Ser Arg Asp Glu Leu Thr
130                 135                 140

Lys Asn Gln Val Ser Leu Trp Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn Arg Tyr Thr Gln Lys
210                 215                 220

Ser Leu Ser Leu Ser Pro
225                 230
```

<210> SEQ ID NO 140
<211> LENGTH: 449
<212> TYPE: PRT
<213> ORGANISM: Artificial Sequence
<220> FEATURE:
<223> OTHER INFORMATION: an artificially synthesized sequence

<400> SEQUENCE: 140

```
Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110
```

```
Ser Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 141
<211> LENGTH: 214
<212> TYPE: PRT
<213> ORGANISM: Artificial Sequence
<220> FEATURE:
<223> OTHER INFORMATION: an artificially synthesized sequence

<400> SEQUENCE: 141

Asp Ile Gln Met Thr Gln Ser Pro Ser Ser Leu Ser Ala Ser Val Gly
1               5                   10                  15
```

```
Asp Arg Val Thr Ile Thr Cys Arg Ala Ser Gln Asp Ile Ser Ser Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
50                      55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Asn Thr Leu Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 142
<211> LENGTH: 7
<212> TYPE: PRT
<213> ORGANISM: Artificial Sequence
<220> FEATURE:
<223> OTHER INFORMATION: an artificially synthesized sequence

<400> SEQUENCE: 142

Gly Gly Ser Gly Gly Gly Ser
1               5

<210> SEQ ID NO 143
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 143

Gly Gly Gly Ser Gly Gly Gly Ser
1               5

<210> SEQ ID NO 144
<211> LENGTH: 458
<212> TYPE: PRT
<213> ORGANISM: Artificial Sequence
<220> FEATURE:
<223> OTHER INFORMATION: an artificially synthesized sequence

<400> SEQUENCE: 144

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Ser Asn Ala
```

```
                20              25              30
Trp Met His Trp Val Arg Gln Ala Pro Gly Lys Gly Leu Glu Trp Val
        35              40              45
Ala Gln Ile Lys Asp Lys Ser Asn Asn Tyr Ala Thr Tyr Tyr Ala Glu
50              55              60
Ser Val Lys Gly Arg Phe Thr Ile Ser Arg Asp Asp Ser Lys Asn Ser
65              70              75              80
Ile Tyr Leu Gln Met Asn Ser Leu Lys Thr Glu Asp Thr Ala Val Tyr
                85              90              95
Tyr Cys Arg Tyr Val His Tyr Ala Ala Tyr Tyr Gly Val Asp Ala Trp
            100             105             110
Gly Gln Gly Thr Thr Val Thr Val Ser Ser Ala Ser Thr Lys Gly Pro
        115             120             125
Ser Val Phe Pro Leu Ala Pro Ser Ser Lys Ser Thr Ser Gly Gly Thr
    130             135             140
Ala Ala Leu Gly Cys Leu Val Lys Asp Tyr Phe Pro Glu Pro Val Thr
145             150             155             160
Val Ser Trp Asn Ser Gly Ala Leu Thr Ser Gly Val His Thr Phe Pro
            165             170             175
Ala Val Leu Gln Ser Ser Gly Leu Tyr Ser Leu Ser Ser Val Val Thr
            180             185             190
Val Pro Ser Ser Ser Leu Gly Thr Gln Thr Tyr Ile Cys Asn Val Asn
            195             200             205
His Lys Pro Ser Asn Thr Lys Val Asp Lys Lys Val Glu Pro Lys Ser
        210             215             220
Cys Asp Lys Thr His Thr Cys Pro Pro Cys Pro Ala Pro Glu Ala Ala
225             230             235             240
Gly Gly Pro Ser Val Phe Leu Phe Pro Pro Lys Pro Lys Asp Thr Leu
            245             250             255
Met Ile Ser Arg Thr Pro Glu Val Thr Cys Val Val Val Asp Val Ser
            260             265             270
His Glu Asp Pro Glu Val Lys Phe Asn Trp Tyr Val Asp Gly Val Glu
        275             280             285
Val His Asn Ala Lys Thr Lys Pro Arg Glu Glu Gln Tyr Ala Ser Thr
    290             295             300
Tyr Arg Val Val Ser Val Leu Thr Val Leu His Gln Asp Trp Leu Asn
305             310             315             320
Gly Lys Glu Tyr Lys Cys Lys Val Ser Asn Lys Ala Leu Pro Ala Pro
            325             330             335
Ile Glu Lys Thr Ile Ser Lys Ala Lys Gly Gln Pro Arg Glu Pro Gln
            340             345             350
Val Tyr Thr Leu Pro Pro Ser Arg Cys Glu Leu Thr Lys Asn Gln Val
        355             360             365
Ser Leu Ser Cys Ala Val Lys Gly Phe Tyr Pro Ser Asp Ile Ala Val
    370             375             380
Glu Trp Glu Ser Asn Gly Gln Pro Glu Asn Asn Tyr Lys Thr Thr Pro
385             390             395             400
Pro Val Leu Asp Ser Asp Gly Ser Phe Phe Leu Val Ser Lys Leu Thr
            405             410             415
Val Asp Lys Ser Arg Trp Gln Gln Gly Asn Val Phe Ser Cys Ser Val
            420             425             430
Met His Glu Ala Leu His Asn His Tyr Thr Gln Lys Ser Leu Ser Leu
        435             440             445
```

```
Ser Pro Asp Tyr Lys Asp Asp Asp Lys
    450                 455

<210> SEQ ID NO 145
<211> LENGTH: 28
<212> TYPE: PRT
<213> ORGANISM: Homo sapiens
<220> FEATURE:
<221> NAME/KEY: misc_feature
<222> LOCATION: (1)..(1)
<223> OTHER INFORMATION: Xaa = pyroglutamic acid

<400> SEQUENCE: 145

Xaa Asp Gly Asn Glu Glu Met Gly Gly Ile Thr Gln Thr Pro Tyr Lys
1               5                   10                  15

Val Ser Ile Ser Gly Thr Thr Val Ile Leu Thr Cys
            20                  25

<210> SEQ ID NO 146
<211> LENGTH: 163
<212> TYPE: PRT
<213> ORGANISM: Homo sapiens

<400> SEQUENCE: 146

Leu Gln Asp Pro Cys Ser Asn Cys Pro Ala Gly Thr Phe Cys Asp Asn
1               5                   10                  15

Asn Arg Asn Gln Ile Cys Ser Pro Cys Pro Pro Asn Ser Phe Ser Ser
            20                  25                  30

Ala Gly Gly Gln Arg Thr Cys Asp Ile Cys Arg Gln Cys Lys Gly Val
        35                  40                  45

Phe Arg Thr Arg Lys Glu Cys Ser Ser Thr Ser Asn Ala Glu Cys Asp
    50                  55                  60

Cys Thr Pro Gly Phe His Cys Leu Gly Ala Gly Cys Ser Met Cys Glu
65                  70                  75                  80

Gln Asp Cys Lys Gln Gly Gln Glu Leu Thr Lys Lys Gly Cys Lys Asp
                85                  90                  95

Cys Cys Phe Gly Thr Phe Asn Asp Gln Lys Arg Gly Ile Cys Arg Pro
            100                 105                 110

Trp Thr Asn Cys Ser Leu Asp Gly Lys Ser Val Leu Val Asn Gly Thr
        115                 120                 125

Lys Glu Arg Asp Val Val Cys Gly Pro Ser Pro Ala Asp Leu Ser Pro
    130                 135                 140

Gly Ala Ser Ser Val Thr Pro Pro Ala Pro Ala Arg Glu Pro Gly His
145                 150                 155                 160

Ser Pro Gln

<210> SEQ ID NO 147
<211> LENGTH: 21
<212> TYPE: DNA
<213> ORGANISM: Artificial Sequence
<220> FEATURE:
<223> OTHER INFORMATION: an artificially synthesized sequence

<400> SEQUENCE: 147
cgacgtacct ctagccttga c                                            21

<210> SEQ ID NO 148
<211> LENGTH: 98
<212> TYPE: DNA
<213> ORGANISM: Artificial Sequence
```

```
<220> FEATURE:
<223> OTHER INFORMATION: an artificially synthesized sequence

<400> SEQUENCE: 148 ctataggggag accacaacgg tttccctcta gaaataattt tgtttaactt taagaaggag    60
atatatccat ggcccaagtt caactggtcg aaagcggc                            98

<210> SEQ ID NO 149
<211> LENGTH: 45
<212> TYPE: DNA
<213> ORGANISM: Artificial Sequence
<220> FEATURE:
<223> OTHER INFORMATION: an artificially synthesized sequence

<400> SEQUENCE: 149
atacgaaatt aatacgactc actataggga gaccacaacg gtttc                    45

<210> SEQ ID NO 150
<211> LENGTH: 21
<212> TYPE: DNA
<213> ORGANISM: Artificial Sequence
<220> FEATURE:
<223> OTHER INFORMATION: an artificially synthesized sequence

<400> SEQUENCE: 150
cgacgtacct ctagccttga c                                              21

<210> SEQ ID NO 151
<211> LENGTH: 73
<212> TYPE: DNA
<213> ORGANISM: Artificial Sequence
<220> FEATURE:
<223> OTHER INFORMATION: an artificially synthesized sequence

<400> SEQUENCE: 151
tctcgagtca tttatcgtcg tcgtctttgt agtcggcacc cgaggcttta atttccagtt    60
tggtgccttg acc                                                       73

<210> SEQ ID NO 152
<211> LENGTH: 39
<212> TYPE: DNA
<213> ORGANISM: Artificial Sequence
<220> FEATURE:
<223> OTHER INFORMATION: an artificially synthesized sequence

<400> SEQUENCE: 152
gcgcagccgg cgctagccca agttcaactg gtcgaaagc                           39

<210> SEQ ID NO 153
<211> LENGTH: 45
<212> TYPE: DNA
<213> ORGANISM: Artificial Sequence
<220> FEATURE:
<223> OTHER INFORMATION: an artificially synthesized sequence

<400> SEQUENCE: 153
cgatgggccc ttggtcgacg cgctgctgac ggtcacggtg gtgcc                    45

<210> SEQ ID NO 154
<211> LENGTH: 42
<212> TYPE: DNA
<213> ORGANISM: Artificial Sequence
<220> FEATURE:
<223> OTHER INFORMATION: an artificially synthesized sequence
```

```
<400> SEQUENCE: 154
ctcctggtgt tggcccagcc ggccatggcg gatatcgtga tg                    42

<210> SEQ ID NO 155
<211> LENGTH: 53
<212> TYPE: DNA
<213> ORGANISM: Artificial Sequence
<220> FEATURE:
<223> OTHER INFORMATION: an artificially synthesized sequence

<400> SEQUENCE: 155
catgtctgtc gagcggccgc tcaacactct cccctgttga agctctttgt gac         53

<210> SEQ ID NO 156
<211> LENGTH: 26
<212> TYPE: DNA
<213> ORGANISM: Artificial Sequence
<220> FEATURE:
<223> OTHER INFORMATION: an artificially synthesized sequence

<400> SEQUENCE: 156
ttaatttcca gtttggtacc ttgacc                                       26

<210> SEQ ID NO 157
<211> LENGTH: 18
<212> TYPE: DNA
<213> ORGANISM: Artificial Sequence
<220> FEATURE:
<223> OTHER INFORMATION: an artificially synthesized sequence

<400> SEQUENCE: 157
gcgtcacact ttgctatg                                                18

<210> SEQ ID NO 158
<211> LENGTH: 21
<212> TYPE: DNA
<213> ORGANISM: Artificial Sequence
<220> FEATURE:
<223> OTHER INFORMATION: an artificially synthesized sequence

<400> SEQUENCE: 158
tgagttccac gacaccgtca c                                            21

<210> SEQ ID NO 159
<211> LENGTH: 55
<212> TYPE: DNA
<213> ORGANISM: Artificial Sequence
<220> FEATURE:
<223> OTHER INFORMATION: an artificially synthesized sequence

<400> SEQUENCE: 159
gttattactc gcggcccagc cggccatggc ggatatcgtg atgacccagt ctccg       55

<210> SEQ ID NO 160
<211> LENGTH: 27
<212> TYPE: DNA
<213> ORGANISM: Artificial Sequence
<220> FEATURE:
<223> OTHER INFORMATION: an artificially synthesized sequence

<400> SEQUENCE: 160
tttaatttcc agtttggtac cttgacc                                      27

<210> SEQ ID NO 161
<211> LENGTH: 8
```

```
<212> TYPE: PRT
<213> ORGANISM: Artificial Sequence
<220> FEATURE:
<223> OTHER INFORMATION: an artificially synthesized sequence

<400> SEQUENCE: 161

Asp Tyr Lys Asp Asp Asp Asp Lys
1               5

<210> SEQ ID NO 162
<211> LENGTH: 4
<212> TYPE: PRT
<213> ORGANISM: Artificial Sequence
<220> FEATURE:
<223> OTHER INFORMATION: an artificially synthesized sequence

<400> SEQUENCE: 162

Gly Gly Gly Ser
1

<210> SEQ ID NO 163
<211> LENGTH: 4
<212> TYPE: PRT
<213> ORGANISM: Artificial Sequence
<220> FEATURE:
<223> OTHER INFORMATION: an artificially synthesized sequence

<400> SEQUENCE: 163

Ser Gly Gly Gly
1

<210> SEQ ID NO 164
<211> LENGTH: 5
<212> TYPE: PRT
<213> ORGANISM: Artificial Sequence
<220> FEATURE:
<223> OTHER INFORMATION: an artificially synthesized sequence

<400> SEQUENCE: 164

Gly Gly Gly Gly Ser
1               5

<210> SEQ ID NO 165
<211> LENGTH: 5
<212> TYPE: PRT
<213> ORGANISM: Artificial Sequence
<220> FEATURE:
<223> OTHER INFORMATION: an artificially synthesized sequence

<400> SEQUENCE: 165

Ser Gly Gly Gly Gly
1               5

<210> SEQ ID NO 166
<211> LENGTH: 6
<212> TYPE: PRT
<213> ORGANISM: Artificial Sequence
<220> FEATURE:
<223> OTHER INFORMATION: an artificially synthesized sequence

<400> SEQUENCE: 166

Gly Gly Gly Gly Gly Ser
1               5

<210> SEQ ID NO 167
<211> LENGTH: 6
<212> TYPE: PRT
```

<213> ORGANISM: Artificial Sequence
<220> FEATURE:
<223> OTHER INFORMATION: an artificially synthesized sequence

<400> SEQUENCE: 167

Ser Gly Gly Gly Gly Gly
1               5

<210> SEQ ID NO 168
<211> LENGTH: 7
<212> TYPE: PRT
<213> ORGANISM: Artificial Sequence
<220> FEATURE:
<223> OTHER INFORMATION: an artificially synthesized sequence

<400> SEQUENCE: 168

Gly Gly Gly Gly Gly Gly Ser
1               5

<210> SEQ ID NO 169
<211> LENGTH: 7
<212> TYPE: PRT
<213> ORGANISM: Artificial Sequence
<220> FEATURE:
<223> OTHER INFORMATION: an artificially synthesized sequence

<400> SEQUENCE: 169

Ser Gly Gly Gly Gly Gly Gly
1               5

<210> SEQ ID NO 170
<211> LENGTH: 549
<212> TYPE: DNA
<213> ORGANISM: Homo sapiens

<400> SEQUENCE: 170
atggaacagg ggaagggcct ggctgtcctc atcctggcta tcattcttct tcaaggtact      60
ttggcccagt caatcaaagg aaaccacttg gttaaggtgt atgactatca agaagatggt     120
tcggtacttc tgacttgtga tgcagaagcc aaaaatatca catggtttaa agatgggaag     180
atgatcggct tcctaactga agataaaaaa aaatggaatc tgggaagtaa tgccaaggac     240
cctcgaggga tgtatcagtg taaaggatca cagaacaagt caaaaccact ccaagtgtat     300
tacagaatgt gtcagaactg cattgaacta atgcagcca ccatatctgg ctttctcttt     360
gctgaaatcg tcagcatttt cgtccttgct gttggggtct acttcattgc tggacaggat     420
ggagttcgcc agtcgagagc ttcagacaag cagactctgt tgcccaatga ccagctctac     480
cagccctca aggatcgaga agatgaccag tacagccacc ttcaaggaaa ccagttgagg     540
aggaattga                                                             549

<210> SEQ ID NO 171
<211> LENGTH: 182
<212> TYPE: PRT
<213> ORGANISM: Homo sapiens

<400> SEQUENCE: 171

Met Glu Gln Gly Lys Gly Leu Ala Val Leu Ile Leu Ala Ile Ile Leu
1               5                   10                  15

Leu Gln Gly Thr Leu Ala Gln Ser Ile Lys Gly Asn His Leu Val Lys
                20                  25                  30

Val Tyr Asp Tyr Gln Glu Asp Gly Ser Val Leu Leu Thr Cys Asp Ala
        35                  40                  45

Glu Ala Lys Asn Ile Thr Trp Phe Lys Asp Gly Lys Met Ile Gly Phe
 50                   55                  60

Leu Thr Glu Asp Lys Lys Trp Asn Leu Gly Ser Asn Ala Lys Asp
 65              70                  75                  80

Pro Arg Gly Met Tyr Gln Cys Lys Gly Ser Gln Asn Lys Ser Lys Pro
                 85                  90                  95

Leu Gln Val Tyr Tyr Arg Met Cys Gln Asn Cys Ile Glu Leu Asn Ala
            100                 105                 110

Ala Thr Ile Ser Gly Phe Leu Phe Ala Glu Ile Val Ser Ile Phe Val
            115                 120                 125

Leu Ala Val Gly Val Tyr Phe Ile Ala Gly Gln Asp Gly Val Arg Gln
        130                 135                 140

Ser Arg Ala Ser Asp Lys Gln Thr Leu Leu Pro Asn Asp Gln Leu Tyr
145                 150                 155                 160

Gln Pro Leu Lys Asp Arg Glu Asp Gln Tyr Ser His Leu Gln Gly
                165                 170                 175

Asn Gln Leu Arg Arg Asn
            180

<210> SEQ ID NO 172
<211> LENGTH: 516
<212> TYPE: DNA
<213> ORGANISM: Homo sapiens

<400> SEQUENCE: 172
atggaacata gcacgtttct ctctggcctg gtactggcta cccttctctc gcaagtgagc        60
cccttcaaga tacctataga ggaacttgag acagagtgtt ttgtgaattg caataccagc       120
atcacatggg tagagggaac ggtgggaaca ctgctctcag acattacaag actggacctg       180
ggaaaacgca tcctggaccc acgaggaata tataggtgta atgggacaga tatatacaag       240
gacaaagaat ctaccgtgca agttcattat cgaatgtgcc agagctgtgt ggagctggat       300
ccagccaccg tggctggcat cattgtcact gatgtcattg ccactctgct ccttgctttg       360
ggagtcttct gctttgctgg acatgagact ggaaggctgt ctggggctgc cgacacacaa       420
gctctgttga ggaatgacca ggtctatcag cccctccgag atcgagatga tgctcagtac       480
agccaccttg aggaaactg ggctcggaac aagtga                                  516

<210> SEQ ID NO 173
<211> LENGTH: 171
<212> TYPE: PRT
<213> ORGANISM: Homo sapiens

<400> SEQUENCE: 173

Met Glu His Ser Thr Phe Leu Ser Gly Leu Val Leu Ala Thr Leu Leu
  1               5                  10                  15

Ser Gln Val Ser Pro Phe Lys Ile Pro Ile Glu Glu Leu Glu Asp Arg
                20                  25                  30

Val Phe Val Asn Cys Asn Thr Ser Ile Thr Trp Val Glu Gly Thr Val
            35                  40                  45

Gly Thr Leu Leu Ser Asp Ile Thr Arg Leu Asp Leu Gly Lys Arg Ile
 50                  55                  60

Leu Asp Pro Arg Gly Ile Tyr Arg Cys Asn Gly Thr Asp Ile Tyr Lys
 65              70                  75                  80

Asp Lys Glu Ser Thr Val Gln Val His Tyr Arg Met Cys Gln Ser Cys
                85                  90                  95

```
Val Glu Leu Asp Pro Ala Thr Val Ala Gly Ile Ile Val Thr Asp Val
            100                 105                 110

Ile Ala Thr Leu Leu Ala Leu Gly Val Phe Cys Phe Ala Gly His
        115                 120                 125

Glu Thr Gly Arg Leu Ser Gly Ala Ala Asp Thr Gln Ala Leu Leu Arg
130                 135                 140

Asn Asp Gln Val Tyr Gln Pro Leu Arg Asp Arg Asp Ala Gln Tyr
145                 150                 155                 160

Ser His Leu Gly Gly Asn Trp Ala Arg Asn Lys
                165                 170
```

```
<210> SEQ ID NO 174
<211> LENGTH: 624
<212> TYPE: DNA
<213> ORGANISM: Homo sapiens

<400> SEQUENCE: 174
atgcagtcgg gcactcactg gagagttctg ggcctctgcc tcttatcagt tggcgtttgg      60
gggcaagatg gtaatgaaga aatgggtggt attacacaga caccatataa agtctccatc    120
tctggaacca cagtaatatt gacatgccct cagtatcctg gatctgaaat actatggcaa    180
cacaatgata aaacatagg cggtgatgag gatgataaaa acataggcag tgatgaggat     240
cacctgtcac tgaaggaatt ttcagaattg agcaaagtg gttattatgt ctgctacccc     300
agaggaagca accagaaga tgcgaacttt tatctctacc tgagggcaag agtgtgtgag    360
aactgcatgg agatggatgt gatgtcggtg gccacaattg tcatagtgga catctgcatc    420
actgggggct gctgctgct ggtttactac tggagcaaga atagaaaggc caaggccaag    480
cctgtgacac gaggagcggg tgctggcggc aggcaaaggg gacaaaacaa ggagaggcca    540
ccacctgttc ccaacccaga ctatgagccc atccggaaag ccagcgggaa cctgtattct    600
ggcctgaatc agagacgcat ctga                                           624
```

```
<210> SEQ ID NO 175
<211> LENGTH: 207
<212> TYPE: PRT
<213> ORGANISM: Homo sapiens

<400> SEQUENCE: 175

Met Gln Ser Gly Thr His Trp Arg Val Leu Gly Leu Cys Leu Leu Ser
1               5                  10                  15

Val Gly Val Trp Gly Gln Asp Gly Asn Glu Glu Met Gly Gly Ile Thr
            20                  25                  30

Gln Thr Pro Tyr Lys Val Ser Ile Ser Gly Thr Thr Val Ile Leu Thr
        35                  40                  45

Cys Pro Gln Tyr Pro Gly Ser Glu Ile Leu Trp Gln His Asn Asp Lys
    50                  55                  60

Asn Ile Gly Gly Asp Glu Asp Asp Lys Asn Ile Gly Ser Asp Glu Asp
65                  70                  75                  80

His Leu Ser Leu Lys Glu Phe Ser Glu Leu Glu Gln Ser Gly Tyr Tyr
                85                  90                  95

Val Cys Tyr Pro Arg Gly Ser Lys Pro Glu Asp Ala Asn Phe Tyr Leu
            100                 105                 110

Tyr Leu Arg Ala Arg Val Cys Glu Asn Cys Met Glu Met Asp Val Met
        115                 120                 125

Ser Val Ala Thr Ile Val Ile Val Asp Ile Cys Ile Thr Gly Gly Leu
```

-continued

```
                130                   135                   140
Leu Leu Leu Val Tyr Tyr Trp Ser Lys Asn Arg Lys Ala Lys Ala Lys
145                     150                 155                 160

Pro Val Thr Arg Gly Ala Gly Ala Gly Gly Arg Gln Arg Gly Gln Asn
                    165                 170                 175

Lys Glu Arg Pro Pro Val Pro Asn Pro Asp Tyr Glu Pro Ile Arg
            180                 185                 190

Lys Gly Gln Arg Asp Leu Tyr Ser Gly Leu Asn Gln Arg Arg Ile
            195                 200                 205
```